(12) United States Patent
Baggott

(10) Patent No.: US 12,365,661 B2
(45) Date of Patent: *Jul. 22, 2025

(54) ADVANTAGEOUS BENZOFURAN COMPOSITIONS FOR MENTAL DISORDERS OR ENHANCEMENT

(71) Applicant: Tactogen Inc, Palo Alto, CA (US)

(72) Inventor: Matthew Baggott, Redwood City, CA (US)

(73) Assignee: Tactogen Inc, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/371,935

(22) Filed: Sep. 22, 2023

(65) Prior Publication Data

US 2024/0083864 A1    Mar. 14, 2024

Related U.S. Application Data

(63) Continuation of application No. 18/077,966, filed on Dec. 8, 2022, now Pat. No. 11,767,305, which is a continuation of application No. PCT/US2021/036479, filed on Jun. 8, 2021.

(60) Provisional application No. 63/165,731, filed on Mar. 24, 2021, provisional application No. 63/149,223, filed on Feb. 13, 2021, provisional application No. 63/062,434, filed on Aug. 6, 2020, provisional application No. 63/055,897, filed on Jul. 23, 2020, provisional application No. 63/048,616, filed on Jul. 6, 2020, provisional application No. 63/046,496, filed on Jun. 30, 2020, provisional application No. 63/036,382, filed on Jun. 8, 2020.

(51) Int. Cl.
     *C07D 307/81*    (2006.01)
     *A61P 25/18*    (2006.01)
     *A61P 25/24*    (2006.01)

(52) U.S. Cl.
     CPC ............ *C07D 307/81* (2013.01); *A61P 25/18* (2018.01); *A61P 25/24* (2018.01)

(58) Field of Classification Search
     CPC ......... C07D 307/81; A61P 25/18; A61P 25/24
     USPC ........................................................ 514/469
     See application file for complete search history.

(56) References Cited

U.S. PATENT DOCUMENTS

| | | | |
|---|---|---|---|
| 7,045,545 B1 | 5/2006 | Briner et al. | |
| 7,368,477 B2 | 5/2008 | Gross et al. | |
| 7,396,857 B2 | 7/2008 | Jandura et al. | |
| 11,767,305 B2 * | 9/2023 | Baggott ............... | C07D 307/81 514/469 |
| 2005/0032873 A1 | 2/2005 | Hatzenbuhler et al. | |
| 2006/0241172 A1 | 10/2006 | Zhou et al. | |
| 2008/0200541 A1 | 8/2008 | Gross et al. | |
| 2009/0048288 A1 | 2/2009 | Ebert et al. | |
| 2020/0000747 A1 | 1/2020 | Golan | |
| 2020/0179349 A1 | 6/2020 | Yun et al. | |
| 2022/0096429 A1 | 3/2022 | Liechti | |

FOREIGN PATENT DOCUMENTS

| | | |
|---|---|---|
| WO | WO 1994/029290 A1 | 12/1994 |
| WO | WO 1997/043272 A2 | 11/1997 |
| WO | WO 2000/044737 A1 | 8/2000 |
| WO | WO 2007/146890 A2 | 12/2007 |
| WO | WO 2021/173273 A1 | 1/2021 |
| WO | WO 2021/257169 A1 | 12/2021 |
| WO | WO 2022/031566 A1 | 2/2022 |
| WO | WO 2022/106947 A1 | 5/2022 |
| WO | WO 2022/109050 A1 | 5/2022 |
| WO | WO 2022/120289 A1 | 6/2022 |

OTHER PUBLICATIONS

Taschwer et al. Electrophoresis, 2014, 35, 2793-2799 (Year: 2014).*
Baggott, Matthew J. et al. Effects of 3,4-methylenedioxymethamphetamine on socioemotional feelings, authenticity, and autobiographical disclosure in healthy volunteers in a controlled setting. J Psychopharmacol. Apr. 2016;30(4):378-87.
Barnett, Gene et al. QuaSAR, Quantitative Structure Activity Relationships of Analgesics, Narcotic Antagonists, and Hallucinogens. Rockville, Maryland: Department of Health, Education, and Welfare, Public Health Service, Alcohol, Drug Abuse, and Mental Health Administration, 1978. Print.
Brandt, Simon D. et al. The psychoactive aminoalkylbenzofuran derivatives, 5-APB and 6-APB, mimic the effects of 3,4-methylenedioxyamphetamine (MDA) on monoamine transmission in male rats. Psychopharmacology (Berl). Dec. 2020;237(12):3703-3714.
Clinicaltrials.gov. A Multi-Site Phase 3 Study of MDMA-Assisted Psychotherapy for PTSD (MAPP1)-NCT03537014. May 25, 2018.
EMCDDA—Europol 2015 annual report on the implementation of council decision 2005/387/JHA. European Monitoring Centre for Drugs and Drug Addiction. https://www.emcdda.europa.eu/system/files/publications/2880/TDAS16001ENN.pdf.
European Drug Report, Trends and Developments. 2020. European Monitoring Centre for Drugs and Drug Addiction. https://www.emcdda.europa.eu/system/files/publications/13236/TDAT20001ENN_web.pdf.
Eshleman, Amy J. et al. Structure-activity relationships of bath salt components: substituted cathinones and benzofurans at biogenic amine transporters. Psychopharmacology (Berl). Mar. 2019;236(3):939-952.
Feduccia Allison A. et al. Breakthrough for Trauma Treatment: Safety and Efficacy of MDMA-Assisted Psychotherapy Compared to Paroxetine and Sertraline. Front Psychiatry. Sep. 12, 2019;10:650.
Fuwa, Tatsu et al. Novel psychoactive benzofurans strongly increase extracellular serotonin level in mouse corpus striatum. J Toxicol Sci. 2016;41(3):329-37.

(Continued)

*Primary Examiner* — Yevgeny Valenrod
(74) *Attorney, Agent, or Firm* — Knowles Intellectual Property Strategies, LLC

(57) ABSTRACT

Pharmaceutically active benzofuran compositions for the treatment of mental disorders or for mental enhancement, including for entactogenic therapy. The present invention also includes benzofuran compounds, compositions, and methods for generally modulating central nervous system activity and treating central nervous system disorders.

30 Claims, 31 Drawing Sheets

(56) References Cited

OTHER PUBLICATIONS

Hysek Cedric M. et al. MDMA enhances emotional empathy and prosocial behavior. Soc Cogn Affect Neurosci. Nov. 2014;9(11):1645-52.
International Search Report and Written Opinion for PCT/US21/36479 dated Dec. 2, 2021, 15 pages.
Iovino Michele et al. Vasopressin secretion control: central neural pathways, neurotransmitters and effects of drugs. Curr Pharm Des. 2012;18(30):4714-24.
Johnson, C., Burroughs, R., Baggot, M., Davidson, C., Perrine, S., Baker, L. (2022) Locomotor stimulant effects and persistent serotonin depletions following 1-Benzofuran-5-yl- N-methylpropan-2-amine (5-MAPB) treatment in Sprague-Dawley rats. Society for Neuroscience Conference, Nov. 14, 2022, San Diego, CA.
Johnson, C., Burroughs, R., Baggot, M., Baker, L. (2022) Evaluation of Benzofuran and Benzothiophene Molecules for MDMA-like Discriminative Stimulus Effects in Sprague-Dawley Rats. Society for Neuroscience Conference, Nov. 14, 2022, San Diego, CA.
Johnson, C. (2022) Benzofuran derivatives substitute for the discriminative stimulus effects of MDMA in male Sprague-Dawley rats. Behavior, Biology, and Chemistry Conference, Feb. 26-27, 2022, San Antonio, TX.
Joyce, BM et al. Adderall produces increased striatal dopamine release and a prolonged time course compared to amphetamine isomers. Psychopharmacology (Berl). Apr. 2007;191(3):669-77.
Johnson, C. (2021) Benzofuran derivatives are potent serotonin releasers and substitute for the discriminative stimulus effects of MDMA in male Sprague-Dawley rats. Michigan Chapter Society for Neuroscience, Oct. 2, 2021, Rochester Hills, MI.
Johnson, C. (2021) Benzofuran derivatives are potent serotonin releasers and substitute for the discriminative stimulus effects of MDMA in male Sprague-Dawley rats. Poster presented Society for Neuroscience, Nov. 8-11, 2021, Chicago, IL.
Johnson, Candace, Benzofuran Derivatives Substitute for the Discriminative Stimulus Effects of 3,4Methylenedioxymethamphetamine (MDMA) in Male Sprague-Dawley Rats (2022). Masters Theses. 5343.
Kadkhodaei et al. Separation of enantiomers of new psychoactive substances by high-performance liquid chromatography, Journal of Separation Science, vol. 41, No. 6, Mar. 2018, pp. 1274-1286.
Kim, M., Yang, C.H., Lee, Y.S. et al. Effects of aromatic ring-substituted phenethylamines on the release of dopamine and serotonin. Forensic Toxicol. 2019; 37, 104-112.
Luethi D; and Liechti, ME. Monoamine Transporter and Receptor Interaction Profiles in Vitro Predict Reported Human Doses of Novel Psychoactive Stimulants and Psychedelics. Int J Neuropsychopharmacol. Oct. 1, 2018;21(10):926-931.
Ly, Calvin et al. Psychedelics Promote Structural and Functional Neural Plasticity. Cell Reports. Jun. 12, 2018, 23 (11): 3170-3182.
Masand, PS; and Gupta, S. Selective serotonin-reuptake inhibitors: an update. Harv Rev Psychiatry. Jul.-Aug. 1999;7(2):69-84.
Nichols, David E. Differences Between the Mechanism of Action of MDMA, MBDB, and the Classic Hallucinogens. Identification of a New Therapeutic Class: Entactogens, Journal of Psychoactive Drugs. Jan. 20, 2012, 18:4, 305-313.
Oeri Hans E. Beyond ecstasy: Alternative entactogens to 3,4-methylenedioxymethamphetamine with potential applications in psychotherapy. J Psychopharmacol. May 2021;35(5):512-536.
Pitts, Elizabeth G. et al. (±)-MDMA and its enantiomers: potential therapeutic advantages of R(−)-MDMA. Psychopharmacology (Berl). Feb. 2018;235(2):377-392.
Popper, Charles W. The Story of Four Salts. J. Child and Adolescent Psychopharmac. 1994, 4 (4): 217-223.
Preller KH, Vollenweider FX. Modulation of Social Cognition via Hallucinogens and "Entactogens". Front Psychiatry. Dec. 3, 2019;10:881.
Pubchem, SID 386269688, Available Date: Oct. 23, 2019 [retrieved on Aug. 5, 2021], Retrieve from the Internet: URL: https://pubchem.ncbi.nlm.nih.gov/substance/386269688.
Pubchem, SID 341724093, Available Date: Sep. 13, 2017 [retrieved on Aug. 5, 2021], Retrieve from the Internet: URL: https://pubchem.ncbi.nlm.nih.gov/substance/341724093.
Pubchem, SID 375664176, Available Date: Aug. 28, 2018 [retrieved on Aug. 5, 2021], Retrieve from the Internet: URL: https://pubchem.ncbi.nlm.nih.gov/substance/375664176.
Pubchem, SID 383456249, Available Date: Apr. 26, 2019 [retrieved on Aug. 5, 2021], Retrieve from the Internet: URL: https://pubchem.ncbi.nlm.nih.gov/substance/383456249.
Rickli, Anna et al. Pharmacological profile of novel psychoactive benzofurans. Br J Pharmacol. Jul. 2015;172(13):3412-25.
Rosen et al. Effects of SSRIs on sexual function: a critical review. J Clin Psychopharmacol. Feb. 1999;19(1):67-85.
Sahai, Michelle A et al. Combined in vitro and in silico approaches to the assessment of stimulant properties of novel psychoactive substances—The case of the benzofuran 5-MAPB. Prog Neuropsychopharmacol Biol Psychiatry. Apr. 3, 2017;75:1-9.
Sessa, Ben et al. A Review of 3,4-methylenedioxymethamphetamine (MDMA)-Assisted Psychotherapy. Front Psychiatry. Mar. 20, 2019;10:138.
Shimshoni, Jakob A. et al. Neurochemical binding profiles of novel indole and benzofuran MDMA analogues. Naunyn Schmiedebergs Arch Pharmacol. Jan. 2017;390(1):15-24.
Simmler, Linda D. et al. Journal of Pharmacology and Experimental Therapeutics Apr. 1, 2016, 357 (1) 134-144.
Simmler, Linda D.; and Liechti, Matthias E. Pharmacology of MDMA- and Amphetamine-Like New Psychoactive Substances. Handb Exp Pharmacol. 2018;252:143-164.
Spitzer, Manfred et al. Enantio-selective cognitive and brain activation effects of N-ethyl-3,4-methylenedioxyamphetamine in humans. Neuropharmacology. Aug. 2001;41(2):263-71.
Taschwer M, Hofer MG, Schmid MG. Enantioseparation of benzofurys and other novel psychoactive compounds by CE and sulfobutylether ß-cyclodextrin as chiral selector added to the BGE. Electrophoresis. Oct. 2014;35(19):2793-9.
Vollenweider, Franz X. et al. Psychological and cardiovascular effects and short-term sequelae of MDMA ("ecstasy") in MDMA-naïve healthy volunteers. Neuropsychopharmacology. Oct. 1998;19(4):241-51.
Wee, Sunmee et al. Relationship between the serotonergic activity and reinforcing effects of a series of amphetamine analogs. J Pharmacol Exp Ther. May 2005;313(2):848-54.
U.S. Pat. No. 11,767,305, B2, U.S. Appl. No. 18/077,966, Matthew Baggott, filed Sep. 26, 2023.
US, 2023/0159487, A1, U.S. Appl. No. 18/093,773, Matthew Baggott, filed May 25, 2023.
US, 2023/0183199, A1, U.S. Appl. No. 18/106,273, Matthew Baggott, filed Jun. 15, 2023.
US, 2023/0257347, A1, U.S. Appl. No. 18/123,812, Matthew Baggott, filed Aug. 17, 2023.
Albert-Ludwigs-Universität Freiburg durchgeführt. Datum der mündlichen Prüfung, 262 p., Sep. 19, 2019 [on-line] [found Nov. 28, 2023] found in https://freidok.uni-freiburg.de/fedora/objects/freidok:150730/datastreams/FILE1/content [524 pages machine translation].
Grumann, Christina et al. "Separation of positional isomers of nine 2 phenethylamine-derived designer drugs by liquid chromatography tandem mass Spectrometry," Short Communication, Drug Test Anal., 1184-1191, Feb. 6, 2018.
Kadkhodaei, Kian et al. Successful use of a novel lux® i-Amylose-1 chiral column for enantioseparation of "legal highs," by HPLC, Chirality, vol. 32, No. 1:11, Sep. 3, 2019.
Kucerova, Gabriela et al. "Enantioselective potential of polysaccharide-based chiral stationary phases in supercritical fluid chromatography," Chirality, vol. 29, No. 6, 8, 1-8, Feb. 21, 2017.
Weib, Jennifer A. et al. "Indirect Chiral Separation of New Recreational Drugs by Gas Chromatography—Mass Spectrometry Using Trifuoroacetyl-L-Prolyl Chloride as Chiral Derivatization Reagent," Chirality, vol. 27, No. 3, 5, Sep. 8, 2014.
PubChem CID 102336592, Dec. 25, 2015 [on-line] [found Nov. 28, 2023]; https://pubchem.ncbi.nlm.nih.gov/compound/102336592.
PubChem CID 122202866, Nov. 21, 2016 [on-line] [found Nov. 28, 2023]; https://pubchem.ncbi.nlm.nih.gov/compound/122202866.

(56) References Cited

OTHER PUBLICATIONS

PubChem CID 139033209, Sep. 23, 2019 [on-line] [found Nov. 28, 2023]; https://pubchem.ncbi.nlm.nih.gov/compound/139033209.
Pubchem, SID:331482821, Retrieve from the Internet: URL:https://pubchem.ncbi.nlm.nih.gov/substance/331482821, Available Date: Apr. 10, 2017.
Pubchem, SID:381994431, Retrieve from the Internet: URL: https://pubchem.ncbi.nlm.nih.gov/substance/381994431, Available Date: Apr. 10, 2019.
Pubchem, SID:340515045, Retrieve from the Internet: URL: https://pubchem.ncbi.nlm.nih.gov/substance/340515045, Available Date: Aug. 18, 2017.
Pubchem, SID:370226125, Retrieve from the Internet: URL: https://pubchem.ncbi.plm.nih.gov/substance/370226125, Available Date: May 25, 2018.
Richter, Lilian H. J. et al. "Pooled human liver preparations, HepaRG, or HepG2 cell lines for metabolism studies of new psychoactive substances? A study using MDMA, MDBD, butylone, MDPPP, MDPV, MDPB, 5-MAPB, and 5-API as examples" J. Pharm. Biomed. Anal., 143:32-42, May 18, 2017.
US, 2024/0308999, A1, U.S. Appl. No. 18/653,750, Matthew J. Baggott, filed Sep. 19, 2024.
US, 2024/0335414, A1, U.S. Appl. No. 18/737,589, Matthew J. Baggott, filed Oct. 10, 2024.
US, 2025/0019357, A1, U.S. Appl. No. 18/737,506, Matthew J. Baggott, filed Jan. 16, 2025.
US, 2025/0034102, A1, U.S. Appl. No. 18/895,095, Matthew J. Baggott, filed Jan. 30, 2025.
US, 2025/0042900, A1, U.S. Appl. No. 18/893,750, Matthew J. Baggott, filed Feb. 6, 2025.

* cited by examiner

ADVANTAGEOUS BENZOFURAN COMPOSITIONS FOR MENTAL DISORDERS OR ENHANCEMENT

CROSS-REFERENCE TO RELATED APPLICATIONS

This application is a continuation of U.S. patent application Ser. No. 18/077,966, filed Dec. 8, 2022, which is a continuation of International Application No. PCT/US2021/036479, filed in the U.S. Receiving Office on Jun. 8, 2021, which claims the benefit of U.S. Provisional Application No. 63/036,382, filed Jun. 8, 2020; U.S. Provisional Application No. 63/046,496, filed Jun. 30, 2020; U.S. Provisional Application No. 63/048,616, filed Jul. 6, 2020; U.S. Provisional Application No. 63/055,897, filed Jul. 23, 2020; U.S. Provisional Application No. 63/062,434, filed Aug. 6, 2020; U.S. Provisional Application No. 63/149,223, filed Feb. 13, 2021; and U.S. Provisional Application No. 63/165,731, filed Mar. 24, 2021. The entirety of each of these applications is hereby incorporated by reference herein for all purposes.

FIELD OF THE INVENTION

The present invention is in area of pharmaceutically active benzofuran compositions for the treatment of mental disorders or for mental enhancement, including for entactogenic therapy. The present invention also includes benzofuran compounds, compositions, and methods for generally modulating central nervous system activity and treating central nervous system disorders.

BACKGROUND

Mental disorders, including Post-Traumatic Stress Disorder (PTSD), are more common in society than most recognize, as they can be silent or hidden. The U.S. National Institute of Mental Health (NIMH) reports that 70% of all adults have experienced at least one traumatic event in their lives, and 20% of these people will get PTSD. NIMH estimates that about 3.6% of U.S. adults have PTSD in a one-year period. PTSD can significantly impair a person's ability to function at work, at home and socially. While many people associate PTSD with veterans and combat, in fact, it is prevalent in all aspects of society.

The World Health Organization reports that depression is a serious medical disorder affecting at least 264 million people globally of all ages. When long lasting and with even moderate intensity or severe intensity, depression can become a serious health condition. It is a leading cause of disability and if not treated can lead to suicidal thoughts and ideation which can progress to suicide as well as addiction. According to WHO, suicide is the second leading cause of death globally in 15-29 year olds.

Other mental disorders that can profoundly affect a person's ability to function normally in society include anxiety disorders such as generalized anxiety disorder, phobia, panic disorder, separation anxiety disorder, stress-related disorders, adjustment disorder, dissociative disorder, eating disorders (e.g., bulimia, anorexia, etc.), attention deficit disorder, sleep disorders, disruptive disorders, neurocognitive disorders, obsessive compulsive disorders, and personality disorders, among others.

While medications are available or in clinical testing for a range of mental disorders, these disorders remain a large burden of disease globally and are insufficiently treated. Further, many of the medications have a long ramp-up time of weeks or more, during which period some patients needing therapy stop the medication out of impatience or belief it doesn't work.

Many mental disorders are caused by, affected by and/or may be treated by altered levels of neurotransmitters, which are chemicals that transmit a signal from a neuron across the synapse to another neuron. Brain neurotransmitter systems include the serotonin system, the noradrenaline (norepinephrine) system, the dopamine system and the cholinergic system. Dopamine, serotonin and noradrenaline (norepinephrine) are classed as phenylethylamines, and noradrenaline is also a catecholamine. Drugs that prevent a neurotransmitter from binding to its receptor are called receptor antagonists. Drugs that bind to a receptor and mimic the normal neurotransmitter are receptor agonists. Other drugs interfere with the deactivation of a neurotransmitter after it has been released, which prolongs its action. This can be accomplished by blocking the re-uptake of the transmitter (reuptake inhibitor) or by inhibiting enzymes that degrade the transmitter. A direct agonist binds directly to its associated receptor site. An indirect agonist increases the binding of a neurotransmitter at the target receptor by stimulating the release or preventing the reuptake of the neurotransmitter.

Dopamine receptors are involved in many neurological processes such as motivation, pleasure, cognition, memory, learning, and fine motor control. It is the primary neurotransmitter involved in the reward pathway. Drugs that increase dopamine may produce euphoria. Some widely used drugs such as methamphetamines alter the functioning of the dopamine transporter (DAT), which is responsible for removing dopamine from the neural synapse.

Norepinephrine, also called noradrenaline, mobilizes the body for activity, and is at a high level during stress or danger. It focuses attention and increases arousal and alertness.

Serotonin (5-hydroxytryptamine or "5-HT") receptors influence various neurological functions such as aggression, anxiety, appetite, cognition, learning, memory, mood and sleep. 5-HT receptors are the target of FDA approved drugs and unapproved drugs, including antidepressants, antipsychotics, hallucinogens (psychedelics), and entactogens (empathogens). There are seven families of 5-HT receptors and each has subtypes, creating a highly complex signaling system. For example, when $5-HT_{2A}$ is agonized it often induces hallucinogenic effects, whereas $5-HT_{2B}$, which is more predominantly in the periphery than in the brain, when chronically agonized, can cause toxicity such as valvulopathy. In contrast, $5-HT_{1B}$ when agonized regulates serotonergic neurons and likely contributes to the social effects of entactogens.

Current treatments for a range of mental disorders typically involve the use of selective serotonin reuptake inhibitors (SSRIs), such as citalopram (Celexa), Escitalopram (Lexapro), Fluoxetine (Prozac), Paroxetine (Paxil) and Sertraline (Zoloft). SSRIs block the reabsorption (i.e., reuptake) of serotonin into neurons, thereby increasing levels of serotonin in the brain. However, SSRIs are generally slow to achieve clinically meaningful benefit, requiring weeks to produce therapeutic effects. Moreover, many patients are nonresponders and show no benefit at all (Masand et al., Harv. Rev. Psychiatry, 1999, 4: 69-84; Rosen et al., J. Clin. Psychopharmacol., 1999, 19: 67-85).

Bupropion (Wellbutrin), in contrast, is an anti-depressant that is a norepinephrine-dopamine reuptake inhibitor, which provides more stimulant effects, including weight loss.

Another class of drugs for treatment of CNS mental disorders is monoamine releasers. Monoamine releasers induce the release of one or more monoamine neurotransmitters (e.g., dopamine, serotonin, or epinephrine) from neurons in the brain. Monoamine releasers rapidly modulate the brain systems that are more slowly affected by SSRIs. However, their stimulant and euphoric effects frequently lead them to have high abuse liability. Hence, although the monoamine releasers based on the phenethylamine structure, such as amphetamine (Benzedrine, Dexedrine) and methamphetamine (Obetrol, Pervitin), were widely employed as antidepressants in the mid-20th century, such agents are now used much more cautiously, and primarily treat attention deficit hyperactivity disorder (ADHD).

In the search for alternatives to the flawed existing CNS mental disorder therapies, various other classes of chemical structures have been investigated. For example, U.S. Publication 2020/0000747A1 discloses rigid 2-aminoindan derivatives for use as regulators of binge behavior. Aminoalkyl dihydrobenzofurans with aryl substituents on the benzofuran ring have been disclosed for the treatment of depression and related disorders in U.S. Pat. No. 7,396,857, and for the treatment of schizophrenia and related disorders in U.S. Pat. No. 7,368,477 and U.S. Publication 2008/0200541A1. A number of secondary amines have also been disclosed as antidiabetic and antiobesity agents in edible animals in PCT Application WO1994029290A1.

While the above drugs may be helpful in certain patients or settings, better alternatives are strongly needed. The prevalent use of unapproved drugs for self-medication urges a solution with additional approved drugs that more adequately treat mental disorders or are able to provide mental enhancement.

Entactogens (empathogens) have become the focus of more attention to solve some of these serious health problems. They increase feelings of authenticity and emotional openness while decreasing social anxiety (Baggott et al., Journal of Psychopharmacology 2016, 30.4: 378-87). Entactogens are typically monoamine releasers that appear to produce their effects in part by releasing serotonin which stimulates hypothalamic serotonergic receptors, thus triggering release of the hormone oxytocin, while also stimulating serotonergic 5-HT$_{1B}$ receptors on cells in the nucleus accumbens area of the brain. They can be distinguished from drugs that are primarily hallucinogenic or psychedelic, and amphetamines, which are primarily stimulants. The most well-known entactogen is MDMA (3,4-methylenedioxymethamphetamine). Other examples of entactogens are MDA, MBDB, MDOH, and MDEA, however, these drugs do have varying and complex effects that result from binding to a range of 5-HT receptors.

The aminoalkylbenzofurans 1-(1-benzofuran-5-yl)-N-methylpropan-2-amine (5-MAPB) and 1-(1-benzofuran-6-yl)-N-methylpropan-2-amine (6-MAPB), among others, are reported to share some effects with entactogens and have undergone preliminary pharmacological profiling (Rickli et al. British Journal of Pharmacology, 2015, 172: 3412-3425; Sahai et al., Progress in Neuropsychopharmacology & Biological Psychiatry, 2017, 75(1-9); Fuwa et al., The Journal of Toxicological Sciences, 2016, 41(3), 329-37).

Before being studied in a laboratory setting, these compounds, and a small number of similar compounds such as 1-(benzofuran-5-yl)-N-methylbutan-2-amine (5-MBPB), were initially sold on the black or gray market and used for self-medication or their euphoric effects (EMCDDA-Europol (2015) Annual Report on the Implementation of Council Decision 2005/387/JHA and European Drug Report, Trends and Developments (2020), European Monitoring Centre for Drugs and Drug Addiction). Additionally, U.S. Pat. No. 7,045,545 discloses certain aminoalkyl benzofurans as agonists of serotonin 5-HT$_{2C}$ receptors.

5-MAPB and 6-MAPB have been demonstrated to act on a number of enzymes that regulate neurotransmitter levels. Significantly, racemic 5-MAPB and 6-MAPB inhibit the serotonin transporter (SERT), dopamine transporter (DAT), and norepinephrine transporter (NET) (i.e., inhibit reuptake at SERT, DAT, and NET) (Eshleman et al., Psychopharmacology, 2019, 236: 939-952; Shimshoni et al., Naunyn-Schmiedeberg's Archives Pharmacol., 2017, 390(1), 15-24). They have also been shown to affect agonism at 5-HT$_{2A}$, 5-HT$_{2B}$, and 5-HT$_{2C}$ receptors, as well as interact with muscarinic, nicotinic acetylcholine α4β2, noradrenergic (alpha-1, alpha-2, beta-1, beta-2), GABA, and dopamine (DA$_1$, DA$_{2S}$, DA$_3$, DA$_4$) receptors (Shimshoni et al., Naunyn-Schmiedeberg's Archives Pharmacol., 2017, 390(1), 15-24). Additionally, they have been shown to be a substrate or inhibitor for the enzyme MAO-A and, to a lesser extent, catechol-o-methyltransferase (Shimshoni et al., Naunyn-Schmiedeberg's Archives Pharmacol., 2017, 390(1), 15-24).

By interacting with DAT, 5-MAPB increases extracellular concentrations of dopamine in the brain consistent with it having some abuse liability (Sahai et al., Progress in Neuropsychopharmacology & Biological Psychiatry, 2017, 75(1-9)). While the mechanism was not studied, 5-MAPB has also been shown to increase extracellular serotonin, dopamine, and norepinephrine in the mouse striatum (Fuwa et al., The Journal of toxicological sciences, 2016, 41(3), 329-37). A microdialysis study of racemic 5-MAPB also found that it increased serotonin and decreased levels of the dopamine metabolite, 3,4-dihydroxyphenylacetic acid, in the rat nucleus accumbens (Kim et al., Forensic Toxicology, 2019, 37(1), 104-12). The same report identified racemic 5-MAPB as inhibiting reuptake at DAT (IC$_{50}$ 3.1 μM) and SERT (IC$_{50}$ 8.5 μM).

MDMA is currently in human clinical trials in the United States (clinicaltrials.gov; NCT03537014) and Europe for approval for use in psychotherapy sessions for severe PTSD and has been suggested as useful for aiding social cognition (Preller & Vollenweider, Frontiers in Psychiatry, 2019, 10; Hysek et al., Social cognitive and affective neuroscience, 2015, 9.11, 1645-52). The FDA granted breakthrough therapy designation for the trial and has also agreed to an expanded access program, both indicative of promising results. (Feduccia et al., Frontiers in Psychiatry, 2019, 10: 650; Sessa et al., Frontiers in Psychiatry, 2019, 10: 138). While MDMA has significant therapeutic potential, it has a number of features that potentially make it contraindicated for some patients. This includes its ability to produce acute euphoria, acute hypertensive effects, risk of hyponatremia, and oxidative stress.

The urgent need for more effective therapies for mental disorders, mental enhancement and other CNS disorders is clear and requires substantial new research and attention.

It is an object of the present invention to provide advantageous compositions and their use and manufacture for the treatment of mental disorders and enhancement. Additional objects are to provide drugs with a more rapid onset to be used in a clinical setting such as counseling, e.g., PTSD and other disorder counseling or a home setting, which open the patient to empathy, sympathy and acceptance. A further object is to provide effective treatments for a range of CNS disorders.

SUMMARY OF THE INVENTION

The present invention provides multiple embodiments of compounds, compositions, and methods to treat mental disorders and more generally central nervous disorders, as well as for mental enhancement. The compounds of the present invention provide advantageous pharmacological properties that are highly desirable as therapeutics for the treatment of mental disorders, particularly as psychotherapeutics and neurotherapeutics.

The embodiments of the invention are presented to meet the goal of assisting persons with mental disorders, who desire mental enhancement or suffer from other CNS disorders by providing milder therapeutics that are fast acting and that reduce the properties that decrease the patient experience, are counterproductive to the therapy or are undesirably toxic. One goal of the invention is to provide therapeutic compositions that increase empathy, sympathy, openness and acceptance of oneself and others, which can be taken if necessary, as part of therapeutic counseling sessions, or when necessary, episodically, or even consistently, as prescribed by a healthcare provider.

It has been surprisingly discovered that the compositions and compounds of the present invention demonstrate permeability properties that indicate the compounds are fast-acting in humans. This represents a significant improvement over SSRIs, the current standard of care for many CNS and psychological disorders. The slow onset of effects is one of the most pronounced shortcomings of SSRI therapeutics. In contrast, in one embodiment, the compounds of the present invention act as fast-acting treatments, which represents a significant advance for clinical use. It is advantageous to use a fast-acting therapeutic in a clinical therapeutic setting that typically lasts for one, two, or several hours.

In a first embodiment, it has been discovered that the entactogenic properties of certain compounds can be improved by administering an effective amount to a host such as a human, in need thereof, in a composition of an enantiomerically enriched composition that has an abundance of one enantiomer over the other, or for some of the compounds described herein, a substantially pure enantiomer (or diastereomer, where relevant). It has been discovered that certain entactogens in enantiomerically enriched form act differently from the racemate on various 5-HT receptors, dopamine receptors, nicotinic acetylcholine receptors, and norepinephrine receptors, producing variable effects, and that those effects can be selected for based on desired outcome for the patient. This could not be predicted in advance given the complexity of the neurotransmitter system.

The entactogenic properties of a drug can be assessed by multiple published methods, including but not limited to those described in Example 28 (Evaluation of the Entactogenic Effect of Decreased Neuroticism) and Example 29 (Evaluation of the Entactogenic Effect of Authenticity).

In one aspect of this embodiment, therefore, the invention provides pharmaceutical compositions comprising enantiomerically enriched or for some indications, substantially enantiomerically pure, R-5-MAPB, S-5-MAPB, R-6-MAPB, or R-6-MAPB or a pharmaceutically acceptable salt or salt mixture thereof. In certain aspects, a pharmaceutical composition is provided that comprises an enantiomerically-enriched mixture of the R- or S-enantiomer of 5-MAPB or 6-MAPB:

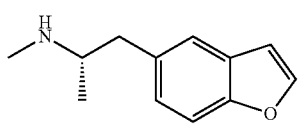

S-5-MAPB

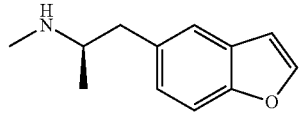

R-5-MAPB

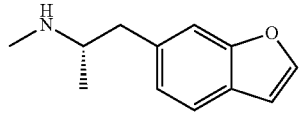

S-6-MAPB

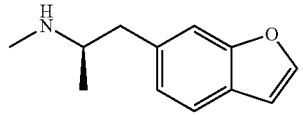

R-6-MAPB

In certain embodiments, isolated enantiomers of the compounds of the present invention show improved binding at the desired receptors and transporters relevant to the goal of treatment for the mental disorder or for mental enhancement.

It has been discovered that it is preferred to have an S- or R-enantiomerically enriched mixture of these entactogenic compounds that is not a racemic mixture. It has been surprisingly discovered that enantiomerically enriched mixtures that have a greater amount of the S-enantiomer 5-MAPB or 6-MAPB maximize serotonin-receptor-dependent therapeutic effects, and that enantiomerically enriched mixtures that have a greater amount of R-enantiomer of 5-MAPB or 6-MAPB maximize nicotinic-receptor-dependent therapeutic effects. Therefore, one aspect of the present invention is a balanced mixture of S-5-MAPB and R-5-MAPB or a balanced mixture of S-6-MAPB and R-6-MAPB that achieves a predetermined combination of serotonin-receptor-dependent therapeutic effects and nicotinic-receptor-dependent or dopaminergic therapeutic effects. The effect can be modulated as desired for optimal therapeutic effect.

Accordingly, in one embodiment, an enantiomerically enriched mixture of S-5-MAPB or an enantiomerically enriched mixture of S-6-MAPB maximize serotonin-receptor-dependent therapeutic effects and minimize unwanted nicotinic effects or dopaminergic effects when administered to a host in need thereof, for example a mammal, including a human.

In another embodiment, an enantiomerically enriched mixture of R-5-MAPB or an enantiomerically enriched mixture of R-6-MAPB maximize nicotinic-receptor-dependent or dopaminergic-receptor dependent therapeutic effects while minimizing unwanted effects, when administered to a host in need thereof, including a mammal, for example, a human.

It has been surprisingly discovered that enantiomerically enriched mixtures of 5-MAPB that are non-racemic have a relatively greater amount of some therapeutic effects (such as emotional openness) while having lesser effects associated with abuse liability (such as perceptible 'good drug effects'). Additionally, any such abuse liability would be expected to be attenuated to the extent that the substance also increases extracellular serotonin (see, e.g., Wee et al., Journal of Pharmacology and Experimental Therapeutics, 2005, 313(2), 848-854). Therefore, one aspect of the present invention is a balanced non-racemic mixture of S-5-MAPB and R-5-MAPB or a balanced non-racemic mixture of S-6-MAPB and R-6-MAPB that achieves a predetermined combination of emotional therapeutic effects and perceptible mood effects. The effect can be modulated as desired for optimal therapeutic effect.

Accordingly, in one embodiment, an enantiomerically enriched mixture of S-5-MAPB or an enantiomerically enriched mixture of S-6-MAPB balances emotional openness and perceptible mood effects when administered to a host in need thereof, for example a mammal, including a human.

The present invention also provides a method for the modulation of CNS activity and/or a method for treatment of mental disorders, including, but not limited to post-traumatic stress and adjustment disorders or any other disorder described herein, comprising administering 5-MBPB, 6-MBPB, Bk-5-MAPB or Bk-6-MAPB or a pharmaceutically acceptable salt or mixture of salts thereof, in an effective amount to a patient such as a human, in enantiomerically enriched form to achieve the desired properties:

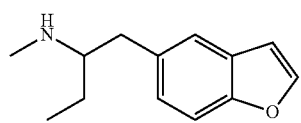

5-MBPB

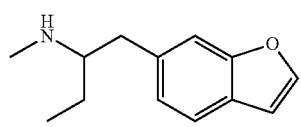

6-MBPB

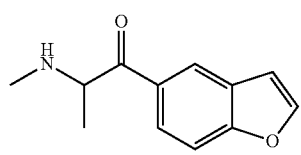

Bk-5-MAPB

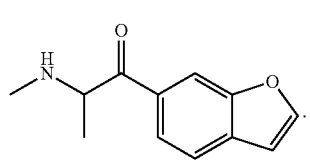

Bk-6-MAPB

In yet other embodiments, the present invention provides a enantiomerically enriched compound of Formula A, Formula B, Formula C, Formula D, Formula E, or Formula F or a pharmaceutically acceptable salt or mixed salt thereof, for any of the uses described herein by administering to a patient, such as a human, the enantiomerically enriched compound in an effective amount to achieve the desired effect:

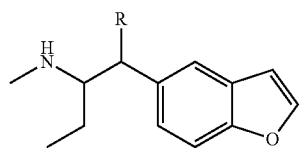

Formula A

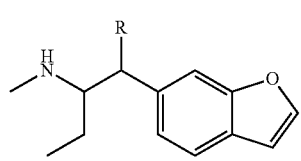

Formula B

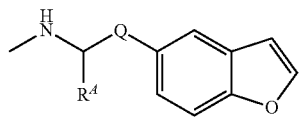

Formula C

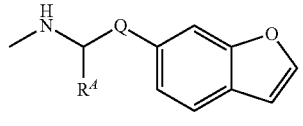

Formula D

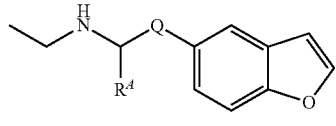

Formula E

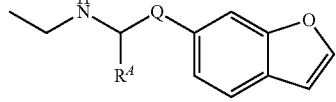

Formula F wherein
R is hydrogen or hydroxyl.
$R^A$ is —$CH_3$, —$CH_2Y$, —$CHY_2$, —$CY_3$, —$CH_2CH_3$, —$CH_2CH_2Y$, —$CH_2CHY_2$, —$CH_2CY_3$, —$CH_2OH$, or —$CH_2CH_2OH$;
Q is selected from:

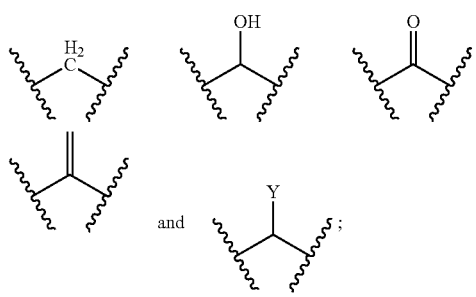

and
Y is halogen.

Non-limiting examples of unwanted effects that can be minimized by carefully selecting the balance of enantiomers include hallucinogenic effects, psychoactive effects (such as excess stimulation or sedation), physiological effects (such as transient hypertension or appetite suppression), toxic effects (such as to the brain or liver), effects contributing to abuse liability (such as euphoria or dopamine release), and/or other side effects.

The present invention includes compounds with beneficial selectivity profiles for neurotransmitter transporters. The balance of weakly activating NET (to reduce cardiovascular toxicity risk) and decreasing the DAT to SERT ratio over the racemate (to increase therapeutic effect relative to addictive liability) is a desirable feature of an entactogenic therapy displayed by the compounds and compositions of the present invention.

An enantiomerically enriched mixture is a mixture that contains one enantiomer in a greater amount than the other. An enantiomerically enriched mixture of an S-enantiomer contains at least 55% of the S-enantiomer, and, typically at least about 60%, 65%, 70%, 75%, 80%, 85%, 90%, 95% of the S-enantiomer. An enantiomerically enriched mixture of an R-enantiomer contains at least 55% of the R-enantiomer, and typically at least about 60%, 65%, 70%, 75%, 80%, 85%, 90%, 95% of the R-enantiomer. The specific ratio of S or R enantiomer can be selected for the need of the patient according to the health care specialist to balance the desired effect.

The term enantiomerically enriched mixture as used herein does not include either a racemic mixture or a pure or substantially pure enantiomer.

The present invention also provides new medical uses for the described compounds, including but not limited to, administration in an effective amount to a host in need thereof such as a human for depression, dysthymia, anxiety, generalized anxiety, social anxiety, panic, adjustment disorders, feeding and eating disorders, binge behaviors, body dysmorphic syndromes, addiction, drug abuse or dependence disorders, disruptive behavior disorders impulse control disorders, gaming disorders, gambling disorders, memory loss, dementia of aging, attention deficit hyperactivity disorder, personality disorders, attachment disorders, autism or dissociative disorders or any other disorder described herein, including in the Background. One particular treatment is for adjustment disorder, which is highly prevalent in society and currently insufficiently addressed. In nonlimiting aspects, the compound used in the treatment includes, for example, an enantiomerically enriched composition or substantially pure R- or S-enantiomer of 5-MAPB, 6-MAPB, 5-MBPB, 6-MBPB, 5-Bk-5-MAPB, 6-Bk-MAPB, Bk-5-MBPB, Bk-6-MBPB, or a combination thereof.

It has been discovered that several of the benzofuran derivatives of the current invention are direct $5\text{-HT}_{1B}$ agonists. Very few substances are known that are 5-HT1B agonists and also 5-HT releasers and these have significant toxicities. For example, meta-chlorophenylpiperazine (mCPP) is one example but is anxiogenic and induces headaches, limiting any clinical use.

However, MDMA itself does not bind directly to the $5\text{-HT}_{1B}$ (Ray. 2010. *PloS one*, 5(2), e9019). $5\text{-HT}_{1B}$ agonism is noteworthy because indirect stimulation of these receptors, secondary to elevated extracellular serotonin, has been hypothesized to be required for the prosocial effects of MDMA (Heifets et al. 2019. *Science translational medicine*, 11(522)), while other aspects of entactogen effects have been attributed to monoamine release (e.g., Luethi & Liechti. 2020. *Archives of toxicology*, 94(4), 1085-1133). Thus, the unique ratios of $5\text{-HT}_{1B}$ stimulation and monoamine release displayed by the disclosed compounds enable different profiles of therapeutic effects that appear not achieved by MDMA or other known entactogens.

The general pharmacology of entactogen enantiomers and enantiomeric compositions has been poorly understood to date. They have been difficult to separate, and it is not currently easily predicted what the therapeutic effects of individual enantiomers or enantiomerically enriched compositions might be based on individual complex receptor binding. Further, trends in the contribution of individual enantiomers often do not translate to other members of the same class of compounds. For example, the S-(+)-enantiomer of MDMA is more psychoactive than the R-(–)-enantiomer, but in 3,4-methylenedioxyamphetamine (MDA, differing from MDMA only by the absence of an N-methyl group), the S-(+)-enantiomer is less active than its corresponding R-(–)-enantiomer (Anderson et al., NIDA Res Monogr, 1978, 22: 8-15; Nichols. J. Psychoactive Drugs, 1986, 18: 305-13).

In the case of amphetamine, a non-entactogenic stimulant, it has been observed that an enantiomerically enriched mixture of enantiomers displays properties superior to the racemic mix or either enantiomer alone (Joyce et al., Psychopharmacology, 2007, 191: 669-677). The drug Adderall is a paradigm example of a mixture of enantiomers of amphetamine. The mixture has equal parts racemic amphetamine and dextroamphetamine mixed salts (sulfate, aspartate, and saccharate) which results in an approximately 3:1 ratio between the dextroamphetamine and levoamphetamine. The two enantiomers are different enough to give Adderall an effect profile different from the racemate or the d-enantiomer. However, to date, it has not been reported or predictable what properties a mixture of enantiomers of the entactogenic compounds described herein would produce or how to use the mixture in therapy.

Understanding the pharmacology of the entactogen enantiomers was further complicated by the fact that the therapeutic effects of entactogens are not identical to the more readily identifiable psychoactive effects. Moreover, different enantiomers may differ in potency and activity in dissimilar and unpredictable ways. For instance, when the enantiomers of 3,4-methylenedioxy-N-ethylamphetamine (MDE) were compared in humans, it was concluded that the therapeutic effects of MDE were due to the S-(+)-enantiomer while the R-(–)-enantiomer primarily contributed to unwanted and toxic effects (Spitzer et al., Neuropharmacology, 2001, 41.2: 263-271). In contrast, it has been argued that the R-(–)-enantiomer of MDMA may maintain the therapeutic effects of (±)-MDMA with a reduced side effect profile (Pitts et al., Psychopharmacology, 2018, 235.2: 377-392). Thus, it is not possible to predict which enantiomers will best retain or provide therapeutic activity. While the enantiomers of 5-MAPB have been at least partially separated (Kadkhodaei et al. Journal of Separation Science, 2018, 41(6): 1274-1286), to the inventor's knowledge, there have not yet been any studies characterizing the pharmacological effects of the isolated enantiomers of a benzofuran entactogen before this invention.

As described in the non-limiting illustrative Example 9, in one embodiment, the compounds of the present invention are rapid releasers of serotonin. This mechanism of action works in parallel with the inhibition of serotonin reuptake. The combination of inhibiting reuptake and increasing release significantly raises levels of serotonin and enhances therapeutic effect.

Further, select compounds of the present invention retain antagonism of the serotonin transporter (SERT), which is believed to be the principal mechanism of action for SSRIs. In this way the present invention provides compounds and methods that act in a similar way to the current standard of care for many CNS disorders including mental disorders, but do not present the crucial drawback of delayed onset.

Finally, the compounds of the present invention show a 5-HT selectivity pattern that is important to therapeutic use. Agonism of the $5\text{-HT}_{2A}$ receptor can cause feelings of fear and hallucinations, but agonism of $5\text{-HT}_{1B}$ is believed to be tied to the pro-social effects of entactogens.

It has been surprisingly discovered that enantiomerically enriched compositions of the present invention can be selected to be poor agonists of $5\text{-HT}_{2A}$, but exhibit activity toward $5\text{-HT}_{1B}$. For example, as described in the non-limiting illustrative Example 6, the majority of the compounds do not exhibit $5\text{-HT}_{2A}$ agonist activity but do exhibit $5\text{-HT}_{1B}$ agonist activity in the nonlimiting range of approximately 5 to 0.05 µM, or even 3 to 0.10 µM. Importantly, $5\text{-HT}_{1B}$ agonist activity effect occurs through direct action on the receptor, rather than as an indirect consequence of serotonin release. This is an unexpected discovery because this property has not been observed in an entactogen, including MDMA, before. In one embodiment, the selectivity of the $5\text{-HT}_{1B}$ receptor over $5\text{-HT}_{2A}$ receptor allows for a more relaxed and therapeutically productive experience for the patient undergoing treatment with a compound of the present invention. In other embodiments, a compound or composition of the present invention is provided in an effective amount to treat a host, typically a human, with a CNS disorder that can be either a neurological condition (one that is typically treated by a neurologist) or a psychiatric condition (one that is typically treated by a psychiatrist). Neurological disorders are typically those affecting the structure, biochemistry, or normal electrical functions of the brain, spinal cord or other nerves. Psychiatric conditions are more typically thought of as mental disorders, which are primarily abnormalities of thought, feeling or behavior that cause significant distress or impairment of personal functioning.

Thus, the disclosed compounds can be used in an effective amount to improve neurological or psychiatric functioning in a patient in need thereof. Neurological indications include, but are not limited to improved neuroplasticity, including treatment of stroke, brain trauma, dementia, and neurodegenerative diseases. MDMA has an $EC_{50}$ of 7.41 nM for promoting neuritogenesis and an Emax approximately twice that of ketamine, which has fast acting psychiatric benefits that are thought to be mediated by its ability to promote neuroplasticity, including the growth of dendritic spines, increased synthesis of synaptic proteins, and strengthening synaptic responses (Ly et al. Cell reports 23, no. 11 (2018): 3170-3182; Figure S3). The compounds of the current invention can similarly be considered psychoplastogens, that is, small molecules that are able to induce rapid neuroplasticity (Olson, 2018, Journal of experimental neuroscience, 12, 1179069518800508. https://doi.org/10.1177%2F1179069518800508). For example, in certain embodiments, the disclosed compounds and compositions can be used to improve stuttering and other dyspraxias or to treat Parkinson's disease or schizophrenia.

The term "improving psychiatric function" is intended to include mental health and life conditions that are not traditionally treated by neurologists but sometimes treated by psychiatrists and can also be treated by psychotherapists, life coaches, personal fitness trainers, meditation teachers, counselors, and the like. For example, it is contemplated that the disclosed compounds will allow individuals to effectively contemplate actual or possible experiences that would normally be upsetting or even overwhelming. This includes individuals with fatal illnesses planning their last days and the disposition of their estate. This also includes couples discussing difficulties in their relationship and how to address them. This also includes individuals who wish to more effectively plan their career.

In other embodiments, the compositions and compounds of the present invention may be used in an effective amount to treat a host, typically a human, to modulate an immune or inflammatory response. The compounds disclosed herein alter extracellular serotonin, which is known to alter immune functioning. MDMA produces acute time-dependent increases and decreases in immune response.

In other embodiments, the invention provides an active compound for any of the uses described herein of Formula I, Formula II, Formula III, Formula IV, Formula V, Formula VI, Formula VII, Formula VIII, Formula IX, Formula X or a pharmaceutically acceptable salt or mixed salt or composition thereof. The compounds of Formula I, Formula II, Formula III, Formula IV, Formula V, Formula VI, Formula VII, Formula VIII, Formula IX, and Formula X are:

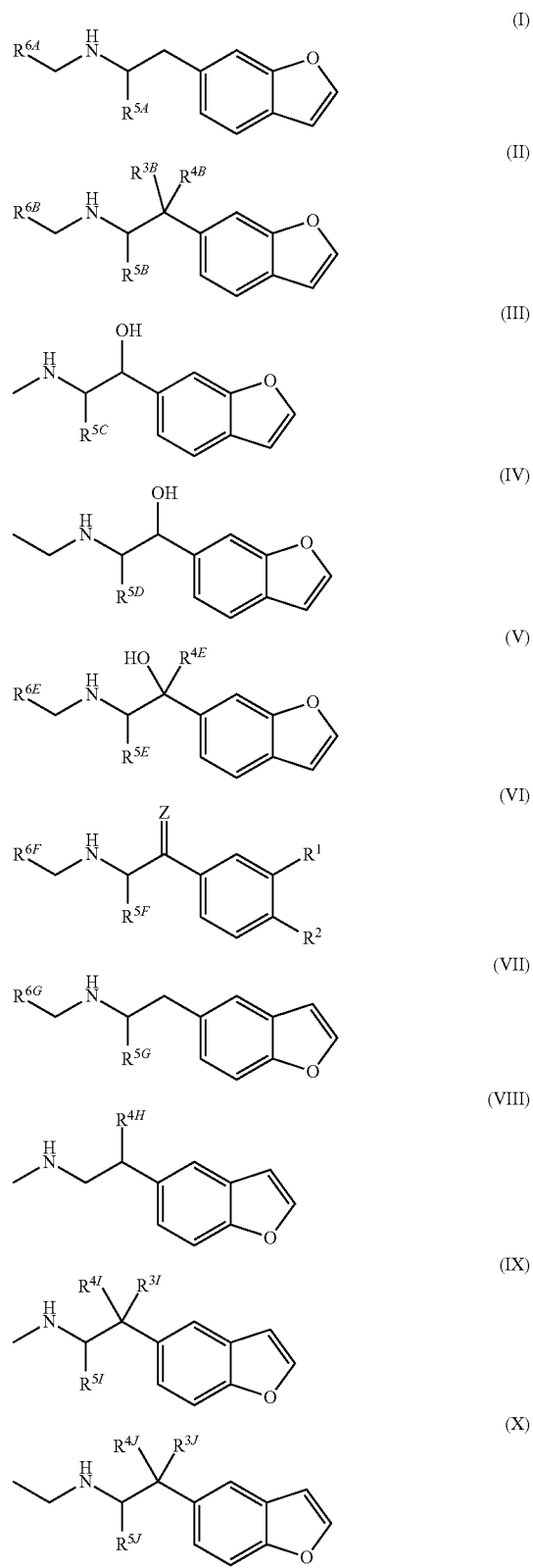

wherein:
R¹ and R² are taken together as —OCH=CH— or —CH=CHO—;
$R^{3B}$ and $R^{4B}$ are independently selected from —H, —X, $C_1$-$C_4$ alkyl, —CH₂OH, —CH₂X, —CHX₂, and —CX₃, wherein at least one of $R^{3B}$ and $R^{4B}$ is not —H;
$R^{3I}$ and $R^{4I}$ are independently selected from —H, —X, —OH, —CH₂OH, —CH₂X, —CHX₂, —CX₃, and $C_1$-$C_4$ alkyl; wherein at least one of $R^{3I}$ and $R^{4I}$ is not —H;
$R^{3J}$ and $R^{4J}$ are independently selected from —H, —X, —OH, $C_1$-$C_4$ alkyl, —CH₂OH, —CH₂X, —CHX₂, and —CX₃;
$R^{4E}$ is selected from $C_1$-$C_4$ alkyl, —CH₂OH, —CH₂X, —CHX₂, and —CX₃;
$R^{4H}$ is selected from —X, —CH₂CH₂CH₃, —CH₂OH, —CH₂X, and —CHX₂;
$R^{5A}$ and $R^{5G}$ are independently selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_2$-$C_4$ alkyl, when $R^{5A}$ is $C_2$ alkyl or H, $R^{6A}$ is not —H, and when $R^{5G}$ is —H or $C_2$ alkyl, $R^{6G}$ is not —H;
$R^{5B}$ is selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_1$-$C_4$ alkyl;
$R^{5C}$ is selected from —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_2$-$C_4$ alkyl;
$R^{5D}$, $R^{5E}$, $R^{5F}$, and $R^{5J}$ are independently selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_1$-$C_4$ alkyl, when $R^{5F}$ is —H or $C_1$ alkyl, $R^{6F}$ cannot be —H, and when $R^{5J}$ is $C_1$ alkyl, at least one of $R^{3J}$ and $R^{4J}$ is not H;
$R^{5I}$ is selected from —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_1$-$C_4$ alkyl; wherein at least one of $R^{3I}$, $R^{4I}$, and $R^{5I}$ is not $C_1$ alkyl;
$R^{6A}$, $R^{6B}$, $R^{6E}$, $R^{6F}$, and $R^{6G}$ are independently selected from —H and —CH₃;
X is independently selected from —F, —Cl, and —Br; and
Z is selected from O and CH₂.

In certain embodiments, a compound of Formulas I-X is used as described herein in enantiomerically enriched form to achieve the goals of the invention. In other embodiments, the compound is used as a racemate or a pure, including a substantially pure enantiomer.

The invention additionally includes methods to treat a neurological or psychiatric central nervous system disorder as further described herein, including a mental disorder, or to provide a mental enhancement, with a compound of Formula I, Formula II, Formula III, Formula IV, Formula V, Formula VI, Formula VII, Formula VIII, Formula IX, and Formula X or a pharmaceutically acceptable salt or mixed salt thereof.

In further embodiments, the invention includes methods to treat a neurological or psychiatric central nervous system disorder as further described herein with an enantiomerically enriched compound of Formula XI, Formula XII, and Formula XIII or a pharmaceutically acceptable salt or mixed salt thereof:

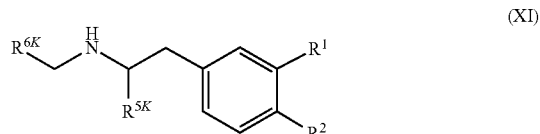

(XI)

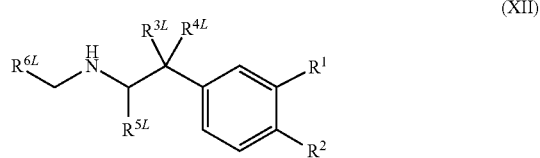

(XII)

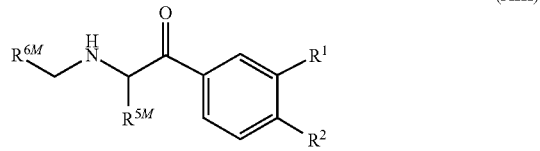

(XIII)

wherein:
R¹ and R² are taken together as —OCH=CH— or —CH=CHO—;
$R^{3L}$ and $R^{4L}$ are independently selected from —H, —X, —OH, $C_1$-$C_4$ alkyl, —CH₂OH, —CH₂X, —CHX₂, and —CX₃, wherein at least one of $R^{3L}$ and $R^{4L}$ is not —H;
$R^{5K}$ is selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_2$-$C_4$ alkyl;
$R^{5L}$ and $R^{5M}$ are independently selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_1$-$C_4$ alkyl; and
$R^{6K}$, $R^{6L}$, and $R^{6M}$ are independently selected from —H and —CH₃.

In certain aspects of these embodiments, one or more selected compounds can be improved or "tuned" by administering an effective amount to a host such as a human, in need thereof, in a composition of an enantiomerically enriched composition that has an abundance of one enantiomer over the other or a substantially pure enantiomer (or diastereomer, where relevant), or a mixture thereof. As described above, the enantiomers act differently from each other on various 5-HT receptors, dopamine receptors, nicotinic acetylcholine receptors, and norepinephrine receptors, producing variable effects, and that those effects can be selected for based on desired outcome for the patient.

In certain embodiments, any of the selected compounds or mixtures of the present invention are administered to a human patient in an effective amount in conjunction with psychotherapy, cognitive enhancement, or life coaching (pharmacotherapy), or as part of routine medical therapy.

Any of the compounds, including the enantiomerically enriched compounds, can be used in the form of a pharmaceutically acceptable salt or a mixture of salts. Nonlimiting examples include those wherein the pharmaceutically acceptable salt(s) is selected from HCl, sulfate, aspartate, saccharate, phosphate, oxalate, acetate, amino acid anion, gluconate, maleate, malate, citrate, mesylate, nitrate or tartrate, or a mixture thereof.

The present invention thus includes at least the following aspects:
(i) An enantiomerically enriched compound of 5-MAPB, 6-MAPB, 5-MBPB, 6-MBPB, Bk-5-MAPB, Bk-6-

MAPB, Formula I, Formula II, Formula III, Formula IV, Formula V, Formula VI, Formula VII, Formula VIII, Formula IX, Formula X, Formula XI, Formula XII, or Formula XIII, or Formula A, Formula B, Formula C, Formula D, Formula E, or Formula F or a pharmaceutically acceptable salt, or mixture of salts, an isotopic derivative, or prodrug thereof, or diastereomerically enriched form, as relevant;

(ii) A compound of Formula I, Formula II, Formula III, Formula IV, Formula V, Formula VI, Formula VII, Formula VIII, Formula IX, or Formula X, or a pharmaceutically acceptable salt or salt mixture, isotopic derivative, or prodrug thereof;

(iii) An enantiomerically enriched compound of Formula XI, Formula XII, or Formula XIII or a pharmaceutically acceptable salt or salt mixture, isotopic derivative, or prodrug thereof, (iv) A pharmaceutical composition comprising an effective patient-treating amount of a compound of (i), (ii) or (iii) or a pharmaceutically acceptable salt or salt mixture, isotopic derivative, or prodrug thereof, optionally with a pharmaceutically acceptable carrier or diluent;

(v) The pharmaceutically acceptable composition of (iv) in a solid or liquid, systemic, oral, topical or parenteral dosage form;

(vi) A method for treating a patient with any neurological or psychological CNS disorder as described herein that includes administering an effective amount of a compound of (i), (ii) or (iii) to a patient such as a human in need thereof, (vii) A method for treating PTSD, depression, dysthymia, anxiety, generalized anxiety, social anxiety, panic, adjustment disorders, feeding and eating disorders, binge behaviors, body dysmorphic syndromes, addiction, drug abuse or dependence disorders, disruptive behavior disorders impulse control disorders, gaming disorders, gambling disorders, memory loss, dementia of aging, attention deficit hyperactivity disorder, personality disorders, attachment disorders, autism or dissociative disorders comprising administering an effective amount of a compound of (i), (ii) or (iii) or a pharmaceutically acceptable salt, isotopic derivative, or prodrug thereof, as described herein, to a patient, typically a human, in need thereof;

(viii) A compound of (i), (ii) or (iii) or a pharmaceutically acceptable salt, salt mixture, isotopic derivative, or prodrug thereof, for use to treat any disorder as described herein in an effective amount as further described herein;

(ix) A compound (i), (ii) or (iii) for use in the manufacture of a medicament for the treatment of any of the disorders described herein;

(x) Use of a compound (i), (ii) or (iii) or a pharmaceutically acceptable salt, salt mixture, isotopic derivative, or prodrug thereof, to treat any disorder as described herein in an effective amount as further described herein;

(xi) Processes for the preparation of therapeutic products that contain an effective amount of a compound, including in enantiomerically enriched form, of 5-MAPB, 6-MAPB, 5-MBPB, 6-MBPB, Bk-5-MAPB, Bk-6-MAPB Formula I, Formula II, Formula III, Formula IV, Formula V, Formula VI, Formula VII, Formula VIII, Formula IX, Formula X, Formula XI, Formula XII, Formula XIII, Formula A, Formula B, Formula C, Formula D, Formula E, or Formula F, or a pharmaceutically acceptable salt or mixed salts, isotopic derivatives, or prodrugs thereof, as described herein.

DETAILED DESCRIPTION OF THE INVENTION

Figure 1:
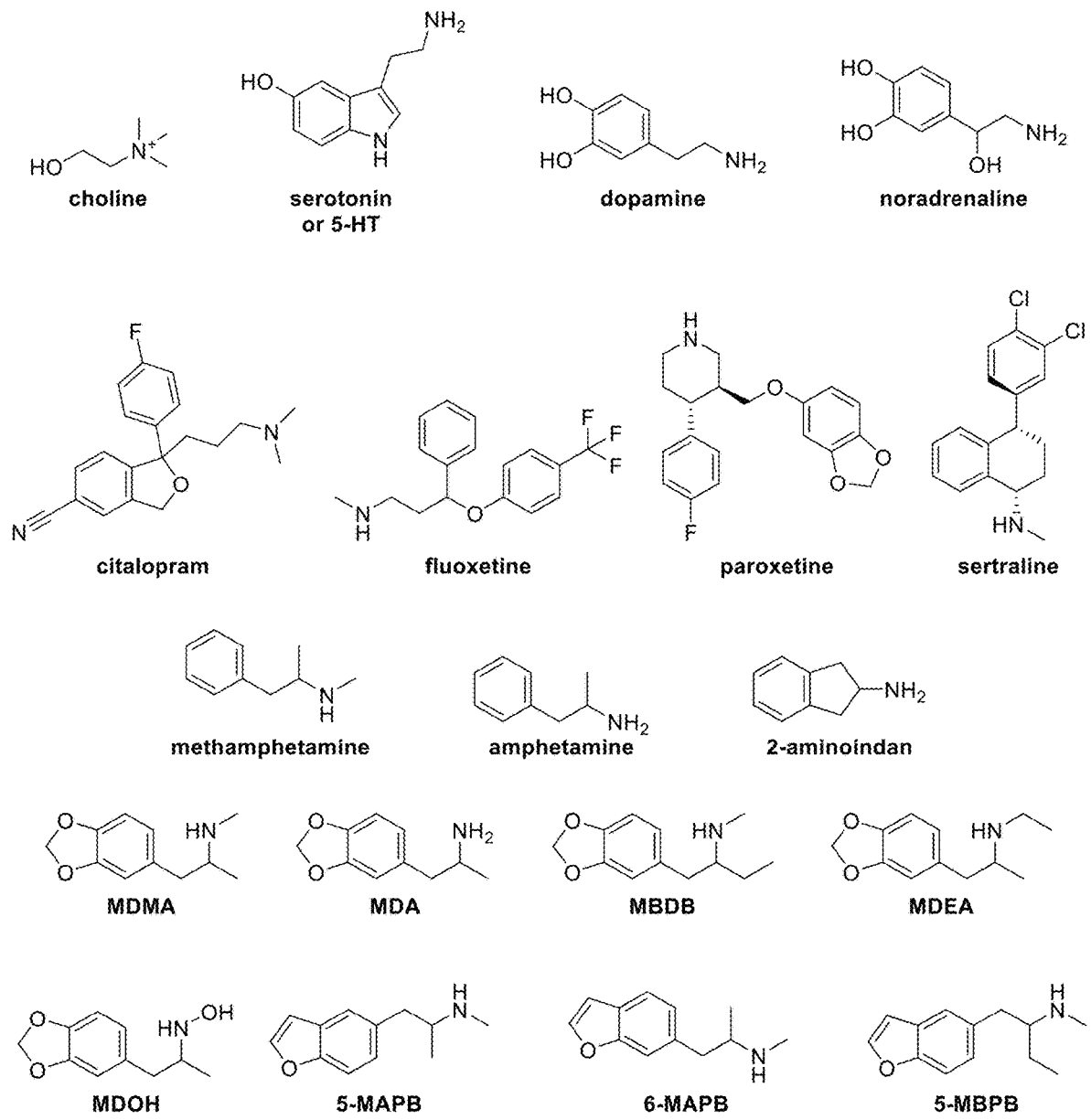
FIG. 1 provides the structures and names of several compounds referred to herein.
Figure 2:
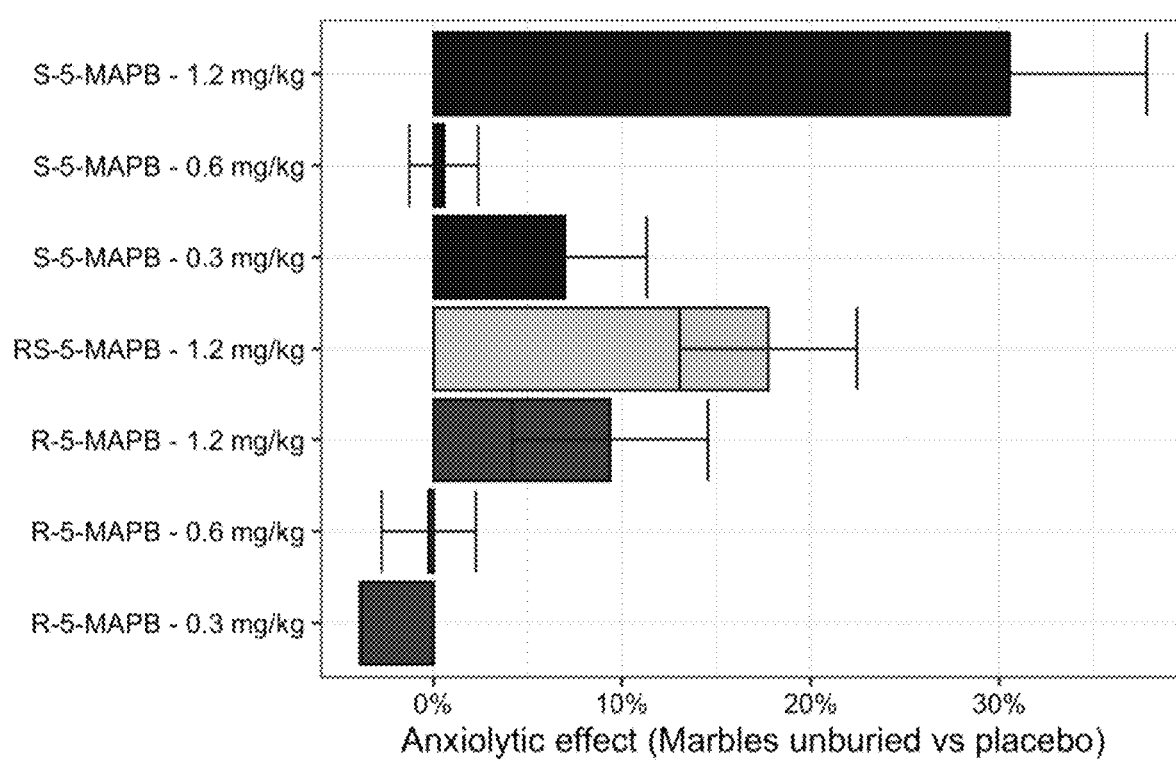
FIG. 2 is a chart showing results from the marble burying assay to measure decreased anxiety and neuroticism resulting from treatment with S-5-MAPB, RS-5-MAPB, and R-5-MAPB. The x-axis of the chart displays anxiolytic effect, described as the percent of marbles left unburied versus placebo. The y-axis gives the compound and dose. Error bars indicate 95% confidence intervals. Details and procedural information for this assay are described in Example 5.
Figure 3:
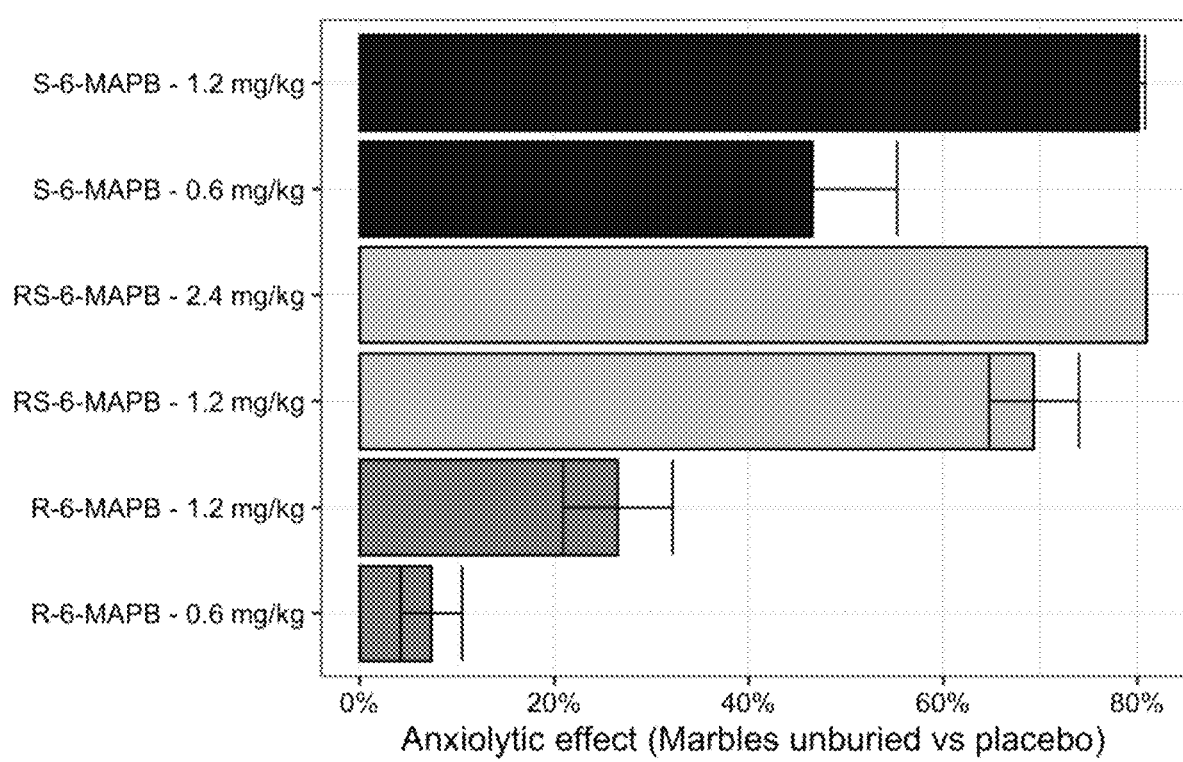
FIG. 3 is a chart showing results from the marble burying assay to measure decreased anxiety and neuroticism resulting from treatment with S-6-MAPB, RS-6-MAPB, and R-6-MAPB. The x-axis of the chart displays anxiolytic effect, described as the percent of marbles left unburied versus placebo. The y-axis gives the compound and dose. Error bars indicate 95% confidence intervals. Details and procedural information for this assay are described in Example 5.
Figure 4:
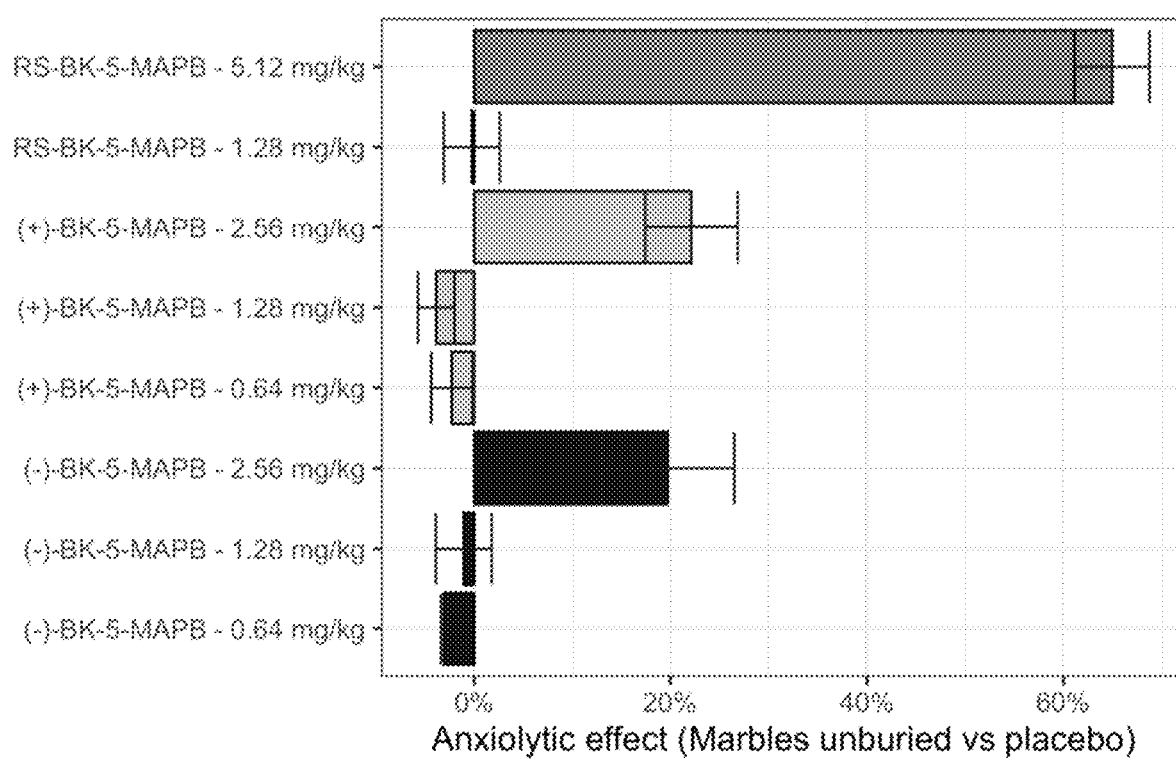
FIG. 4 is a chart showing results from the marble burying assay to measure decreased anxiety and neuroticism resulting from treatment with (+)-Bk-5-MAPB, RS-Bk-5-MAPB, and (−)-Bk-R-5-MAPB. The x-axis of the chart displays anxiolytic effect, described as the percent of marbles left unburied versus placebo. The y-axis gives the compound and dose. Error bars indicate 95% confidence intervals. Details and procedural information for this assay are described in Example 5.

The present invention provides multiple embodiments of compounds, compositions, and methods to treat mental disorders, and more generally central nervous disorders, as well as for mental enhancement. The compounds of the present invention provide advantageous pharmacological properties that are highly desirable as therapeutics for the treatment of mental disorders, particularly as psychotherapeutics and neurotherapeutics.

The embodiments of the invention are presented to meet the goal of assisting persons with mental disorders, who desire mental enhancement, or who suffer from other CNS disorders by providing milder therapeutics that are fast acting and that reduce the properties that decrease the patient experience, are counterproductive to the therapy or are undesirably toxic. One goal of the invention is to provide therapeutic compositions that increase empathy, sympathy, openness and acceptance of oneself and others, which can be taken if necessary as part of therapeutic counseling sessions, when necessary episodically or even consistently, as prescribed by a healthcare provider.

It has been surprisingly discovered that the compositions compounds of the present invention demonstrate permeability properties that indicate the compounds will be fast-acting in humans. This represents a significant improvement over SSRIs, the current standard of care for many CNS and psychological disorders. The slow onset of effects is one of the most pronounced shortcomings of SSRI therapeutics. In contrast, in one embodiment, the compounds of the present invention act as a fast-acting treatment, which represents a significant advance for clinical use. It is advantageous to use a fast-acting therapeutic in a clinical therapeutic setting that typically lasts for one or two hours.

1. In certain embodiments an enantiomerically enriched mixture of the S-enantiomer and R-enantiomer of 5-MAPB:

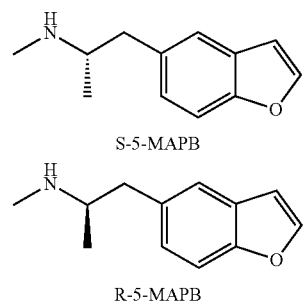

S-5-MAPB

R-5-MAPB or a pharmaceutically acceptable salt or mixed salts thereof is provided.

2. In certain embodiments an enantiomerically enriched mixture of the S-enantiomer and R-enantiomer of 6-MAPB:

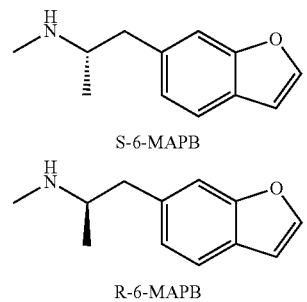

S-6-MAPB

R-6-MAPB or a pharmaceutically acceptable salt or mixed salts thereof is provided.

3. In certain embodiments an enantiomerically enriched mixture of the S-enantiomer and R-enantiomer of 5-MBPB:

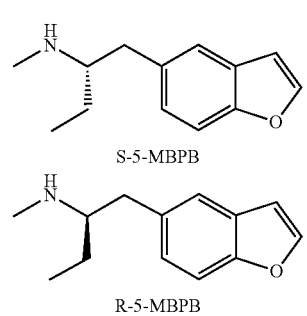

S-5-MBPB

R-5-MBPB or a pharmaceutically acceptable salt or mixed salts thereof provided.

4. In certain embodiments an enantiomerically enriched mixture of the S-enantiomer and R-enantiomer of 6-MBPB:

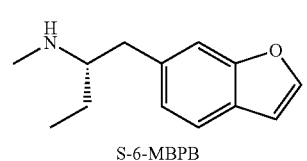

S-6-MBPB

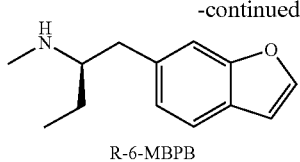

R-6-MBPB or a pharmaceutically acceptable salt or mixed salts thereof is provided.

5. In certain embodiments an enantiomerically enriched mixture of the S-enantiomer and R-enantiomer of 6-Bk-5-MAPB:

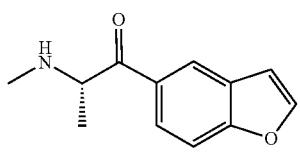

S-Bk-5-MAPB

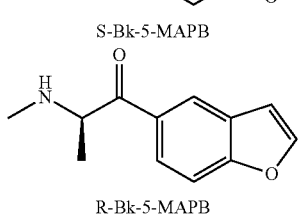

R-Bk-5-MAPB or a pharmaceutically acceptable salt or mixed salts thereof is provided.

6. In certain embodiments an enantiomerically enriched mixture of the S-enantiomer and R-enantiomer of 6-Bk-6-MAPB:

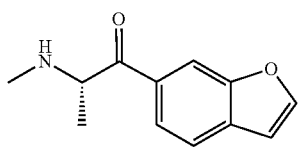

S-Bk-6-MAPB

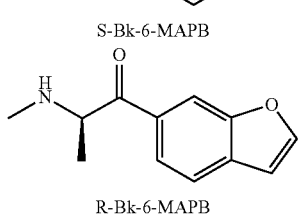

R-Bk-6-MAPB or a pharmaceutically acceptable salt or mixed salts thereof is provided.

7. In certain embodiments an enantiomerically enriched mixture of the S-enantiomer and R-enantiomer of 6-Bk-5-MBPB:

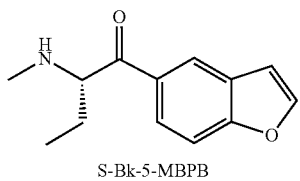

S-Bk-5-MBPB

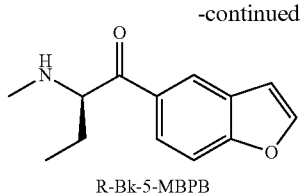

R-Bk-5-MBPB or a pharmaceutically acceptable salt or mixed salts thereof is provided.

8. In certain embodiments an enantiomerically enriched mixture of the S-enantiomer and R-enantiomer of 6-Bk-6-MBPB,

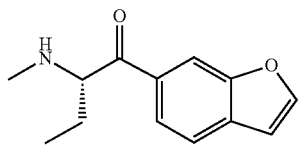

S-Bk-6-MBPB

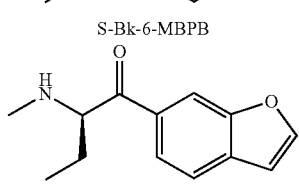

R-Bk-6-MBPB or a pharmaceutically acceptable salt or mixed salts thereof is provided.

9. The enantiomerically enriched mixture of any of embodiments 1-8, wherein the mixture has more entactogenic effects than the corresponding racemic mixture in a human.

10. The enantiomerically enriched mixture of any of embodiments 1-8, that have a greater amount of nicotinic-receptor-dependent therapeutic effects than the corresponding racemic mixture in a human.

11. The enantiomerically enriched mixture of any of embodiments 1-8, that have a greater amount of serotonin-receptor-dependent therapeutic effects than the corresponding racemic mixture in a human.

12. The enantiomerically enriched mixture of any of embodiments 1-8, that enhance serotonin-receptor-dependent therapeutic effects and decrease nicotinic effects or dopaminergic effects in a human.

13. The enantiomerically enriched mixture of any of embodiments 1-8, that comprise a balance of enantiomers that decrease an hallucinogenic effect over the racemate.

14. The enantiomerically enriched mixture of any of embodiments 1-8, that comprise a balance of enantiomers that decrease an unwanted psychoactive effect over the racemate.

15. The enantiomerically enriched mixture of any of embodiments 1-8, that comprise a balance of enantiomers that decrease a physiological effect over the racemate.

16. The enantiomerically enriched mixture of any of embodiments 1-8, that comprise a balance of enantiomers that decrease a toxic effect over the racemate.

17. The enantiomerically enriched mixture of any of embodiments 1-8, that comprise a balance of enantiomers that decrease abuse potential over the racemate.

18. The enantiomerically enriched mixture of any of embodiments 1-8 that have at least about 60% S-enantiomer.
19. The enantiomerically enriched mixture of any of embodiments 1-8 that have at least about 70% S-enantiomer.
20. The enantiomerically enriched mixture of any of embodiments 1-8 that have at least about 80% S-enantiomer.
21. The enantiomerically enriched mixture of any of embodiments 1-8 that have at least about 90% S-enantiomer.
22. The enantiomerically enriched mixture of any of embodiments 1-8 that have at least about 60% R-enantiomer.
23. The enantiomerically enriched mixture of any of embodiments 1-8 that have at least about 70% R-enantiomer.
24. The enantiomerically enriched mixture of any of embodiments 1-8 that have at least about 80% R-enantiomer.
25. The enantiomerically enriched mixture of any of embodiments 1-8 that have at least about 90% R-enantiomer.
26. The enantiomerically enriched mixture of any of embodiments 1-25 that shows a greater amount of the therapeutic effect of emotional openness than the corresponding racemic mixture.
27. The enantiomerically enriched mixture of any of embodiments 1-26 wherein the pharmaceutically acceptable salt(s) is selected from HCl, sulfate, aspartate, saccharate, phosphate, oxalate, acetate, amino acid anion, gluconate, maleate, malate, citrate, mesylate, nitrate or tartrate, or a mixture thereof.
28. The enantiomerically enriched mixture of any of embodiments 1-27 that is both a direct 5-HT$_{1B}$ agonist and a serotonin releasing agent.
29. The enantiomerically enriched mixture of embodiment 28 that is also a serotonin reuptake inhibitor.
30. The enantiomerically enriched mixture of any of embodiments 1-29 that has minimal or no agonism of 5-HT$_{2A}$.
31. In certain embodiments a compound of Formula I, Formula II, Formula III, Formula IV, Formula V, Formula VI, Formula VII, Formula VIII, Formula IX, or Formula X:

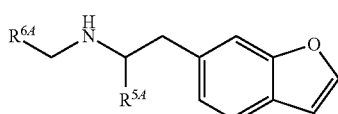

(I)

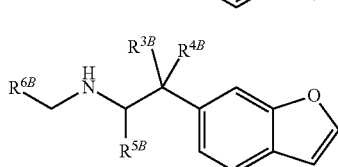

(II)

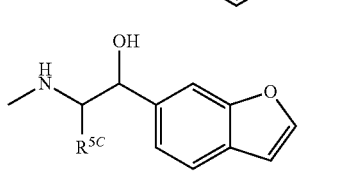

(III)

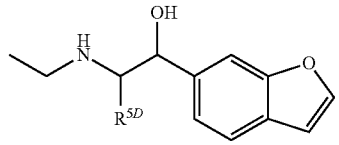

(IV)

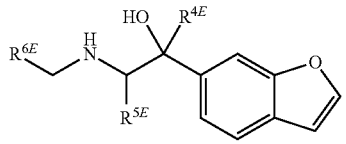

(V)

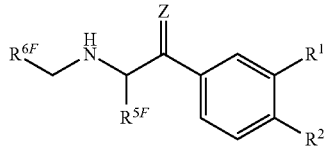

(VI)

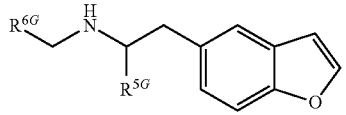

(VII)

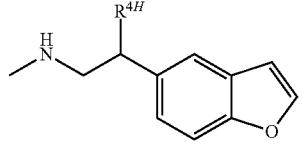

(VIII)

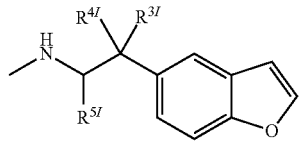

(IX)

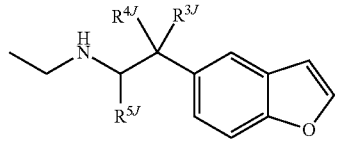

(X)

or a pharmaceutically acceptable salt or mixed salt or isotopic derivative thereof is provided, wherein:

$R^1$ and $R^2$ are taken together as —OCH=CH— or —CH=CHO—;

$R^{3B}$ and $R^{4B}$ are independently selected from —H, —X, $C_1$-$C_4$ alkyl, —CH$_2$OH, —CH$_2$X, —CHX$_2$, and —CX$_3$, wherein at least one of $R^{3B}$ and $R^{4B}$ is not —H;

$R^{3I}$ and $R^{4I}$ are independently selected from —H, —X, —OH, —CH$_2$OH, —CH$_2$X, —CHX$_2$, —CX$_3$, and $C_1$-$C_4$ alkyl; wherein at least one of $R^{3I}$ and $R^{4I}$ is not —H;

$R^{3J}$ and $R^{4J}$ are independently selected from —H, —X, —OH, $C_1$-$C_4$ alkyl, —CH$_2$OH, —CH$_2$X, —CHX$_2$, and —CX$_3$;

$R^{4E}$ is selected from $C_1$-$C_4$ alkyl, —CH$_2$OH, —CH$_2$X, —CHX$_2$, and —CX$_3$;

$R^{4H}$ is selected from —X, —CH$_2$CH$_2$CH$_3$, —CH$_2$OH, —CH$_2$X, and —CHX$_2$;

$R^{5A}$ and $R^{5G}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_2$-C$_4$ alkyl, when R$^{5A}$ is C$_2$ alkyl or H, R$^{6A}$ is not —H, and when R$^{5G}$ is —H or C$_2$ alkyl, R$^{6G}$ is not —H;

R$^{5B}$ is selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_1$-C$_4$ alkyl;

R$^{5C}$ is selected from —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_2$-C$_4$ alkyl;

R$^{5D}$, R$^{5E}$, R$^{5F}$, and R$^{5J}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_1$-C$_4$ alkyl, when R$^{5F}$ is —H or C$_1$ alkyl, R$^{6F}$ cannot be —H, and when R$^{5J}$ is C$_1$ alkyl, at least one of R$^{3J}$ and R$^{4J}$ is not H;

R$^{5I}$ is selected from —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_1$-C$_4$ alkyl; wherein at least one of R$^{3I}$, R$^{4I}$, and R$^{5I}$ is not C$_1$ alkyl;

R$^{6A}$, R$^{6B}$, R$^{6E}$, R$^{6F}$, and R$^{6G}$ are independently selected from —H and —CH$_3$;

X is independently selected from —F, —Cl, and —Br; and

Z is selected from O and CH$_2$.

32. The compound of embodiment 31 wherein the compound is of Formula I:

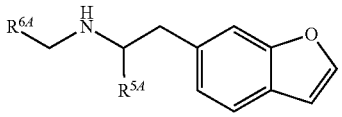

(I)

or a pharmaceutically acceptable salt or mixed salt.

33. The compound of embodiment 31 wherein the compound is of Formula II:

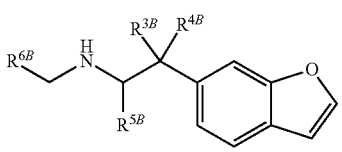

(II)

or a pharmaceutically acceptable salt or mixed salt.

34. The compound of embodiment 31 wherein the compound is of Formula III:

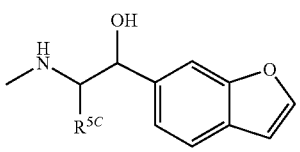

(III)

or a pharmaceutically acceptable salt or mixed salt

35. The compound of embodiment 31 wherein the compound is of Formula IV:

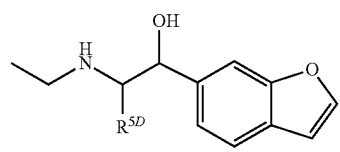

(IV)

or a pharmaceutically acceptable salt or mixed salt.

36. The compound of embodiment 31 wherein the compound is of Formula V:

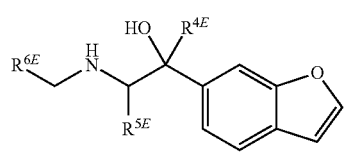

(V)

or a pharmaceutically acceptable salt or mixed salt.

37. The compound of embodiment 31 wherein the compound is of Formula VI:

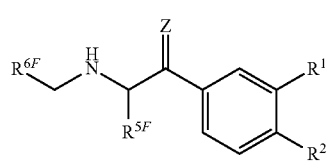

(VI)

or a pharmaceutically acceptable salt or mixed salt

38. The compound of embodiment 31 wherein the compound is of Formula VII:

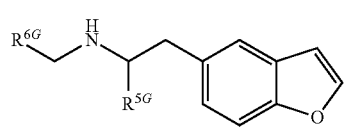

(VII)

or a pharmaceutically acceptable salt or mixed salt

39. The compound of embodiment 31 wherein the compound is of Formula VIII:

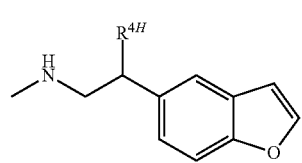

(VIII)

or a pharmaceutically acceptable salt or mixed salt.

40. The compound of embodiment 31 wherein the compound is of Formula IX:
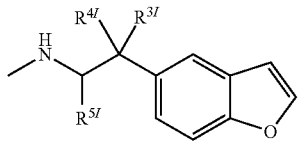
(IX)
or a pharmaceutically acceptable salt or mixed salt
41. The compound of embodiment 31 wherein the compound is of Formula X:
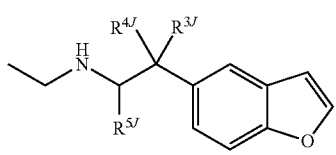
(X)
or a pharmaceutically acceptable salt or mixed salt
42. The compound of embodiment 31 or 32 wherein the compound is selected from:
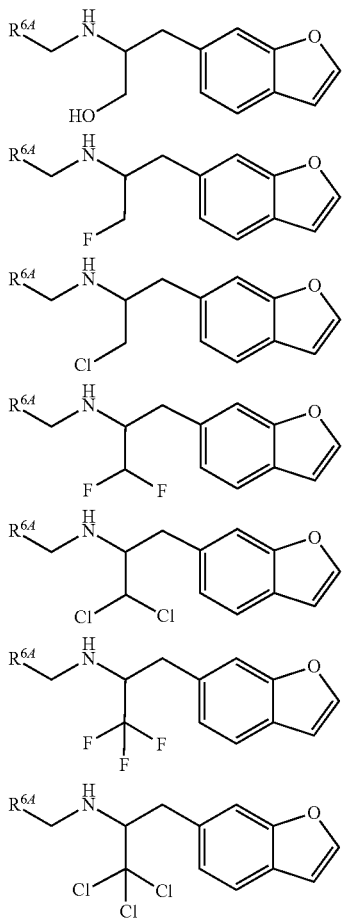
-continued
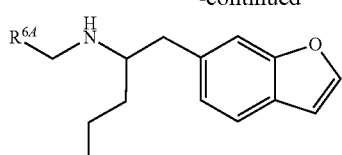
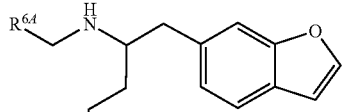
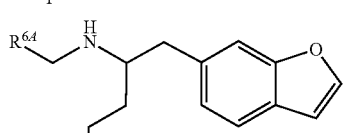
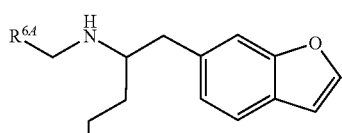
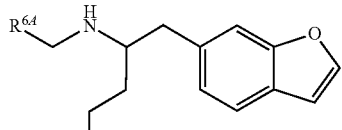
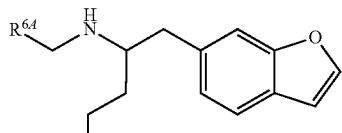
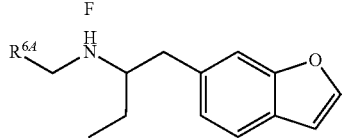
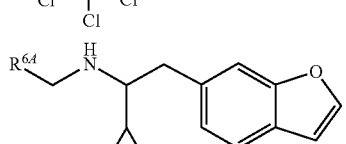

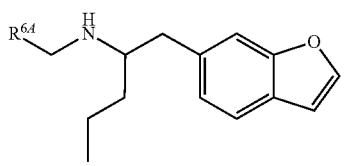
and
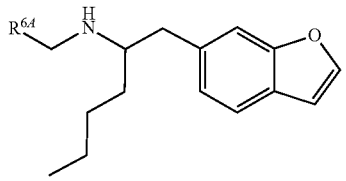
or a pharmaceutically acceptable salt or mixed salt.
43. The compound of embodiment 31 or 33 wherein the compound is selected from:
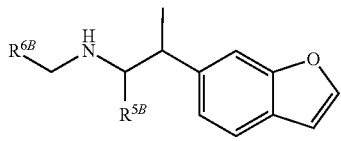
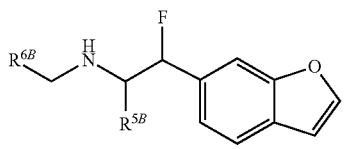
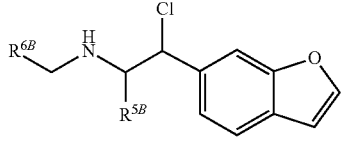
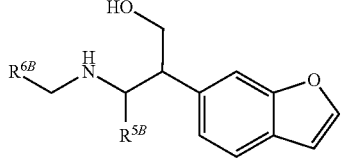
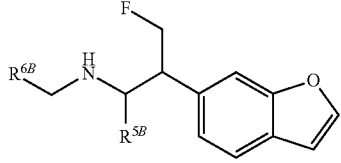
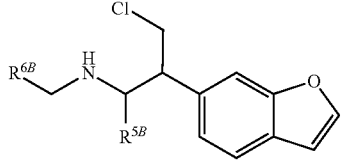
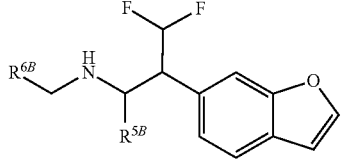
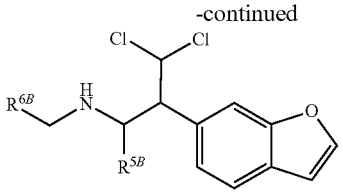
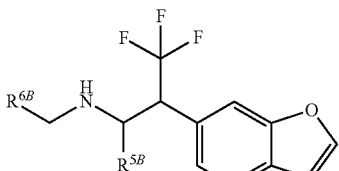
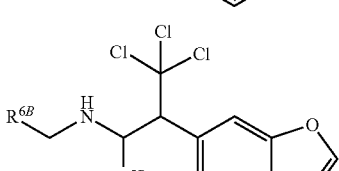
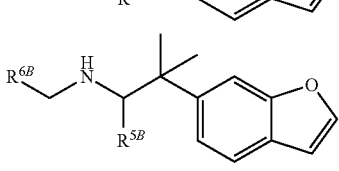
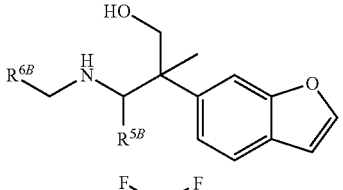
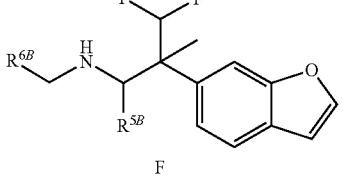
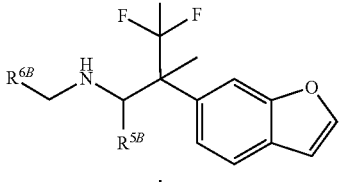
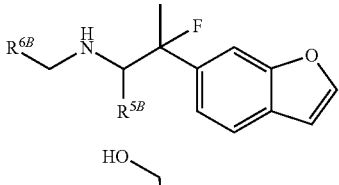
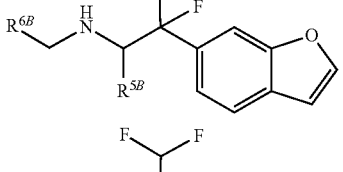
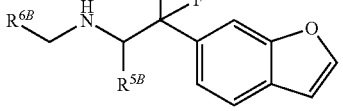
and

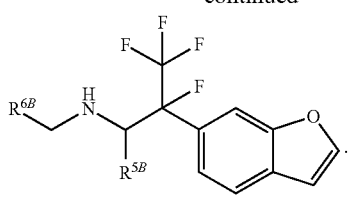
or a pharmaceutically acceptable salt or mixed salt.
44. The compound of embodiment 31 or 37 wherein the compound is selected from:
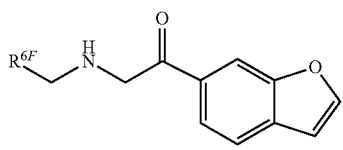
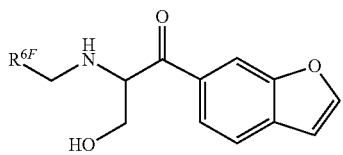
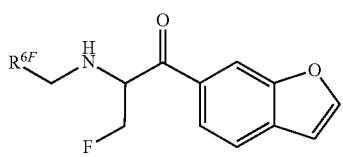
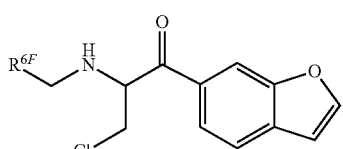
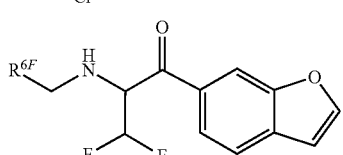
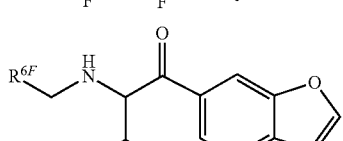
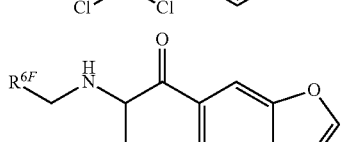
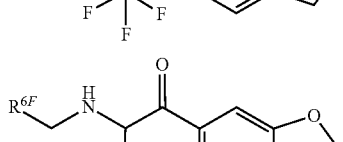
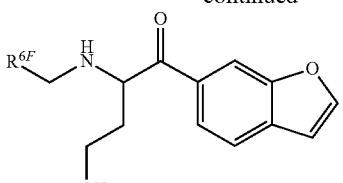
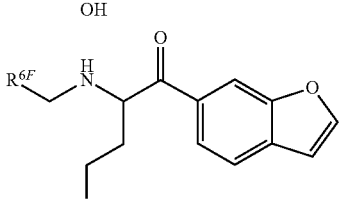
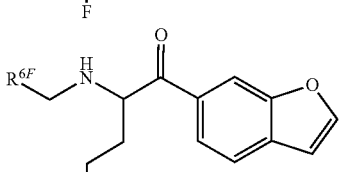
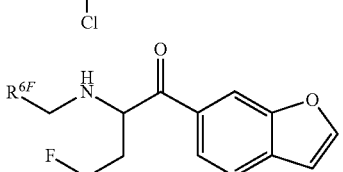
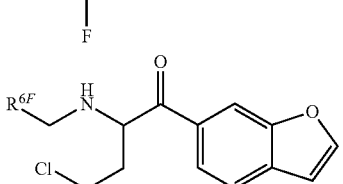
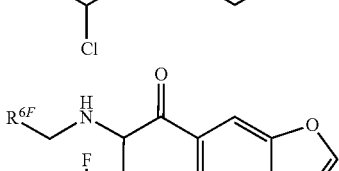
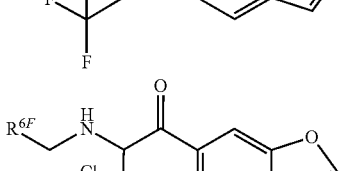
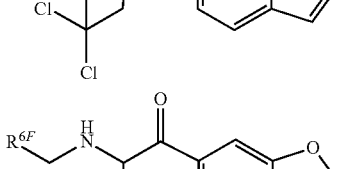
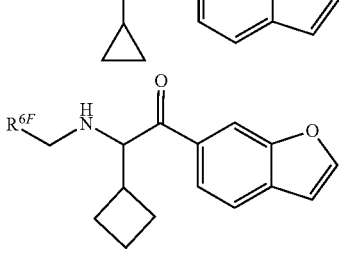

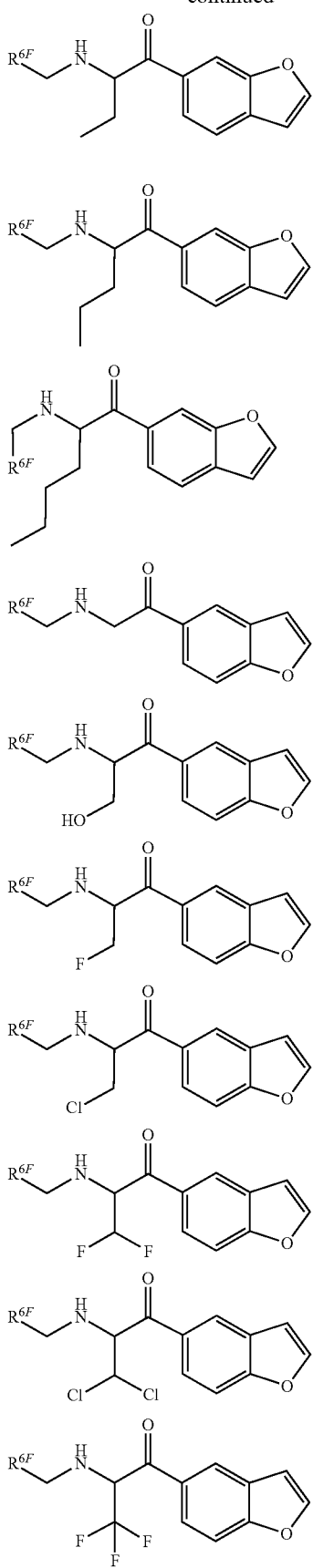
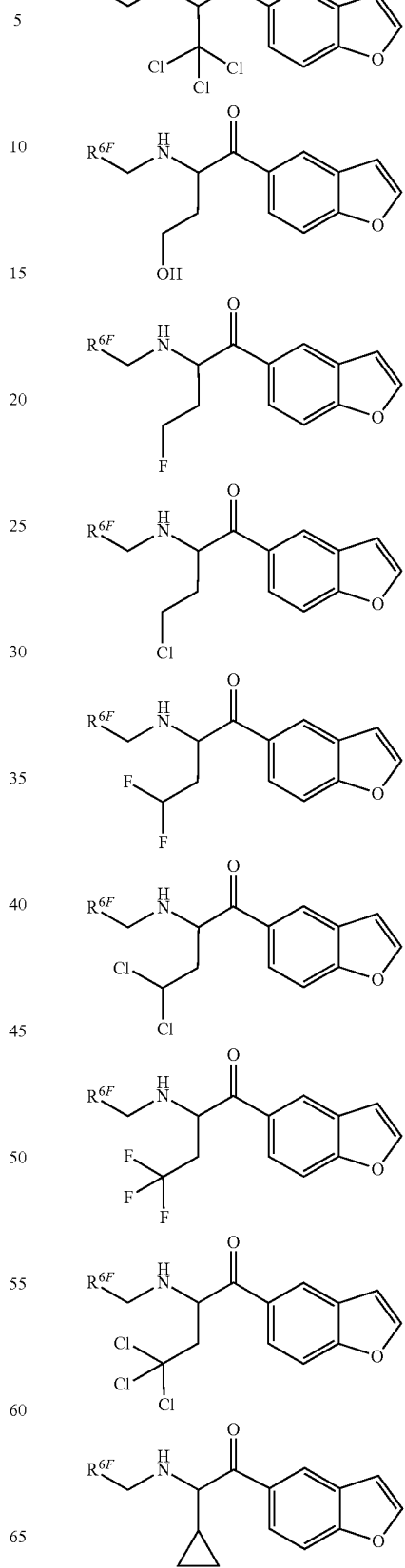

-continued
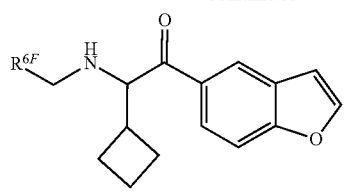
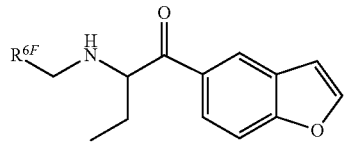
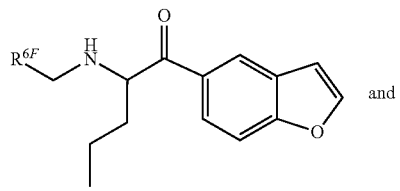 and
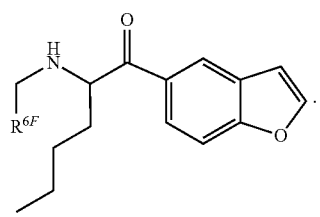
or a pharmaceutically acceptable salt or mixed salt
45. The compound of embodiment 31 or 38 wherein the compound is selected from:
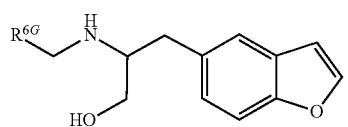
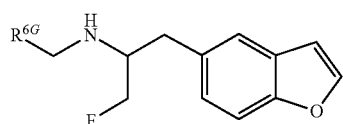
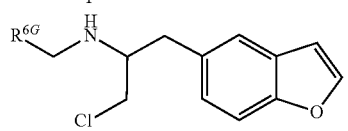
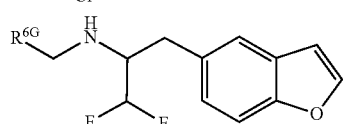
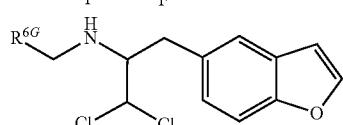
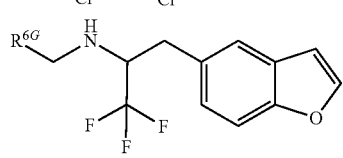
-continued
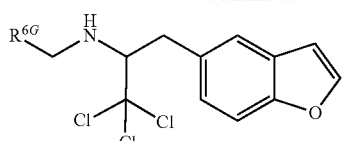
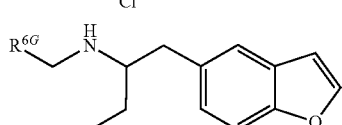
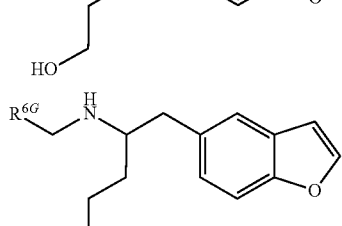
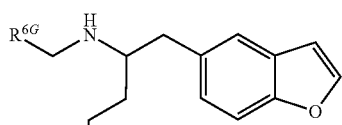
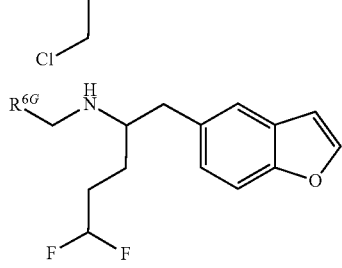
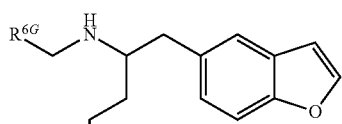
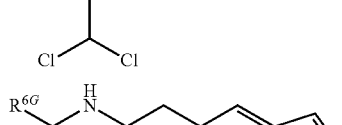
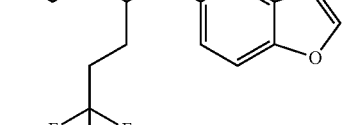
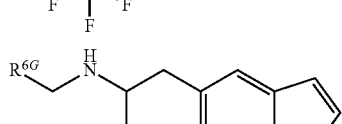
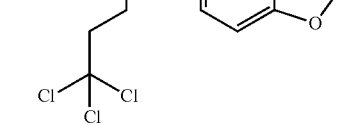
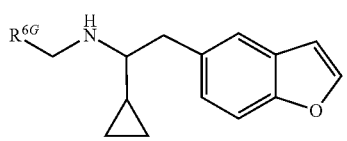

-continued
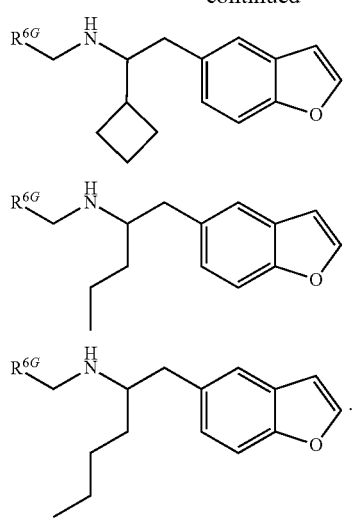
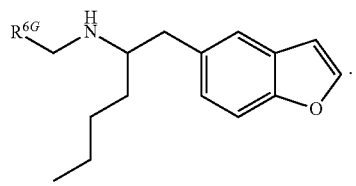
or a pharmaceutically acceptable salt or mixed salt.
46. The compound of embodiment 31 or 40 wherein the compound is selected from:
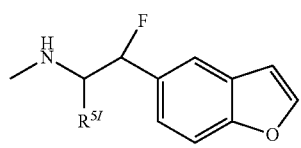
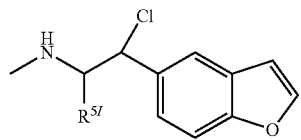
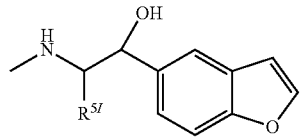
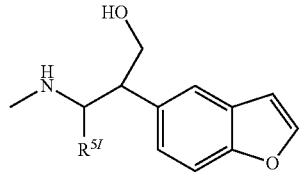
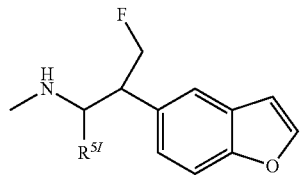
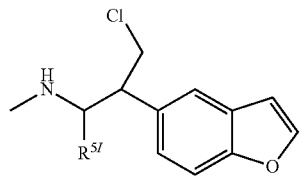
-continued
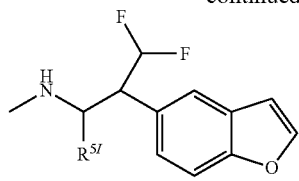
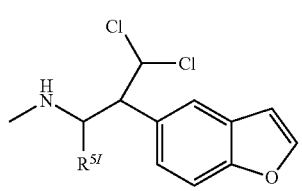
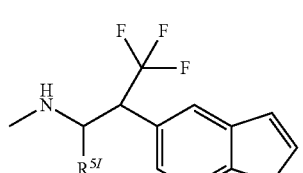
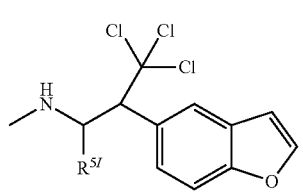
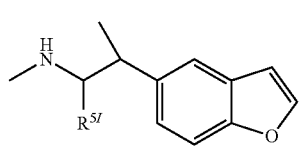
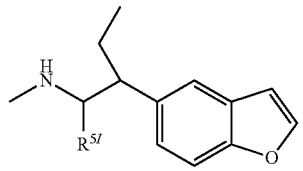
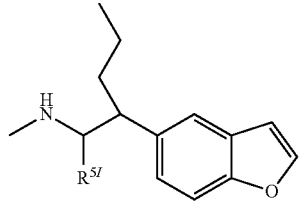
and
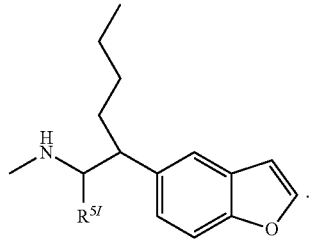
or a pharmaceutically acceptable salt or mixed salt.

47. The compound of embodiment 42 wherein the compound is selected from:
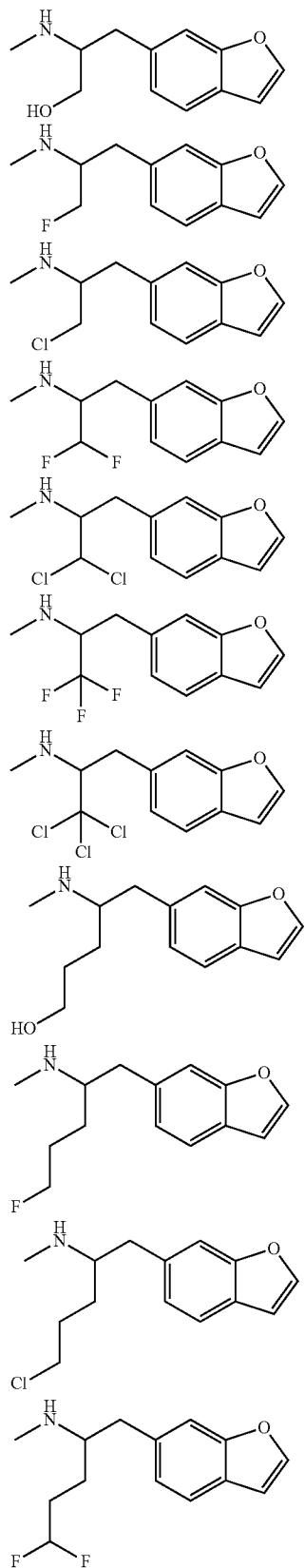
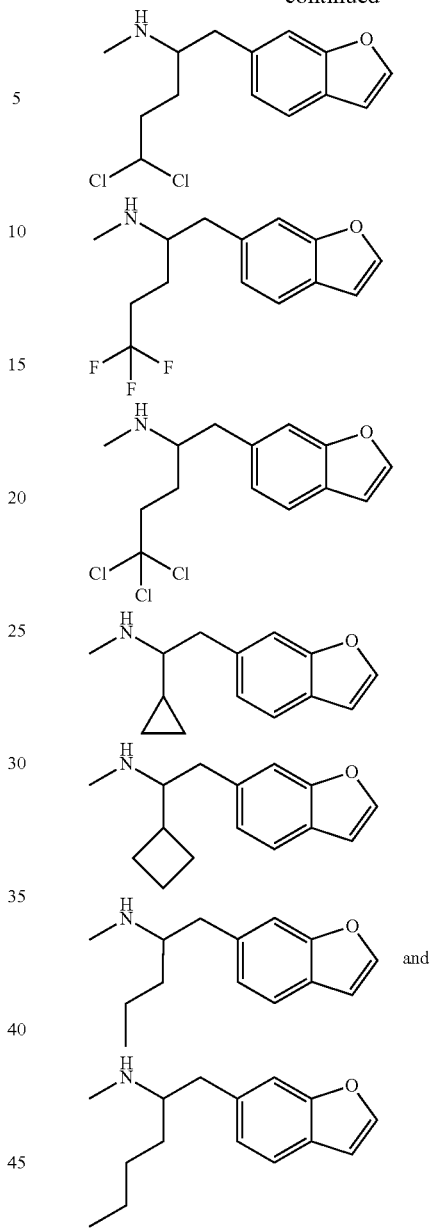
or a pharmaceutically acceptable salt or mixed salt thereof.
48. The compound of embodiment 43 wherein the compound is selected from:
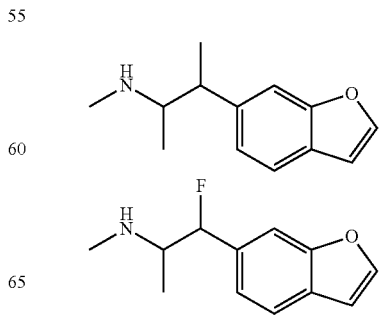

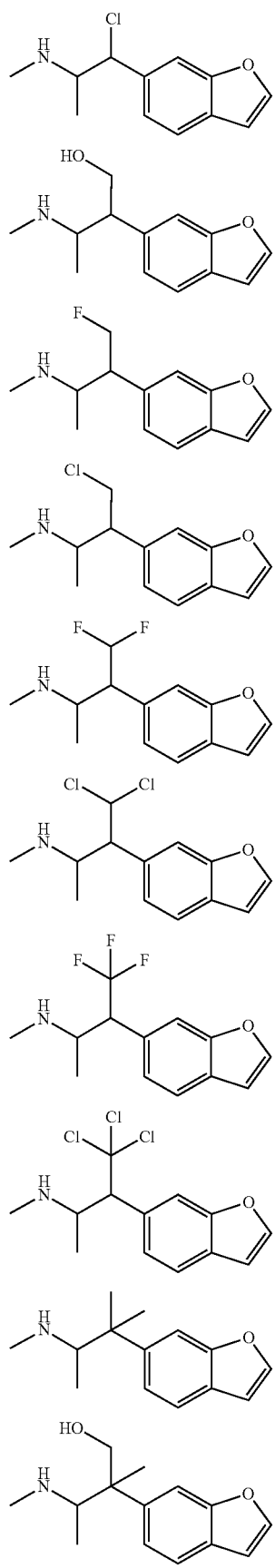
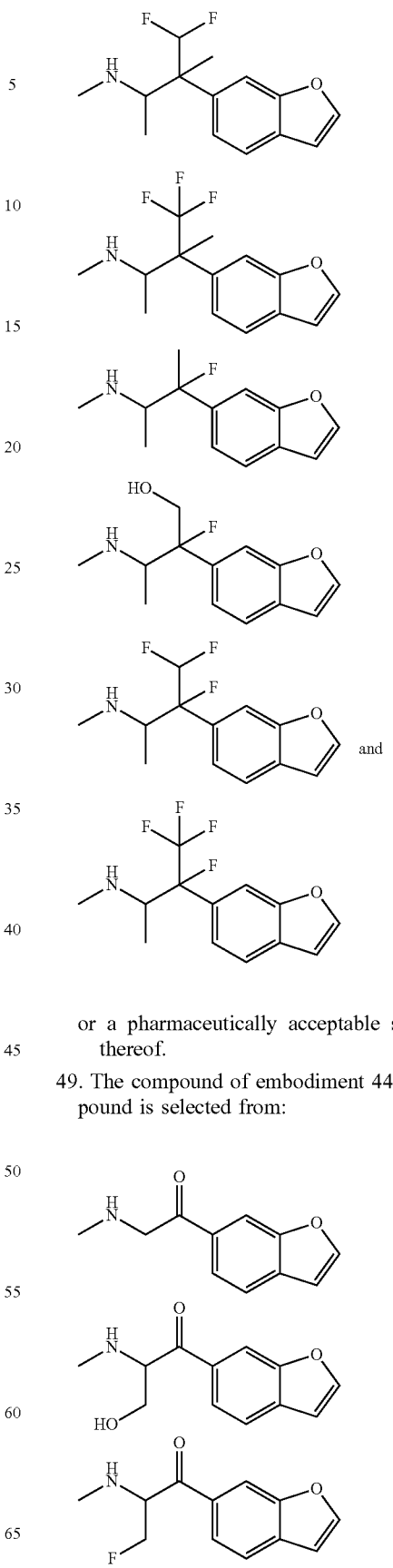
or a pharmaceutically acceptable salt or mixed salt thereof.
49. The compound of embodiment 44 wherein the compound is selected from:

-continued
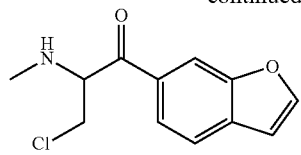
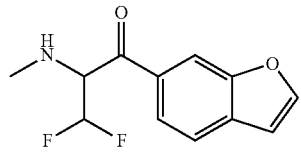
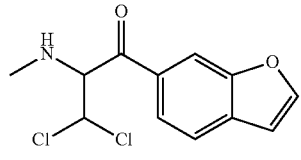
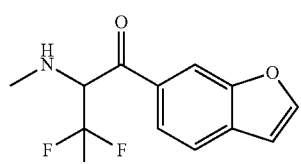
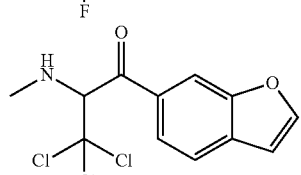
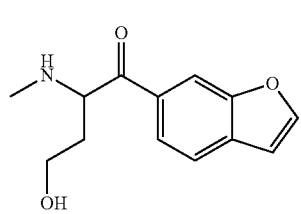
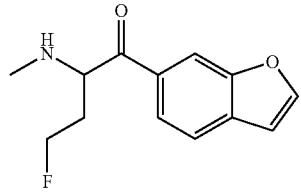
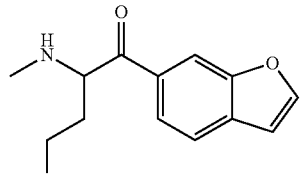
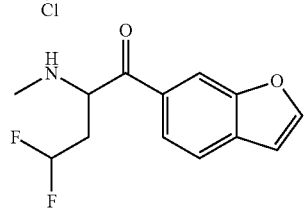
-continued
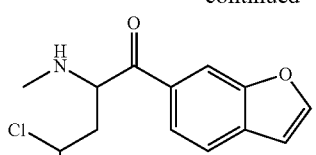
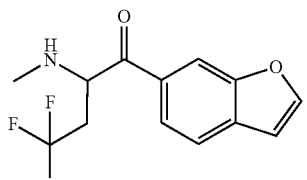
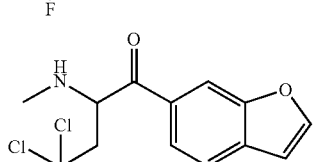
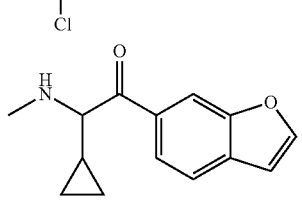
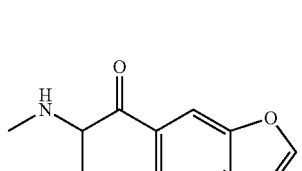
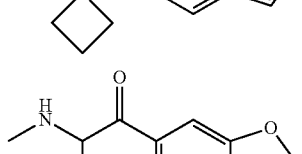
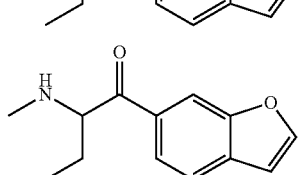
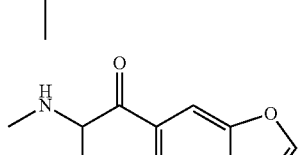
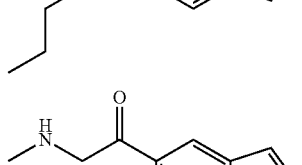

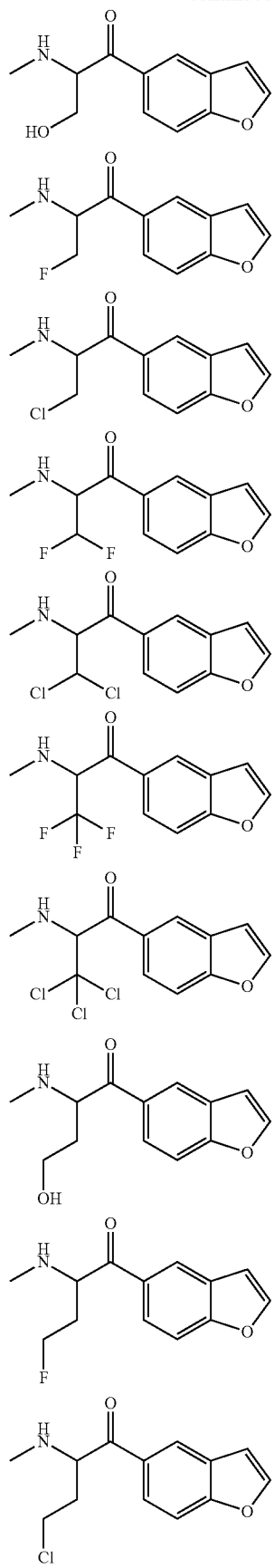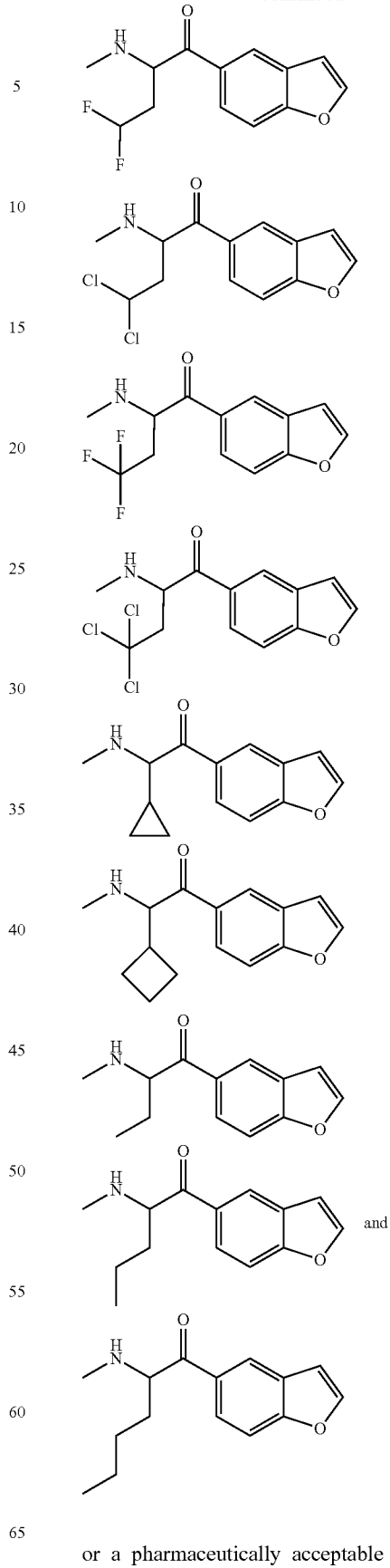
or a pharmaceutically acceptable salt or mixed salt thereof.

50. The compound of embodiment 45 wherein the compound is selected from:
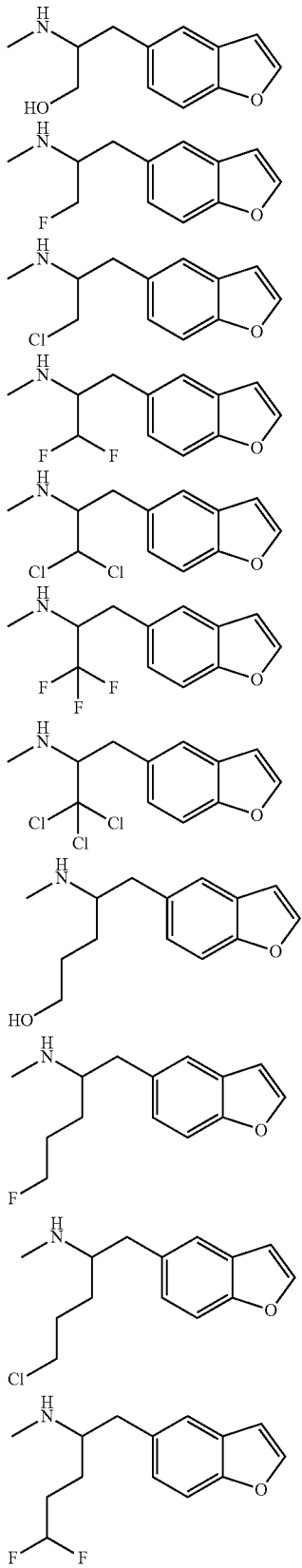
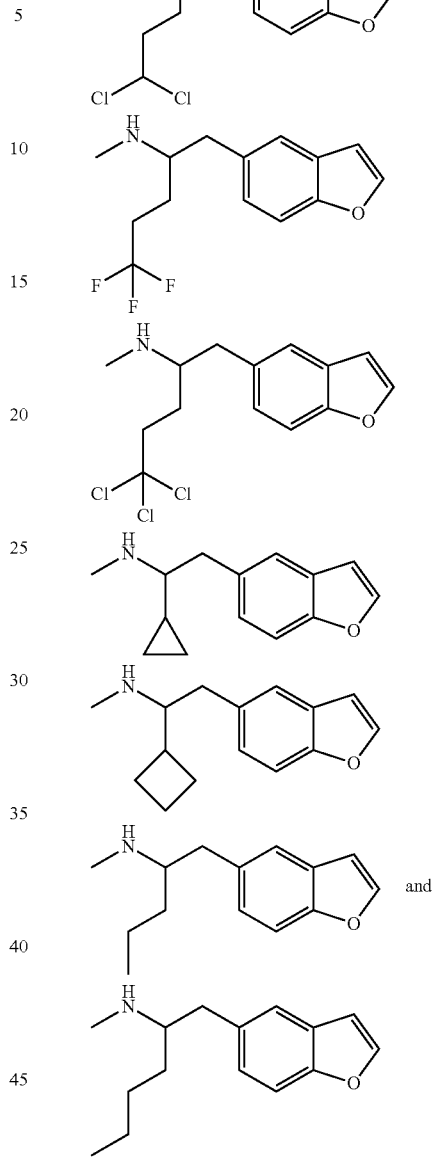
or a pharmaceutically acceptable salt or mixed salt thereof.
51. The compound of embodiment 46 wherein the compound is selected from:
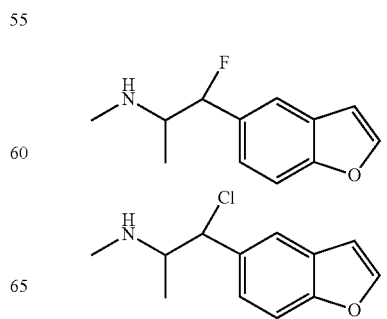

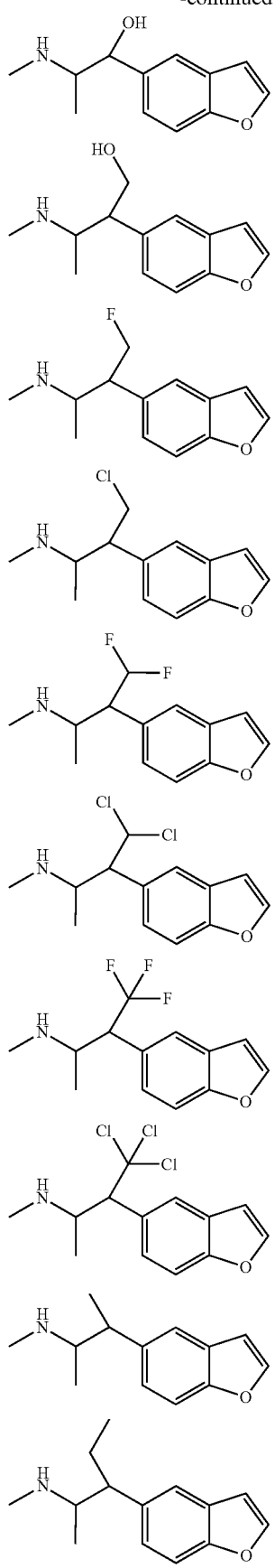

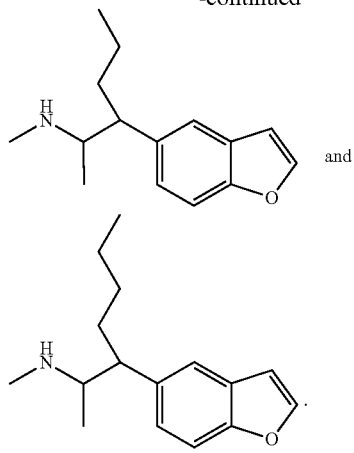

or a pharmaceutically acceptable salt or mixed salt thereof.

52. The compound of embodiment 31 or 37 wherein the compound is selected from:

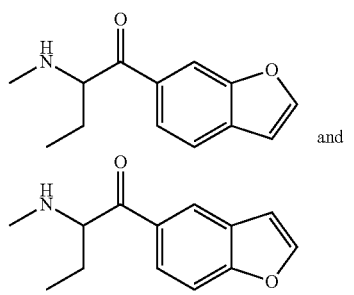

or a pharmaceutically acceptable salt or mixed salt thereof.

53. The compound of any one of embodiments 31, 37, or 52, wherein the compound is of structure

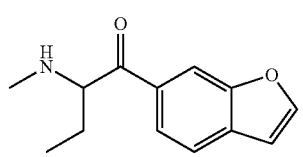 [SMILES: CCC(NC)C(=O)c1ccc2ccoc2c1]

or a pharmaceutically acceptable salt or mixed salt thereof.

54. The compound of any one of embodiments 31, 37, or 52, wherein the compound is of structure

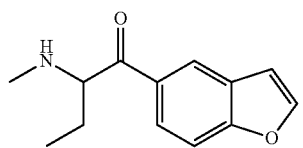 [SMILES: CCC(NC)C(=O)c1ccc2occc2c1]

or a pharmaceutically acceptable salt or mixed salt thereof.

55. In certain embodiments an enantiomerically enriched mixture of the S-enantiomer and R-enantiomer of a compound of Formula I, Formula II, Formula III, Formula IV, Formula V, Formula VI, Formula VII, Formula VIII, Formula IX, or Formula X:

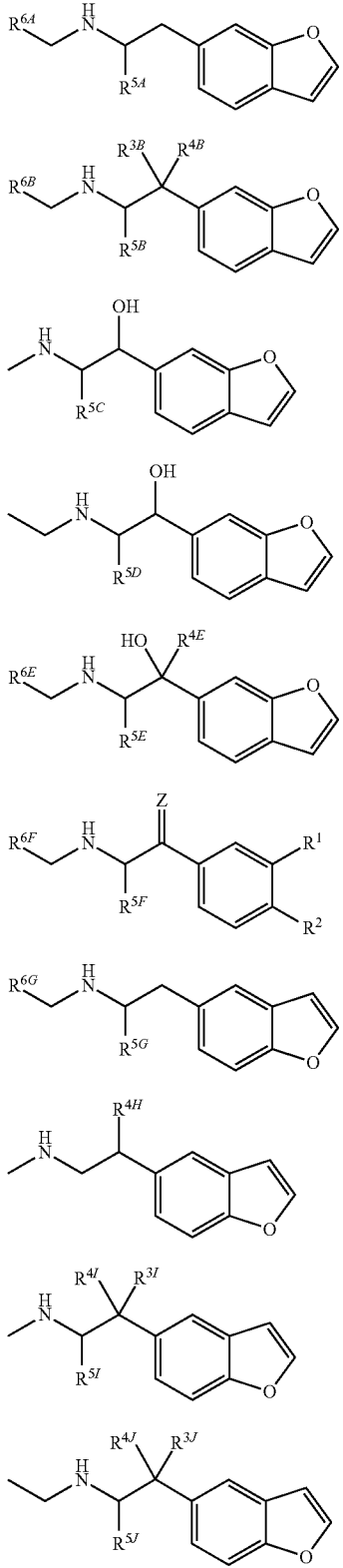

or a pharmaceutically acceptable salt or mixed salt thereof is provided, wherein:
- $R^1$ and $R^2$ are taken together as —OCH=CH— or —CH=CHO—;
- $R^{3B}$ and $R^{4B}$ are independently selected from —H, —X, $C_1$-$C_4$ alkyl, —CH$_2$OH, —CH$_2$X, —CHX$_2$, and —CX$_3$, wherein at least one of $R^{3B}$ and $R^{4B}$ is not —H;
- $R^{3I}$ and $R^{4I}$ are independently selected from —H, —X, —OH, —CH$_2$OH, —CH$_2$X, —CHX$_2$, —CX$_3$, and $C_1$-$C_4$ alkyl; wherein at least one of $R^{3I}$ and $R^{4I}$ is not —H;
- $R^{3J}$ and $R^{4J}$ are independently selected from —H, —X, —OH, $C_1$-$C_4$ alkyl, —CH$_2$OH, —CH$_2$X, —CHX$_2$, and —CX$_3$;
- $R^{4E}$ is selected from $C_1$-$C_4$ alkyl, —CH$_2$OH, —CH$_2$X, —CHX$_2$, and —CX$_3$;
- $R^{4H}$ is selected from —X, —CH$_2$CH$_2$CH$_3$, —CH$_2$OH, —CH$_2$X, and —CHX$_2$;
- $R^{5A}$ and $R^{5G}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_2$-$C_4$ alkyl, when $R^{5A}$ is $C_2$ alkyl or H, $R^{6A}$ is not —H, and when $R^{5G}$ is —H or $C_2$ alkyl, $R^{6G}$ is not —H;
- $R^{5B}$ is selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl;
- $R^{5C}$ is selected from —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_2$-$C_4$ alkyl;
- $R^{5D}$, $R^{5E}$, $R^{5F}$, and $R^{5J}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl, when $R^{5F}$ is —H or $C_1$ alkyl, $R^{6F}$ cannot be —H, and when $R^{5J}$ is $C_1$ alkyl, at least one of $R^{3J}$ and $R^{4J}$ is not H;
- $R^{5I}$ is selected from —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl; wherein at least one of $R^{3I}$, $R^{4I}$, and $R^{5I}$ is not $C_1$ alkyl;
- $R^{6A}$, $R^{6B}$, $R^{6E}$, $R^{6F}$, and $R^{6G}$ are independently selected from —H and —CH$_3$;
- X is independently selected from —F, —Cl, and —Br; and
- Z is selected from O and CH$_2$.

56. The enantiomerically enriched mixture of embodiment 55 wherein the compound is of Formula I:

(I)

[structure]

or a pharmaceutically acceptable salt or mixed salt thereof.-

57. The enantiomerically enriched mixture of embodiment 55 wherein the compound is of Formula II:

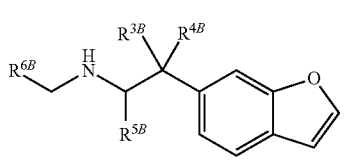

(II)

or a pharmaceutically acceptable salt or mixed salt.

58. The enantiomerically enriched mixture of embodiment 55 wherein the compound is of Formula III:

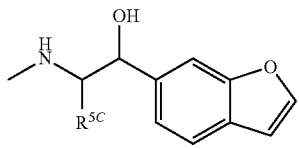

(III)

or a pharmaceutically acceptable salt or mixed salt.

59. The enantiomerically enriched mixture of embodiment 55 wherein the compound is of Formula IV:

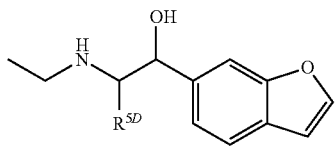

(IV)

or a pharmaceutically acceptable salt or mixed salt thereof.

60. The enantiomerically enriched mixture of embodiment 55 wherein the compound is of Formula V:

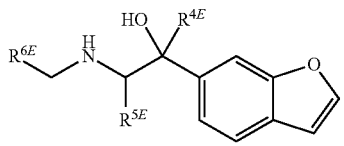

(V)

or a pharmaceutically acceptable salt or mixed salt.

61. The enantiomerically enriched mixture of embodiment 55 wherein the compound is of Formula VI:

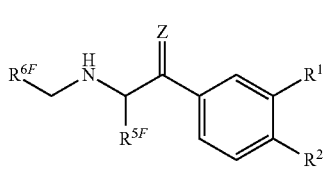

(VI)

or a pharmaceutically acceptable salt or mixed salt.

62. The enantiomerically enriched mixture of embodiment 55 wherein the compound is of Formula VII:

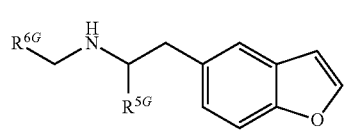

(VII)

or a pharmaceutically acceptable salt or mixed salt.

63. The enantiomerically enriched mixture of embodiment 55 wherein the compound is of Formula VIII:

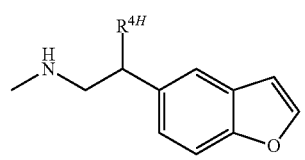

(VIII)

or a pharmaceutically acceptable salt or mixed salt.

64. The enantiomerically enriched mixture of embodiment 55 wherein the compound is of Formula IX:

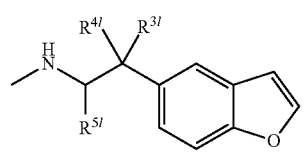

(IX)

or a pharmaceutically acceptable salt or mixed salt.

65. The enantiomerically enriched mixture of embodiment 55 wherein the compound is of Formula X:

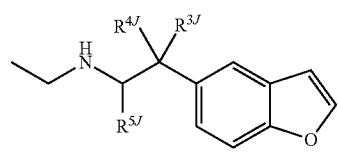

(X)

or a pharmaceutically acceptable salt or mixed salt.

66. The enantiomerically enriched mixture of embodiment 55 or 56 wherein the compound is selected from:

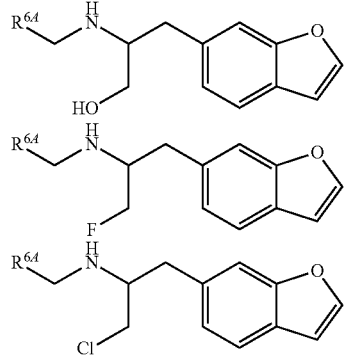

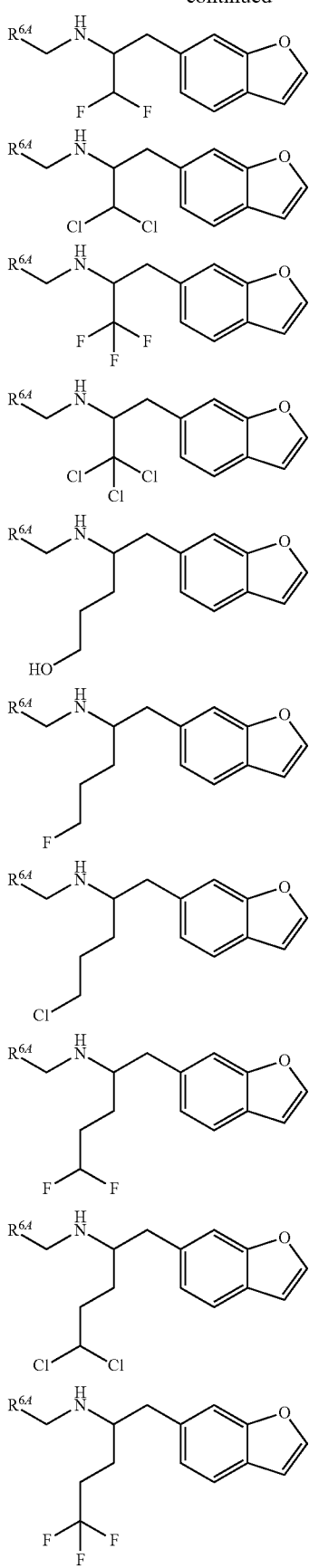
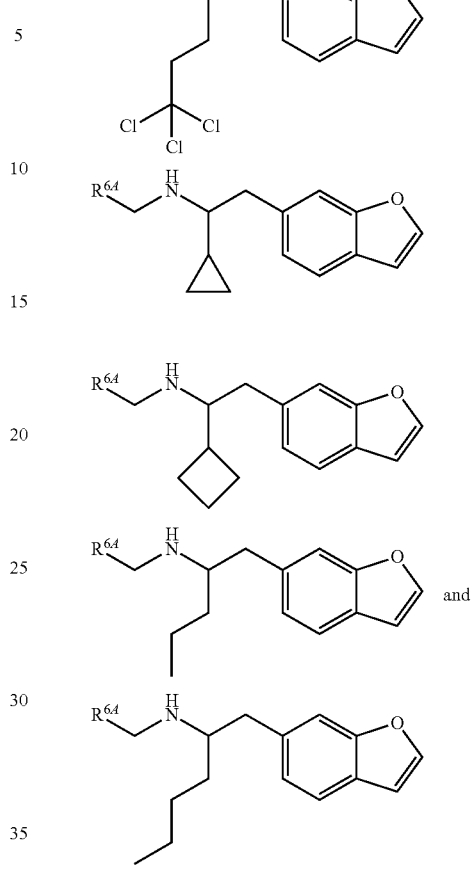
or a pharmaceutically acceptable salt or mixed salt.
67. The enantiomerically enriched mixture of embodiment 55 or 57 wherein the compound is selected from:
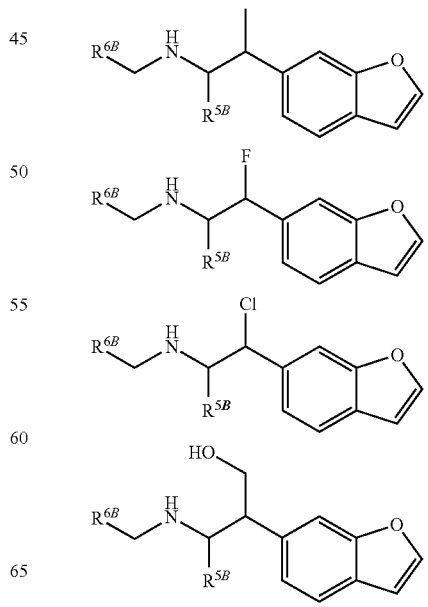

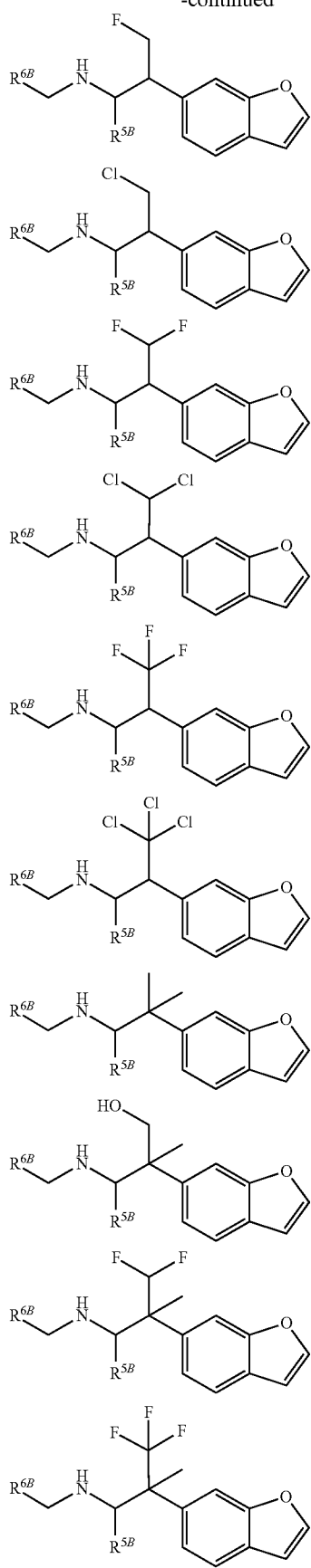
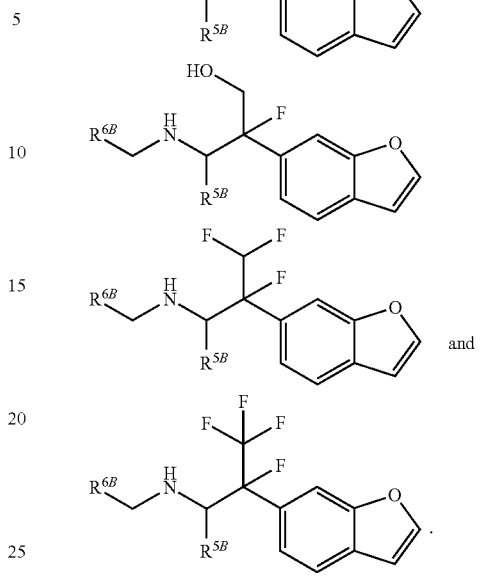
or a pharmaceutically acceptable salt or mixed salt.
68. The enantiomerically enriched mixture of embodiment 55 or 61 wherein the compound is selected from:
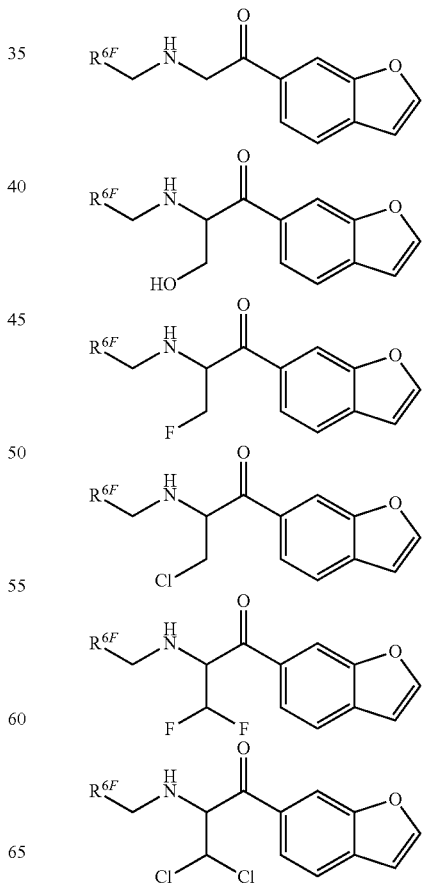

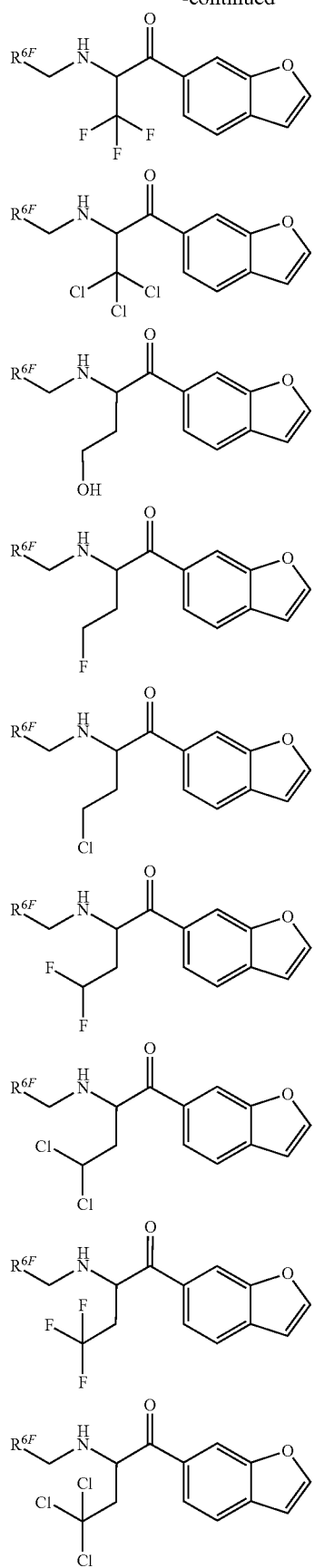
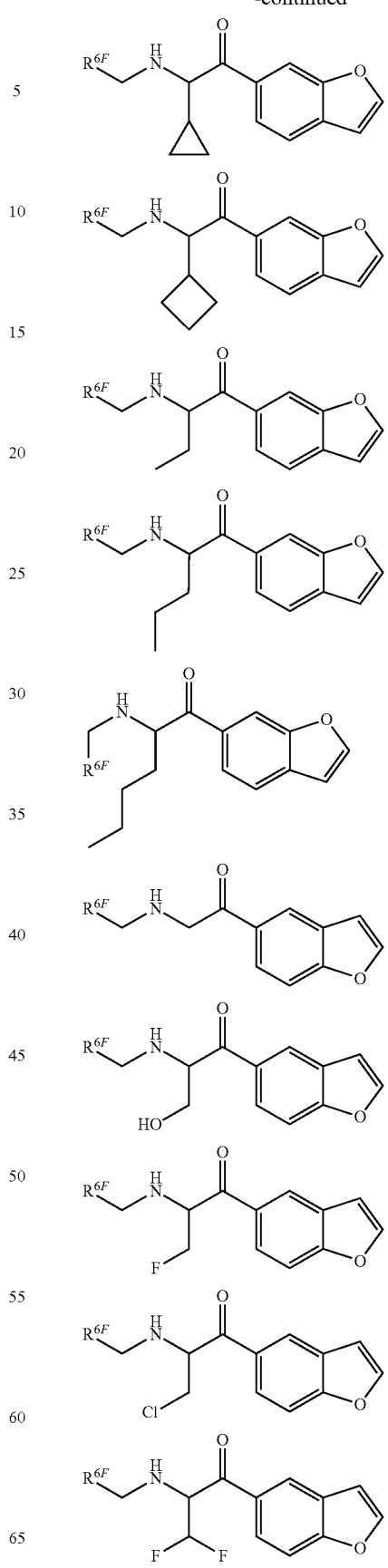

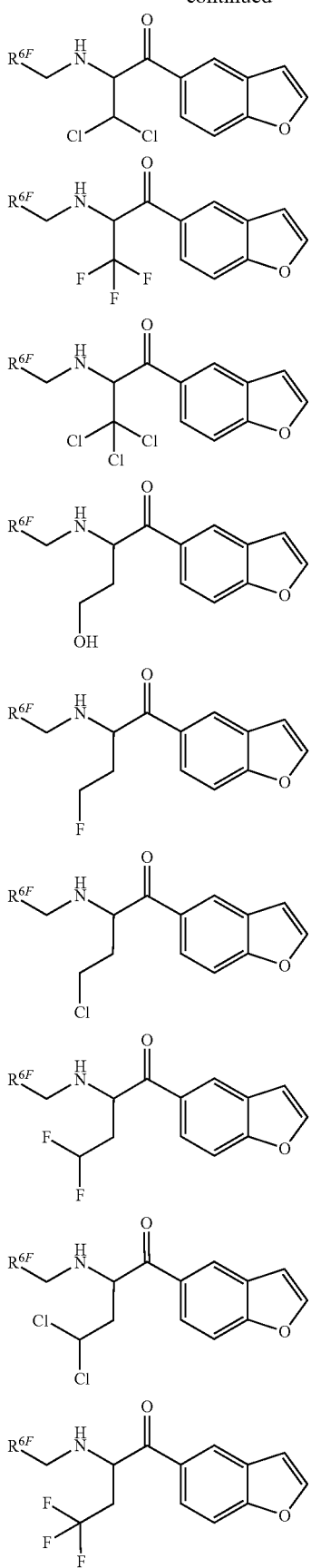
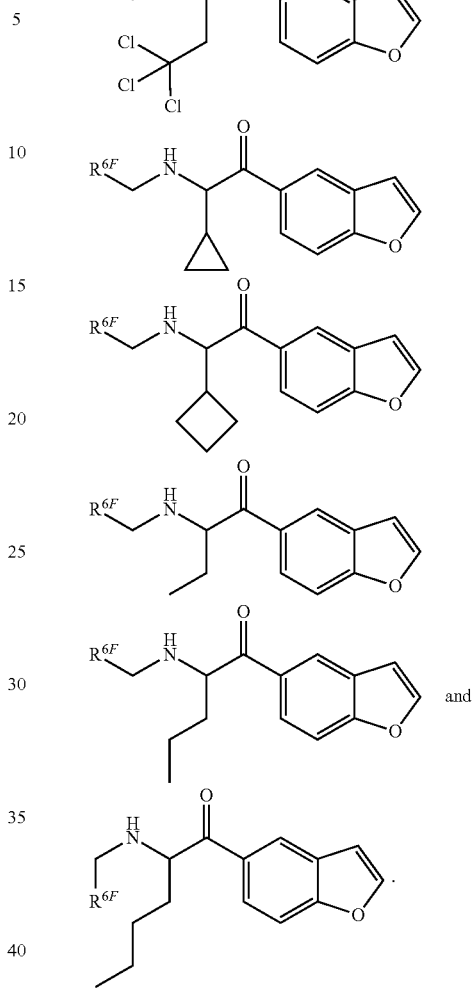
or a pharmaceutically acceptable salt or mixed salt.
69. The enantiomerically enriched mixture of embodiment 55 or 62 wherein the compound is selected from:
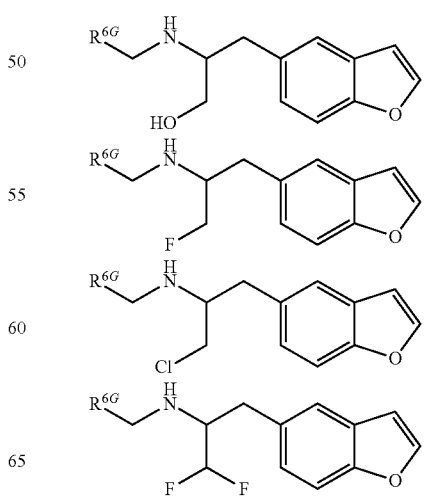

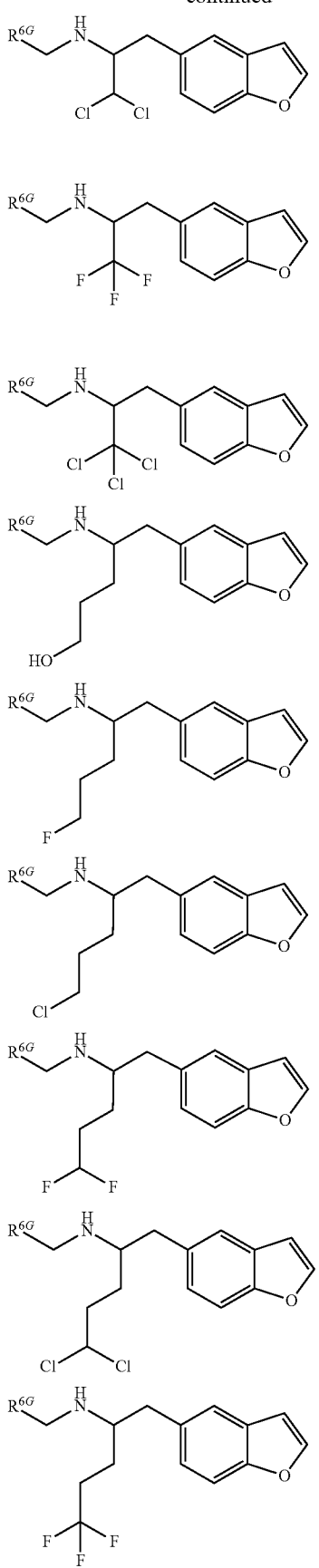
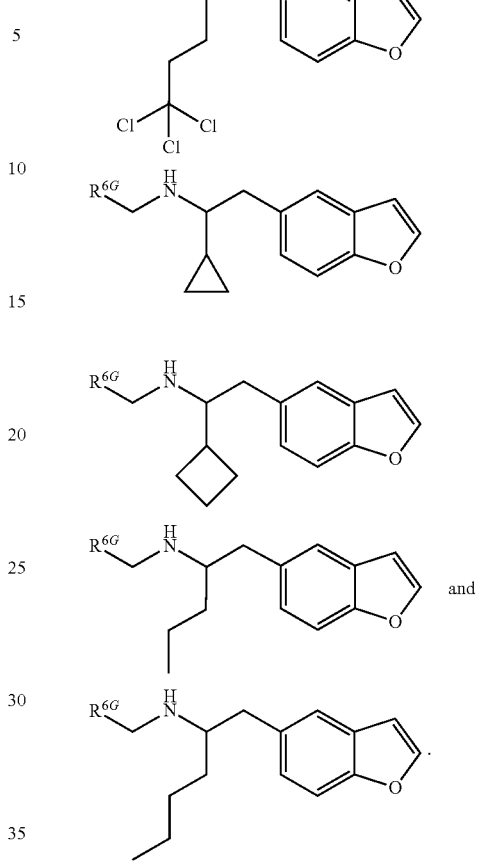
and
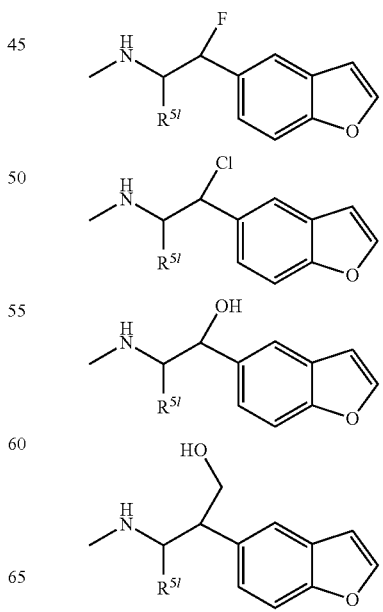
or a pharmaceutically acceptable salt or mixed salt.
70. The enantiomerically enriched mixture of embodiment 55 or 64 wherein the compound is selected from:

-continued
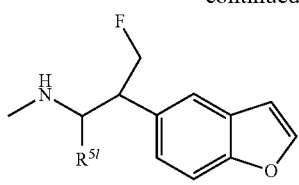
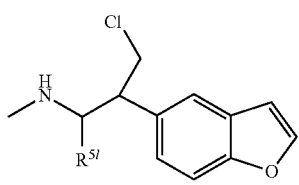
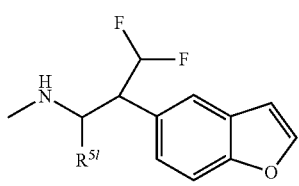
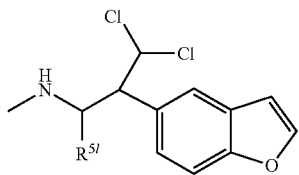
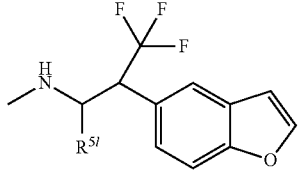
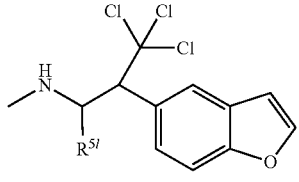
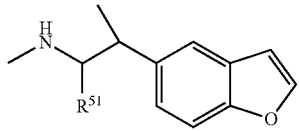
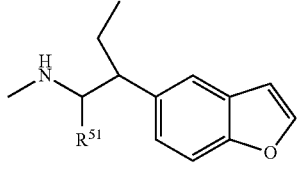
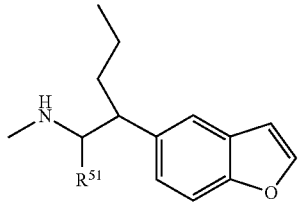 and
-continued
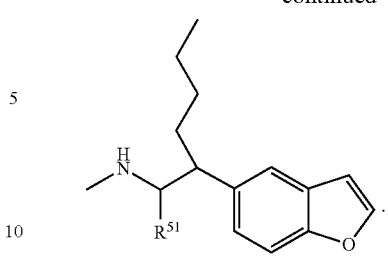
or a pharmaceutically acceptable salt or mixed salt.
71. The enantiomerically enriched mixture of embodiment 55 or 66 wherein the compound is selected from:
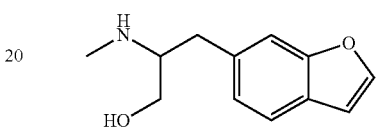
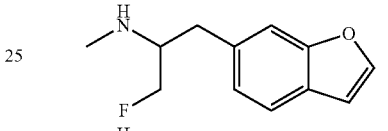
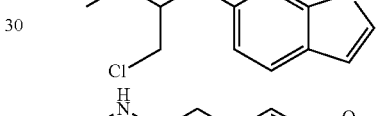
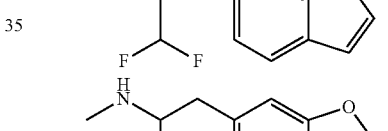
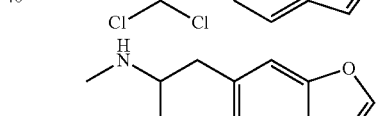
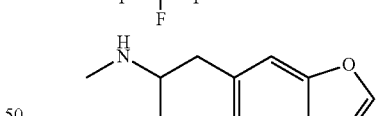
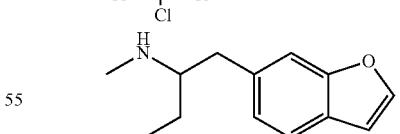
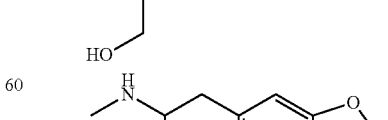
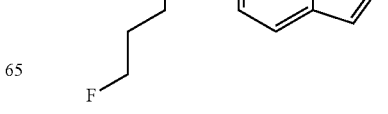

-continued
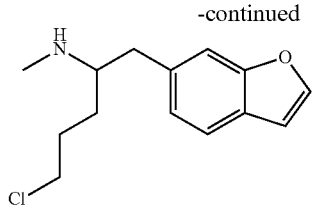
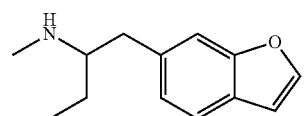
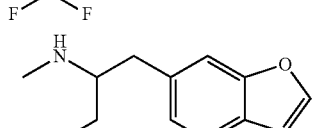
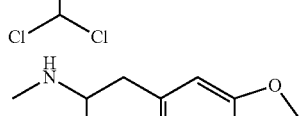
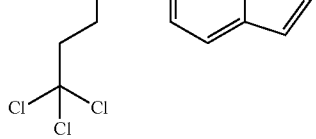
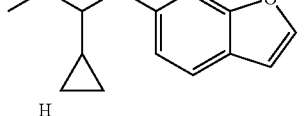
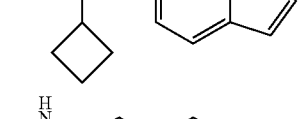 and
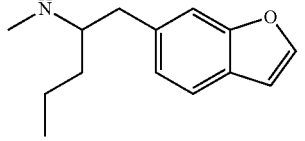
or a pharmaceutically acceptable salt or mixed salt.
72. The enantiomerically enriched mixture of embodiment 55 or 67 wherein the compound is selected from:
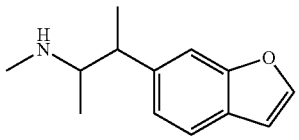
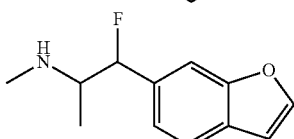
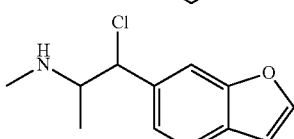
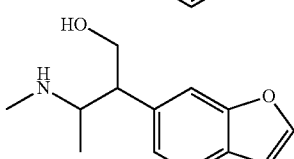
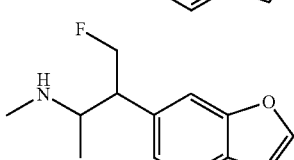
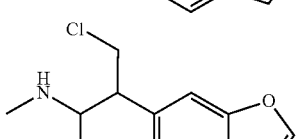
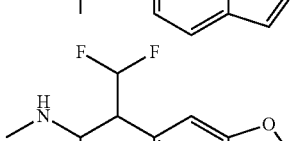
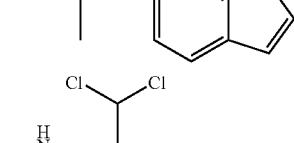
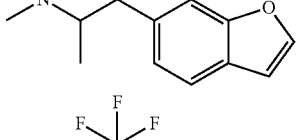
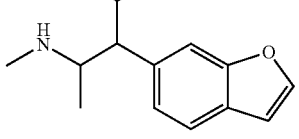
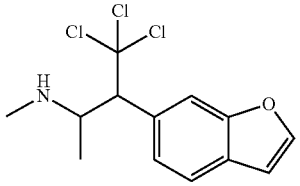

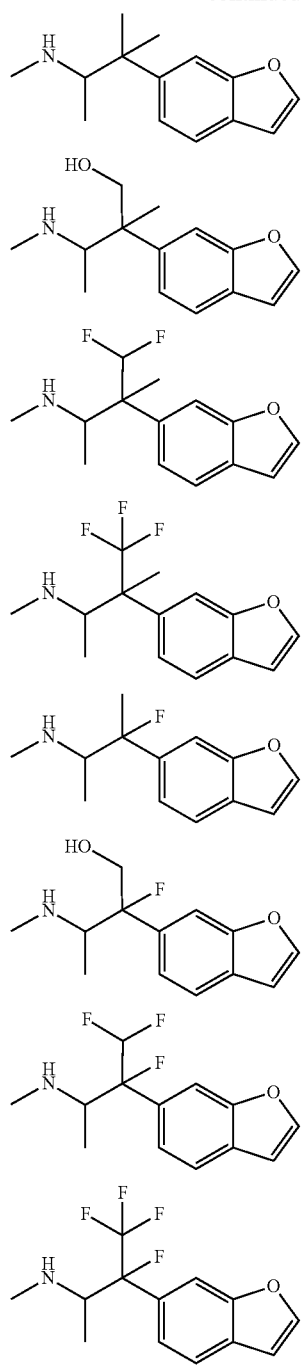
or a pharmaceutically acceptable salt or mixed salt thereof.
73. The enantiomerically enriched mixture of embodiment 55 or 68 wherein the compound is selected from:
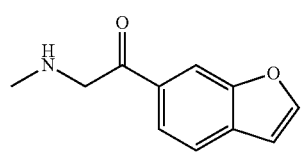
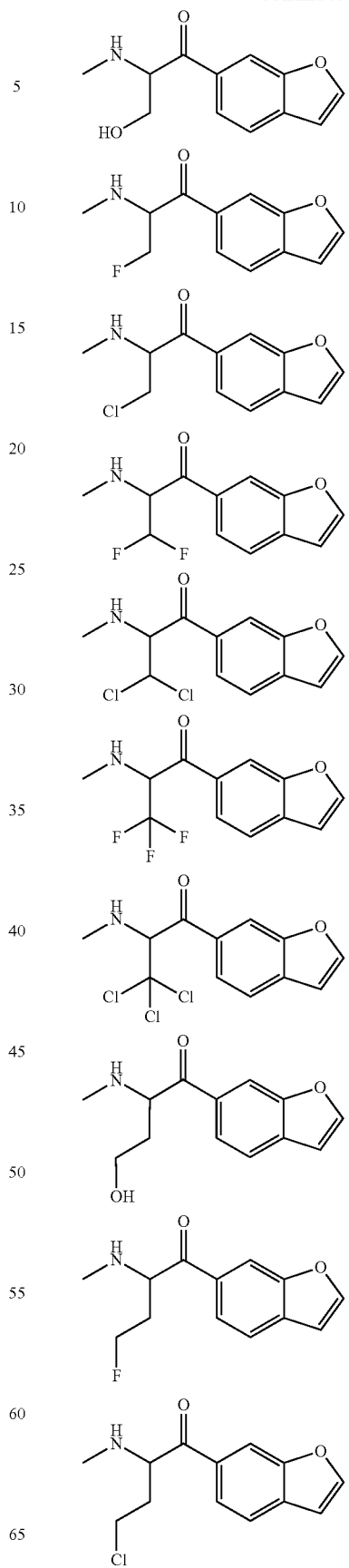

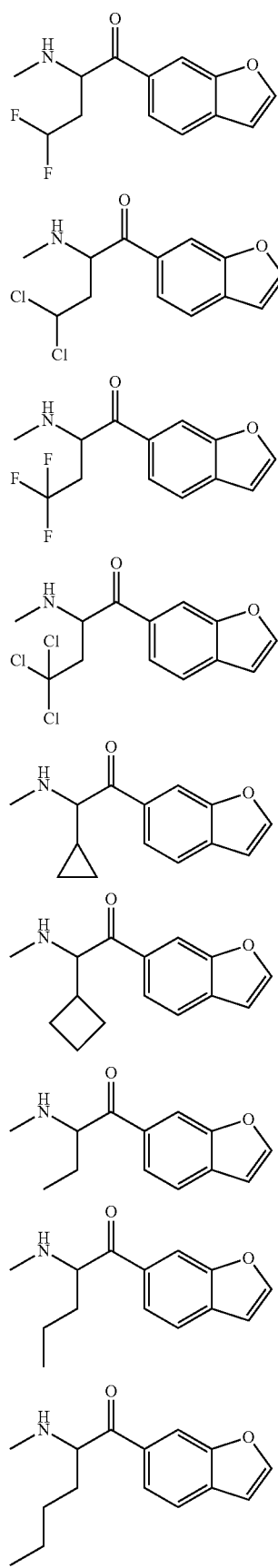
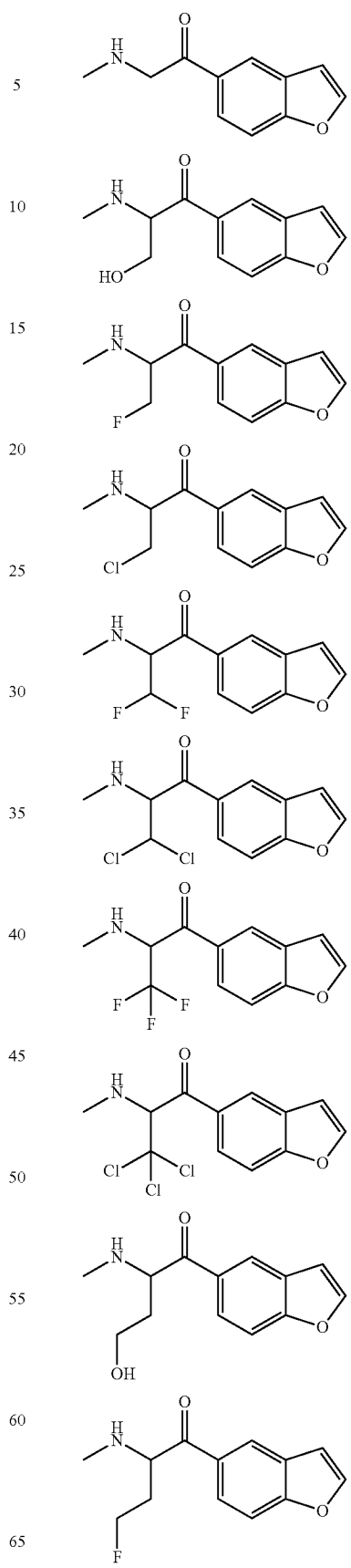

77
-continued
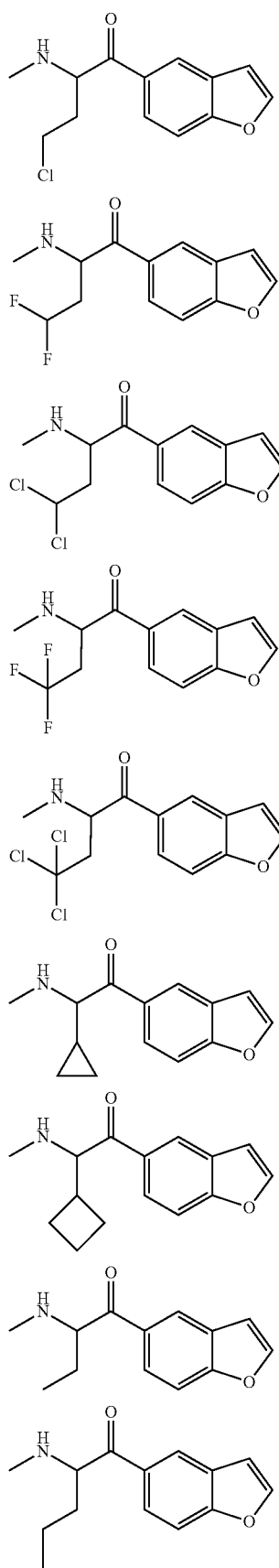
and
78
-continued
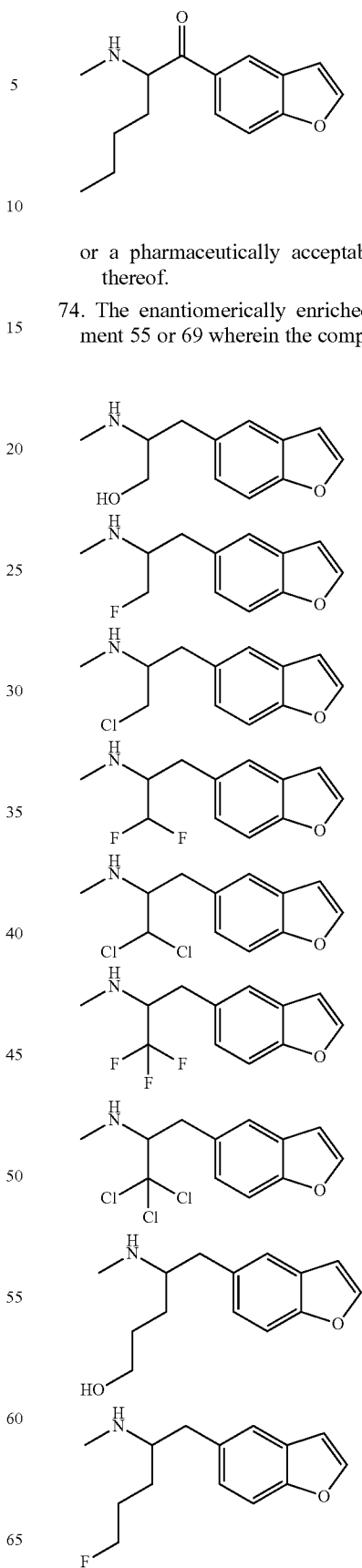
or a pharmaceutically acceptable salt or mixed salt thereof.
74. The enantiomerically enriched mixture of embodiment 55 or 69 wherein the compound is selected from:

-continued
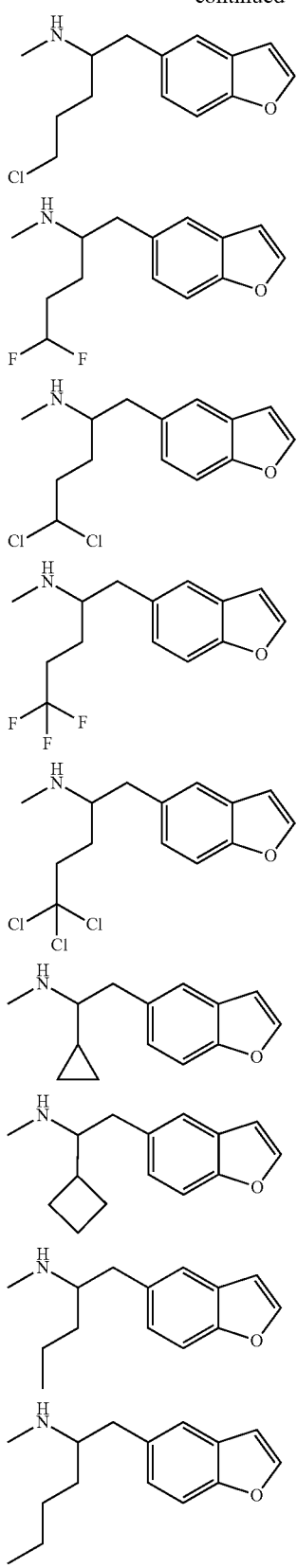
or a pharmaceutically acceptable salt or mixed salt thereof.
75. The enantiomerically enriched mixture of embodiment 55 or 70 wherein the compound is selected from:
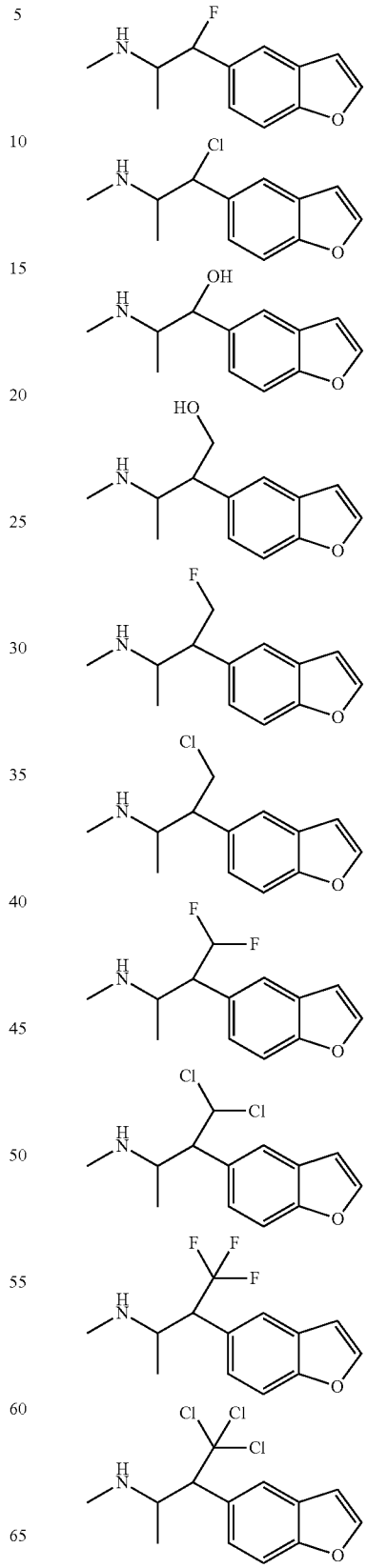

-continued

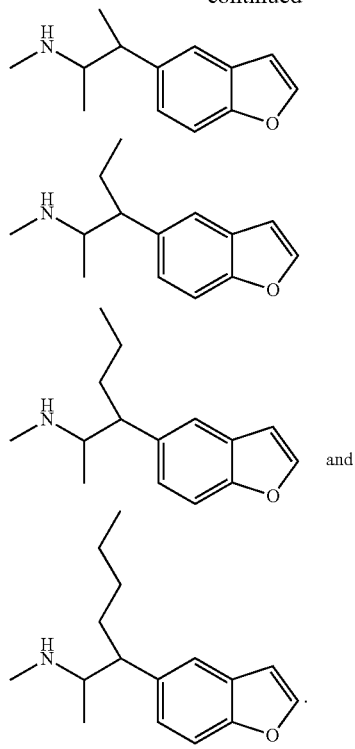

76. The enantiomerically enriched mixture of embodiment 55 or 61 wherein the compound is selected from:

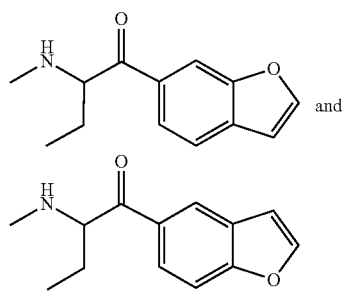

or a pharmaceutically acceptable salt or mixed salt thereof.

77. An enantiomerically enriched mixture of the S-enantiomer and R-enantiomer of a compound of Formula XI, Formula XII, or Formula XIII:

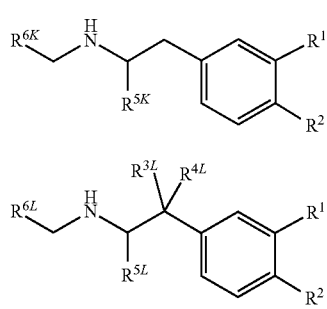

-continued

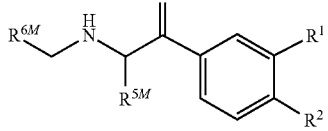

(XIII)

or a pharmaceutically acceptable salt or mixed salt thereof, wherein:

$R^1$ and $R^2$ are taken together as —OCH=CH— or —CH=CHO—;

$R^{3L}$ and $R^{4L}$ are independently selected from —H, —X, —OH, $C_1$-$C_4$ alkyl, —CH$_2$OH, —CH$_2$X, —CHX$_2$, and —CX$_3$, wherein at least one of $R^{3L}$ and $R^{4L}$ is not —H;

$R^{5K}$ is selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_2$-$C_4$ alkyl;

$R^{5L}$ and $R^{5M}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl;

$R^{6K}$, $R^{6L}$, and $R^{6M}$ are independently selected from —H and —CH$_3$; and X is independently selected from —F, —Cl, and —Br.

78. The enantiomerically enriched mixture of embodiment 77 wherein the compound is of Formula XI

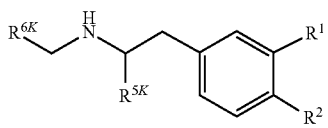

(XI)

or a pharmaceutically acceptable salt or mixed salt thereof.

79. The enantiomerically enriched mixture of embodiment 77 wherein the compound is of Formula XII

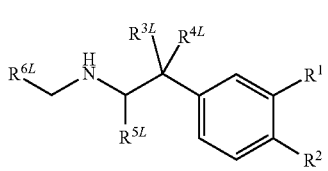

(XII)

or a pharmaceutically acceptable salt or mixed salt thereof.-

80. The enantiomerically enriched mixture of embodiment 77 wherein the compound is of Formula XIII

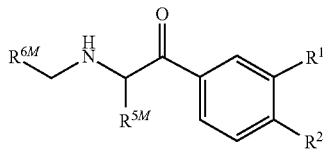
(XIII)

or a pharmaceutically acceptable salt or mixed salt thereof.

81. In certain embodiments an enantiomerically enriched mixture of the S-enantiomer and R-enantiomer of a compound of Formula A, Formula B, Formula C, Formula D, Formula E, or Formula F:

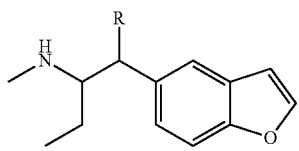
(A)

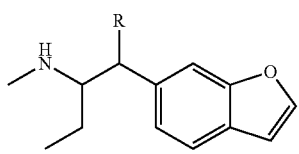
(B)

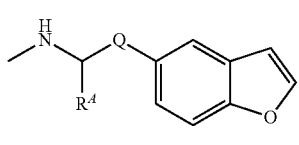
(C)

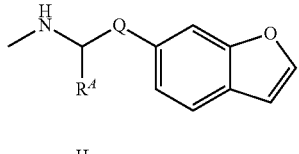
(D)

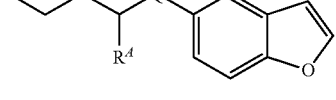
(E)

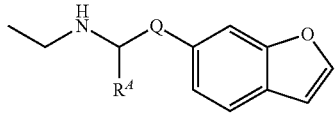
(F)

or a pharmaceutically acceptable salt or mixed salt thereof is provided,
wherein:
R is hydrogen or hydroxyl;
$R^A$ is —$CH_3$, —$CH_2Y$, —$CHY_2$, —$CY_3$, —$CH_2CH_3$, —$CH_2CH_2Y$, —$CH_2CHY_2$, —$CH_2CY_3$, —$CH_2OH$, or —$CH_2CH_2OH$;

Q is selected from:

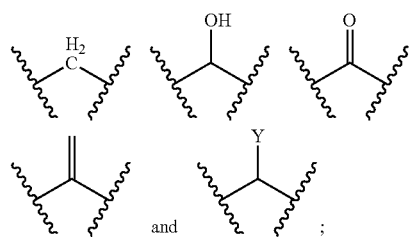
and ;

and
Y is halogen.

82. The enantiomerically enriched mixture of embodiment 81 wherein the compound is of Formula A

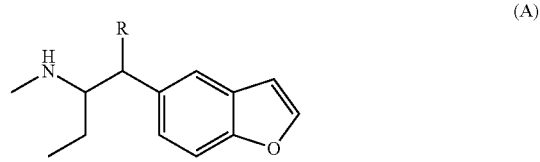
(A)

or a pharmaceutically acceptable salt or mixed salt thereof.

83. The enantiomerically enriched mixture of embodiment 81 wherein the compound is of Formula B

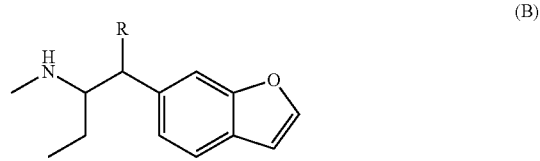
(B)

or a pharmaceutically acceptable salt or mixed salt thereof.

84. The enantiomerically enriched mixture of embodiment 81 wherein the compound is of Formula C

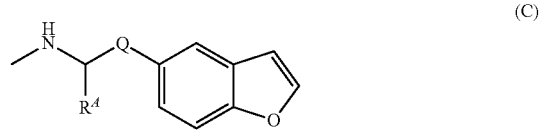
(C)

or a pharmaceutically acceptable salt or mixed salt thereof.

85. The enantiomerically enriched mixture of embodiment 81 wherein the compound is of Formula D

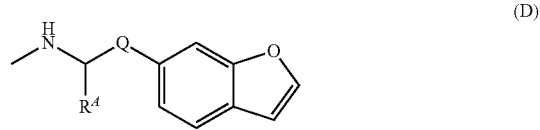
(D)

or a pharmaceutically acceptable salt or mixed salt thereof.

86. The enantiomerically enriched mixture of embodiment 81 wherein the compound is of Formula E

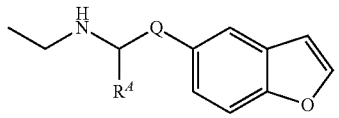
(E)

or a pharmaceutically acceptable salt or mixed salt thereof.

87. The enantiomerically enriched mixture of embodiment 81 wherein the compound is of Formula F

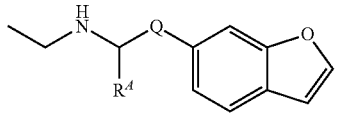
(F)

or a pharmaceutically acceptable salt or mixed salt thereof.

88. The enantiomerically enriched mixture of embodiment 81 wherein the compound is selected from:

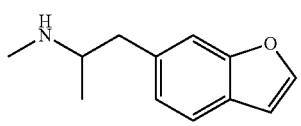

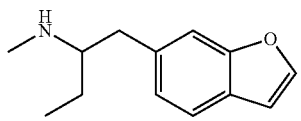

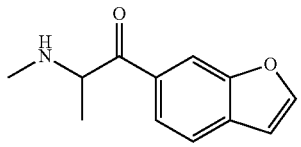


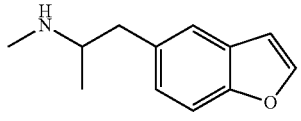

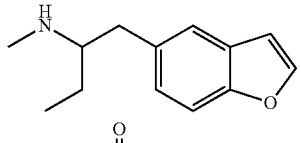
and

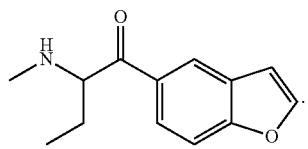

or a pharmaceutically acceptable salt or mixed salt thereof.

89. The enantiomerically enriched mixture of embodiment 81 or 88 wherein the compound is selected from:

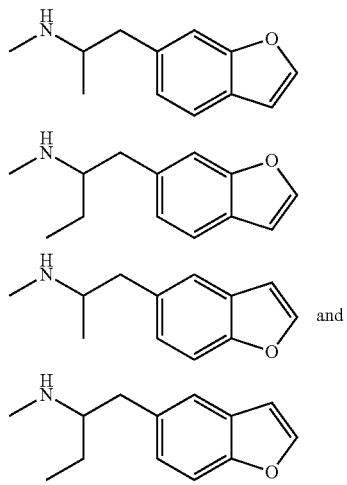
and or a pharmaceutically acceptable salt or mixed salt thereof.

90. The enantiomerically enriched mixture of embodiment 81 or 88 wherein the compound is selected from:

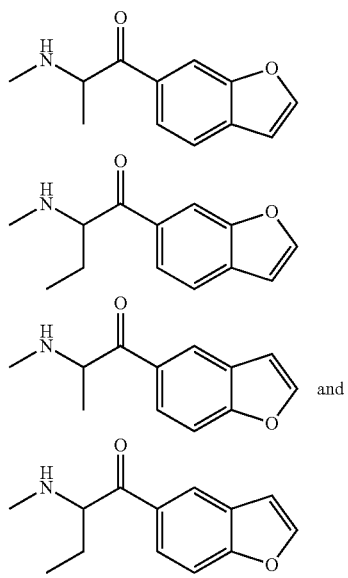
and or a pharmaceutically acceptable salt or mixed salt thereof.

91. The enantiomerically enriched mixture of embodiment 81 or 88 wherein the compound is selected from:

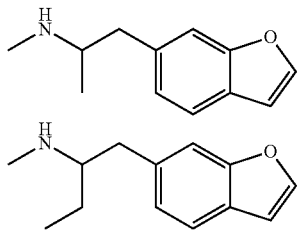

or a pharmaceutically acceptable salt or mixed salt thereof.

92. The enantiomerically enriched mixture of embodiment 81 or 88 wherein the compound is:

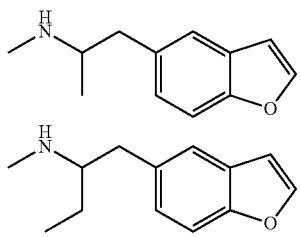

or a pharmaceutically acceptable salt or mixed salt thereof.

93. The enantiomerically enriched mixture of embodiment 81 or 88 wherein the compound is selected from:

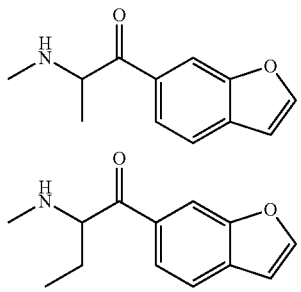

or a pharmaceutically acceptable salt or mixed salt thereof.

94. The enantiomerically enriched mixture of embodiment 81 or 88 wherein the compound is:

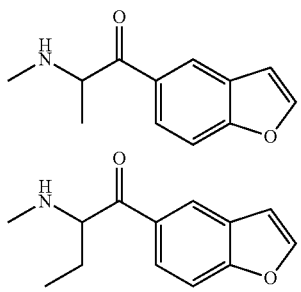

or a pharmaceutically acceptable salt or mixed salt thereof.

95. The compound of any of embodiments 31-54, wherein the compound has entactogenic effects in a human.

96. The compound of any of embodiments 31-54, wherein the compound has nicotinic-receptor-dependent therapeutic effects in a human.

97. The compound of any of embodiments 31-54, wherein the compound has serotonin-receptor-dependent therapeutic effects in a human.

98. The compound of any of embodiments 31-54, wherein the compound enhances serotonin-receptor-dependent therapeutic effects and decreases nicotinic effects or dopaminergic effects in a human.

99. The compound of any of embodiments 31-54, in an enantiomerically enriched form that decreases a hallucinogenic effect relative to the racemate.

100. The compound of any of embodiments 31-54, in an enantiomerically enriched form that decreases an unwanted psychoactive effect relative to the racemate.

101. The compound of any of embodiments 31-54, in an enantiomerically enriched form that decreases a physiological effect relative to the racemate.

102. The compound of any of embodiments 31-54, in an enantiomerically enriched form that decreases a toxic effect relative to the racemate.

103. The compound of any of embodiments 31-54, in an enantiomerically enriched form that decreases abuse potential relative to the racemate.

104. The compound of any of embodiments 31-54 in an enantiomerically enriched form that has at least about 60% S-enantiomer.

105. The compound of any of embodiments 31-54 in an enantiomerically enriched form that has at least about 70% S-enantiomer.

106. The compound of any of embodiments 31-54 in an enantiomerically enriched form that has at least about 80% S-enantiomer.

107. The compound of any of embodiments 31-54 in an enantiomerically enriched form that has at least about 90% S-enantiomer.

108. The compound of any of embodiments 31-54 in an enantiomerically enriched form that has at least about 60% R-enantiomer.

109. The compound of any of embodiments 31-54 in an enantiomerically enriched form that has at least about 70% R-enantiomer.

110. The compound of any of embodiments 31-54 in an enantiomerically enriched form that has at least about 80% R-enantiomer.

111. The compound of any of embodiments 31-54 in an enantiomerically enriched form that has at least about 90% R-enantiomer.

112. The compound of any of embodiments 31-54 or 95-111 that shows the therapeutic effect of emotional openness.

113. The compound of any of embodiments 31-54 or 95-112 wherein the pharmaceutically acceptable salt(s) is selected from HCl, sulfate, aspartate, saccharate, phosphate, oxalate, acetate, amino acid anion, gluconate, maleate, malate, citrate, mesylate, nitrate or tartrate, or a mixture thereof.

114. The compound of any of embodiments 31-54 or 95-113 that is both a direct 5-$HT_{1B}$ agonist and a serotonin releasing agent.

115. The compound of embodiment 114 that is also a serotonin reuptake inhibitor.

116. The compound of any one of embodiments 31-54 or 95-115 that has minimal or no agonism of 5-HT$_{2A}$.
117. The enantiomerically enriched mixture of any of embodiments 55-94, wherein the mixture has more entactogenic effects than the corresponding racemic mixture in a human.
118. The enantiomerically enriched mixture of any of embodiments 55-94, that has a greater amount of nicotinic-receptor-dependent therapeutic effects than the corresponding racemic mixture in a human.
119. The enantiomerically enriched mixture of any of embodiments 55-94, that has a greater amount of serotonin-receptor-dependent therapeutic effects than the corresponding racemic mixture in a human.
120. The enantiomerically enriched mixture of any of embodiments 55-94, that enhances serotonin-receptor-dependent therapeutic effects and decreases nicotinic effects or dopaminergic effects in a human.
121. The enantiomerically enriched mixture of any of embodiments 55-94, that comprises a balance of enantiomers that decreases a hallucinogenic effect over the racemate.
122. The enantiomerically enriched mixture of any of embodiments 55-94, that comprises a balance of enantiomers that decreases an unwanted psychoactive effect over the racemate.
123. The enantiomerically enriched mixture of any of embodiments 55-94, that comprises a balance of enantiomers that decreases a physiological effect over the racemate.
124. The enantiomerically enriched mixture of any of embodiments 55-94, that comprises a balance of enantiomers that decreases a toxic effect over the racemate.
125. The enantiomerically enriched mixture of any of embodiments 55-94, that comprises a balance of enantiomers that decreases abuse potential over the racemate.
126. The enantiomerically enriched mixture of any of embodiments 55-94 that have at least about 60% S-enantiomer.
127. The enantiomerically enriched mixture of any of embodiments 55-94 that have at least about 70% S-enantiomer.
128. The enantiomerically enriched mixture of any of embodiments 55-94 that have at least about 80% S-enantiomer.
129. The enantiomerically enriched mixture of any of embodiments 55-94 that have at least about 90% S-enantiomer.
130. The enantiomerically enriched mixture of any of embodiments 55-94 that have at least about 60% R-enantiomer.
131. The enantiomerically enriched mixture of any of embodiments 55-94 that have at least about 70% R-enantiomer.
132. The enantiomerically enriched mixture of any of embodiments 55-94 that have at least about 80% R-enantiomer.
133. The enantiomerically enriched mixture of any of embodiments 55-94 that have at least about 90% R-enantiomer.
134. The enantiomerically enriched mixture of any of embodiments 55-94 or 117-133 that shows a greater amount of the therapeutic effect of emotional openness than the corresponding racemic mixture.
135. The enantiomerically enriched mixture of any of embodiments 55-94 or 117-134 wherein the pharmaceutically acceptable salt(s) is selected from HCl, sulfate, aspartate, saccharate, phosphate, oxalate, acetate, amino acid anion, gluconate, maleate, malate, citrate, mesylate, nitrate or tartrate, or a mixture thereof.
136. The enantiomerically enriched mixture of any of embodiments 55-94 or 117-135 that is both a direct 5-HT$_{1B}$ agonist and a serotonin releasing agent.
137. The enantiomerically enriched mixture of embodiment 136 that is also a serotonin reuptake inhibitor.
138. The enantiomerically enriched mixture of embodiments 55-94 or 117-137 that has minimal or no agonism of 5-HT$_{2A}$.
139. In certain embodiments a method for treating a central nervous system disorder comprising administering an effective amount of an enantiomerically enriched mixture of any one of embodiments 1-138 to a host in need thereof is provided.
140. In certain embodiments a method for treating a central nervous system disorder in a host in need thereof comprising administering an effective amount of a compound of Formula XI, Formula XII, or Formula XIII:

(XI)

(XII)

(XIII)

or a pharmaceutically acceptable salt or mixed salt thereof,
wherein:
R$^1$ and R$^2$ are taken together as —OCH=CH— or —CH=CHO—;
R$^{3L}$ and R$^{4L}$ are independently selected from —H, —X, —OH, C$_1$-C$_4$ alkyl, —CH$_2$OH, —CH$_2$X, —CHX$_2$, and —CX$_3$, wherein at least one of R$^{3L}$ and R$^{4L}$ is not —H;
R$^{5K}$ is selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_2$-C$_4$ alkyl;
R$^{5L}$ and R$^{5M}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_1$-C$_4$ alkyl;
R$^{6K}$, R$^{6L}$, and R$^{6M}$ are independently selected from —H and —CH$_3$; and
X is independently selected from —F, —Cl, and —Br.
141. In certain embodiments a method for treating a central nervous system disorder selected from: depression, dysthymia, anxiety, generalized anxiety, social anxiety, panic, adjustment disorders, feeding and eating disorders, binge behaviors, body dysmorphic syndromes, addiction, drug abuse or dependence disorders, disruptive behavior disorders impulse control disorders, gaming disorders, gambling disorders, memory loss, dementia of aging, attention deficit hyperactivity disorder, personality disorders, attachment disorders, autism and dissociative disorders in a host in need thereof comprising administering an effective amount of enantiomerically enriched 5-MAPB, 6-MAPB, 5-MBPB, 6-MBPB, Bk-5-MAPB, Bk-6-MAPB, Bk-5-MBPB, Bk-6-MBPB, or a pharmaceutically acceptable salt or mixed salt thereof is provided.

142. The method of any one of embodiments 139-141 wherein the host is a human.

143. The method of any one of embodiments 139-142 wherein the central nervous system disorder is generalized anxiety.

144. The method of any one of embodiments 139-142 wherein the central nervous system disorder is social anxiety.

145. The method of any one of embodiments 139-142 wherein the central nervous system disorder is depression.

146. The method of any one of embodiments 139-142 wherein the central nervous system disorder is addiction.

147. The method of any one of embodiments 139-142 wherein the central nervous system disorder is an eating disorder.

148. The method of embodiment 147 wherein the eating disorder is bulimia.

149. The method of embodiment 147 wherein the eating disorder is binge eating.

150. The method of embodiment 147 wherein the eating disorder is anorexia.

151. The method of any one of embodiments 139-142 wherein the central nervous system disorder is an attachment disorder.

152. The method of any one of embodiments 139-142 wherein the central nervous system disorder is schizophrenia.

153. The method of any one of embodiments 139-152 wherein the compound or enantiomerically enriched mixture is administered in a clinical setting.

154. The method of any one of embodiments 139-152 wherein the compound or enantiomerically enriched mixture is administered in an at-home or other non-clinical setting.

155. The method of any one of embodiments 139-152 wherein the compound or enantiomerically enriched mixture is administered during a psychotherapy session.

156. The method of any one of embodiments 139-152 wherein the compound or enantiomerically enriched mixture is administered during a counseling session.

157. In certain embodiments a pharmaceutical composition comprising an effective patient-treating amount of a compound of any one of embodiments 31-54 and a pharmaceutically acceptable carrier or excipient is provided.

158. In certain embodiments a pharmaceutical composition comprising an effective patient-treating amount of an enantiomerically enriched mixture or compound of any one of embodiments 1-138 and a pharmaceutically acceptable carrier or excipient is provided.

159. The pharmaceutical composition of embodiment 157 or 158 wherein the composition is administered systemically.

160. The pharmaceutical composition of embodiment 157 or 158 wherein the composition is administered orally.

161. The pharmaceutical composition of embodiment 157 or 158 wherein the composition is administered to mucosal tissue.

162. The pharmaceutical composition of embodiment 157 or 158 wherein the composition is administered rectally.

163. The pharmaceutical composition of embodiment 157 or 158 wherein the composition is administered topically.

164. The pharmaceutical composition of embodiment 157 or 158 wherein the composition is administered subcutaneously.

165. The pharmaceutical composition of embodiment 157 or 158 wherein the composition is administered intravenously.

166. The pharmaceutical composition of embodiment 157 or 158 wherein the composition is administered intramuscularly.

167. The pharmaceutical composition of embodiment 157 or 158 wherein the composition is administered via inhalation.

168. The pharmaceutical composition of embodiment 157 wherein the composition is administered as a tablet.

169. The pharmaceutical composition of embodiment 157 wherein the composition is administered as a gelcap.

170. The pharmaceutical composition of embodiment 157 wherein the composition is administered as a capsule.

171. The pharmaceutical composition of embodiment 157 wherein the composition is administered as an aqueous emulsion.

172. The pharmaceutical composition of embodiment 157 wherein the composition is administered as an aqueous solution.

173. The pharmaceutical composition of embodiment 157 wherein the composition is administered as a pill.

174. The pharmaceutical composition of embodiment 158 wherein the composition is administered as a buccal tablet.

175. The pharmaceutical composition of embodiment 158 wherein the composition is administered as a sublingual tablet.

176. The pharmaceutical composition of embodiment 158 wherein the composition is administered as a sublingual strip.

177. The pharmaceutical composition of embodiment 163 wherein the composition is administered as a cream.

178. The pharmaceutical composition of embodiment 163 wherein the composition is administered as a topical solution.

179. The pharmaceutical composition of embodiment 160 wherein the composition is administered as an aqueous solution.

180. The pharmaceutical composition of embodiment 160 wherein the composition is administered as a powder.

181. The pharmaceutical composition of embodiment 160 wherein the composition is administered as an aerosol.

182. In certain embodiments a compound or enantiomerically enriched mixture or pharmaceutically acceptable salt thereof according to any one of embodiments 1-138 or a pharmaceutical composition thereof for use in the treatment of a central nervous system disorder in a host is provided.

183. In certain embodiments a compound of Formula XI, Formula XII, or Formula XIII or pharmaceutically acceptable salt thereof or a pharmaceutical composition thereof for use in the treatment of a central nervous system disorder in a host is provided:

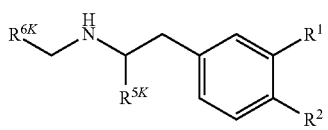
(XI)

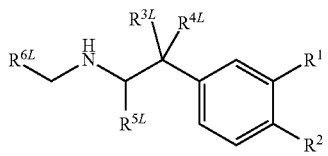
(XII)

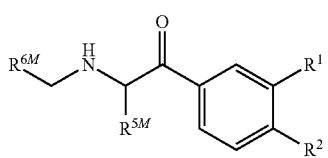
(XIII)

wherein:
$R^1$ and $R^2$ are taken together as —OCH=CH— or —CH=CHO—;
$R^{3L}$ and $R^{4L}$ are independently selected from —H, —X, —OH, $C_1$-$C_4$ alkyl, —CH$_2$OH, —CH$_2$X, —CHX$_2$, and —CX$_3$, wherein at least one of $R^{3L}$ and $R^{4L}$ is not —H;
$R^{5K}$ is selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_2$-$C_4$ alkyl;
$R^{5L}$ and $R^{5M}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl;
$R^{6K}$, $R^{6L}$, and $R^{6M}$ are independently selected from —H and —CH$_3$; and
X is independently selected from —F, —Cl, and —Br.

184. In certain embodiments a compound or pharmaceutically acceptable salt thereof or a pharmaceutical composition thereof for use in the treatment of a central nervous system disorder selected from: depression, dysthymia, anxiety, generalized anxiety, social anxiety, panic, adjustment disorders, feeding and eating disorders, binge behaviors, body dysmorphic syndromes, addiction, drug abuse or dependence disorders, disruptive behavior disorders impulse control disorders, gaming disorders, gambling disorders, memory loss, dementia of aging, attention deficit hyperactivity disorder, personality disorders, attachment disorders, autism or a dissociative disorder in a host in need thereof wherein the compound is enantiomerically enriched 5-MAPB, 6-MAPB, 5-MBPB, 6-MBPB, Bk-5-MAPB, Bk-6-MAPB, Bk-5-MBPB, or Bk-6-MBPB is provided.

185. The compound or enantiomerically enriched mixture of any one of embodiments 182-184 wherein the host is a human.

186. The compound or enantiomerically enriched mixture of any one of embodiments 182-185 wherein the central nervous system disorder is an anxiety disorder.

187. The compound or enantiomerically enriched mixture of embodiment 186 wherein the anxiety disorder is generalized anxiety.

188. The compound or enantiomerically enriched mixture of embodiment 186 wherein the anxiety disorder is social anxiety.

189. The compound or enantiomerically enriched mixture of any one of embodiments 182-185 wherein the central nervous system disorder is depression.

190. The compound or enantiomerically enriched mixture of any one of embodiments 182-185 wherein the central nervous system disorder is post-traumatic stress disorder.

191. The compound or enantiomerically enriched mixture of any one of embodiments 182-185 wherein the central nervous system disorder is addiction.

192. The compound or enantiomerically enriched mixture of any one of embodiments 182-185 wherein the central nervous system disorder is an eating disorder.

193. The compound or enantiomerically enriched mixture of embodiment 192 wherein the eating disorder is bulimia.

194. The compound or enantiomerically enriched mixture of embodiment 192 wherein the eating disorder is binge eating.

195. The compound or enantiomerically enriched mixture of embodiment 192 wherein the eating disorder is anorexia.

196. The compound or enantiomerically enriched mixture of any one of embodiments 182-185 wherein the central nervous system disorder is an attachment disorder.

197. The compound or enantiomerically enriched mixture of any one of embodiments 182-185 wherein the central nervous system disorder is schizophrenia.

198. The compound or enantiomerically enriched mixture of any one of embodiments 182-197 wherein the compound or enantiomerically enriched mixture is administered in a clinical setting.

199. The compound or enantiomerically enriched mixture of any one of embodiments 182-197 wherein the compound or enantiomerically enriched mixture is administered in an at-home setting.

200. The compound or enantiomerically enriched mixture of any one of embodiments 182-197 wherein the compound or enantiomerically enriched mixture is administered during a psychotherapy session.

201. The compound or enantiomerically enriched mixture of any one of embodiments 182-197 wherein the compound or enantiomerically enriched mixture is administered during a counseling session.

202. In certain embodiments a use of a compound or enantiomerically enriched mixture or pharmaceutically acceptable salt thereof according to any one of embodiments 55-138 or a pharmaceutical composition thereof in the treatment of a central nervous system disorder in a host is provided.

203. In certain embodiments a use of a compound of Formula XI, Formula XII, or Formula XIII or pharmaceutically acceptable salt thereof or a pharmaceutical composition thereof in the treatment of a central nervous system disorder in a host is provided:

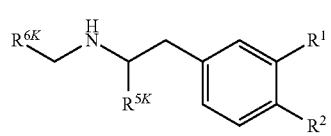
(XI)

-continued

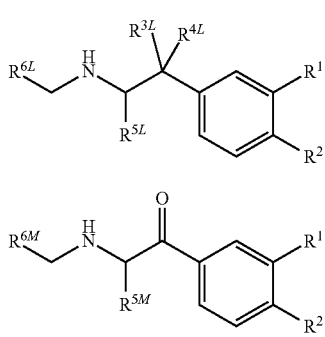
(XII)

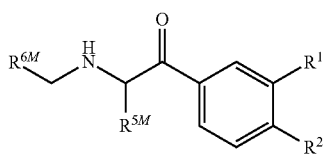
(XIII)

wherein:
R¹ and R² are taken together as —OCH=CH— or —CH=CHO—;
$R^{3L}$ and $R^{4L}$ are independently selected from —H, —X, —OH, $C_1$-$C_4$ alkyl, —CH₂OH, —CH₂X, —CHX₂, and —CX₃, wherein at least one of $R^{3L}$ and $R^{4L}$ is not —H;
$R^{5K}$ is selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_2$-$C_4$ alkyl;
$R^{5L}$ and $R^{5M}$ are independently selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_1$-$C_4$ alkyl;
$R^{6K}$, $R^{6L}$, and $R^{6M}$ are independently selected from —H and —CH₃; and
X is independently selected from —F, —Cl, and —Br.

204. In certain embodiments a use of a compound or pharmaceutically acceptable salt thereof or a pharmaceutical composition thereof in the treatment of a central nervous system disorder selected from: depression, dysthymia, anxiety, generalized anxiety, social anxiety, panic, adjustment disorders, feeding and eating disorders, binge behaviors, body dysmorphic syndromes, addiction, drug abuse or dependence disorders, disruptive behavior disorders impulse control disorders, gaming disorders, gambling disorders, memory loss, dementia of aging, attention deficit hyperactivity disorder, personality disorders, attachment disorders, autism or a dissociative disorder in a host in need thereof wherein the compound is enantiomerically enriched 5-MAPB, 6-MAPB, 5-MBPB, 6-MBPB, Bk-5-MAPB, Bk-6-MAPB, Bk-5-MBPB, or Bk-6-MBPB is provided.

205. In certain embodiments a use of a compound or pharmaceutically acceptable salt thereof according to any one of embodiments 55-138 or a pharmaceutical composition thereof in the manufacture of a medicament for the treatment of a central nervous system disorder in a host is provided.

206. In certain embodiments a use of a compound of Formula XI, Formula XII, or Formula XIII or pharmaceutically acceptable salt thereof or a pharmaceutical composition thereof in the manufacture of a medicament for the treatment of a central nervous system disorder in a host is provided:

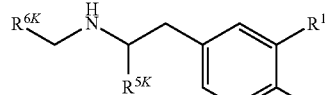
(XI)

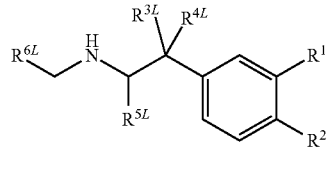
(XII)

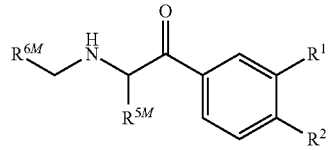
(XIII)

wherein:
R¹ and R² are taken together as —OCH=CH— or —CH=CHO—;
$R^{3L}$ and $R^{4L}$ are independently selected from —H, —X, —OH, $C_1$-$C_4$ alkyl, —CH₂OH, —CH₂X, —CHX₂, and —CX₃, wherein at least one of $R^{3L}$ and $R^{4L}$ is not —H;
$R^{5K}$ is selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_2$-$C_4$ alkyl;
$R^{5L}$ and $R^{5M}$ are independently selected from —H, —CH₂OH, —CH₂X, —CHX₂, —CX₃, —CH₂CH₂OH, —CH₂CH₂X, —CH₂CHX₂, —CH₂CX₃, $C_3$-$C_4$ cycloalkyl, and $C_1$-$C_4$ alkyl;
$R^{6K}$, $R^{6L}$, and $R^{6M}$ are independently selected from —H and —CH₃; and
X is independently selected from —F, —Cl, and —Br.

207. In certain embodiments a use of a compound or pharmaceutically acceptable salt thereof or a pharmaceutical composition thereof in the manufacture of a medicament for the treatment of a central nervous system disorder selected from: depression, dysthymia, anxiety, generalized anxiety, social anxiety, panic, adjustment disorders, feeding and eating disorders, binge behaviors, body dysmorphic syndromes, addiction, drug abuse or dependence disorders, disruptive behavior disorders impulse control disorders, gaming disorders, gambling disorders, memory loss, dementia of aging, attention deficit hyperactivity disorder, personality disorders, attachment disorders, autism or a dissociative disorder in a host in need thereof wherein the compound is enantiomerically enriched 5-MAPB, 6-MAPB, 5-MBPB, 6-MBPB, Bk-5-MAPB, Bk-6-MAPB, Bk-5-MBPB, or Bk-6-MBPB is provided.

208. The use of any one of embodiments 202-207 wherein the host is a human.

209. The use of any one of embodiments 202-208 wherein the central nervous system disorder is an anxiety disorder.

210. The use of embodiment 209 wherein the anxiety disorder is generalized anxiety.

211. The use of embodiment 209 wherein the anxiety disorder is social anxiety.

212. The use of any one of embodiments 202-208 wherein the central nervous system disorder is depression.

213. The use of any one of embodiments 202-208 wherein the central nervous system disorder is post-traumatic stress disorder.
214. The use of any one of embodiments 202-208 wherein the central nervous system disorder is addiction.
215. The use of any one of embodiments 202-208 wherein the central nervous system disorder is an eating disorder.

I. Definitions

When introducing elements of the present invention or the preferred embodiments thereof, the articles "a," "an," "the," and "said" are intended to mean that there are one or more of the elements. The terms "comprising," "including," and "having" are intended to be inclusive and not exclusive (i.e., there may be other elements in addition to the recited elements). Thus, the terms "including," "may include," and "include," as used herein mean, and are used interchangeably with, the phrase "including but not limited to."

Where a range of values is provided, it is understood that the upper and lower limit, and each intervening value between the upper and lower limit of the range is encompassed within the embodiments.

Unless defined otherwise, all technical and scientific terms herein have the meaning as commonly understood by one of ordinary skill in the art to which this invention belongs. In the event there is a plurality of definitions for a term herein, those in this section prevail unless stated otherwise. Further definitions that may assist the reader to understand the disclosed embodiments are as follows, and such definitions may be used to interpret the defined terms, when those terms are used herein. However, the examples given in the definitions are generally non-exhaustive and must not be construed as limiting the invention. It also will be understood that a substituent should comply with chemical bonding rules and steric compatibility constraints in relation to the particular molecule to which it is attached.

The term "CNS disorder" as used herein refers to either a neurological condition (one that is typically treated by a neurologist) or a psychiatric condition (one that is typically treated by a psychiatrist). Neurological disorders are typically those affecting the structure, biochemistry or normal electrical functioning of the brain, spinal cord or other nerves. Psychiatric conditions are more typically thought of as mental disorders, which are primarily abnormalities of thought, feeling or behavior that cause significant distress or impairment of personal functioning. Thus, the disclosed compounds can be used in an effective amount to improve neurological or psychiatric functioning in a patient in need thereof. Neurological indications include, but are not limited to improved neuroplasticity, including treatment of stroke, brain trauma, dementia, and neurodegenerative diseases. Compounds of the current invention can be considered psychoplastogens, that is, small molecules that are able to induce rapid neuroplasticity. For example, in certain embodiments, the disclosed compounds and compositions can be used to improve stuttering and other dyspraxias or to treat Parkinson's disease or schizophrenia.

The term "improving psychiatric function" is intended to include mental health and life conditions that are not traditionally treated by neurologists but sometimes treated by psychiatrists and can also be treated by psychotherapists, life coaches, personal fitness trainers, meditation teachers, counselors, and the like. For example, it is contemplated that the disclosed compounds will allow individuals to effectively contemplate actual or possible experiences that would normally be upsetting or even overwhelming. This includes individuals with fatal illness planning their last days and the disposition of their estate. This also includes couples discussing difficulties in their relationship and how to address them. This also includes individuals who wish to more effectively plan their career.

The term "inadequate functioning of neurotransmission" is used synonymously with a CNS disorder that adversely affects normal healthy neurotransmission.

The present invention also includes compounds, including enantiomerically enriched compounds and their use, such as 5-MAPB, 6-MAPB, 5-MBPB, 6-MBPB, Bk-5-MAPB, Bk-6-MAPB Formula I, Formula II, Formula III, Formula IV, Formula V, Formula VI, Formula VII, Formula VIII, Formula IX, Formula X, Formula XI, Formula XII, Formula XII, Formula A, Formula B, Formula C, Formula D, Formula E, and Formula F with at least one desired isotopic substitution of an atom, at an amount above the natural abundance of the isotope, i.e., isotopically enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, fluorine and chlorine such as $^{2}H$, $^{3}H$, $^{11}C$, $^{13}C$, $^{14}C$, $^{5}N$, $^{17}O$, $^{18}O$, $^{18}F$, $^{36}Cl$, and respectively. In one non-limiting embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is at least 60, 70, 80, 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in a compounds or compositions described herein. In one non-limiting embodiment, the substitution of a hydrogen atom for a deuterium atom occurs within a group selected from any of Q, Z, $R^1$, $R^2$, $R^3$, $R^4$, $R^5$ or $R^6$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). The compounds of the invention also include isotopically labeled compounds where one or more atoms have an atomic mass different from the atomic mass conventionally found in nature. Examples of isotopes that may be incorporated into the compounds of the invention include $^2$H, $^3$H, $^{13}$C, $^{14}$C, $^{15}$N, $^{18}$O, $^{17}$O, $^{31}$P, $^{32}$P, $^{18}$F, and $^{36}$Cl.

For example, the methyl group on the nitrogen of 5-MAPB, 6-MAPB, 5-MBPB, 6-MBPB, Bk-5-MAPB and Bk-6-MAPB is subject to metabolic removal, which produces pharmacologically active metabolites. In some embodiments, 5-MAPB or 6-MAPB is prepared with deuterium replacing some or all of the three hydrogens on the N-methyl group. In one embodiment, 5-MBPB or 6-MBPB is prepared with deuterium replacing some or all of the three hydrogens on the N-methyl group. In one embodiment, Bk-5-MAPB or Bk-6-MAPB is prepared with deuterium replacing some or all of the three hydrogens on the N-methyl group. This creates a higher activation energy for bond cleavage and a slower formation of the methyl metabolites. Analogously, the two hydrogens on the furan ring may be replaced with one or two deuteriums to decrease metabolic opening of the furan ring and formation of hydroxyl-substituted metabolites.

Similarly, the methyl group on the nitrogen of Formula A, Formula B, Formula C, and Formula D of the invention is subject to metabolic removal, which produces pharmacologically active metabolites. In one embodiment, Formula A or Formula B is prepared with deuterium replacing some or all of the three hydrogens on the N-methyl group. In one embodiment, Formula C or Formula D is prepared with deuterium replacing some or all of the three hydrogens on the N-methyl group. The primary amines of Formula C and Formula D of the invention retain therapeutic effects while presenting a different profile of pharmacological effects. Accordingly, the present disclosure also includes the primary amine variants of Formula C and Formula D, where applicable.

The ethyl group on the nitrogen of Formula E and Formula F is also subject to metabolic removal, which produces pharmacologically active metabolites. In one embodiment, Formula E or Formula F is prepared with deuterium replacing some or all of the three hydrogens on the N-ethyl group. The primary amines of Formula E and Formula F of the invention retain therapeutic effects while presenting a different profile of pharmacological effects. Accordingly, the present disclosure also includes the primary amine variants of Formula E and Formula F, where applicable.

The methyl or ethyl group on the nitrogen where applicable of 5-MAPB, 6-MAPB, 5-MBPB, 6-MBPB, Bk-5-MAPB, Bk-6-MAPB, Formula I, Formula II, Formula III, Formula IV, Formula V, Formula VI, Formula VII, Formula VIII, Formula IX, Formula X, Formula XI, Formula XII, or Formula XII is also subject to metabolic removal, which produces pharmacologically active metabolites. In one embodiment, Formula I, Formula II, Formula III, Formula IV, Formula V, Formula VI, Formula VII, Formula VIII, Formula IX, Formula X, Formula XI, Formula XII, or Formula XII is prepared with deuterium replacing some or all of the three hydrogens on the N-ethyl or N-methyl group. The primary amines of Formula I, Formula II, Formula III, Formula IV, Formula V, Formula VI, Formula VII, Formula VIII, Formula IX, Formula X, Formula XI, Formula XII, and Formula XII of the invention retain therapeutic effects while presenting a different profile of pharmacological effects.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is at least 60, 70, 80 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

"Alkyl" refers to a saturated or unsaturated, branched, straight-chain, or cyclic monovalent hydrocarbon radical derived by the removal of one hydrogen atom from a single carbon atom of a parent alkane, alkene or alkyne. Typical alkyl groups include methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Alkyl will be understood to include cyclic alkyl radicals such as cyclopropyl, cyclobutyl, and cyclopentyl.

"Alkyl" includes radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 26 carbon atoms, more preferably, from 1 to 10 carbon atoms.

"Halogen" or "halo" means fluoro (F), chloro (Cl), bromo (Br), or iodo (I). For groups containing two or more halogens, such as —CHX$_2$ or —CX$_3$, and for example "where X is halogen," it will be understood that each Y independently will be selected from the group of halogens.

"Hydroxy" means the radical —OH.

"Oxo" means the divalent radical =O.

"Stereoisomers" includes enantiomers, diastereomers, the components of racemic mixtures, and combinations thereof. Stereoisomers can be prepared or separated as described herein or by using other methods.

"Isomers" includes stereo and geometric isomers, as well as diastereomers. Examples of geometric isomers include cis isomers or trans isomers across a double bond. Other isomers are contemplated among the compounds of the present disclosure. The isomers may be used either in pure form or in admixture with other isomers of the compounds described herein.

"Agonism" refers to the activation of a receptor or enzyme by a modulator, or agonist, to produce a biological response.

"Agonist" refers to a modulator that binds to a receptor or enzyme and activates the receptor to produce a biological response. As a nonlimiting example, "$5HT_{1B}$ agonist" can be used to refer to a compound that exhibits an $EC_{50}$ with respect to $5HT_{1B}$ activity of no more than about 10, 25 or even 50 µM. In some embodiments, "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

"DAT to SERT ratio" refers to the tendency of a substance (e.g., a compound or a drug) to increase extracellular dopamine versus increasing extracellular 5-HT concentrations. Higher numbers of this ratio indicate a greater increase of dopamine than serotonin, while lower number indicate an increasing 5-HT more than dopamine. The exact numbers depend on the assay used. The ratio is calculated herein as (DAT EC50)$^{-1}$/(SERT EC50)$^{-1}$. Some publications use IC50s for inhibiting uptake instead of EC50s for causing release to calculate this ratio, which will often yield very different results for substances that are monoamine releasers. Thus, it is important to review the numbers in view of the assay and measurement used.

"IC50" refers to the concentration of a substance (e.g., a compound or a drug) that is required for 50% inhibition of a biological process. For example, IC50 refers to the half maximal (50%) inhibitory concentration (IC) of a substance as determined in a suitable assay. Similarly, EC50 refers to the concentration of a substance that provokes a response halfway between the baseline activity and maximum response. In some instances, an IC50 or EC50 is determined in an in vitro assay system. In some embodiments as used herein, IC50 (or EC50) refers to the concentration of a modulator that is required for 50% inhibition (or excitation) of a receptor, for example, 5HT$_{1B}$.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., positive allosteric modulator) of a G protein-coupled receptor (e.g., 5-HT$_{1B}$) are modulators of the receptor.

"Neuroplasticity" refers to the ability of the brain to change its structure and/or function throughout a subject's life. Examples of the changes to the brain include, but are not limited to, the ability to adapt or respond to internal and/or external stimuli, such as due to an injury, and the ability to produce new neurites, dendritic spines, and synapses.

"Treating" or "treatment" of a disease, as used in context, includes (i) inhibiting the disease, i.e., arresting or reducing the development or progression of the disease or its clinical symptoms; or (ii) relieving the disease, i.e., causing regression of the disease or its clinical symptoms. Inhibiting the disease, for example, would include prophylaxis. Hence, one of skill in the art will understand that a therapeutic amount necessary to effect treatment for purposes of this invention will, for example, be an amount that provides for objective indicia of improvement in patients having clinically-diagnosable symptoms. Other such measurements, benefits, and surrogate or clinical endpoints, whether alone or in combination, would be understood to those of ordinary skill.

II. Compounds of the Present Invention

An enantiomerically enriched mixture is a mixture that contains one enantiomer in a greater amount than the other. An enantiomerically enriched mixture of an S-enantiomer contains at least 55% of the S-enantiomer, and, typically at least about 60%, 65%, 70%, 75%, 80%, 85%, 90%, or 95% or more of the S-enantiomer. An enantiomerically enriched mixture of an R-enantiomer contains at least 55% of the R-enantiomer, and typically at least about 60%, 65%, 70%, 75%, 80%, 85%, 90% or 95% of the R-enantiomer. The specific ratio of S or R enantiomer can be selected for the need of the patient according to the health care specialist to balance the desired effect.

The term enantiomerically enriched mixture as used in this application does not include a racemic mixture and does not include a pure isomer or substantially pure isomer. Notwithstanding, it should be understood that any compound described herein in enantiomerically enriched form can be used as a substantially pure isomer if it achieves the goal of any of the specifically itemized methods of treatment described herein, including but not limited to 5-MAPB, 6-MAPB, 5-MBPB, 6-MBPB, 5-Bk-5-MAPB, 6-Bk-MAPB, Bk-5-MBPB or Bk-6-MBPB.

The chiral carbon typically referred to in this application is the carbon alpha to the amine in the phenylethylamine motif. Of course, the compounds can have additional chiral centers that result in diastereomers. Notwithstanding, in the present application, the primary chiral carbon referred to in the term "enantiomerically enriched" is that carbon alpha to the amine in the provided structures.

In one aspect of the invention, compounds are provided comprising enantiomerically enriched or enantiomerically substantially pure R-5-MAPB, S-5-MAPB, R-6-MAPB, or R-6-MAPB or a pharmaceutically acceptable salt or mixed salt thereof. In one embodiment, a pharmaceutical composition is provided that comprises an enantiomerically-enriched mixture of the R- or S-enantiomer of 5-MAPB or 6-MAPB:

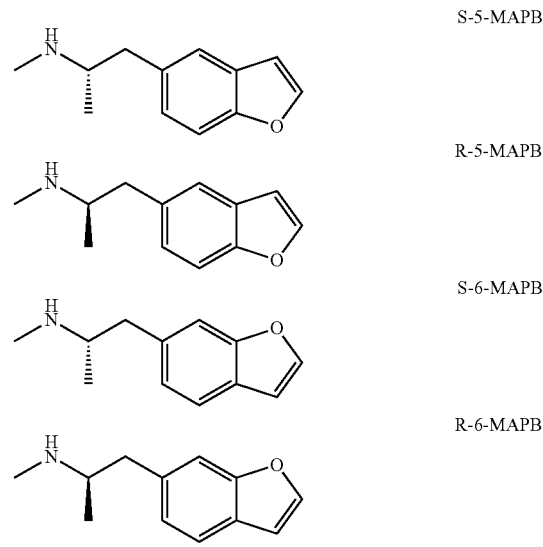

In certain embodiments, isolated enantiomers of the compounds of the present invention show improved binding at the desired receptors and transporters relevant to the goal of treatment for the mental disorder or for mental enhancement.

It has been discovered that it is useful to have an S- or R-enantiomerically enriched mixture of these entactogenic compounds that is not a racemic mixture. It has been surprisingly discovered that enantiomerically enriched mixtures that have a greater amount of the S-enantiomer 5-MAPB or 6-MAPB maximize serotonin-receptor-dependent therapeutic effects, whereas the enantiomerically enriched R-enantiomer of 5-MAPB or 6-MAPB maximize nicotinic-receptor-dependent therapeutic effects. Therefore, one aspect of the present invention is a balanced mixture of S-5-MAPB and R-5-MAPB or a balanced mixture of S-6-MAPB and R-6-MAPB that achieves a predetermined combination of serotonin-receptor-dependent therapeutic effects and nicotinic-receptor-dependent or dopaminergic therapeutic effects. The effect can be modulated as desired for optimal therapeutic effect.

Accordingly, in one embodiment, an enantiomerically enriched mixture of S-5-MAPB or an enantiomerically enriched mixture of S-6-MAPB maximize serotonin-receptor-dependent therapeutic effects and minimize unwanted nicotinic effects or dopaminergic effects when administered to a host in need thereof, for example a mammal, including a human.

In another embodiment, an enantiomerically enriched mixture of R-5-MAPB or an enantiomerically enriched mixture of R-6-MAPB maximize nicotinic-receptor-dependent or dopaminergic-receptor dependent therapeutic effects while minimizing unwanted effects, when administered to a host in need thereof, including a mammal, for example, a human.

Non-limiting examples of unwanted effects that can be minimized by carefully selecting the balance of enantiomers include hallucinogenic effects, psychoactive effects (such as excess stimulation or sedation), physiological effects (such as transient hypertension or appetite suppression), toxic effects (such as to the brain or liver), effects contributing to abuse liability (such as euphoria or dopamine release), and/or other side effects.

It has been surprisingly discovered that enantiomerically enriched mixtures of 5-MAPB that are non-racemic have a relatively greater amount of some therapeutic effects (such as emotional openness) while having lesser effects associated with abuse liability (such as perceptible 'good drug effects' which can lead to abuse versus openness, which leads to more tranquility and peace). Therefore, one aspect of the present invention is a balanced mixture of S-5-MAPB and R-5-MAPB or a balanced mixture of S-6-MAPB and R-6-MAPB that achieves a predetermined combination of emotional therapeutic effects and perceptible mood effects. The effect can be modulated as desired for optimal therapeutic effect.

Accordingly, in one embodiment, an enantiomerically enriched mixture of S-5-MAPB or an enantiomerically enriched mixture of S-6-MAPB balances emotional openness and perceptible mood effects when administered to a host in need thereof, for example a mammal, including a human.

In certain embodiments, it is preferred to have an S- or R-enantiomerically enriched mixture. It has been surprisingly discovered that enantiomerically enriched mixtures that have a greater amount of the R-enantiomer of 5-MAPB or 6-MAPB maximize nicotinic-receptor-dependent therapeutic effects and that enantiomerically enriched mixtures that have a greater amount of the S-enantiomer 5-MAPB or 6-MAPB maximize serotonin-receptor-dependent therapeutic effects. Therefore, one aspect of the present invention is a balanced mixture of S-5-MAPB and R-5-MAPB or a balanced mixture of S-6-MAPB and R-6-MAPB that achieves a predetermined combination of serotonin-receptor-dependent therapeutic effects and nicotinic-receptor-dependent therapeutic effects.

Accordingly, in one embodiment, an enantiomerically enriched mixture of S-5-MAPB or an enantiomerically enriched mixture of S-6-MAPB maximize serotonin-receptor-dependent therapeutic effects and minimized unwanted nicotinic effects when administered to a host in need thereof, for example a mammal, including a human.

In another embodiment, an enantiomerically enriched mixture of R-5-MAPB or an enantiomerically enriched mixture of R-6-MAPB maximize nicotinic-receptor-dependent therapeutic effects while minimizing unwanted effects, when administered to a host in need thereof, including a mammal, for example, a human.

The present invention also provides new medical uses for the compounds of Formulas I-X and enantiomerically enriched compositions of 5-MAPB, 6-MAPB, 5-MBPB, 6-MBPB, 5-Bk-5-MAPB, 6-Bk-MAPB, Bk-5-MBPB, Bk-6-MBPB, or the compounds of Formulas A-F by administering an effective amount to a patient such as a human to treat a CNS disorder including but not limited to, the treatment of depression, dysthymia, anxiety, generalized anxiety, social anxiety, panic, adjustment disorders, feeding and eating disorders, binge behaviors, body dysmorphic syndromes, addiction, drug abuse or dependence disorders, disruptive behavior disorders impulse control disorders, gaming disorders, gambling disorders, memory loss, dementia of aging, attention deficit hyperactivity disorder, personality disorders, attachment disorders, autism or dissociative disorders or any other disorder described herein, including in the Background.

It has been discovered that several of the benzofuran derivatives of the current invention are direct $5\text{-HT}_{1B}$ agonists. Very few substances are known that are $5\text{-HT}_{1B}$ agonists and also 5-HT releasers and of those, some show significant toxicities. For example, m-chlorophenylpiperazine (mCPP) is one example but is anxiogenic and induces headaches, limiting any clinical use. MDMA itself does not bind to the $5\text{-HT}_{1B}$ (Ray. 2010. *PloS one*, 5(2), e9019). $5\text{-HT}_{1B}$ agonism is noteworthy because indirect stimulation of these receptors, secondary to elevated extracellular serotonin, has been hypothesized to be required for the prosocial effects of MDMA (Heifets et al. 2019. *Science translational medicine*, 11(522)), while other aspects of entactogen effects have been attributed to monoamine release (e.g., Luethi & Liechti. 2020. *Archives of Toxicology*, 94(4), 1085-1133). Thus, the unique ratios of $5\text{-HT}_{1B}$ stimulation and monoamine release displayed by the disclosed compounds enable different profiles of therapeutic effects that cannot be achieved by MDMA or other known entactogens.

The compounds of the present invention show a 5-HT selectivity pattern that is important to therapeutic use. Various subtypes of 5-HT receptor can induce different felt experiences on a patient. Agonism of the $5\text{-HT}_{2A}$ receptor can cause feelings of fear and hallucinations, but agonism of $5\text{-HT}_{1B}$ is believed to be tied to the pro-social effects of entactogens. Various subtypes of 5-HT receptor can also contribute to different toxicity risks for a patient. Administration of MDMA and other serotonergic drugs is associated with elevated acute risk of hyponatremia. It is known that stimulation of $5\text{-HT}_2$ receptors is an important trigger of release of antidiuretic hormone (Iovino et a. Current pharmaceutical design 18, no. 30 (2012): 4714-4724).

It has been surprisingly discovered that the enantiomeric compositions of the present invention can be selected to be poor agonists of $5\text{-HT}_{2A}$, but exhibit activity toward $5\text{-HT}_{1B}$. For example, as described in the non-limiting illustrative Example 6, the majority of the compounds do not exhibit $5\text{-HT}_{2A}$ agonist activity but do exhibit $5\text{-HT}_{1B}$ agonist activity in the range of about 5 to 0.0005 μM, or 3 to 0.10 μM. Importantly, 5-$HT_{1B}$ agonist activity effect occurs through direct action on the receptor, rather than as an indirect consequence of serotonin release. This is an unexpected discovery because this property has not been observed in an entactogen, including MDMA, before. In one embodiment, the selectivity toward the 5-$HT_{1B}$ receptor over 5-$HT_{2A}$ receptor allows for a more relaxed and therapeutically productive experience for the patient undergoing treatment with a compound of the present invention.

The unique ratios of 5-$HT_{1B}$ stimulation and 5-HT release displayed by the disclosed compounds enable different profiles of therapeutic effects and side effects that may not be achieved by MDMA or other known entactogens. An undesirable effect of releasing 5-HT can be hyponatremia or loss of appetite. Drugs such as d-fenfluramine that release 5-HT by interacting with SERT and thereby increase agonism of all serotonin receptors have been used as anorectics. Similarly, MDMA is known to acutely suppress appetite (see, e.g., Vollenweider et al. Neuropsychopharmacology 19, no. 4 (1998): 241-251.).

Accordingly, as described in the non-limiting illustrative Example 9, the enantiomeric compositions of the present invention have ability to release 5-HT with potencies (EC50s) in the range of approximately 5 to 0.001 μM or 1.3 to 0.003 μM. In another embodiment, therefore, the selectivity toward the 5-$HT_{1B}$ receptor over SERT-mediated 5-HT release allows for a therapeutically productive experience for the patient undergoing treatment with a compound of the present invention with fewer other side effects from serotonin release, such as loss of appetite or risk of hyponatremia.

The present invention also includes compounds with beneficial selectivity profiles for neurotransmitter transporters. The balance of weakly activating NET (to reduce cardiovascular toxicity risk) and having a relatively low DAT to SERT ratio (to increase therapeutic effect relative to addictive liability) is a desirable feature of an entactogenic therapy displayed by the compounds and compositions of the present invention.

In other embodiments, the invention provides an active compound of Formula I, Formula II, Formula III, Formula IV, Formula V, Formula VI, Formula VII, Formula VIII, Formula IX, Formula X:

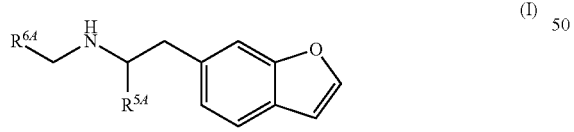

(I)

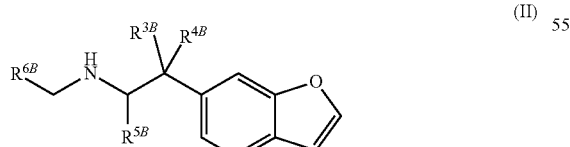

(II)

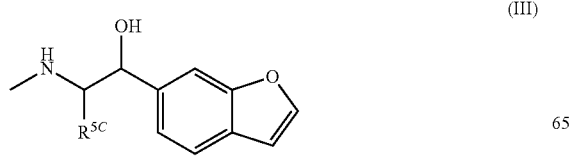

(III)

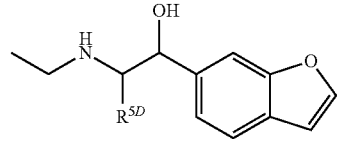

(IV)

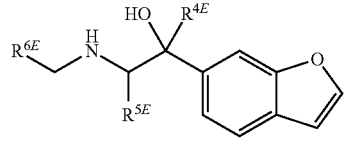

(V)

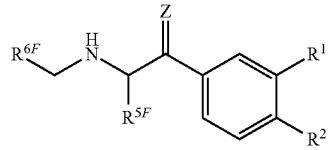

(VI)

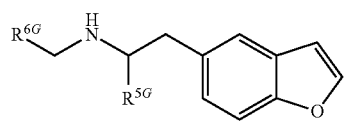

(VII)

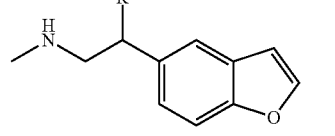

(VIII)

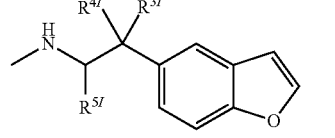

(IX)

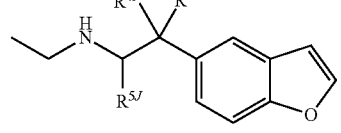

(X)

wherein:
$R^1$ and $R^2$ are taken together as —OCH=CH— or —CH=CHO—;
$R^{3B}$ and $R^{4B}$ are independently selected from —H, —X, $C_1$-$C_4$ alkyl, —$CH_2OH$, —$CH_2X$, —$CHX_2$, and —$CX_3$, wherein at least one of $R^{3B}$ and $R^{4B}$ is not —H;
$R^{3I}$ and $R^{4I}$ are independently selected from —H, —X, —OH, —$CH_2OH$, —$CH_2X$, —$CHX_2$, —$CX_3$, and $C_1$-$C_4$ alkyl; wherein at least one of $R^{3I}$ and $R^{4I}$ is not —H;
$R^{3J}$ and $R^{4J}$ are independently selected from —H, —X, —OH, $C_1$-$C_4$ alkyl, —$CH_2OH$, —$CH_2X$, —$CHX_2$, and —$CX_3$;
$R^{4E}$ is selected from $C_1$-$C_4$ alkyl, —$CH_2OH$, —$CH_2X$, —$CHX_2$, and —$CX_3$;
$R^{4H}$ is selected from —X, —$CH_2CH_2CH_3$, —$CH_2OH$, —$CH_2X$, and —$CHX_2$;
$R^{5A}$ and $R^{5G}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_2$-$C_4$ alkyl, when $R^{5A}$ is $C_2$ alkyl or H, $R^{6A}$ is not —H, and when $R^{5G}$ is —H or $C_2$ alkyl, $R^{6G}$ is not —H;

$R^{5B}$ is selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl;

$R^{5C}$ is selected from —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_2$-$C_4$ alkyl;

$R^{5D}$, $R^{5E}$, $R^{5F}$, and $R^{5J}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl, when $R^{5F}$ is —H or $C_1$ alkyl, $R^{6F}$ cannot be —H, and when $R^{5J}$ is $C_1$ alkyl, at least one of $R^{3J}$ and $R^{4J}$ is not H;

$R^{5I}$ is selected from —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl; wherein at least one of $R^{3I}$, $R^{4I}$, and $R^{5I}$ is not $C_1$ alkyl;

$R^{6A}$, $R^{6B}$, $R^{6E}$, $R^{6F}$, and $R^{6G}$ are independently selected from —H and —CH$_3$;

X is independently selected from —F, —Cl, and —Br; and

Z is selected from O and CH$_2$.

The compounds of Formulas I-X can be used as racemic mixtures, enantiomerically or diastereomerically enriched or substantially pure or pure isomers, as desired to achieve the goal of therapy.

In further embodiments, the invention includes enantiomerically enriched compounds of Formula XI, Formula XII, and Formula XIII or a pharmaceutically acceptable salt or mixed salt thereof:

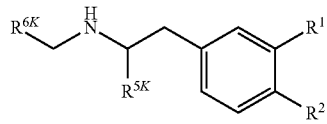

(XI)

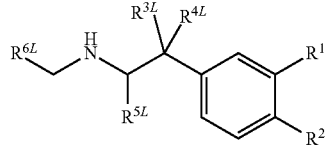

(XII)

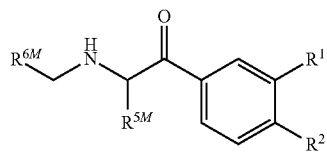

(XIII)

wherein:
$R^1$ and $R^2$ are taken together as —OCH=CH— or —CH=CHO—;

$R^{3L}$ and $R^{4L}$ are independently selected from —H, —X, —OH, $C_1$-$C_4$ alkyl, —CH$_2$OH, —CH$_2$X, —CHX$_2$, and —CX$_3$, wherein at least one of $R^{3L}$ and $R^{4L}$ is not —H;

$R^{5K}$ is selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_2$-$C_4$ alkyl;

$R^{5L}$ and $R^{5M}$ are independently selected from —H, —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, $C_3$-$C_4$ cycloalkyl, and $C_1$-$C_4$ alkyl; and $R^{6K}$, $R^{6L}$, and $R^{6M}$ are selected from —H and —CH$_3$.

In other embodiments, the present invention provides a enantiomerically enriched compound of Formula A, Formula B, Formula C, Formula D, Formula E, or Formula F or a pharmaceutically acceptable salt or mixed salt thereof, for any of the uses described herein by administering to a patient, such as a human, the enantiomerically enriched compound in an effective amount to achieve the desired effect:

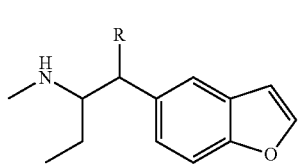 [SMILES: CCC(NC)C(=O)c1ccc2occc2c1]

Formula A

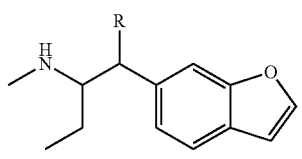 [SMILES: CCC(NC)C(=O)c1ccc2ccoc2c1]

Formula B

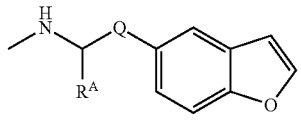

Formula C

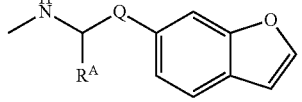

Formula D

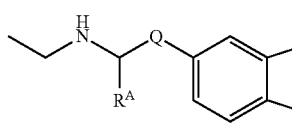

Formula E

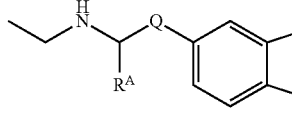

Formula F wherein
R is hydrogen or hydroxyl.

$R^A$ is —CH$_3$, —CH$_2$Y, —CHY$_2$, —CY$_3$, —CH$_2$CH$_3$, —CH$_2$CH$_2$Y, —CH$_2$CHY$_2$, —CH$_2$CY$_3$, —CH$_2$OH, or —CH$_2$CH$_2$OH;

Q is selected from:

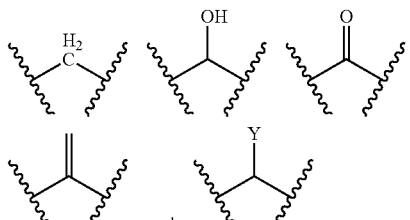

and
Y is halogen.

In certain aspects of these embodiments, one or more selected compounds of Formulas I-XIII or Formulas A-F can be improved or "tuned" by administering an effective amount to a host such as a human, in need thereof, in a composition of a substantially pure enantiomer (or diastereomer, where relevant), or alternatively, an enantiomerically enriched composition that has an abundance of one enantiomer over the other. In this way, as described above, the enantiomeric forms act differently from each other on various 5-HT receptors, dopamine receptors, nicotinic acetylcholine receptors, and norepinephrine receptors, producing variable effects, and that those effects can be selected for based on desired outcome for the patient.

In certain embodiments, any of the selected compounds or mixture of the present invention is administered to a patient in an effective amount in conjunction with psychotherapy, cognitive enhancement, or life coaching (pharmacotherapy), or as part of routine medical therapy.

In one embodiment, compounds of Formula A and Formula B are halogenated, for example by having one or more halogens in place of one or more hydrogens on the ethyl group attached at the alpha carbon.

The present invention also provides compounds that in certain embodiments can be in methods for the modulation of CNS activity and/or a method for treatment of CNS disorders, including, but not limited to post-traumatic stress and adjustment disorders, comprising administering Formula C or Formula D or a pharmaceutically acceptable salt thereof:

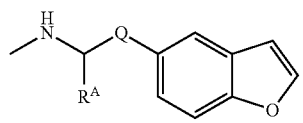

Formula C

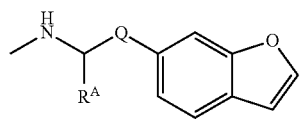

Formula D wherein $R^A$ is —$CH_3$, —$CH_2Y$, —$CHY_2$, —$CY_3$, —$CH_2CH_3$, —$CH_2CH_2Y$, —$CH_2CHY_2$, —$CH_2CY_3$, —$CH_2OH$, or —$CH_2CH_2OH$;

Q is selected from:

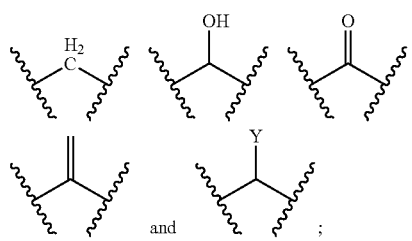

and

Y is halogen.

In one embodiment, compounds of Formula C and Formula D are halogenated, for example by having one or more halogens in place of one or more hydrogens on the alkyl group attached at the alpha carbon, e.g., as defined at position $R^A$ (e.g., halogenated alpha-ethyl or alpha-methyl compounds).

The present invention also provides compounds that can be used in a method for the modulation of CNS activity and/or a method for treatment of CNS disorders, including, but not limited to post-traumatic stress and adjustment disorders, comprising administering Formula E or Formula F or a pharmaceutically acceptable salt thereof:

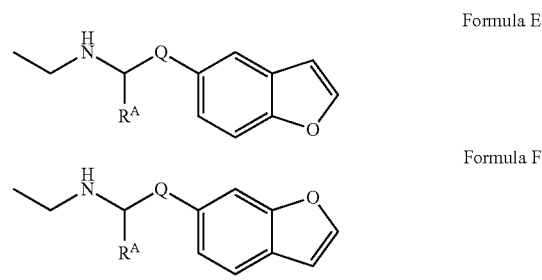

Formula E

Formula F wherein $R^A$ is —$CH_3$, —$CH_2Y$, —$CHY_2$, —$CY_3$, —$CH_2CH_3$, —$CH_2CH_2Y$, —$CH_2CHY_2$, —$CH_2CY_3$, —$CH_2OH$, or —$CH_2CH_2OH$;

Q is selected from:

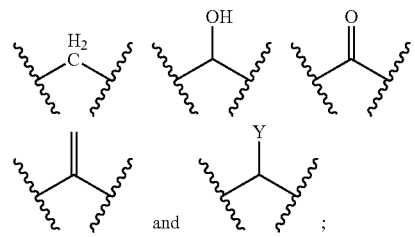

and

Y is halogen.

In one embodiment, compounds of Formula E and Formula F are halogenated, for example by having one or more halogens in place of one or more hydrogens on the alkyl group attached at the alpha carbon, e.g., as defined at position $R^A$ (e.g., halogenated alpha-ethyl or alpha-methyl compounds).

The present invention also provides enantiomerically enriched compounds Bk-5-MAPB and Bk-6-MAPB or a pharmaceutically acceptable salt or mixed salt thereof:

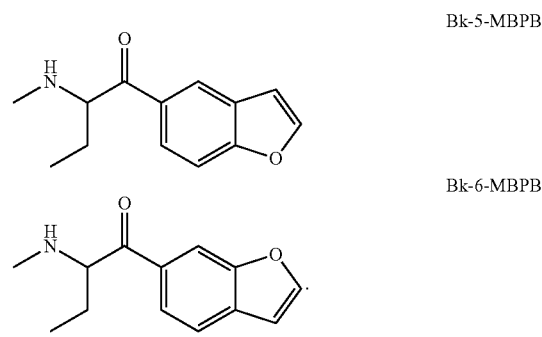

Bk-5-MBPB

Bk-6-MBPB

In some embodiments, disclosed are 1-(benzofuran-5-yl)-2-(ethylamino)-1-propanone and 1-(benzofuran-6-yl)-2-(ethylamino)-1-propanone.

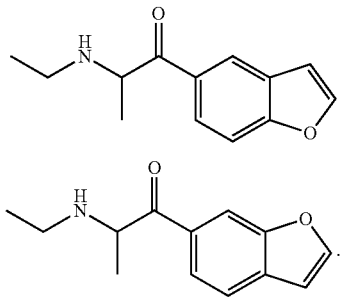

The compounds may be provided in a composition that is enantiomerically enriched, such as a mixture of enantiomers in which one enantiomer is present in excess, in particular to the extent of 60% or more, 70% or more, 75% or more, 80% or more, 90% or more, 95% or more, or 98% or more, including 100%.

In certain embodiments, the compound of the present invention is selected from:

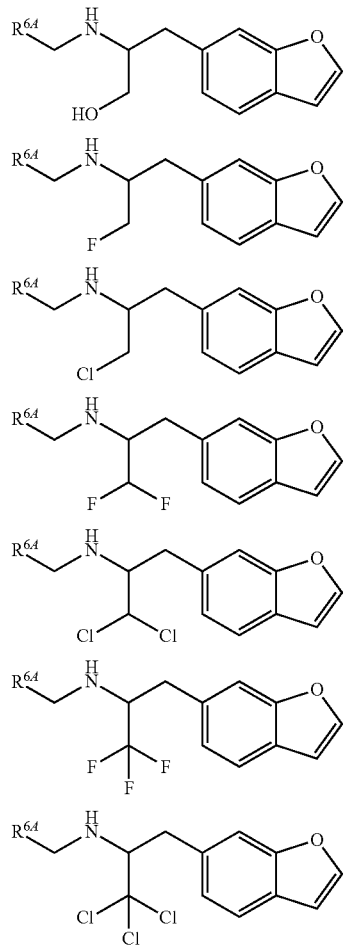

-continued

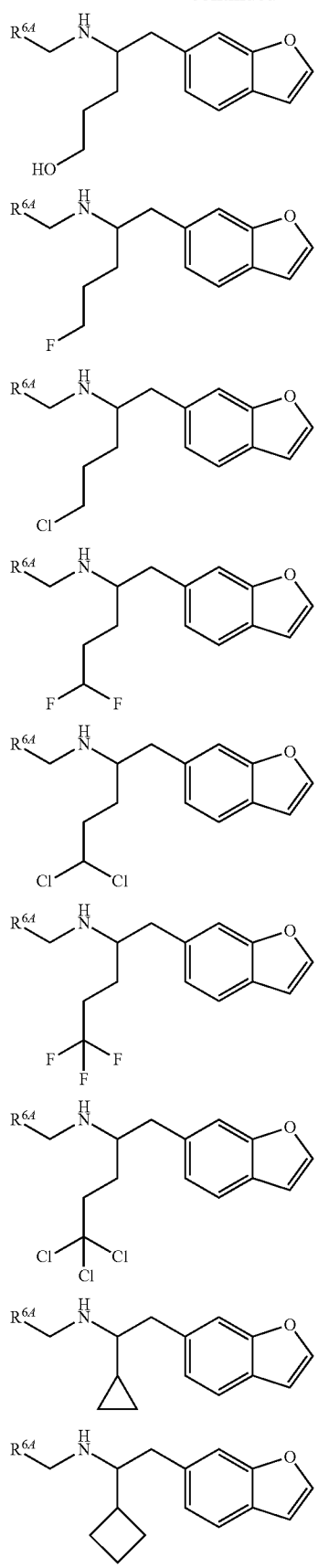

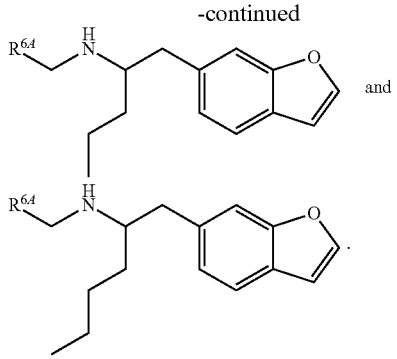
In certain embodiments, the compound of the present invention is selected from:
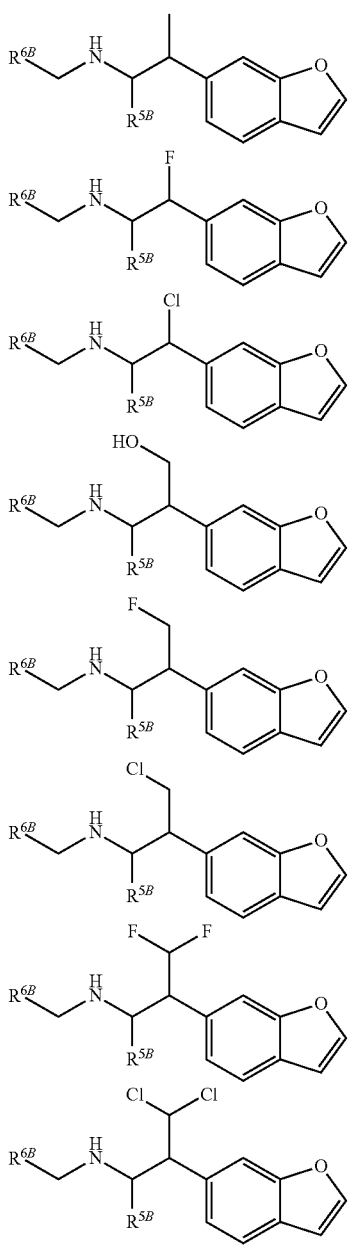
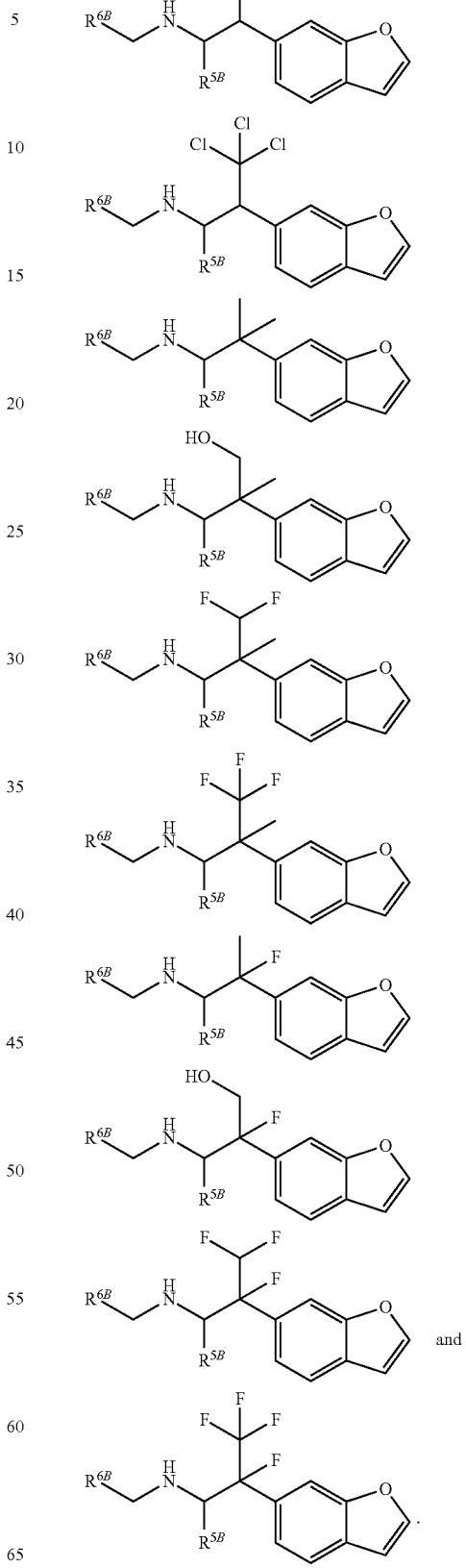

In certain embodiments, the compound of the present invention is selected from:
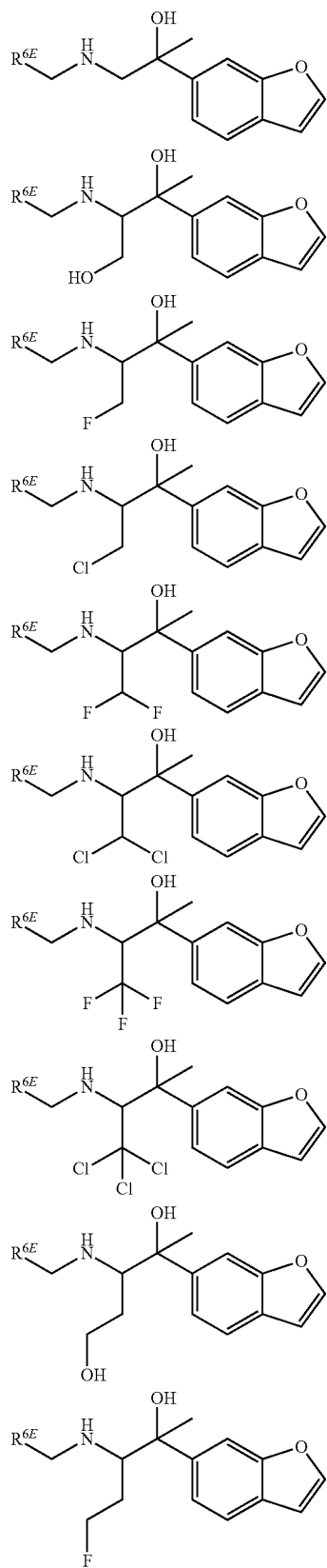
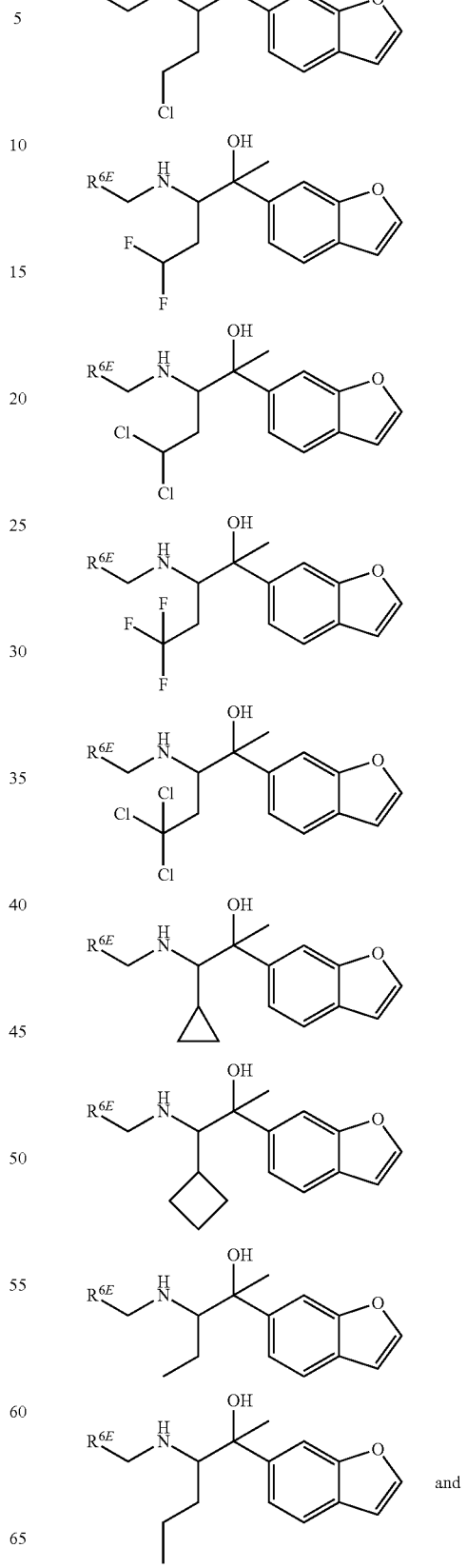

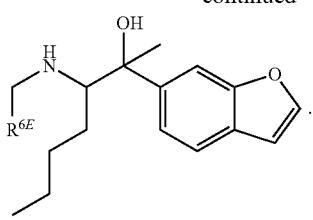
In certain embodiments, the compound of the present invention is selected from:
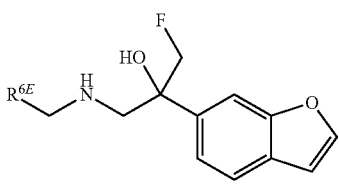
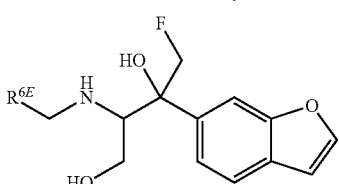
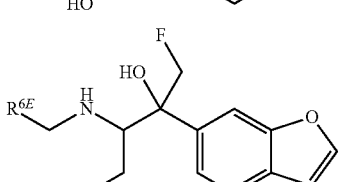
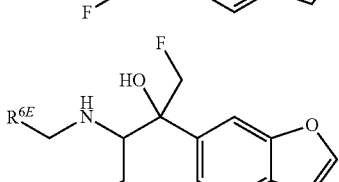
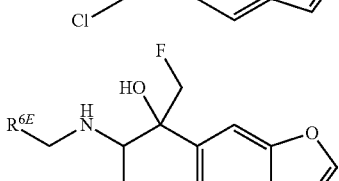
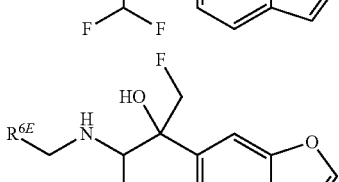
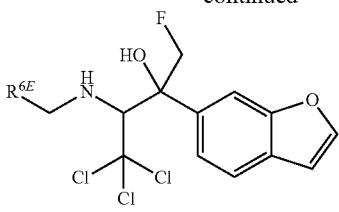
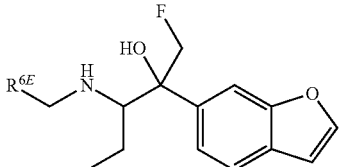
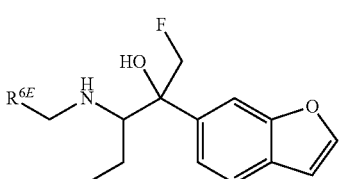
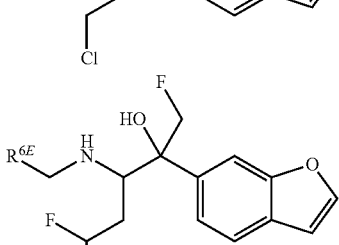
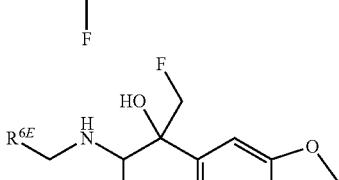
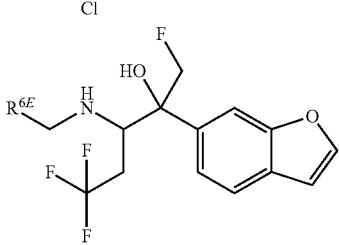

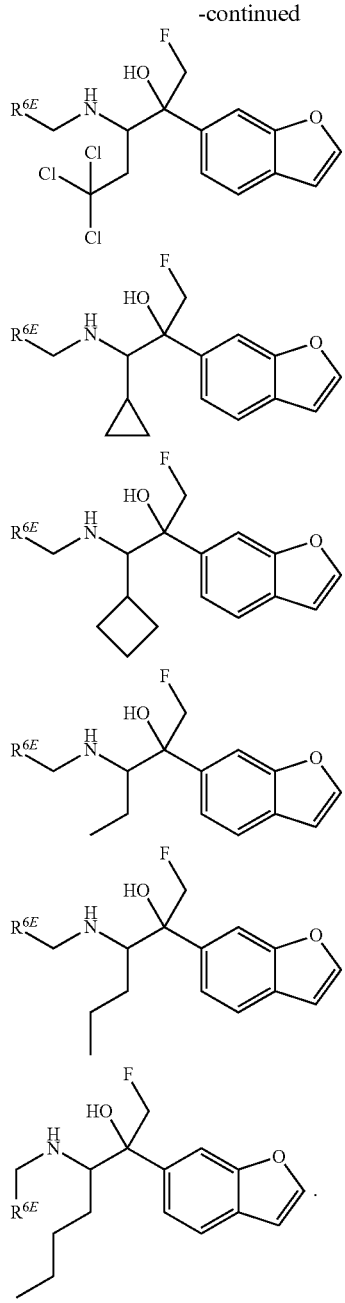
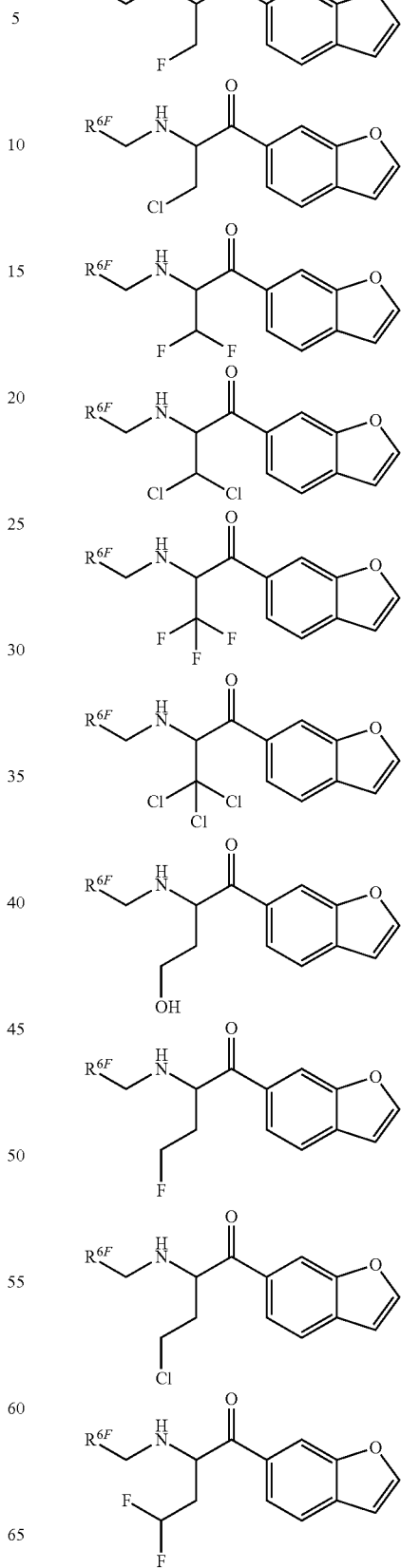
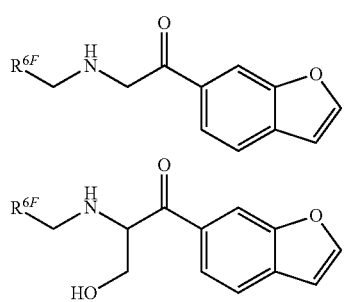
In certain embodiments, the compound of the present invention is selected from:

-continued
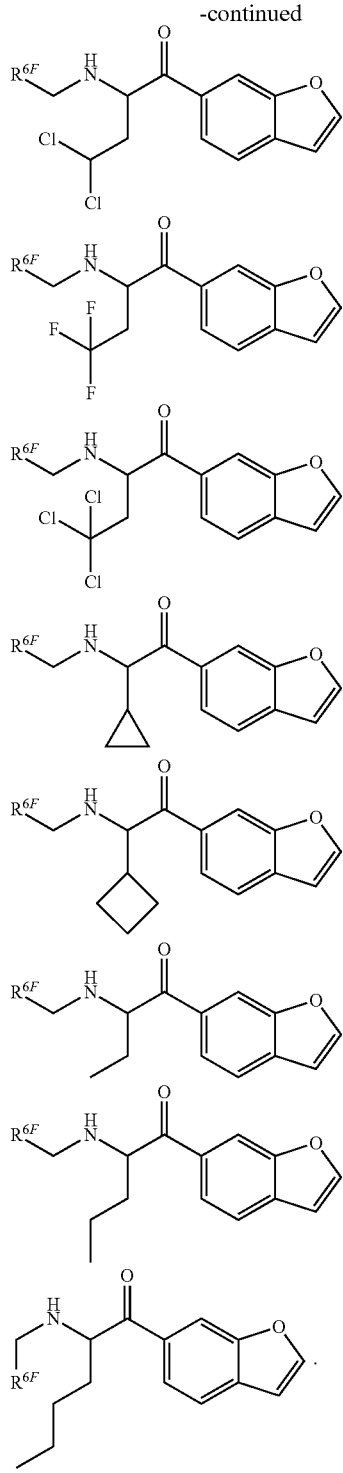
In certain embodiments, the compound of the present invention is selected from:
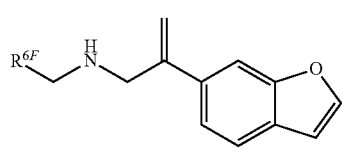
-continued
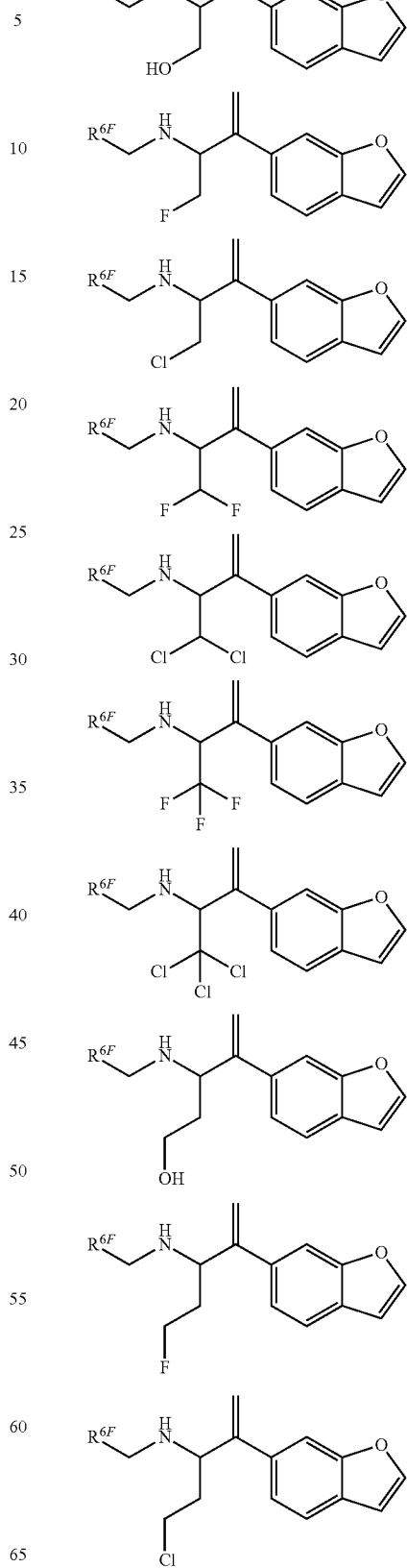

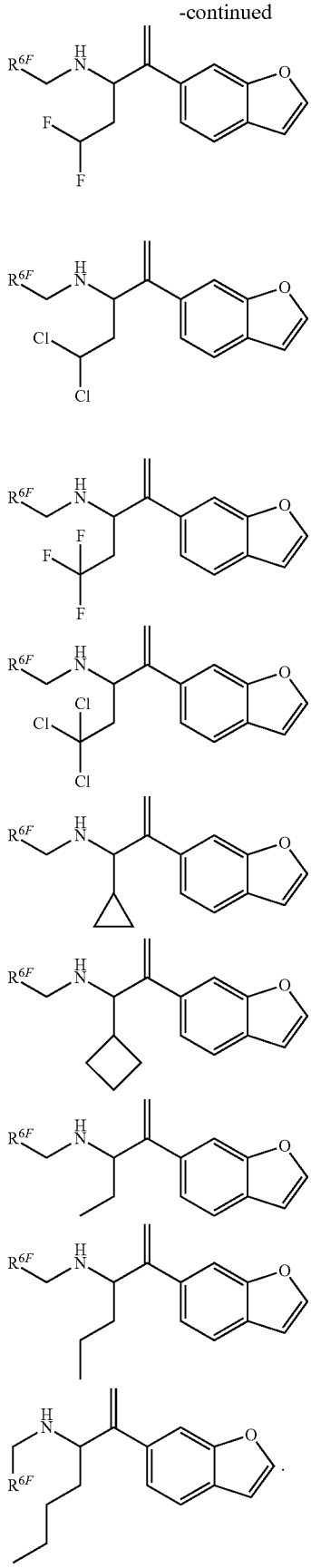
In certain embodiments, the compound of the present invention is selected from:
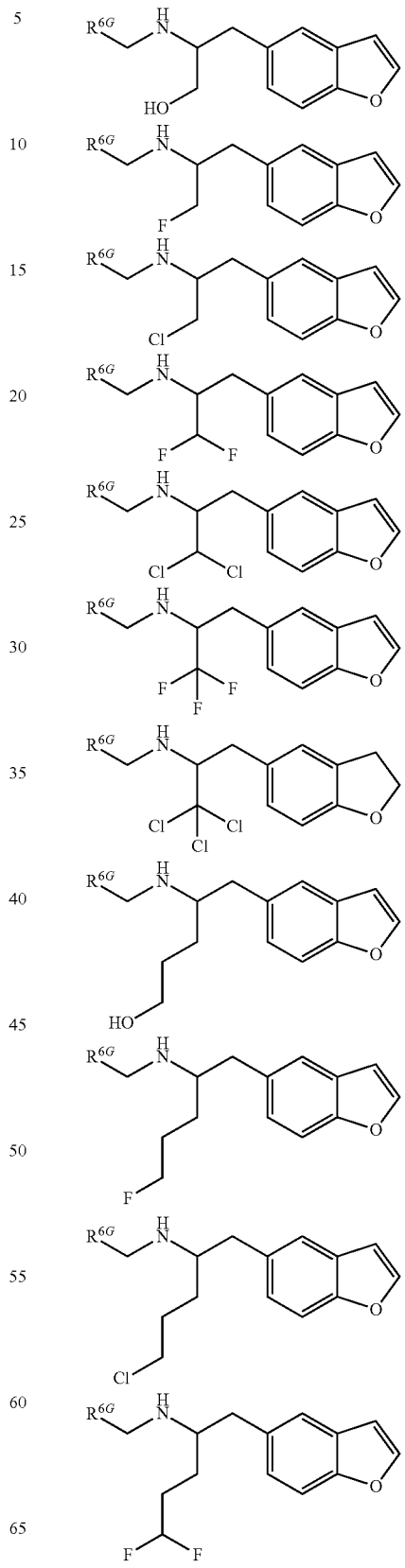

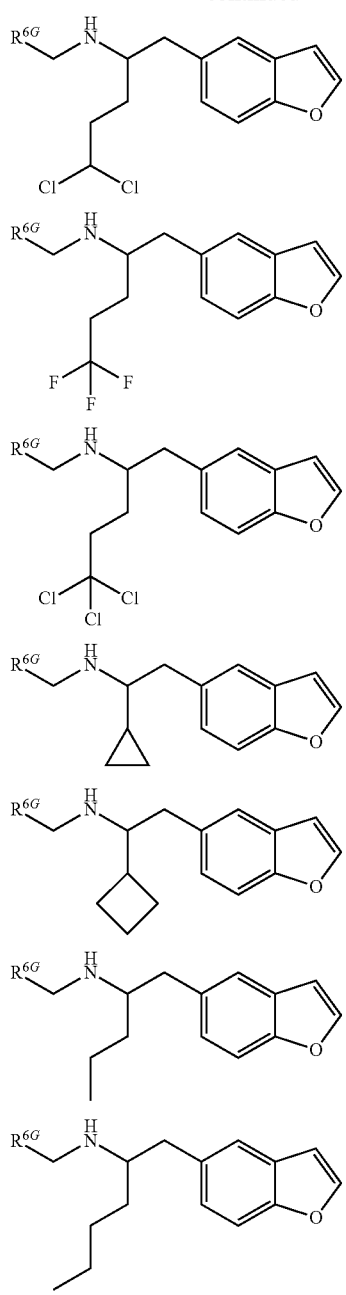
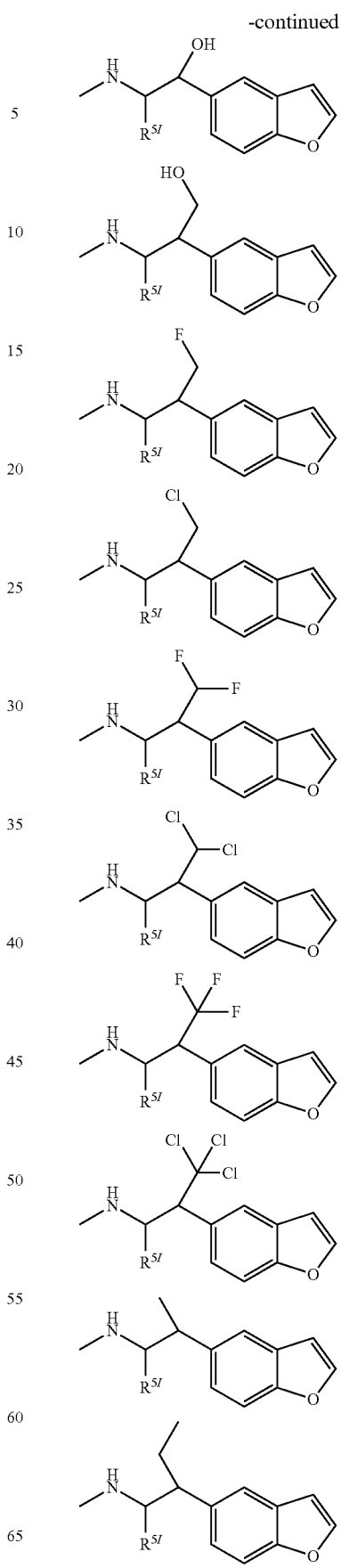
In certain embodiments, the compound of the present invention is selected from:
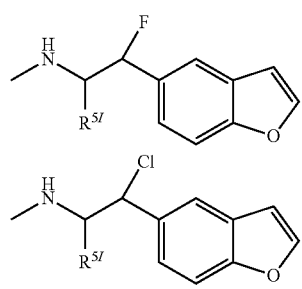

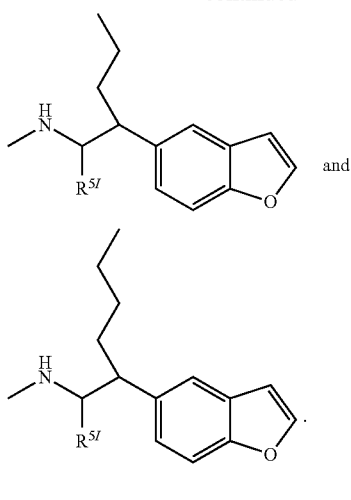
In certain embodiments, the compound of the present invention is selected from:
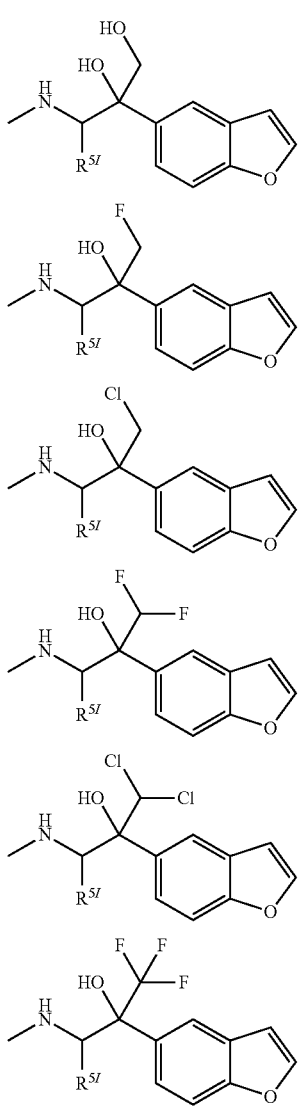
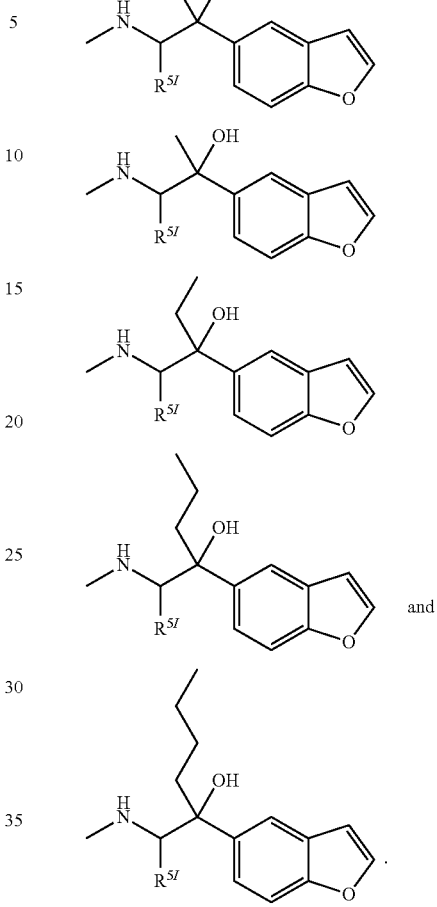
In certain embodiments, the compound of the present invention is selected from:
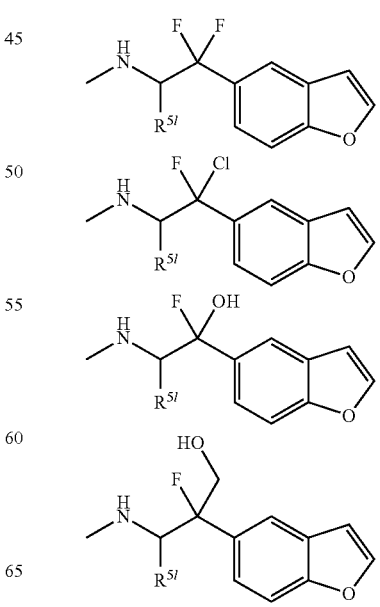

-continued
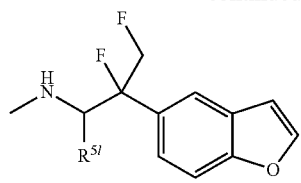
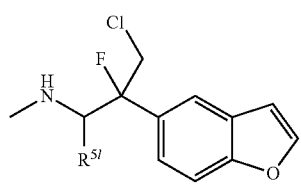
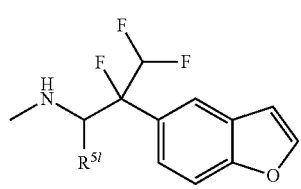
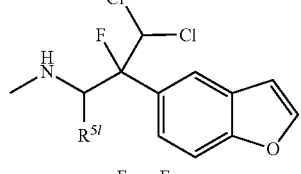
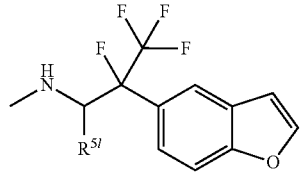
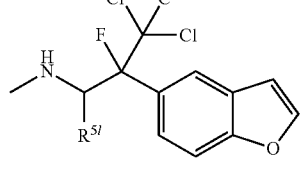
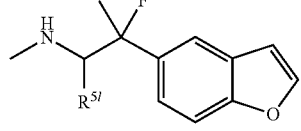
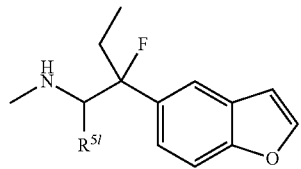
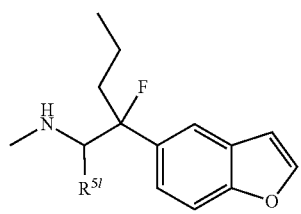 and
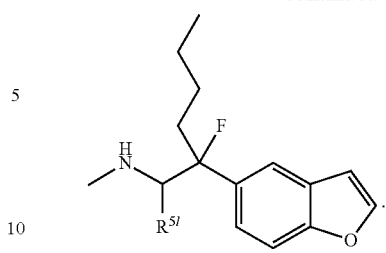
In certain embodiments, the compound of the present invention is selected from:
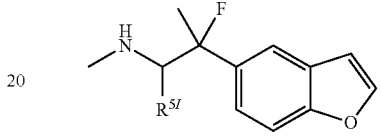
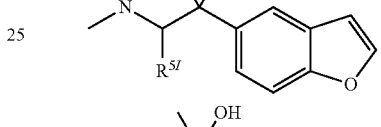
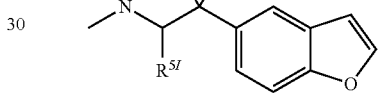
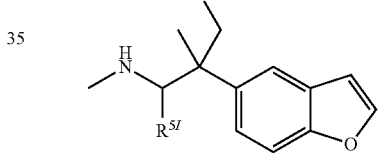
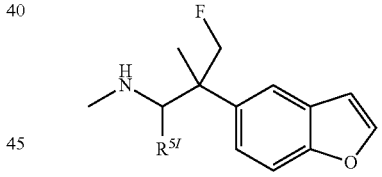
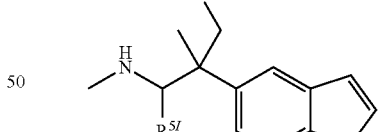
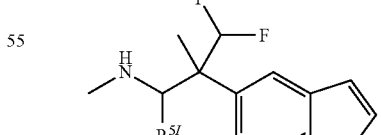
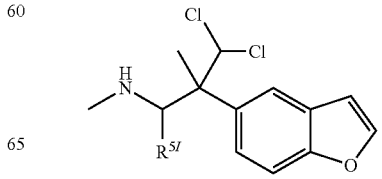

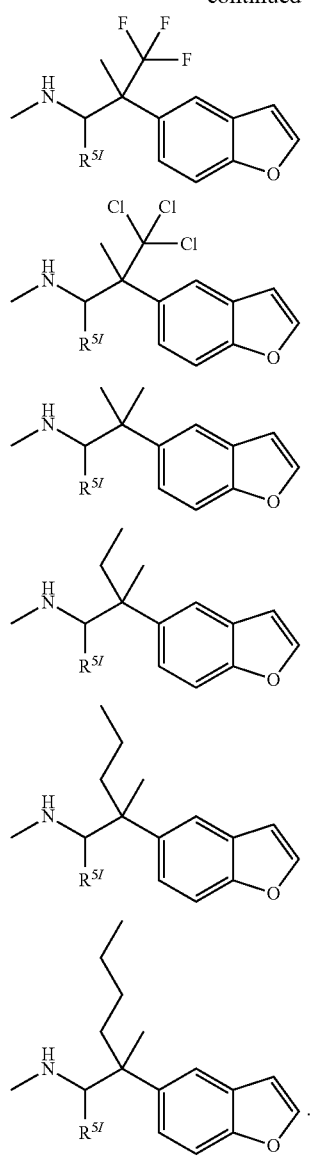
In certain embodiments, the compound of the present invention is selected from:
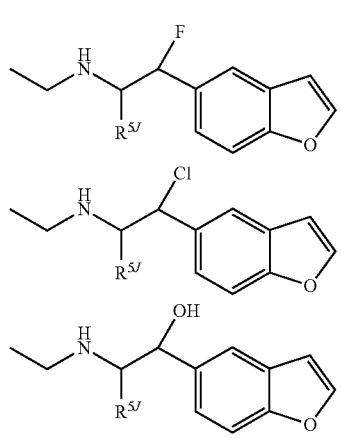
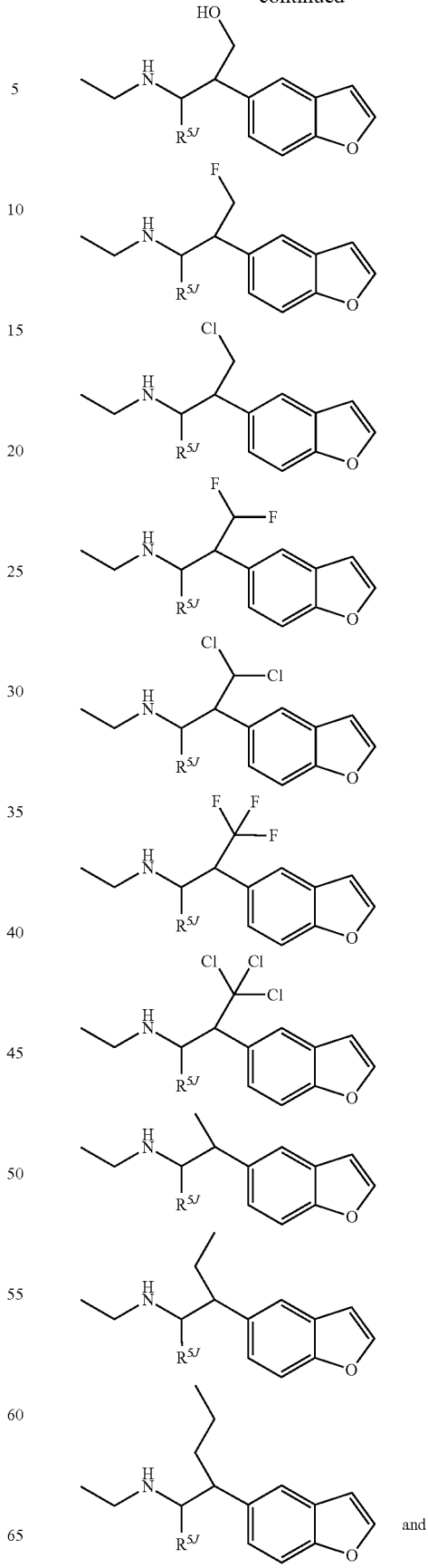
and -continued
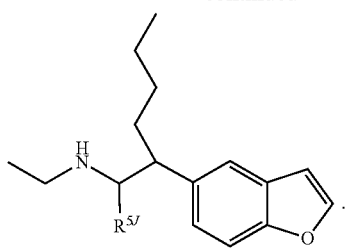
In certain embodiments, the compound of the present invention is selected from:
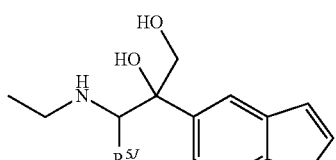
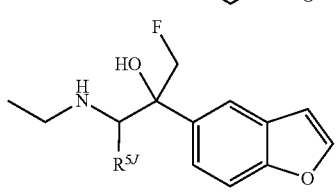
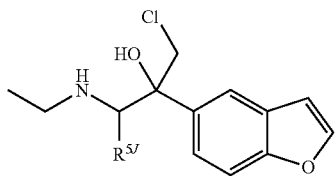
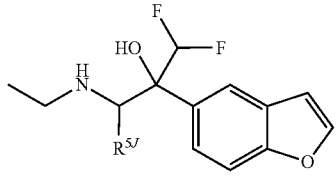
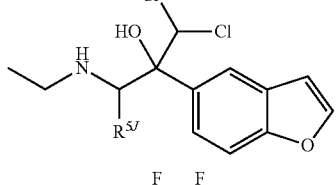
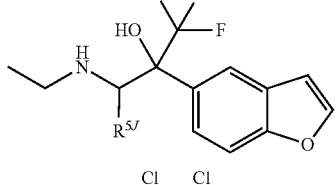
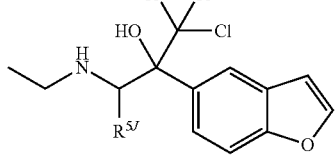
-continued
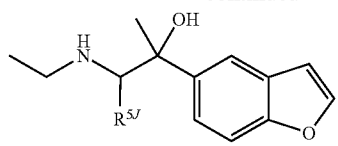
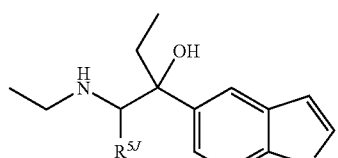
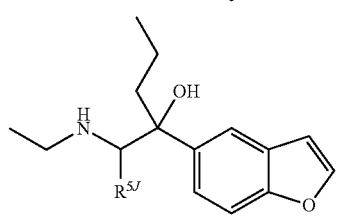
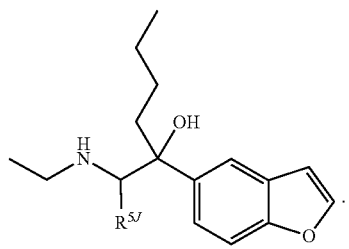
and
In certain embodiments, the compound of the present invention is selected from:
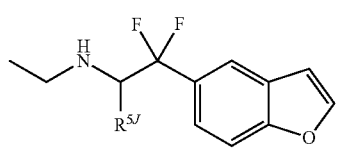
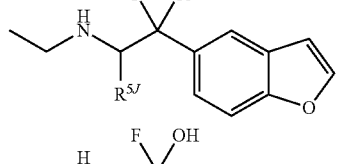
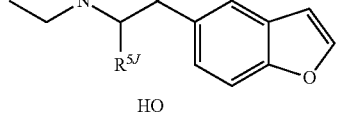
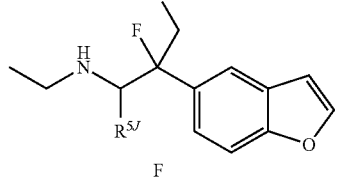
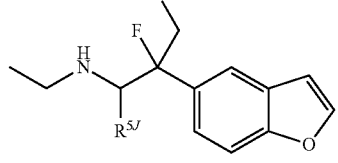

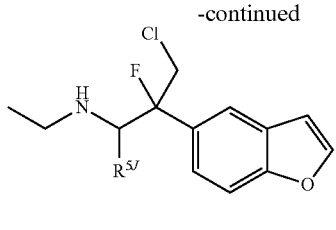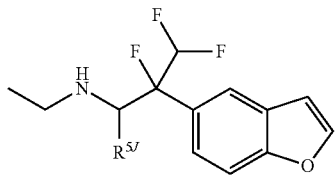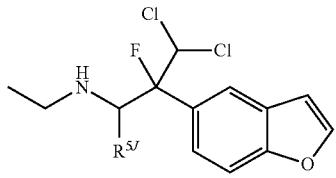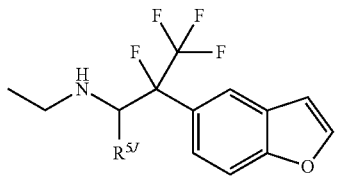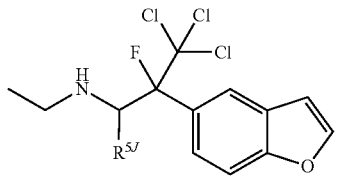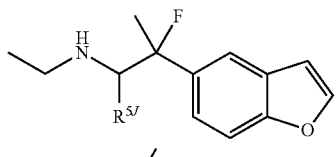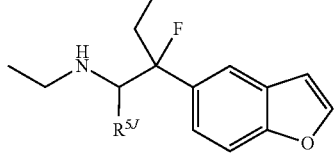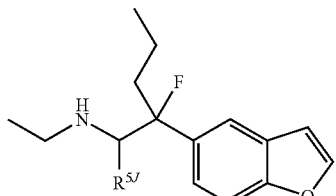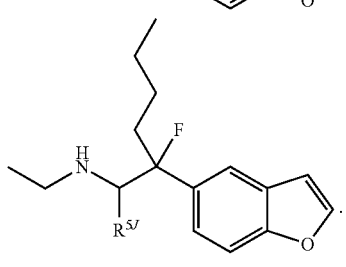
In certain embodiments, the compound of the present invention is selected from:
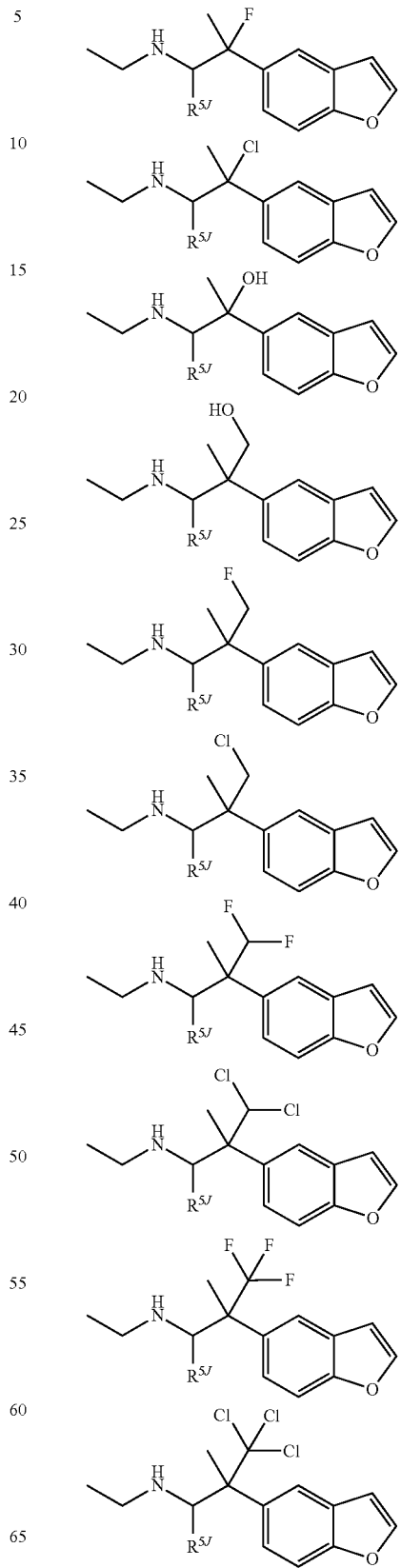

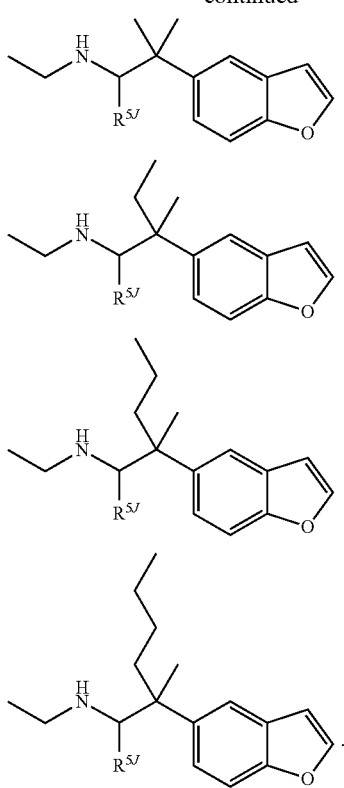
In certain embodiments, the compound of the present invention is selected from:
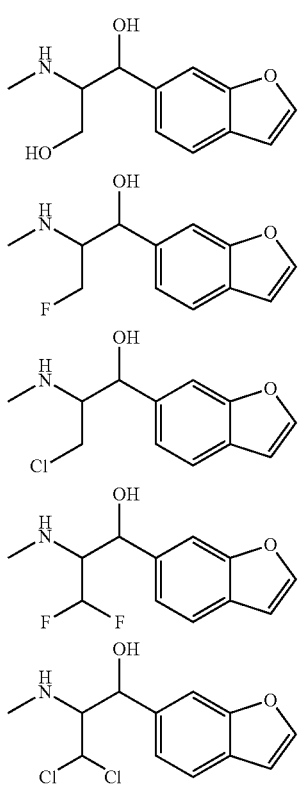
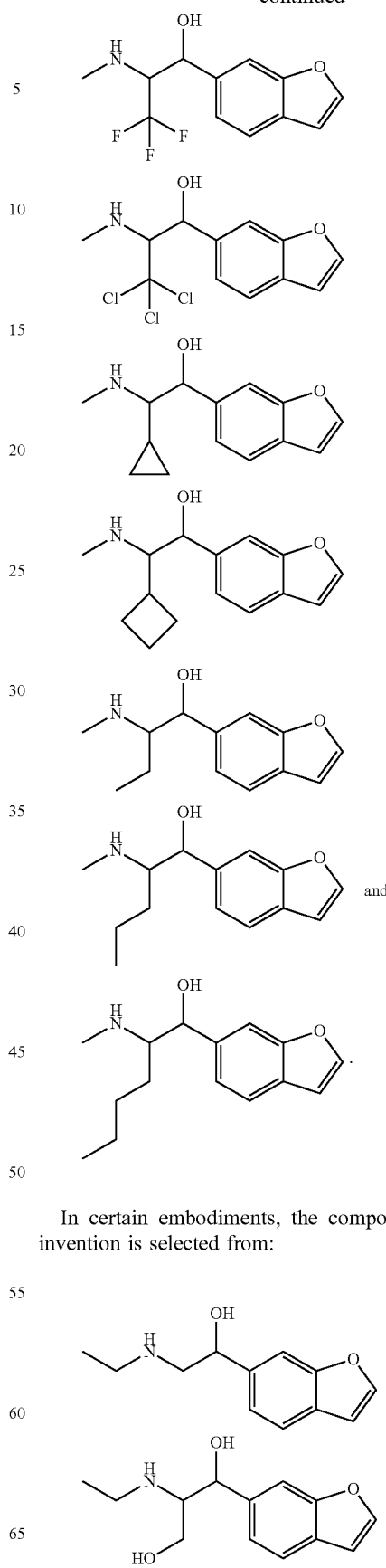
In certain embodiments, the compound of the present invention is selected from:
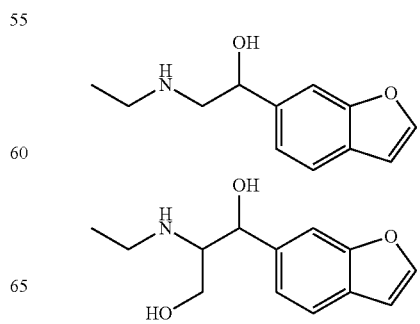

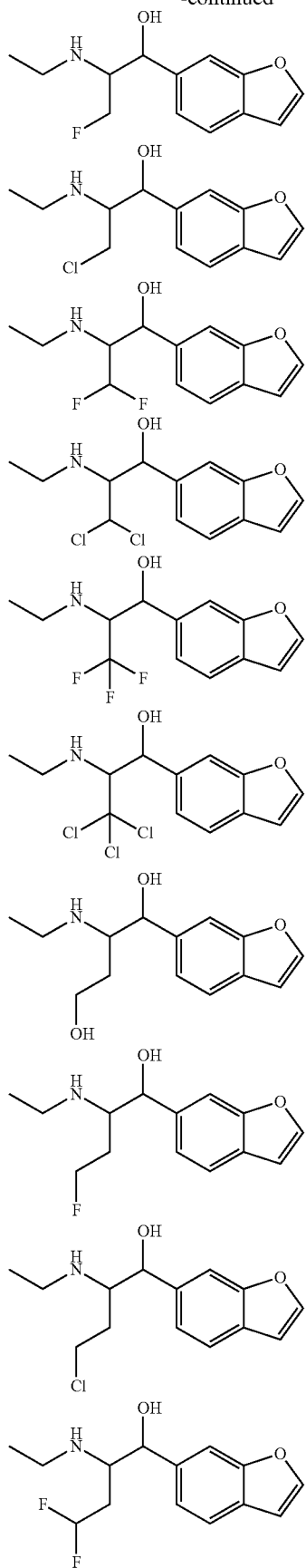
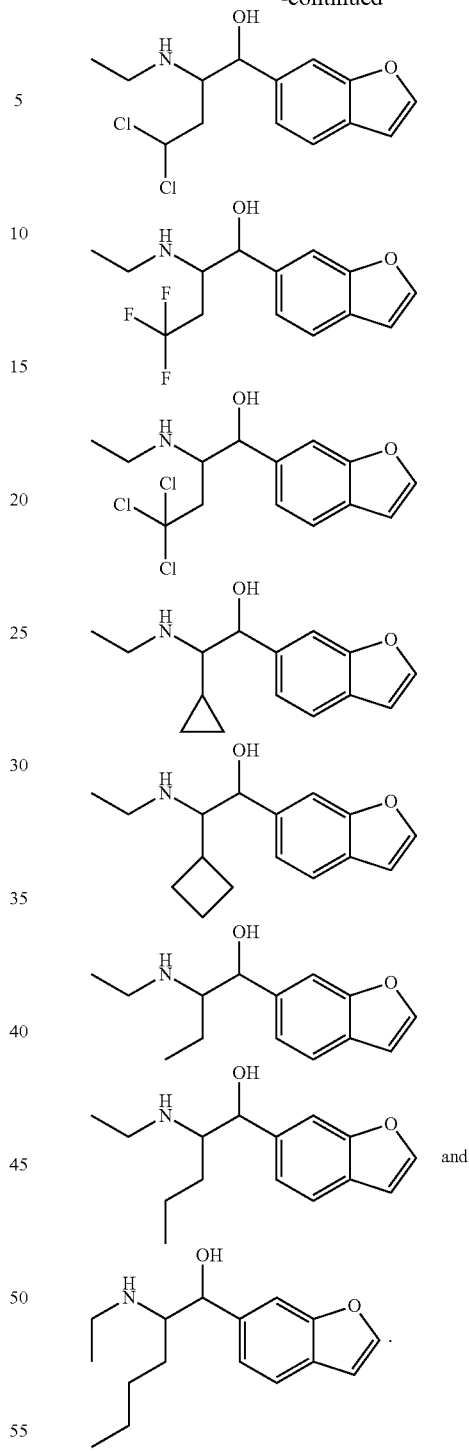
In certain embodiments, the compound of the present invention is selected from:
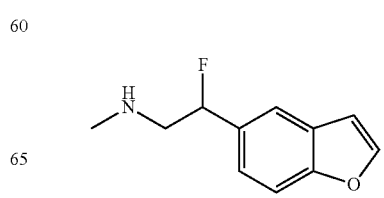

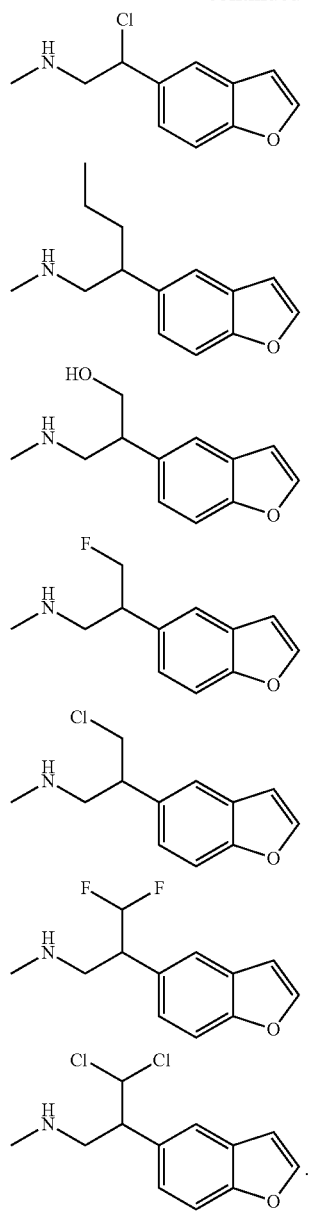
In certain embodiments, the compound of the present invention is selected from:
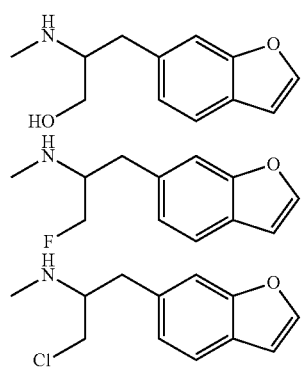
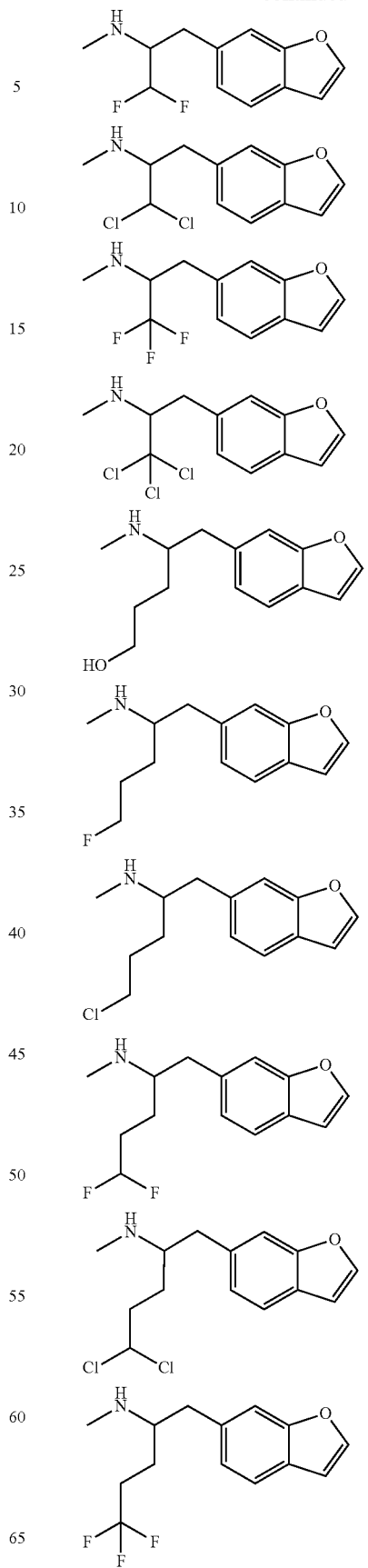

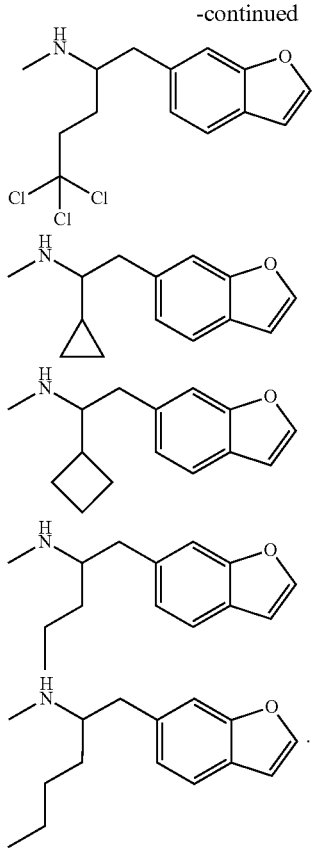
In certain embodiments, the compound of the present invention is selected from:
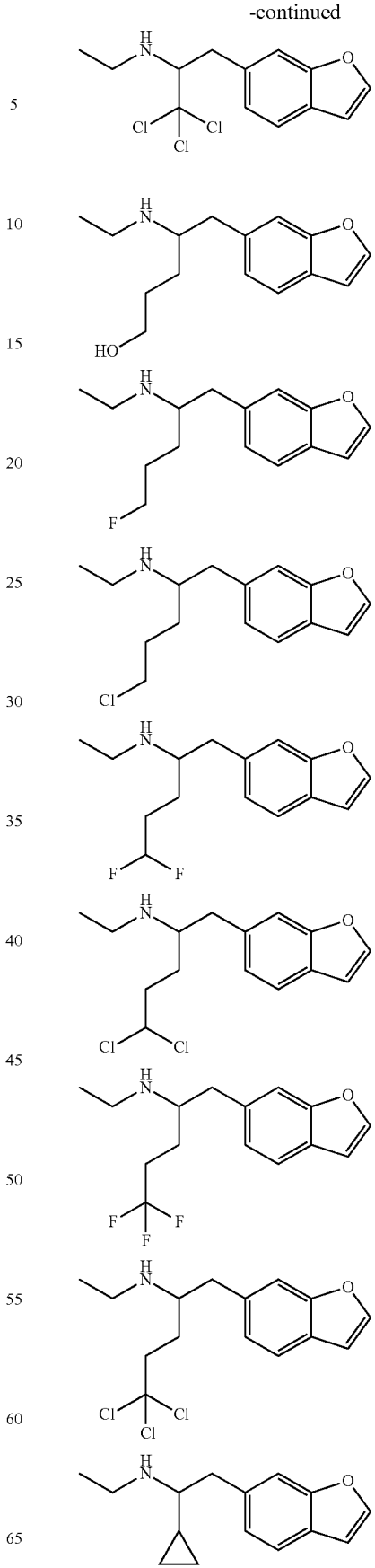

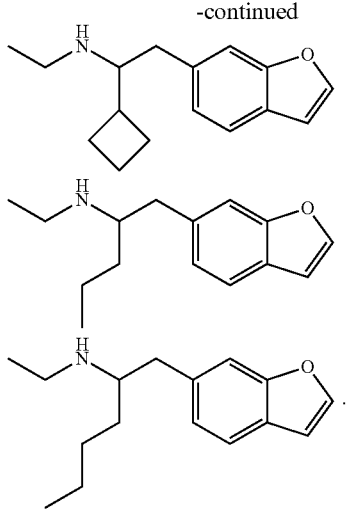

In certain embodiments, the compound of the present invention is selected from:
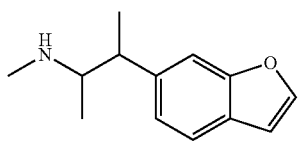
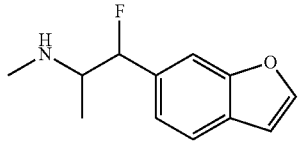
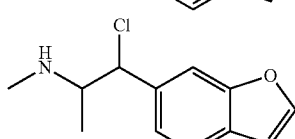
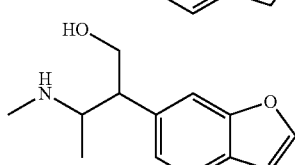
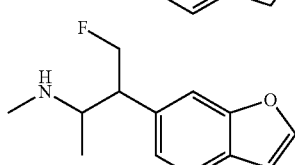
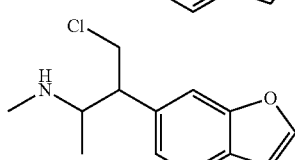
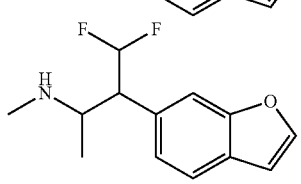
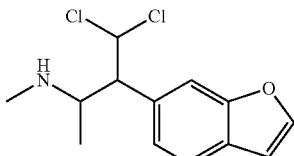
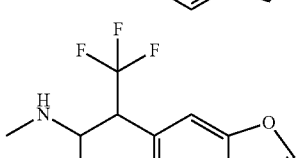
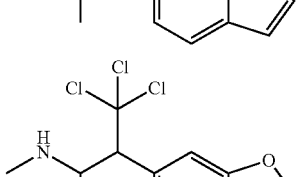
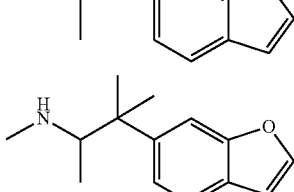
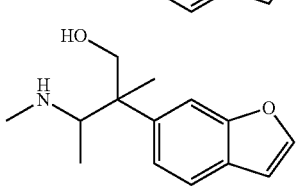
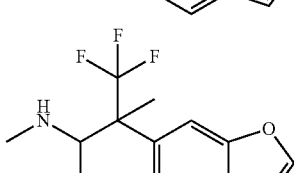
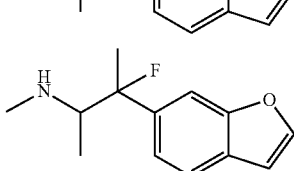
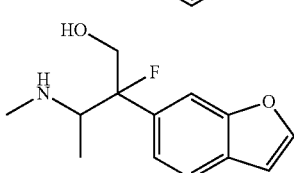
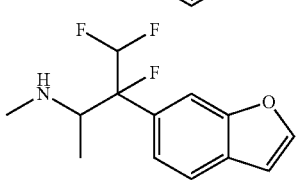
and

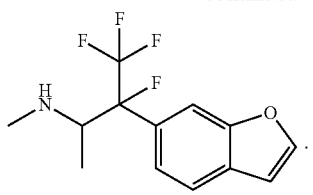
In certain embodiments, the compound of the present invention is selected from:
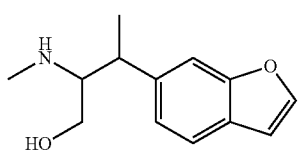
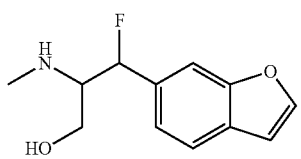
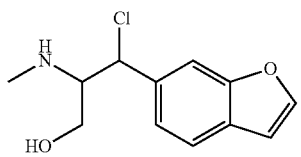
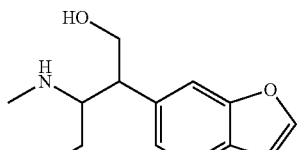
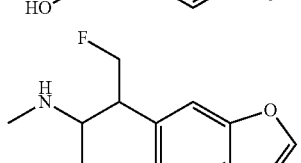
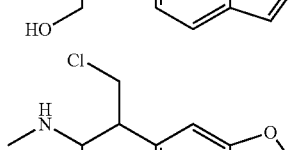
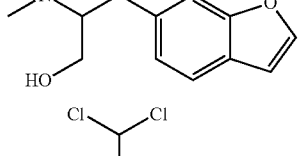
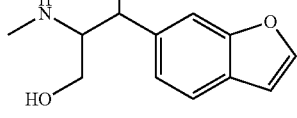
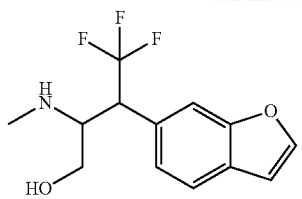
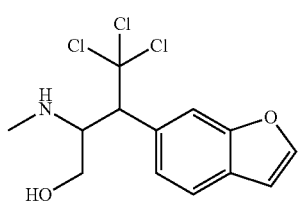
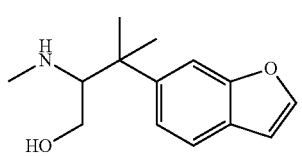
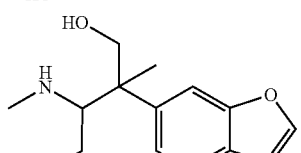
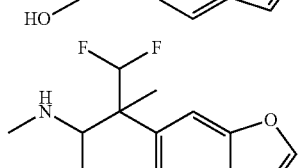
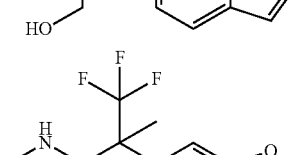
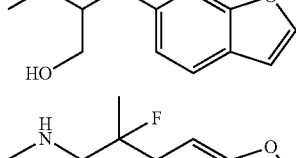
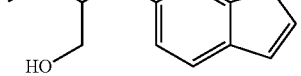
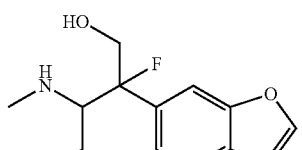
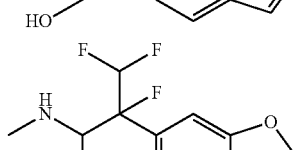
and -continued
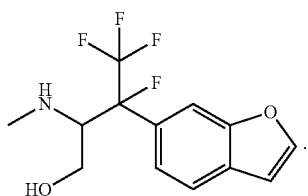
In certain embodiments, the compound of the present invention is selected from:
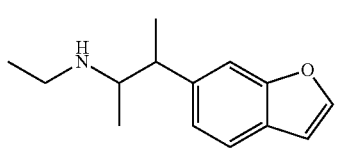
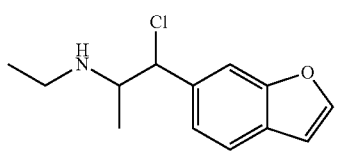
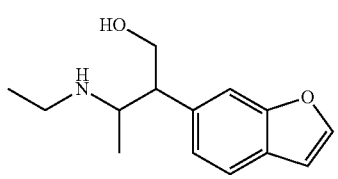
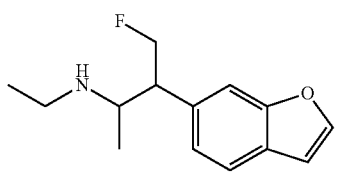
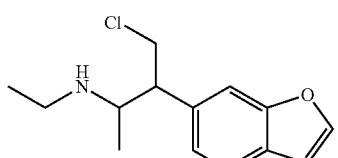
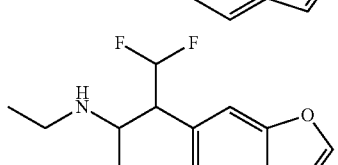
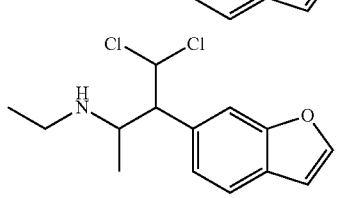
-continued
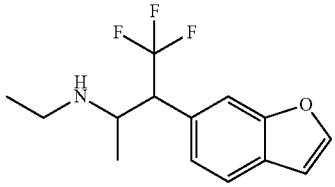
and In certain embodiments, the compound of the present invention is selected from:
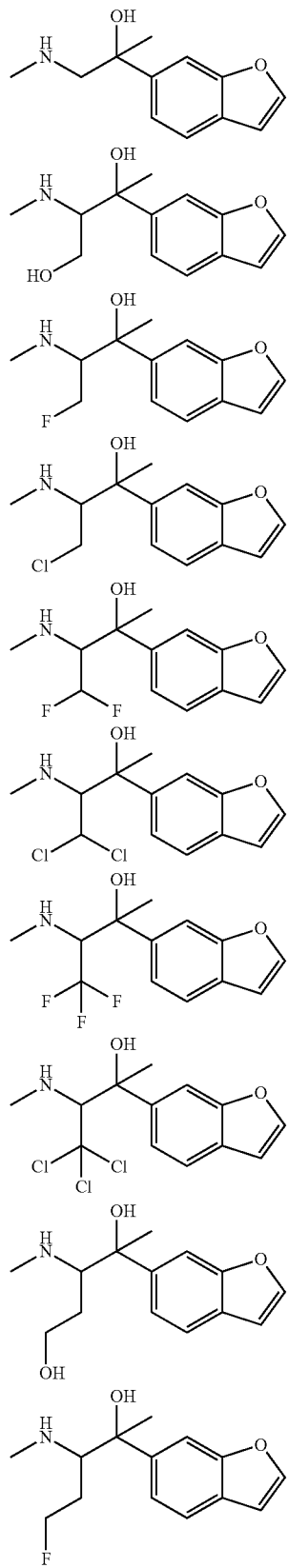
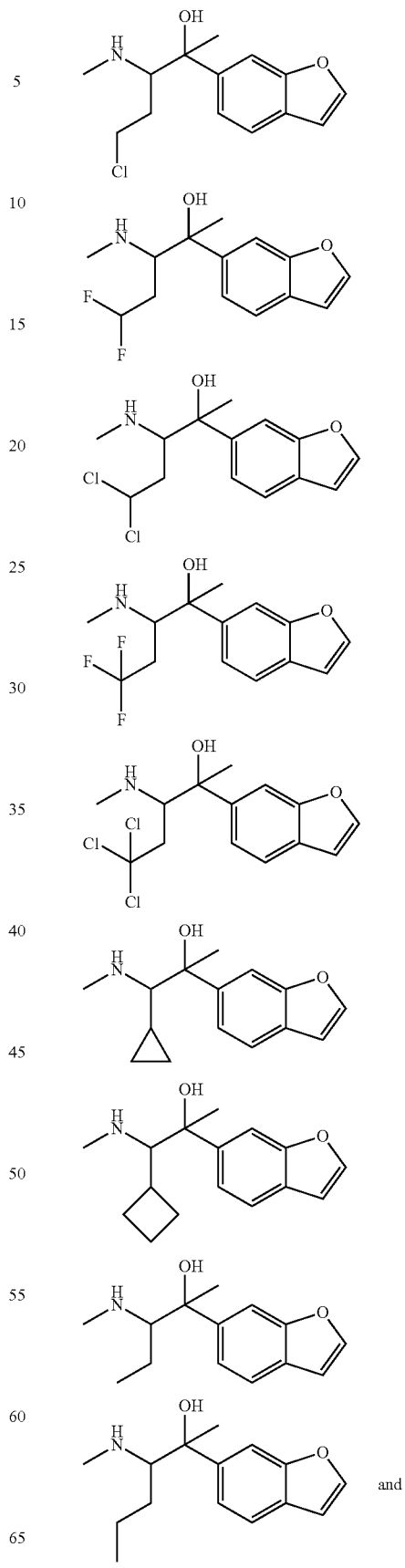
and

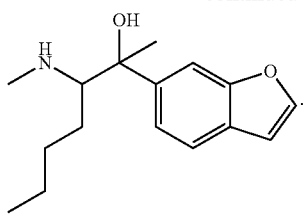
In certain embodiments, the compound of the present invention is selected from:
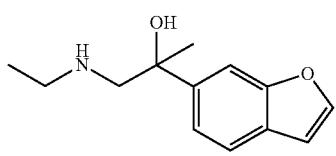
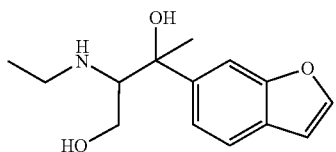
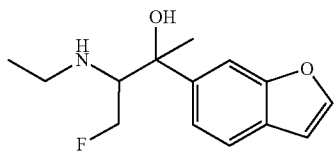
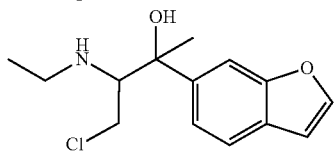
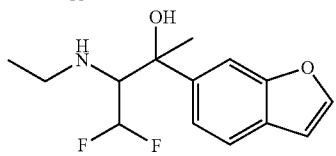
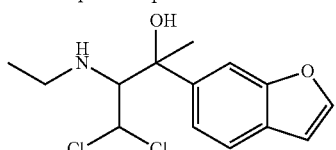
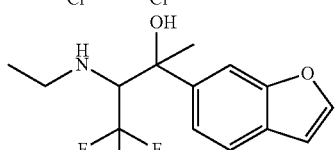
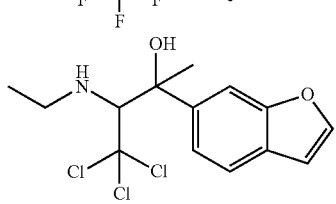
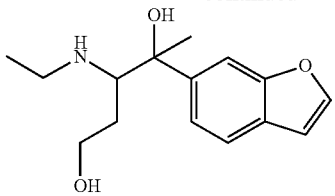
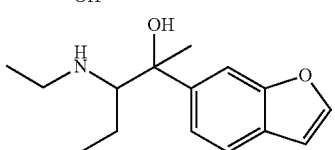
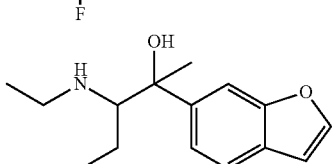
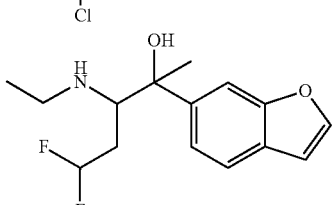
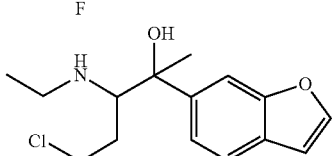
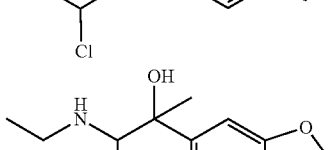
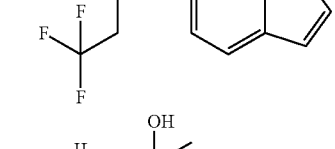
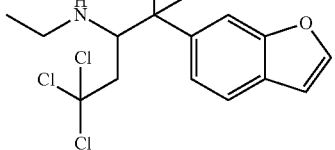
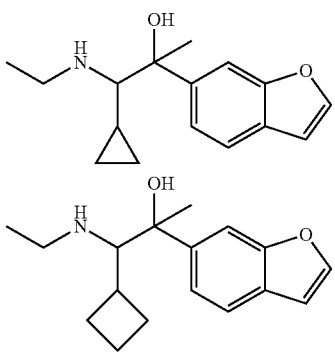

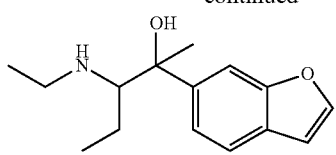
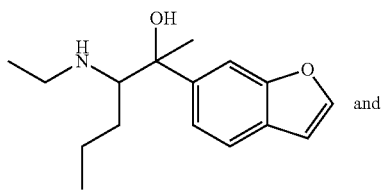
and
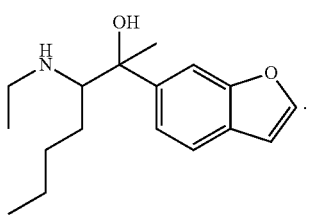
In certain embodiments, the compound of the present invention is selected from:
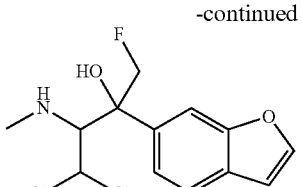
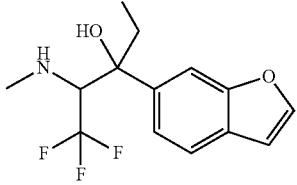
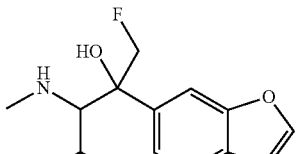
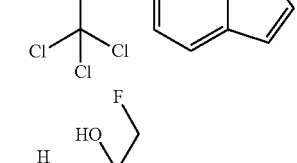
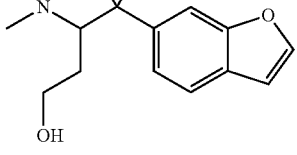
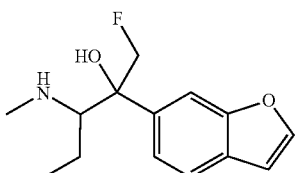
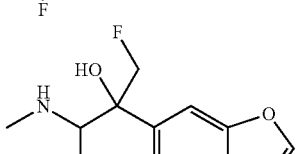
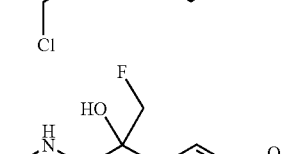
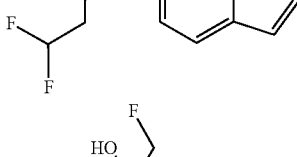

-continued
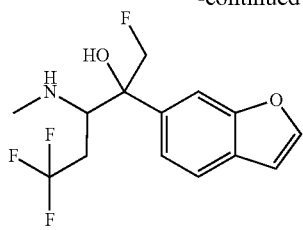
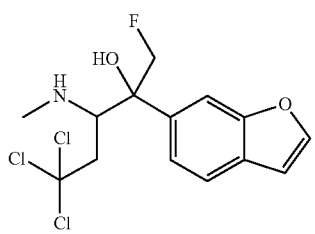
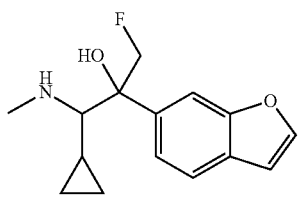
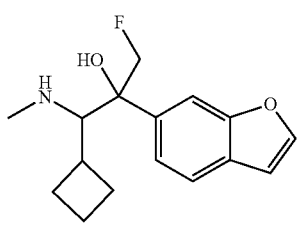
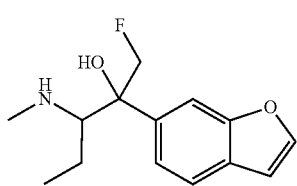
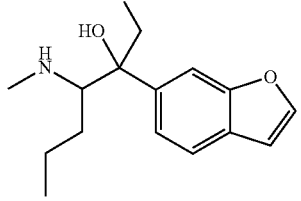
and
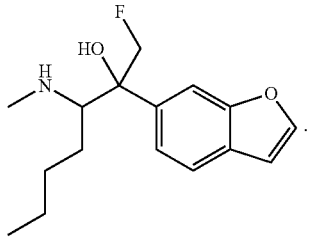
In certain embodiments, the compound of the present invention is selected from:
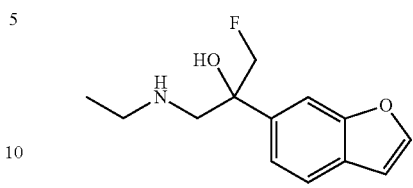
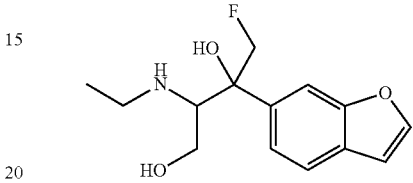
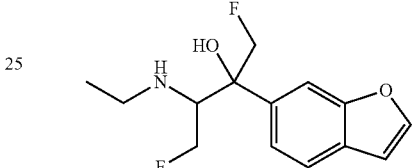
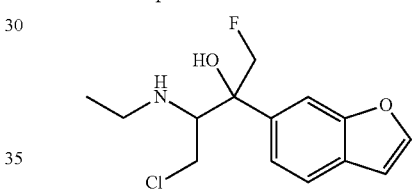
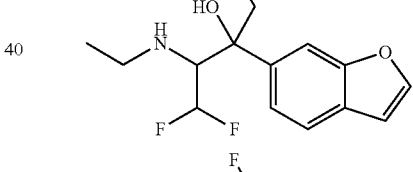
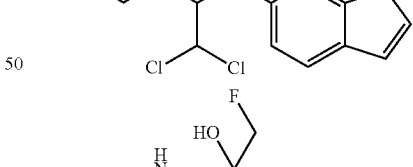
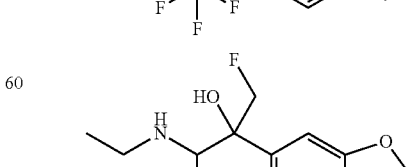

-continued
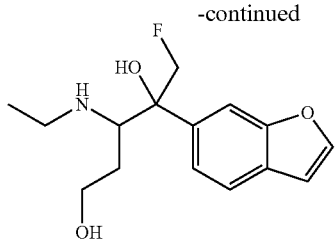
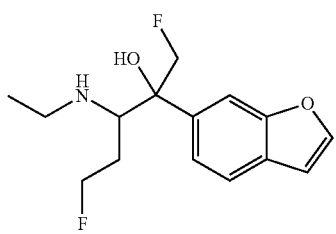
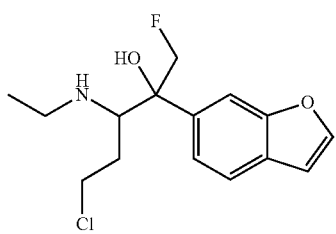
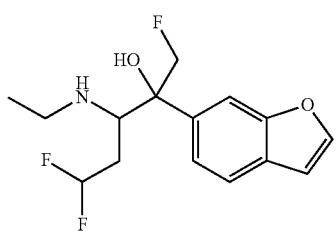
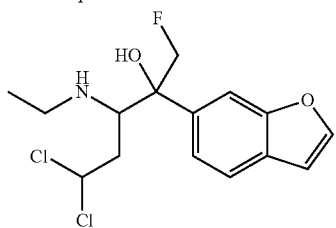
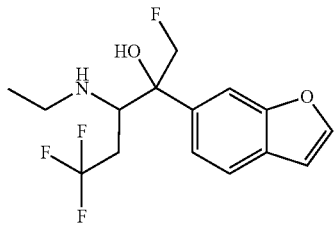
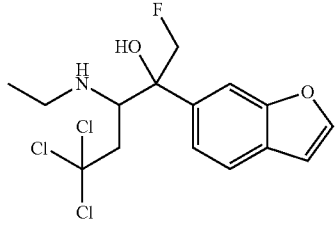
-continued
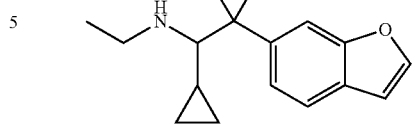
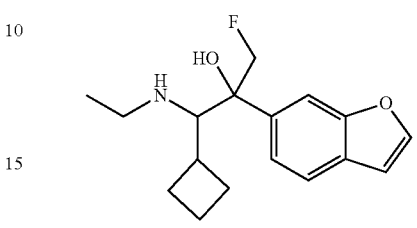
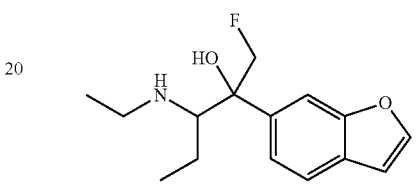
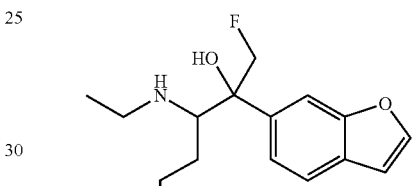
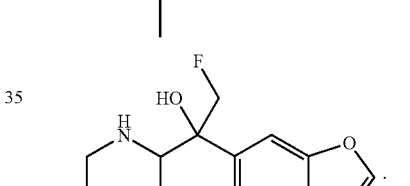
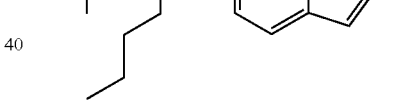 and
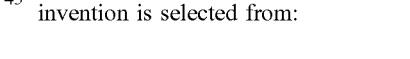.
In certain embodiments, the compound of the present invention is selected from:
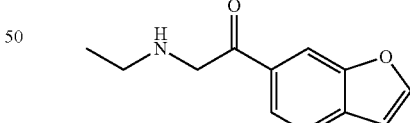
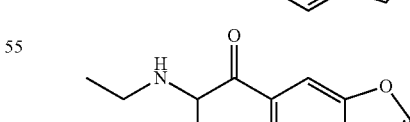
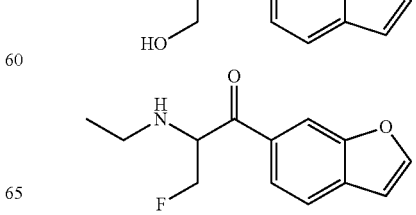

-continued
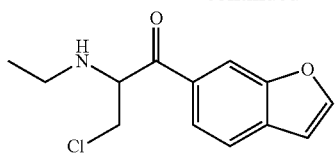
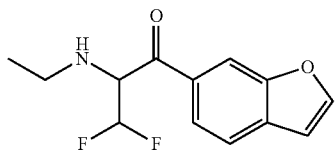
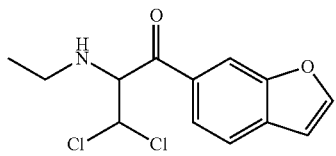
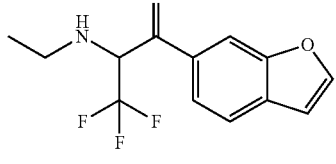
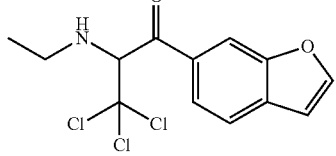
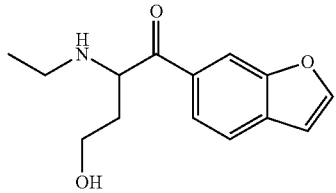
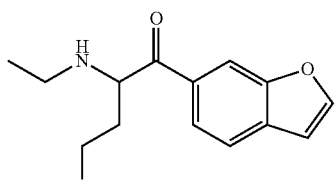
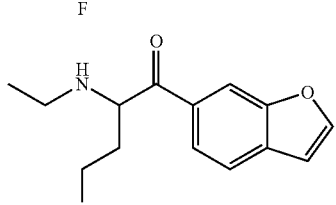
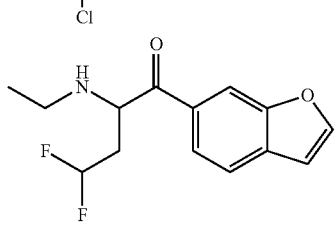
-continued
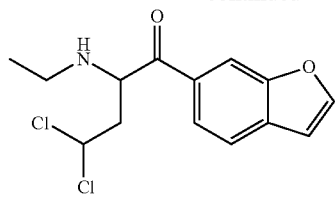
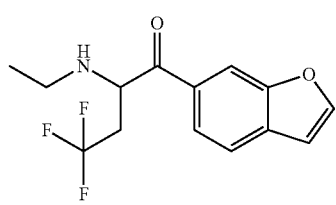
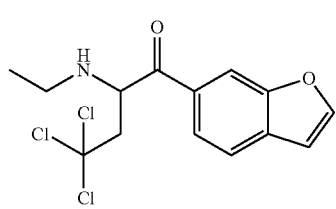
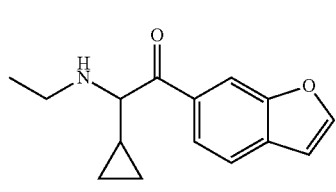
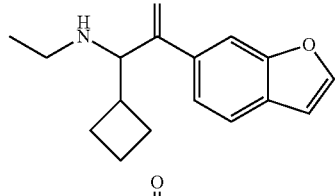
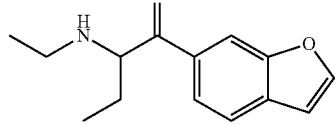
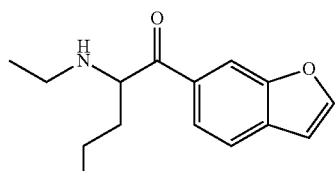 and
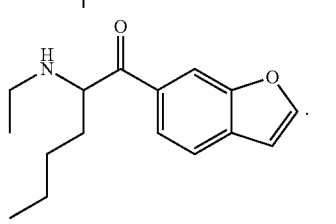

In certain embodiments, the compound of the present invention is selected from:
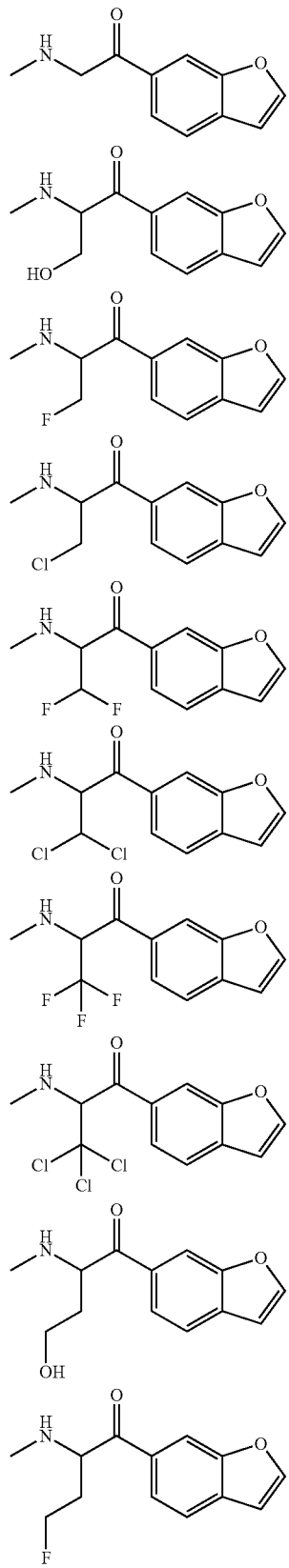
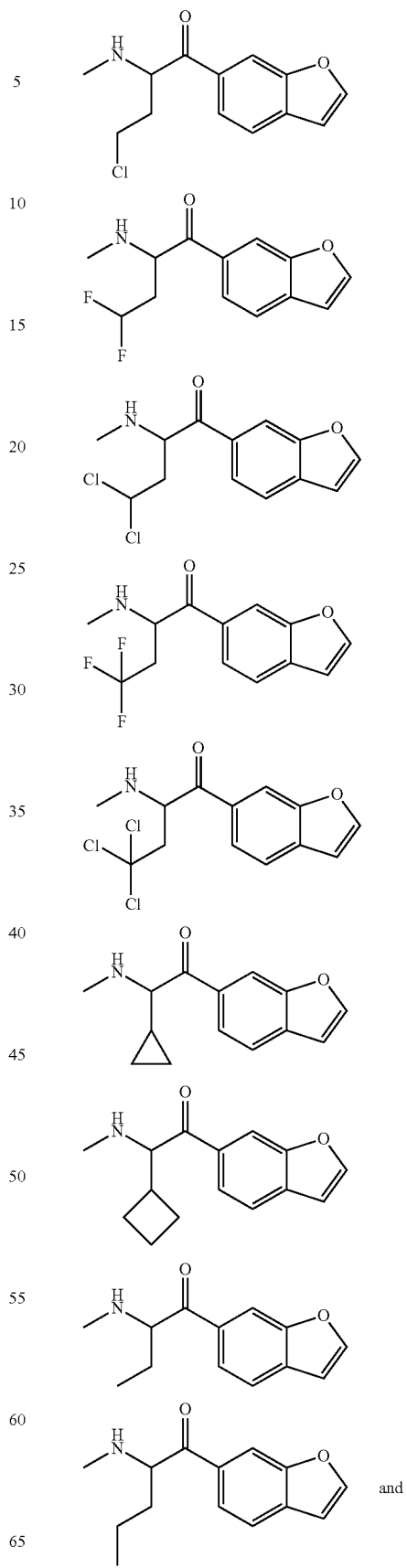
and

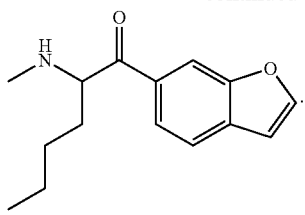
In certain embodiments, the compound of the present invention is selected from:
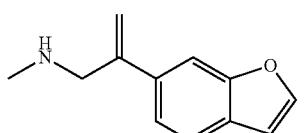
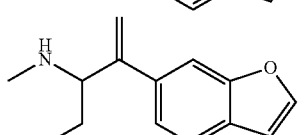
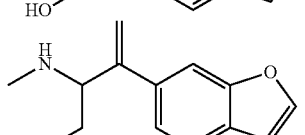
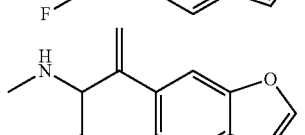
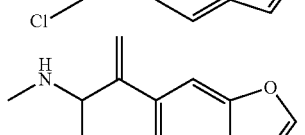
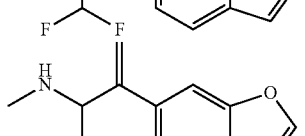
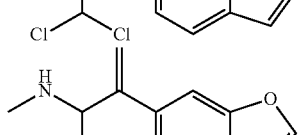
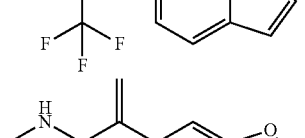
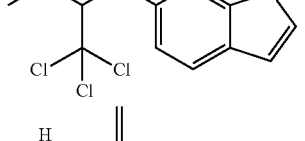
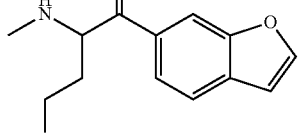
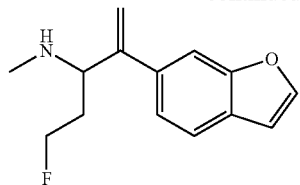
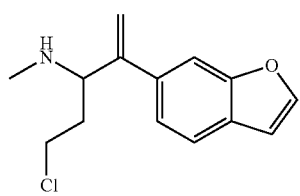
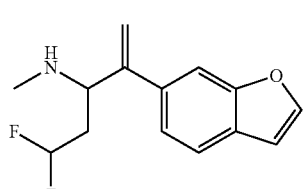
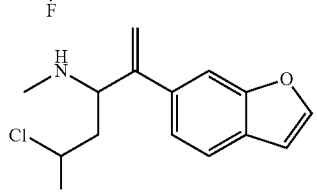
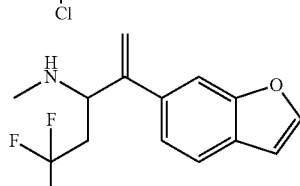
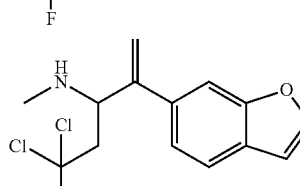
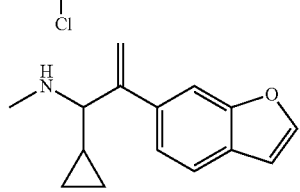
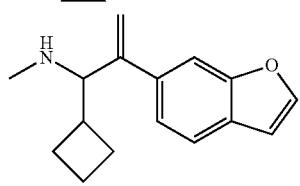
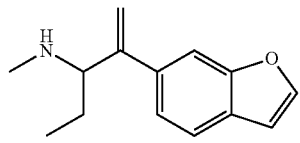

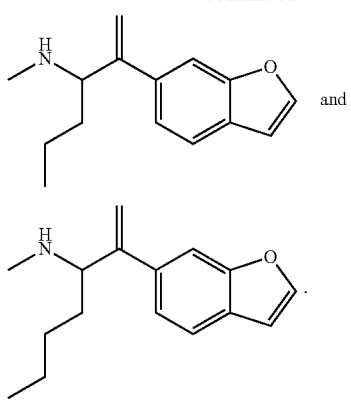
In certain embodiments, the compound of the present invention is selected from:
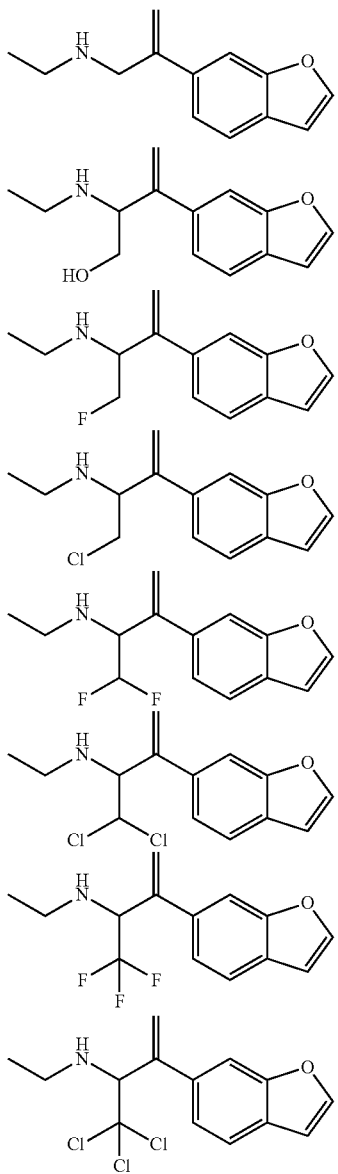
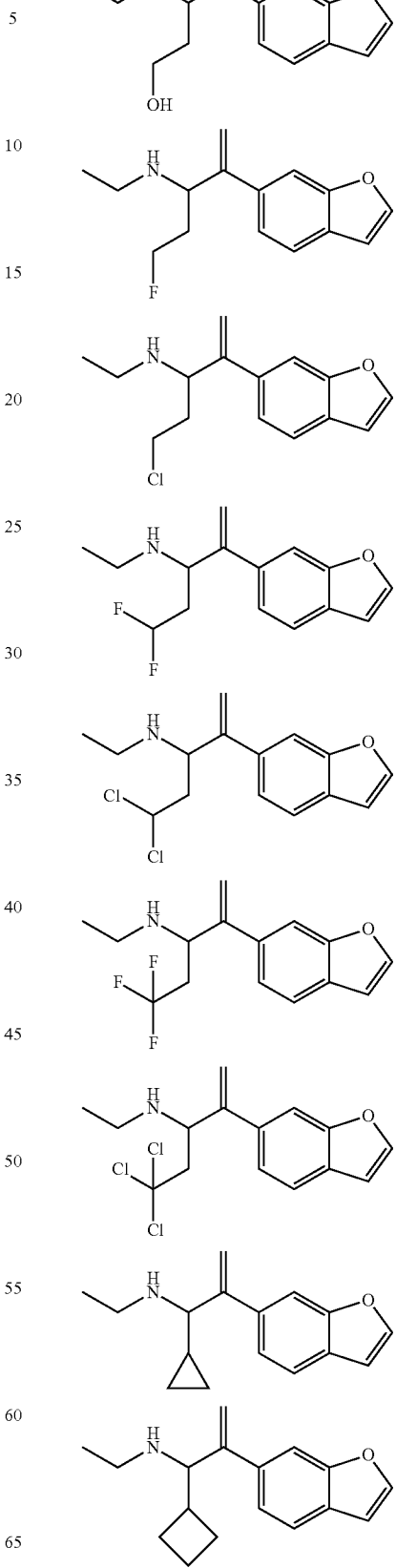

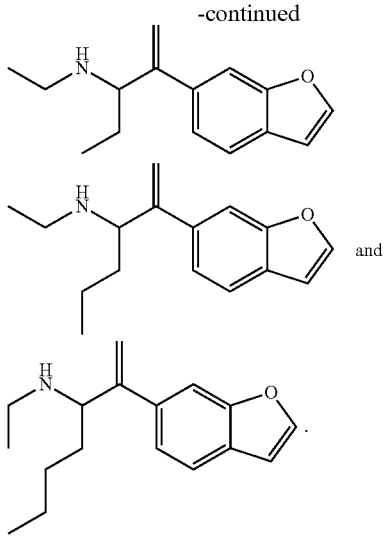
In certain embodiments, the compound of the present invention is selected from:
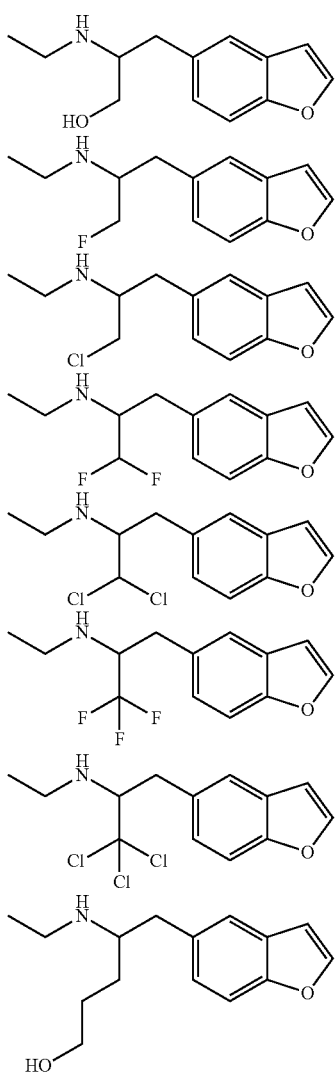
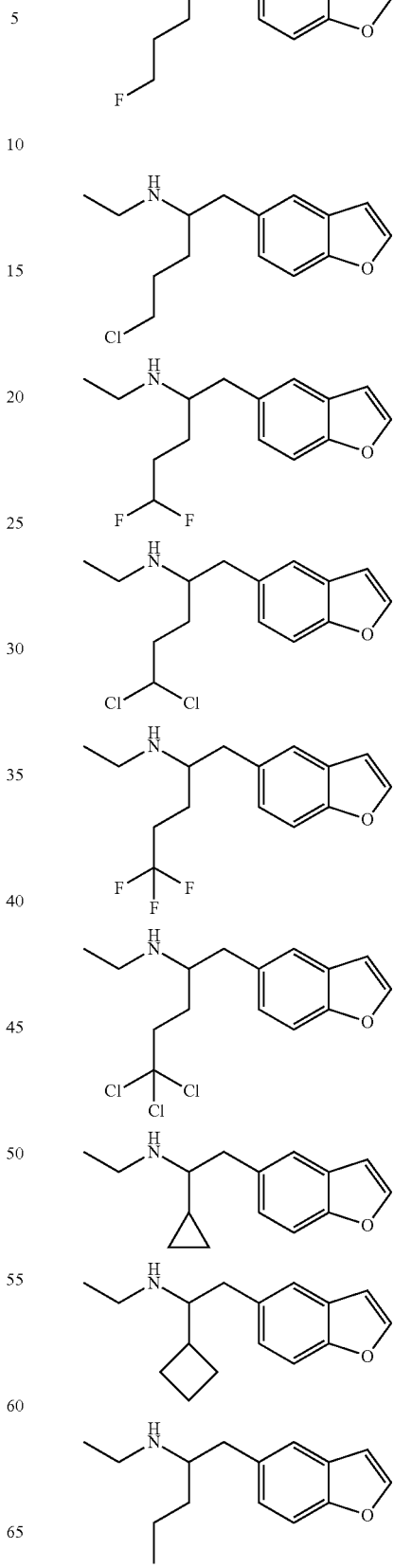

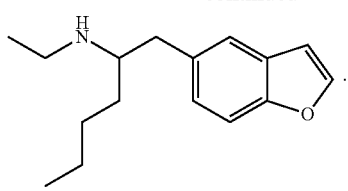
In certain embodiments, the compound of the present invention is selected from:
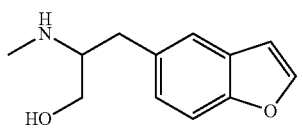
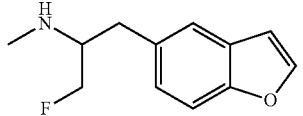
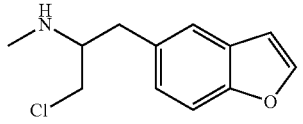
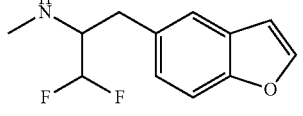
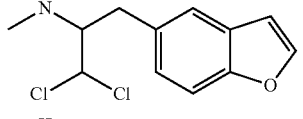
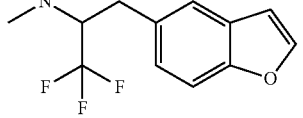
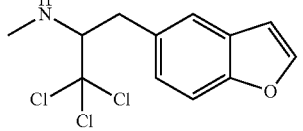
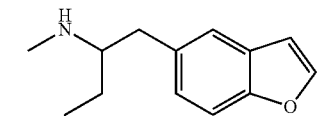
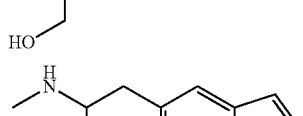
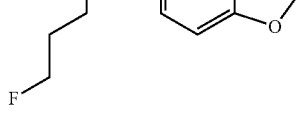
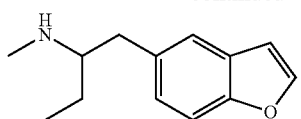
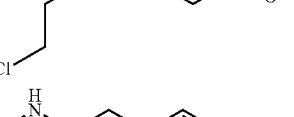
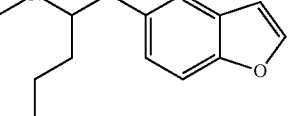
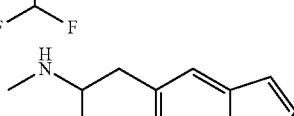
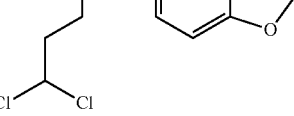
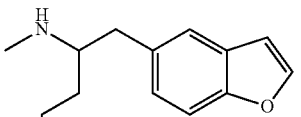
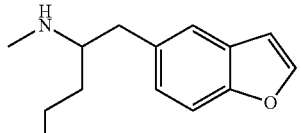
and
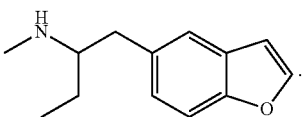

In certain embodiments, the compound of the present invention is selected from:
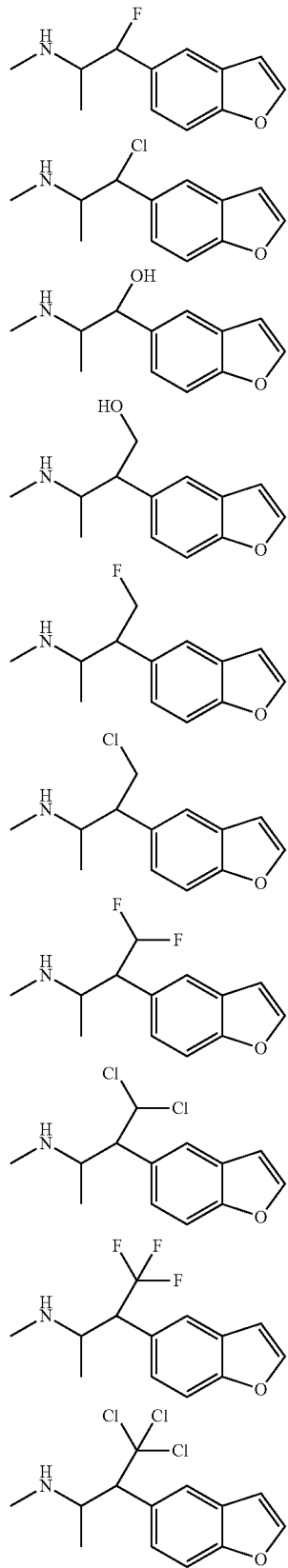
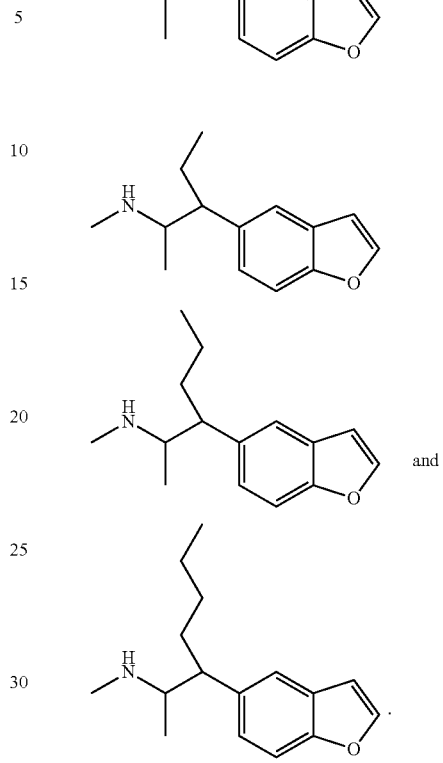
In certain embodiments, the compound of the present invention is selected from:
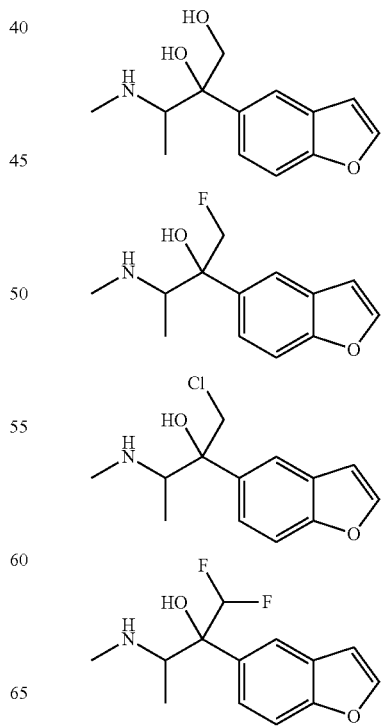

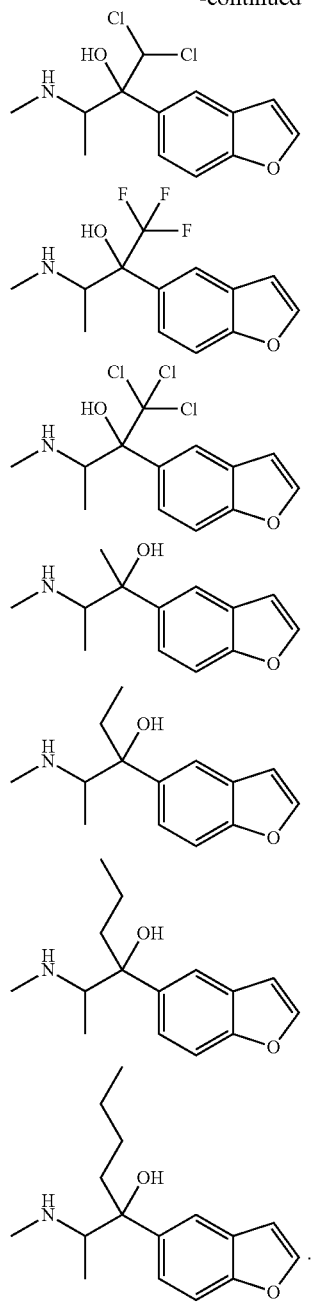
In certain embodiments, the compound of the present invention is selected from:
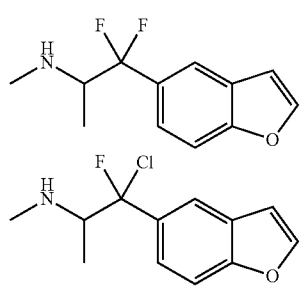
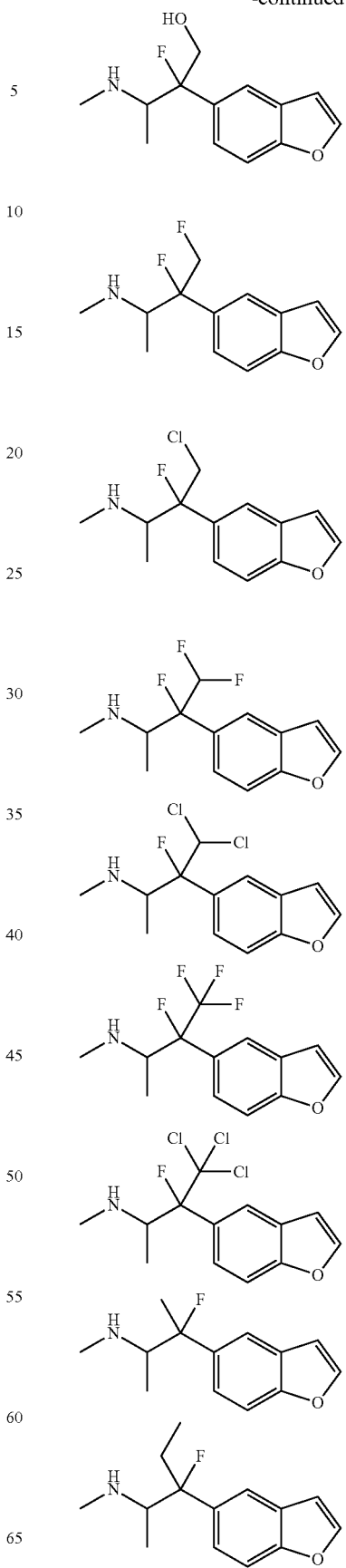

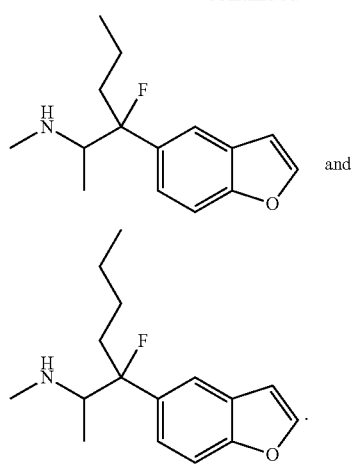
and
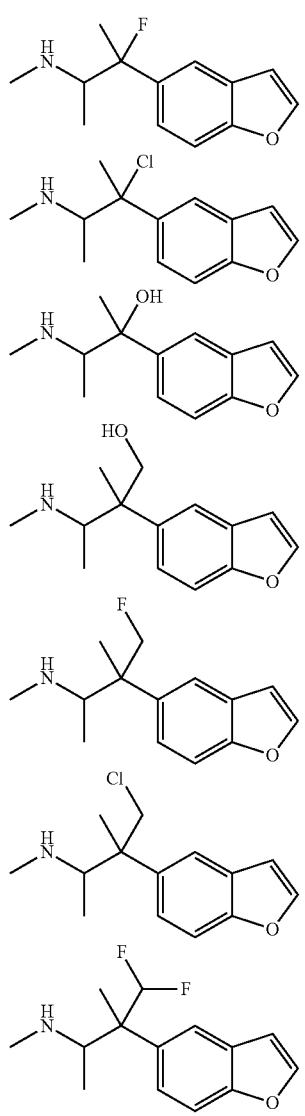
In certain embodiments, the compound of the present invention is selected from:
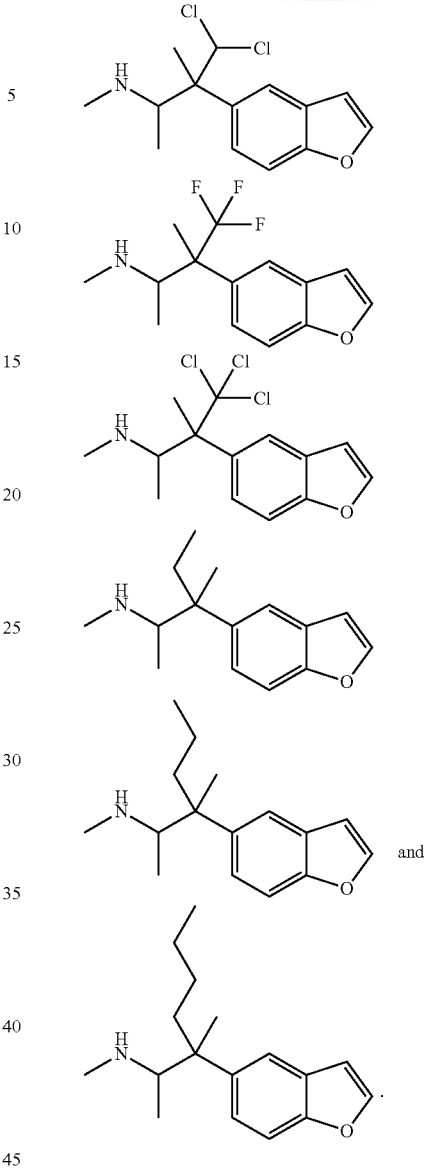
and
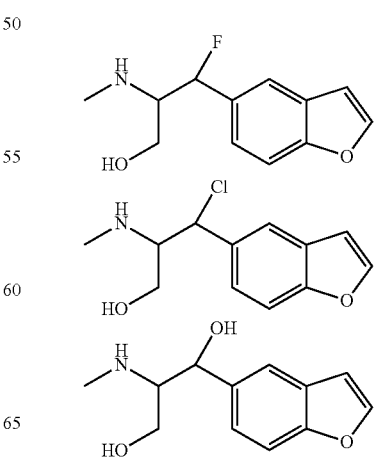
In certain embodiments, the compound of the present invention is selected from:

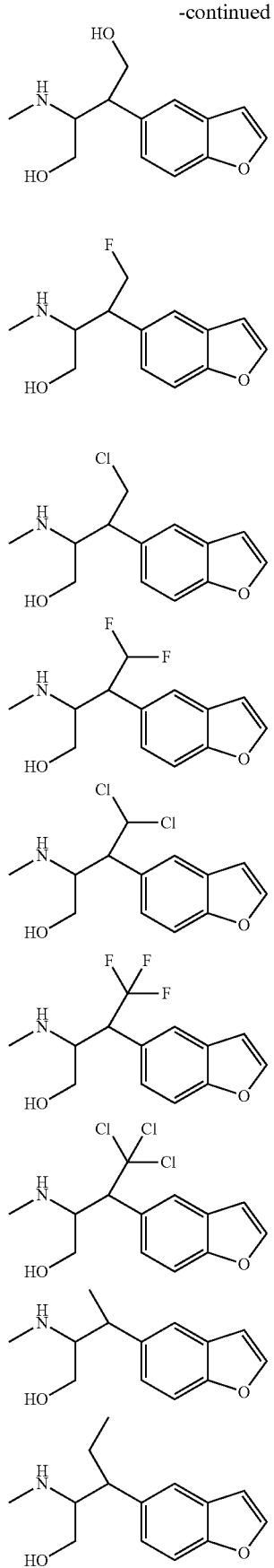
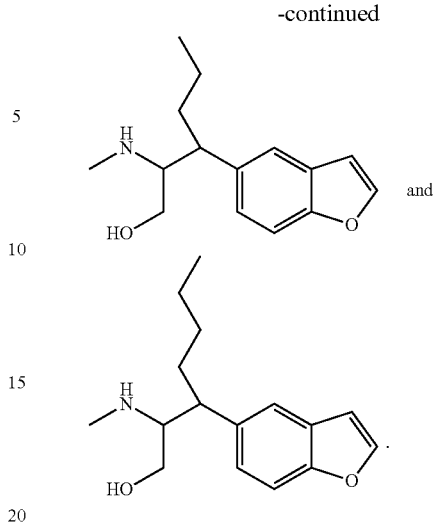
In certain embodiments, the compound of the present invention is selected from:
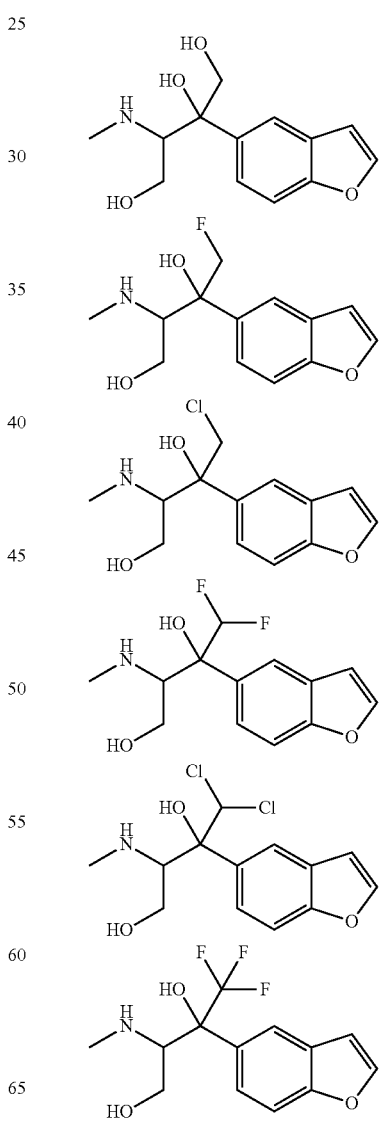

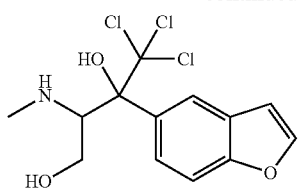
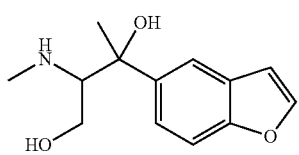
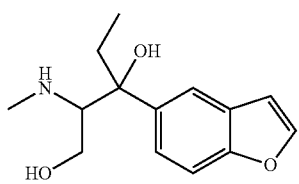
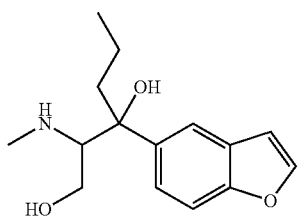
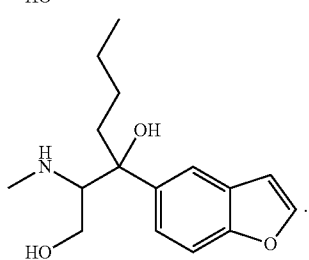
and
In certain embodiments, the compound of the present invention is selected from:
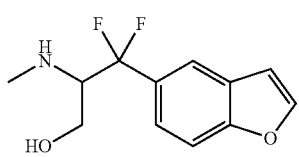
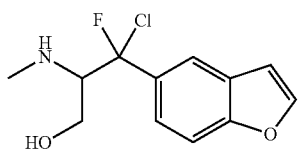
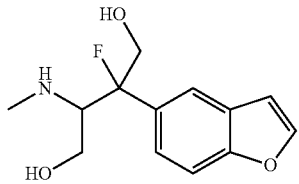
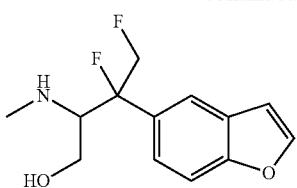
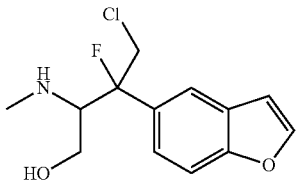
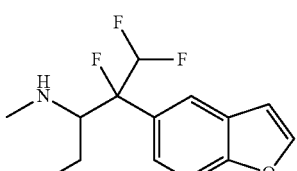
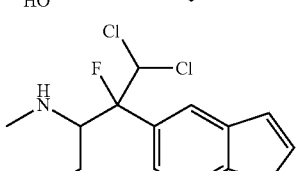
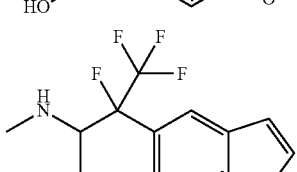
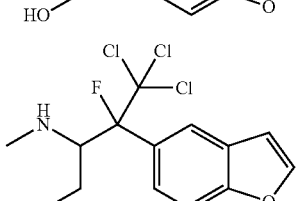
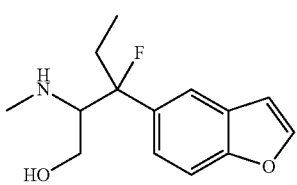
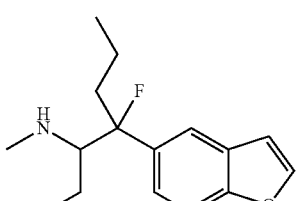
and

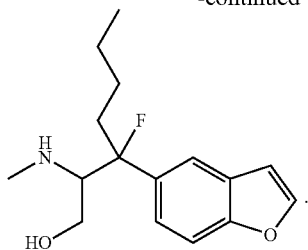
In certain embodiments, the compound of the present invention is selected from:
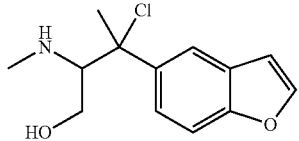
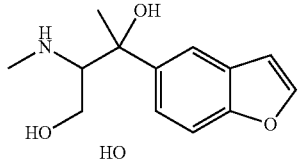
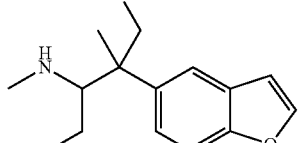
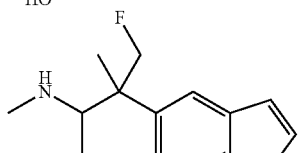
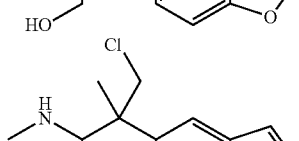
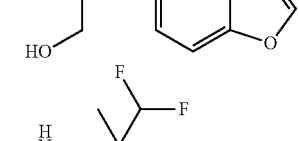
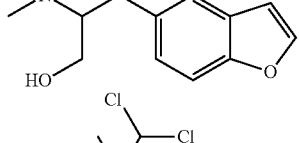
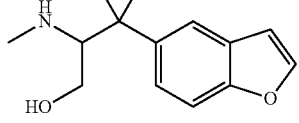
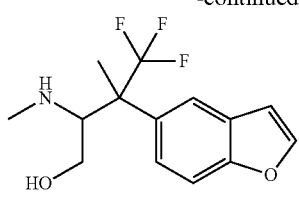
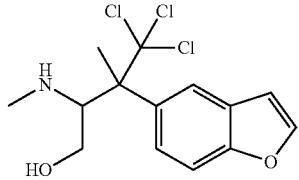
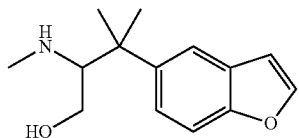
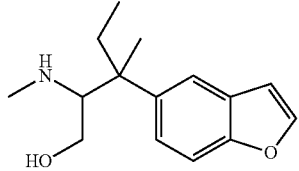
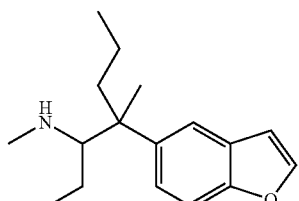
and
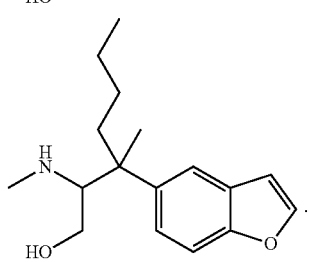
In certain embodiments, the compound of the present invention is selected from:
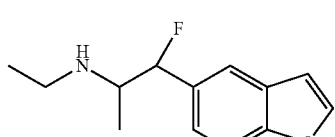
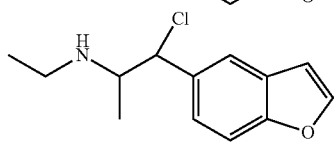
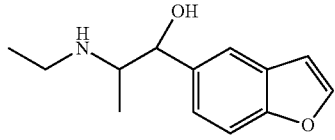

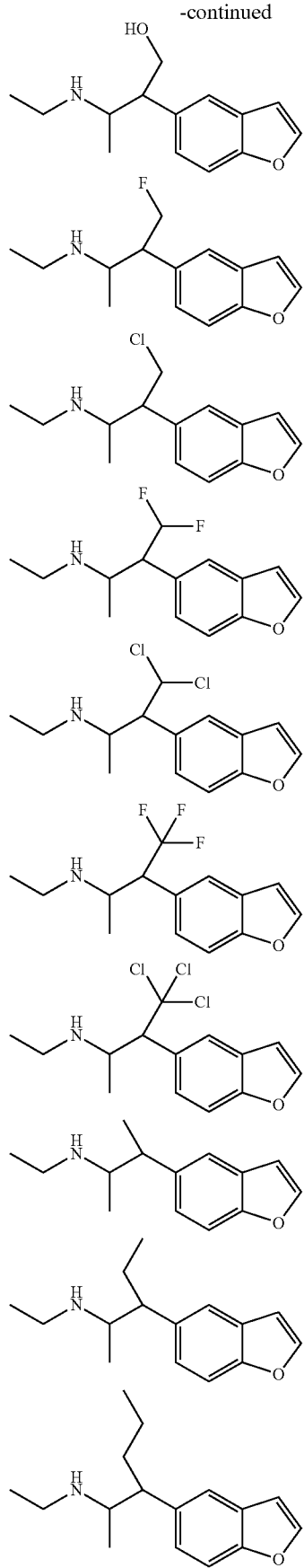
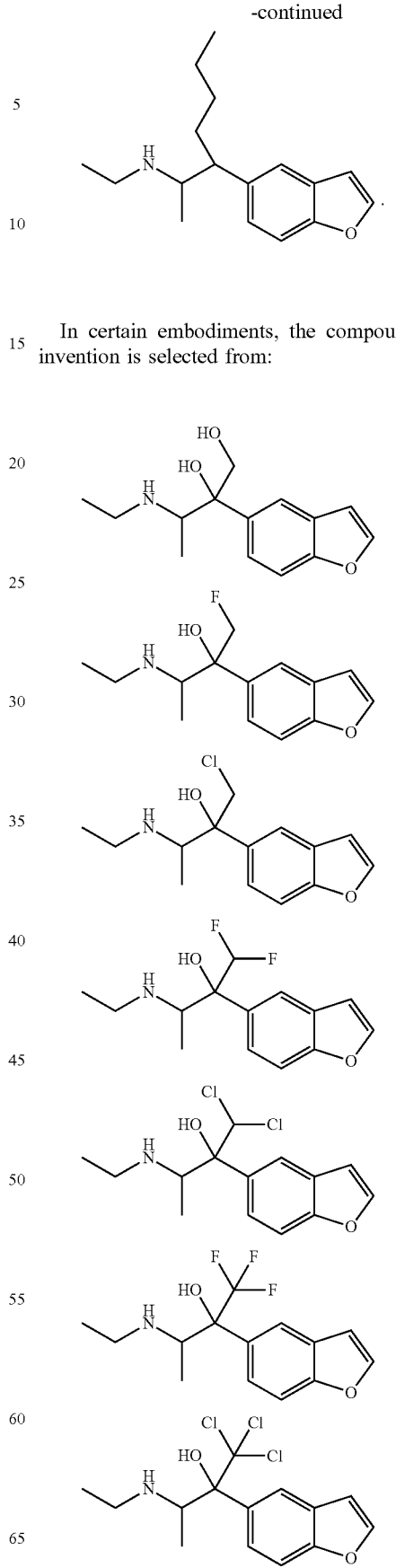
In certain embodiments, the compound of the present invention is selected from:
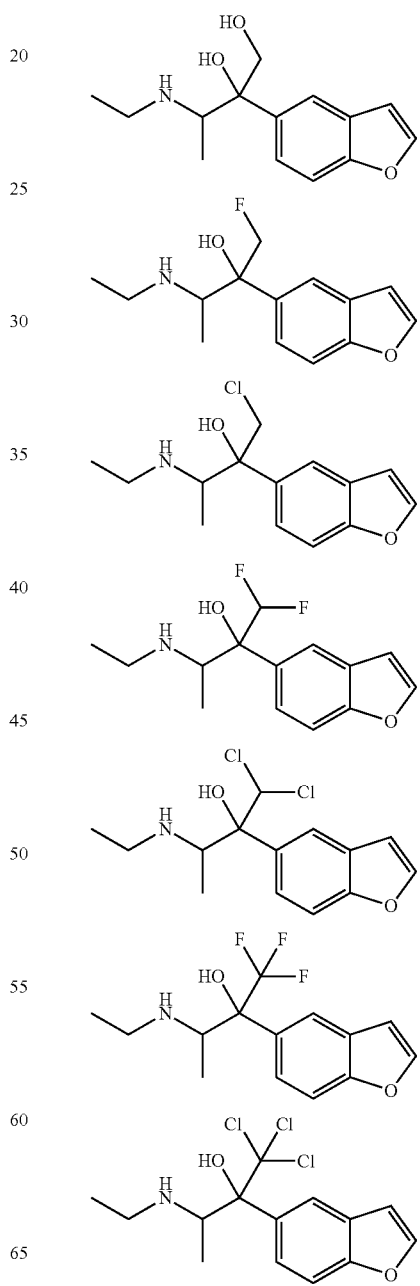

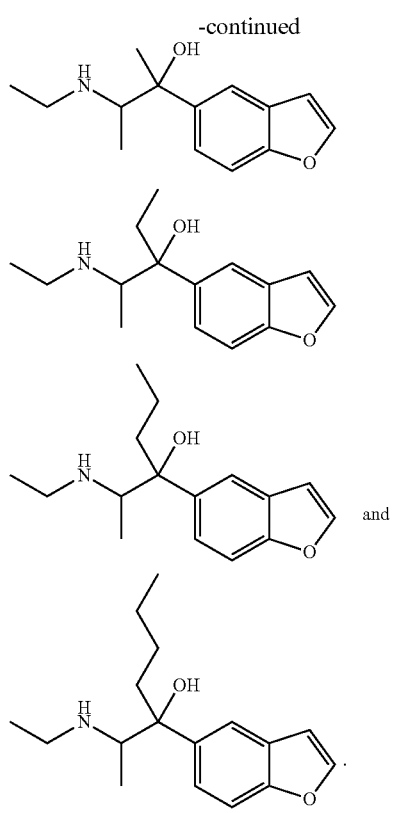
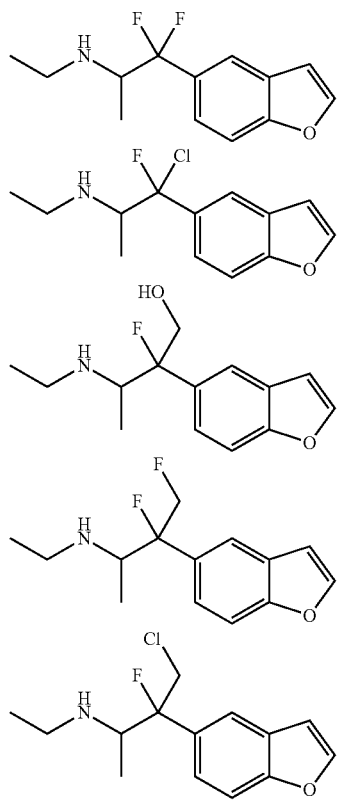
In certain embodiments, the compound of the present invention is selected from:
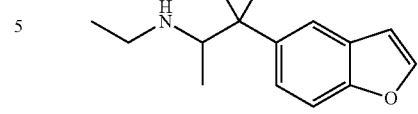
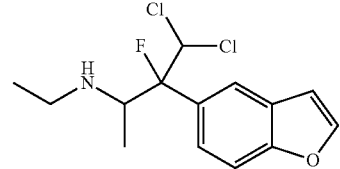
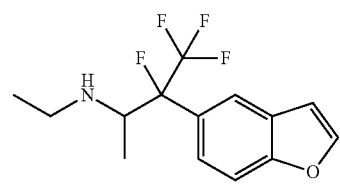
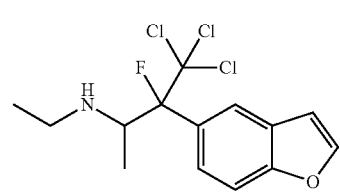
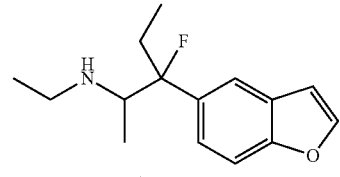
and

In certain embodiments, the compound of the present invention is selected from:
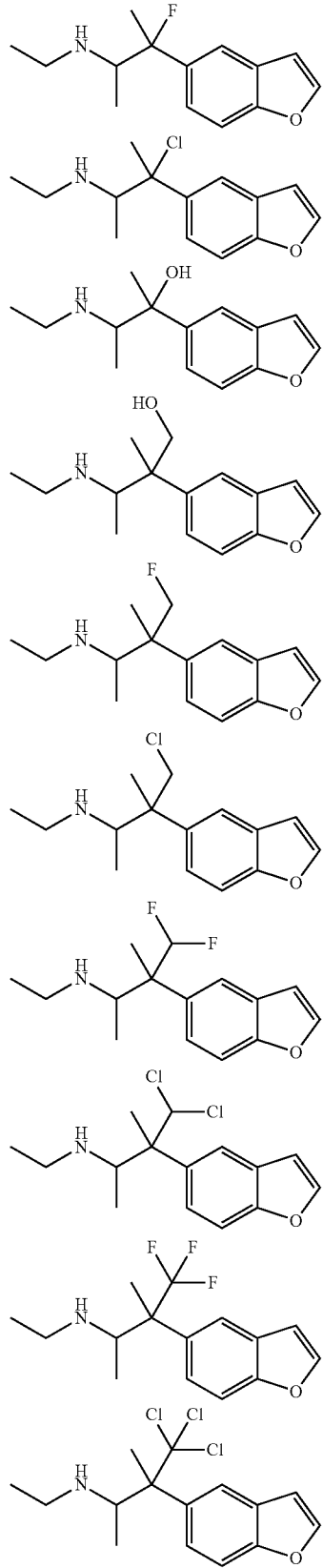
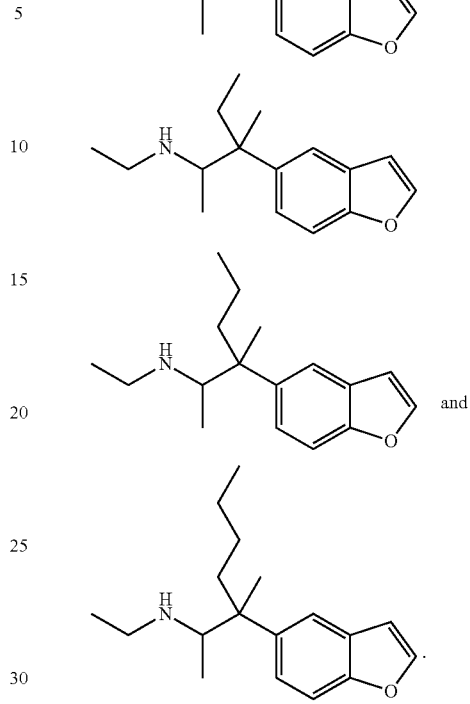
In certain embodiments, the compound of the present invention is selected from:
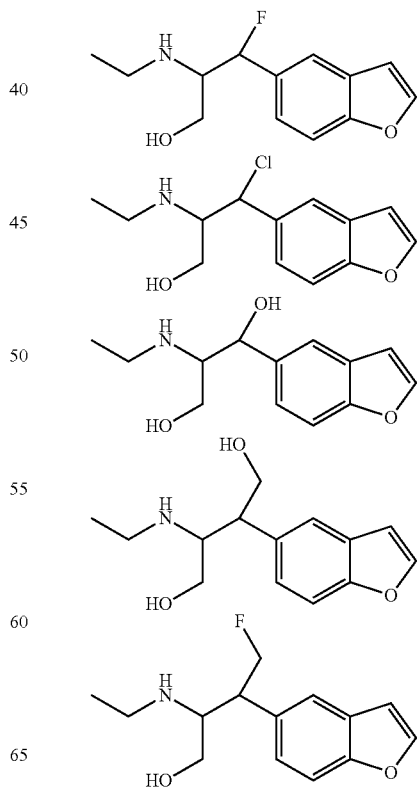

191
-continued
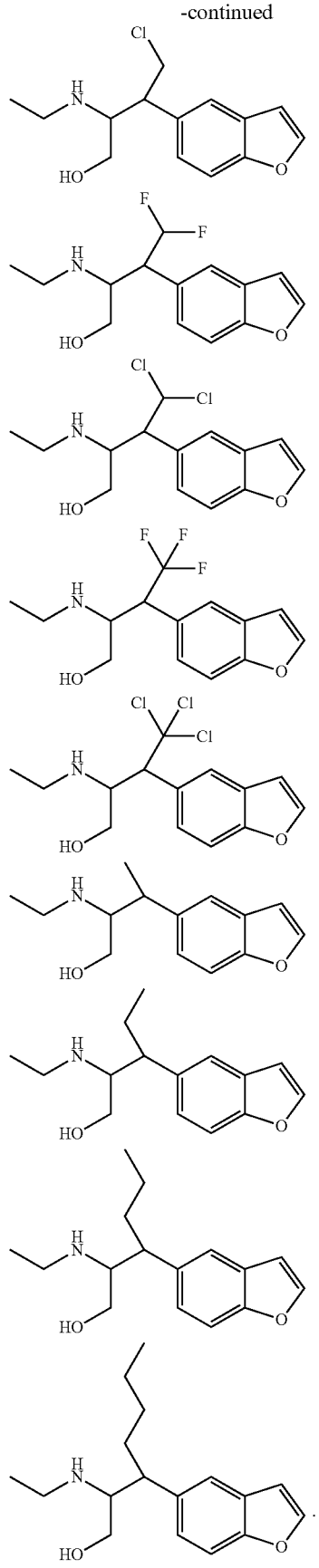
192
In certain embodiments, the compound of the present invention is selected from:
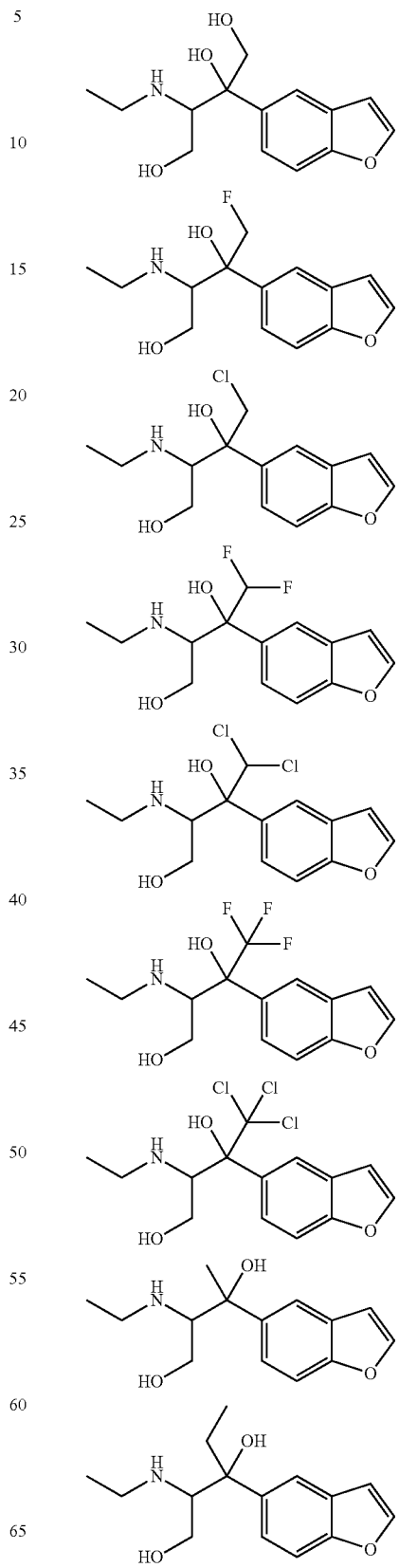
and

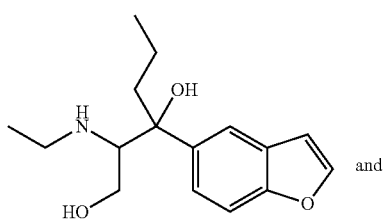
and
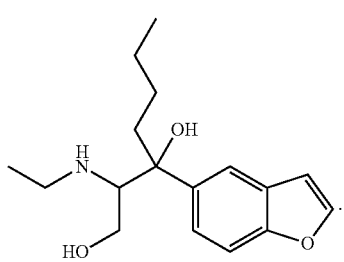
In certain embodiments, the compound of the present invention is selected from:
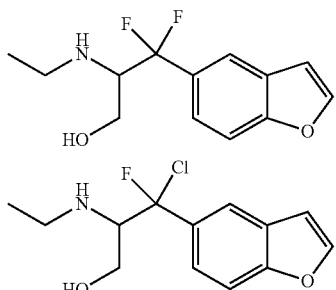
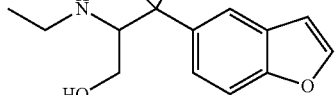
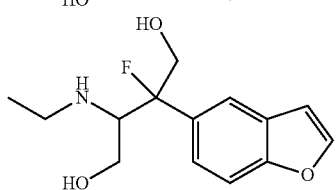
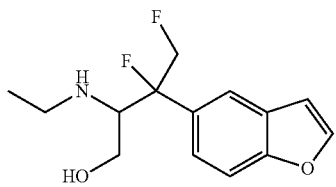
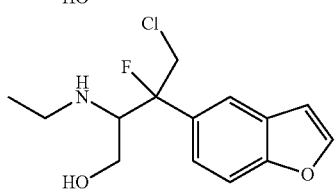
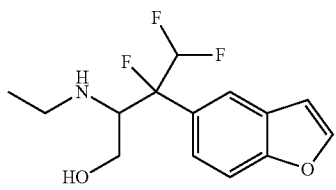
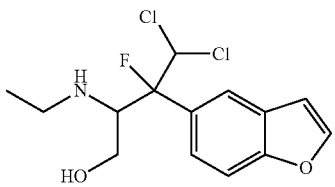
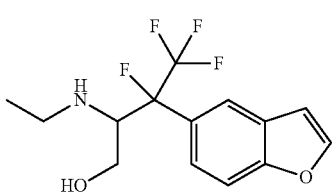
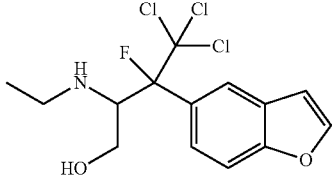
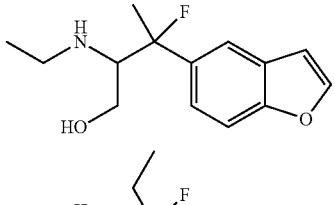
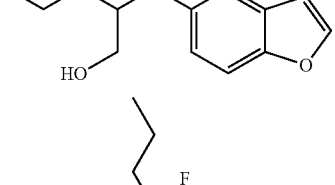
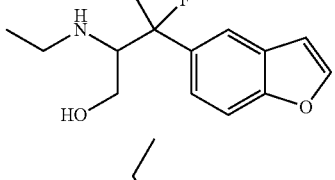
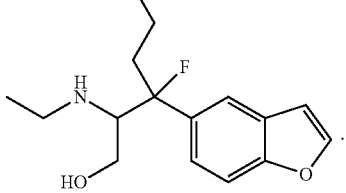
and
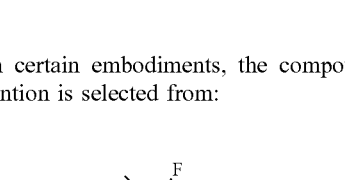
In certain embodiments, the compound of the present invention is selected from:
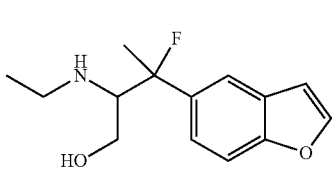

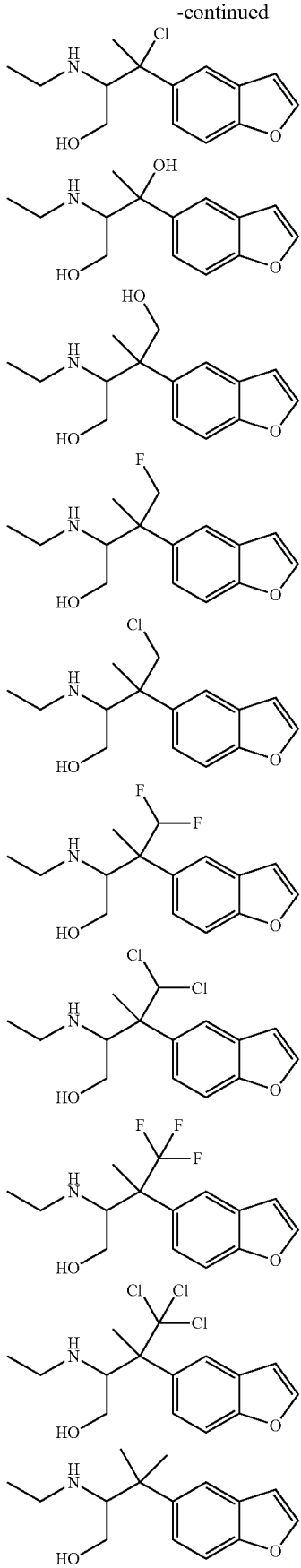

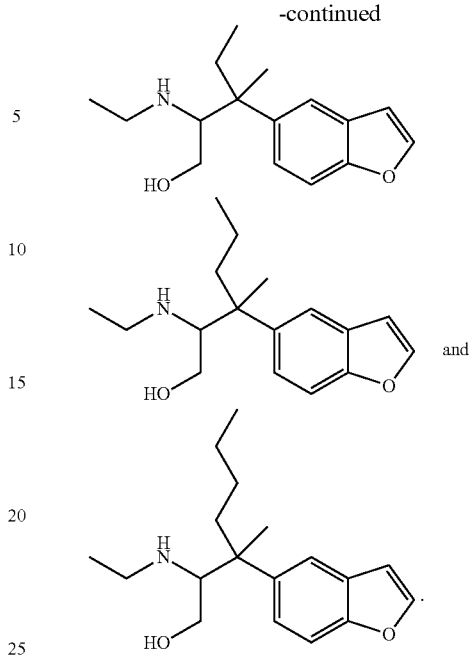

Certain compounds of the invention may also exist in several tautomeric forms including the enol form, the keto form, and mixtures thereof. Accordingly, the chemical structures depicted herein encompass all possible tautomeric forms of the illustrated compounds. Keto-enol tautomerism, for example, is the reversible transfer of a hydrogen from the alpha carbon adjacent to a carbonyl group followed by a double bond transfer. In solution, compounds will spontaneously undergo a kinetic transformation from one tautomer to the other until equilibrium is reached, generally strongly favoring the keto tautomer over the enol tautomer, but dependent on factors such as solvent, pH, and temperature. Keto and enol tautomers may have distinguishable physicochemical properties; however, because they will interconvert in solution, reference to a compound in its keto form (e.g., where Q is

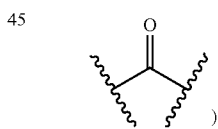

)

will be understood to refer to and include the compound in its enol form (e.g., where Q is

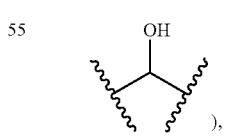

), unless context clearly indicates otherwise. The compounds may also exist as ring-chain tautomers, as discussed below.

Preparation of Enantiomeric Compounds

Various methods are known in the art for preparing optically active forms and determining activity. Such methods include standard processes described herein and other similar assays which are well known in the art. Examples of methods that can be used to obtain optical isomers of the compounds according to the present disclosure include but are not limited to the following:

a) physical separation of crystals whereby macroscopic crystals of the individual enantiomers are manually separated. This technique may particularly be used if crystals of the separate enantiomers exist (i.e., the material is a conglomerate), and the crystals are visually distinct;

b) simultaneous crystallization whereby the individual enantiomers are separately crystallized from a solution of the racemate, possible only if the latter is a conglomerate in the solid state;

c) enzymatic resolutions whereby partial or complete separation of a racemate by virtue of differing rates of reaction for the enantiomers with an enzyme;

d) enzymatic asymmetric synthesis, a synthetic technique whereby at least one step of the synthesis uses an enzymatic reaction to obtain an enantiomerically pure or enriched synthetic precursor of the desired enantiomer;

e) chemical asymmetric synthesis whereby the desired enantiomer is synthesized from an achiral precursor under conditions that produce asymmetry (i.e., chirality) in the product, which may be achieved using chiral catalysts or chiral auxiliaries;

f) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

g) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

h) kinetic resolutions comprising partial or complete resolution of a racemate (or of a further resolution of a partially resolved compound) by virtue of unequal reaction rates of the enantiomers with a chiral, enantiomerically enriched reagent or catalyst under kinetic conditions;

i) enantiospecific synthesis from enantiomerically enriched precursors whereby the desired enantiomer is obtained from non-chiral starting materials and where the stereochemical integrity is not or is only minimally compromised over the course of the synthesis;

j) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

k) chiral gas chromatography whereby the racemate is volatilized and enantiomers are separated by virtue of their differing interactions in the gaseous mobile phase with a column containing a fixed enantiomerically enriched chiral adsorbent phase;

l) extraction with chiral solvents whereby the enantiomers are separated by virtue of preferential dissolution of one enantiomer into a particular chiral solvent; and m) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the enantiomerically enriched chiral nature of the membrane, which allows only one enantiomer of the racemate to pass through.

Where diastereomers exist, the compounds can be used in any diastereomeric form or mixture of forms that provides the appropriate therapeutic effect for the patient, as taught herein. Therefore, in one embodiment, the compounds of the present invention can be administered in a racemic mixture, as the R-enantiomer, as the S-enantiomer, or as an enantiomerically enriched mixture, or a diastereomeric form.

The following compounds indicate where primary stereocenters exist when the designated R group is not hydrogen. In certain embodiments, the enantiomers of the present invention include:

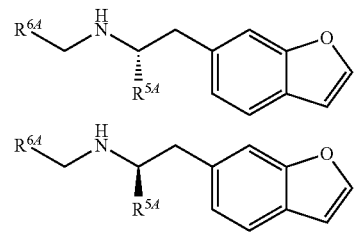

wherein $R^{5A}$ is not hydrogen.

In certain embodiments, the enantiomers of the present invention include:

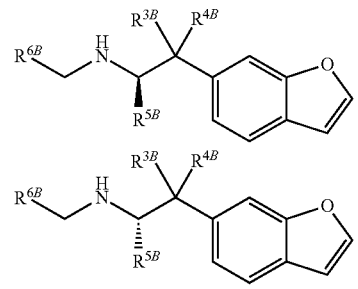

wherein $R^{5B}$ is not hydrogen.

In certain embodiments, the enantiomers of the present invention include:

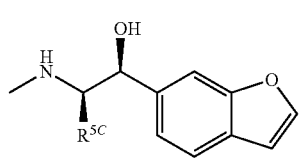

-continued

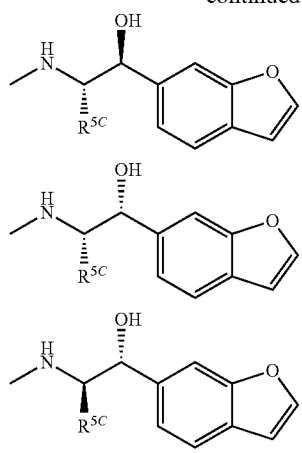

wherein R$^{5C}$ is not hydrogen.

In certain embodiments, the enantiomers of the present invention include:

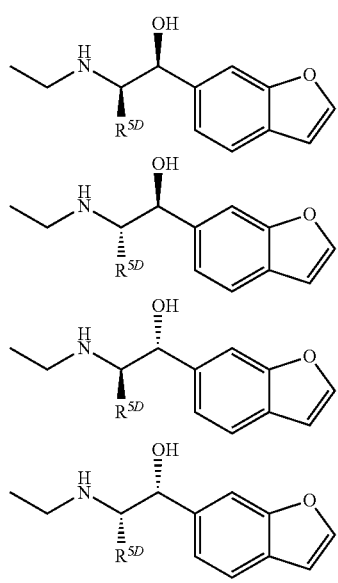

wherein R$^{5D}$ is not hydrogen.

In certain embodiments, the enantiomers of the present invention include:

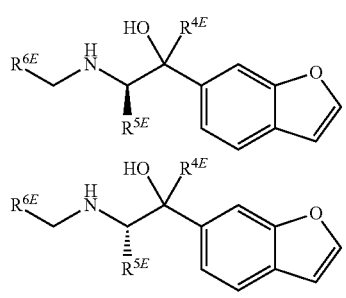

wherein R$^{5E}$ is not hydrogen.

In certain embodiments, the enantiomers of the present invention include:

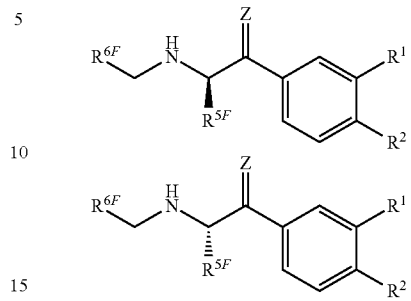

wherein R$^{5F}$ is not hydrogen.

In certain embodiments, the enantiomers of the present invention include:

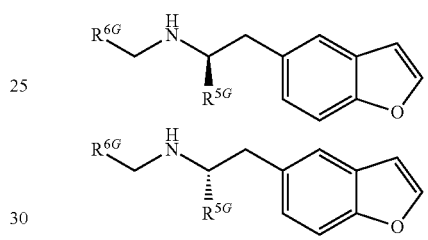

wherein R$^{5G}$ is not hydrogen.

In certain embodiments, the enantiomers of the present invention include:

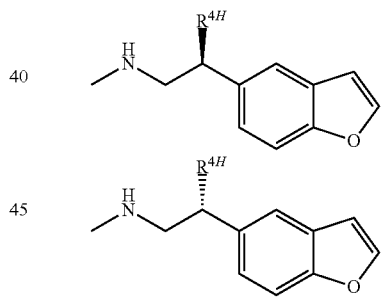

wherein R$^{4H}$ is not hydrogen.

In certain embodiments, the enantiomers of the present invention include:

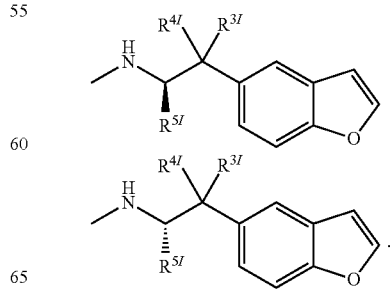

In certain embodiments, the enantiomers of the present invention include:

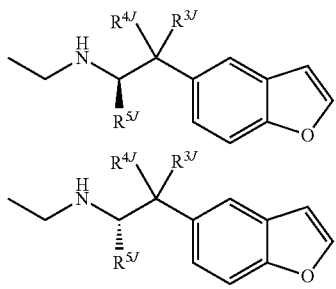

wherein $R^{5J}$ is not hydrogen.

In certain embodiments, the enantiomers of the present invention include:

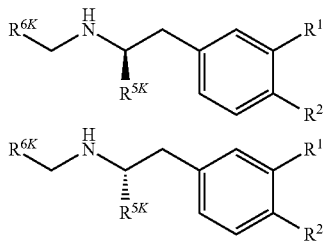

wherein $R^{5K}$ is not hydrogen.

In certain embodiments, the enantiomers of the present invention include:

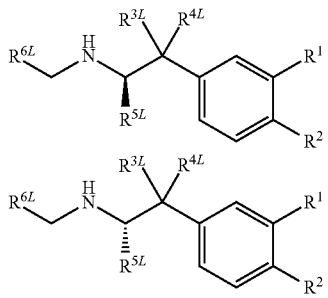

wherein $R^{5L}$ is not hydrogen.

In certain embodiments, the enantiomers of the present invention include:

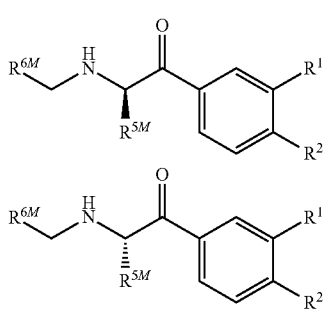

wherein $R^{5M}$ is not hydrogen.

Enantiomerically Enriched Pharmaceutical Compositions

Chiral compounds of the invention may be prepared by chiral chromatography from the racemic or enantiomerically enriched free amine. Pharmaceutically acceptable salts of chiral compounds may be prepared from fractional crystallization of salts from a racemic or an enantiomerically enriched free amine and a chiral acid. Alternatively, the free amine may be reacted with a chiral auxiliary and the enantiomers separated by chromatography followed by removal of the chiral auxiliary to regenerate the free amine. Furthermore, separation of enantiomers may be performed at any convenient point in the synthesis of the compounds of the invention. The compounds of the invention may also be prepared using a chiral synthesis.

An enantiomerically enriched mixture is a mixture that contains one enantiomer in a greater amount than the other. An enantiomerically enriched mixture of an S-enantiomer contains at least 55% of the S-enantiomer, and more typically at least about 60%, 65%, 70%, 75%, 80%, 85%, 90%, 95% of the S-enantiomer. An enantiomerically enriched mixture of an R-enantiomer contains at least 55% of the R-enantiomer, more typically at least about 55%, 60%, 65%, 70%, 75%, 80%, 85%, 90%, 95% of the R-enantiomer.

In one embodiment, enantiomerically enriched mixtures that have a greater amount of the R-enantiomer maximize nicotinic-receptor-dependent therapeutic effects. In one embodiment, enantiomerically enriched mixtures that have a greater amount of the S-enantiomer maximize serotonin-receptor-dependent therapeutic effects. Accordingly, in one embodiment, an enantiomerically enriched mixture of S-5-MAPB or an enantiomerically enriched mixture of S-6-MAPB maximize serotonin-receptor-dependent therapeutic effects and minimized unwanted nicotinic effects when administered to a host in need thereof, for example a mammal, including a human. In another embodiment, an enantiomerically enriched mixture of R-5-MAPB or an enantiomerically enriched mixture of R-6-MAPB maximize nicotinic-receptor-dependent therapeutic effects while minimizing unwanted effects, when administered to a host in need thereof, including a mammal, for example, a human.

Non-limiting examples of unwanted effects that can be minimized include psychoactive effects (such as excess stimulation or sedation), physiological effects (such as transient hypertension or appetite suppression), toxic effects (such as to the brain or liver), effects contributing to abuse liability (such as euphoria or dopamine release), and other side effects.

One aspect of the present invention is a balanced mixture of S-5-MAPB and R-5-MAPB (not the racemate) or a balanced mixture of S-6-MAPB and R-6-MAPB (not the racemate) that achieves a predetermined combination of serotonin-receptor-dependent therapeutic effects and nicotinic-receptor-dependent therapeutic effects.

In certain embodiments, pharmaceutical compositions of enantiomerically enriched preparations of 5-MAPB or 6-MAPB are provided. In one embodiment, the pharmaceutical composition is enriched with S-5-MAPB. In one embodiment, the pharmaceutical composition is enriched with R-5-MAPB. In one embodiment, the pharmaceutical composition is enriched with S-6-MAPB. In one embodiment, the pharmaceutical composition is enriched with R-6-MAPB.

Example 1 below provides a non-limiting example for the preparation of certain enantiomerically enriched preparations of 5-MAPB (i.e., comprising S-5-MAPB and R-5-MAPB). Enantiomerically enriched preparations of 6-MAPB (i.e., S-6-MAPB, R-6-MAPB) can be similarly produced using racemic 6-MAPB HCl.

Particular embodiments for pharmaceutical compositions, including enantiomerically enriched pharmaceutical compositions, of the present invention include:

a) S-5-MAPB;
b) R-5-MAPB;
c) S-6-MAPB;
d) R-6-MAPB;
e) Embodiments (a)-(d) wherein the compound is a free base;
f) Embodiments (a)-(d) wherein the compound is a salt;
g) Embodiment (f) wherein the compound is the hydrochloride salt;
h) A mixture of S-5-MAPB, R-5-MAPB and there is more S-enantiomer than R-enantiomer;
i) A mixture of S-5-MAPB, R-5-MAPB and there is less S-enantiomer than R-enantiomer;
j) A mixture of S-6-MAPB, R-6-MAPB and there is more S-enantiomer than R-enantiomer;
k) A mixture of S-6-MAPB, R-6-MAPB and there is less S-enantiomer than R-enantiomer;
l) A mixture of S-5-MAPB, R-5-MAPB and about 65% is the S-enantiomer while about 35% is the R-enantiomer;
m) A mixture of S-5-MAPB, R-5-MAPB and greater than 65% is the S-enantiomer while less than 35% is the R-enantiomer;
n) A mixture of S-5-MAPB, R-5-MAPB and greater than 90% is the S-enantiomer while less than 10% is the R-enantiomer;
o) A mixture of S-5-MAPB, R-5-MAPB and about 35% is the S-enantiomer while about 65% is the R-enantiomer;
p) A mixture of S-5-MAPB, R-5-MAPB and less than 35% is the S-enantiomer while greater than 65% is the R-enantiomer;
q) A mixture of S-5-MAPB, R-5-MAPB and less than 10% is the S-enantiomer while greater than 90% is the R-enantiomer;
r) A mixture of S-6-MAPB, R-6-MAPB and about 65% is the S-enantiomer while about 35% is the R-enantiomer;
s) A mixture of S-6-MAPB, R-6-MAPB and greater than 65% is the S-enantiomer while less than 35% is the R-enantiomer;
t) A mixture of S-6-MAPB, R-6-MAPB and greater than 90% is the S-enantiomer while less than 10% is the R-enantiomer;
u) A mixture of S-6-MAPB, R-6-MAPB and 35% or less is the S-enantiomer while 65% or more is the R-enantiomer;
v) A mixture of S-6-MAPB, R-6-MAPB and about 35% is the S-enantiomer while about 65% is the R-enantiomer; and
w) A mixture of S-6-MAPB, R-6-MAPB and less than 10% is the S-enantiomer while greater than 90% is the R-enantiomer.
x) S-5-MBPB;
y) R-5-MBPB;
z) S-6-MBPB;
aa) R-6-MBPB;
bb) Embodiments (x)-(aa) wherein the compound is a free base;
cc) Embodiments (x)-(aa) wherein the compound is a salt;
dd) Embodiment (cc) wherein the compound is the hydrochloride salt;
ee) A mixture of S-5-MBPB, R-5-MBPB and there is more S-enantiomer than R-enantiomer;
ff) A mixture of S-5-MBPB, R-5-MBPB and there is less S-enantiomer than R-enantiomer;
gg) A mixture of S-6-MBPB, R-6-MBPB and there is more S-enantiomer than R-enantiomer;
hh) A mixture of S-6-MBPB, R-6-MBPB and there is less S-enantiomer than R-enantiomer;
ii) A mixture of S-5-MBPB, R-5-MBPB and about 65% is the S-enantiomer while about 35% is the R-enantiomer;
jj) A mixture of S-5-MBPB, R-5-MBPB and greater than about 65% is the S-enantiomer while less than about 35% is the R-enantiomer;
kk) A mixture of S-5-MBPB, R-5-MBPB and greater than about 90% is the S-enantiomer while less than about 10% is the R-enantiomer;
ll) A mixture of S-5-MBPB, R-5-MBPB and about 35% is the S-enantiomer while about 65% is the R-enantiomer;
mm) A mixture of S-5-MBPB, R-5-MBPB and less than about 35% is the S-enantiomer while greater than about 65% is the R-enantiomer;
nn) A mixture of S-5-MBPB, R-5-MBPB and less than about 10% is the S-enantiomer while greater than about 90% is the R-enantiomer;
oo) A mixture of S-6-MBPB, R-6-MBPB and about 65% is the S-enantiomer while about 35% is the R-enantiomer;
pp) A mixture of S-6-MBPB, R-6-MBPB and greater than about 65% is the S-enantiomer while less than about 35% is the R-enantiomer;
qq) A mixture of S-6-MBPB, R-6-MBPB and greater than about 90% is the S-enantiomer while less than about 10% is the R-enantiomer;
rr) A mixture of S-6-MBPB, R-6-MBPB and about 35% or less is the S-enantiomer while about 65% or more is the R-enantiomer;
ss) A mixture of S-6-MBPB, R-6-MBPB and about 35% is the S-enantiomer while about 65% is the R-enantiomer; and
tt) A mixture of S-6-MBPB, R-6-MBPB and less than about 10% is the S-enantiomer while greater than about 90% is the R-enantiomer.
uu) S-Bk-5-MAPB;
vv) R-Bk-5-MAPB;
ww) S-Bk-6-MAPB;
xx) R-Bk-6-MAPB;
yy) Embodiments (uu)-(xx) wherein the compound is a free base;
zz) Embodiments (uu)-(xx) wherein the compound is a salt;
aaa) Embodiment (zz) wherein the compound is the hydrochloride salt;
bbb) A mixture of S-Bk-5-MAPB, R-Bk-5-MAPB and there is more S-enantiomer than R-enantiomer;
ccc) A mixture of S-Bk-5-MAPB, R-Bk-5-MAPB and there is less S-enantiomer than R-enantiomer;
ddd) A mixture of S-Bk-6-MAPB, R-Bk-6-MAPB and there is more S-enantiomer than R-enantiomer;
eee) A mixture of S-Bk-6-MAPB, R-Bk-6-MAPB and there is less S-enantiomer than R-enantiomer;
fff) A mixture of S-Bk-5-MAPB, R-Bk-5-MAPB and about 65% is the S-enantiomer while about 35% is the R-enantiomer;
ggg) A mixture of S-Bk-5-MAPB, R-Bk-5-MAPB and greater than about 65% is the S-enantiomer while less than about 35% is the R-enantiomer;
hhh) A mixture of S-Bk-5-MAPB, R-Bk-5-MAPB and greater than about 90% is the S-enantiomer while less than about 10% is the R-enantiomer;

iii) A mixture of S-Bk-5-MAPB, R-Bk-5-MAPB and about 35% is the S-enantiomer while about 65% is the R-enantiomer;
jjj) A mixture of S-Bk-5-MAPB, R-Bk-5-MAPB and less than about 35% is the S-enantiomer while greater than about 65% is the R-enantiomer;
kkk) A mixture of S-Bk-5-MAPB, R-Bk-5-MAPB and less than about 10% is the S-enantiomer while greater than about 90% is the R-enantiomer;
lll) A mixture of S-Bk-6-MAPB, R-Bk-6-MAPB and about 65% is the S-enantiomer while about 35% is the R-enantiomer;
mmm) A mixture of S-Bk-6-MAPB, R-Bk-6-MAPB and greater than about 65% is the S-enantiomer while less than about 35% is the R-enantiomer;
nnn) A mixture of S-Bk-6-MAPB, R-Bk-6-MAPB and greater than about 90% is the S-enantiomer while less than about 10% is the R-enantiomer;
ooo) A mixture of S-Bk-6-MAPB, R-Bk-6-MAPB and about 35% or less is the S-enantiomer while about 65% or more is the R-enantiomer;
ppp) A mixture of S-Bk-6-MAPB, R-Bk-6-MAPB and about 35% is the S-enantiomer while about 65% is the R-enantiomer; and
qqq) A mixture of S-Bk-6-MAPB, R-Bk-6-MAPB and less than about 10% is the S-enantiomer while greater than about 90% is the R-enantiomer.
rrr) S-Bk-5-MBPB;
sss) R-Bk-5-MBPB;
ttt) S-Bk-6-MBPB;
uuu) R-Bk-6-MBPB;
vvv) Embodiments (rrr)-(uuu) wherein the compound is a free base;
www) Embodiments (rrr)-(uuu) wherein the compound is a salt;
xxx) Embodiment (www) wherein the compound is the hydrochloride salt;
yyy) A mixture of S-Bk-5-MBPB, R-Bk-5-MBPB and there is more S-enantiomer than R-enantiomer;
zzz) A mixture of S-Bk-5-MBPB, R-Bk-5-MBPB and there is less S-enantiomer than R-enantiomer;
aaaa) A mixture of S-Bk-6-MBPB, R-Bk-6-MBPB and there is more S-enantiomer than R-enantiomer;
bbbb) A mixture of S-Bk-6-MBPB, R-Bk-6-MBPB and there is less S-enantiomer than R-enantiomer;
cccc) A mixture of S-Bk-5-MBPB, R-Bk-5-MBPB and about 65% is the S-enantiomer while about 35% is the R-enantiomer;
dddd) A mixture of S-Bk-5-MBPB, R-Bk-5-MBPB and greater than about 65% is the S-enantiomer while less than about 35% is the R-enantiomer;
eeee) A mixture of S-Bk-5-MBPB, R-Bk-5-MBPB and greater than about 90% is the S-enantiomer while less than about 10% is the R-enantiomer;
ffff) A mixture of S-Bk-5-MBPB, R-Bk-5-MBPB and about 35% is the S-enantiomer while about 65% is the R-enantiomer;
gggg) A mixture of S-Bk-5-MBPB, R-Bk-5-MBPB and less than about 35% is the S-enantiomer while greater than about 65% is the R-enantiomer;
hhhh) A mixture of S-Bk-5-MBPB, R-Bk-5-MBPB and less than about 10% is the S-enantiomer while greater than about 90% is the R-enantiomer;
iiii) A mixture of S-Bk-6-MBPB, R-Bk-6-MBPB and about 65% is the S-enantiomer while about 35% is the R-enantiomer;
jjjj) A mixture of S-Bk-6-MBPB, R-Bk-6-MBPB and greater than about 65% is the S-enantiomer while less than about 35% is the R-enantiomer;
kkkk) A mixture of S-Bk-6-MBPB, R-Bk-6-MBPB and greater than about 90% is the S-enantiomer while less than about 10% is the R-enantiomer;
llll) A mixture of S-Bk-6-MBPB, R-Bk-6-MBPB and about 35% or less is the S-enantiomer while about 65% or more is the R-enantiomer;
mmmm) A mixture of S-Bk-6-MBPB, R-Bk-6-MBPB and about 35% is the S-enantiomer while about 65% is the R-enantiomer; and
nnnn) A mixture of S-Bk-6-MBPB, R-Bk-6-MBPB and less than about 10% is the S-enantiomer while greater than about 90% is the R-enantiomer.

It will be understood that the above embodiments and classes of embodiments can be combined to form additional preferred embodiments.

III. Methods to Treat CNS Disorders Including Mental Disorders and for Mental Enhancement The present invention provides methods and uses for the treatment of CNS disorders, including, but not limited to, mental disorders as described herein, including post-traumatic stress and adjustment disorders, comprising administering the benzofuran compounds or composition or a pharmaceutically acceptable salt or mixture of salts thereof as described herein. It has been surprisingly discovered that these compounds display many pharmacological properties that are beneficial to their use as therapeutics and represent an improvement over existing therapeutics.

The present invention also provides, for example, methods for the treatment of disorders, including, but not limited to depression, dysthymia, anxiety and phobia disorders (including generalized anxiety, social anxiety, panic, post-traumatic stress and adjustment disorders), feeding and eating disorders (including binge eating, bulimia, and anorexia nervosa), other binge behaviors, body dysmorphic syndromes, alcoholism, tobacco abuse, drug abuse or dependence disorders, disruptive behavior disorders, impulse control disorders, gaming disorders, gambling disorders, memory loss, dementia of aging, attention deficit hyperactivity disorder, personality disorders (including antisocial, avoidant, borderline, histrionic, narcissistic, obsessive compulsive, paranoid, schizoid and schizotypal personality disorders), attachment disorders, autism, and dissociative disorders.

In addition to treating various diseases and disorders, the employed methods of modulating activity of the serotonergic system in particular can be used to improve CNS functioning in non-disease states, such as reducing neuroticism and psychological defensiveness, increasing openness to experience, increasing creativity, and aiding decision-making.

In other embodiments, a compound or composition of the present invention is provided in an effective amount to treat a host, typically a human, with a CNS disorder that can be either a neurological condition (one that is typically treated by a neurologist) or a psychiatric condition (one that is typically treated by a psychiatrist). Neurological disorders are typically those affecting the structure, biochemistry or cause electrical abnormalities of the brain, spinal cord or other nerves. Psychiatric conditions are more typically thought of as mental disorders, which are primarily abnormalities of thought, feeling or behavior that cause significant distress or impairment of personal functioning.

Thus, the disclosed compounds can be used in an effective amount to improve neurological or psychiatric functioning in a patient in need thereof. Neurological indications include, but are not limited to improved neuroplasticity, including treatment of stroke, brain trauma, dementia, and neurodegenerative diseases. MDMA has been reported to have an EC50 of 7.41 nM for promoting neuritogenesis and an Emax approximately twice that of ketamine, which has fast acting psychiatric benefits that are thought to be mediated by its ability to promote neuroplasticity, including the growth of dendritic spines, increased synthesis of synaptic proteins, and strengthening synaptic responses. Figure S3. in Ly et al. (Cell reports 23, no. 11 (2018): 3170-3182, https://doi.org/1016/j.celrep.2018.05.022). The compounds of the current invention can similarly be considered psychoplastogens, that is, small molecules that are able to induce rapid neuroplasticity (Olson, 2018, Journal of experimental neuroscience, 12, 1179069518800508. https://doi.org/10.1177%2F1179069518800508). For example, in certain embodiments, the disclosed compounds and compositions can be used to improve stuttering and other dyspraxias or to treat Parkinson's disease or schizophrenia.

The term "improving psychiatric function" is intended to include mental health and life conditions that are not traditionally treated by neurologists but sometimes treated by psychiatrists and can also be treated by psychotherapists, life coaches, personal fitness trainers, meditation teachers, counselors, and the like. For example, it is contemplated that the disclosed compounds will allow individuals to effectively contemplate actual or possible experiences that would normally be upsetting or even overwhelming. This includes individuals with fatal illness planning their last days and the disposition of their estate. This also includes couples discussing difficulties in their relationship and how to address them. This also includes individuals who wish to more effectively plan their career.

In other embodiments, the compositions and compounds of the present invention may be used in an effective amount to treat a host, typically a human, to modulate an immune or inflammatory response. The compounds disclosed herein alter extracellular serotonin, which is known to alter immune functioning. MDMA produces acute time-dependent increases and decreases in immune response.

The following nonlimiting examples are relevant to any of the disorders, indications, methods of use or dosing regimes described herein.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of S enantiomer is greater than about 99 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of S enantiomer is greater than about 95 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of S enantiomer is greater than about 90 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of S enantiomer is greater than about 85 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of S enantiomer is greater than about 80 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of S enantiomer is greater than about 75 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of S enantiomer is greater than about 70 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of S enantiomer is greater than about 65 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of S enantiomer is greater than about 60 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of S enantiomer is greater than about 55 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of S enantiomer is greater than about 55 or 60 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of R enantiomer is greater than about 95 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt mixed salt, isotopic derivative, or prodrug thereof, wherein the percent of R enantiomer is greater than about 90 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of R enantiomer is greater than about 85 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of R enantiomer is greater than about 80 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt or mixed salt, isotopic derivative, or prodrug thereof, wherein the percent of R enantiomer is greater than about 75 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of R enantiomer is greater than about 70 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of R enantiomer is greater than about 65 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of R enantiomer is greater than about 60 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of R enantiomer is greater than about 55 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, mixed salt, isotopic derivative, or prodrug thereof, wherein the percent of R enantiomer is greater than about 55 or 60 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 95 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 90 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 85 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 80 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 75 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 70 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 65 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 60 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 55 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of S enantiomer is greater than about 55 or 60 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 99 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 95 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 90 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 85 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 80 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 75 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 70 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 65 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 60 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, mixed salt, isotopic derivative, or prodrug thereof, wherein the percent of R enantiomer is greater than about 55 percent.

In certain embodiments, a host, for example a human, is treated with an effective amount of an enantiomerically enriched mixture of enantiomers of compounds of Formula A, Formula B, Formula C, Formula D, Formula E, or Formula F, or a pharmaceutically acceptable salt, mixed salt, isotopic derivative, or prodrug thereof, wherein the percent of R enantiomer is greater than about 55 or 60 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 99 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 95 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-

MBPB, or Bk-6-MBPB, or a pharmaceutically acceptable salt, mixed salt, isotopic derivative, or prodrug thereof, wherein the percent of R enantiomer is greater than about 90 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 85 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 80 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 75 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 70 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 65 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 60 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 55 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of R enantiomer is greater than about 55 or 60 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 99 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 95 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 90 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 85 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 80 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 75 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 70 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 65 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 60 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 55 percent.

In certain embodiments, a host, for example a human, is treated with an effective amount of an enantiomerically enriched mixture of enantiomers of 5-MAPB, 6-MAPB, 5-MBPB, 6-MBPB, Bk-5-MAPB, Bk-6-MAPB, Bk-5-MBPB, or Bk-6-MBPB, or a pharmaceutically acceptable salt, mixed salt, isotopic derivative, or prodrug thereof, wherein the percent of S enantiomer is greater than about 55 or 60 percent.

The present invention also provides methods for modulating the CNS in a mammal in need thereof, including a human, by administering a pharmaceutically effective amount of a compound of the present invention, including S-5-MAPB, R-5-MAPB, S-6-MAPB, and/or R-6-MAPB or a pharmaceutically acceptable salt or mixed salt thereof.

In some embodiments, a method is provided for modulating the CNS in a mammal in need thereof, including a human, by administering a pharmaceutically effective amount of 5-MBPB and/or 6-MBPB or a pharmaceutically acceptable salt thereof. In one embodiment, a method is provided for modulating the CNS in a mammal in need thereof, including a human, by administering a pharmaceutically effective amount of Formula A and/or Formula B or a pharmaceutically acceptable salt thereof. In one embodiment, a method is provided for modulating the CNS in a mammal in need thereof, including a human, by administering a pharmaceutically effective amount of Formula C and/or Formula D or a pharmaceutically acceptable salt thereof. In one embodiment, a method is provided for modulating the CNS in a mammal in need thereof, including a human, by administering a pharmaceutically effective amount of Formula E and/or Formula F or a pharmaceutically acceptable salt thereof. In one embodiment, a method is provided for modulating the CNS in a mammal in need thereof, including a human, by administering a pharmaceutically effective amount of a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof. In one embodiment, a method is provided for modulating the CNS in a mammal in need thereof, including a human, by administering a pharmaceutically effective amount of a compound of Formula XI, Formula XII, and/or Formula XIII or a pharmaceutically acceptable salt thereof.

In one embodiment, a method is provided to treat diseases or disorders linked to inadequate functioning of neurotransmission in the CNS comprising administering 5-MBPB and 6-MBPB or a pharmaceutically acceptable salt thereof in a host in need thereof.

In one embodiment, a method is provided to treat diseases or disorders linked to inadequate functioning of neurotransmission in the CNS comprising administering 5-MBPB and 6-MBPB or a pharmaceutically acceptable salt thereof in a host in need thereof.

In one embodiment, a method is provided to treat diseases or disorders linked to inadequate functioning of neurotransmission in the CNS comprising administering Bk-5-MAPB and Bk-6-MAPB or a pharmaceutically acceptable salt thereof in a host in need thereof.

In one embodiment, a method is provided to treat diseases or disorders linked to inadequate functioning of neurotransmission in the CNS comprising administering Bk-5-MBPB and Bk-6-MBPB or a pharmaceutically acceptable salt thereof in a host in need thereof.

In one embodiment, a method is provided to treat diseases or disorders linked to inadequate functioning of neurotransmission in the CNS comprising administering Formula A and Formula B or a pharmaceutically acceptable salt thereof in a host in need thereof.

In one embodiment, a method is provided to treat diseases or disorders linked to inadequate functioning of neurotransmission in the CNS comprising administering Formula C and Formula D or a pharmaceutically acceptable salt thereof in a host in need thereof.

In one embodiment, a method is provided to treat diseases or disorders linked to inadequate functioning of neurotransmission in the CNS comprising administering Formula E and Formula F or a pharmaceutically acceptable salt thereof in a host in need thereof.

In one embodiment, a method is provided to treat diseases or disorders linked to inadequate functioning of neurotransmission in the CNS comprising administering a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof in a host in need thereof.

In one embodiment, a method is provided to treat diseases or disorders linked to inadequate functioning of neurotransmission in the CNS comprising administering a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof in a host in need thereof.

This invention also provides the use S-5-MAPB, R-5-MAPB, S-6-MAPB, and/or R-6-MAPB or a pharmaceutically acceptable salt or composition to treat a maladaptive response to perceived psychological threats. In one embodiment, S-5-MAPB, R-5-MAPB, S-6-MAPB, and/or R-6-MAPB or a pharmaceutically acceptable salt or composition is administered in the context of psychotherapy. In one embodiment, S-5-MAPB, R-5-MAPB, S-6-MAPB, and/or R-6-MAPB or a pharmaceutically acceptable salt or composition is administered as a stand-alone treatment.

This invention also provides the administration of an effective amount of 5-MBPB and/or 6-MBPB or a pharmaceutically acceptable salt or composition to a host, typically a human, to treat a maladaptive response to perceived psychological threats. In one embodiment, 5-MBPB and/or 6-MBPB or a pharmaceutically acceptable salt or composition is administered in the context of psychotherapy. In one embodiment, 5-MBPB and/or 6-MBPB or a pharmaceutically acceptable salt or composition is administered as a stand-alone treatment.

This invention also provides the use Formula A or Formula B or a pharmaceutically acceptable salt or composition in an effective amount to treat a maladaptive response to perceived psychological threats. In one embodiment, Formula A or Formula B or a pharmaceutically acceptable salt or composition is administered in the context of psychotherapy. In one embodiment, Formula A or Formula B or a pharmaceutically acceptable salt or composition is administered as a stand-alone treatment.

This invention also provides the use Formula C or Formula D or a pharmaceutically acceptable salt or composition to treat a maladaptive response to perceived psychological threats. In one embodiment, Formula C or Formula D or a pharmaceutically acceptable salt or composition is administered in the context of psychotherapy. In one embodiment, Formula C or Formula D or a pharmaceutically acceptable salt or composition is administered as a stand-alone treatment.

This invention also provides the use Formula E and/or Formula F or a pharmaceutically acceptable salt or composition to treat a maladaptive response to perceived psychological threats. In one embodiment, Formula E and/or Formula F or a pharmaceutically acceptable salt or composition is administered in the context of psychotherapy. In one embodiment, Formula E and/or Formula F or a pharmaceutically acceptable salt or composition is administered as a stand-alone treatment.

This invention also provides the use Bk-5-MAPB and/or Bk-6-MAPB or a pharmaceutically acceptable salt or composition to treat a maladaptive response to perceived psychological threats. In one embodiment, Bk-5-MAPB and/or Bk-6-MAPB or a pharmaceutically acceptable salt or composition is administered in the context of psychotherapy. In one embodiment, Bk-5-MAPB and/or Bk-6-MAPB or a pharmaceutically acceptable salt or composition is administered as a stand-alone treatment.

This invention also provides the use Bk-5-MBPB and/or Bk-6-MBPB or a pharmaceutically acceptable salt or composition to treat a maladaptive response to perceived psychological threats. In one embodiment, Bk-5-MBPB and/or Bk-6-MBPB or a pharmaceutically acceptable salt or composition is administered in the context of psychotherapy. In one embodiment, Bk-5-MBPB and/or Bk-6-MBPB or a pharmaceutically acceptable salt or composition is administered as a stand-alone treatment.

Non-Limiting Examples of Pharmacotherapeutic Use

Psychotherapy, cognitive enhancement, or life coaching conducted with the compounds or pharmaceutically acceptable salts as described herein employed as an adjunct (hereafter, "pharmacotherapy") is typically conducted in widely spaced sessions with one, two, or rarely three or more administrations of an entactogen per session. These sessions can be as frequent as weekly, but are more often approximately monthly or even less frequently. In most cases, a small number of pharmacotherapy sessions, on the order of one to three, is needed for the patient to experience significant clinical progress, as indicated, for example, by a reduction in signs and symptoms of mental distress, by improvement in functioning in some domain of life, by arrival at a satisfactory solution to some problem, or by increased feelings of closeness to and understanding of some other person. In some embodiments, the psychotherapy, cognitive enhancement, or life coaching is conducted with an effective amount of enantiomerically enriched S-5-MAPB, R-5-MAPB, S-6-MAPB, and/or R-6-MAPB or a pharmaceutically acceptable salt thereof. In some embodiments, the psychotherapy, cognitive enhancement, or life coaching is conducted with an effective amount of enantiomerically enriched Bk-5-MAPB and/or Bk-6-MAPB or a pharmaceutically acceptable salt thereof. Alternatively, the psychotherapy, cognitive enhancement, or life coaching is conducted with an effective amount of enantiomerically enriched Bk-5-MBPB and/or Bk-6-MBPB or a pharmaceutically acceptable salt thereof. In one embodiment, the psychotherapy, cognitive enhancement, or life coaching is conducted with an effective amount of enantiomerically enriched Formula A and/or Formula B or a pharmaceutically acceptable salt thereof. In one embodiment, the psychotherapy, cognitive enhancement, or life coaching is conducted with an effective amount of enantiomerically enriched Formula C and/or Formula D or a pharmaceutically acceptable salt thereof. In one embodiment, the psychotherapy, cognitive enhancement, or life coaching is conducted with an effective amount of enantiomerically enriched Formula E and/or Formula F or a pharmaceutically acceptable salt thereof.

In one embodiment, the psychotherapy, cognitive enhancement, or life coaching is conducted with an effective amount of Formula I, Formula II, Formula III, Formula IV, Formula V, Formula VI, Formula VII, Formula VIII, Formula IX, Formula X, Formula XI, Formula XII, and/or Formula XIII or a pharmaceutically acceptable salt thereof.

In one embodiment, the psychotherapy, cognitive enhancement, or life coaching is conducted with an effective amount of Formula XI, Formula XII, and/or Formula XIII or a pharmaceutically acceptable salt thereof.

The following sections provide detailed examples of pharmacotherapy. While common procedures are described, these are intended as illustrative, non-limiting examples. It is anticipated that the prescribing physician and therapy team may wish to specify different procedures than those described here based on their clinical judgment concerning the needs of the patient.

The example methods of treatment can also be modified with very minor changes to treat multiple patients at once, including couples or families. Hence, "patient" should be understood to mean one or more individuals.

Use of a Compound or Composition of the Present Invention in Conjunction with Conventional Psychotherapy or Coaching In one embodiment, the use of a compound or composition of the present invention as pharmacotherapy is integrated into the patient's ongoing psychotherapy or coaching (hereafter abbreviated as "psychotherapy"). If a patient in need of the pharmacotherapy is not in ongoing psychotherapy, then psychotherapy may be initiated and the pharmacotherapy added later, after the prescribing physician and treating psychotherapist, physician, coach, member of the clergy, or other similar professional or someone acting under the supervision of such a professional (hereafter, "therapist") agree that the pharmacotherapy is indicated and that there have been sufficient meetings between the patient and therapist to establish an effective therapeutic alliance.

If the patient is not experienced with the pharmacotherapy, a conversation typically occurs in which the therapist or other members of the therapy team addresses the patient's questions and concerns about the medicine and familiarizes the patient with the logistics of pharmacotherapy-assisted session. The therapist describes the kinds of experience that can be expected during the pharmacotherapy session. Optionally, parts of this conversation employ written, recorded, or interactive digital explanations, as might be used in the informed consent process in a clinical trial. The therapist may additionally make commitments to support the participant's healthcare and wellness process. In turn, the patient may be asked to make commitments of their own (such as not to hurt themselves or others and to abstain from contraindicated medicines or drugs for an adequate period before and after the pharmacotherapy).

The compounds and compositions of the invention (or alternately herein for convenience, the "medicine") is administered shortly before or during a scheduled psychotherapy session, with timing optionally selected so that therapeutic effects begin by the time the psychotherapy session begins. Either shortly before or after administration of the medicine, it is common for the therapist to provide some reminder of their mutual commitments and expected events during the session.

The psychotherapy session is carried out by the therapist, who, optionally, may be remote and in communication with the patient using a communication means suitable for telehealth or telemedicine, such as a phone, video, or other remote two-way communication method. Optionally, video or other monitoring of the patient's response or behavior is used to document or measure the session. The therapist uses their clinical judgment and available data to adjust the session to the needs of the patient. Many therapists view their responsibility as being to facilitate rather than direct the patient's experience. This may sometimes involve silent empathic listening, while other times it may include more active support to help the patient arrive at new perspectives on their life.

It is anticipated that the therapeutic effects of the medicine will allow the patient to make more rapid therapeutic progress than would normally be possible. These effects include decreased neuroticism and increased feelings of authenticity. Patients are often able to calmly contemplate actual or possible experiences that would normally be upsetting or even overwhelming. This can facilitate decision making and creativity in addition to mental wellness.

Optionally, the prescribing physician may allow a second or even third administration of the medicine or another psychotherapeutic agent in order to extend the therapeutic effects. Optionally, a pharmaceutical preparation with modified release is employed to make this unnecessary.

Because the duration of the scheduled psychotherapy session may be shorter than the therapeutic effects of the medicine, the therapist may suggest to the patient activities to support further psychotherapeutic progress after the psychotherapy session has ended. Alternatively, the therapist may continue to work with the patient until the therapeutic effects of the medicine have become clinically minimal.

In a subsequent non-pharmacological psychotherapy session, the therapist and patient will typically discuss the patient's experiences from the pharmacotherapy session and the therapist will often aid the patient in recalling the therapeutic effects and help them to incorporate the experiences into their everyday lives.

Pharmacotherapy sessions may be repeated as needed, based on the judgment of the treating physician and therapy team regarding the needs of the patient.

Use of a Compound or Composition of the Present Invention Outside of Conventional Psychotherapy In one embodiment, a compound or composition of the present invention is administered outside of a conventional psychotherapy. This example method is a broader, more flexible approach to pharmacotherapy that is not centered on supervision by a therapist. These pharmacotherapy sessions can take place in many different quiet and safe settings, including the patient's home. The setting is typically chosen to offer a quiet setting, with minimal disruptions, where the patient feels psychologically safe and emotionally relaxed. The setting may be the patient's home but may alternatively be a clinic, retreat center, or hotel room.

In one alternative embodiment, the medicine is taken by the patient regularly to maintain therapeutic concentrations of the active compound in the blood. In another alternative embodiment, the medicine is taken, as needed, for defined psychotherapy sessions.

Optionally, a checklist may be followed to prepare the immediate environment to minimize distractions and maximize therapeutic or decision-making benefits. This checklist can include items such as silencing phones and other communications devices, cleaning and tidying the environment, preparing light refreshments, preparing playlists of appropriate music, and pre-arranging end-of-session transportation if the patient is not undergoing pharmacotherapy at home.

Before the pharmacotherapy session, there may be an initial determination of the therapeutic or other life-related goals (for example, decision-making, increasing creativity, or simply appreciation of life) that will be a focus of the session. These goals can optionally be determined in advance with support from a therapist.

Optionally, the therapist may help the patient select stimuli, such as photographs, videos, augmented or virtual reality scenes, or small objects such as personal possessions, that will help focus the patient's attention on the goals of the session or on the patient's broader life journey. As examples that are intended to be illustrative and not restrictive, these stimuli can include photographs of the patient from when they were young, which can increase self-compassion, or can include stimuli relating to traumatic events or phobias experienced by the patient, which can help the patient reevaluate and change their response to such stimuli. Optionally, the patient selects these stimuli without assistance (e.g., without the involvement of the therapist) or does not employ any stimuli. Optionally, stimuli are selected in real time by the therapist or an algorithm based on the events of the session with the goal of maximizing benefits to the patient.

If the patient is not experienced with the pharmacotherapy, a conversation occurs in which the therapist addresses the patient's questions and concerns about the medicine and familiarizes the patient with the logistics of a pharmacotherapy-assisted session. The therapist describes the kinds of experience that can be expected during the pharmacotherapy-assisted session. Optionally, parts of this conversation employ written, recorded, or interactive digital explanations, as might be used in the informed consent process in a clinical trial. The therapist may additionally make commitments to support the participant's healthcare and wellness process. In turn, the patient may be asked to make commitments of their own (such as not to hurt themselves or others and to abstain from contraindicated medicines or drugs for an adequate period before and after the pharmacotherapy).

Selected session goals and any commitments or other agreements regarding conduct between the patient and therapy team are reviewed immediately before administration of the medicine. Depending on the pharmaceutical preparation and route of administration, the therapeutic effects of the medicine usually begin within one hour. Typical therapeutic effects include decreased neuroticism and increased feelings of authenticity. Patients are often able to calmly contemplate experiences or possible experiences that would normally be upsetting or even overwhelming. This can facilitate decision making and creativity in addition to mental wellness.

Optionally, sleep shades and earphones with music or soothing noise may be used to reduce distractions from the environment. Optionally, a virtual reality or immersive reality system may be used to provide stimuli that support the therapeutic process. Optionally, these stimuli are preselected; optionally, they are selected in real time by a person or an algorithm based on events in the session with the goal of maximizing benefits to the patient. Optionally, a therapist or other person well-known to the patient is present or available nearby or via phone, video, or other communication method in case the patient wishes to talk, however the patient may optionally undergo a session without the assistance of a therapist. Optionally, the patient may write or create artwork relevant to the selected session goals. Optionally, the patient may practice stretches or other beneficial body movements, such as yoga ("movement activity").

Optionally, in other embodiments the patient may practice movement activity that includes more vigorous body movements, such as dance or other aerobic activity. Movement activity also may make use of exercise equipment such as a treadmill or bicycle.

In some additional embodiments, the patient may be presented with music, video, auditory messages, or other perceptual stimuli. Optionally, these stimuli may be adjusted based on the movements or other measurable aspects of the patient. Such adjustment may be done by the therapist with or without the aid of a computer, or by a computer alone in response to said patient aspects, including by an algorithm or artificial intelligence, and "computer" broadly meaning any electronic tool suitable for such purposes, whether worn or attached to a patient (e.g., watches, fitness trackers, "wearables," and other personal devices; biosensors or medical sensors; medical devices), whether directly coupled or wired to a patient or wirelessly connected (and including desktop, laptop, and notebook computers; tablets, smartphones, and other mobile devices; and the like), and whether within the therapy room or remote (e.g., cloud-based systems).

For example, measurable aspects of a patient (e.g., facial expression, eye movements, respiration rate, pulse rate, skin color change, patient voice quality or content, patient responses to questions) from these tools may be individually transformed into scores on standardized scales by subtracting a typical value and then multiplying by a constant and these scores may be further multiplied by constants and added together to create an overall score that can optionally be transformed by multiplication with a link function, such as the logit function, to create an overall score. This score may be used to select or adjust stimuli such as selecting music with higher or lower beats-per-minute or with faster or slower notes, selecting images, audio, or videos with different emotionality or autobiographical meaning, or selecting activities for the patient to engage in (such as specific movements, journaling prompts, or meditation mantras).

It should be readily appreciated that a patient can participate in numerous therapeutically beneficial activities, where such participation follows or is in conjunction with the administration of a compound or composition of the invention, including writing about a preselected topic, engaging in yoga or other movement activity, meditating, creating art, viewing of photographs or videos or emotionally evocative objects, using a virtual reality or augmented reality system, talking with a person, and thinking about a preselected problem or topic, and it should be understood that such participation can occur with or without the participation or guidance of a therapist.

Optionally, the prescribing physician may allow a second or even third administration of the medicine or another psychotherapeutic agent in order to extend the therapeutic effects. Optionally, a pharmaceutical preparation with modified release is employed to make this unnecessary.

The patient typically remains in the immediate environment until the acute therapeutic effects of the medicine are clinically minimal, usually within eight hours. After this point, the session is considered finished.

The treatment plan will often include a follow-up session with a therapist. This follow-up session occurs after the pharmacotherapy session has ended, often the next day but sometimes several days later. In this session, the patient discusses their experiences from the pharmacotherapy session with the therapist, who can aid them in recalling the therapeutic effects and help them to incorporate the experiences into their everyday lives.

Pharmacotherapy sessions may be repeated as needed, based on the judgment of the treating physician and therapy team regarding the needs of the patient.

IV. Pharmaceutical Compositions and Salts

The compounds and compositions described herein can be administered in an effective amount as the neat chemical but are more typically administered as a pharmaceutical composition for a host, typically a human, in need of such treatment in an effective amount for any of the disorders described herein. The compounds or compositions disclosed herein may be administered orally, topically, systemically, parenterally, by inhalation, insufflation, or spray, mucosally (e.g., buccal, sublingual), sublingually, transdermally, rectally, intravenous, intra-aortal, intracranial, subdermal, intraperitoneal, intramuscularly, inhaled, intranasal, subcutaneous, transnasal, or by other means, in dosage unit formulations containing conventional pharmaceutically acceptable carriers. Such compositions are prepared in a manner well known in the pharmaceutical art and comprise at least one active compound. (See, e.g., Remington, 2005, Remington: The science and practice of pharmacy, 21st ed., Lippincott Williams & Wilkins.)

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, a suppository, a buccal or sublingual formulation, a parenteral formulation, an ophthalmic solution, or in a medical device. Some dosage forms, such as tablets and capsules, are subdivided into suitably sized unit doses containing appropriate quantities of the active components, e.g., an effective amount to achieve the desired purpose.

A "pharmaceutically acceptable composition" thus refers to at least one compound (which may be a mixture of enantiomers or diastereomers, as fully described herein) of the invention and a pharmaceutically acceptable vehicle, excipient, diluent or other carrier in an effective amount to treat a host, typically a human, who may be a patient.

In certain nonlimiting embodiments the pharmaceutical composition is a dosage form that contains from about 0.1 mg to about 1500 mg, from about 10 mg to about 1000 mg, from about 100 mg to about 800 mg, or from about 200 mg to about 600 mg of the active compound and optionally from about 0.1 mg to about 1500 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 20, 25, 40, 50, 100, 125, 150, 200, 250, 300, 400, 500, 600, 700, or 750 mg of active compound, or its salt or mixed salt.

The pharmaceutical compositions described herein can be formulated into any suitable dosage form, including tablets, capsules, gelcaps, aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilized formulations, pills, powders, delayed-release formulations, immediate-release formulations, modified release formulations, extended-release formulations, pulsatile release formulations, multi particulate formulations, and mixed immediate release and controlled release formulations. Generally speaking, the composition should be administered in an effective amount to administer an amount of the active agents of the present invention achieves a plasma level commensurate with the concentrations found to be effective in vivo for a period of time effective to elicit a desired therapeutic effect without abuse liability.

In making the compositions employed in the present invention the active ingredient is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets (including orally disintegrating, swallowable, sublingual, buccal, and chewable tablets), pills, powders, lozenges, troches, oral films, thin strips, sachets, cachets, elixirs, suspensions, emulsions, solutions, slurries, syrups, aerosols (as a solid or in a liquid medium), ointments containing for example up to 10% by weight of the active compound, soft and hard gelatin capsules, suppositories, dry powders for inhalation, liquid preparations for vaporization and inhalation, topical preparations, transdermal patches, sterile injectable solutions, and sterile packaged powders. Compositions may be formulated as immediate release, controlled release, sustained (extended) release or modified release formulations.

The compositions of the present invention can be administered by multiple routes, which may differ in different patients according to their preference, co-morbidities, side effect profile, and other factors (IV, PO, transdermal, etc.). In one embodiment, the pharmaceutical composition includes the presence of other substances with the active drugs, known to those skilled in the art, such as fillers, carriers, gels, skin patches, lozenges, or other modifications in the preparation to facilitate absorption through various routes (such as, but not limited to, gastrointestinal, transdermal, etc.) and/or to extend the effect of the drugs, and/or to attain higher or more stable serum levels or to enhance the therapeutic effect of the active drugs in the combination.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, but are not limited to, lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from at least about 0.05 to about 350 mg or less, more preferably at least about 5.0 to about 180 mg or less, of the active ingredients. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier, diluent, or excipient.

The active compounds are effective over a wide dosage range. For example, as-needed dosages normally fall within the range of at least about 0.01 to about 4 mg/kg or less. In the treatment of adult humans, the range of at least about 0.2 to about 3 mg/kg or less, in single dose, is especially preferred.

It will be understood that the amount of the compound actually administered will be determined by a physician, in light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way.

In some instances, dosage levels below the lower limit of the aforesaid range may be more than adequate, while in other cases still larger doses may be employed without causing any harmful side effects, provided for instance that such larger doses may be first divided into several smaller doses for administration.

Generally, the pharmaceutical compositions of the invention may be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Starting and maintenance dosage levels thus may differ from patient to patient, for individual patients across time, and for different pharmaceutical compositions, but shall be able to be determined with ordinary skill.

In one embodiment, a powder comprising the active agents of the present invention described herein may be formulated to comprise one or more pharmaceutical excipients and flavors. Such a powder may be prepared, for example, by mixing the active agents of the present invention and optional pharmaceutical excipients to form a bulk blend composition. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

Oral Formulations

In certain embodiments, any selected compound(s) of the present invention is formulated in an effective amount in an pharmaceutically acceptable oral dosage form. In one embodiment, the compound(s) is 5-MBPB and/or 6-MBPB or a pharmaceutically acceptable salt thereof. In one embodiment, the compound(s) is Bk-5-MAPB and/or Bk-6-MAPB or a pharmaceutically acceptable salt thereof. In one embodiment, the compound(s) is Bk-5-MBPB and/or Bk-6-MBPB or a pharmaceutically acceptable salt thereof. In one embodiment, the compound(s) is Formula A and/or Formula B or a pharmaceutically acceptable salt thereof. In one embodiment, the compound(s) is Formula C and/or Formula D or a pharmaceutically acceptable salt thereof. In one embodiment, the compound(s) is Formula E and/or Formula F or a pharmaceutically acceptable salt thereof. In one embodiment, the compound(s) is a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof. Oral dosage forms may include, but are not limited to, oral solid dosage forms and oral liquid dosage forms. Oral solid dosage forms may include but are not limited to, tablets, capsules, caplets, powders, pellets, multiparticulates, beads, spheres and/or any combinations thereof. The oral solid dosage forms may be formulated as immediate release, controlled release, sustained (extended) release or modified release formulations.

The oral solid dosage forms of the present invention may also contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof.

In some embodiments, the solid dosage forms of the present invention may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including a fast-melt tablet. Additionally, pharmaceutical formulations of the present invention may be administered as a single capsule or in multiple capsule dosage form. In some embodiments, the pharmaceutical formulation is administered in two, or three, or four, capsules or tablets.

The pharmaceutical solid dosage forms described herein can comprise the active agent of the present invention compositions described herein and one or more pharmaceutically acceptable additives such as a compatible carrier, binder, complexing agent, ionic dispersion modulator, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

Alternatively, the pharmaceutical solid dosage forms described herein can comprise the active agent or agents of the present invention (i.e., the "active agent(s)"; but for convenience herein, both "active agent" and "active agents" shall mean "active agent(s)" unless context clearly indicates that what is intended or would be suitable is only one agent or only two or more agents) and one or more pharmaceutically acceptable additives such as a compatible carrier, binder, complexing agent, ionic dispersion modulator, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the active agent of the present invention formulation. In one embodiment, some or all of the active agent of the present invention particles are coated. In another embodiment, some or all of the active agent of the present invention particles are microencapsulated. In yet another embodiment, some or all of the active agent of the present invention is amorphous material coated and/or microencapsulated with inert excipients. In still another embodiment, the active agent of the present invention particles are not microencapsulated and are uncoated.

Suitable carriers for use in the solid dosage forms described herein include acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include lactose, calcium carbonate, calcium phosphate, dibasic calcium phosphate, calcium sulfate, microcrystalline cellulose (e.g., Avicel®, Avicel® PH101, Avicel® PH102, Avicel® PH105, etc.), cellulose powder, dextrose, dextrates, dextrose, dextran, starches, pregelatinized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

If needed, suitable disintegrants for use in the solid dosage forms described herein include natural starch such as corn starch or potato starch, a pregelatinized starch such as National 1551 or Amijel®, or a sodium starch glycolate such as Promogel® or Explotab®, a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, Ac-Di-Sol, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder-filled capsule formulation, they aid in plug formation that can be filled into soft- or hard-shell capsules and in tablet formulation, binders ensure that the tablet remains intact after compression and help assure blend uniformity prior to a compression or fill step. Materials suitable for use as binders in the solid dosage forms described herein include carboxymethylcellulose, methylcellulose (e.g., Methocel®), hydroxypropylmethylcellulose (e.g., Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crosspovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like. In general, binder levels of 20-70% are typically used in powder-filled gelatin capsule formulations. Binder usage level in tablet formulations is a function of whether direct compression, wet granulation, roller compaction, or usage of other excipients such as fillers which itself can act as moderate binders are used. Formulators skilled in the art can determine the binder level for the formulations, but binder usage level of up to 70% in tablet formulations is common.

Suitable lubricants or glidants for use in the solid dosage forms described herein include stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include sugars (including lactose, sucrose, and dextrose), polysaccharides (including dextrates and maltodextrin), polyols (including mannitol, xylitol, and sorbitol), cyclodextrins and the like.

Non-water-soluble diluents are compounds typically used in the formulation of pharmaceuticals, such as calcium phosphate, calcium sulfate, starches, modified starches and microcrystalline cellulose, and micro cellulose (e.g., having a density of about 0.45 g/cm3, e.g. Avicel®, powdered cellulose), and talc.

Suitable wetting agents for use in the solid dosage forms described herein include oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like. Wetting agents include surfactants.

Suitable surfactants for use in the solid dosage forms described herein include docusate and its pharmaceutically acceptable salts, sodium lauryl sulfate, sorbitan monooleate, polyoxyethylene sorbitan monooleate, polysorbates, poloxamers, bile salts, glyceryl monostearate, copolymers of ethylene oxide and propylene oxide, e.g., Pluronic® (BASF), and the like.

Suitable suspending agents for use in the solid dosage forms described here include polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 18000, vinylpyrrolidone/vinyl acetate copolymer (S630), sodium alginate, gums, such as, e.g., gum tragacanth and gum acacia, guar gum, xanthans, including xanthan gum, sugars, cellulosic, such as, e.g., sodium carboxymethylcellulose, methylcellulose, sodium carboxymethylcellulose, hydroxypropylmethylcellulose, hydroxyethylcellulose, polysorbate-80, polyethoxylated sorbitan monolaurate, polyethoxylated sorbitan monolaurate, povidone and the like.

Suitable antioxidants for use in the solid dosage forms described herein include, e.g., butylated hydroxytoluene (BHT), butyl hydroxyanisole (BHA), sodium ascorbate, Vitamin E TPGS, ascorbic acid, sorbic acid and tocopherol.

Immediate-release formulations may be prepared by combining superdisintegrants such as Croscarmellose sodium and different grades of microcrystalline cellulose in different ratios. To aid disintegration, sodium starch glycolate will be added.

The above-listed additives should be taken as merely examples and not limiting, of the types of additives that can be included in solid dosage forms of the present invention. The amounts of such additives can be readily determined by one skilled in the art, according to the particular properties desired.

Oral liquid dosage forms include solutions, emulsions, suspensions, and syrups. These oral liquid dosage forms may be formulated with any pharmaceutically acceptable excipient known to those of skill in the art for the preparation of liquid dosage forms. For example, water, glycerin, simple syrup, alcohol, and combinations thereof.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as but not limited to, an oil, water, an alcohol, and combinations of these pharmaceutically suitable surfactants, suspending agents, emulsifying agents, may be added for oral or parenteral administration. Suspensions may include oils. Such oils include peanut oil, sesame oil, cottonseed oil, corn oil, and olive oil. Suspension preparation may also contain esters of fatty acids such as ethyl oleate, isopropyl myristate, fatty acid glycerides, and acetylated fatty acid glycerides. Suspension formulations may include alcohols, such as ethanol, isopropyl alcohol, hexadecyl alcohol, glycerol, and propylene glycol. Ethers, such as poly(ethylene glycol), petroleum hydrocarbons such as mineral oil and petrolatum, and water may also be used in suspension formulations.

In some embodiments, formulations are provided comprising particles of 5-MAPB and/or 6-MAPB and at least one dispersing agent or suspending agent for oral administration to a subject in need thereof. In some embodiments, formulations are provided comprising particles of 5-MBPB and/or 6-MBPB and at least one dispersing agent or suspending agent for oral administration to a subject in need thereof. In some embodiments, formulations are provided comprising particles of Bk-5-MAPB and/or Bk-6-MAPB and at least one dispersing agent or suspending agent for oral administration to a subject in need thereof. In some embodiments, formulations are provided comprising particles of Bk-5-MBPB and/or Bk-6-MBPB and at least one dispersing agent or suspending agent for oral administration to a subject in need thereof. In some embodiments, formulations are provided comprising particles of compounds of Formula A and/or Formula B and at least one dispersing agent or suspending agent for oral administration to a subject in need thereof. In some embodiments, formulations are provided comprising particles of compounds of Formula C and/or Formula D and at least one dispersing agent or suspending agent for oral administration to a subject in need thereof. In some embodiments, formulations are provided comprising particles of compounds of Formula E and/or Formula F and at least one dispersing agent or suspending agent for oral administration to a subject in need thereof. In some embodiments, formulations are provided comprising particles of Formula I, Formula II, Formula III, Formula IV, Formula V, Formula VI, Formula VII, Formula VIII, Formula IX, or Formula X or a pharmaceutically acceptable salt thereof and at least one dispersing agent or suspending agent for oral administration to a subject in need thereof. In some embodiments, formulations are provided comprising particles of Formula XI, Formula XII, or Formula XIII, or a pharmaceutically acceptable salt thereof and at least one dispersing agent or suspending agent for oral administration to a subject in need thereof.

The formulation may be a powder and/or granules for suspension, and upon admixture with water, a substantially uniform suspension is obtained. As described herein, the aqueous dispersion can comprise amorphous and non-amorphous particles consisting of multiple effective particle sizes such that the drug is absorbed in a controlled manner over time. In certain embodiments, the aqueous dispersion or suspension is an immediate-release formulation. In another embodiment, an aqueous dispersion comprising amorphous particles is formulated such that a portion of the particles of the present invention are absorbed within, e.g., about 0.75 hours after administration and the remaining particles are absorbed 2 to 4 hours after absorption of the earlier particles.

In other embodiments, addition of a complexing agent to the aqueous dispersion results in a larger span of the particles to extend the drug absorption phase of the active agent such that 50-80% of the particles are absorbed in the first hour and about 90% are absorbed by about 4 hours. Dosage forms for oral administration can be aqueous suspensions selected from the group including pharmaceutically acceptable aqueous oral dispersions, emulsions, solutions, and syrups. See, e.g., Singh et al., Encyclopedia of Pharm. Tech., 2nd Ed., 754-757 (2002). In addition to the active agents of the present invention particles, the liquid dosage forms may comprise additives, such as (a) disintegrating agents; (b) dispersing agents; (c) wetting agents; (d) at least one preservative; (e) viscosity enhancing agents; (f) at least one sweetening agent; and (g) at least one flavoring agent.

Examples of disintegrating agents for use in the aqueous suspensions and dispersions include a starch, e.g., a natural starch such as corn starch or potato starch, a pregelatinized starch such as National 1551 or Amijel®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corp., Parsippany, N.J.)).

In other embodiments, the dispersing agent is selected from a group not comprising one of the following agents: hydrophilic polymers; electrolytes; Tween® 60 or 80; PEG; polyvinylpyrrolidone (PVP); hydroxypropyl cellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethylcellulose phthalate; hydroxypropylmethylcellulose acetate stearate; noncrystalline cellulose; magnesium aluminum silicate; triethanolamine; polyvinyl alcohol (PVA); 4-(1,1,3, 3-tetramethyl butyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908® or Poloxamine 908®).

Wetting agents (including surfactants) suitable for the aqueous suspensions and dispersions described herein are known in the art and include acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphatidylcholine and the like.

Suitable preservatives for the aqueous suspensions or dispersions described herein include potassium sorbate, parabens (e.g., methylparaben and propylparaben) and their salts, benzoic acid and its salts, other esters of para hydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

In one embodiment, the aqueous liquid dispersion can comprise methylparaben and propylparaben in a concentration ranging from at least about 0.01% to about 0.3% or less methylparaben by weight to the weight of the aqueous dispersion and at least about 0.005% to about 0.03% or less propylparaben by weight to the total aqueous dispersion weight. In yet another embodiment, the aqueous liquid dispersion can comprise methylparaben from at least about 0.05 to about 0.1 or less weight % and propylparaben from at least about 0.01 to about 0.02 or less weight % of the aqueous dispersion.

Suitable viscosity enhancing agents for the aqueous suspensions or dispersions described herein include methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity-enhancing agent will depend upon the agent selected and the viscosity desired.

In addition to the additives listed above, the liquid formulations of the present invention can also comprise inert diluents commonly used in the art, such as water or other solvents, solubilizing agents, emulsifiers, and/or sweeteners.

In one embodiment, the formulation for oral delivery is an effervescent powder containing 5-MAPB and/or 6-MAPB or a pharmaceutically acceptable salt thereof. In one embodiment, the formulation for oral delivery is an effervescent powder containing 5-MBPB and/or 6-MBPB or a pharmaceutically acceptable salt thereof. In one embodiment, the formulation for oral delivery is an effervescent powder containing Bk-5-MAPB and/or Bk-6-MAPB or a pharmaceutically acceptable salt thereof. In one embodiment, the formulation for oral delivery is an effervescent powder containing Bk-5-MBPB and/or Bk-6-MBPB or a pharmaceutically acceptable salt thereof. In one embodiment, the formulation for oral delivery is an effervescent powder containing Formula A and/or Formula B or a pharmaceutically acceptable salt thereof. In one embodiment, the formulation for oral delivery is an effervescent powder containing Formula C and/or Formula D or a pharmaceutically acceptable salt thereof. Effervescent salts have been used to disperse medicines in water for oral administration. In one embodiment, the formulation for oral delivery is an effervescent powder containing Formula E and/or Formula F or a pharmaceutically acceptable salt thereof. In one embodiment, the formulation for oral delivery is an effervescent powder containing a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof. Effervescent salts have been used to disperse medicines in water for oral administration. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the present invention are added to water, the acids and the base react to liberate carbon dioxide gas, thereby causing "effervescence." Examples of effervescent salts include sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

Tablets of the invention described here can be prepared by methods well known in the art. Various methods for the preparation of the immediate release, modified release, controlled release, and extended-release dosage forms (e.g., as matrix tablets, tablets having one or more modified, controlled, or extended-release layers, etc.) and the vehicles therein are well known in the art. Generally recognized compendia of methods include: Remington: The Science and Practice of Pharmacy, Alfonso R. Gennaro, Editor, 20th Edition, Lippincott Williams & Wilkins, Philadelphia, PA; and Sheth et al. (1980), Compressed tablets, in Pharmaceutical dosage forms, Vol. 1, edited by Lieberman and Lachtman, Dekker, NY.

In certain embodiments, solid dosage forms, e.g., tablets, effervescent tablets, and capsules, are prepared by mixing the active agents of the present invention particles with one or more pharmaceutical excipients to form a bulk blend composition. When referring to these bulk blend compositions as homogeneous, it is meant that the active agents of the present invention particles are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluents. These the active agents of the present invention formulations can be manufactured by conventional pharmaceutical techniques.

Conventional pharmaceutical techniques for preparation of solid dosage forms include, e.g., one or a combination of methods: (1) dry mixing, (2) direct compression, (3) milling, (4) dry or non-aqueous granulation, (5) wet granulation, or (6) fusion. See, e.g., Lachman et al., Theory and Practice of Industrial Pharmacy (1986). Other methods include, e.g., spray drying, pan coating, melt granulation, granulation, fluidized bed spray drying or coating (e.g., Wurster coating), tangential coating, top spraying, tableting, extruding and the like.

Compressed tablets are solid dosage forms prepared by compacting the bulk blend the active agents of the present invention formulations described above. In various embodiments, compressed tablets which are designed to dissolve in the mouth will comprise one or more flavoring agents. In other embodiments, the compressed tablets will comprise a film surrounding a final compressed tablet. In some embodiments, the film coating can provide a delayed release of the active agents of the present invention formulation. In other embodiments, the film coating aids in patient compliance (e.g., Opadry® coatings or sugar coating). Film coatings comprising Opadry® typically range from about 1% to about 3% of the tablet weight. Film coatings for delayed-release usually comprise 2-6% of a tablet weight or 7-15% of a spray-layered bead weight. In other embodiments, the compressed tablets comprise one or more excipients.

A capsule may be prepared, e.g., by placing the bulk blend of the active agents of the present invention formulation, described above, inside of a capsule. In some embodiments, the formulations of the present invention (non-aqueous suspensions and solutions) are placed in a soft gelatin capsule. In other embodiments, the formulations of the present invention are placed in standard gelatin capsules or non-gelatin capsules such as capsules comprising HPMC. In other embodiments, the formulations of the present invention are placed in a sprinkle capsule, wherein the capsule may be swallowed whole or the capsule may be opened and the contents sprinkled on food prior to eating. In some embodiments of the present invention, the therapeutic dose is split into multiple (e.g., two, three, or four) capsules. In some embodiments, the entire dose of the active agents of the present invention is delivered in a capsule form.

In certain embodiments, ingredients (including or not including the active agent) of the invention are wet granulated. The individual steps in the wet granulation process of tablet preparation include milling and sieving of the ingredients, dry powder mixing, wet massing, granulation, drying, and final grinding. In various embodiments, the active agents of the present invention composition are added to the other excipients of the pharmaceutical formulation after they have been wet granulated. Alternatively, the ingredients may be subjected to dry granulation, e.g., via compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps.

In some embodiments, the active agents of the present invention formulation are dry granulated with other excipients in the pharmaceutical formulation. In other embodiments, the active agents of the present invention formulation are added to other excipients of the pharmaceutical formulation after they have been dry granulated.

In other embodiments, the formulation of the present invention formulations described herein is a solid dispersion. Methods of producing such solid dispersions are known in the art and include U.S. Pat. Nos. 4,343,789; 5,340,591; 5,456,923; 5,700,485; 5,723,269; and U.S. Pub. No. 2004/0013734. In some embodiments, the solid dispersions of the invention comprise both amorphous and non-amorphous active agents of the present invention and can have enhanced bioavailability as compared to conventional active agents of the present invention formulations. In still other embodiments, the active agents of the present invention formulations described herein are solid solutions. Solid solutions incorporate a substance together with the active agent and other excipients such that heating the mixture results in the dissolution of the drug and the resulting composition is then cooled to provide a solid blend that can be further formulated or directly added to a capsule or compressed into a tablet.

Non-Limiting Examples of Formulations for Oral Delivery

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| S-6-MAPB | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| 6-MBPB (100% R-enantiomer) | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| Compound of Formula B (100% R-enantiomer) | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| compound of Formula D (100% R-enantiomer) | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| Bk-6-MAPB (100% R-enantiomer) | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
| --- | --- |
| Compound of Formula F (100% R-enantiomer) | 30.0 |
| Starch | 205.0 |
| Alpha lipoic acid | 100.0 |
| Magnesium stearate | 5.0 |

In one non-limiting embodiment, a tablet formulation is prepared comprising the ingredients below. The components are blended and compressed to form tablets, each weighing 240 mg.

| Ingredient | Quantity (mg/tablet) |
| --- | --- |
| R-5-MAPB | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
| --- | --- |
| 6-MBPB (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
| --- | --- |
| Compound of Formula B (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
| --- | --- |
| Compound of Formula D (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
| --- | --- |
| Bk-6-MAPB (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
| --- | --- |
| Compound of Formula F (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet, comprising the components below, including R-6-MAPB and S-6-MAPB, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
| --- | --- |
| R-6-MAPB | 20.0 |
| S-6-MAPB | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including R-5-MBPB and 6-MBPB, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
| --- | --- |
| 5-MBPB (R-enantiomer) | 20.0 |
| 6-MBPB (Racemic) | 10.0 |
| Starch | 45.0 |

| Ingredient | Quantity (mg/tablet) |
| --- | --- |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including an R-enantiomer of a compound of Formula A and a racemic compound of Formula B, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
| --- | --- |
| Compound of Formula A (R-enantiomer) | 20.0 |
| Compound of Formula B (Racemic) | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including an R-enantiomer of a compound of Formula C and a racemic compound of Formula D, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
| --- | --- |
| compound of Formula C (R-enantiomer) | 20.0 |
| compound of Formula D (Racemic) | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including R-Bk-5-MAPB and Bk-6-MAPB, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
| --- | --- |
| Bk-5-MAPB (R-enantiomer) | 20.0 |
| Bk-6-MAPB (Racemic) | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including an R-enantiomer of a compound of Formula E and a racemic compound of Formula F, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
| --- | --- |
| Compound of Formula E (R-enantiomer) | 20.0 |
| Compound of Formula F (Racemic) | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a capsule, comprising the components below, including R-5-MAPB and S-5-MAPB, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| S-5-MAPB | 10.0 |
| R-5-MAPB | 30.0 |
| Starch | 109.0 |
| Magnesium stearate | 1.0 |

In one non-limiting embodiment, a capsule, comprising the components below, including R-6-MBPB and 5-MBPB, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| 5-MBPB (racemic) | 10.0 |
| 6-MBPB (R-enantiomer) | 30.0 |
| Starch | 109.0 |
| Magnesium stearate | 1.0 |

In one non-limiting embodiment, a capsule, comprising the components below, including a racemic compound of Formula A and an R-enantiomer of a compound of Formula B, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| Compound of Formula A (racemic) | 10.0 |
| Compound of Formula B (R-enantiomer) | 30.0 |
| Starch | 109.0 |
| Magnesium stearate | 1.0 |

In one non-limiting embodiment, a capsule, comprising the components below, including a racemic compound of Formula C and an R-enantiomer of a compound of Formula D, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| compound of Formula C (racemic) | 10.0 |
| compound of Formula D (R-enantiomer) | 30.0 |
| Starch | 109.0 |
| Magnesium stearate | 1.0 |

In one non-limiting embodiment, a capsule, comprising the components below, including R-Bk-6-MAPB and Bk-5-MAPB, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| Bk-5-MAPB (racemic) | 10.0 |
| Bk-6-MAPB (R-enantiomer) | 30.0 |
| Starch | 109.0 |
| Magnesium stearate | 1.0 |

In one non-limiting embodiment, a capsule, comprising the components below, including a racemic compound of Formula E and an R-enantiomer of a compound of Formula F, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| Compound of Formula E (racemic) | 10.0 |
| Compound of Formula F (R-enantiomer) | 30.0 |
| Starch | 109.0 |
| Magnesium stearate | 1.0 |

In one non-limiting embodiment, a capsule, comprising 15 mg of S-5-MAPB, is prepared using the ingredients below. The active ingredient, cellulose, starch, and magnesium stearate are blended, passed through a No. 20 mesh U.S. sieve, and filled into hard gelatin capsules in 425 mg quantities.

| Ingredient | Amount (mg/capsule) |
| --- | --- |
| S-5-MAPB | 15.0 |
| Starch | 407.0 |
| Magnesium stearate | 3.0 |

In one non-limiting embodiment, a capsule, comprising 100 mg of R-5-MBPB, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
| --- | --- |
| 5-MBPB (R-enantiomer) | 100.0 |
| Starch | 407.0 |
| Magnesium stearate | 3.0 |

In one non-limiting embodiment, a capsule, comprising 100 mg of an R-enantiomer of a compound of Formula A, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
| --- | --- |
| Compound of Formula A (R-enantiomer) | 100.0 |
| Starch | 407.0 |
| Magnesium stearate | 3.0 |

In one non-limiting embodiment, a capsule, comprising 100 mg of an R-enantiomer of a compound of Formula C, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
| --- | --- |
| compound of Formula C (R-enantiomer) | 100.0 |
| Starch | 407.0 |
| Magnesium stearate | 3.0 |

In one non-limiting embodiment, a capsule, comprising 100 mg of R-Bk-5-MAPB, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
| --- | --- |
| Bk-5-MAPB (R-enantiomer) | 100.0 |
| Starch | 407.0 |
| Magnesium stearate | 3.0 |

In one non-limiting embodiment, a capsule, comprising 100 mg of an R-enantiomer of a compound of Formula E, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
| --- | --- |
| Compound of Formula E (R-enantiomer) | 100.0 |
| Starch | 407.0 |
| Magnesium stearate | 3.0 |

Extended-Release Formulations

Depending on the desired release profile, the pharmaceutical formulation, for example, an oral solid dosage form, may contain a suitable amount of controlled-release agents, extended-release agents, and/or modified-release agents (e.g., delayed-release agents). The pharmaceutical solid oral dosage forms comprising the active agents of the present invention described herein can be further formulated to provide a modified or controlled release of the active agents of the present invention. In some embodiments, the solid dosage forms described herein can be formulated as a delayed release dosage form such as an enteric-coated delayed release oral dosage forms, i.e., as an oral dosage form of a pharmaceutical composition as described herein which utilizes an enteric coating to affect release in the small intestine of the gastrointestinal tract. The enteric-coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated. Enteric coatings may also be used to prepare other controlled release dosage forms including extended-release and pulsatile release dosage forms.

In other embodiments, the active agents of the formulations described herein are delivered using a pulsatile dosage form. Pulsatile dosage forms comprising the active agents of the present invention described herein may be administered using a variety of formulations known in the art. For example, such formulations include those described in U.S. Pat. Nos. 5,011,692; 5,017,381; 5,229,135; and 5,840,329. Other dosage forms suitable for use with the active agents of the present invention are described in, for example, U.S. Pat. Nos. 4,871,549; 5,260,068; 5,260,069; 5,508,040; 5,567, 441; and 5,837,284.

In one embodiment, the controlled release dosage form is pulsatile release solid oral dosage form comprising at least two groups of particles, each containing active agents of the present invention as described herein. The first group of particles provides a substantially immediate dose of the active agents of the present invention upon ingestion by a subject. The first group of particles can be either uncoated or comprise a coating and/or sealant. The second group of particles comprises coated particles, which may comprise from at least about 2% to about 75% or less, preferably from at least about 2.5% to about 70% or less, or from at least about 40% to about 70% or less, by weight of the total dose of the active agents of the present invention in said formulation, in admixture with one or more binders.

In one embodiment, a coating for providing a controlled, delayed, or extended-release is applied to 5-MAPB and/or 6-MAPB or to a core containing 5-MAPB and/or 6-MAPB. In one embodiment, a coating for providing a controlled, delayed, or extended-release is applied to 5-MBPB and/or 6-MBPB or to a core containing 5-MBPB and/or 6-MBPB. In one embodiment, a coating for providing a controlled, delayed, or extended-release is applied to Bk-5-MAPB and/or Bk-6-MAPB or to a core containing Bk-5-MAPB and/or Bk-6-MAPB. In one embodiment, a coating for providing a controlled, delayed, or extended-release is applied to Bk-5-MBPB and/or Bk-6-MBPB or to a core containing Bk-5-MBPB and/or Bk-6-MBPB. In one embodiment, a coating for providing a controlled, delayed, or extended-release is applied to Formula A and/or Formula B or to a core containing Formula A and/or Formula B. In one embodiment, a coating for providing a controlled, delayed, or extended-release is applied to Formula C and/or Formula D or to a core containing Formula C and/or Formula D. In one embodiment, a coating for providing a controlled, delayed, or extended-release is applied to Formula E and/or Formula F or to a core containing Formula E and/or Formula F. In one embodiment, a coating for providing a controlled, delayed, or extended-release is applied to Formula I, Formula II, Formula III, Formula IV, Formula V, Formula VI, Formula VII, Formula VIII, Formula IX, Formula X, Formula XI, Formula XII, or Formula XIII or to a core containing Formula I, Formula II, Formula III, Formula IV, Formula V, Formula VI, Formula VII, Formula VIII, Formula IX, Formula X, Formula XI, Formula XII, or Formula XIII.

The coating may comprise a pharmaceutically acceptable ingredient in an amount sufficient, e.g., to provide an extended release from e.g., about 1 hours to about 7 hours following ingestion before release of the active agent. Suitable coatings include one or more differentially degradable coatings such as, by way of example only, pH-sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the active agents of the present invention formulation.

Many other types of controlled/delayed/extended-release systems known to those of ordinary skill in the art and are suitable for use with the active agents of the present invention formulations described herein. Examples of such delivery systems include polymer-based systems, such as polylactic and polyglycolic acid, polyanhydrides and polycaprolactone, cellulose derivatives (e.g., ethylcellulose), porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp.

751-753 (2002); U.S. Pat. Nos. 4,327,725; 4,624,848; 4,968,509; 5,461,140; 5,456,923, 5,516,527; 5,622,721, 5,686,105; 5,700,410; 5,977,175; 6,465,014 and 6,932,983.

In certain embodiments, the controlled release systems may comprise the controlled/delayed/extended-release material incorporated with the drug(s) into a matrix, whereas in other formulations, the controlled release material may be applied to a core containing the drug(s). In certain embodiments, one drug may be incorporated into the core while the other drug is incorporated into the coating. In some embodiments, materials include shellac, acrylic polymers, cellulosic derivatives, polyvinyl acetate phthalate, and mixtures thereof. In other embodiments, materials include Eudragit® series E, L, RL, RS, NE, L, L300, S, 100-55, cellulose acetate phthalate, Aquateric, cellulose acetate trimellitate, ethyl cellulose, hydroxypropylmethylcellulose phthalate, hydroxypropylmethylcellulose acetate succinate, polyvinyl acetate phthalate, and Cotteric.

The controlled/delayed/extended-release systems may utilize a hydrophilic polymer, including a water-swellable polymer (e.g., a natural or synthetic gum). The hydrophilic polymer may be any pharmaceutically acceptable polymer which swells and expands in the presence of water to slowly release the active agents of the present invention. These polymers include polyethylene oxide, methylcellulose, hydroxypropyl cellulose, hydroxypropylmethylcellulose, and the like.

The performance of acrylic polymers (primarily their solubility in biological fluids) can vary based on the degree and type of substitution. Examples of suitable acrylic polymers which may be used in matrix formulations or coatings include methacrylic acid copolymers and ammonia methacrylate copolymers. The Eudragit series E, L, S, RL, RS and NE (Rohm Pharma) are available as solubilized in an organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in the stomach and dissolve in the intestine; Opadry Enteric is also insoluble in the stomach and dissolves in the intestine.

Examples of suitable cellulose derivatives for use in matrix formulations or coatings include ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous-based system and is a spray-dried CAP psuedolatex with particles <1 μm. Other components in Aquateric can include pluronic, Tweens, and acetylated monoglycerides. Other suitable cellulose derivatives include cellulose acetate trimellitate (Eastman); methylcellulose (Pharmacoat, Methocel); hydroxypropylmethylcellulose phthalate (HPMCP); hydroxypropylmethylcellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, HP-55F grades are suitable. The performance can vary based on the degree and type of substitution. For example, suitable grades of hydroxypropylmethylcellulose acetate succinate include AS-LG (LF), which dissolves at pH 5, AS-MG (MF), which dissolves at pH 5.5, and AS-HG (HF), which dissolves at higher pH. These polymers are offered as granules or as fine powders for aqueous dispersions. Other suitable cellulose derivatives include hydroxypropylmethylcellulose.

In some embodiments, the coating may contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate, and triacetin. Conventional coating techniques such as spray or pan coating are employed to apply coatings. The coating thickness must be sufficient to ensure that the oral dosage form remains intact until the desired site of topical delivery in the intestinal tract is reached.

Multilayer tablet delivery (e.g., such as that used in the GeoMatrix™ technology) comprises a hydrophilic matrix core containing the active ingredient and one or two impermeable or semi-permeable polymeric coatings. This technology uses films or compressed polymeric barrier coatings on one or both sides of the core. The presence of polymeric coatings (e.g., such as that used in the GeoMatrix™ technology) modifies the hydration/swelling rates of the core and reduces the surface area available for drug release. These partial coatings provide modulation of the drug dissolution profile: they reduce the release rate from the device and shift the typical time-dependent release rate toward constant release. This technology enables customized levels of controlled release of specific active agents and/or simultaneous release of two different active agents at different rates that can be achieved from a single tablet. The combination of layers, each with different rates of swelling, gelling and erosion, is used for the rate of drug release in the body. Exposure of the multilayer tablet as a result of the partial coating may affect the release and erosion rates, therefore, transformation of a multilayered tablet with exposure on all sides to the gastrointestinal fluids upon detachment of the barrier layer will be considered.

Multi-layered tablets containing combinations of immediate release and modified/extended release of two different active agents or dual release rate of the same drug in a single dosage form may be prepared by using hydrophilic and hydrophobic polymer matrices. Dual release repeat action multi-layered tablets may be prepared with an outer compression layer with an initial dose of rapidly disintegrating matrix in the stomach and a core inner layer tablet formulated with components that are insoluble in the gastric media but release efficiently in the intestinal environment.

In one embodiment, the dosage form is a solid oral dosage form which is an immediate release dosage form whereby >80% of the active agents of the present invention are released within 2 hours after administration. In other embodiments, the invention provides an (e.g., solid oral) dosage form that is a controlled release or pulsatile release dosage form. In such instances, the release may be, e.g., 30 to 60% of the active agents of the present invention particles by weight are released from the dosage form within about 2 hours after administration and about 90% by weight of the active agents of the present invention released from the dosage form, e.g., within about 4 hours after administration. In yet other embodiments, the dosage form includes at least one active agent in an immediate-release form and at least one active agent in the delayed-release form or sustained-release form. In yet other embodiments, the dosage form includes at least two active agents that are released at different rates as determined by in-vitro dissolution testing or via oral administration.

The various release dosage formulations discussed above, and others known to those skilled in the art can be characterized by their disintegration profile. A profile is characterized by the test conditions selected. Thus, the disintegration profile can be generated at a pre-selected apparatus type, shaft speed, temperature, volume, and pH of the dispersion media. Several disintegration profiles can be obtained. For example, a first disintegration profile can be measured at a pH level approximating that of the stomach (about pH 1.2); a second disintegration profile can be measured at a pH level approximating that of one point in the intestine or several pH levels approximating multiple points in the intestine (about 6.0 to about 7.5, more specifically, about 6.5 to 7.0). Another disintegration profile can be measured using distilled water. The release of formulations may also be characterized by their pharmacokinetic parameters, for example, Cmax, Tmax, and AUC (0-τ).

In certain embodiments, the controlled, delayed or extended-release of one or more of the active agents of the fixed-dose combinations of the invention may be in the form of a capsule having a shell comprising the material of the rate-limiting membrane, including any of the coating materials previously discussed, and filled with the active agents of the present invention particles. A particular advantage of this configuration is that the capsule may be prepared independently of the active agent of the present invention particles; thus, process conditions that would adversely affect the drug can be used to prepare the capsule.

Alternatively, the formulation may comprise a capsule having a shell made of a porous or a pH-sensitive polymer made by a thermal forming process. Another alternative is a capsule shell in the form of an asymmetric membrane, i.e., a membrane that has a thin skin on one surface and most of whose thickness is constituted of a highly permeable porous material. The asymmetric membrane capsules may be prepared by a solvent exchange phase inversion, wherein a solution of polymer, coated on a capsule-shaped mold, is induced to phase separate by exchanging the solvent with a miscible non-solvent. In another embodiment, spray layered active agents of the present invention particles are filled in a capsule.

An exemplary process for manufacturing the spray layered the active agents of the present invention is the fluidized bed spraying process. The active agents of the present invention suspensions or the active agents of the present invention complex suspensions described above may be sprayed onto sugar or microcrystalline cellulose (MCC) beads (20-35 mesh) with Wurster column insert at an inlet temperature of 50° C. to 60° C. and air temp of 30° C. to 50° C. A 15 to 20 wt % total solids content suspension containing 45 to 80 wt % the active agents of the present invention, 10 to 25 wt % hydroxymethylpropylcellulose, 0.25 to 2 wt % of SLS, 10 to 18 wt % of sucrose, 0.01 to 0.3 wt % simethicone emulsion (30% emulsion) and 0.3 to 10% NaCl, based on the total weight of the solid content of the suspension, are sprayed (bottom spray) onto the beads through 1.2 mm nozzles at 10 mL/min and 1.5 bar of pressure until a layering of 400 to 700% wt % is achieved as compared to initial beads weight. The resulting spray layered the active agents of the present invention particles, or the active agents of the present invention complex particles comprise about 30 to 70 wt % of the active agents of the present invention based on the total weight of the particles.

In one embodiment the capsule is a size 0 soft gelatin capsule. In one embodiment, the capsule is a swelling plug device. In another embodiment, the swelling plug device is further coated with cellulose acetate phthalate or copolymers of methacrylic acid and methylmethacrylate. In some embodiments, the capsule includes at least 40 mg (or at least 100 mg or at least 200 mg) of the active agents of the present invention and has a total weight of less than 800 mg (or less than 700 mg). The capsule may contain a plurality of the active agents of the present invention-containing beads, for example, spray layered beads. In some embodiments, the beads are 12-25% the active agents of the present invention by weight. In some embodiments, some or all of the active agents of the present invention containing beads are coated with a coating comprising 6 to 15% (or 8 to 12%) of the total bead weight. Optimization work typically involves lower loading levels, and the beads constitute 30 to 60% of the finished bead weight. The capsule may contain a granulated composition, wherein the granulated composition comprises the active agents of the present invention.

The capsule may provide pulsatile release of the active agents of the present invention oral dosage form. In one embodiment, the formulations comprise: (a) a first dosage unit comprising 5-MBPB and/or 6-MBPB that is released substantially immediately following oral administration of the dosage form to a patient; (b) a second dosage unit comprising 5-MBPB and/or 6-MBPB that is released approximately 2 to 6 hours following administration of the dosage form to a patient.

The capsule may provide pulsatile release of the active agents of the present invention oral dosage form. In one embodiment, the formulations comprise: (a) a first dosage unit comprising 5-MAPB and/or 6-MAPB that is released substantially immediately following oral administration of the dosage form to a patient; (b) a second dosage unit comprising 5-MAPB and/or 6-MAPB that is released approximately 2 to 6 hours following administration of the dosage form to a patient.

In one embodiment, the formulation comprises: (a) a first dosage unit comprising compounds of Formula A and/or Formula B that is released substantially immediately following oral administration of the dosage form to a patient; (b) a second dosage unit comprising compounds of Formula A and/or Formula B that is released approximately 2 to 6 hours following administration of the dosage form to a patient.

In one embodiment, the formulations comprises: (a) a first dosage unit comprising compounds of Formula C and/or Formula D that is released substantially immediately following oral administration of the dosage form to a patient; (b) a second dosage unit comprising compounds of Formula C and/or Formula D that is released approximately 2 to 6 hours following administration of the dosage form to a patient.

In one embodiment, the formulation comprises: (a) a first dosage unit comprising compounds of Formula E and/or Formula F that is released substantially immediately following oral administration of the dosage form to a patient; (b) a second dosage unit comprising compounds of Formula E and/or Formula F that is released approximately 2 to 6 hours following administration of the dosage form to a patient.

In one embodiment, the formulation comprises: (a) a first dosage unit comprising Bk-5-MAPB and/or Bk-6-MAPB that is released substantially immediately following oral administration of the dosage form to a patient; (b) a second dosage unit comprising Bk-5-MAPB and/or Bk-6-MAPB that is released approximately 2 to 6 hours following administration of the dosage form to a patient.

In one embodiment, the formulation comprises: (a) a first dosage unit comprising Bk-5-MBPB and/or Bk-6-MBPB that is released substantially immediately following oral administration of the dosage form to a patient; (b) a second dosage unit comprising Bk-5-MBPB and/or Bk-6-MBPB that is released approximately 2 to 6 hours following administration of the dosage form to a patient.

In one embodiment, the formulation comprises: (a) a first dosage unit comprising a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof that is released substantially immediately following oral administration of the dosage form to a patient; (b) a second dosage unit comprising a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof that is released approximately 2 to 6 hours following administration of the dosage form to a patient.

For pulsatile release capsules containing beads, the beads can be coated with a coating comprising 6 to 15% (or 8 to 12%) of the total bead weight. In some embodiments, the coating is a coating that is insoluble at pH 1 to 2 and soluble at pH greater than 5.5. In other embodiments, the pulsatile release capsule contains a plurality of beads formulated for modified release and the at least one agent of the present invention is, for example, spray granulated for immediate release.

In some embodiments, the release of the active agents of the present invention particles can be modified with a modified release coating, such as an enteric coating using cellulose acetate phthalate or a sustained release coating comprising copolymers of methacrylic acid and methylmethacrylate. In one embodiment, the enteric coating may be present in an amount of about 0.5 to about 15 wt %, more specifically, about 8 to about 12 wt %, based on the weight of, e.g., the spray layered particles. In one embodiment, the spray layered particles coated with the delayed and/or sustained release coatings can be filled in a modified release capsule in which both enteric-coated particles and immediate release particles of the present invention beads are filled into a soft gelatin capsule. Additional suitable excipients may also be filled with the coated particles in the capsule. The uncoated particles release the active agent of the present invention immediately upon administration while the coated particles do not release the active agent of the present invention until these particles reach the intestine. By controlling the ratios of the coated and uncoated particles, desirable pulsatile release profiles also may be obtained. In some embodiments, the ratios between the uncoated and the coated particles are e.g., 20/80, or 30/70, or 40/60, or 50/50, w/w to obtain desirable release.

In certain embodiments, spray layered active agents of the present invention can be compressed into tablets with commonly used pharmaceutical excipients. Any appropriate apparatus for forming the coating can be used to make the enteric coated tablets, e.g., fluidized bed coating using a Wurster column, powder layering in coating pans or rotary coaters; dry coating by double compression technique; tablet coating by film coating technique, and the like. See, e.g., U.S. Pat. No. 5,322,655; Remington's Pharmaceutical Sciences Handbook: Chapter 90 "Coating of Pharmaceutical Dosage Forms," 1990.

In certain embodiments, the spray layered active agents of the present invention described above and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the active agents of the present invention formulation into the gastrointestinal fluid. In other embodiments, the spray layered active agents of the present invention particles or spray layered active agents complex particles with enteric coatings described above and one or more excipients are dry blended and compressed into a mass, such as a tablet.

In certain embodiments, a pulsatile release of the active agent of the present invention formulation comprises a first dosage unit comprising a formulation made from the active agent of the present invention containing granules made from a spray drying or spray granulated procedure or a formulation made from the active agent of the present invention complex containing granules made from a spray drying or spray granulated procedure without enteric or sustained-release coatings and a second dosage unit comprising spray layered the active agent of the present invention particles or spray layered the active agent of the present invention complex particles with enteric or sustained-release coatings. In one embodiment, the active agent is wet or dry blended and compressed into a mass to make a pulsatile release tablet.

In certain embodiments, binding, lubricating and disintegrating agents are blended (wet or dry) to the spray layered active agent of the present invention to make a compressible blend. In one embodiment, the dosage unit containing 5-MBPB and/or 6-MBPB and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing 5-MBPB and/or 6-MBPB. In yet another embodiment, the dosage unit containing 5-MBPB and/or 6-MBPB is in the form of an overcoat and completely covers the second dosage unit containing the other pharmacological agent.

In certain embodiments, binding, lubricating and disintegrating agents are blended (wet or dry) to the spray layered active agent of the present invention to make a compressible blend. In one embodiment, the dosage unit containing 5-MAPB and/or 6-MAPB and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing 5-MAPB and/or 6-MAPB. In yet another embodiment, the dosage unit containing 5-MAPB and/or 6-MAPB is in the form of an overcoat and completely covers the second dosage unit containing the other pharmacological agent.

In one embodiment, the dosage unit containing Bk-5-MAPB and/or Bk-6-MAPB and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing Bk-5-MAPB and/or Bk-6-MAPB. In yet another embodiment, the dosage unit containing Bk-5-MAPB and/or Bk-6-MAPB is in the form of an overcoat and completely covers the second dosage unit containing the other pharmacological agent.

In one embodiment, the dosage unit containing Bk-5-MBPB and/or Bk-6-MBPB and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing Bk-5-MBPB and/or Bk-6-MBPB. In yet another embodiment, the dosage unit containing Bk-5-MBPB and/or Bk-6-MBPB is in the form of an overcoat and completely covers the second dosage unit containing the other pharmacological agent.

In one embodiment, the dosage unit containing Formula A and/or Formula B and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing Formula A and/or Formula B. In yet another embodiment, the dosage unit containing Formula A and/or Formula B is in the form of an overcoat and completely covers the second dosage unit containing the other pharmacological agent.

In one embodiment, the dosage unit containing Formula C and/or Formula D and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing Formula C and/or Formula D. In yet another embodiment, the dosage unit containing Formula C and/or Formula D is in the form of an overcoat and completely covers the second dosage unit containing the other pharmacological agent.

In one embodiment, the dosage unit containing Formula E and/or Formula F and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing Formula E and/or Formula F. In yet another embodiment, the dosage unit containing Formula E and/or Formula F is in the form of an overcoat and completely covers the second dosage unit containing the other pharmacological agent.

In one embodiment, the dosage unit containing a compound of Formula I, Formula II, Formula III, Formula IV, Formula V, Formula VI, Formula VII, Formula VIII, Formula IX, Formula X, Formula XI, Formula XII, or Formula XIII and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing a compound of Formula I, Formula II, Formula III, Formula IV, Formula V, Formula VI, Formula VII, Formula VIII, Formula IX, Formula X, Formula XI, Formula XII, or Formula XIII. In yet another embodiment, the dosage unit containing a compound of Formula I, Formula II, Formula III, Formula IV, Formula V, Formula VI, Formula VII, Formula VIII, Formula IX, Formula X, Formula XI, Formula XII, or Formula XIII is in the form of an overcoat and completely covers the second dosage unit containing the other pharmacological agent.

Systemic Formulations

The formulations of the present invention can include any selected compound of the present invention for any of the disclosed indications in a form suitable for intramuscular, subcutaneous, or intravenous injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethylene-glycol, glycerol, cremophor and the like), suitable mixtures thereof, vegetable oils (such as olive oil) and injectable organic esters such as ethyl oleate. Additionally, the active agents of the present invention can be dissolved at concentrations of greater than about 1 mg/ml using water-soluble beta cyclodextrins (e.g., beta-sulfobutyl-cyclodextrin and 2-hydroxypropyl-beta-cyclodextrin. Proper fluidity can be maintained, for example, by the use of a coating such as a lecithin, by the maintenance of the required particle size in the case of dispersions, and by the use of surfactants.

The formulations of the present invention suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. The formulations of the present invention designed for extended-release via subcutaneous or intramuscular injection can avoid first-pass metabolism and lower dosages of the active agents of the present invention will be necessary to maintain plasma levels of about 50 ng/ml. In such formulations, the particle size of the active agents of the present invention and the range of the particle sizes of the active agents of the present invention particles can be used to control the release of the drug by controlling the rate of dissolution in fat or muscle.

In one embodiment, a pharmaceutical composition containing 5-MAPB and/or 6-MAPB or a pharmaceutically acceptable salt thereof is formulated into a dosage form suitable for parenteral use. In one embodiment, a pharmaceutical composition containing 5-MBPB and/or 6-MBPB or a pharmaceutically acceptable salt thereof is formulated into a dosage form suitable for parenteral use. In one embodiment, pharmaceutical compositions containing compounds of Formula A and/or Formula B or a pharmaceutically acceptable salt thereof is formulated into a dosage form suitable for parenteral use. In one embodiment, pharmaceutical compositions containing compounds of Formula C and/or Formula D or a pharmaceutically acceptable salt thereof is formulated into a dosage form suitable for parenteral use. In one embodiment, pharmaceutical compositions containing Bk-5-MAPB and/or Bk-6-MAPB or a pharmaceutically acceptable salt thereof is formulated into a dosage form suitable for parenteral use. In one embodiment, pharmaceutical compositions containing Bk-5-MBPB and/or Bk-6-MBPB or a pharmaceutically acceptable salt thereof is formulated into a dosage form suitable for parenteral use. In one embodiment, pharmaceutical compositions containing compounds of Formula E and/or Formula F or a pharmaceutically acceptable salt thereof is formulated into a dosage form suitable for parenteral use. In one embodiment, pharmaceutical compositions containing a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof is formulated into a dosage form suitable for parenteral use. The dosage form may be selected from, but not limited to, a lyophilized powder, a solution, or a suspension (e.g., a depot suspension).

In one embodiment, a pharmaceutical composition containing 5-MBPB and/or 6-MBPB or a pharmaceutically acceptable salt thereof is formulated into a topical dosage form. In one embodiment, a pharmaceutical composition containing Bk-5-MAPB and/or Bk-6-MAPB or a pharmaceutically acceptable salt thereof is formulated into a topical dosage form. In one embodiment, a pharmaceutical composition containing 5-MAPB and/or 6-MAPB or a pharmaceutically acceptable salt thereof is formulated into a topical dosage form. In one embodiment, a pharmaceutical composition containing Bk-5-MBPB and/or Bk-6-MBPB or a pharmaceutically acceptable salt thereof is formulated into a topical dosage form. In one embodiment, a pharmaceutical composition containing Formula A and/or Formula B or a pharmaceutically acceptable salt thereof is formulated into a topical dosage form. In one embodiment, a pharmaceutical composition containing Formula C and/or Formula D or a pharmaceutically acceptable salt thereof is formulated into a topical dosage form. In one embodiment, a pharmaceutical composition containing Formula E and/or Formula F or a pharmaceutically acceptable salt thereof is formulated into a topical dosage form. In one embodiment, a pharmaceutical composition containing a compound of Formula I, Formula II, Formula III, Formula IV, Formula V, Formula VI, Formula VII, Formula VIII, Formula IX, Formula X, Formula XI, Formula XII, or Formula XIII or a pharmaceutically acceptable salt thereof is formulated into a topical dosage form. The topical dosage form is selected from, but not limited to, a patch, a gel, a paste, a cream, an emulsion, a liniment, a balm, a lotion, and an ointment.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Non-Limiting Examples of Formulations for Systemic Delivery

In one non-limiting embodiment, a suppository, comprising 25 mg of S-6-MAPB, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| S-6-MAPB | 25.0 |
| Saturated fatty acid glycerides | 2000.0 |

In one non-limiting embodiment, a suppository, comprising 25 mg of R-5-MBPB, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| R-5-MBPB | 25.0 |
| Saturated fatty acid glycerides | 2000.0 |

In one non-limiting embodiment, a suppository, comprising 25 mg of a compound of Formula A, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| Compound of Formula A (R-enantiomer) | 25.0 |
| Saturated fatty acid glycerides | 2000.0 |

In one non-limiting embodiment, a suppository, comprising 25 mg of a compound of Formula C, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| compound of Formula C (R-enantiomer) | 25.0 |
| Saturated fatty acid glycerides | 2000.0 |

In one non-limiting embodiment, a suppository, comprising 25 mg of R-Bk-5-MAPB, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| R-Bk-5-MAPB | 25.0 |
| Saturated fatty acid glycerides | 2000.0 |

In one non-limiting embodiment, a suppository, comprising 25 mg of a compound of Formula E, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| Compound of Formula E (R-enantiomer) | 25.0 |
| Saturated fatty acid glycerides | 2000.0 |

In one non-limiting embodiment, a suspension comprising 50 mg of S-5-MAPB per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| S-5-MAPB | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of R-5-BPB per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| 5-MBPB (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of an R-enantiomer of a compound of Formula A per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| Compound of Formula A (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of an R-enantiomer of a compound of Formula C per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| compound of Formula C (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of R-Bk-5-MAPB per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| Bk-5-MAPB (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of an R-enantiomer of a compound of Formula E per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
| --- | --- |
| Compound of Formula E (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, an intravenous formulation is prepared using the following ingredients:

| Ingredient | Amount |
| --- | --- |
| R-6-MAPB | 250.0 mg |
| Isotonic saline | 1000 ml |

In one non-limiting embodiment, an intravenous formulation is prepared using the following ingredients:

| Ingredient | Amount |
| --- | --- |
| Compound of Formula B (R-enantiomer of beta-ketone) | 250.0 mg |
| Isotonic saline | 1000 ml |

In one non-limiting embodiment, an intravenous formulation is prepared using the following ingredients:

| Ingredient | Amount |
| --- | --- |
| compound of Formula D (R-enantiomer of beta-ketone) | 250.0 mg |
| Isotonic saline | 1000 ml |

In one non-limiting embodiment, an intravenous formulation is prepared using the following ingredients:

| Ingredient | Amount |
| --- | --- |
| Bk-6-MAPB (R-enantiomer) | 250.0 mg |
| Isotonic saline | 1000 ml |

In one non-limiting embodiment, an intravenous formulation is prepared using the following ingredients:

| Ingredient | Amount |
| --- | --- |
| Compound of Formula F (R-enantiomer) | 250.0 mg |
| Isotonic saline | 1000 ml |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
| --- | --- |
| R-5-MAPB | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
| --- | --- |
| 6-MBPB (S-enantiomer) | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
| --- | --- |
| Compound of Formula B (S-enantiomer) | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
| --- | --- |
| compound of Formula D (S-enantiomer) | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
| --- | --- |
| Bk-6-MAPB (S-enantiomer) | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
|---|---|
| Compound of Formula F (70% S-enantiomer, 30% R) | 10.0 |
| Emulsifying Wax | 30.0 |
| Liquid Paraffin | 20.0 |
| White Soft Paraffin | To 100 |

In one embodiment, a sublingual or buccal tablet, comprising 10 mg of S-5-MAPB, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| S-5-MAPB | 10.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of R-5-MBPB, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| 5-MBPB (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of an R-enantiomer of a compound of Formula A, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| Compound of Formula A (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of an R-enantiomer of a compound of Formula C, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| compound of Formula C (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of R-Bk-5-MAPB, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| Bk-5-MAPB (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of an R-enantiomer of a compound of Formula E, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
| --- | --- |
| Compound of Formula E (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one non-limiting embodiment, a liquid formulation for vaporization comprising R-5-MPBP, is prepared using the ingredients below. The active mixture is mixed and added to a liquid vaporization appliance.

| Ingredient | Quantity (units) |
| --- | --- |
| 5-MPBP (R-enantiomer) | 500 mg |
| Propylene Glycol | 2 ml |
| Glycerin | 2 ml |

In one non-limiting embodiment, a liquid formulation for vaporization comprising a compound of Formula A, is prepared using the ingredients below. The active mixture is mixed and added to a liquid vaporization appliance.

| Ingredient | Quantity (units) |
| --- | --- |
| Compound of Formula A (R-enantiomer) | 500 mg |
| Propylene Glycol | 2 ml |
| Glycerin | 2 ml |

In one non-limiting embodiment, a liquid formulation for vaporization comprising a compound of Formula C, is prepared using the ingredients below. The active mixture is mixed and added to a liquid vaporization appliance.

| Ingredient | Quantity (units) |
| --- | --- |
| compound of Formula C (R-enantiomer) | 500 mg |
| Propylene Glycol | 2 ml |
| Glycerin | 2 ml |

In one non-limiting embodiment, a liquid formulation for vaporization comprising R-Bk-5-MAPB, is prepared using the ingredients below. The active mixture is mixed and added to a liquid vaporization appliance.

| Ingredient | Quantity (units) |
| --- | --- |
| Bk-5-MAPB (R-enantiomer) | 500 mg |
| Propylene Glycol | 2 ml |
| Glycerin | 2 ml |

In one non-limiting embodiment, a liquid formulation for vaporization comprising a compound of Formula E, is prepared using the ingredients below. The active mixture is mixed and added to a liquid vaporization appliance.

| Ingredient | Quantity (units) |
| --- | --- |
| Compound of Formula E (R-enantiomer) | 500 mg |
| Propylene Glycol | 2 ml |
| Glycerin | 2 ml |

In one non-limiting embodiment, a formulation of dry powder for insufflation is prepared comprising the components below. The active mixture is mixed with the lactose and the mixture is added to a dry powder inhaling appliance.

| Ingredient | Weight % |
| --- | --- |
| S-5-MAPB | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
| --- | --- |
| 5-MAPB (R-enantiomer) | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
| --- | --- |
| Compound of Formula A (R-enantiomer) | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
| --- | --- |
| compound of Formula C (R-enantiomer) | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
| --- | --- |
| Bk-5-MAPB (R-enantiomer) | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
| --- | --- |
| Compound of Formula E (R-enantiomer) | 5 |
| Lactose | 95 |

Pharmaceutically Acceptable Salts

The compounds described herein, including enantiomerically enriched mixtures, can be administered if desired as a pharmaceutically acceptable salt or a mixed salt. A mixed salt may be useful to increase solubility of the active substances, to alter pharmacokinetics, or for controlled release or other objective.

The compounds of the present invention are amines and thus basic, and therefore, react with inorganic and organic acids to form pharmaceutically acceptable acid addition salts. In some embodiments, the compounds of the present invention as free amines are oily and have decreased stability at room temperature. In this case it may be preferable to convert the free amines to their pharmaceutically acceptable acid addition salts for ease of handling and administration because in some embodiments, the pharmaceutically acceptable salt is solid at room temperature.

Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. In one embodiment, the compounds of the present invention are administered as oxalate salts. In one embodiment of the present invention, the compounds are administered as phosphate salts.

Exemplary salts include, but are not limited to, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isethionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like.

Alternatively, exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, finnarate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, sethiona, hybenzate, hydrabamine, hydrobromide, hydrobromide/bromide, hydrochloride, hydroiodide, hydroxide, hydroxybenzoate, hydroxynaphthoate, iodide, isethionate, sethionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. (See Berge et al. (1977) "Pharmaceutical Salts," J. Pharm. Sci. 66:1-19.) Preferred pharmaceutically acceptable salts are those employing a hydrochloride anion.

Working Examples 12-15, 17-19, 21-24, and 26 provide nonlimiting examples of salts of exemplary compounds of the present invention or for use in the methods of the present invention. While salts of 5-MAPB or 6-MAPB are illustrated, any of the compounds described herein can be substituted, including but not limited to 5-MBPB, 6-MBPB, Bk-5-MAPB, Bk-6-MAPB, Bk-5-MBPB or Bk-6-MBPB. The compounds can be used as salts or mixed salts in enantiomerically enriched form, or in substantially pure enantiomeric form Nonlimiting examples are the oxalate and phosphate salts (and wherein MAPB is used solely for exemplary purposes for ease of drafting, but can be substituted for any of the other compounds herein):

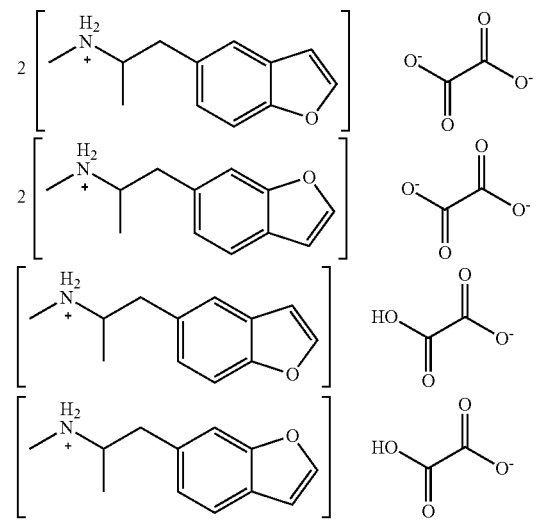

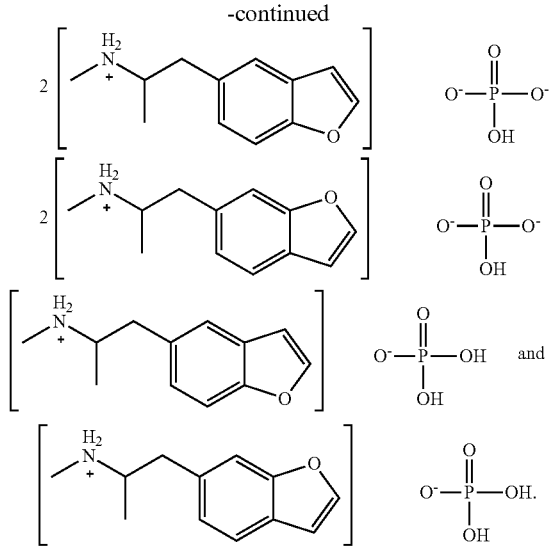

In certain illustrative nonlimiting embodiments, the pharmaceutically acceptable salt of 5-MAPB or 6-MAPB, including enantiomerically enriched 5-MAPB or 6-MAPB, is selected from:

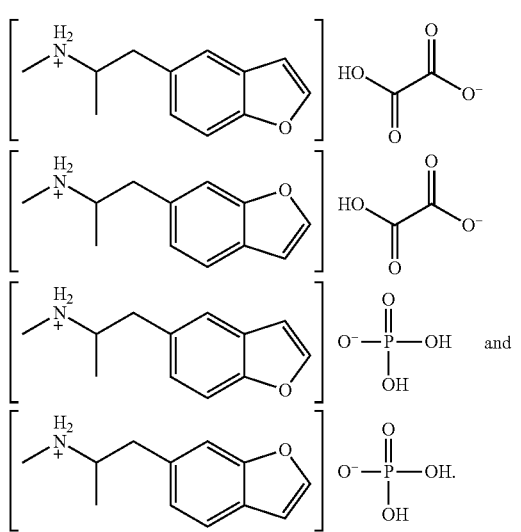

In certain illustrative nonlimiting embodiments, the pharmaceutically acceptable salt of 5-MAPB or 6-MAPB, including enantiomerically enriched 5-MAPB or 6-MAPB, is selected from:

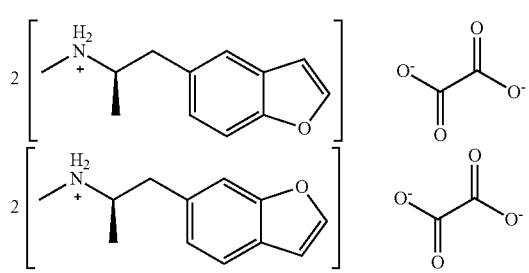

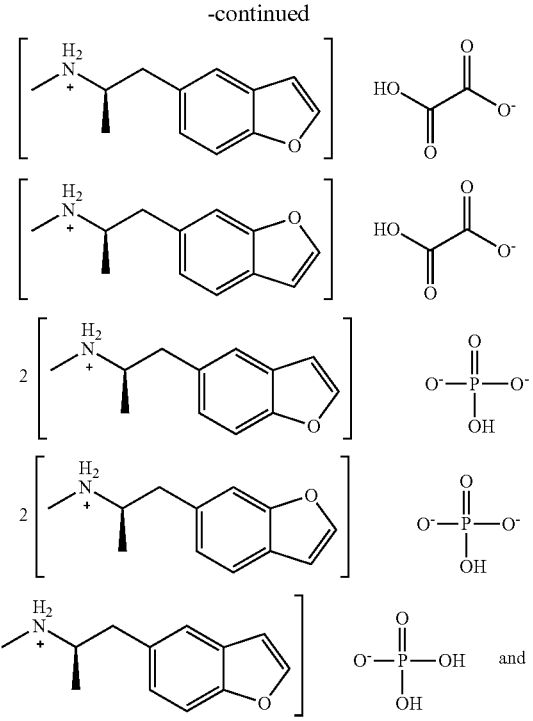

In certain illustrative nonlimiting embodiments, the pharmaceutically acceptable salt of 5-MAPB or 6-MAPB, including enantiomerically enriched 5-MAPB or 6-MAPB, is selected from:

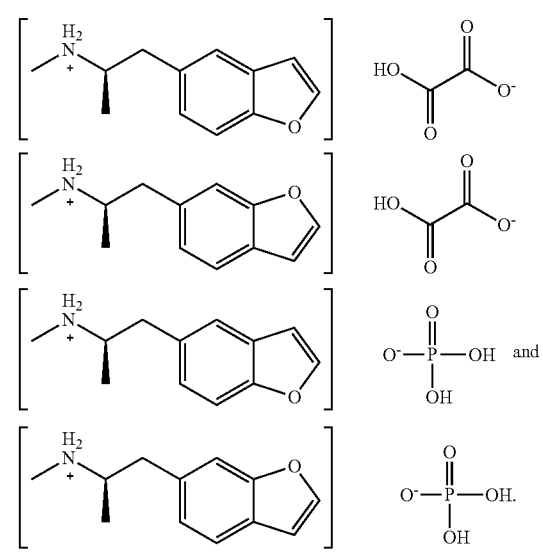

In certain illustrative nonlimiting embodiments, the pharmaceutically acceptable salt of 5-MAPB or 6-MAPB, including enantiomerically enriched 5-MAPB or 6-MAPB, is selected from:

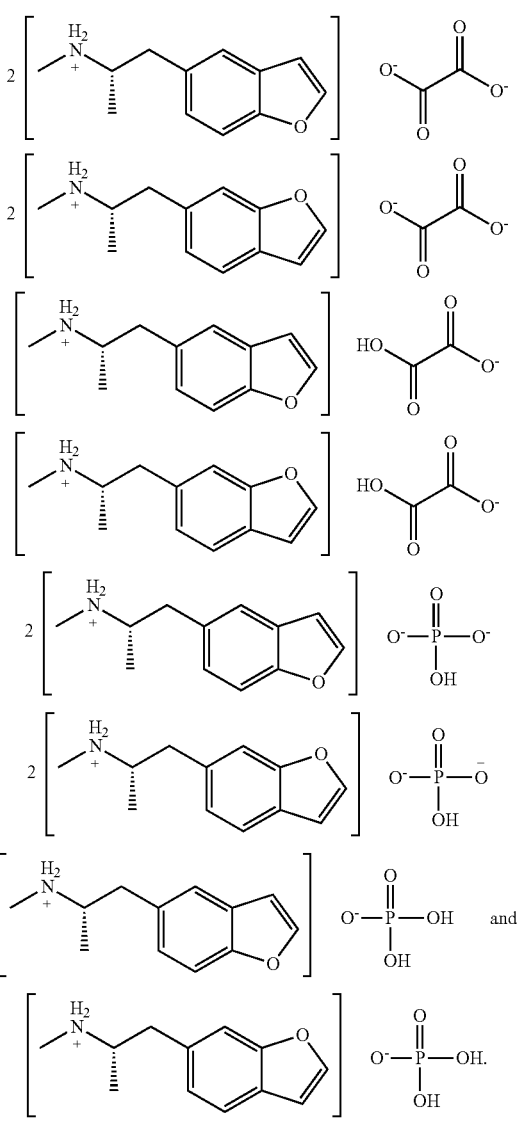

In certain illustrative nonlimiting embodiments, the pharmaceutically acceptable sale of 5-MAPB or 6-MAPB, including enantiomerically enriched 5-MAPB or 6-MAPB, is selected from:

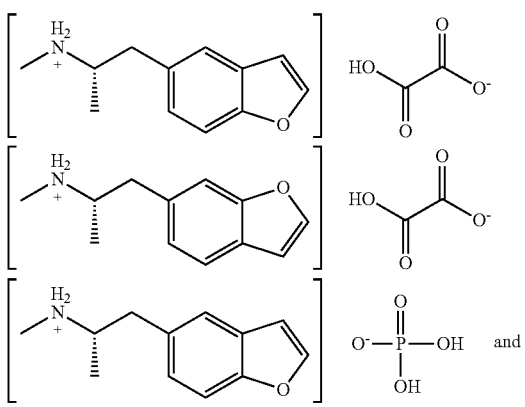

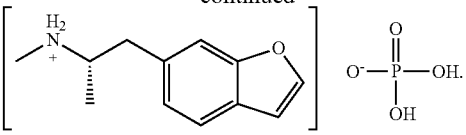

Prodrugs

In certain aspects, the compounds of the present invention are administered as prodrugs. Prodrugs are compounds that are metabolized or otherwise transformed inside the body to the active pharmacologic agent(s) of interest. Thus, prodrug will contain the "active" component (for example, Bk-5-MBPB, Bk-6-MBPB, 5-MBPB, 6-MBPB, 5-MAPB, 6-MAPB, Bk-6-MAPB, Bk-5-MAPB, or a compound of Formula A, Formula B, Formula C, Formula D, Formula E, or Formula F and a prodrug moiety). Examples include addition of amino acids to the amine, which can be removed within the body by esterases or similar enzymes, and reactions at the keto-group to form enol ethers, enol esters, and imines. Prodrugs are frequently (though not necessarily) pharmacologically less active or inactive until converted to the parent drug. This is done in the body by a chemical or biological reaction. In some cases, the moiety or chemicals formed from it may also have beneficial effects, including increasing therapeutic effects, decreasing undesirable side effects, or otherwise altering the pharmacokinetics or pharmacodynamics of the active drug. When the chemical formed from the prodrug moiety has beneficial effects that contribute to the overall beneficial effects of administering the prodrug, then the formed chemical is considered a "codrug."

Types of prodrugs contemplated to be within the scope of the invention include compounds that are transformed in various organs or locations in the body (e.g., liver, kidney, G.I., lung, tissue) to release the active compound. For example, liver prodrugs will include active compounds conjugated with a polymer or chemical moiety that is not released until acted upon by liver cytochrome enzymes and CYP metabolism includes dealkylation, dehydrogenation, reduction, hydrolysis, oxidation, and the breakdown of aromatic rings. Kidney prodrugs will include active compounds conjugated to L-gamma-glutamyl or N-acetyl-L-gamma glutamic moieties so that they are metabolized by gamma-glutamyl transpeptidase before they are bioactive. Alternatively, the compounds may be conjugated to alkyl-glucoside moieties to create glycosylation-based prodrugs. Digestive or G.I. prodrugs will include those where an active compound is, e.g., formulated into microspheres or nanospheres that do not degrade until the spheres are subjected to an acidic pH; formulated with an amide that will resist biochemical degradation until colonic pH is achieved; or, conjugated with a linear polysaccharide such as pectin that will delay activation until the combination reaches the bacteria in the colon. Besides these exemplary prodrug forms, many others will be known to those of ordinary skill.

V. Combination Therapy

In certain embodiments, a pharmaceutical composition can be provided to the host, for example a human who can be a patient, with an effective amount of one or more other compounds either of the present invention or other active compounds, in combination, together with one or more other active compounds, and one or more pharmaceutically acceptable carriers, diluents, and/or excipients.

In some aspects, a compound of the present invention is formulated in a pharmaceutical preparation with other active compounds to increase therapeutic efficacy, decrease unwanted effects, increase stability/shelf-life, and/or alter pharmacokinetics. Such other active compounds include, but are not limited to antioxidants (such alpha-lipoate in acid or salt form, ascorbate in acid or salt form, selenium, or N-acetylcysteine); H2-receptor agonists or antagonists (such as famotidine); stimulants (such as dextroamphetamine, amphetamine, lisdexamphetamine, or methamphetamine); entactogens (such as MDMA); anti-inflammatories (such as ibuprofen or ketoprofen); matrix metalloproteinase inhibitors (such as doxycycline); NOS inhibitors (such as S-methyl-L-thiocitrulline); proton pump inhibitors (such as omeprazole); phosphodiesterase 5 inhibitors (such as sildenafil); drugs with cardiovascular effects (beta antagonists such as propranolol, mixed alpha and beta antagonists such as carvedilol, alpha antagonists such as prazosin, imidazoline receptor agonists such as rilmenidine or moxonidine; serotonin antagonists such as ketanserin or lisuride); norepinephrine transporter blockers (such as reboxetine); acetylcholine nicotinic receptor modulators (such as bupropion, hydroxybupropion, methyllycaconitine, memantine, or mecamylamine); gastrointestinal acidifying agents (such as ascorbic acid or glutamic acid hydrochloride); alkalinizing agents (such as sodium bicarbonate), NMDA receptor antagonists (such as ketamine); or serotonin receptor agonists (such as 5-methoxy-N-methyl-N-isopropyltryptamine, psilocin, or psilocybin). The ingredients may be in ion, freebase, or salt form and may be isomers or prodrugs.

The pharmacological agents that make up the combination therapy disclosed herein may be a combined dosage form or in separate dosage forms intended for substantially simultaneous administration. The pharmacological agents that make up the combination therapy may also be administered sequentially, with either therapeutic compound being administered by a regimen calling for two-step administration. The two-step administration regimen may call for sequential administration of the active agents or spaced-apart administration of the separate active agents.

The time period between the multiple administration steps may range from, a few minutes to several hours, depending upon the properties of each pharmacological agent, such as potency, solubility, bioavailability, plasma half-life and kinetic profile of the pharmacological agent. Circadian variation of the target molecule concentration may also determine the optimal dose interval. For example, a compound of the present invention may be administered while the other pharmacological agent is being administered (concurrent administration) or may be administered before or after other pharmacological agent is administered (sequential administration).

In cases where the two (or more) drugs are included in the fixed-dose combinations of the present invention are incompatible, cross-contamination can be avoided, e.g., by incorporation of the drugs in different drug layers in the oral dosage form with the inclusion of a barrier layer(s) between the different drug layers, wherein the barrier layer(s) comprise one or more inert/non-functional materials.

In certain preferred embodiments, the formulations of the present invention are fixed-dose combinations of a compound of the present invention or a pharmaceutically acceptable salt thereof and at least one other pharmacological agent. Fixed-dose combination formulations may contain, but are not limited to, the following combinations in the form of single-layer monolithic tablet or multi-layered monolithic tablet or in the form of a core tablet-in-tablet or multi-layered multi-disk tablet or beads inside a capsule or tablets inside a capsule.

In one embodiment, the fixed-dose combination is a therapeutically efficacious fixed-dose combinations of immediate-release formulations of compounds of 5-MBPB and/or 6-MBPB and other pharmacological agents.

In one embodiment, the fixed-dose combination is a therapeutically efficacious fixed-dose combinations of extended-release compounds of 5-MBPB and/or 6-MBPB and delayed and/or extended-release other pharmacological agents contained in a single dosage form.

In one embodiment, the fixed-dose combination is a therapeutically efficacious fixed-dose combinations of immediate-release formulations of compounds of 5-MAPB and/or 6-MAPB and other pharmacological agents.

In one embodiment, the fixed-dose combination is a therapeutically efficacious fixed-dose combinations of extended-release compounds of 5-MAPB and/or 6-MAPB and delayed and/or extended-release other pharmacological agents contained in a single dosage form.

In one embodiment, the fixed-dose combination is a therapeutically efficacious fixed-dose combinations of immediate-release formulations of compounds of Formula A and/or Formula B and other pharmacological agents.

In one embodiment, the fixed-dose combination is a therapeutically efficacious fixed-dose combinations of extended-release compounds of Formula A and/or Formula B and delayed and/or extended-release other pharmacological agents contained in a single dosage form.

In one embodiment, the fixed-dose combination is a therapeutically efficacious fixed-dose combinations of immediate-release formulations of compounds of Formula C and/or Formula D and other pharmacological agents.

In one embodiment, the fixed-dose combination is a therapeutically efficacious fixed-dose combinations of extended-release compounds of Formula C and/or Formula D and delayed and/or extended-release other pharmacological agents contained in a single dosage form.

In one embodiment, the fixed-dose combination is a therapeutically efficacious fixed-dose combinations of immediate-release formulations of compounds of Bk-5-MAPB and/or Bk-6-MAPB and other pharmacological agents.

In one embodiment, the fixed-dose combination is a therapeutically efficacious fixed-dose combinations of extended-release compounds of Bk-5-MAPB and/or Bk-6-MAPB and delayed and/or extended-release other pharmacological agents contained in a single dosage form.

In one embodiment, the fixed-dose combination is a therapeutically efficacious fixed-dose combinations of immediate-release formulations of compounds of Bk-5-MBPB and/or Bk-6-MBPB and other pharmacological agents.

In one embodiment, the fixed-dose combination is a therapeutically efficacious fixed-dose combinations of extended-release compounds of Bk-5-MBPB and/or Bk-6-MBPB and delayed and/or extended-release other pharmacological agents contained in a single dosage form.

In one embodiment, the fixed-dose combination is a therapeutically efficacious fixed-dose combinations of immediate-release formulations of compounds of Formula E and/or Formula F and other pharmacological agents.

In one embodiment, the fixed-dose combination is a therapeutically efficacious fixed-dose combinations of extended-release compounds of Formula E and/or Formula F and delayed and/or extended-release other pharmacological agents contained in a single dosage form.

In one embodiment, the fixed-dose combination is a therapeutically efficacious fixed-dose combinations of immediate-release formulations of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof, and other pharmacological agents.

In one embodiment, the fixed-dose combination is a therapeutically efficacious fixed-dose combinations of immediate-release formulations of compounds of Formula XI, Formula XII, or Formula XIII, or a pharmaceutically acceptable salt thereof, and other pharmacological agents.

In one embodiment, the fixed-dose combination is a therapeutically efficacious fixed-dose combinations of extended-release formulations of compounds of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof, and other pharmacological agents.

In one embodiment, the fixed-dose combination is a therapeutically efficacious fixed-dose combinations of extended-release formulations of compounds of Formula XI, Formula XII, or Formula XIII, or a pharmaceutically acceptable salt thereof, and other pharmacological agents.

In one embodiment, the fixed-dose combination is a therapeutically efficacious fixed-dose combinations of immediate-release formulations of compounds of 5-MAPB and/or 6-MAPB and other pharmacological agents.

In one embodiment, extended-release multi-layered matrix tablets are prepared using fixed-dose combinations of 5-MAPB and/or 6-MAPB with another pharmacological agent. In one embodiment, extended-release multi-layered matrix tablets are prepared using fixed-dose combinations of 5-MBPB and/or 6-MBPB with another pharmacological agent. In one embodiment, extended-release multi-layered matrix tablets are prepared using fixed-dose combinations of Formula A and/or Formula B with another pharmacological agent. In one embodiment, extended-release multi-layered matrix tablets are prepared using fixed-dose combinations of Formula C and/or Formula D with another pharmacological agent. In one embodiment, extended-release multi-layered matrix tablets are prepared using fixed-dose combinations of Formula E and/or Formula F with another pharmacological agent. In one embodiment, extended-release multi-layered matrix tablets are prepared using fixed-dose combinations of Bk-5-MAPB and/or Bk-6-MAPB with another pharmacological agent. In one embodiment, extended-release multi-layered matrix tablets are prepared using fixed-dose combinations of Bk-5-MBPB and/or Bk-6-MBPB with another pharmacological agent. Such formulations may comprise one or more of the active agents within a hydrophilic or hydrophobic polymer matrix. In one embodiment, extended-release multi-layered matrix tablets are prepared using fixed-dose combinations of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof, with another pharmacological agent. In one embodiment, extended-release multi-layered matrix tablets are prepared using fixed-dose combinations of Formula XI, Formula XII, or Formula XIII, or a pharmaceutically acceptable salt thereof, with another pharmacological agent. In one embodiment, extended-release multi-layered matrix tablets are prepared using fixed-dose combinations of 5-MAPB and/or 6-MAPB with another pharmacological agent. For example, a hydrophilic polymer may comprise guar gum, hydroxypropylmethylcellulose, and xanthan gum as matrix formers. Lubricated formulations may be compressed by a wet granulation method.

Another embodiment of the invention includes multiple variations in the pharmaceutical dosages of each drug in the combination as further outlined below. Another embodiment of the invention includes various forms of preparations including using solids, liquids, immediate or delayed or extended-release forms. Many types of variations are possible as known to those skilled in the art.

Pharmaceutical Combinations with Dextroamphetamine

In one embodiment, 5-MBPB and/or 6-MBPB or a pharmaceutically acceptable salt thereof is formulated in a pharmaceutical composition that also contains dextroamphetamine or a pharmaceutically acceptable salt thereof in the amount of at least about 2 mg, 4 mg, 5 mg, 7 mg, 10 mg, 15 mg, 20 mg, or 25 mg. The required amount of dextroamphetamine will vary depending on the needs of the patient. The compound of 5-MBPB and/or 6-MBPB can be a racemic compound, an R- or S-enantiomer, or an enantiomerically enriched mixture of R- or S-enantiomers. In one embodiment, the compound of 5-MBPB and/or 6-MBPB is deuterated wherein one to five hydrogens have been replaced with deuterium.

In one embodiment, the ratio of dextroamphetamine (with or without salt) to 5-MBPB and/or 6-MBPB (with or without salt) is about 1:2, about 1:3, about 1:4, or about 1:5 by weight.

In one embodiment, 5-MAPB and/or 6-MAPB or a pharmaceutically acceptable salt thereof is formulated in a pharmaceutical composition that also contains dextroamphetamine or a pharmaceutically acceptable salt thereof in the amount of at least about 2 mg, 4 mg, 5 mg, 7 mg, 10 mg, 15 mg, 20 mg, or 25 mg. The required amount of dextroamphetamine will vary depending on the needs of the patient. The compound of 5-MAPB and/or 6-MAPB can be a racemic compound, an R- or S-enantiomer, or an enantiomerically enriched mixture of R- or S-enantiomers. In one embodiment, the compound of 5-MAPB and/or 6-MAPB is deuterated wherein one to five hydrogens have been replaced with deuterium.

In one embodiment, the ratio of dextroamphetamine (with or without salt) to 5-MAPB and/or 6-MAPB (with or without salt) is about 1:2, about 1:3, about 1:4, or about 1:5 by weight.

In one embodiment, a compound of Formula A and/or Formula B or a pharmaceutically acceptable salt thereof is formulated in a pharmaceutical composition that also contains dextroamphetamine or a pharmaceutically acceptable salt thereof in the amount of at least about 2 mg, 4 mg, 5 mg, 7 mg, 10 mg, 15 mg, 20 mg, or 25 mg. The required amount of dextroamphetamine will vary depending on the needs of the patient. The compound of Formula A and/or Formula B can be a racemic compound, an R- or S-enantiomer, or an enantiomerically enriched mixture of R- or S-enantiomers. In one embodiment, the compound of Formula A and/or B is deuterated wherein one to five hydrogens have been replaced with deuterium.

In one embodiment, the ratio of dextroamphetamine (with or without salt) to the compound of Formula A and/or Formula B (with or without salt) is about 1:2, about 1:3, about 1:4, or about 1:5 by weight.

In one embodiment, a compound of Formula C and/or Formula D or a pharmaceutically acceptable salt thereof is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Formula C and/or Formula D can be a racemic compound, an R- or S-enantiomer, or an enantiomerically enriched mixture of R- or S-enantiomers. In one embodiment, the compound of Formula C and/or D is deuterated wherein one to five hydrogens have been replaced with deuterium.

In one embodiment, the ratio of dextroamphetamine (with or without salt) to the compound of Formula C and/or Formula D (with or without salt) is about 1:2, about 1:3, about 1:4, or about 1:5 by weight.

In one embodiment, Bk-5-MAPB and/or Bk-6-MAPB is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Bk-5-MAPB and/or Bk-6-MAPB can be a racemic compound, an R- or S-enantiomer, or an enantiomerically enriched mixture of R- or S-enantiomers. In one embodiment, the compound of Bk-5-MAPB and/or Bk-6-MAPB is deuterated wherein one to five hydrogens have been replaced with deuterium.

In one embodiment, the ratio of dextroamphetamine (with or without salt) to Bk-5-MAPB and/or Bk-6-MAPB (with or without salt) is at least about 1:2, about 1:3, about 1:4, about 1:5, about 1:6, about 1:7, about 1:8, about 1:9, or about 1:10 by weight.

In one embodiment, Bk-5-MBPB and/or Bk-6-MBPB is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Bk-5-MBPB and/or Bk-6-MBPB can be a racemic compound, an R- or S-enantiomer, or an enantiomerically enriched mixture of R- or S-enantiomers. In one embodiment, the compound of Bk-5-MBPB and/or Bk-6-MBPB is deuterated wherein one to five hydrogens have been replaced with deuterium.

In one embodiment, the ratio of dextroamphetamine (with or without salt) to Bk-5-MBPB and/or Bk-6-MBPB (with or without salt) is at least about 1:2, about 1:3, about 1:4, about 1:5, about 1:6, about 1:7, about 1:8, about 1:9, or about 1:10 by weight.

In one embodiment, a compound of Formula E and/or Formula F is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Formula E and/or Formula F can be a racemic compound, an R- or S-enantiomer, or an enantiomerically enriched mixture of R- or S-enantiomers. In one embodiment, the compound of Formula E and/or F is deuterated wherein one to five hydrogens have been replaced with deuterium.

In one embodiment, the ratio of dextroamphetamine (with or without salt) to the compound of Formula E and/or Formula F (with or without salt) is at least about 1:2, about 1:3, about 1:4, about 1:5, about 1:6, about 1:7, about 1:8, about 1:9, or about 1:10 by weight.

In one embodiment, a compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof, can be a racemic compound, an R- or S-enantiomer, or an enantiomerically enriched mixture of R- or S-enantiomers. In one embodiment, the compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof is deuterated wherein one to five hydrogens have been replaced with deuterium.

In one embodiment, the ratio of dextroamphetamine (with or without salt) to the compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof is at least about 1:2, about 1:3, about 1:4, about 1:5, about 1:6, about 1:7, about 1:8, about 1:9, or about 1:10 by weight.

In one embodiment, a compound of Formula XI, Formula XII, or Formula XIII, or a pharmaceutically acceptable salt thereof is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Formula XI, Formula XII, or Formula XIII, or a pharmaceutically acceptable salt thereof, can be a racemic compound, an R- or S-enantiomer, or an enantiomerically enriched mixture of R- or S-enantiomers. In one embodiment, the compound of Formula X, Formula XI, Formula XII, or Formula XIII, or a pharmaceutically acceptable salt thereof is deuterated wherein one to five hydrogens have been replaced with deuterium.

In one embodiment, the ratio of dextroamphetamine (with or without salt) to the compound of Formula XI, Formula XII, or Formula XIII, or a pharmaceutically acceptable salt thereof is at least about 1:2, about 1:3, about 1:4, about 1:5, about 1:6, about 1:7, about 1:8, about 1:9, or about 1:10 by weight.

In one embodiment, 5-MAPB and/or 6-MAPB or a pharmaceutically acceptable salt thereof is formulated in a pharmaceutical composition that also contains dextroamphetamine or a pharmaceutically acceptable salt thereof in the amount of at least about 2 mg, 4 mg, 5 mg, 7 mg, 10 mg, 15 mg, 20 mg, or 25 mg. The required amount of dextroamphetamine will vary depending on the needs of the patient. The compound of 5-MAPB and/or 6-MAPB can be a racemic compound, an R- or S-enantiomer, or an enantiomerically enriched mixture of R- or S-enantiomers. In one embodiment, the compound of 5-MAPB and/or 6-MAPB is deuterated wherein one to five hydrogens have been replaced with deuterium.

In one embodiment, the ratio of dextroamphetamine (with or without salt) to 5-MAPB and/or 6-MAPB (with or without salt) is at least about 1:2, about 1:3, about 1:4, about 1:5, about 1:6, about 1:7, about 1:8, about 1:9, or about 1:10 by weight.

Pharmaceutical Combinations with MDMA

In one embodiment, 5-MBPB and/or 6-MBPB is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The required amount of MDMA will vary depending on the needs of the patient. The compound of 5-MBPB and/or 6-MBPB can be a racemic compound, an R- or S-enantiomer, or an enantiomerically enriched mixture of R- or S-enantiomers. In one embodiment, the compound of 5-MBPB and/or 6-MBPB is deuterated wherein one to five hydrogens have been replaced with deuterium.

In one embodiment, the ratio of MDMA (with or without salt) to 5-MBPB and/or 6-MBPB (with or without salt) is at least about 3:1, about 2:1, about 1:1, about 1:2, about 1:3, about 1:4, or about 1:5 by weight.

In one embodiment, 5-MAPB and/or 6-MAPB is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The required amount of MDMA will vary depending on the needs of the patient. The compound of 5-MAPB and/or 6-MAPB can be a racemic compound, an R- or S-enantiomer, or an enantiomerically enriched mixture of R- or S-enantiomers. In one embodiment, the compound of 5-MAPB and/or 6-MAPB is deuterated wherein one to five hydrogens have been replaced with deuterium.

In one embodiment, the ratio of MDMA (with or without salt) to 5-MAPB and/or 6-MAPB (with or without salt) is at least about 3:1, about 2:1, about 1:1, about 1:2, about 1:3, about 1:4, or about 1:5 by weight.

In one embodiment, Formula A and/or Formula B is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Formula A and/or Formula B can be a racemic compound, an R- or S-enantiomer, or an enantiomerically enriched mixture of R- or S-enantiomers. In one embodiment, the compound of Formula A and/or Formula B is deuterated wherein one to five hydrogens have been replaced with deuterium.

In one embodiment, the ratio of MDMA (with or without salt) to Formula A and/or Formula B (with or without salt) is at least about 3:1, about 2:1, about 1:1, about 1:2, about 1:3, about 1:4, or about 1:5 by weight.

In one embodiment, Formula C and/or Formula D is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Formula C and/or Formula D can be a racemic compound, an R- or S-enantiomer, or an enantiomerically enriched mixture of R- or S-enantiomers. In one embodiment, the compound of Formula C and/or Formula D is deuterated wherein one to five hydrogens have been replaced with deuterium.

In one embodiment, the ratio of MDMA (with or without salt) to Formula C and/or Formula D (with or without salt) is at least about 3:1, about 2:1, about 1:1, about 1:2, about 1:3, about 1:4, or about 1:5 by weight.

In one embodiment, Bk-5-MAPB and/or Bk-6-MAPB is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Bk-5-MAPB and/or Bk-6-MAPB can be a racemic compound, an R- or S-enantiomer, or an enantiomerically enriched mixture of R- or S-enantiomers. In one embodiment, the compound of Bk-5-MAPB and/or Bk-6-MAPB is deuterated wherein one to five hydrogens have been replaced with deuterium.

In one embodiment, the ratio of MDMA (with or without salt) to Bk-5-MAPB and/or Bk-6-MAPB (with or without salt) is at least about 3:1, about 2:1, about 1:1, about 1:2, about 1:3, about 1:4, or about 1:5 by weight.

In one embodiment, Bk-5-MBPB and/or Bk-6-MBPB is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Bk-5-MBPB and/or Bk-6-MBPB can be a racemic compound, an R- or S-enantiomer, or an enantiomerically enriched mixture of R- or S-enantiomers. In one embodiment, the compound of Bk-5-MBPB and/or Bk-6-MBPB is deuterated wherein one to five hydrogens have been replaced with deuterium.

In one embodiment, the ratio of MDMA (with or without salt) to Bk-5-MBPB and/or Bk-6-MBPB (with or without salt) is at least about 3:1, about 2:1, about 1:1, about 1:2, about 1:3, about 1:4, or about 1:5 by weight.

In one embodiment, Formula E and/or Formula F is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Formula E and/or Formula F can be a racemic compound, an R- or S-enantiomer, or an enantiomerically enriched mixture of R- or S-enantiomers. In one embodiment, the compound of Formula E and/or Formula F is deuterated wherein one to five hydrogens have been replaced with deuterium.

In one embodiment, the ratio of MDMA (with or without salt) to Formula E and/or Formula F (with or without salt) is at least about 3:1, about 2:1, about 1:1, about 1:2, about 1:3, about 1:4, or about 1:5 by weight.

In one embodiment, Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof can be a racemic compound, an R- or S-enantiomer, or an enantiomerically enriched mixture of R- or S-enantiomers. In one embodiment, the compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof is deuterated wherein one to five hydrogens have been replaced with deuterium.

In one embodiment, the ratio of MDMA (with or without salt) to Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof (with or without salt) is at least about 3:1, about 2:1, about 1:1, about 1:2, about 1:3, about 1:4, or about 1:5 by weight.

In one embodiment, Formula XI, Formula XII, or Formula XIII, or a pharmaceutically acceptable salt thereof is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Formula XI, Formula XII, or Formula XIII, or a pharmaceutically acceptable salt thereof can be a racemic compound, an R- or S-enantiomer, or an enantiomerically enriched mixture of R- or S-enantiomers. In one embodiment, the compound of Formula XI, Formula XII, or Formula XIII, or a pharmaceutically acceptable salt thereof is deuterated wherein one to five hydrogens have been replaced with deuterium.

In one embodiment, the ratio of MDMA (with or without salt) to Formula XI, Formula XII, or Formula XIII, or a pharmaceutically acceptable salt thereof (with or without salt) is at least about 3:1, about 2:1, about 1:1, about 1:2, about 1:3, about 1:4, or about 1:5 by weight.

Pharmaceutical Combinations with Psilocybin

In one embodiment, 5-MBPB and/or 6-MBPB or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of 5-MBPB and/or 6-MBPB can be a racemic compound, an R- or S-enantiomer, or an enantiomerically enriched mixture of R- or S-enantiomers. In one embodiment, the compound of 5-MBPB and/or 6-MBPB is deuterated wherein one to five hydrogens have been replaced with deuterium.

In one embodiment, a compound of Formula A and/or Formula B or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Formula A and/or Formula B can be a racemic compound, an R- or S-enantiomer, or an enantiomerically enriched mixture of R- or S-enantiomers. In one embodiment, the compound of Formula A and/or B is deuterated wherein one to five hydrogens have been replaced with deuterium.

In one embodiment, a compound of Formula C and/or Formula D or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Formula C and/or Formula D can be a racemic compound, an R- or S-enantiomer, or an enantiomerically enriched mixture of R- or S-enantiomers. In one embodiment, the compound of Formula C and/or D is deuterated wherein one to five hydrogens have been replaced with deuterium.

In one embodiment, Bk-5-MAPB and/or Bk-6-MAPB is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Bk-5-MAPB and/or Bk-6-MAPB can be a racemic compound, an R- or S-enantiomer, or an enantiomerically enriched mixture of R- or S-enantiomers. In one embodiment, the compound of Bk-5-MAPB and/or Bk-6-MAPB is deuterated wherein one to five hydrogens have been replaced with deuterium.

In one embodiment, a compound of Formula E and/or Formula F is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Formula E and/or Formula F can be a racemic compound, an R- or S-enantiomer, or an enantiomerically enriched mixture of R- or S-enantiomers. In one embodiment, the compound of Formula E and/or F is deuterated wherein one to five hydrogens have been replaced with deuterium.

In one embodiment, a compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof, can be a racemic compound, an R- or S-enantiomer, or an enantiomerically enriched mixture of R- or S-enantiomers. In one embodiment, the compound of Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt thereof is deuterated wherein one to five hydrogens have been replaced with deuterium.

In one embodiment, a compound of Formula XI, Formula XII, or Formula XIII, or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Formula XI, Formula XII, or Formula XIII, or a pharmaceutically acceptable salt thereof, can be a racemic compound, an R- or S-enantiomer, or an enantiomerically enriched mixture of R- or S-enantiomers. In one embodiment, the compound of Formula X, Formula XI, Formula XII, or Formula XIII, or a pharmaceutically acceptable salt thereof is deuterated wherein one to five hydrogens have been replaced with deuterium.

In one embodiment, 5-MAPB and/or 6-MAPB or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of 5-MAPB and/or 6-MAPB can be a racemic compound, an R- or S-enantiomer, or an enantiomerically enriched mixture of R- or S-enantiomers. In one embodiment, the compound of 5-MAPB and/or 6-MAPB is deuterated wherein one to five hydrogens have been replaced with deuterium.

In one embodiment, Bk-5-MBPB and/or Bk-6-MBPB is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Bk-5-MBPB and/or Bk-6-MBPB can be a racemic compound, an R- or S-enantiomer, or an enantiomerically enriched mixture of R- or S-enantiomers. In one embodiment, the compound of Bk-5-MBPB and/or Bk-6-MBPB is deuterated wherein one to five hydrogens have been replaced with deuterium.

Non-Limiting Examples of Combination Formulations

In one non-limiting embodiment, a capsule comprising S-5-MAPB, R-5-MAPB, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| S-5-MAPB | 30.0 |
| R-5-MAPB | 10.0 |
| Amphetamine sulfate | 5.0 |
| Starch | 109.0 |
| Magnesium stearate | 1.0 |

In one non-limiting embodiment, a capsule comprising deuterated R-5-MBPB, R-6-MBPB, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| 5-MBPB (R-enantiomer, D3-N-Deuterated) | 10.0 |
| 6-MBPB (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising a deuterated compound of Formula A, a deuterated compound of Formula B, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| Compound of Formula A (R-enantiomer, D3-N-Deuterated) | 10.0 |
| Compound of Formula B (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising a deuterated compound of Formula C, a deuterated compound of Formula D, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| compound of Formula C (R-enantiomer, D3-N-Deuterated) | 10.0 |
| compound of Formula D (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising deuterated R-Bk-5-MAPB, deuterated R-Bk-6-MAPB, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| Bk-5-MAPB (R-enantiomer, D3-N-Deuterated) | 10.0 |
| Bk-6-MAPB (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising a deuterated compound of Formula E, a deuterated compound of Formula F, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| Compound of Formula E (R-enantiomer, D3-N-Deuterated) | 10.0 |
| Compound of Formula F (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising deuterated R-6-MBPB and amphetamine sulfate, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| 6-MBPB (R-enantiomer, D3-N-Deuterated) | 40.0 |
| Amphetamine sulfate | 5.0 |
| Starch | 109.0 |
| Magnesium stearate | 1.0 |

In one non-limiting embodiment, a capsule, comprising R-6-MAPB, S-6-MAPB, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| R-6-MAPB | 30.0 |
| S-6-MAPB | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising enantiomerically enriched 5-MBPB, enantiomerically enriched 6-MBPB, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| 5-MBPB (70% R-enantiomer) | 30.0 |
| 6-MBPB (70% S-enantiomer) | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising an enantiomerically enriched compound of Formula A, an enantiomerically enriched compound of Formula B, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| Compound of Formula A (70% R-enantiomer) | 30.0 |
| Compound of Formula B (70% S-enantiomer) | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising an enantiomerically enriched compound of Formula C, an enantiomerically enriched compound of Formula D, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| compound of Formula C (70% R-enantiomer) | 30.0 |
| compound of Formula D (70% S-enantiomer) | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising enantiomerically enriched Bk-5-MAPB, enantiomerically enriched Bk-6-MAPB, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| Bk-5-MAPB (70% R-enantiomer) | 30.0 |
| Bk-6-MAPB (70% S-enantiomer) | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising an enantiomerically enriched compound of Formula E, an enantiomerically enriched compound of Formula F, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
| --- | --- |
| Compound of Formula E (70% R-enantiomer) | 30.0 |
| Compound of Formula F (70% S-enantiomer) | 10.0 |

-continued

| Ingredient | Quantity (mg/capsule) |
|---|---|
| Psilocybin hydrochloride | 2.0 |
| Alpha lipoic acid | 40.0 |
| Starch | 72.0 |
| Magnesium stearate | 1.0 |

It should be readily appreciated that the above formulation examples are illustrative only. Accordingly, it should be understood that reference to particular compounds(s) is likewise illustrative, and the compounds(s) in any of the non-limiting examples of combination formulations may be substituted by other compounds(s) of the invention. Likewise, any of the other active compounds (e.g., amphetamine sulfate or psilocybin hydrochloride as described above) may be substituted by a different other active compound, as may the inactive compounds.

Moreover, for any of S-5-MAPB, R-5-MAPB, S-6-MAPB, R-6-MAPB, 5-MBPB, 6-MBPB, Bk-5-MAPB, Bk-6-MAPB Formula A, Formula B, Formula C, Formula D, Formula E, and Formula F, or for any other active compounds of the invention, substitution of the compound by its prodrug, free base, salt, or hydrochloride salt shall be understood to provide merely an alternative embodiment still within the scope of the invention. Further, compositions within the scope of the invention should be understood to be open-ended and may include additional active or inactive compounds and ingredients.

The type of formulation employed for the administration of the compounds employed in the methods of the present invention generally may be dictated by the compound(s) employed, the type of pharmacokinetic profile desired from the route of administration and the compound(s), and the state of the patient.

VI. Dosage Regimes

The compounds or pharmaceutically acceptable formulations of the present invention can be administered to the host in any amount, and with any frequency, that achieves the goals of the invention as used by the healthcare provider, or otherwise by the host in need thereof, typically a human, as necessary or desired.

In certain embodiments, the composition as described herein is provided only in a controlled counseling session, and administered only once, or perhaps 2, 3, 4, or 5 or more times in repeated counseling sessions to address a mental disorder as described herein.

In other embodiments, the composition as described herein is provided outside of a controlled counseling session, and perhaps self-administered, as needed to perhaps 2, 3, 4, or 5 or more times in to address a mental disorder as described herein.

In other embodiments, the composition of the present invention may be administered on a routine basis for mental wellbeing or for entactogenic treatment.

The compounds of the current invention can be administered in a variety of doses, routes of administration, and dosing regimens, based on the indication and needs of the patient. Non-limiting examples of therapeutic use include discrete psychotherapeutic sessions, ad libitum use for treatment of episodic disorders, and ongoing use for treatment of subchronic and chronic disorders.

Psychotherapeutic Sessions

For some indications, the medicine is taken in discrete psychotherapy or other beneficial sessions. It is anticipated that these sessions will typically be separated by more than 5 half-lifes of the medicine and, for most patients, will typically occur only 1 to 5 times each year.

For these sessions, it will typically be desirable to induce clearly perceptible entactogenic effects that will facilitate fast therapeutic progress. Non-exhaustive examples of oral doses of medicine that produce clearly perceptible entactogenic effects include: about 40 to about 120 mg of non-racemic 5-MAPB, about 40 to about 120 mg of non-racemic 6-MAPB, about 50 to about 300 mg of 5-MBPB, about 50 to about 300 mg of 6-MBPB, about 75 to about 500 mg of BK-5-MAPB, about 75 to about 500 mg of BK-6-MAPB, about 75 to about 800 mg of BK-5-MBPB, about 75 to about 800 mg of BK-6-MBPB.

It is anticipated that the medicine would be taken once or, more rarely, two or three times in a single therapeutic session. In these cases, it is common for each subsequent dose to be half of the previous dose or lower. Multiple doses within a session typically occur because either the patient's sensitivity to the medicine was unknown and too low of an initial dose was employed or because the patient is experiencing a productive session and it is desirable to extend the duration of therapeutic effects. Controlled release preparations may be used to lengthen the duration of therapeutic effects from a single administration of the medicine. In cases where multiple administrations are used in a session, it is anticipated that individual doses will be lower so that plasma concentrations remain within a desired therapeutic range.

Non-limiting, non-exhaustive examples of indications that may benefit from psychotherapeutic sessions include depression, dysthymia, anxiety and phobia disorders, feeding, eating, and binge disorders, body dysmorphic syndromes, alcoholism, tobacco abuse, drug abuse or dependence disorders, disruptive behavior disorders, impulse control disorders, gaming disorders, gambling disorders, personality disorders, attachment disorders, autism, and dissociative disorders. Also included as exemplary situations where an individual would benefit from a psychotherapeutic session are situations from a reduction of neuroticism or psychological defensiveness, an increase in openness to experience, an increase in creativity, or an increase in decision-making ability.

Ad Libitum Use for Treatment of Episodic Disorders

For some indications, such as social anxiety, where the patient has need for relief from episodic occurrence of a disorder, it is anticipated that the medicine would be taken as needed but that uses should be separated by more than 5 half-lifes of the medicine to avoid bioaccumulation and formation of tolerance.

For treating episodic disorders, clearly perceptible entactogenic effects are often not desirable, as they can impair some aspects of functioning. Non-exhaustive examples of oral doses of medicine that produce subtle, barely perceptible therapeutic effects include: about 10 to about 60 mg of non-racemic 5-MAPB, about 10 to about 60 mg of non-racemic 6-MAPB, about 10 to about 100 mg of 5-MBPB, about 10 to about 100 mg of 6-MBPB, about 20 to about 150 mg of BK-5-MAPB, about 20 to about 150 mg of BK-6-MAPB, about 20 to about 200 mg of BK-5-MBPB, and about 20 to about 200 mg of BK-6-MBPB.

Non-limiting, non-exhaustive examples of indications that may benefit from episodic treatment are the same as those listed in the previous section provided that clinically significant signs and symptoms worsen episodically or in predictable contexts.

Ongoing Use for Treatment of Subchronic and Chronic Disorders

For some indications, such as substance use disorders, inflammatory conditions, and neurological indications, including treatment of stroke, brain trauma, dementia, and neurodegenerative diseases, where the patient has need for ongoing treatment, it is anticipated that the medicine would be taken daily, twice daily, or three times per day. With some indications (subchronic disorders), such as treatment of stroke or traumatic brain injury, it is anticipated that treatment duration will be time-limited and dosing will be tapered when the patient has recovered. An example dose taper regimen is a reduction in dose of 10% of the original dose per week for nine weeks. With other, chronic disorders, such as dementia, it is anticipated that treatment will be continued as long as the patient continues to receive clinically significant benefits.

For treating subchronic and chronic disorders, clearly perceptible entactogenic effects are often not desirable. Non-exhaustive examples of oral doses of medicine that produce subtle, barely perceptible therapeutic effects with ongoing dosing include: about 5 to about 60 mg of non-racemic 5-MAPB, about 5 to about 60 mg of non-racemic 6-MAPB, about 5 to about 100 mg of 5-MBPB, about 5 to about 100 mg of 6-MBPB, about 10 to about 150 mg of BK-5-MAPB, about 10 to about 150 mg of BK-6-MAPB, about 10 to about 200 mg of BK-5-MBPB, and about 10 to about 200 mg of BK-6-MBPB.

Non-limiting, non-exhaustive examples of subchronic and chronic disorders that may benefit from regular treatment include migraine, headaches (e.g., cluster headache), neurodegenerative disorders, Alzheimer's disease, Parkinson's disease, schizophrenia, stroke, traumatic brain injury, phantom limb syndrome, and other conditions where increasing neuronal plasticity is desirable.

VII. Examples

Example 1: Production of Enantiomerically Enriched Preparations

Racemic 5-MAPB HCl (not less than 99.9% pure) was purchased (Chemical Collective, Netherlands). Enantiomeric enrichment of 2 g of 5-MAPB HCl was performed using supercritical fluid chromatography (SFC), with details listed below:

Preparative SFC Method
  Column: 2.1×25.0 cm Chiralpak AD-H (Chiral Technologies, West Chester, PA)
  $CO_2$ Co-solvent (Solvent B): Isopropanol with 0.25% Isopropylamine
  Isocratic Method: 15% Co-solvent at 90 g/min
  System Pressure: 100 bar
  Column Temperature: 25 degrees C.
  Sample Diluent: 3:2 Isopropanol/Methanol
Analytical SFC Method
  Column: 4.6×250 mm 3 μm Chiralpak AD-H from Chiral Technologies (West Chester, PA)
  $CO_2$ Co-solvent (Solvent B): Isopropanol with 0.1% Isopropylamine
  Isocratic Method: 10% Co-solvent at 3 mL/min System Pressure: 125 bar
  Column Temperature: 40 degrees C.
  Sample Diluent: Isopropanol Because the close retention times of the enantiomers led to overlapping peaks, complete enantiomeric separation did not occur. Collection of three isolates allowed isolation of two enriched samples and a "valley." The collected fractions were dried in a rotary evaporator at 40 C°, rinsed with acetonitrile, and transferred to their final containers using methanol. Isolate one had an enantiomeric excess of 30%, chemical purity of 99.1%, and a dried weight of 227 mg as the freebase. Isolate two had an enantiomeric excess of 33.2%, chemical purity of 98.5%, and a dried weight of 250 mg as the freebase.

Separation of R-5-MAPB and S-5-MAPB

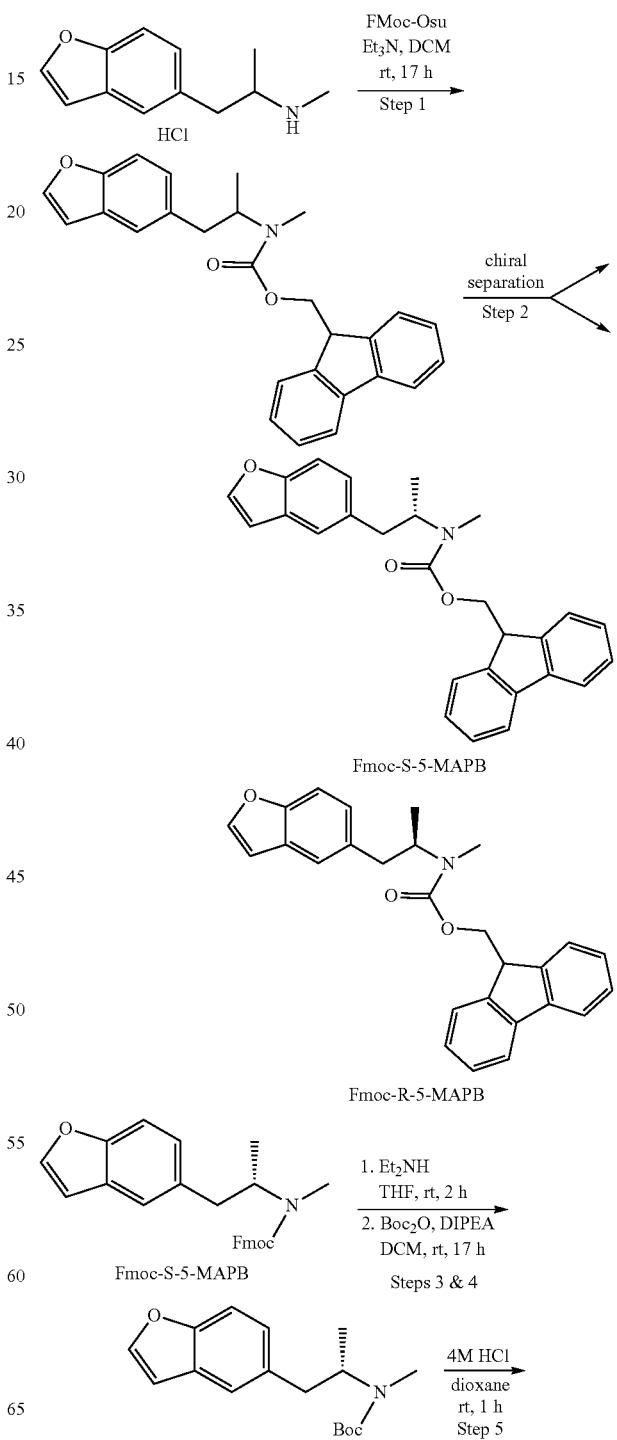

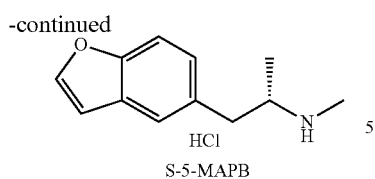

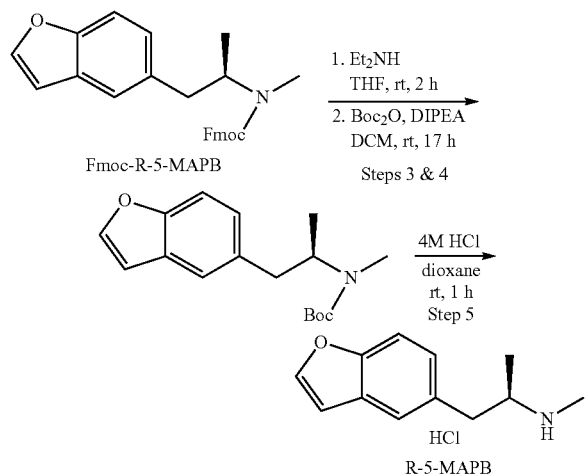

The chiral separation of Step 2 was accomplished with the following method:

Separation SFC Method

Column: 30.0×250 mm Regis Reflect C-Amylose A, 5p (Regis Technologies, Morton Grove, IL)

Mobile Phase: 30% $CO_2$+70% MeOH

Flow: 30 g/min

System Pressure: 140 bar

Column Temperature: 35 degrees C.

UV: 240 nm

Diluent: Methanol

Identity of the enantiomers was confirmed with 1H NMR and LC/MS. Chromatography was used to estimate purity. The S-5-MAPB had a chemical purity of 98.49% and an enantiomeric excess of 99.46. The R-5-MAPB had a chemical purity of 88.13% and an enantiomeric excess of 99.46.

R-6-MAPB and S-6-MAPB were prepared using 6-bromobenzofuran as a starting material, as shown in the following scheme:

Synthesis and Separation of R-6-MAPB and S-6-MAPB

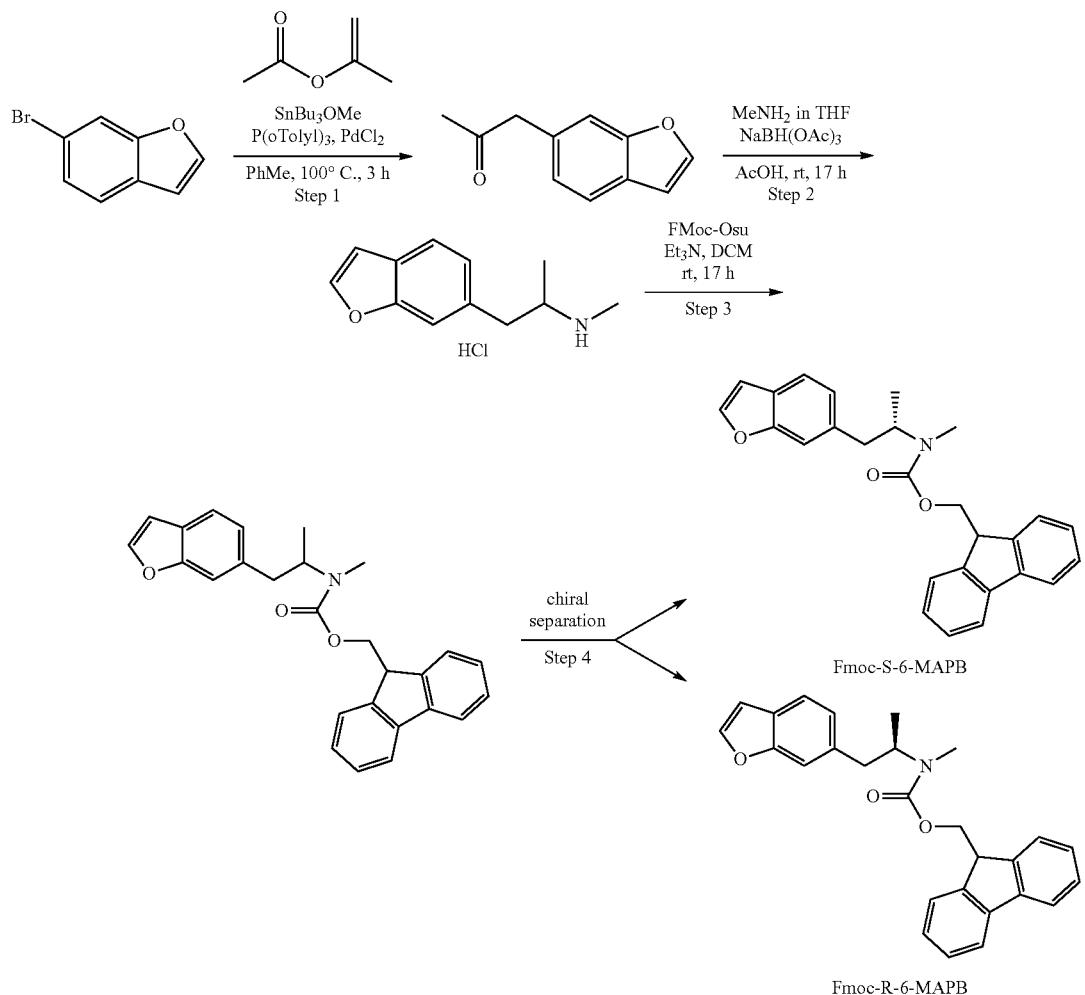

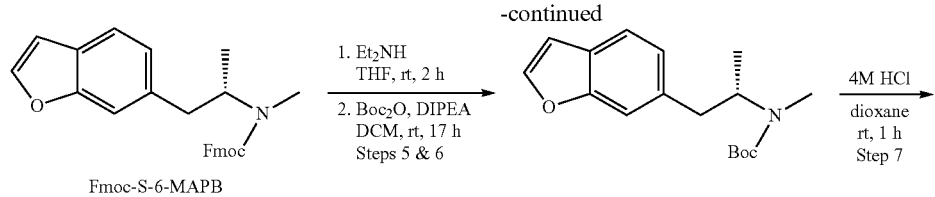
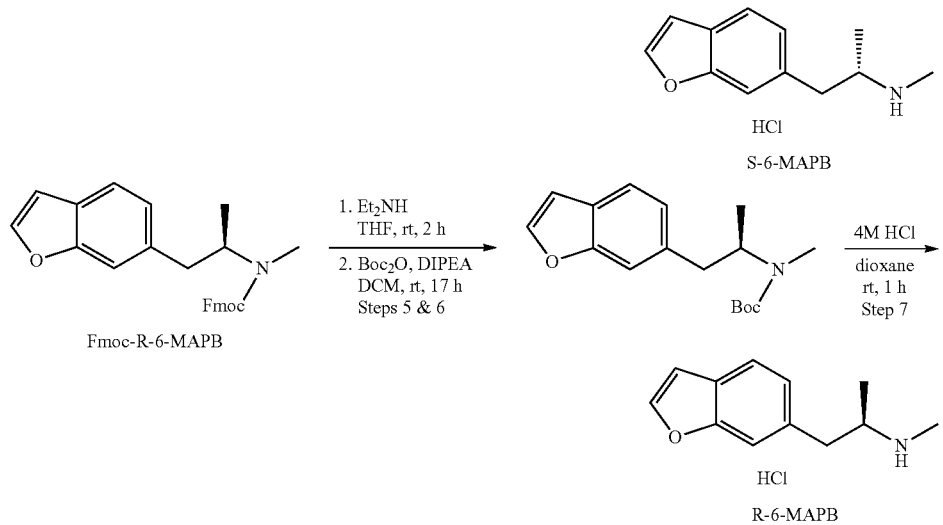
The chiral separation method used in Step 4 was the same as for S-5-MAPB and R-5-MAPB. This resulted in a sample of S-6-MAPB that had chemical purity of 98.86% and an enantiomeric excess of 100, and a sample of R-6-MAPB that had a chemical purity of 96.34% and an enantiomeric excess of 100.
Separation of S-5-MAPB and R-5-MAPB
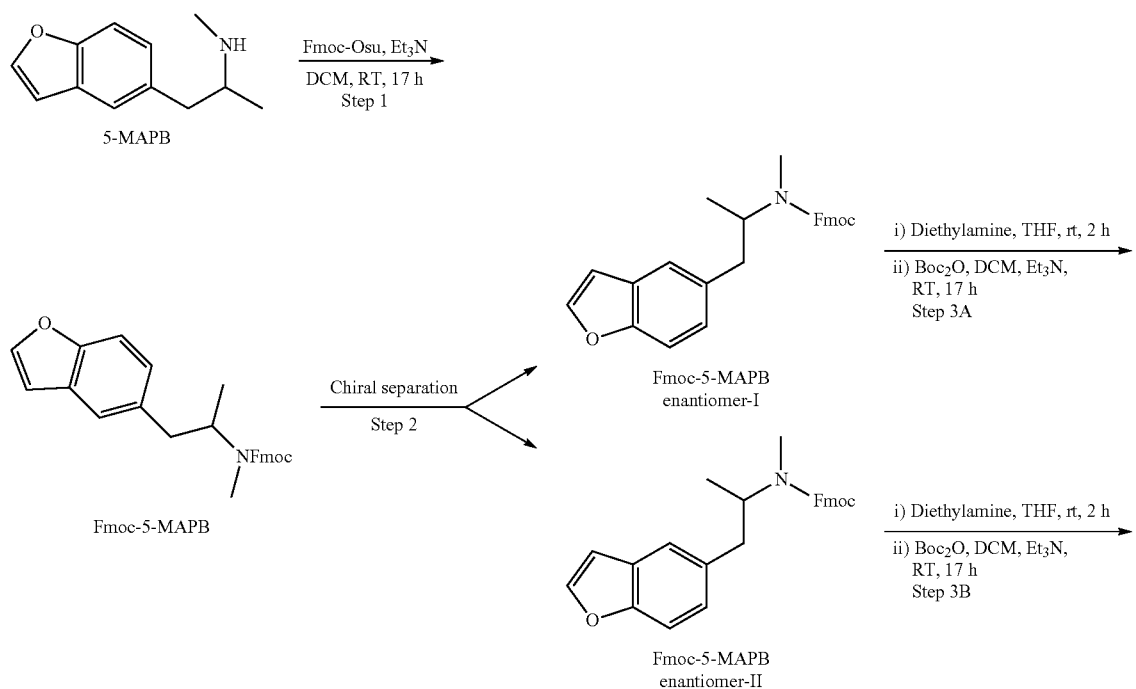

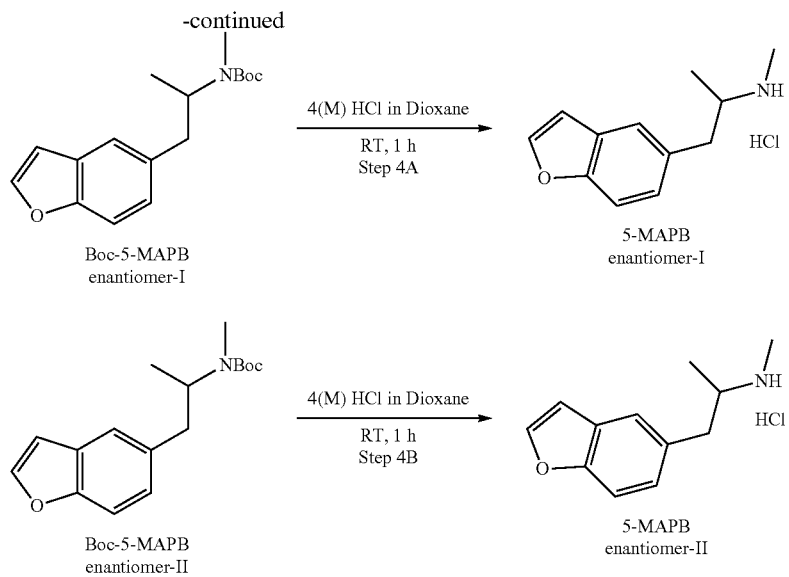

Step 1: To a stirred solution of crude 1-(benzofuran-5-yl)-N-methylpropan-2-amine (5-MAPB) (2.0 g, 10.56 mmol, 1.0 eq.) in DCM (20.0 mL) was added Et₃N (2.94 m 1, 21.13 mmol, 2.0 eq.) and Fmoc-osu (5.34 g, 15.85 mmol, 1.5 eq.) at RT and continue to stir at same temperature for 1 h. After completion of reaction (monitoring by LCMS), water (20 mL) was added to the reaction mixture, organic part was extracted with DCM (20 ml), dried over sodium sulphate, evaporated under reduced pressure to get crude, which was purified by column-chromatography using (0-10%) EA/HEX to get (9H-fluoren-9-yl)methyl (1-(benzofuran-5-yl)propan-2-yl)(methyl)carbamate (Fmoc-5-MAPB) (3.6 g, 83%) as sticky liquid.

Step 2: After chiral (SFC) separation got Fmoc-5-MAPB-enantiomer-I (1.5 g) and Fmoc-5-MAPB-enantiomer-II (1.7 g) as sticky liquid.

Fmoc-5-MAPB-enantiomer-I 1H NMR (400 MHz, DMSO-$d_6$) δ 7.92-7.88 (m, 2H), 7.60 (s, 1H), 7.50 (s, 1H), 7.42-7.38 (m, 4H), 7.27-7.22 (m, 2H), 7.14-7.12 (m, 1H), 6.85 (s, 2H), 4.40 (s, 1H), 4.26 (s, 1H), 4.15 (m, 1H), 3.91 (s, 1H), 2.79 (s, 1H), 2.64 (d, J=19.96 Hz, 3H), 1.23-0.76 (m, 3H), LCMS: (ES) C27H25NO3 requires 411, found 412.4 [M+H]⁺.

Fmoc-5-MAPB-enantiomer-II 1H NMR (400 MHz, DMSO-$d_6$) δ 7.92-7.83 (m, 2H), 7.60-7.25 (m, 8H), 7.12 (m, 1H), 6.88-6.79 (m, 2H), 4.40 (s, 1H), 4.31 (m, 1H), 4.15 (s, 1H), 3.91 (s, 1H), 2.79 (m, 1H), 2.64 (d, J=19.36 Hz, 3H) 1.28-1.06 (m, 3H). LCMS: (ES) $C_{27}H_{25}NO_3$ requires 411, found 412.50 [M+H]⁺.

Step 3A: To stirred solution of (9H-fluoren-9-yl)methyl (1-(benzofuran-5-yl)propan-2-yl)(methyl)carbamate (600 mg, 1.46 mmol, 1.0 eq.) in THF (20 mL) was added diethyl amine (1.52 mL, 14.59 mmol, 10.0 eq.) at RT and reaction was stir at room temperature for 16 h. After completion of reaction, solvent was evaporated, residue was re-dissolved in DCM (20 mL) and Boc-anhydride (0.67 mL, 2.92 mmol, 2.0 eq.) and Et₃N (0.82 mL, 5.839 mmol, 4.0 eq.) was added to it and stirred at room temperature for 12 h. After completion, organic part was washed with water (20 mL), dried over anhydrous sodium sulfate, evaporated under reduced pressure to get the crude which was purified with silica gel (100-200 mesh) eluted with 0-5% ethyl acetate in hexane to afford tert-butyl (1-(benzofuran-5-yl)propan-2-yl)(methyl)carbamate (7-enantiomer-I) (400 mg, 94%) as sticky colorless liquid. ¹HNMR (400 MHz, DMSO-$d_6$) δ 7.92 (s, 1H), 7.48 (d, J=8.32 Hz, 1H), 7.40 (s, 1H), 7.11 (d, J=8.16 Hz, 1H), 6.88 (s, 1H), 4.36-4.30 (m, 1H), 2.77 (d, J=5.6 Hz, 2H), 2.66 (s, 3H), 1.25 (s, 3H), 1.11 (s, 9H), LCMS: (ES) $C_{17}H_{23}NO_3$ requires 289, found 234 [M–tertbutyl]⁺.

Step 3B: To stirred solution of (9H-fluoren-9-yl)methyl (1-(benzofuran-5-yl)propan-2-yl)(methyl)carbamate (1 g, 2.43 mmol, 1.0 eq.) in THF (20 mL) was added diethyl amine (2.5 mL, 24.30 mmol, 10.0 eq.) at RT and the resulting reaction mixture was stirred at room temperature for 16 h. After completion, solvent was evaporated, residue was re-dissolved in DCM (20 mL) and Boc-anhydride (1.1 mL, 4.86 mmol, 2.0 eq.) and Et₃N (1.4 mL, 9.72 mmol, 4.0 eq.) was added to it and continue to stir at RT for 12 h. After completion, organic part was washed with water (30 mL), dried over anhydrous sodium sulfate, evaporated under reduced pressure to get the crude which was purified b column chromatography eluted with 0-5% ethyl acetate in hexane to afford pure tert-butyl (1-(benzofuran-5-yl)propan-2-yl)(methyl)carbamate (600 mg, 79%) as sticky colorless liquid. ¹HNMR (400 MHz, DMSO-$d_6$) δ 7.92 (d, J=1.68 HZ, 1H), 7.48 (d, J=8.04 Hz, 1H), 7.40 (s, 1H), 7.11 (d, J=8.28 Hz, 1H), 6.88 (s, 1H), 4.38-4.30 (m, 1H), 2.77 (d, J=5.8 Hz, 2H), 2.64 (s, 3H), 1.25 (s, 3H), 1.11 (s, 9H), LCMS: (ES) $C_{17}H_{23}NO_3$ requires 289, found 234 [M–tertbutyl]⁺.

Step 4A: To a stirred solution tert-butyl (1-(benzofuran-5-yl)propan-2-yl)(methyl)carbamate (7-enantiomer-1) (1.8 g, 6.228 mmol, 1 eq.) in 1,4 dioxane (10 ml) was added 4(M) HCl in 1,4 dioxane (15 mL) at 0° C. and the resulting reaction mixture was allowed to stir at room temperature for 1 h. Upon completion of reaction (monitored by TLC, 30% EA in Hexane), the solvent were evaporated and the crude was washed twice with diethyl ether (2×30 mL) and pentane finally dried under vacuum to afford 1-(benzofuran-5-yl)-N-methylpropan-2-amine hydrochloride (1.1 g, 93%) as white solid. ¹HNMR (400 MHz, DMSO-$d_6$) δ 8.87-8.82 (bs, 2H), 7.99 (s, 1H), 7.57 (m, 2H), 7.21 (d, J=8.28 Hz, 1H), 6.93 (S, 1H), 3.39 (bs, 1H), 3.26 (q, 1H), 2.77 (q, 3H), 2.57 (s, 3H), 1.11 (d, J=6.4 Hz, 3H). LCMS: (ES) $C_{12}H_{15}NO$ requires 189, found 190 [M+H]+. HPLC: Purity (λ 250 nm): 99.64%. Absolute configuration determined by comparison to authentic samples.

Step 4B: To a stirred solution of tert-butyl (1-(benzofuran-5-yl)propan-2-yl)(methyl)carbamate (7-enantiomer-II) (1.7 g, 5.87 mmol, 1 eq.) in 1,4 dioxane (15 mL) was added 4(M) HCl in 1,4 dioxane (10 mL) at 0° C. and the resulting reaction mixture was allowed to stir at room temperature for 1 h. Upon completion of reaction (monitored by TLC, 30% EA in Hexane), the solvent were evaporated and the crude was washed twice with diethyl ether (2×30 mL) and pentane and dried under vacuum to afford (R)-1-(benzofuran-5-yl)-N-methylpropan-2-amine hydrochloride (Compound-9-en-antiomer-II) (1 g, 99%) as white solid. $^1$HNMR (400 MHz, DMSO-$d_6$) δ 8.82 (bs, 2H), 7.99 (d, J=2.12 HZ, 1H), 7.55 (t, J=8.44 HZ, 6.56 Hz, 2H), 7.21 (dd, J=1.08 Hz, 8.32 Hz, 1H), 6.93 (d, J=1.44 HZ, 1H), 3.39 (bs, 1H), 3.25-3.21 (q, 1H), 2.77-2.71 (q, 1H), 2.57 (s, 3H), 1.10 (t, J=6.48 Hz, 12.12 Hz, 3H). LCMS: (ES) $C_{12}H_{15}NO$ requires 189, found 190.1 [M+H]+. HPLC: Purity (λ 210 nm): 99.84%. Absolute configuration determined by comparison to authentic samples.

Separation of S-6-MAPB and R-6-MAPB

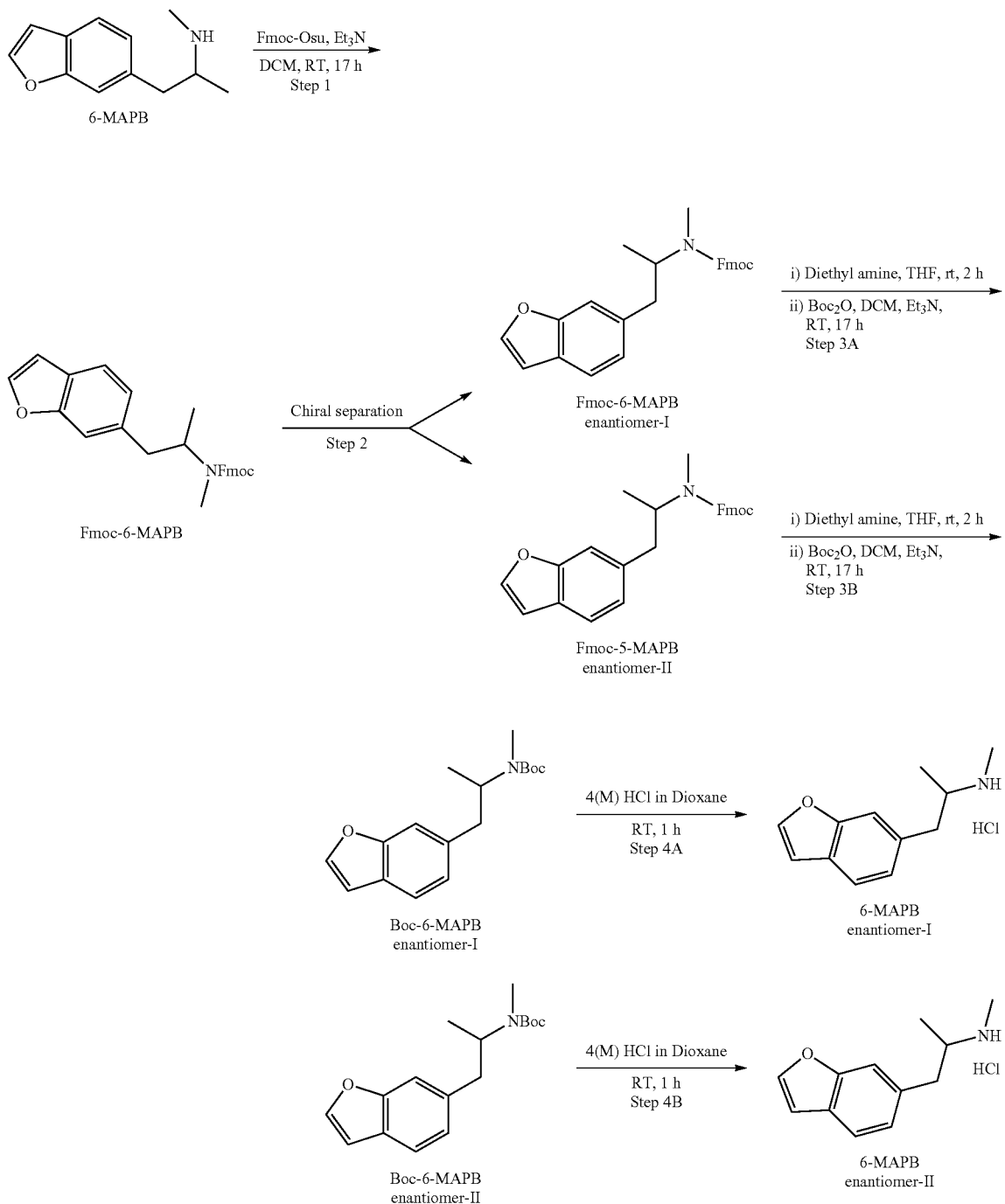

Step 1: To a stirred solution of crude 1-(benzofuran-6-yl)-N-methylpropan-2-amine (6-MAPB) (2.5 g, 13.22 mmol) in DCM (30 mL) was added Et$_3$N (9.27 mL, 66.13 mmol) and Fmoc-Osu (5.34 gm, 15.87 mmol). Resultant reaction mixture was stirred at room temperature for 17 h. After completion, reaction mixture was washed water (10 mL) and organic layer was concentrated under reduced pressure to get the crude which was purified by silica gel (100-200 mesh) column chromatography eluted with 10-20% ethyl acetate in hexane to get (9H-fluoren-9-yl)methyl (1-(benzofuran-6-yl)propan-2-yl)(methyl)carbamate (4.5 g, 82.6%) as a colorless sticky liquid.

Step 2: Isomer separation of Int-3 was done by SFC. The method of SFC separation was given below
Column: REGIS REFLECT C-Amylose A (30.0×250 mm), 5μ
Flow: 30 g/min
Mobile Phase: 30% CO$_2$+70% MeOH
ABPR: 140 bar
Temp: 35° C.
UV: 240 nm
DILUENT: MeOH 6.0 g crude was separated by SFC and ~2.5 g of each fraction (Peak-1 and Peak-2) was obtained.

Peak 1 was obtained at 4.83 min and Peak 2 was obtained at 5.63 min. We observed Fmoc group was removed during chiral separation and generated impurities along with desired compound.

Peak-1 (6-MAPB Enantiomer-I)
$^1$H NMR (DMSO-d$_6$): δ 7.91 (m, 2H), 7.60-7.12 (m, 6H), 6.85 (bs, 1H), 4.40-4.16 (m, 1H), 4.31 (s, 3H), 2.81 (d, J=7.0 Hz, 1H), 2.64 (d, J=17.92 Hz, 1H), 1.14-0.81 (m, 3H). LCMS: (ES) C$_{27}$H$_{25}$NO$_3$ requires 411.18, found 412.3 [M+H]+.

Peak-2 (6-MAPB Enantiomer-II)
$^1$H NMR (DMSO-d$_6$): δ 7.92-7.83 (m, 2H), 7.58-7.32 (m, 4H), 7.27 (bs, 1H), 7.12 (m, 1H), 6.85 (s, 1H), 4.40-4.16 (m, 3H), 2.81 (d, J=7.0 Hz, 1H), 2.64 (d, J=17.18 Hz, 2H), 1.08-0.81 (m, 3H). LCMS: (ES) C$_{27}$H$_{25}$NO$_3$ requires 411, found 412 [M+H]+.

Step 3A and 3B: Each Fmoc protected enantiomer of 6-MAPB (2.5 g, 6 mmol, not fully pure) in THF (20 mL) was treated with diethyl amine (4.4 mL, 60 mmol) and stirred at room temperature for 4 h. After completion, [Monitored with TLC, Mobile Phase 10% EtOAc-hexane], solvent was evaporated, residue was re-dissolved in DCM (30 mL) and then Boc-anhydride (2.7 mL, 11.84 mmol) and Et$_3$N (3.3 mL, 23.68 mmol) was added to it and stirred at room temperature for 17 h. After completion, organic part was washed with water (10 mL), dried over anhydrous sodium sulfate, evaporated under reduced pressure to get the crude which was purified with silica gel (100-200 mesh) elute with 0-5% ethyl acetate hexane to afford boc-6-MAPB enantiomer I and II (1.5 g, 85%) as a sticky colorless liquid.

boc-6-MAPB enantiomer I $^1$H NMR (400 MHz, DMSO-d$_6$): δ 7.90 (d, J=1.68 Hz, 1H), 7.53 (d, J=7.92 Hz, 1H), 7.36 (s, 1H), 7.07 (d, J=7.84 Hz, 1H), 6.88 (s, 1H), 4.33 (s, 1H), 2.79 (s, 2H), 2.63 (s, 3H), 1.24 (s, 3H), 1.10 (s, 9H). LCMS: (ES) C$_{17}$H$_{23}$NO$_3$ requires 289.17, found 290.3 [M+H]+.

boc-6-MAPB enantiomer II $^1$H NMR (400 MHz, DMSO-d$_6$): δ 7.90 (d, J=1.8 Hz, 1H), 7.53 (d, J=7.8 Hz, 1H), 7.36 (s, 1H), 7.07 (d, J=7.84 Hz, 1H), 6.88 (s, 1H), 4.33 (bs, 1H), 2.79 (s, 2H), 2.63 (s, 3H), 1.26 (d, J=6.32 Hz, 3H), 1.10 (s, 9H). LCMS: (ES) C17H23NO3 requires 289.17, found 290.1 [M+H]+.

Step 4A and 4B: (2.0 g, 6.92 mmol, 1 eq.) were separately dissolved in 1,4 dioxane (5 mL) and 4M HCl in 1,4 dioxane (20 mL) was added to it. Resultant solution was stirred at room temperature for 3 h. After completion, solvent was evaporated; residue was triturated with hexane to get the pure desired amine HCl salt as a white solid 6-MAPB enantiomer I (1.24 g, 94%) and 6-MAPB enantiomer II (1.25 g, 95.44%).

6-MAPB enantiomer I $^1$H NMR (400 MHz, DMSO-d$_6$): δ 9.05 (s, 2H), 7.96 (d, J=1.96 Hz, 1H), 7.62 (d, J=7.92 Hz, 1H), 7.53 (s, 1H), 7.16 (d, J=7.84 Hz, 1H), 6.93 (s, 1H), 3.41-3.37 (m, 1H), 3.30-3.26 (m, 1H), 2.80-2.75 (q, 1H), 2.56 (t, J=5.16 Hz, 5.24 Hz, 3H), 1.12 (d, J=6.44 Hz, 3H). LCMS: (ES) C12H15NO requires 189.12, found 190.38 [M+H]$^+$. HPLC: Purity (λ 210 nm): 98.86%. Chiral HPLC: Purity (λ 250 nm): 100%. Absolute stereochemistry assigned by comparison to authentic sample.

6-MAPB enantiomer II $^1$H NMR (400 MHz, DMSO-d$_6$): δ 9.01 (bs, 2H), 7.96 (d, J=2.2 Hz, 1H), 7.62 (d, J=7.92 Hz, 1H), 7.53 (s, 1H), 7.16 (d, J=7.96 Hz, 1H), 6.93 (t, J=1.48 Hz, J=0.6 Hz, 1H), 3.30-3.25 (m, 1H), 2.80-2.75 (q, 1H), 2.57-2.55 (m, 3H), 1.12 (d, J=6.48 Hz, 3H). LCMS: (ES) C12H15NO requires 189.12, found 190.29 [M+H]$^+$. HPLC: Purity (λ 260 nm): 96.34%. Chiral HPLC: Purity (λ 250 nm): 99.93%. Absolute stereochemistry assigned by comparison to authentic sample.

Separation of S-5-MBPB and R-5-MBPB

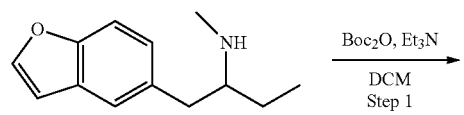

5-MBPB

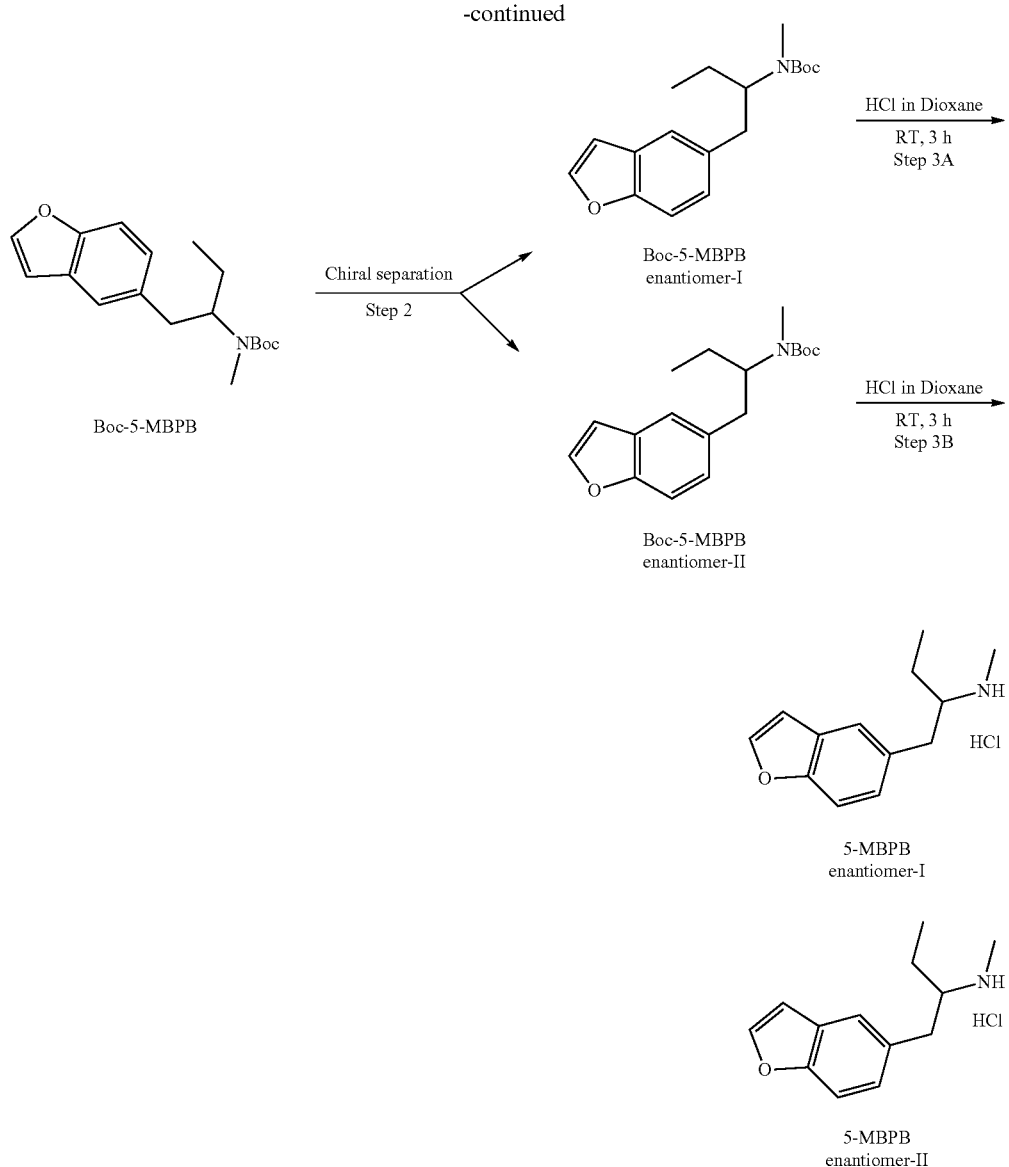

Step 1: To a stirred solution of 1-(benzofuran-5-yl)-N-methylbutan-2-amine (5-MBPB) (3.3 g, 17.55 mmol, 1.0 eq) in DCM (20 mL) was added TEA (7.38 mL, 52.66 mmol, 3.0 eq). Then Boc anhydride (6.04 mL, 26.33 mmol, 1.5 eq) was added to the reaction mixture at 0° C. and stirred at RT for overnight. After the completion [Monitored with TLC, Mobile Phase 5% EtOAc-hexane, Rf-0.5], reaction mixture was diluted with DCM (100 mL) and washed with water (20 mL), and finally NaCl solution. DCM part was dried over magnesium sulphate and concentrated under reduced pressure to afford tert-butyl (1-(benzofuran-5-yl)butan-2-yl)(methyl)carbamate (Boc-5-MBPB) (4.8 g, 90%) as a light yellow liquid. $^1$H NMR (400 MHz, DMSO-d$_6$): δ 7.95 (d, J=15.16 Hz, 1H), 7.47-7.40 (m, 2H), 7.10 (d, J=8.2 Hz, 1H), 6.87 (s, 1H), 4.20-4.09 (m, 1H), 2.79-2.69 (m, 2H), 2.59 (s, 3H), 1.51-1.46 (m, 2H), 1.23 (s, 3H), 1.10 (s, 6H), 0.91-0.77 (m, 3H).

Step 2: Isomer separation of Boc-5-MBPB was done by SFC.
The method of SFC separation was given below
Method of SFC:
  Column Name: Chiralpak AY-H (250×21 mm) 5μ
  Flow rate: 21.0 ml/min
  Mobile phase: Hexane/EtOH/IPAmine—80/20/0.1
  Solubility: MeOH
  Wave length: 246 nm
  Run time: 25 min
4.8 g crude was submitted and after separation ~1.8 g of enantiomer I and enantiomer II was obtained.
  Enantiomer I was obtained at ~4.13 min
  Enantiomer II was obtained at ~5.57 min
  Boc-5-MBPB enantiomer I $^1$H NMR (400 MHz, DMSO-d$_6$): δ 7.91 (s, 1H), 7.47-7.40 (m, 2H), 7.10 (d, J=8.68 Hz, 1H), 6.87 (s, 1H), 4.21-4.09 (m, 1H), 2.79-2.69 (m, 2H), 2.59 (s, 3H), 1.51 (m, 2H), 1.23-1.10 (m, 9H), 0.85-0.79 (m, 3H). Rotamers observed. LCMS: (ES) C18H25NO3 requires 303, found 204 [M−Boc+H]⁺.

Boc-5-MBPB enantiomer II ¹H NMR (400 MHz, DMSO-d₆): δ 7.91 (s, 1H), 7.48-7.40 (m, 2H), 7.10 (d, J=8.12 Hz, 1H), 6.87 (s, 1H), 4.29-4.08 (m, 1H), 2.79-2.69 (m, 2H), 2.59 (s, 3H), 1.51 (m, 2H), 1.23-1.10 (m, 9H), 0.85-0.79 (m, 3H). LCMS: (ES) C18H25NO3 requires 303, found 204 [M−Boc+H]⁺.

Step 3A and 3B: After chiral separation Boc-5-MBPB enantiomer I and Boc-5-MBPB enantiomer II (1.7 g, 5.6 mmol, 1.0 eq.) were separately dissolved in 1,4 dioxane (5 mL) and 4M HCl in 1,4 dioxane (20 mL) was added to it. Resultant solution was stirred at room temperature for 3 h. After completion, solvent was evaporated; residue was triturated with hexane to get the pure desired amine HCl salt as a white solid 5-MBPB enantiomer I (1.3 g, ~100%) and 5-MBPB enantiomer I (1.1 g, 96%).

5-MBPB enantiomer I ¹H NMR (400 MHz, DMSO-d₆): δ 8.97 (s, 1H), 8.82 (s, 1H), 7.99 (d, J=2 Hz, 1H), 7.57 (d, J=8.8 Hz, 2H), 7.24 (d, J=8.36 Hz, 1H), 6.93 (d, J=1.24 Hz, 1H), 3.33 (s, 1H), 3.19-3.14 (m, 1H), 2.91-2.85 (m, 1H), 2.55 (s, 3H), 1.59-1.51 (m, 2H), 0.89 (t, J=7.44 Hz, J=7.48 Hz, 3H). LCMS: (ES) C13H17NO requires 203, found 204 [M+H]⁺. HPLC: Purity (λ 240 nm): 99.65%.

5-MBPB enantiomer II ¹H NMR (400 MHz, DMSO-d₆): δ 8.93 (s, 1H), 8.79 (s, 1H), 7.99 (d, J=2 Hz, 1H), 7.57 (d, J=8.76 Hz, 2H), 7.24 (d, J=8.36 Hz, 1H), 6.93 (d, J=1.4 Hz, 1H), 3.33 (s, 1H), 3.19-3.14 (m, 1H), 2.91-2.85 (m, 1H), 2.55 (s, 3H), 1.59-1.49 (m, 2H), 0.89 (t, J=7.44 Hz, J=7.48 Hz, 3H). LCMS: (ES) C13H17NO requires 203, found 204.1 [M+H]⁺. HPLC: Purity (λ 250 nm): 99.81%.

Separation of S-6-MBPB and R-6-MBPB

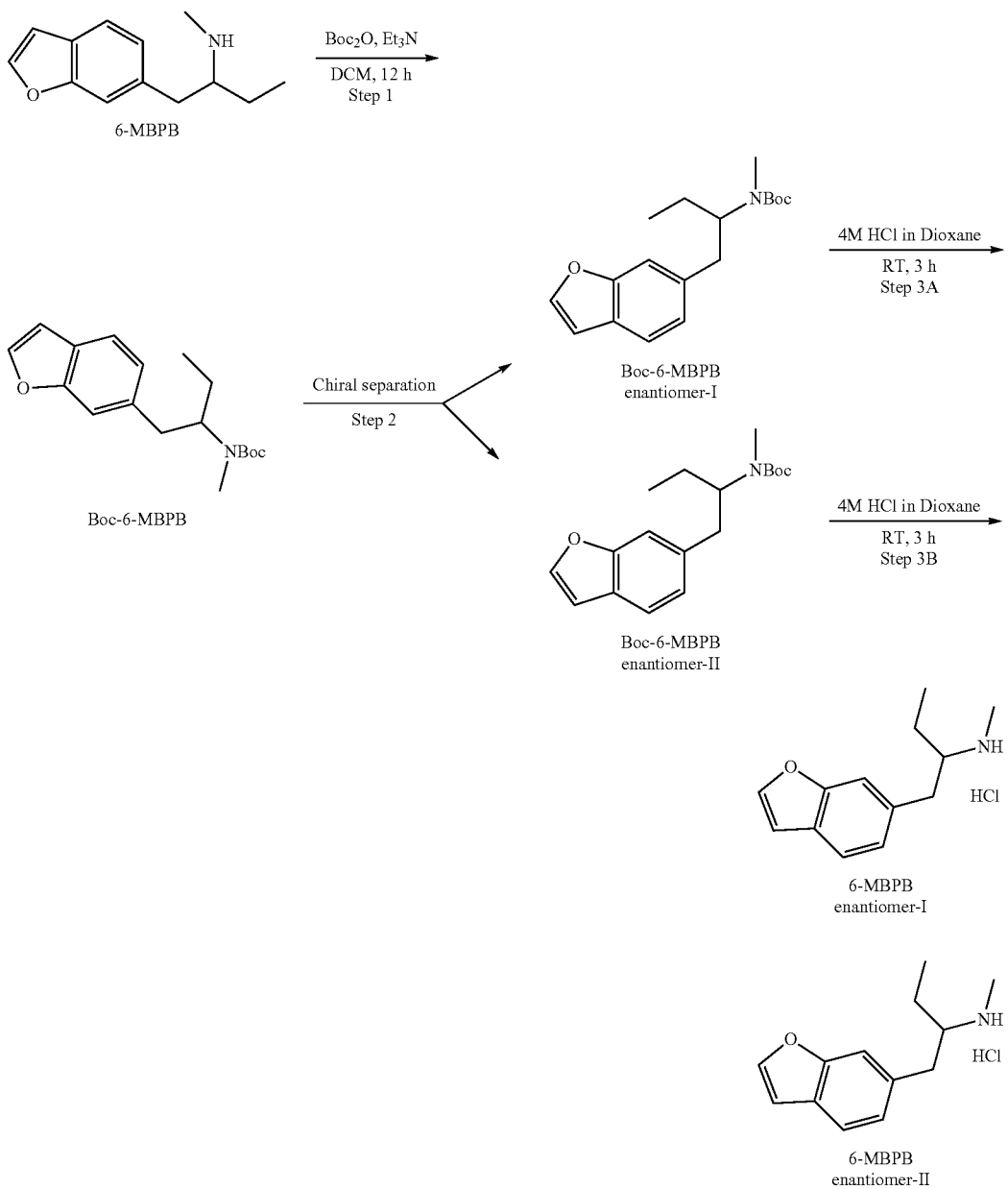

Step 1: To a stirred solution of 1-(benzofuran-6-yl)-N-methylbutan-2-amine (6-MBPB) (5.0 g, 19.70 mmol, 1.0 eq.) in DCM (15 mL) was added TEA (8.29 mL, 59.11 mmol, 3.0 eq.). Then Boc anhydride (6.78 mL, 29.55 mmol, 1.5 eq.) was added to the reaction mixture at 0° C. and stirred at RT for 12 h. After completion [monitored by TLC, mobile Phase 5% EtOAc-hexane]reaction mixture was diluted with DCM (100 mL) and washed with water (20 mL), followed by NaCl solution. Organic layer was dried over magnesium sulphate and concentrated under reduced pressure to afford tert-butyl (1-(benzofuran-6-yl)butan-2-yl)(methyl)carbamate (Boc-6-MPBP) (6.7 g, 83%) as a light yellow liquid. $^1$H NMR (400 MHz, DMSO-$d_6$): δ 7.89 (s, 1H), 7.51 (t, J=7.72 Hz, J=7.32 Hz, 1H), 7.35 (s, 1H), 7.06 (d, J=7.96 Hz, 1H), 6.88 (s, 1H), 4.22-4.12 (m, 1H), 2.86-2.71 (m, 2H), 2.59 (s, 3H), 1.54-1.48 (m, 2H), 1.26-1.10 (m, 9H), 0.82-0.76 (m, 3H). Rotamers observed. LCMS: (ES) C18H25NO3 requires 303, found 304.14 [M+H]+. HPLC: Purity (λ 210 nm): 99.70%. Chiral HPLC: Purity (λ 250 nm): 52.87% and Purity (λ 250 nm): 47.13%.

Step 2: Isomer separation of Int-9 was done by SFC. The method of SFC separation was given below
 Column Name: Chiralpak AY-H (250×21 mm) 5µ
 Flow rate: 21.0 ml/min
 Mobile phase: Hexane/EtOH/IPAmine—80/20/0.1
 Solubility: MeOH
 Wave length: 246 nm
 Run time: 25 min
5.0 g crude was separated by SFC and ~2.2 g of each fraction (enantiomer I and enantiomer II) was obtained.
Enantiomer I was obtained at −3.78 min and enantiomer II was obtained at −9.29 min.

Boc-6-MPBP enantiomer I $^1$H NMR (400 MHz, DMSO-$d_6$): δ 7.89 (s, 1H), 7.51 (t, J=7.72 Hz, J=7.32 Hz, 1H), 7.36 (s, 1H), 7.06 (d, J=7.96 Hz, 1H), 6.88 (bs, 1H), 4.22-4.12 (m, 1H), 3.01-2.71 (m, 2H), 2.59 (s, 3H), 1.54-1.42 (m, 2H), 1.26-1.10 (m, 9H), 0.82 (d, J=7.32 Hz, 3H). Rotamers observed. LCMS: (ES) C18H25NO3 requires 303, found 204.12 [M −Boc H]+. HPLC: Purity (λ 220 nm): 95.08%. Chiral HPLC: Purity (λ 250 nm): 100%.

Boc-6-MPBP enantiomer II $^1$H NMR (400 MHz, DMSO-$d_6$): δ 7.89 (s, 1H), 7.51 (t, J=7.72 Hz, J=7.32 Hz, 1H), 7.36 (s, 1H), 7.06 (d, J=7.96 Hz, 1H), 6.88 (s, 1H), 4.22-4.12 (m, 1H), 2.84-2.71 (m, 2H), 2.59 (s, 3H), 1.54-1.48 (m, 2H), 1.22-1.10 (m, 9H), 0.82-0.75 (m, 3H). Rotamers observed. LCMS: (ES) C18H25NO3 requires 303, found 204.12 [M −Boc H]+. HPLC: Purity (λ 210 nm): 99.68%. Chiral HPLC: Purity (λ 250 nm): 99.95%.

Step 3A and 3B: After chiral separation Boc-6-MPBP enantiomer I and Boc-6-MPBP enantiomer II (2.2 g, 7.26 mmol, 1 eq.) were separately dissolved in 1,4 dioxane (5 mL) and to it was added 4M HCl in 1,4 dioxane (20 mL). Resultant solution was stirred at room temperature for 3 h. After completion, solvent was evaporated; residue was triturated with hexane to get the pure desired amine HCl salt as a white solid 6-MPBP enantiomer I (2.05 g, 95.49%) and 6-MPBP enantiomer II (2.02 g, 94.09%).

6-MPBP enantiomer I $^1$H NMR (400 MHz, DMSO-$d_6$): δ 9.08-8.91 (m, 2H), 7.96 (d, J=2.08 Hz, 1H), 7.62 (d, J=7.92 Hz, 1H), 7.57 (s, 1H), 7.20 (d, J=7.88 Hz, 1H), 6.93 (d, J=1.8 Hz, 1H), 3.23-3.18 (m, 1H), 2.94-2.88 (m, 1H), 2.55-2.53 (m, 3H), 1.62-1.52 (m, 2H), 0.903 (t, J=7.44 Hz, 7.56 Hz, 3H). LCMS: (ES) C13H17NO requires 203, found 204 [M+H]+. HPLC: Purity (λ 210 nm): 97.42%. Chiral HPLC: Purity (λ 250 nm): 100%.

6-MPBP enantiomer II $^1$H NMR (400 MHz, DMSO-$d_6$): δ 8.98-8.83 (m, 2H), 7.96 (d, J=2.16 Hz, 1H), 7.62 (d, J=7.92 Hz, 1H), 7.57 (s, 1H), 7.19 (d, J=7.84 Hz, 1H), 6.93 (d, J=1.84 Hz, 1H), 3.56 (s, 1H), 3.38-3.16 (m, 1H), 2.94-2.88 (m, 1H), 2.55 (t, J=3.2 Hz, J=5.28 Hz, 3H), 1.62-1.50 (m, 2H), 0.92 (t, J=7.44 Hz, 3H). LCMS: (ES) C13H17NO requires 203, found 204 [M+H]+. HPLC: Purity (λ 240 nm): 99.59%. Chiral HPLC: Purity (λ 250 nm): 100%.

Separation of Bk-5-MAPB:
Bk-5-MAPB was Boc-protected. Next, isomeric separation of Boc-Bk-5-MAPB was conducted using the SFC and after chiral separation, both isomers of Boc-Bk-5-MAPB were deprotected to afford (−)-Bk-5-MAPB and (+)-Bk-5-MAPB. Each procedure is described below.

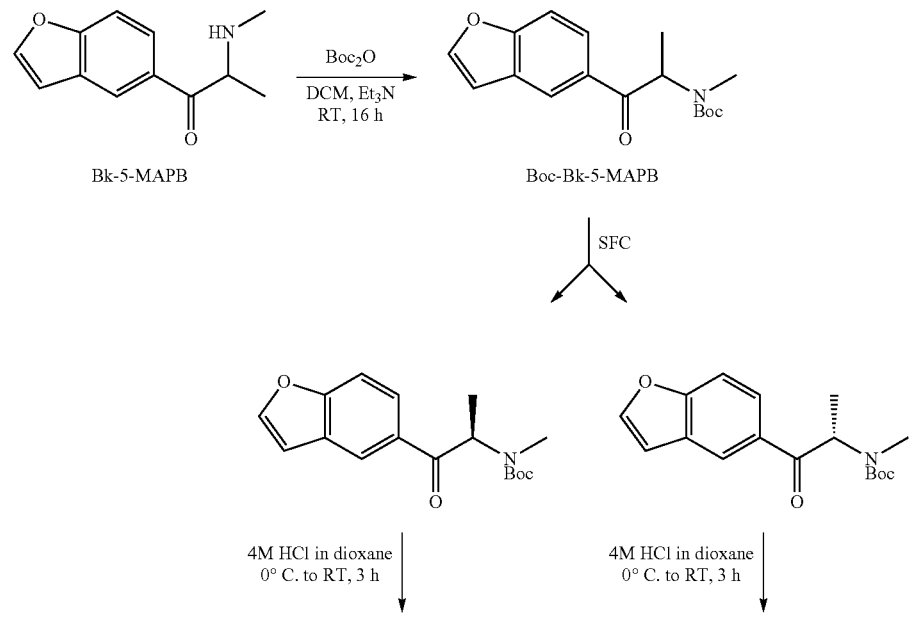

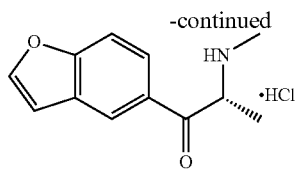

Bk-5-MAPB

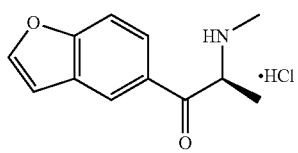

Bk-5-MAPB

Synthesis of Boc-Bk-5-MAPB: To a stirred solution of 1-(benzofuran-5-yl)-2-(methylamino) propan-1-one (16-5) (5.2 g, 25.61 mmol, 1 eq.) in dry DCM (50 ml) was added triethylamine (7.39 ml, 51.23 mmol, 2eq.) and Boc anhydride (11.75 ml, 51.23 mmol, 2 eq.) and the resulting reaction mixture was allowed to stir at room temperature for 4 hours. Upon completion of reaction (monitored by TLC, 10% EA in hexane), the reaction mixture was extracted with DCM (2×100 ml) and washed with water followed by brine solution. Combined organic solvent was dried over anhydrous sodium sulphate and solvent was evaporated under vacuum and purified by silica gel column chromatography using ethyl acetate/hexane (10:90 v/v) as eluent to afford pure tert-butyl (1-(benzofuran-5-yl)-1-oxopropan-2-yl)(methyl)carbamate (Boc-Bk-5-MAPB) as yellow sticky gum (3.9 g, 50%). $^1$H NMR (400 MHz, CDCl$_3$) δ 8.33 (s, 1H), 7.99 (d, J=8.52 Hz, 1H), 7.66 (bs, 1H), 7.52 (d, J=8.56 Hz, 1H), 6.81 (d, J=1.12 Hz, 1H), 5.80 (q, 1H), 2.59 (s, 3H), 1.43 (s, 9H), 1.37 (m, 3H). LCMS: (ES) $C_{17}H_{21}NO_4$ requires 303, found 304 $[M+H]^+$.

Isomeric Separation by SFC:

Isomeric separation of intermediate Boc-Bk-5-MAPB was performed using SFC and the method of SFC separation is given below:

Column: (R,R) Whelk-01 (4.5 mm×250 mm), 5μ
Flow: 2 g/min
Mobile Phase: 75% CO2+25% (ISOPROPANOL)
ABPR: 100 bar
Temp: 35° C.
UV: 220 nm
Diluent: IPA After SFC separation, 1.8 g of intermediate Boc-Bk-5-MAPB-Isomer-1 and 1.9 g of intermediate Boc-Bk-5-MAPB-Isomer-2 were isolated. Characterization of intermediate Boc-Bk-5-MAPB-Isomer-1 and intermediate Boc-Bk-5-MAPB-Isomer-2 are below:

Boc-Bk-5-MAPB-Isomer-1: $^1$HNMR (400 MHz, CDCl$_3$) δ 8.33-8.22 (bs, 1H), 8.00-7.93 (m, 1H), 7.66 (bs, 1H), 7.52 (d, J=7.96 Hz, 1H), 6.82 (s, 1H), 5.79-5.28 (m, 1H), 2.77-2.59 (s, 3H), 1.44 (s, 9H), 1.38 (m, 3H). Rotamers observed. LCMS: (ES) C17H21NO4 requires 303, found 304 [M+H]+. Chiral-HPLC: Purity (λ 235 nm): 99.12%.

Boc-Bk-5-MAPB-Isomer-2: $^1$HNMR (400 MHz, CDCl$_3$) δ 8.30-8.22 (bs, 1H), 8.00-7.91 (m, 1H), 7.66 (bs, 1H), 7.52 (d, J=8.48 Hz, 1H), 6.82 (s, 1H), 5.79-5.28 (m, 1H), 2.77-2.60 (s, 3H), 1.44 (s, 9H), 1.38 (m, 3H). Rotamers observed, LCMS: (ES) C17H21NO4 requires 303, found 304 [M+H]+. Chiral-HPLC: Purity (λ 235 nm): 100%.

Synthesis (−)-Bk-5-MAPB and (+)-Bk-5-MAPB: Both chiral intermediates were then subsequently de-protected using 4(M) HCl in 1,4 dioxane as described in Synthesis 16 to afford the two isomers of Bk-5-MAPB. Characterization of (−)-Bk-5-MAPB-isomer-1 and (+)-Bk-5-MAPB-isomer-2 are below:

(−)-Bk-5-MAPB-Isomer-1: Following the deprotection, Bk-5-MAPB Isomer-1 was afforded as an off-white solid (1.1 g, 96%). $^1$HNMR (400 MHz, DMSO) δ 9.60 (s, 1H), 9.16 (bs, 1H), 8.46 (s, 1H), 8.19 (d, J=1.8 Hz, 1H), 8.02 (d, J=7.56 Hz, 1H), 7.82 (d, J=8.6 Hz, 1H), 7.15 (d, J=1.04 Hz, 1H), 5.25 (d, J=7.04 Hz, 1H), 2.61 (s, 3H), 1.50 (d, J=7.04 Hz, 3H). LCMS: (ES) C12H13NO2 requires 203, found 203.9 [M+H]+. HPLC: Purity (λ 230 nm): 99.19%.

(+)-Bk-5-MAPB-Isomer-1: Following the deprotection, Bk-5-MAPB Isomer-2 was afforded as an off-white solid (1.1 g, 96%). $^1$H NMR (400 MHz, DMSO) δ 9.59 (s, 1H), 9.14 (s, 1H), 8.46 (d, J=1.44 Hz, 1H), 8.19 (d, J=2.16 Hz, 1H), 8.02 (dd, J=1.72 Hz, 8.72 Hz, 1H), 7.82 (d, J=8.68 Hz, 1H), 7.15 (d, J=1.84 Hz, 1H), 5.27 (q, 1H), 2.61 (s, 3H), 1.50 (d, J=7.08 Hz, 3H). LCMS: (ES) C12H13NO2 requires 203, found 204 [M+H]+. HPLC: Purity (λ 240 nm): 99.24%.

Separation of Bk-6-MAPB:

Bk-6-MAPB was Boc-protected. Next, isomeric separation of Boc-Bk-6-MAPB was conducted using the SFC and after chiral separation, both isomers of Boc-Bk-6-MAPB were deprotected to afford (−)-Bk-6-MAPB and (+)-Bk-6-MAPB. Each procedure is described below.

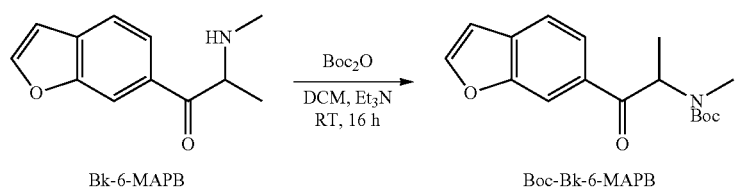

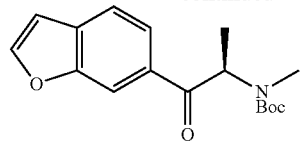

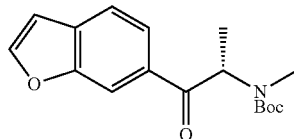

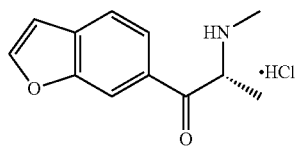

Bk-6-MAPB

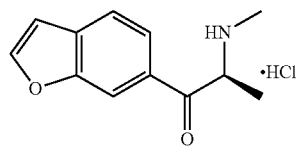

Bk-6-MAPB

Synthesis of Boc-Bk-6-MAPB: To a stirred solution of 1-(benzofuran-6-yl)-2-(methylamino) propan-1-one (Bk-6-MAPB) (3 g, 14.77 mmol, 1 eq.) in dry DCM (30 ml) was added triethylamine (4.26 ml, 29.55 mmol, 2 eq.) and Boc anhydride (6.78 ml, 29.55 mmol, 2 eq.) and the resulting reaction mixture was allowed to stir at room temperature for 4 hours. Upon completion of the reaction (monitored by TLC, 10% EA in hexane), the reaction mixture was extracted with DCM (2×50 ml) and washed with water followed by brine solution. The combined organic solvent was dried over anhydrous sodium sulphate and the solvent was evaporated under vacuum and purified by silica gel column chromatography using ethyl acetate/hexane (10:90 v/v) as eluent to afford tert-butyl (1-(benzofuran-6-yl)-1-oxopropan-2-yl)(methyl) carbamate (Boc-Bk-6-MAPB) as a yellow sticky gum (2.5 g, 55%). 1H NMR (400 MHz, CDCl$_3$) δ 8.20-8.11 (bs, 1H), 7.93-7.85 (bd, 1H), 7.76 (s, 1H), 7.63 (bs, 1H), 6.80 (s, 1H), 5.77-5.31 (m, 1H), 2.76-2.58 (s, 3H), 1.45 (s, 9H), 1.38 (m, 3H). Rotamers observed. LCMS: (ES) C$_{17}$H$_{21}$NO$_4$ requires 303, found 304 [M+H]$^+$.

Isomeric Separation by SFC:

Isomer separation of Boc-Bk-6-MAPB was performed using SFC and the method of SFC separation is given below:

Column: (R,R) Whelk-01 (4.5 mm×250 mm), 5μ
Flow: 2 g/min
Mobile Phase: 75% CO2+25% (isopropanol)
ABPR: 100 bar
Temp: 35° C.
UV: 220 nm
Diluent: IPA After SFC separation 1.5 g of Boc-Bk-6-MAPB-Isomer-1 and 1.2 g of Boc-Bk-6-MAPB-Isomer-2 were isolated. Characterization of intermediate Boc-Bk-6-MAPB-Isomer-1 and intermediate Boc-Bk-6-MAPB-Isomer-2 are below:

Boc-Bk-6-MAPB-Isomer-1: $^1$H NMR (400 MHz, CDCl$_3$) δ 8.20-8.11 (s, 1H), 7.93-7.84 (dd, J=8.36 Hz, 1H), 7.76 (s, 1H), 7.63 (d, J=7.8 Hz, 1H), 6.81 (s, 1H), 5.78-5.28 (m, 1H), 2.77-2.61 (s, 3H), 1.45 (s, 9H), 1.38 (m, 3H). Rotamers observed. LCMS: (ES) C17H21NO4 requires 303, found 304 [M+H]+.

Boc-Bk-6-MAPB-Isomer-2: $^1$H NMR (400 MHz, CDCl$_3$) δ 8.20-8.11 (s, 1H), 7.93-7.83 (dd, J=8.04 Hz, 30.44 Hz, 1H), 7.76 (s, 1H), 7.63 (d, J=7.84 Hz, 1H), 6.81 (s, 1H), 5.77-5.28 (m, 1H), 2.77-2.61 (s, 3H), 1.45 (s, 9H), 1.38 (m, 3H). Rotamers observed. LCMS: MS(ES) C17H21NO4 requires 303, found 304 [M+H]$^+$.

Synthesis (−)-Bk-6-MAPB and (+)-Bk-6-MAPB: Both chiral intermediates were then subsequently de-protected using 4(M) HCl in 1,4 dioxane as described in Synthesis 17 to afford the two isomers of Bk-6-MAPB. Characterization of (−)-Bk-6-MAPB-isomer-1 and (+)-Bk-6-MAPB-isomer-2 are below:

(−)-Bk-6-MAPB: Following the deprotection, (−)-Bk-6-MAPB was afforded as a white solid (1.1 g, 87%). $^1$H NMR (400 MHz, CDCl$_3$) δ 10.65 (s, 1H), 9.26 (s, 1H), 8.13 (s, 1H), 7.85-7.82 (m, 2H), 7.71 (d, J=8.16 Hz, 1H), 6.85 (d, J=1.7 Hz, 1H), 5.01 (bs, 1H), 2.89 (bs, 3H), 1.84 (d, J=7 Hz, 3H). LCMS: (ES) C12H13NO2 requires 203, found 204 [M+H]$^+$. HPLC: Purity (λ 300 nm): 99.63%.

(+)-Bk-6-MAPB: Following the deprotection, (+)-Bk-6-MAPB was afforded as a white solid (1.1 g, 92%). $^1$H NMR (400 MHz, CDCl$_3$) δ 10.57 (s, 1H), 9.33 (s, 1H), 8.13 (s, 1H), 7.85-7.82 (m, 2H), 7.70 (d, J=8.08 Hz, 1H), 6.85 (d, J=1.9 Hz, 1H), 5.03 (bs, 1H), 2.96 (s, 3H), 1.84 (d, J=6.76 Hz, 3H). LCMS: (ES) C12H13NO2 requires 203, found 204 [M+H]$^+$. HPLC: Purity (λ 300 nm): 99.75%.

Separation of Bk-5-MBPB:

Bk-5-MBPB was Boc-protected. Next, isomeric separation of Boc-Bk-5-MBPB was conducted using the SFC and after chiral separation, both isomers of Boc-Bk-5-MBPB were deprotected to afford (−)-Bk-5-MBPB and (+)-Bk-5-MBPB. Each procedure is described below.

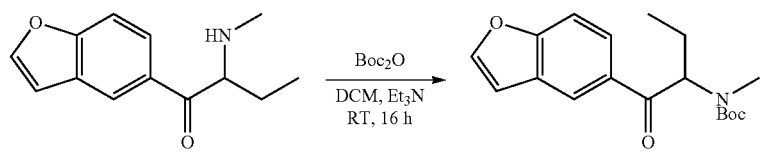

Bk-5-MBPB → Boc-Bk-5-MBPB

Boc₂O, DCM, Et₃N, RT, 16 h

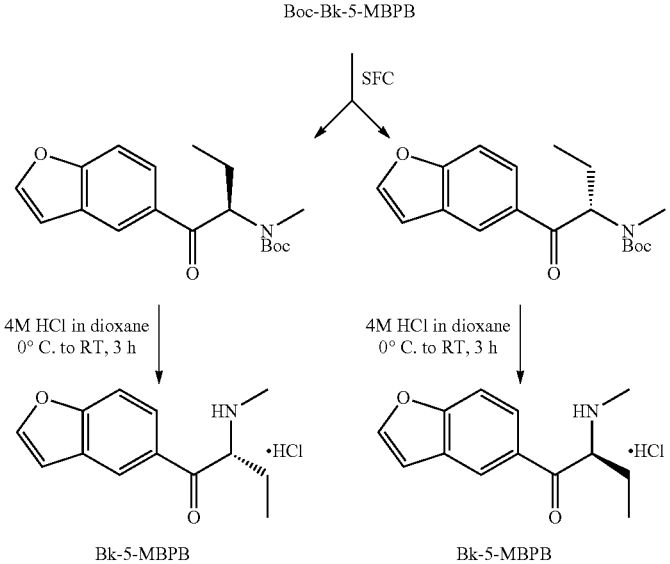

4M HCl in dioxane
0° C. to RT, 3 h

4M HCl in dioxane
0° C. to RT, 3 h

Bk-5-MBPB         Bk-5-MBPB

Synthesis of Boc-Bk-5-MBPB: To a stirred solution of 1-(benzofuran-5-yl)-2-(methylamino) butan-1-one (Bk-5-MBPB) (2.3 g, 10.59 mmol, 1 eq.) in dry DCM (30 ml) was added triethylamine (3.05 ml, 21.19 mmol, 2 eq.) and Boc anhydride (4.86 ml, 21.19 mmol, 2 eq.) and the resulting reaction mixture was allowed to stir at room temperature for 4 hours. Upon completion, (monitored by TLC, 10% EA in hexane), the reaction mixture was extracted with DCM (2×50 ml) and washed with water followed by brine solution. Combined organic solvent was dried over anhydrous sodium sulphate, solvent was evaporated under vacuum and purified by silica gel column chromatography using ethyl acetate/hexane (10:90 v/v) as eluent to get pure tert-butyl (1-(benzofuran-5-yl)-1-oxobutan-2-yl)(methyl)carbamate (Boc-Bk-5-MBPB) as a yellow sticky gum (1.7 g, 50%). $^1$H NMR (400 MHz, CDCl$_3$) δ 8.38 (s, 1H), 8.03 (dd, J=8.76 Hz, 1H), 7.68 (m, 1H), 7.52 (d, J=4.8 Hz, 1H), 6.82 (s, 1H), 5.62 (m, 1H), 2.67 (s, 3H), 1.97 (m, 1H), 1.78 (m, 1H), 1.52 (s, 9H), 0.96 (m, 3H). Rotamer observed. LCMS: (ES) C$_{18}$H$_{23}$NO$_4$ requires 317, found 318 [M+H]$^+$.

Isomeric Separation by SFC:

Isomeric separation of Boc-Bk-5-MBPB was performed using SFC and the method of SFC separation is given below
  Column: (R,R) Whelk-01 (4.5 mm×250 mm), 5μ
  Flow: 2 g/min
  Mobile Phase: 75% CO2+25% (isopropanol)
  ABPR: 100 bar
  Temp: 35° C.
  UV: 220 nm
  Diluent: IPA After SFC separation 1.6 g of Boc-Bk-5-MBPB-Isomer-1 and 1.5 g of Boc-Bk-5-MBPB-Isomer-2 were isolated. Characterization for both isomers is below:

Boc-Bk-5-MBPB-Isomer-1: $^1$H NMR (400 MHz, CDCl$_3$) δ 8.38 (s, 1H), 8.03 (dd, J=8.56 Hz, 1H), 7.68 (d, J=8.28 Hz, 1H), 7.52 (d, J=8.40 Hz, 1H), 6.82 (s, 1H), 5.62 (q, 1H), 2.67 (s, 3H), 1.97 (m, 2H), 1.52 (s, 9H), 0.96 (m, 3H). Rotamer observed. LCMS: (ES) C$_{18}$H$_{23}$NO$_4$ requires 317, found 318 [M+H]$^+$.

Boc-Bk-5-MBPB-Isomer-2: $^1$H NMR (400 MHz, CDCl$_3$) δ 8.38 (s, 1H), 8.03 (dd, J=7.68 Hz, 1H), 7.68 (d, J=8.32 Hz, 1H), 7.52 (d, J=8.4 Hz, 1H), 6.81 (d, J=0.76 Hz, 1H), 5.62 (m, 1H), 2.67 (s, 4H), 1.96 (m, 3H), 1.52 (s, 9H), 0.98 (m, 4H). Extra peak present in aliphatic region. Rotamer observed. LCMS: (ES) C$_{18}$H$_{23}$NO$_4$ requires 317, found 318 [M+H]$^+$.

Synthesis (−)-Bk-5-MBPB and (+)-Bk-5-MBPB: Both chiral intermediates were then subsequently de-protected using 4(M) HCl in 1,4 dioxane as described in Synthesis 18 to afford the two isomers of Bk-5-MBPB. Characterization of (−)-Bk-5-MBPB-isomer-1 and (+)-Bk-5-MBPB-isomer-2 are below:

(−)-Bk-5-MBPB: Following the deprotection, (−)-Bk-5-MBPB was afforded as a white solid (1.43 g, 99%). $^1$HNMR (400 MHz, DMSO-d$_6$) δ 9.53 (s, 1H), 9.18 (s, 1H), 8.48 (s, 1H), 8.19 (d, J=2 Hz, 1H), 8.04 (dd, J=1.32 Hz, 8.68 Hz, 1H), 7.83 (d, J=8.68 Hz, 1H), 7.15 (d, J=1.04 Hz, 1H), 5.31 (s, 1H), 2.58 (s, 3H), 2.10 (m, 1H), 1.94 (m, 1H), 0.78 (t, J=7.44 Hz, 7.48 Hz, 3H). LCMS: (ES) C$_{13}$H$_{15}$NO$_2$ requires 217, found 218 [M+H]$^+$. HPLC: Purity (λ 220 nm): 99.33%.

(+)-Bk-5-MBPB: Following the deprotection, (+)-Bk-5-MBPB was afforded as a white solid (1.33 g, 92%). $^1$HNMR (400 MHz, DMSO-d$_6$) δ 9.50 (bs, 2H), 8.48 (d, J=0.84 Hz, 1H), 8.19 (d, J=1.9 Hz, 1H), 8.04 (d, J=8.6 Hz, 1H), 7.81 (d, J=8.64 Hz, 1H), 7.14 (d, J=1.1 Hz, 1H), 5.32 (s, 1H), 2.57 (s, 3H), 2.13 (m, 1H), 1.95 (m, 1H), 0.78 (t, J=7.4 Hz, 3H). LCMS: MS (ES) C$_{13}$H$_{15}$NO$_2$ requires 217, found 218 [M+H]$^+$. HPLC: Purity (λ 220 nm): 98.15%.

Separation of Bk-6-MBPB:

Bk-6-MBPB was Boc-protected. Next, isomeric separation of Boc-Bk-6-MBPB was conducted using the SFC and after chiral separation, both isomers of Boc-Bk-6-MBPB were deprotected to afford (−)-Bk-6-MBPB and (+)-Bk-6-MBPB. Each procedure is described below.

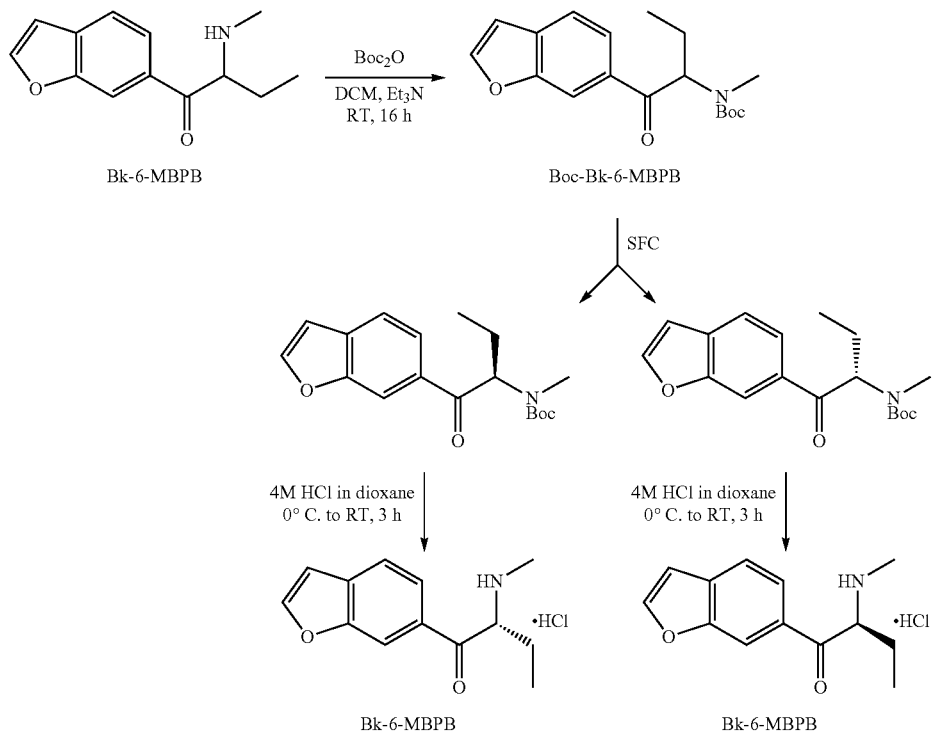

Synthesis of Boc-Bk-6-MBPB: To a stirred solution of 1-(benzofuran-6-yl)-2-(methylamino)butan-1-one (Bk-6-MBPB) (2.75 g, 12.65 mmol, 1 eq.) in dry DCM (30 mL) was added triethylamine (3.65 mL, 25.31 mmol, 2 eq.) and Boc anhydride (5.8 mL, 25.31 mmol, 2 eq.) and the resulting reaction mixture was allowed to stir at room temperature for 4 hours. Upon completion of the reaction (monitored by TLC, 10% EA in hexane), the reaction mixture was extracted with DCM (2×50 ml) and washed with water followed by brine solution. The combined organic layers were dried over anhydrous sodium sulphate, solvent was evaporated under vacuum, and the crude material purified by silica gel column chromatography using ethyl acetate/hexane (10:90 v/v) as eluent to afford pure tert-butyl (1-(benzofuran-6-yl)-1-oxobutan-2-yl)(methyl)carbamate (Boc-Bk-6-MBPB) as yellow sticky gum (3.4 g, 84%). $^1$H NMR (400 MHz, CDCl$_3$) δ 8.24 (s, 1H), 7.97 (dd, J=8.2 Hz, 1H), 7.76 (bs, 1H), 7.63 (bm, 1H), 6.80 (bs, 1H), 5.61 (t, J=5.64 Hz, 8.88 Hz, 1H), 2.66 (s, 3H), 1.99 (q, 2H), 1.55 (s, 9H), 0.98 (m, 3H). Rotamer observed. LCMS: (ES) C$_{18}$H$_{23}$NO$_4$ requires 317, found 318 [M+H]$^+$.

Isomer Separation by SFC

Isomer separation of Boc-Bk-6-MBPB was done by SFC and the method of SFC separation is given below:
Column: (R,R) Whelk-01 (4.5 mm×250 mm), 5μ
Flow: 2 g/min
Mobile Phase: 80% CO2+25% (ISOPROPANOL)
ABPR: 100 bar
Temp: 35° C.
UV: 220 nm
Diluent: IPA After SFC separation, 1 g of Boc-Bk-6-MBPB-Isomer-1 and 900 mg of Boc-Bk-6-MBPB-Isomer-2. Characterization for each isomer is given below:

Boc-Bk-6-MBPB-Isomer-1: $^1$H NMR (400 MHz, CDCl$_3$) δ 8.25 (s, 1H), 7.97 (d, J=8.16 Hz, 1H), 7.89 (bs, 1H), 7.64 (m, 1H), 6.80 (s, 1H), 5.61 (q, 1H), 2.66 (s, 3H), 1.97 (m, 2H), 1.54 (s, 9H), 0.99 (m, 3H). Rotamers observed. LCMS: (ES) C$_{18}$H$_{23}$NO$_4$ requires 317, found 318 [M+H]$^+$.

Boc-Bk-6-MBPB-Isomer-2: $^1$H NMR (400 MHz, CDCl$_3$) δ 8.25 (s, 1H), 7.97 (d, J=8.08 Hz, 1H), 7.76 (s, 1H), 7.64 (m, 1H), 6.80 (s, 1H), 5.61 (m, 1H), 2.66 (s, 3H), 1.97 (m, 2H), 1.45 (s, 9H), 0.99 (m, 3H). Rotamers observed. LCMS: (ES) C$_{18}$H$_{23}$NO$_4$ requires 317, found 218 [M −Boc+H]$^+$.

Synthesis (−)-Bk-6-MBPB and (+)-Bk-6-MBPB: Both chiral intermediates were then subsequently de-protected using 4(M) HCl in 1,4 dioxane as described in Synthesis 19 to afford the two isomers of Bk-6-MBPB. Characterization of (−)-Bk-6-MBPB-isomer-1 and (+)-Bk-6-MBPB-isomer-2 are below:

(−)-Bk-6-MBPB: Following the deprotection, (−)-Bk-6-MBPB was afforded as a white solid (1.4 g, 97%). $^1$H NMR (400 MHz, CDCl$_3$) δ 10.69 (s, 1H), 9.03 (s, 1H), 8.15 (s, 1H), 7.87 (m, 2H), 7.72 (d, J=8.08 Hz, 1H), 6.86 (s, 1H), 5.00 (bs, 1H), 2.85 (s, 3H), 2.45 (m, 1H), 2.26 (m, 1H), 1.02 (t, J=7.48 Hz, 3H). LCMS: (ES) C$_{13}$H$_{15}$NO$_2$ requires 217, found 218 [M+H]$^+$. HPLC: Purity (λ 220 nm): 99.14%.

(+)-Bk-6-MBPB: Following the deprotection, (+)-Bk-6-MBPB was afforded as an off-white solid (1.4 g, 97%). $^1$HNMR (400 MHz, CDCl$_3$) δ 10.61 (s, 1H), 9.09 (s, 1H), 8.16 (s, 1H), 7.88 (m, 2H), 7.72 (d, J=8.08 Hz, 1H), 6.86 (s, 1H), 5.03 (bs, 1H), 2.95 (s, 3H), 2.45 (m, 1H), 2.24 (m, 1H), 1.02 (t, J=7.44 Hz, 3H). LCMS: (ES) C$_{13}$H$_{15}$NO$_2$ requires 217, found 218 [M+H]$^+$. HPLC: Purity (λ 220 nm): 99.44%.

Determination of Specific Rotation

Specific rotation was determined for individual enantiomers using a Jasco P-2000 Polarimeter, 589 nm Na lamp (Path Length 1 dm, 20° C. temperature, Concentration approx. 1 g/100 mL). EtOH was used as solvent for beta-ketone compounds, while distilled water was used for other compounds. Ten measurements were made for each compound.

| Compound | Specific rotation | Standard Deviation |
|---|---|---|
| S 5-MAPB | 13.4 | 0.3 |
| R 5-MAPB | −14.3 | 0.2 |
| S-6-MAPB | 14.7 | 0.1 |
| R-6-MAPB | −14.3 | 0.2 |
| 5-MBPB enantiomer 1 | 18.9 | 0.5 |
| 5-MBPB enantiomer 2 | N/A | N/A |
| 6-MBPB enantiomer 1 | 19.6 | 0.9 |
| 6-MBPB enantiomer 2 | NA | N/A |
| BK-5-MAPB Peak 1 | −53.6 | 0.1 |
| BK-5-MAPB Peak 2 | 56 | 0.2 |
| BK-6-MAPB Peak 1 | −49 | 0.2 |
| BK-6-MAPB Peak 2 | 47.1 | 0.2 |
| BK-5-MBPB Peak 1 | −15.6 | 0.2 |
| BK-5-MBPB Peak 2 | 14.1 | 0.2 |
| BK-6-MBPB Peak 1 | −6.7 | 0.1 |
| BK-6-MBPB Peak 2 | 5.6 | 0.2 |

Example 2: Synthesis of Select Compounds of the Present Invention

Methods for synthesis of the compounds described herein and/or starting materials are either described in the art or will be readily apparent to the skilled artisan in view of general 5 references well-known in the art (see, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the compounds of the invention.

Additional references include: Taniguchi et al. 2010. Journal of mass spectrometry, 45(12), 1473-1476; Shulgin & Shulgin. 1992. PiHKAL. A chemical love story, Transform Press, Berkeley CA; Glennon et al. 1986. J. Med. Chem., 29(2), 194-199; Nichols et al. 1991. J. Med. Chem., 34(1), 276-281; Kedrowski et al. 2007. Organic Letters, 9(17), 3205-3207; Heravi & Zadsirjan. 2016. Current Organic Synthesis, 13(6), 780-833; Keri et al. 2017. European J. Med. Chem., 138, 1002-1033; Perez-Silanes et al. 2001. J. Heterocyclic Chem, 38(5), 1025-1030; and references therein.

Synthesis 1. 5-MBPB:

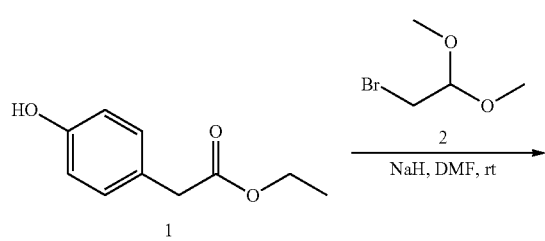

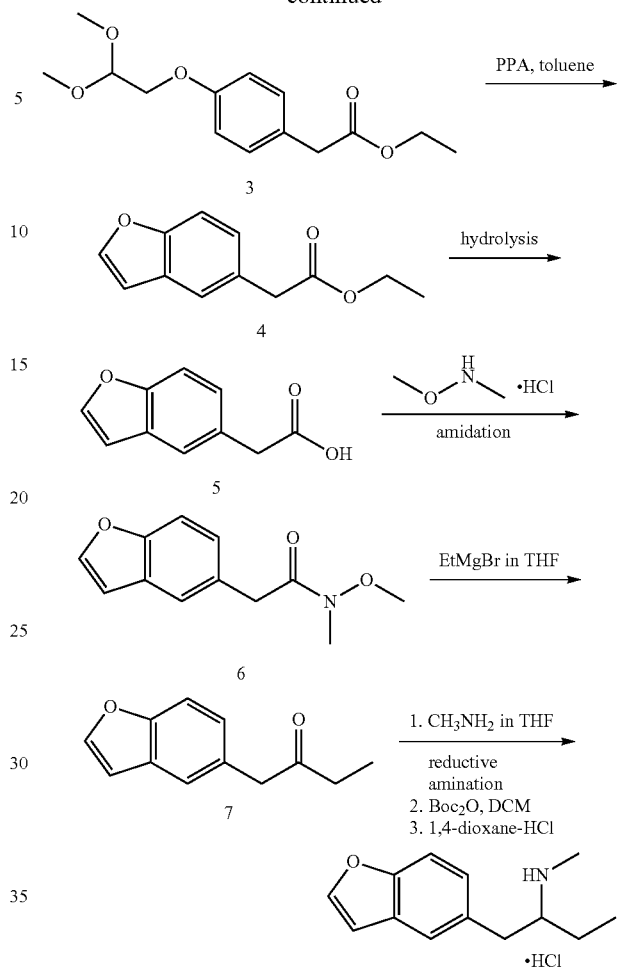

Synthesis 2. 6-MBPB:

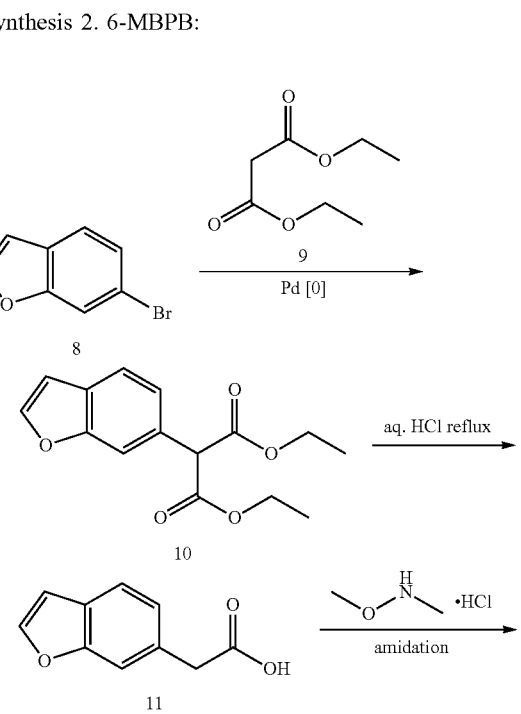

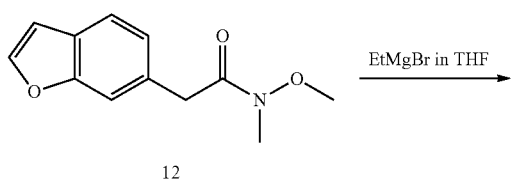

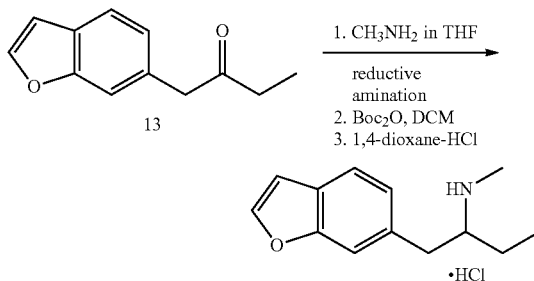

Other versions of these molecules can, for example, be synthesized following the methods of López and colleagues (López et al. 2012. British Journal of Pharmacology. 167 (2): 407-420). Additionally, the 5-MAPB and 6-MAPB can be made by analogy using the syntheses herein for 5-MBPB and 6-MBPB, using MeMgBr in THF in place of EtMgBr in THF in the third step.

Synthesis 3. Bk-5-MAPB:

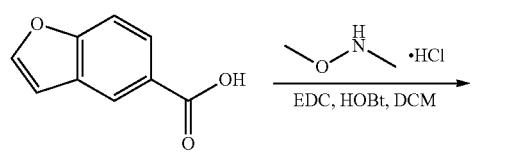

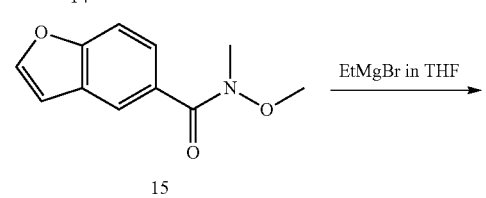

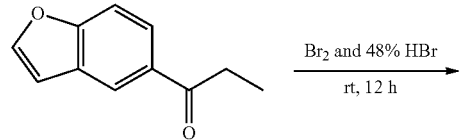

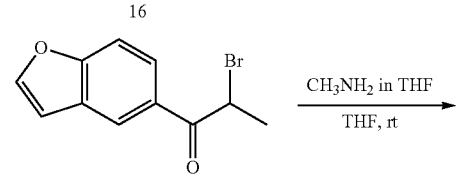

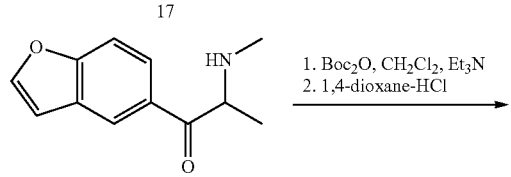

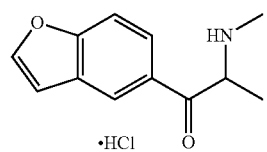

Synthesis 4. Bk-5-MAPB:

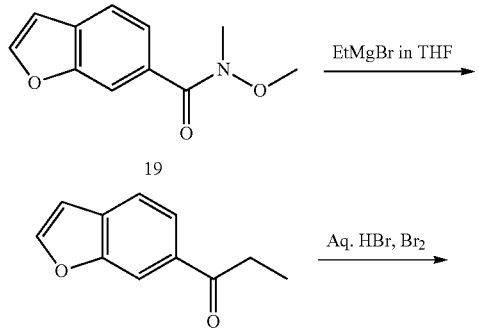

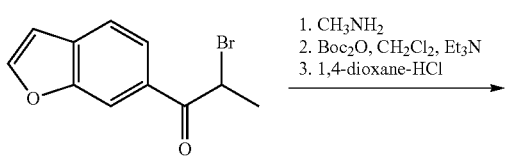

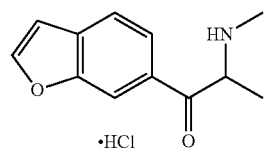

Other versions of these molecules can, for example, be synthesized following the methods of López and colleagues (López et al. 2012. British Journal of Pharmacology. 167 (2): 407-420). Additionally, the Bk-5-MBPB and Bk-66-MBPB can be made by analogy using the syntheses herein for Bk-5-MAPB and Bk-6-MAPB, using propyl magnesium bromide in THF in place of EtMgBr in THF in the second step.

Synthesis 5. Alternative Method of Synthesis of Bk-5-MAPB and Bk-6-MAPB

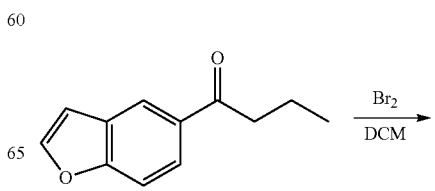

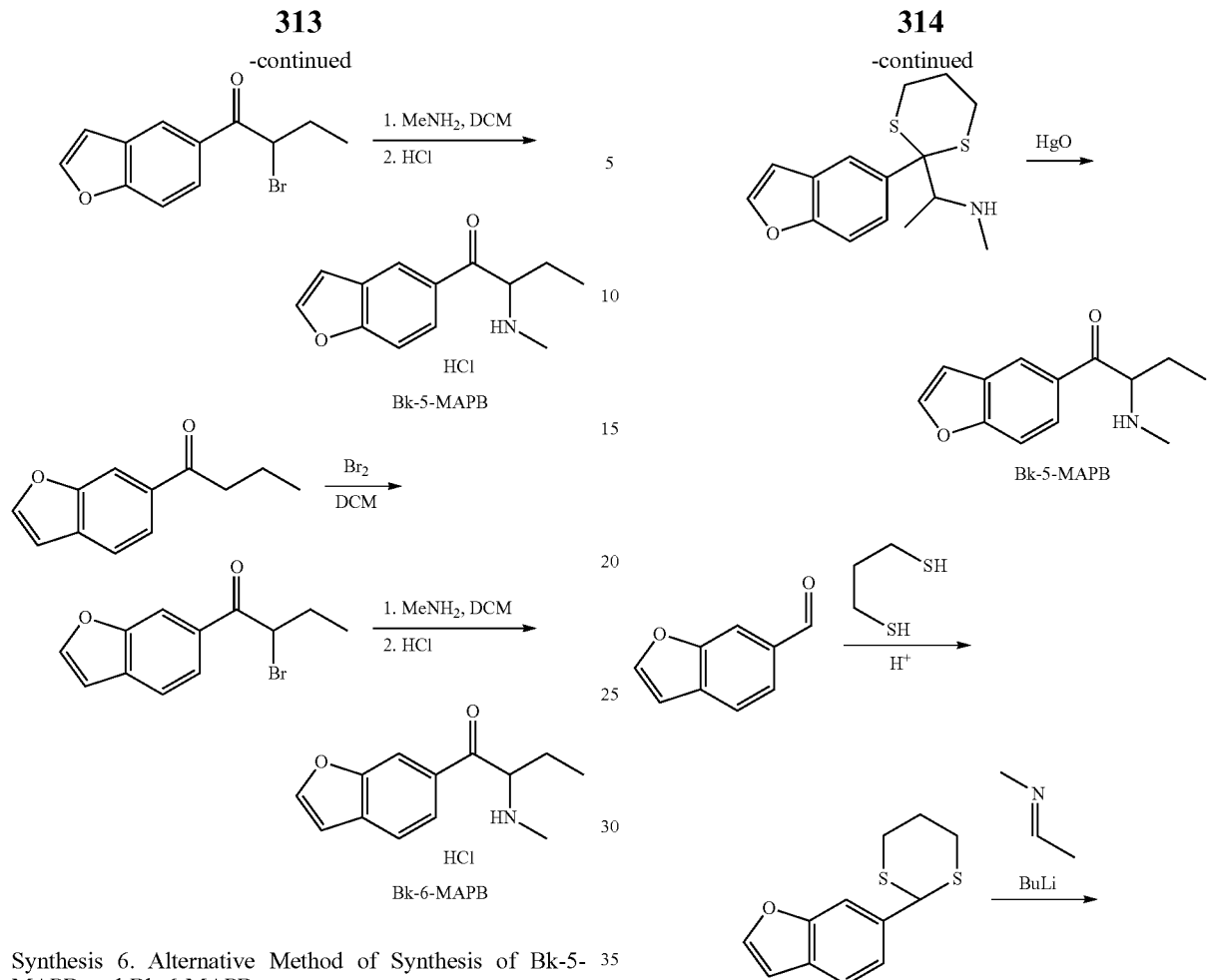
Synthesis 6. Alternative Method of Synthesis of Bk-5-MAPB and Bk-6-MAPB
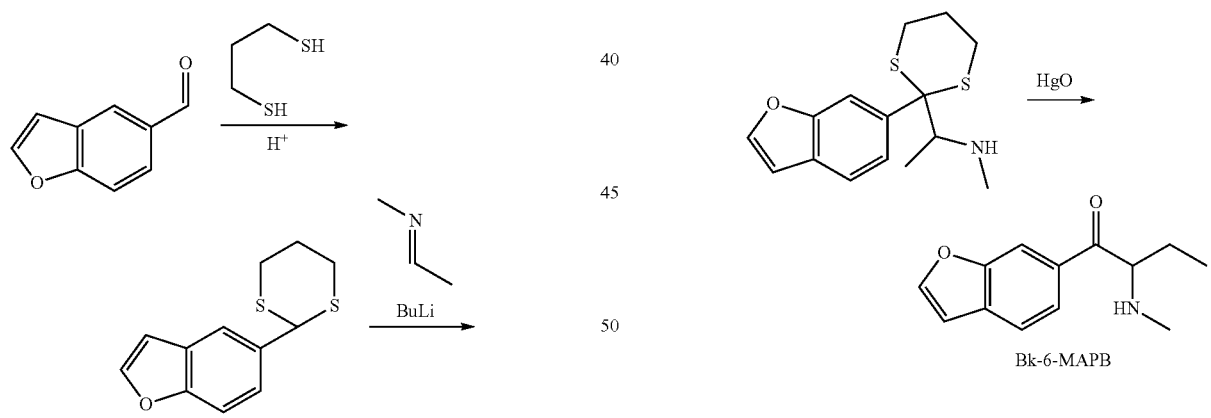
Synthesis 7. Derivatization from Bk-5-MAPB:
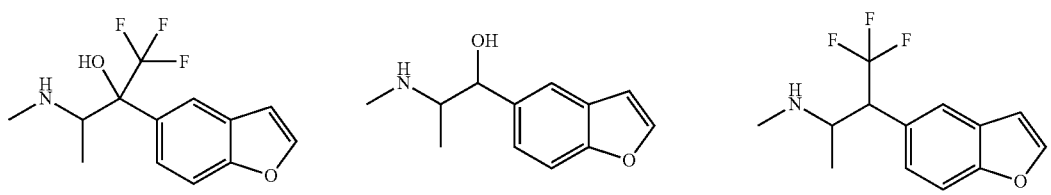

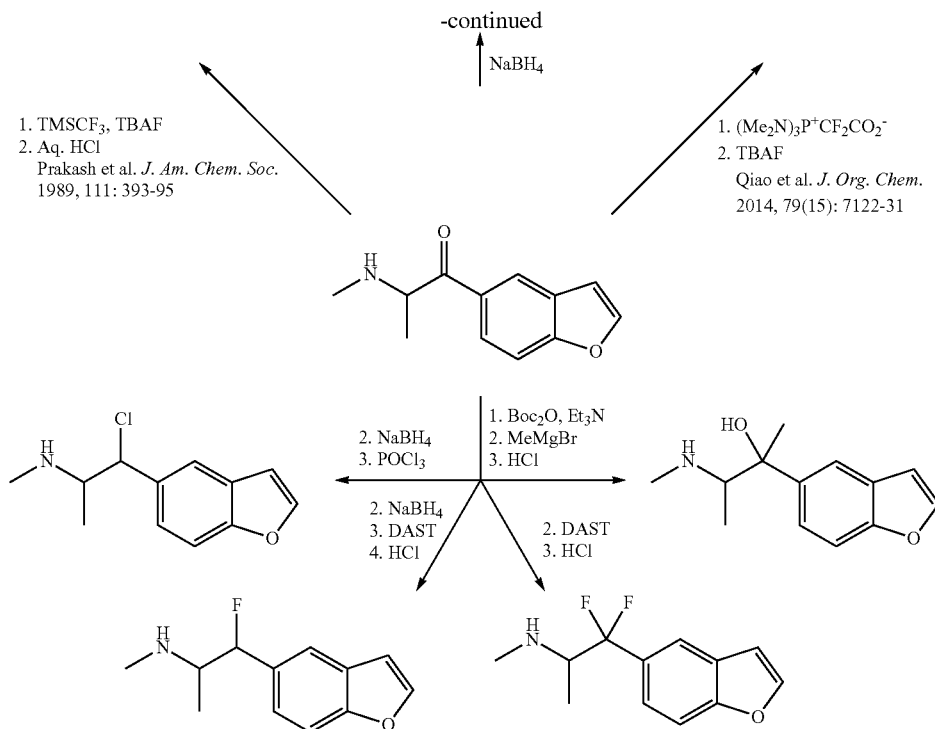

Synthesis 8. Synthesis of 3-(benzofuran-6-yl)-N-methylbut-3-en-2-amine (Compound 1-4)

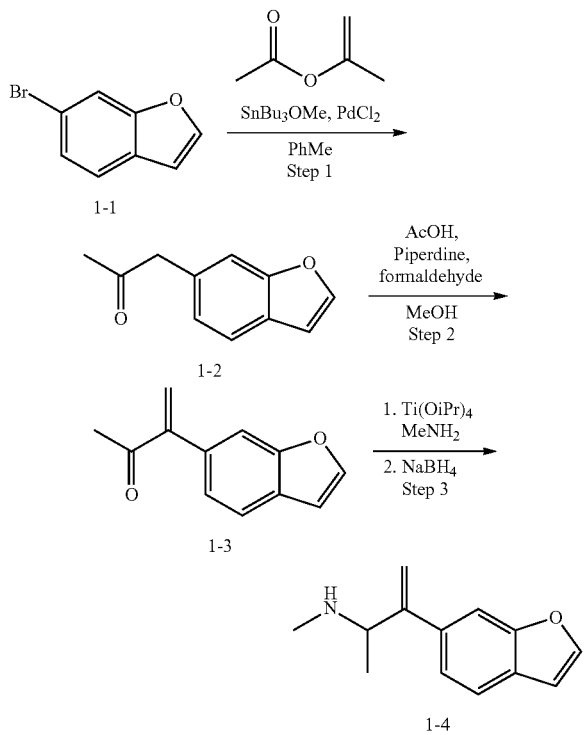

Step 1: A round-bottom flask is charged with 1-1, tributyltin methoxide, and palladium(II) chloride. The flask is then evacuated and refilled with anhydrous nitrogen three times before adding toluene and isopropenyl acetate. The reaction solution is then stirred with heating under nitrogen until the reaction is judged complete by TLC, HPLC, or other analytical method.

Following the reaction, the mixture is cooled to room temperature, diluted with ethyl acetate, and washed three times with water. The organic layer is then dried over anhydrous $Na_2SO_4$, filtered, and concentrated to collect crude 1-2. This crude material can be taken to the next step without further purification or purified by standard techniques of the art to obtain the pure compound.

Step 2: A round-bottom flask is charged with 1-2, acetic acid, piperdine, and formaldehyde. Methanol is then added to dissolve the reaction components and the mixture is stirred until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 1-3. This crude material can be taken to the next step without further purification or purified by standard techniques of the art to obtain the pure compound.

Step 3: In a round-bottom flask, 1-3, methylamine, and titanium (IV) isopropoxide are dissolved in ethanol and stirred under nitrogen. Once there is no remaining 1-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 1-4. This crude material can be purified by standard techniques of the art to obtain the pure compound.

The individual enantiomers of 1-4 can be separated using the methods described herein. For example, chiral SFC conditions are provided in Example 1. Following isolation of the pure enantiomers, they can be mixed again in any ratio necessary to obtain the desired effects.

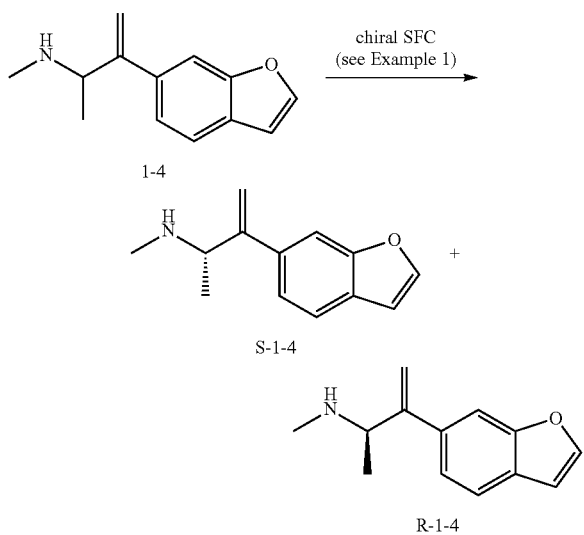

Synthesis 9. Synthesis of 2-(benzofuran-6-yl)-3-(methylamino)butan-1-ol (Compound 2-6)

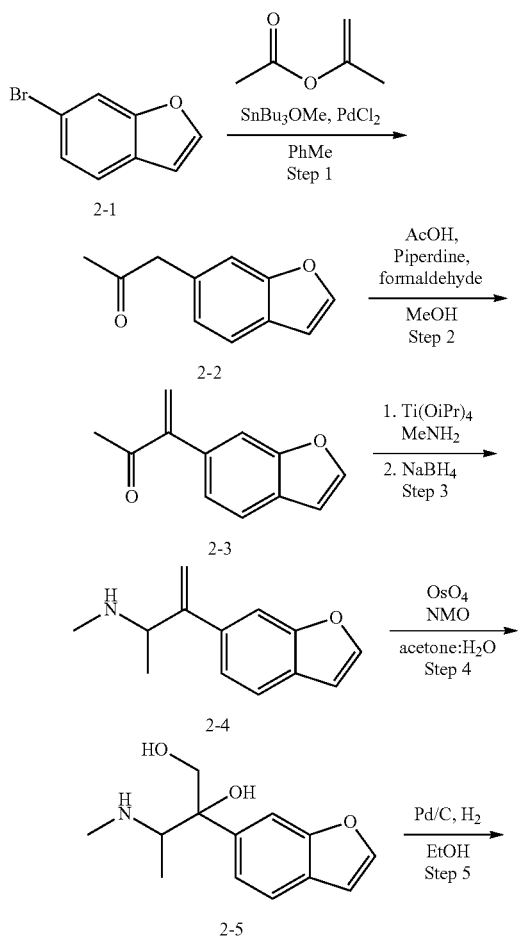

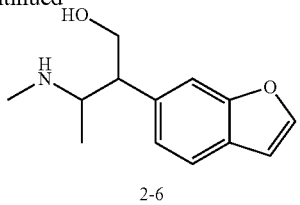

Step 1: A round-bottom flask is charged with 2-1, tributyltin methoxide, and palladium(II) chloride. The flask is then evacuated and refilled with anhydrous nitrogen three times before adding toluene and isopropenyl acetate. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 2-2. This crude material can be taken to the next step without further purification or purified by standard techniques of the art to obtain the pure compound.

Step 2: A round-bottom flask is charged with 2-2, acetic acid, piperdine, and formaldehyde. Methanol is then added to dissolve the reaction components and the mixture is stirred until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 2-3. This crude material can be taken to the next step without further purification or purified by standard techniques of the art to obtain the pure compound.

Step 3: In a round-bottom flask, 2-3, methylamine, and titanium (IV) isopropoxide are dissolved in ethanol and stirred under nitrogen. Once there is no remaining 2-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 2-4. This crude material can be purified by standard techniques of the art to obtain the pure compound.

Step 4: To a round-bottom flask containing 2-4 dissolved in acetone:$H_2O$ is added NMO and a catalytic amount of osmium tetroxide. The resulting mixture is stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 2-5. This crude material can be taken to the next step without further purification or purified by standard techniques of the art to obtain the pure compound.

Step 5: A round-bottom flask containing 2-5 and palladium on carbon is evacuated under vacuum and backfilled with nitrogen three times. Ethanol is then added to the flask and the resulting mixture is sparged with hydrogen gas while stirring. Once the nitrogen atmosphere is displaced by hydrogen, the reaction is stirred at room temperature until the reaction is judged complete by TLC, HPLC, or other analytical method. Following the reaction, the mixture is diluted with ethyl acetate, filtered through diatomaceous earth, and concentrated to collect crude 2-6. This crude material can be purified by standard techniques of the art to obtain the pure compound.

The individual enantiomers of 2-6 can be separated using the methods described herein. For example, chiral SFC conditions are provided in Example 1. Following isolation of the pure enantiomers, they can be mixed again in any ratio necessary to obtain the desired effects.

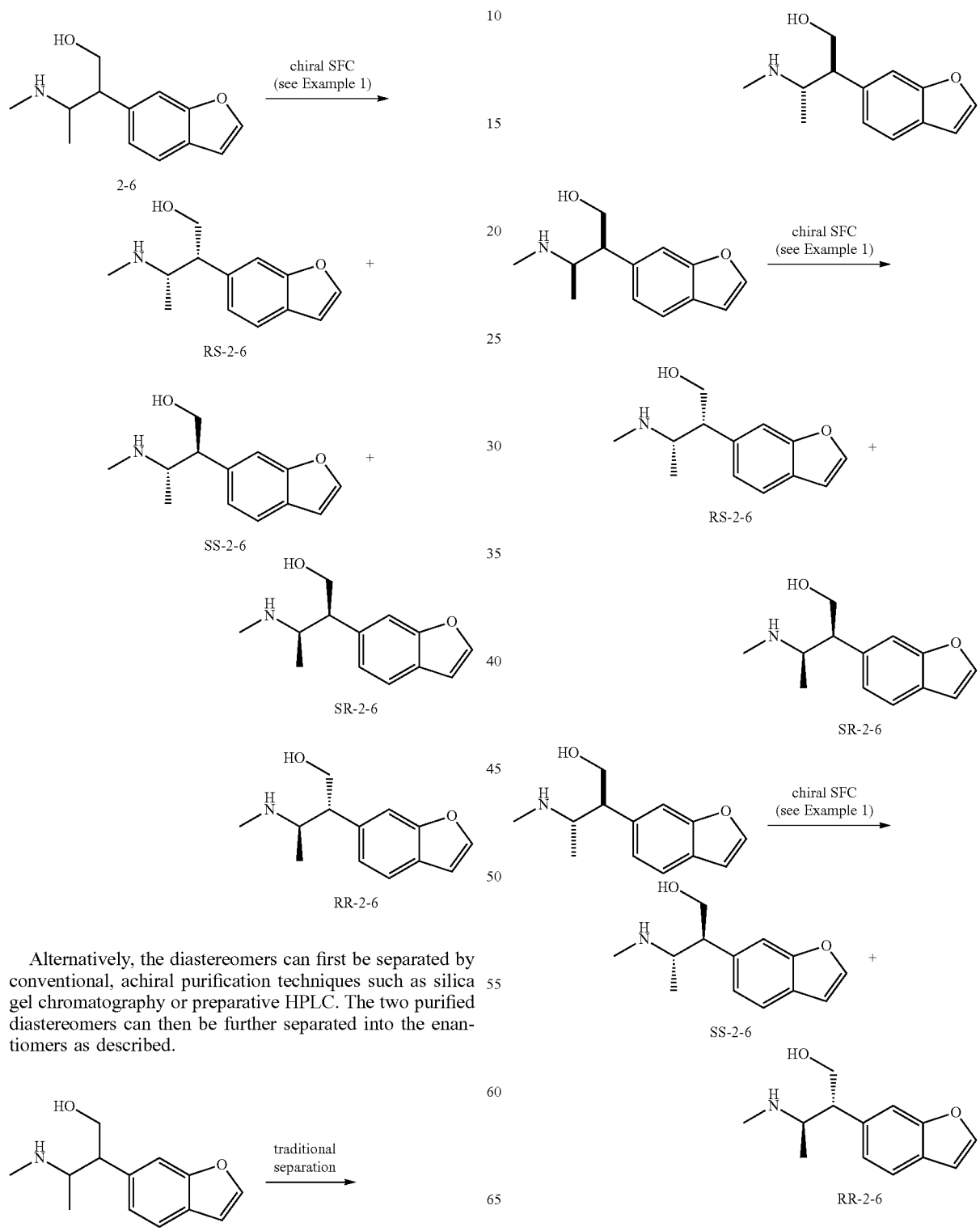

Alternatively, the diastereomers can first be separated by conventional, achiral purification techniques such as silica gel chromatography or preparative HPLC. The two purified diastereomers can then be further separated into the enantiomers as described.

Synthesis 10. Synthesis of 2-(benzofuran-6-yl)-1-cyclopropyl-N-ethylethan-1-amine (Compound 3-5)

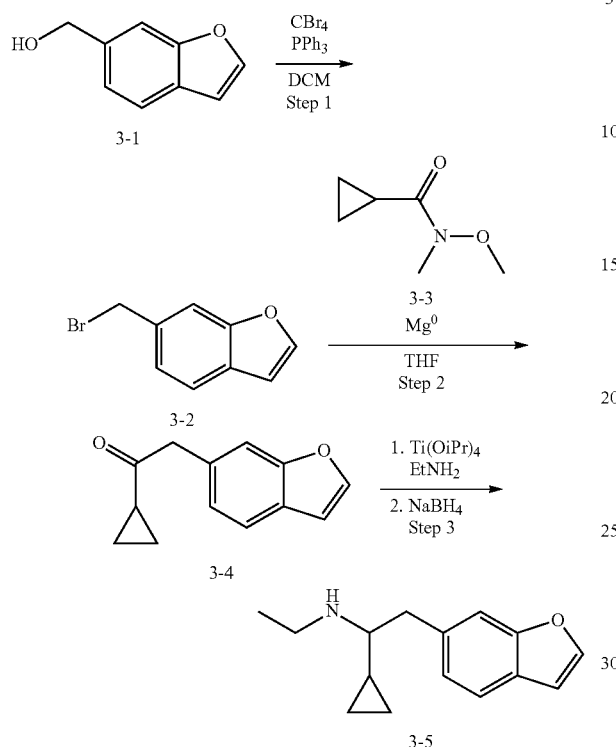

Step 1: To a round-bottom flask containing 3-1 dissolved in DCM is added triphenylphosphine and tetrabromomethane. The resulting mixture is stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 3-2. This crude material can be purified by standard techniques of the art to obtain the pure compound.

Step 2: A round-bottom flask is charged with freshly activated magnesium metal then evacuated under reduced pressure and back-filled with nitrogen three times. Anhydrous THF is then added, and the reaction solution cooled to −78° C. followed by the slow addition of 3-2. Once reaction mixture ceases to self-heat, an anhydrous solution of 3-3 is added slowly. The resulting mixture is allowed to gradually warm to room temperature overnight. The reaction is then quenched under nitrogen using a saturated solution of aqueous $NH_4Cl$. The resulting mixture is then diluted with EtOAc, washed three times with water, dried over anhydrous $Na_2SO_4$, and filtered. The filtrate is then concentrated to collect crude 3-4. This crude material can be taken to the next step without further purification or purified by standard techniques of the art to obtain the pure compound.

Step 3: In a round-bottom flask, 3-4, ethylamine, and titanium (IV) isopropoxide are dissolved in ethanol and stirred under nitrogen. Once there is no remaining 3-4 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 3-5. This crude material can be purified by standard techniques of the art to obtain the pure compound.

The individual enantiomers of 3-5 can be separated using the methods described herein. For example, chiral SFC conditions are provided in Example 1. Following isolation of the pure enantiomers, they can be mixed again in any ratio necessary to obtain the desired effects.

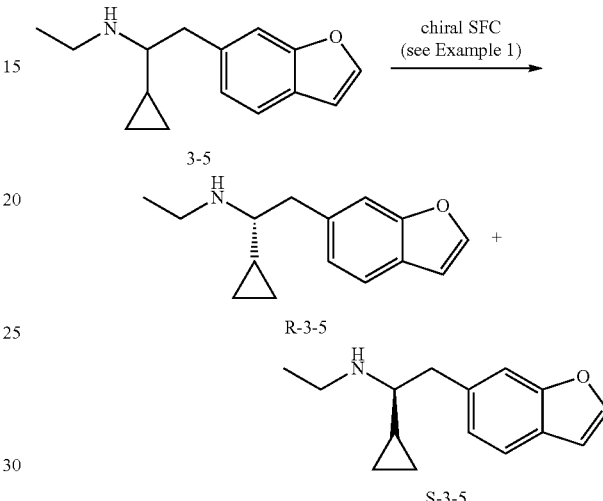

Synthesis 11. Synthesis of 3-(benzofuran-6-yl)-4-fluoro-2-(methylamino)butane-1,3-diol (Compound 4-8)

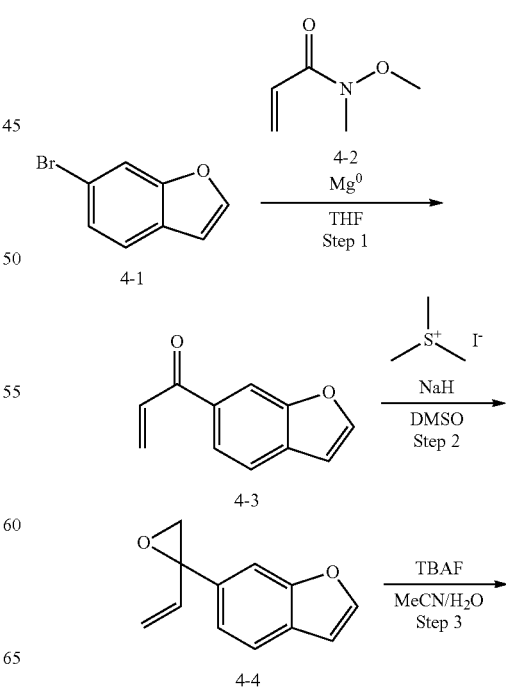

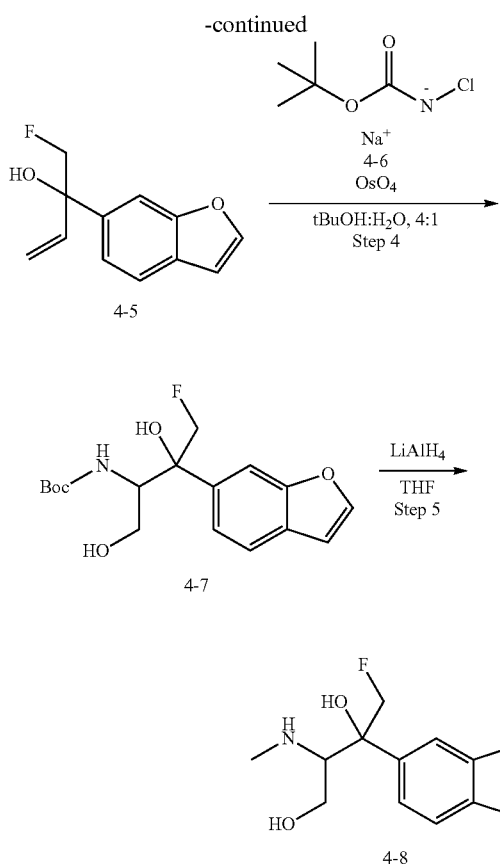

Step 1: A round-bottom flask is charged with freshly activated magnesium metal then evacuated under reduced pressure and back-filled with nitrogen three times. Anhydrous THF is then added, and the reaction solution cooled to −78° C. followed by the slow addition of 4-1. Once the reaction mixture ceases to self-heat, an anhydrous solution of 4-2 is added slowly. The resulting mixture is allowed to gradually warm to room temperature overnight. The reaction is then quenched under nitrogen using a saturated solution of aqueous NH$_4$Cl. The resulting mixture is then diluted with EtOAc, washed three times with water, dried over anhydrous Na$_2$SO$_4$, and filtered. The filtrate is then concentrated to collect crude 4-3. This crude material can be taken to the next step without further purification or purified by standard techniques of the art to obtain the pure compound.

Step 2: A round-bottom flask is charged with a stirbar, anhydrous DMSO, and trimethylsulfonium iodide. After evacuating the flask of ambient air and refilling with dry nitrogen three times, NaH is added slowly to the flask. Once the reaction solution has stopped giving off hydrogen gas, an anhydrous solution of 4-3 in DMSO is added slowly. The reaction is allowed to stir overnight and warm to room temperature. The reaction is then quenched under nitrogen using a saturated solution of aqueous NH$_4$Cl. The resulting mixture is then diluted with EtOAc, washed three times with water, dried over anhydrous Na$_2$SO$_4$, and filtered. The filtrate is then concentrated to collect crude 4-4. This crude material can be taken to the next step without further purification or purified by standard techniques of the art to obtain the pure compound.

Step 3: A round-bottom flask is charged with a stirbar, 4-4, and TBAF. The reagents are then dissolved in a solution of MeCN/H$_2$O, heated to just below reflux temperature, and stirred overnight. The reaction is monitored until completion by TLC, HPLC, or other analytical method. Following the reaction, the mixture is diluted with ethyl acetate and washed three times with water. The organic layer is then dried over anhydrous Na$_2$SO$_4$, filtered, and concentrated to collect crude 3-5. This crude material can be purified by standard techniques of the art to obtain the pure compound.

Step 4: A round-bottom flask is charged with a stirbar, 4-6, osmium tetroxide, and 4-5. The reagents are then dissolved in a solution of 4:1 tBuOH:H$_2$O. The resulting mixture is stirred at room temperature until the reaction is judged complete by TLC, HPLC, or other analytical method. Following the reaction, the mixture is diluted with ethyl acetate and washed three times with water. The organic layer is then dried over anhydrous Na$_2$SO$_4$, filtered, and concentrated to collect crude a mixture of regio- and diastereoisomers of 4-7. This crude material can be purified by standard techniques of the art to obtain the pure compound.

Step 5: To a flame-dried round-bottom flask is added a stirbar, 4-7, and anhydrous THF. The resulting solution is cooled to −78° C. before adding LiAlH$_4$ slowly via syringe. The resulting mixture is allowed to slowly warm to room temperature and stirred until the reaction is judged complete by TLC, HPLC, or other analytical method. Following the reaction, the mixture is diluted with ether, slowly quenched with aqueous NaOH, then further quenched with water. The resulting slurry is diluted with EtOAc and washed three times with water. The organic layer is then dried over anhydrous Na$_2$SO$_4$, filtered, and concentrated to crude 4-8. This crude material can be purified by standard techniques of the art to obtain the pure compound.

The individual enantiomers of 4-8 can be separated using the methods described herein. For example, chiral SFC conditions are provided in Example 1. Following isolation of the pure enantiomers, they can be mixed again in any ratio necessary to obtain the desired effects.

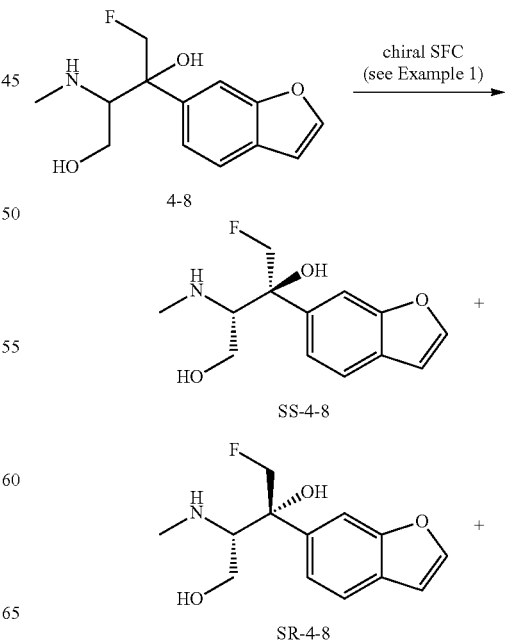

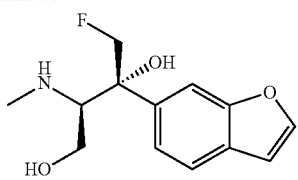

RR-4-8

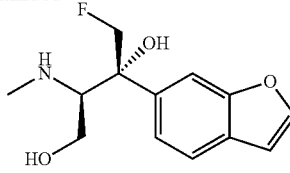

RR-4-8

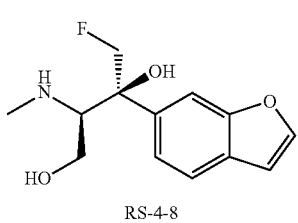

RS-4-8

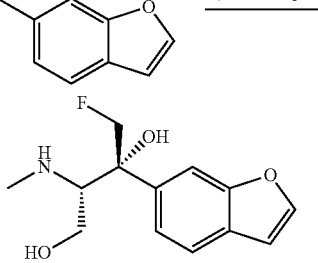

SR-4-8 +

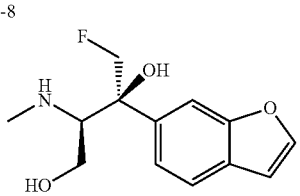

RS-4-8

Alternatively, the diastereomers can first be separated by conventional, achiral purification techniques such as silica gel chromatography or preparative HPLC. The two purified diastereomers can then be further separated into the enantiomers as described.

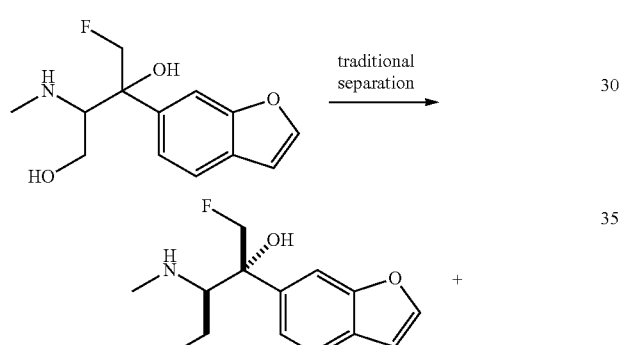

racemic racemic

Synthesis 12. Synthesis of 1-(benzofuran-5-yl)-N-methylpropan-2-amine (5-MAPB)

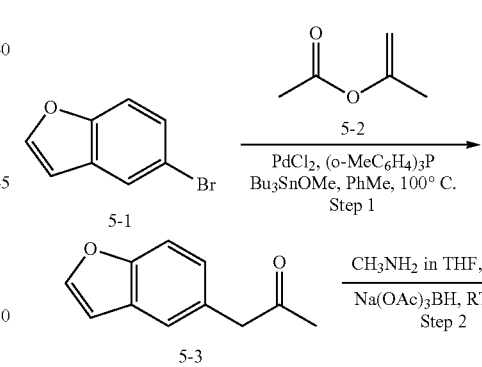

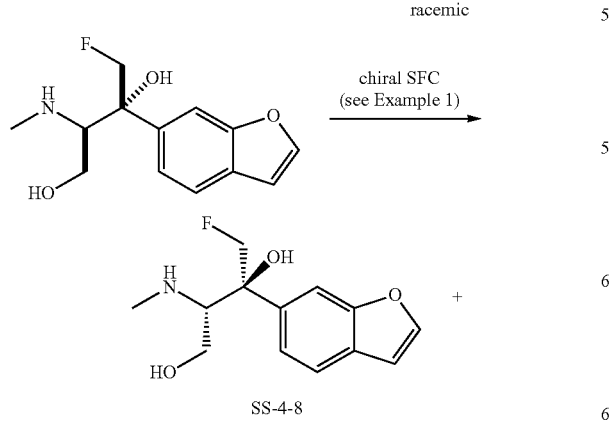

SS-4-8

Step 1: To a stirred solution of 5-bromobenzofuran (5-1) (20 g, 101.52 mmol, 1 eq.) in dry toluene (400 mL) was added tri(o-tolyl)phosphine (1.84 g, 6.09 mmol, 0.06 eq.), tributyl tin methoxide (48.89 mL, 152.28 mmol, 1.5 eq.) and Isopropenyl acetate (16.99 mL, 156.34 mmol, 1.54 eq.) then the resulting reaction mixture was degassed under nitrogen for 15 minutes. Then palladium (II) chloride (1.26 g, 7.10 mmol, 0.07 eq.) was added to the reaction mixture and the resulting reaction mixture was heated to 100° C. for 16 h. Upon completion, monitored by TLC (10% EA in Hexane), the reaction mixture was cooled to RT, evaporate under vacuum. Then the residue was dissolved in ethyl acetate and filtered through celite bed, washed with water, and saturated potassium fluoride solution, followed by brine solution. Combined organic layer was dried over anhydrous sodium sulphate, solvent was removed under vacuum and purified by silica gel column chromatography using ethyl acetate/hexane (10:90 v/v) as eluent to afford 1-(benzofuran-5-yl)propan-2-one (5-3) as light yellow gum (17 g, 96%). $^1$H NMR (400 MHz, DMSO-d$_6$) δ 7.96 (d, J=2.0 Hz, 1H), 7.53 (d, J=8.48 Hz, 1H), 7.46 (s, 1H), 7.13 (dd, J=1.52 Hz, 8.44 Hz, 1H), 6.92 (bs, 1H), 3.83 (s, 2H), 2.12 (s, 3H). LCMS: (ES) $C_{11}H_{10}O_2$ requires 174, found 175 [M+H]$^+$.

Step 2: To a stirred solution of 1-(benzofuran-5-yl)propan-2-one (5-3) (16.0 g, 91.84 mmol, 1.0 eq.) in AcOH (70 ml) was added Methyl Amine (2M in THF) (230 mL, 460 mmol, 5 eq.) at RT and the resulting reaction mixture was stirred at RT for 1 h. Then Na(OAc)$_3$BH (29.2 g, 137.77 mmol, 1.5 eq.) was added portion wise to the reaction mixture and continue to stir at RT for 16 h. After completion of reaction (TLC and LCMS) the reaction mixture was diluted with water (100 mL), and extracted with DCM (50 mL×2). Combined organic layer was dried over anhydrous sodium sulphate, solvent was removed under vacuum to got crude 1-(benzofuran-5-yl)-N-methylpropan-2-amine (5-MAPB) (16.0 g, 92%). 1H NMR (400 MHz, DMSO-d$_6$) δ 7.93 (s, 1H), 7.49 (d, J=8.36 Hz, 1H), 7.43 (s, 1H), 7.12 (d, J=7.56 Hz, 1H), 6.88 (s, 1H), 2.84-2.79 (m, 1H), 2.74-2.69 (m, 1H), 2.49 (bs, 1H), 2.94 (s, 3H), 0.91 (d, J=6.08 Hz, 3H). LCMS: (ES) $C_{12}H_{15}NO$ requires 189, found 190 [M+H]$^+$.

Synthesis 13. Synthesis of 1-(benzofuran-6-yl)-N-methylpropan-2-amine (6-MAPB)

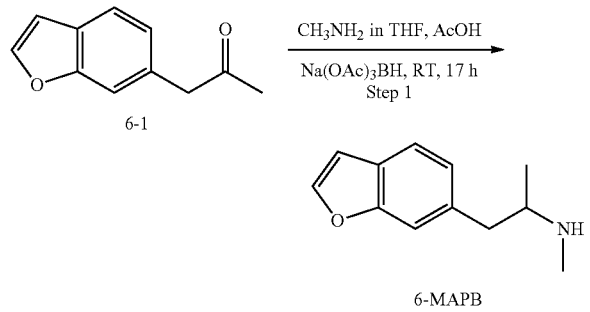

Step 1: To a stirred solution of 1-(benzofuran-6-yl)propan-2-one (6-1) (7 g, 40.23 mmol) in ACOH (15 mL), methyl amine (100 mL, 2M in methanol, 200 mmol) was added to it. After stirring for 15 mins, Na(OAc)$_3$BH (12.7 g, 60.34 mmol) was added to the reaction mixture and continue to stir at room temperature for 17 h. After the completion [Monitored with TLC, Mobile Phase 10% MeOH-DCM], the excess solvent was evaporated under reduced pressure and basified by sodium carbonate solution (30 mL) and extracted with DCM (2×50 mL). The obtained crude 1-(benzofuran-6-yl)-N-methylpropan-2-amine (6-MAPB) (7 g) was forwarded to the next step without further purification. $^1$H NMR (400 MHz, DMSO-d$_6$): δ 7.90 (d, J=1.92 Hz, 1H), 7.54 (d, J=7.88 Hz, 1H), 7.39 (s, 1H), 7.08 (d, J=7.68 Hz, 1H), 6.89 (s, 1H), 2.85-2.80 (m, 1H), 2.74-2.65 (m, 2H), 2.28 (s, 3H), 0.91-0.85 (m, 3H). LCMS: (ES) C12H15NO requires 189.12, found 190.07 [M+H]+.

Synthesis 14. Synthesis of 1-(benzofuran-5-yl)-N-methylbutan-2-amine (5-MBPB)

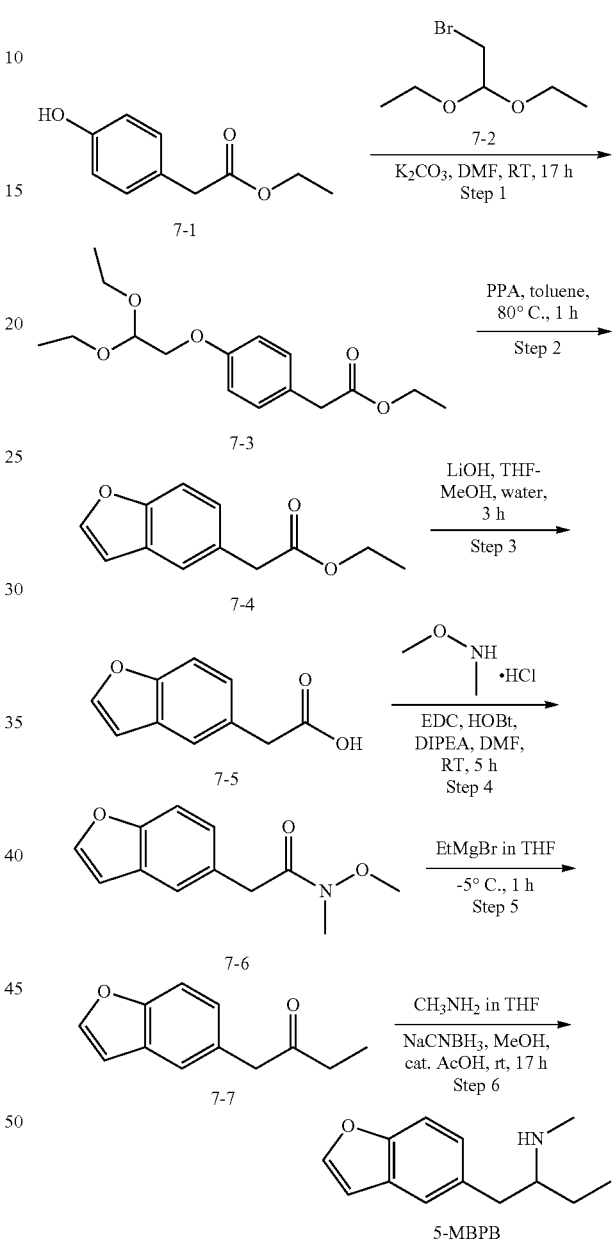

Step 1: To a stirred solution of ethyl 2-(4-hydroxyphenyl) acetate (7-1) (40 g, 222.22 mmol, 1.0 eq.) and 2-bromo-1,1-diethoxyethane (36.76 mL, 244.4 mmol, 1.1 eq.) in DMF (250 mL) was added K$_2$CO$_3$ (92 g, 666.66 mmol, 3.0 eq.) and heated to 100° C. for 17 h. After the completion [Monitored by TLC, mobile phase 10% EtOAc-Hexane], mixture was quenched with ice cold water (500 mL) and extracted with 30% ethyl acetate in hexane (1 L). Then the organic part was washed with saturated solution of NaCl, dried over anhydrous magnesium sulphate and concentrated under vacuum to afford the crude which was purified by silica gel (100-200 mesh) column chromatography eluted with 0-10% ethyl acetate in hexane to get the desired compound ethyl 2-(4-(2,2-diethoxyethoxy)phenyl)acetate (7-3) (20 g, 30%) as a colorless liquid. $^1$H NMR (400 MHz, DMSO-$d_6$): δ 7.17 (d, J=8.56 Hz, 2H), 6.90 (d, J=8.52 Hz, 2H), 4.78 (t, J=5.2 Hz, 1H), 4.08 (m, 2H), 3.93 (d, J=5.2 Hz, 2H), 3.70-3.44 (m, 6H), 1.18-1.08 (m, 9H).

Step 2: To a stirred solution of ethyl 2-(4-(2,2-diethoxyethoxy)phenyl)acetate (7-3) (20 g, 74.62 mmol, 1.0 eq.) in toluene (100 mL) was added PPA (21.94 g, 223.8 mmol, 3.0 eq.) and heated to 80° C. for 3 h under nitrogen atmosphere. After the completion [Monitored with TLC, mobile phase 10% EtOAc-Hexane], reaction mixture was quenched with ice cold water (100 mL) and extracted with 30% ethyl acetate in hexane (300 mL). Then the organic part washed with saturated solution of NaCl, dried over anhydrous magnesium sulphate and concentrated under vacuum to afford the crude which was purified by silica gel (100-200 mesh) column chromatography eluted with 0-2% ethyl acetate in hexane to get the desired ethyl 2-(benzofuran-5-yl)acetate (7-4) (4.0 g, 26%) as a colorless liquid. $^1$H NMR (400 MHz, DMSO-$d_6$): δ 7.97 (d, J=2.08 Hz, 1H), 7.54 (d, J=8.44 Hz, 2H), 7.20 (t, J=1.36 Hz, J=8.48 Hz, 1H), 6.93 (d, J=1.92 Hz, 1H), 4.10-4.04 (m, 2H), 3.73 (s, 2H), 1.17 (t, J=7 Hz, J=7.2 Hz, 3H).

Step 3: To a stirred solution of ethyl 2-(benzofuran-5-yl) acetate (7-4) (4 g, 19.6 mmol, 1.0 eq.) in THF (20 mL), MeOH (20 mL) was added followed by addition of lithium hydroxide (1.4 g, 58.82 mmol, 3.0 eq.) in water (20 mL). Reaction was stirred at RT for 2 hrs. After the completion [Monitored with TLC, Mobile Phase 60% EtOAc-Hexane], excess solvent was evaporated and acidified with 1(N) HCL in ice cooling condition and extracted with 10% MeOH in DCM. Organic part was washed with saturated solution of NaCl, dried over anhydrous magnesium sulphate and concentrated under vacuum to afford 2-(benzofuran-5-yl)acetic acid (7-5) (3.3 g, 95%) as an off white solid. $^1$H NMR (400 MHz, DMSO-$d_6$): δ 12.28 (s, 1H), 7.96 (d, J=2.0 Hz, 1H), 7.52 (d, J=8.68 Hz, 2H), 7.20-7.18 (m, 1H), 6.92 (bs, 1H), 3.64 (s, 2H).

Step 4: To a stirred solution of 2-(benzofuran-5-yl)acetic acid (7-5) (3.3 g, 18.75 mmol, 1.0 eq.) in DMF (20 mL) were added DIPEA (9.8 mL, 56.25 mmol, 3.0 eq.), EDCI (3.93 g, 20.62 mmol, 1.1 eq.) and HOBT (3.79 g, 28.12 mmol, 1.5 eq.). Reaction was stirred at RT for 5 min followed by addition of weinreb amide (2 g, 20.62 mmol, 1.1 eq.). Reaction was stirred at RT for overnight. After the completion [Monitored with TLC, Mobile Phase 30% EtOAc-Hexane], reaction mixture was diluted with ethyl acetate (200 mL), washed 2-3 times with cold water. Organic phase was dried over magnesium sulphate and concentrated under reduced pressure to afford 2-(benzofuran-5-yl)-N-methoxy-N-methylacetamide (7-6) (4 g, 97%) as a light yellow sticky solid. $^1$H NMR (400 MHz, DMSO-$d_6$): δ 7.95 (d, J=2.08 Hz, 1H), 7.51-7.49 (m, 2H), 7.18 (dd, J=1.36 Hz, 8.6 Hz, 1H), 6.91 (d, J=1.8 Hz, 1H), 3.80 (s, 2H), 3.67 (s, 3H), 3.11 (s, 3H).

Step 5: To a stirred solution of 2-(benzofuran-5-yl)-N-methoxy-N-methylacetamide (7-6) (4 g, 18.26 mmol, 1.0 eq.) in THF (20 mL), ethyl magnesium bromide (1 M, 27.39 mL, 27.39 mmol, 1.5 eq.) was added drop wise at 0° C. under nitrogen atmosphere. The reaction mixture was stirred at 0° C. for 1 hr. After completion [Monitored with TLC, mobile Phase 10% EtOAc-Hexane], it was quenched by saturated ammonium chloride solution (5 mL) and extracted with ethyl acetate (50 mL) and washed with NaCl solution. Organic phase was dried over magnesium sulphate and concentrated under reduced pressure. Crude compound was purified by silica gel (100-200 mesh) column chromatography eluted with 10-20% ethyl acetate in hexane to afford the desired 1-(benzofuran-5-yl)butan-2-one (7-7) (3.2 g, 93%) as a yellow liquid. $^1$H NMR (400 MHz, DMSO-$d_6$): δ 7.96 (d, J=1.92 Hz, 1H), 7.52 (d, J=8.4 Hz, 1H), 7.46 (s, 1H), 7.12 (d, J=7.36 Hz, 1H), 6.91 (bs, 1H), 3.82 (s, 2H), 2.53 (m, 2H), 0.91 (t, J=7.24 Hz, J=7.28 Hz, 3H).

Step 6: To a stirred solution of 1-(benzofuran-5-yl)butan-2-one (7-7) (3.2 g, 17.02 mmol, 1.0 eq) and methanol (20 mL), methyl amine (43 mL, 2M in methanol, 85.1 mmol, 5.0 eq) was added followed by addition of catalytic amount of AcOH (0.5 mL). After stirring for 15 mins, NaCNBH3 (3.2 g, 51.06 mmol, 3.0 eq) was added. The resultant mixture was stirred at room temperature for 17 h. After the completion [Monitored with TLC, Mobile Phase 5% MeOH-EtOAc, Rf-0.2], the excess solvent was evaporated under reduced pressure and basified by sodium carbonate solution (30 mL) and extracted with DCM (2×100 mL). The obtained crude 1-(benzofuran-5-yl)-N-methylbutan-2-amine (5-MBPB) (3.3 g, 95%). $^1$H NMR (400 MHz, DMSO-$d_6$): δ 7.94-7.91 (m, 1H), 7.50-7.46 (m, 2H), 7.15 (d, J=8.4 Hz, 1H), 6.89 (d, J=1.72 Hz, 1H), 2.82-2.61 (m, 3H), 2.32 (s, 3H), 1.40-1.30 (m, 2H), 0.95-0.75 (m, 3H). LCMS: (ES) C13H17NO requires 203, found 204 [M+H]$^+$.

Synthesis 15. Synthesis of 1-(benzofuran-6-yl)-N-methylbutan-2-amine (6-MBPB)

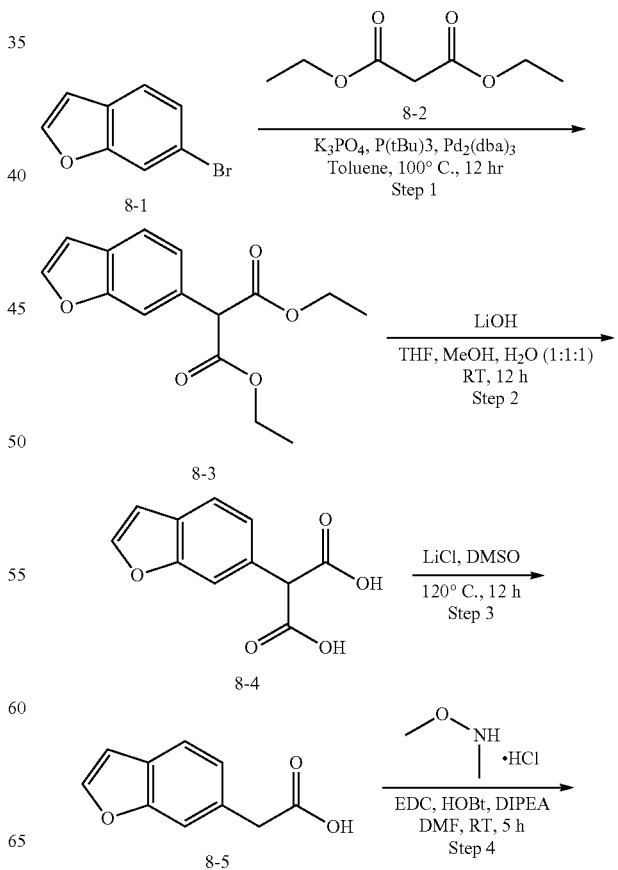

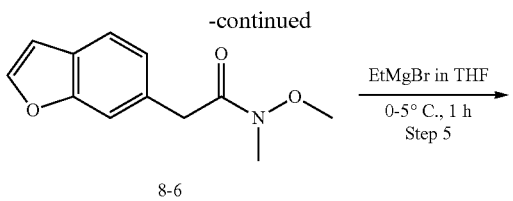

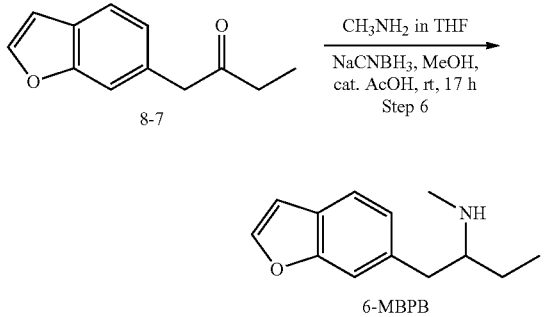

Step 1: A solution of diethyl malonate (8-2) (20.42 mL, 134.01 mmol, 1.1 eq.) and $K_3PO_4$ (51.65 g, 243.65 mmol, 2 eq.) in toluene (120 mL) was purged with nitrogen for 10 min. Then $P(tBu)_3$ (12.45 g, 24.36 mmol, 0.2 eq.) was added to the reaction mixture followed by 6-bromobenzofuran (8-1) (24 g, 121.82 mmol, 1.0 eq.) and $Pd_2(dba)_3$ (2.31 g, 2.43 mmol, 0.02 eq.). Reaction mixture was stir at RT and continue at 100° C. for 12 h. After completion of reaction monitored by TLC and LCMS, the mixture was cooled to room temperature and concentrated under reduced pressure. Then the reaction mixture was diluted with water [500 mL] and extracted with EtOAc [500 mL×2]. Organic layer was separated, dried over sodium sulphate and concentrated under vacuum. Then the crude was purified by silica gel (100-200 mesh) column chromatography eluted with 0-10% ethyl acetate in hexane to afford diethyl 2-(benzofuran-6-yl)malonate (8-3) (15 g, 44%) as a colorless liquid. $^1H$ NMR (400 MHz, DMSO-$d_6$): δ 8.01 (d, J=2.12 Hz, 1H), 7.63 (t, J=8.04 Hz, J=7.44 Hz, 2H), 7.28-7.26 (m, 1H), 6.96 (bs, 1H), 5.07 (s, 1H), 4.21-4.08 (m, 4H), 1.20-1.15 (m, 6H). LCMS: (ES) C15H16O5 requires 276, found 277 [M+H]+.

Step 2: To a stirred solution of diethyl 2-(benzofuran-6-yl)malonate (8-3) (15 g, 54.34 mmol, 1.0 eq.) in THF (50 mL), MeOH (50 mL) was added followed by addition of lithium hydroxide (5.7 g, 135.87 mmol, 2.5 eq.) in water (50 mL). Then the reaction was stir at RT for 12 h. After the completion [Monitored by TLC, mobile Phase 5% MeOH-DCM], excess solvent was evaporated and acidified with 1(N) HCL in ice cooling condition and extracted with 10% MeOH in DCM. Organic part was washed with saturated solution of NaCl, dried over anhydrous magnesium sulphate and concentrated under vacuum to afford 2-(benzofuran-6-yl)malonic acid (8-4) (11.5 g, 96%) as an off white solid. $^1H$ NMR (400 MHz, DMSO-$d_6$): δ 12.71 (s, 2H), 7.99 (d, J=2.08 Hz, 1H), 7.62-7.58 (m, 2H), 7.29 (d, J=14.68 Hz, 1H), 6.95 (d, J=1.84 Hz, 1H). LCMS: (ES) C11H8O5 requires 220, found 219 [M−H]+.

Step 3: To a stirred solution of 2-(benzofuran-6-yl)malonic acid (8-4) (11.5 g, 52.27 mmol, 1.0 eq) in DMSO (50 mL) were added LiCl (4.39 g, 104.54 mmol, 2.0 eq) and $H_2O$ (5 mL) heated to 120° C. temperature for 12 hrs. After completion [Monitored with TLC, Mobile Phase 100% EtOAc, Rf-0.6], reaction mixture was diluted with water [250 mL] and extracted with EtOAc [500 mL×2]. Then the organic layer was extracted and dried over magnesium sulphate and concentrated under vacuum to afford 2-(benzofuran-6-yl)acetic acid (8-5) (9 g, 97.73%) as an off white solid crude. $^1H$ NMR (400 MHz, DMSO-$d_6$): δ 12.03 (s, 1H), 7.95 (d, J=2.0 Hz, 1H), 7.58 (d, J=7.92 Hz, 1H), 7.48 (s, 1H), 7.16 (d, J=7.88 Hz, 1H), 6.92 (d, J=0.92 Hz, 1H), 3.68 (s, 2H).

Step 4: To a stirred solution of 2-(benzofuran-6-yl)acetic acid (8-5) (9.0 g, 51.13 mmol, 1.0 eq.) in DMF (15 mL) were added DIPEA (26.74 mL, 153.40 mmol, 3.0 eq.), EDCI (10.74 g, 56.25 mmol, 1.1 eq.) and HOBT (8.62 g, 63.92 mmol, 1.5 eq.). The reaction mixture was stirred at RT for 5 min followed by addition of weinreb amide (5.45 g, 56.25 mmol, 1.1 eq.), then it was stir at RT for 5 h. After the completion [monitored by TLC, mobile Phase 30% EtOAc-hexane], reaction mixture was diluted with ethyl acetate (500 mL), washed 2-3 times with cold water and dried over magnesium sulphate and concentrated under reduced pressure to afford 2-(benzofuran-6-yl)-N-methoxy-N-methylacetamide (8-6) (8.0 g, 71%) as a light yellow sticky solid. $^1H$ NMR (400 MHz, DMSO-$d_6$): δ 7.94 (d, J=2.04 Hz, 1H), 7.57 (d, J=7.92 Hz, 1H), 7.45 (s, 1H), 7.13 (d, J=7.96 Hz, 1H), 6.91 (bs, 1H), 3.83 (s, 2H), 3.68 (s, 3H), 3.11 (s, 3H). LCMS: (ES) C12H13NO3 requires 219, found 220 [M+H]+.

Step 5: To a stirred solution of 2-(benzofuran-6-yl)-N-methoxy-N-methylacetamide (8-6) (8.0 g, 36.53 mmol, 1.0 eq.) in THF (50 mL), ethyl magnesium bromide (1 M, 54.79 mL, 54.79 mmol, 1.5 eq.) was added drop wise at 0° C. under nitrogen atmosphere. The reaction mixture was stirred at 0° C. for 1 h. After completion [monitored by TLC, mobile Phase 10% EtOAc-hexane], it was quenched by saturated ammonium chloride solution (5 mL) and extracted with ethyl acetate (100 mL) and washed with NaCl solution then dried over magnesium sulphate and concentrated under reduced pressure. The crude compound was purified by silica gel (100-200 mesh) column chromatography eluted with 10-20% ethyl acetate in hexane to afford 1-(benzofuran-6-yl)butan-2-one (8-7) (6.0 g, 87%) as a yellow liquid. $^1H$ NMR (400 MHz, DMSO-$d_6$): δ 7.94 (d, J=2.16 Hz, 1H), 7.58 (d, J=7.92 Hz, 1H), 7.42 (s, 1H), 7.08 (d, J=8.0 Hz, 1H), 6.92 (d, J=0.76 Hz, J=1.12 Hz, 1H), 3.85 (s, 1H), 2.54-2.49 (m, 2H), 0.91 (t, J=7.2 Hz, 3H). LCMS: (ES) C12H12O2 requires 188, found 189 [M+H]+.

Step 6: To a stirred solution of 1-(benzofuran-6-yl)butan-2-one (8-7) (6.0 g, 31.91 mmol, 1.0 eq.) in methanol (30 mL), methyl amine (79.78 mL, 2M in methanol, 159.57 mmol, 5.0 eq.) was added followed by the addition of catalytic amount of AcOH (1.0 mL). After stirring for 15 min, $NaCNBH_3$ (56.03 g, 95.74 mmol, 3.0 eq.) was added to it. The resultant mixture was stirred at room temperature for 17 h. After completion [monitored by TLC, mobile Phase 10% MeOH-EtOAc], the excess solvent was evaporated under reduced pressure and basified by sodium carbonate solution (60 mL) then extracted with DCM (2×200 mL). Then dried over magnesium sulphate and concentrated under reduced pressure to obtained crude 1-(benzofuran-6-yl)-N-methylbutan-2-amine (6-MBPB) (5.0 g, 77%) which was forwarded to the next step without purification. $^1H$ NMR (400 MHz, DMSO-$d_6$): δ 7.90 (d, J=2.08 Hz, 1H), 7.54 (d, J=7.88 Hz, 1H), 7.40 (s, 1H), 7.09 (d, J=7.8 Hz, 1H), 6.89 (d, J=1.08 Hz, 1H), 2.77-2.72 (m, 1H), 2.67-2.62 (m, 1H), 2.58-2.53 (m, 1H), 2.26 (s, 3H), 1.35-1.23 (m, 2H), 0.84 (t, J=7.36 Hz, J=7.40 Hz, 3H). LCMS: (ES) C13H17NO requires 203, found 204.43 [M+H]+.

Synthesis 16. Synthesis of Bk-5-MAPB HCl

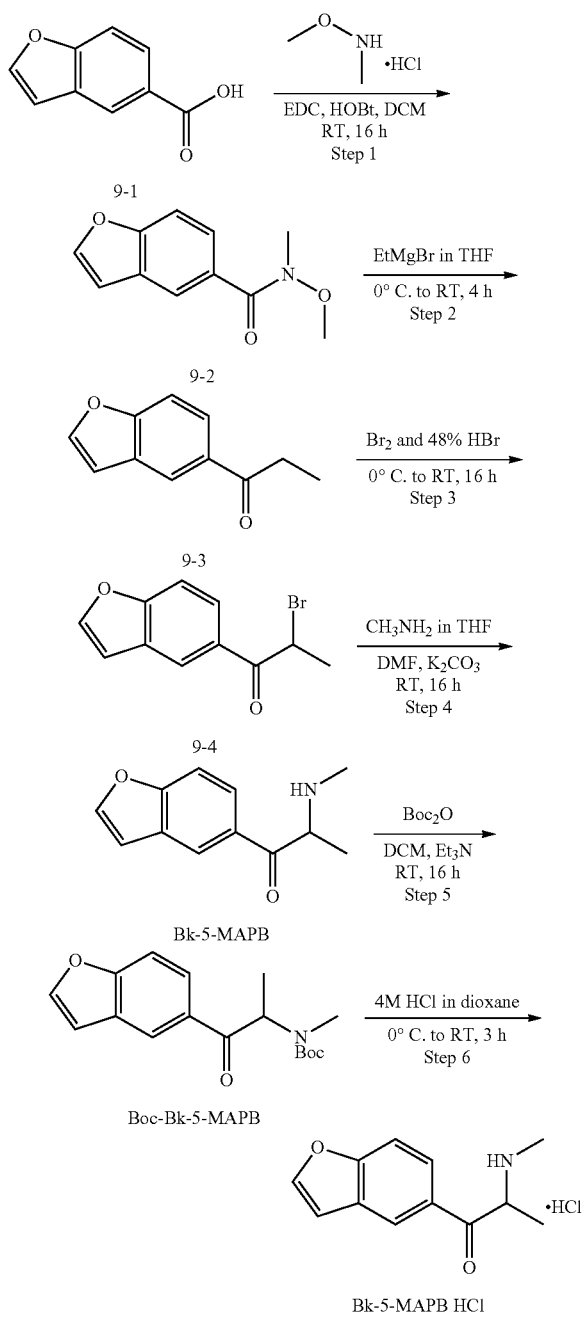

Step 1: Synthesis of N-Methoxy-N-methylbenzofuran-5-carboxamide (9-2): To a stirred solution of benzofuran-5-carboxylic acid (9-1) (10 g, 61.72 mmol, 1 eq.) in dry DCM (100 ml) was added DIPEA (32 ml, 185.18 mmol, 3 eq.) followed by EDC·HCl (13 g, 67.90 mmol, 1.1 eq.) and HOBT (12.5 g, 92.59 mmol, 1.5 eq.) under N2 atmosphere at room temperature and the resulting reaction mixture was allowed to stir at room temperature for 15 minutes. Then, N,O-dimethylhydroxylamine hydrochloride (6.62 g, 67.90 mmol, 1.1 eq.) was added to the resulting reaction mixture and was allowed to stir at room temperature for 16 hours. Completion of the reaction was monitored by TLC (20% EA in hexane). Upon completion, the reaction mixture was extracted with DCM twice (2×200 ml) and washed with water followed by brine solution. The combined organic layers were dried over anhydrous sodium sulphate, solvent was removed under vacuum and purified by silica gel column chromatography using ethyl acetate/hexane (20:80 v/v) as eluent to afford pure N-methoxy-N-methylbenzofuran-5-carboxamide (9-2) as yellow sticky gum (10.6 g, 83%). $^1$H NMR (400 MHz, CDCl$_3$) δ 7.97 (s, 1H), 7.66 (m, 2H), 7.50 (d, J=8.56 Hz, 1H), 6.80 (d, J=1.08 Hz, 1H), 3.54 (s, 3H), 3.37 (s, 3H). LCMS: (ES) C$_{11}$H$_{11}$NO$_3$ requires 205, found 206 [M+H]$^+$.

Step 2: Synthesis of 1-(Benzofuran-5-yl) propan-1-one (9-3): To a stirred solution of N-methoxy-N-methylbenzofuran-5-carboxamide (9-2) (14 g, 68.22 mmol, 1 eq.) was added dry THF (250 ml) at 0° C. and was added 3 (M) solution of EtMgBr in diethyl ether (45 ml, 136.44 mmol, 2 eq.) to the reaction mixture and allowed to stir at room temperature for 4 hours. Upon completion of reaction (monitored by TLC, 20% EA in hexane) was quenched with saturated NH$_4$C$_1$ solution and extracted with ethyl acetate, twice (2×100 ml), then washed with water followed by brine solution. The combined organic layers were dried over anhydrous sodium sulphate, solvent was evaporated under vacuum to afford crude compound 1-(benzofuran-5-yl) propan-1-one (9-3) as yellow solid (10 g, 84%). $^1$H NMR (400 MHz, CDCl$_3$) δ 8.25 (d, J=1.48 Hz, 1H), 7.97 (dd, J=1.72 Hz, 8.72 Hz, 1H), 7.67 (d, J=6.68 Hz, 1H), 7.53 (d, J=8.72 Hz, 1H), 6.84 (d, J=1.56 Hz, 1H), 3.08 (q, 2H), 1.24 (t, J=7.24 Hz, 3H). LCMS: (ES) C$_{11}$H$_{10}$O$_2$ requires 174, found 175 [M+H]$^+$.

Step 3: Synthesis of 1-(Benzofuran-5-yl)-2-bromopropan-1-one (9-4): To a stirred solution of 1-(benzofuran-5-yl)propan-1-one (9-3) (9 g, 51.66 mmol, 1 eq.) in dry THF (90 ml) was added hydrobromic acid 48% in water (133 ml, 1653.27 mmol, 32 eq.) and bromine (2.91 ml, 56.83 mmol, 1.1 eq.) dropwise at 0° C. and the reaction mixture was allowed to stir at room temperature for 16 hours. Upon completion, the reaction mixture (monitored by TLC, 10% EA in hexane) was quenched with saturated sodium carbonate solution, extracted with ethyl acetate (2×100 ml), and washed with water and brine solution. The combined organic layers were dried over anhydrous sodium sulphate, solvent was evaporated under vacuum and purified by silica gel column chromatography using ethyl acetate/hexane (10:90 v/v) as eluent to afford pure compound 1-(benzofuran-5-yl)-2-bromopropan-1-one (9-4) as yellow sticky gum (9 g, 68%). $^1$H NMR (400 MHz, CDCl$_3$) δ 8.32 (d, J=1.52 Hz, 1H), 8.02 (dd, J=1.76 Hz, 8.72 Hz, 1H), 7.69 (d, J=2.2 Hz, 1H), 7.57 (d, J=8.72 Hz, 1H), 6.86 (d, J=1.96 Hz, 1H), 5.39 (q, 1H), 1.93 (t, J=6.6 Hz, 3H). LCMS: (ES) C$_{11}$H$_{19}$BrO$_2$ requires 253, found 254 [M+H]$^+$.

Step 4: Synthesis of 1-(Benzofuran-5-yl)-2-(methylamino) propan-1-one (9-5): To a stirred solution of 1-(benzofuran-5-yl)-2-bromopropan-1-one (9-4) (9 g, 35.57 mmol, 1 eq.) in dry DMF (90 ml) was added potassium carbonate (7.36 g, 53.36 mmol, 1.5eq.) and methyl amine 2(M) in THF (106.5 ml, 213.43 mmol, 6eq.) in a sealed round bottom flask and the resulting reaction mixture was allowed to stir at room temperature for 16 hours. Upon completion of reaction (monitored by TLC, 10% EA in hexane) the crude was extracted with ethyl acetate (2×100 ml), and washed with water (2×100 ml) and brine solution. The combined organic solvent was dried over anhydrous sodium sulphate and solvent was evaporated under vacuum to afford crude 1-(benzofuran-5-yl)-2-(methylamino) propan-1-one (9-5) as yellow sticky gum (5.4 g, 74%). $^1$H NMR (400 MHz, CDCl$_3$) δ 8.27 (s, 1H), 7.98 (dd, J=1.52 Hz, 8.68 Hz, 1H), 7.69 (d, J=2 Hz, 1H), 7.57 (d, J=8.56 Hz, 1H), 6.86 (s, 1H), 4.31 (q, 1H), 2.38 (s, 3H), 1.33 (d, J=7 Hz, 3H). LCMS: (ES) $C_{12}H_{13}NO_2$ requires 203, found 204 [M+H]$^+$.

Step 5: Synthesis of tert-Butyl (1-(benzofuran-5-yl)-1-oxopropan-2-yl) (methyl) carbamate (Boc-Bk-5-MAPB): To a stirred solution of 1-(benzofuran-5-yl)-2-(methylamino) propan-1-one (9-5) (5.2 g, 25.61 mmol, 1 eq.) in dry DCM (50 ml) was added triethylamine (7.39 ml, 51.23 mmol, 2eq.) and Boc anhydride (11.75 ml, 51.23 mmol, 2 eq.) and the resulting reaction mixture was allowed to stir at room temperature for 4 hours. Upon completion of reaction (monitored by TLC, 10% EA in hexane), the reaction mixture was extracted with DCM (2×100 ml) and washed with water followed by brine solution. Combined organic solvent was dried over anhydrous sodium sulphate and solvent was evaporated under vacuum and purified by silica gel column chromatography using ethyl acetate/hexane (10: 90 v/v) as eluent to afford pure tert-butyl (1-(benzofuran-5-yl)-1-oxopropan-2-yl)(methyl)carbamate (Boc-Bk-5-MAPB) as yellow sticky gum (3.9 g, 50%). $^1$H NMR (400 MHz, CDCl$_3$) δ 8.33 (s, 1H), 7.99 (d, J=8.52 Hz, 1H), 7.66 (bs, 1H), 7.52 (d, J=8.56 Hz, 1H), 6.81 (d, J=1.12 Hz, 1H), 5.80 (q, 1H), 2.59 (s, 3H), 1.43 (s, 9H), 1.37 (m, 3H). LCMS: (ES) $C_{17}H_{21}NO_4$ requires 303, found 304 [M+H]$^+$.

Step 6: Synthesis of 1-(Benzofuran-5-yl)-2-(methylamino) propan-1-one hydrochloride (Bk-5-MAPB HCl): To a stirred solution of tert-butyl (1-(benzofuran-5-yl)-1-oxopropan-2-yl)(methyl) carbamate (Boc-Bk-5-MAPB) (1.8 g, 5.94 mmol, 1 eq.) in dry DCM (15 ml) was added 4(M) HCl in 1,4 dioxane (15 ml) at 0° C. and the resulting reaction mixture was allowed to stir at room temperature for 3 hours. Upon completion of reaction (monitored by TLC, 10% EA in hexane), the solvents were evaporated, the crude was washed twice with diethyl ether (2×50 ml) and pentane, and them dried under vacuum to afford 1-(benzofuran-5-yl)-2-(methylamino)propan-1-one hydrochloride (Bk-5-MAPB HCl) (1.3 g, 91%) as off white solid. $^1$HNMR (400 MHz, CDCl$_3$) δ 10.52 (bs, 1H), 9.28 (bs, 1H), 8.26 (bs, 1H), 7.93 (d, J=8.32 Hz, 1H), 7.71 (d, J=1.72 Hz, 1H), 7.58 (bd, J=9.12 Hz, 1H), 6.86 (bs, 1H), 5.08 (bs, 1H), 2.87 (s, 3H), 1.82 (q, 3H). LCMS: (ES) $C_{12}H_{13}NO_2$ requires 203, found 204 [M+H]$^+$. HPLC: Purity (λ 220 nm): 98.40%.

Synthesis 17. Synthesis of Bk-6-MAPB HCl

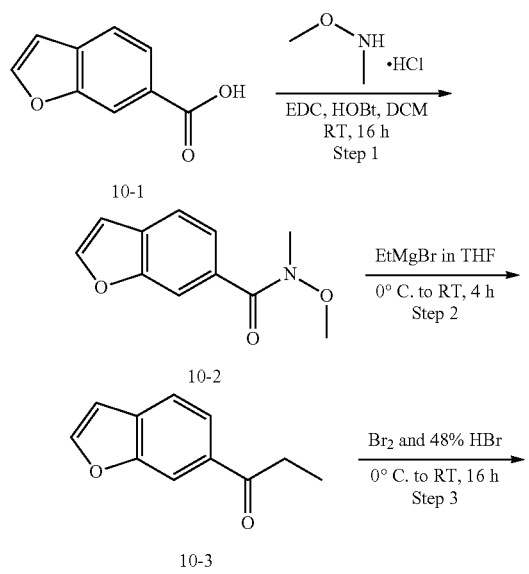

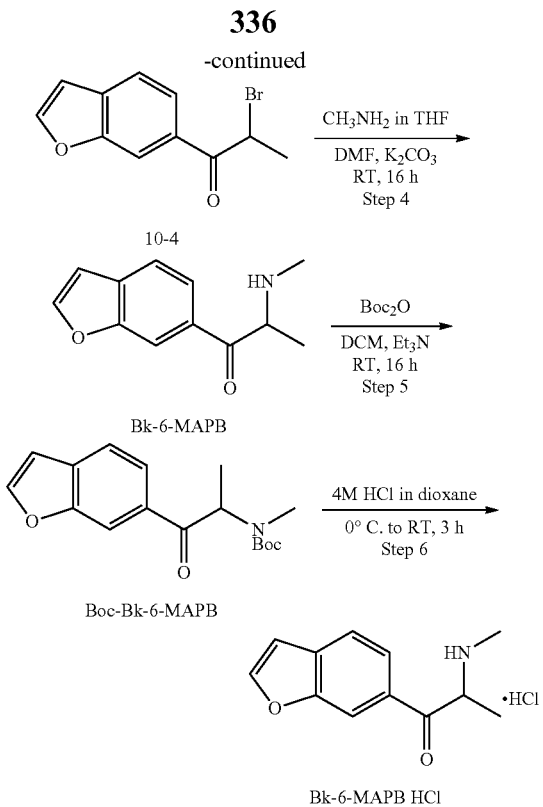

Step 1: Synthesis of N-methoxy-N-methylbenzofuran-6-carboxamide (10-2): To a stirred solution of benzofuran-6-carboxylic acid (10-1) (10 g, 61.72 mmol, 1 eq.) in dry DCM (100 ml) was added DIPEA (32 ml, 185.18 mmol, 3 eq.) followed by EDC·HCl (13 g, 67.90 mmol, 1.1 eq.) and HOBT (12.5 g, 92.59 mmol, 1.5 eq.) under N2 atmosphere at room temperature and the resulting reaction mixture was allowed to stir at room temperature for 15 minutes. Then N, O-dimethylhydroxylamine hydrochloride (6.62 g, 67.90 mmol, 1.1 eq.) was added to the resulting reaction mixture and was allowed to stir at room temperature for 16 hours. Completion of the reaction was monitored by TLC (20% EA in hexane). Upon completion, the reaction mixture was extracted with DCM twice (2×200 ml) and washed with water followed by brine solution. The combined organic layers were dried over anhydrous sodium sulphate, solvent was removed under vacuum and purified by silica gel column chromatography using ethyl acetate/hexane (20:80 v/v) as eluent to afford pure N-methoxy-N-methylbenzofuran-6-carboxamide (10-2) as yellow sticky gum (11.4 g, 90%). $^1$H NMR (400 MHz, CDCl$_3$) δ 7.88 (bs, 1H), 7.70 (d, J=2.08 Hz, 1H), 7.60 (s, 2H), 6.79 (d, J=1.16 Hz, 1H), 3.55 (s, 3H), 3.38 (s, 3H). LCMS: (ES) $C_{11}H_{11}NO_3$ requires 205, found 206 [M+H]$^+$.

Step 2: Synthesis of 1-(benzofuran-6-yl) propan-1-one (10-3): To a stirred solution of N-methoxy-N-methylbenzofuran-6-carboxamide (10-2) (10 g, 48.73 mmol, 1 eq.) was added dry THF (150 ml) at 0° C. and followed by 3(M) solution of EtMgBr in diethyl ether (32.4 ml, 97.46 mmol, 2 eq.) to the reaction mixture and allowed to stir at room temperature for 4 hours. Upon completion, the reaction (monitored by TLC, 20% EA in hexane) was quenched with saturated NH$_4$C$_1$ solution and extracted with ethyl acetate twice (2×100 ml), and washed with water and brine solution. The combined organic layers were dried over anhydrous sodium sulphate and solvent was evaporated under vacuum to afford crude compound 1-(benzofuran-6-yl) propan-1-one (10-3) as yellow solid (7 g, 82%). $^1$H NMR (400 MHz, CDCl$_3$) δ 8.12 (s, 1H), 7.90 (d, J=8.24 Hz, 1H), 7.76 (d, J=1.96 Hz, 1H), 7.65 (d, J=8.24 Hz, 1H), 6.81 (t, J=0.76 Hz & 0.92 Hz, 1H), 3.08 (q, 2H), 1.25 (t, J=7.28 Hz & 7.24 Hz, 3H). LCMS: (ES) C$_{11}$H$_{10}$O$_2$ requires 174, found 175 [M+H]$^+$.

Step 3: Synthesis of 1-(benzofuran-6-yl)-2-bromopropan-1-one (10-4): To a stirred solution of 1-(benzofuran-6-yl) propan-1-one (10-3) (3 g, 17.22 mmol, 1 eq.) in dry THF (30 ml) was added hydrobromic acid 48% in water (30 ml, 551 mmol, 32 eq.) and bromine (0.97 ml, 18.94 mmol, 1.1 eq.) dropwise at 0° C. and the reaction mixture was allowed to stir at room temperature for 16 hours. Upon completion of the reaction (monitored by TLC, 10% EA in hexane), the reaction mixture was quenched with saturated sodium carbonate solution, extracted with ethyl acetate (2×100 ml), and washed with water and brine solution. The combined organic layers were dried over anhydrous sodium sulphate and solvent was evaporated under vacuum and purified by silica gel column chromatography using ethyl acetate/hexane (10:90 v/v) as eluent to afford pure compound 1-(benzofuran-6-yl)-2-bromopropan-1-one (10-4) as a yellow sticky gum (1.9 g, 43.6%). $^1$H NMR (400 MHz, CDCl$_3$) δ 8.20 (bs, 1H), 7.94 (bd, J=8.16 Hz, 1H), 7.80 (d, J=2 Hz, 1H), 7.68 (bd, J=8.2 Hz, 1H), 6.83 (bs, 1H), 5.37 (q, 1H), 1.93 (d, J=6.68 Hz, 3H). LCMS: (ES) C$_{11}$H$_{19}$BrO$_2$ requires 252, found 253 [M+H]$^+$.

Step 4: Synthesis of 1-(benzofuran-6-yl)-2-(methylamino) propan-1-one (Bk-6-MAPB): To a stirred solution of 1-(benzofuran-6-yl)-2-bromopropan-1-one (16-4) (3.8 g, 15 mmol, 1 eq.) in dry DMF (30 ml) was added potassium carbonate (3.1 g, 22.53 mmol, 1.5 eq.) and methyl amine 2(M) in THF (45 ml, 90.11 mmol, 6 eq.) in a sealed round bottom flask and the resulting reaction mixture was allowed to stir at room temperature for 16 hours. Upon completion of the reaction (monitored by TLC, 10% EA in hexane), the crude was extracted with ethyl acetate (2×50 ml) and washed with water (2×50 ml) and brine solution. The combined organic solvent was dried over anhydrous sodium sulphate and solvent was evaporated under vacuum to afford crude 1-(benzofuran-6-yl)-2-(methylamino) propan-1-one (Bk-6-MAPB) as a yellow sticky gum (3 g, 98%). $^1$H NMR (400 MHz, CDCl$_3$) δ 8.14 (s, 1H), 7.90 (d, J=8.2 Hz, 1H), 7.78 (d, J=1.96 Hz, 1H), 7.68 (d, J=8.2 Hz, 1H), 6.83 (s, 1H), 4.29 (q, 1H), 2.38 (s, 3H), 1.34 (d, J=6.96 Hz, 3H). LCMS: (ES) C$_{12}$H$_{13}$NO$_2$ requires 203, found 204 [M+H]$^+$.

Step 5: Synthesis of tert-butyl (1-(benzofuran-6-yl)-1-oxopropan-2-yl) (methyl) carbamate (Boc-Bk-6-MAPB): To a stirred solution of 1-(benzofuran-6-yl)-2-(methylamino) propan-1-one (Bk-6-MAPB) (3 g, 14.77 mmol, 1 eq.) in dry DCM (30 ml) was added triethylamine (4.26 ml, 29.55 mmol, 2 eq.) and Boc anhydride (6.78 ml, 29.55 mmol, 2 eq.) and the resulting reaction mixture was allowed to stir at room temperature for 4 hours. Upon completion of the reaction (monitored by TLC, 10% EA in hexane), the reaction mixture was extracted with DCM (2×50 ml) and washed with water followed by brine solution. The combined organic solvent was dried over anhydrous sodium sulphate and the solvent was evaporated under vacuum and purified by silica gel column chromatography using ethyl acetate/hexane (10:90 v/v) as eluent to afford tert-butyl (1-(benzofuran-6-yl)-1-oxopropan-2-yl)(methyl) carbamate (Boc-Bk-6-MAPB) as a yellow sticky gum (2.5 g, 55%). 1H NMR (400 MHz, CDCl$_3$) δ 8.20-8.11 (bs, 1H), 7.93-7.85 (bd, 1H), 7.76 (s, 1H), 7.63 (bs, 1H), 6.80 (s, 1H), 5.77-5.31 (m, 1H), 2.76-2.58 (s, 3H), 1.45 (s, 9H), 1.38 (m, 3H). Rotamers observed. LCMS: (ES) C$_{17}$H$_{21}$NO$_4$ requires 303, found 304 [M+H]$^+$.

Step 6: Synthesis of 1-(benzofuran-6-yl)-2-(methylamino) propan-1-one hydrochloride (Bk-6-MAPB HCl): To a stirred solution of tert-butyl (1-(benzofuran-6-yl)-1-oxopropan-2-yl)(methyl) carbamate (Boc-Bk-6-MAPB) (1.5 g, 4.95 mmol, 1 eq.) in dry DCM (15 ml) was added 4(M) HCl in 1,4 dioxane (15 ml) at 0° C. and the resulting reaction mixture was allowed to stir at room temperature for 3 hours. Upon completion of reaction (monitored by TLC, 10% EA in hexane), the solvent was evaporated, and the crude was washed twice with diethyl ether (2×50 ml) and pentane and dried under vacuum to afford 1-(benzofuran-6-yl)-2-(methylamino)propan-1-one hydrochloride (HCl Bk-6-MAPB) (1.1 g, 92%) as off white solid. $^1$HNMR (400 MHz, CDCl$_3$) δ 10.90 (s, 1H), 8.92 (s, 1H), 8.13 (s, 1H), 7.84 (bd, J=6.88 Hz, 1H), 7.72 (bd, J=8.16 Hz, 1H), 6.86 (s, 1H), 4.96 (bs, 1H), 2.86 (s, 3H), 1.85 (d, J=7.08 Hz, 3H). LCMS: (ES) C12H13NO2 requires 203, found 204 [M+H]$^+$. HPLC: Purity (λ 220 nm): 99.85%.

Synthesis 18. Synthesis of Bk-5-MBPB HCl

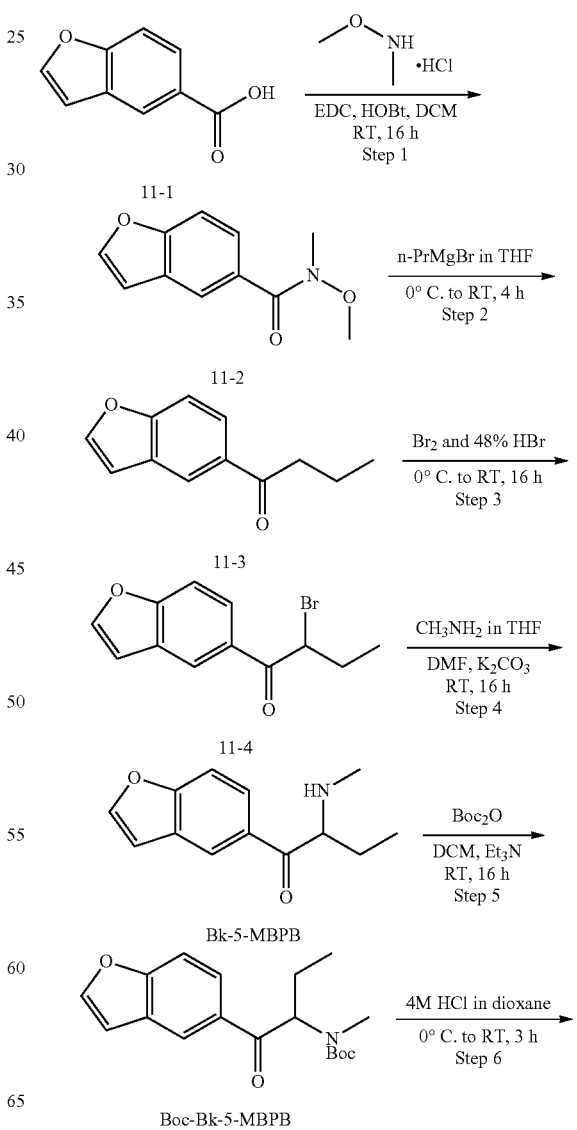

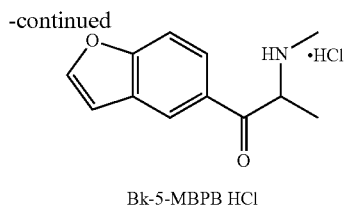

Bk-5-MBPB HCl

Step 1: Synthesis of N-methoxy-N-methylbenzofuran-5-carboxamide (11-2): To a stirred solution of benzofuran-5-carboxylic acid (11-1) (10 g, 61.72 mmol, 1 eq.) in dry DCM (100 ml) was added DIPEA (32 ml, 185.18 mmol, 3 eq.) followed by EDC·HCl (13 g, 67.90 mmol, 1.1 eq.) and HOBT (12.5 g, 92.59 mmol, 1.5 eq.) under N2 atmosphere at room temperature and the resulting reaction mixture was allowed to stir at room temperature for 15 minutes. Then N,O-dimethylhydroxylamine hydrochloride (6.62 g, 67.90 mmol, 1.1 eq.) was added to the resulting reaction mixture and was allowed to stir at room temperature for 16 hours. Upon completion, monitored by TLC (20% EA in hexane), the reaction mixture was extracted with DCM twice (2×200 ml) and washed with water followed by brine solution. The combined organic layers were dried over anhydrous sodium sulphate and solvent was removed under vacuum and purified by silica gel column chromatography using ethyl acetate/hexane (20:80 v/v) as eluent to afford pure N-methoxy-N-methylbenzofuran-5-carboxamide (11-2) as yellow sticky gum (10.6 g, 83%). $^1$H NMR (400 MHz, CDCl3) δ 7.97 (s, 1H), 7.66 (m, 2H), 7.50 (d, J=8.56 Hz, 1H), 6.80 (d, J=1.08 Hz, 1H), 3.54 (s, 3H), 3.37 (s, 3H). LCMS: (ES) $C_{11}H_{11}NO_3$ requires 205, found 206 [M+H]$^+$.

Step 2: Synthesis of 1-(benzofuran-5-yl) butan-1-one (11-3): To a stirred solution of N-methoxy-N-methylbenzofuran-5-carboxamide (11-2) (5 g, 24.37 mmol, 1 eq.) was added in dry THF (50 ml) at 0° C. and was added 2 (M) solution of n-propyl MgBr in THF (24.4 ml, 48.73 mmol, 2 eq.) to the reaction mixture and allowed to stir at room temperature for 4 hours. Upon completion, (monitored by TLC, 20% EA in hexane) the reaction was quenched with saturated NH$_4$C$_1$ solution and extracted with ethyl acetate twice (2×75 ml) and then washed with water followed by brine solution. The combined organic layers were dried over anhydrous sodium sulphate, solvent was evaporated under vacuum to afford crude compound 1-(benzofuran-5-yl) butan-1-one (11-3) as yellow solid (4.5 g, 98%). $^1$H NMR (400 MHz, CDCl$_3$) δ 8.25 (d, J=1.56 Hz, 1H), 7.97 (dd, J=1.72 Hz, 8.72 Hz, 1H), 7.67 (d, J=2.2 Hz, 1H), 7.53 (d, J=8.72 Hz, 1H), 6.84 (d, J=1.88 Hz, 1H), 2.99 (t, J=7.28 Hz, 7.36 Hz, 2H), 1.83 (q, 2H), 1.01 (t, J=7.4 Hz, 3H). LCMS: (ES) $C_{12}H_{12}O_2$ requires 188, found 189 [M+H]$^+$.

Step 3: Synthesis of 1-(benzofuran-5-yl)-2-bromobutan-1-one (11-4): To a stirred solution of 1-(benzofuran-5-yl) butan-1-one (11-3) (3 g, 15.95 mmol, 1 eq.) in dry THF (30 ml) was added hydrobromic acid 48% in water (41.3 ml, 510.63 mmol, 32 eq.) and bromine (0.89 ml, 17.55 mmol, 1.1 eq.) dropwise at 0° C. and the reaction mixture was allowed to stir at room temperature for 16 hours. Upon completion, (monitored by TLC, 10% EA in hexane), the reaction mixture was quenched with saturated sodium carbonate solution, extracted with ethyl acetate (2×50 ml), and washed with water and brine solution. The combined organic layers were dried over anhydrous sodium sulphate and solvent was evaporated under vacuum and purified by silica gel column chromatography using ethyl acetate/hexane (10:90 v/v) as eluent to afford pure compound 1-(benzofuran-5-yl)-2-bromobutan-1-one (11-4) as yellow sticky gum (3.2 g, 75%). $^1$H NMR (400 MHz, CDCl$_3$) δ 8.32 (d, J=1.32 Hz, 1H), 8.02 (dd, J=1.52 Hz, 8.72 Hz, 1H), 7.70 (d, J=2.08 Hz, 1H), 7.57 (d, J=8.72 Hz, 1H), 6.87 (d, J=1.8 Hz, 1H), 5.14 (t, J=7.04 Hz, 7.08 Hz, 1H), 2.30 (m, 2H), 1.09 (t, J=7.64 Hz, 7.28 Hz, 3H). LCMS: (ES) $C_{12}H_{11}BrO_2$ requires 267, found 268 [M+H]$^+$ Step 4: Synthesis of 1-(benzofuran-5-yl)-2-(methylamino) butan-1-one (11-5): To a stirred solution of 1-(benzofuran-5-yl)-2-bromobutan-1-one (11-4) (3.2 g, 11.98 mmol, 1 eq.) in dry DMF (30 ml) was added potassium carbonate (2.48 g, 17.97 mmol, 1.5 eq.) and methyl amine 2(M) in THF (36 ml, 71.91 mmol, 6 eq.) in a sealed round bottom flask and the resulting reaction mixture was allowed to stir at room temperature for 16 hours. Upon completion of the reaction (monitored by TLC, 10% EA in hexane), volatiles were evaporated, and the crude was extracted with ethyl acetate (2×50 ml) and washed with water (2×50 ml) and brine solution. The combined organic solvent was dried over anhydrous sodium sulphate and solvent was evaporated under vacuum to afford crude 1-(benzofuran-5-yl)-2-(methylamino) butan-1-one (Bk-5-MBPB) as yellow sticky gum (2.3 g, 88%). $^1$H NMR (400 MHz, CDCl$_3$) δ 8.26 (d, J=1.12 Hz, 1H), 7.98 (dd, J=1.40 Hz, 8.64 Hz, 1H), 7.69 (d, J=1.96 Hz, 1H), 7.57 (d, J=8.6 Hz, 1H), 6.86 (d, J=1.16 Hz, 1H), 4.15 (t, J=5.76 Hz, 5.80 Hz, 1H), 2.37 (s, 3H), 1.86 (m, 1H), 1.63 (m, 1H), 0.92 (t, J=7.44 Hz, 3H). LCMS: (ES) $C_{13}H_{15}NO_2$ requires 217, found 218 [M+H]$^+$.

Step 5: Synthesis of tert-butyl (1-(benzofuran-5-yl)-1-oxobutan-2-yl) (methyl) carbamate (Boc-Bk-5-MBPB): To a stirred solution of 1-(benzofuran-5-yl)-2-(methylamino) butan-1-one (Bk-5-MBPB) (2.3 g, 10.59 mmol, 1 eq.) in dry DCM (30 ml) was added triethylamine (3.05 ml, 21.19 mmol, 2 eq.) and Boc anhydride (4.86 ml, 21.19 mmol, 2 eq.) and the resulting reaction mixture was allowed to stir at room temperature for 4 hours. Upon completion, (monitored by TLC, 10% EA in hexane), the reaction mixture was extracted with DCM (2×50 ml) and washed with water followed by brine solution. Combined organic solvent was dried over anhydrous sodium sulphate, solvent was evaporated under vacuum and purified by silica gel column chromatography using ethyl acetate/hexane (10:90 v/v) as eluent to afford pure tert-butyl (1-(benzofuran-5-yl)-1-oxobutan-2-yl)(methyl)carbamate (Boc-Bk-5-MBPB) as a yellow sticky gum (1.7 g, 50%). $^1$H NMR (400 MHz, CDCl$_3$) δ 8.38 (s, 1H), 8.03 (dd, J=8.76 Hz, 1H), 7.68 (m, 1H), 7.52 (d, J=4.8 Hz, 1H), 6.82 (s, 1H), 5.62 (m, 1H), 2.67 (s, 3H), 1.97 (m, 1H), 1.78 (m, 1H), 1.52 (s, 9H), 0.96 (m, 3H). Rotamer observed. LCMS: (ES) $C_{18}H_{23}NO_4$ requires 317, found 318 [M+H]$^+$.

Step 6: Synthesis of 1-(benzofuran-5-yl)-2-(methylamino)butan-1-one hydrochloride (Bk-5-MBPB HCl): To a stirred solution of tert-butyl (1-(benzofuran-5-yl)-1-oxobutan-2-yl)(methyl) carbamate (Boc-Bk-5-MBPB) (1.5 g, 4.73 mmol, 1 eq.) in dry DCM (15 ml) was added 4(M) HCl in 1,4 dioxane (15 ml) at 0° C. and the resulting reaction mixture was allowed to stir at room temperature for 3 hours. Upon completion of reaction (monitored by TLC, 10% EA in hexane), the solvent was evaporated, and the crude was washed twice with diethyl ether (2×30 ml) and pentane and dried under vacuum to afford 1-(benzofuran-5-yl)-2-(methylamino)butan-1-one hydrochloride (HCl Bk-5-MBPB) (1.15 g, 95%) as off white solid. $^1$H NMR (400 MHz, CDCl$_3$) δ 10.51 (s, 1H), 9.10 (s, 1H), 8.31 (s, 1H), 7.97 (d, J=8.32 Hz, 1H), 7.72 (s, 1H), 7.60 (d, J=8.32 Hz, 1H), 6.88 (s, 1H), 5.12 (s, 1H), 2.86 (s, 3H), 2.41 (bs, 1H), 2.22 (bs, 1H), 1.87 (s, 2H), 1.03 (t, J=6.28 Hz, 6.48 Hz, 3H). LCMS: (ES) $C_{13}H_{15}NO_2$ requires 217, found 218 [M+H]$^+$. HPLC: Purity (λ 220 nm): 96.94%.

Synthesis 19. Synthesis of Bk-6-MBPB HCl

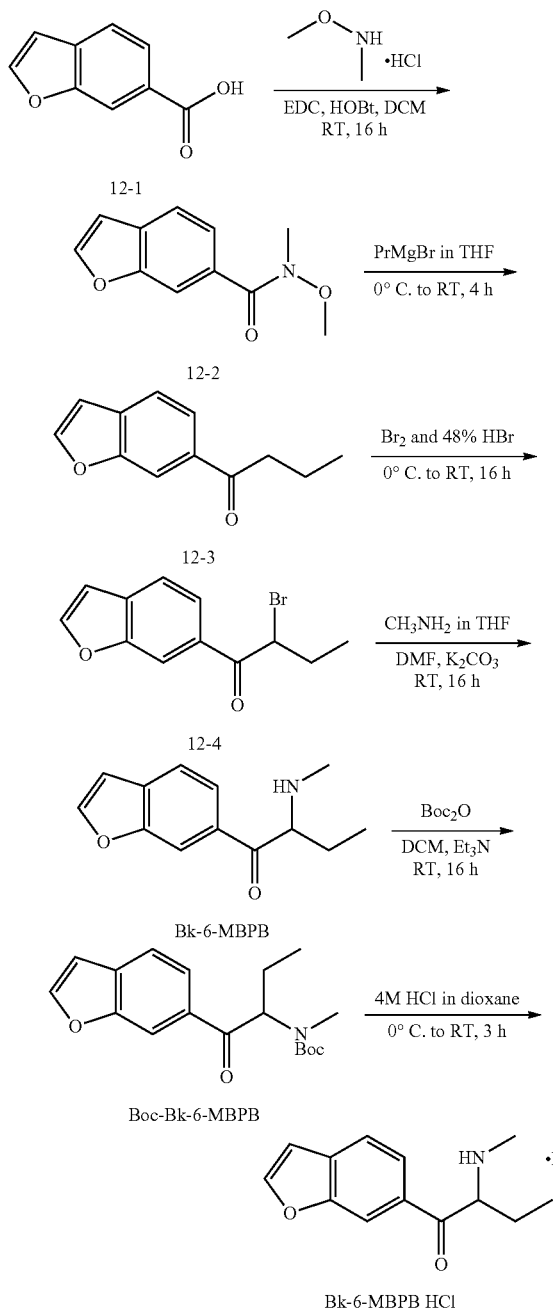

Step 1: Synthesis of N-methoxy-N-methylbenzofuran-6-carboxamide (12-2): To a stirred solution of benzofuran-6-carboxylic acid (12-1) (10 g, 61.72 mmol, 1 eq.) in dry DCM (100 mL) was added DIPEA (32 ml, 185.18 mmol, 3 eq.) followed by EDC·HCl (13 g, 67.90 mmol, 1.1 eq.) and HOBT (12.5 g, 92.59 mmol, 1.5 eq.) under N2 atmosphere at room temperature and the resulting reaction mixture was allowed to stir at room temperature for 15 minutes. Then N,O-dimethylhydroxylamine hydrochloride (6.62 g, 67.90 mmol, 1.1 eq.) was added to the resulting reaction mixture and was allowed to stir at room temperature for 16 hours. Upon completion (monitored by TLC 20% EA in hexane), the reaction mixture was extracted with DCM twice (2×200 ml) and washed with water followed by brine solution. The combined organic layers were dried over anhydrous sodium sulphate and solvent was removed under vacuum and purified by silica gel column chromatography using ethyl acetate/hexane (20:80 v/v) as eluent to afford pure N-methoxy-N-methylbenzofuran-6-carboxamide (12-2) as yellow sticky gum (10.6 g, 83%). $^1$H NMR (400 MHz, CDCl$_3$) δ 7.97 (bs, 1H), 7.66 (m, 2H), 7.50 (d, J=8.56 Hz, 1H), 6.80 (s, 1H), 3.54 (s, 3H), 3.37 (s, 3H). LCMS: (ES) $C_{11}H_{11}NO_3$ requires 205, found 206 [M+H]$^+$.

Step 2: Synthesis of 1-(benzofuran-6-yl)butan-1-one (12-3): To a stirred solution of N-methoxy-N-methylbenzofuran-6-carboxamide (12-2) (10 g, 48.73 mmol, 1 eq.) was added dry THF (100 mL) at 0° C. and 2 (M) solution of n-propylmagnesium bromide in THF (48.73 mL, 97.46 mmol, 2 eq.). The reaction mixture and allowed to stir at room temperature for 4 hours. Upon completion of reaction (monitored by TLC, 20% EA in hexane) was quenched with saturated NH$_4$C$_1$ solution and extracted with ethyl acetate twice (2×200 ml), and then washed with water followed by brine solution. The combined organic layers were dried over anhydrous sodium sulphate and solvent was evaporated under vacuum to afford crude 1-(benzofuran-6-yl)butan-1-one (12-3) as yellow solid (9 g, 98%). $^1$H NMR (400 MHz, CDCl$_3$) δ 8.11 (s, 1H), 7.89 (d, J=8.2 Hz, 1H), 7.76 (d, J=2.04 Hz, 1H), 7.64 (d, J=8.16 Hz, 1H), 6.81 (d, J=1.3 Hz, 1H), 3.04 (m, 2H), 1.84 (m, 2H), 1.03 (t, J=7.4 Hz, 3H). LCMS: (ES) $C_{12}H_{12}O_2$ requires 188, found 189 [M+H]$^+$.

Step 3: Synthesis of 1-(benzofuran-6-yl)-2-bromobutan-1-one (12-4): To a stirred solution of 1-(benzofuran-6-yl) butan-1-one (12-3) (4.6 g, 24.46 mmol, 1 eq.) in dry THF (50 mL) was added hydrobromic acid 48% in water (42.51 ml, 782.97 mmol, 32 eq.) and bromine (1.37 mL, 26.91 mmol, 1.1 eq.) dropwise at 0° C. and the reaction mixture was allowed to stir at room temperature for 16 hours. Upon completion, the reaction mixture (monitored by TLC, 10% EA in hexane) was quenched with saturated sodium carbonate solution, extracted with ethyl acetate (2×100 ml), and washed with water and brine solution. The combined organic layers were dried over anhydrous sodium sulphate, solvent was evaporated under vacuum and purified by silica gel column chromatography using ethyl acetate/hexane (10:90 v/v) as eluent to afford pure 1-(benzofuran-6-yl)-2-bromobutan-1-one (12-4) as yellow sticky gum (3.8 g, 58%). $^1$H NMR (400 MHz, CDCl$_3$) δ 8.18 (s, 1H), 7.93 (d, J=7.16 Hz, 1H), 7.80 (d, J=2.08 Hz, 1H), 7.68 (d, J=8.04 Hz, 1H), 6.83 (s, 1H), 5.12 (t, J=7.12 Hz, 6.72 Hz, 1H), 2.28 (m, 2H), 1.09 (t, J=7.28 Hz, 7.32 Hz, 3H). LCMS: (ES) $C_{12}H_{11}BrO_2$ requires 267, found 268 [M+H]$^+$.

Step 4: Synthesis of 1-(benzofuran-6-yl)-2-(methylamino)butan-1-one (Bk-6-MBPB): To a stirred solution of 1-(benzofuran-6-yl)-2-bromobutan-1-one (12-4) (3.8 g, 14.22 mmol, 1 eq.) in dry DMF (40 mL) was added potassium carbonate (2.94 g, 21.33 mmol, 1.5 eq.) and methyl amine 2(M) in THF (42.5 mL, 85.37 mmol, 6 eq.) in a sealed round bottom flask and the resulting reaction mixture was allowed to stir at room temperature for 16 h. Upon completion of reaction (monitored by TLC, 10% EA in Hexane), volatiles were evaporated, and the crude was extracted with ethyl acetate (2×100 ml), washed with water (2×50 ml) and brine solution. Combined organic solvent was dried over anhydrous sodium sulphate, solvent was evaporated under vacuum to afford crude 1-(benzofuran-6-yl)-2-(methylamino)butan-1-one (Bk-6-MBPB) as yellow sticky gum (2.75 g, 89%). Crude $^1$H NMR (400 MHz, CDCl$_3$) δ 8.14 (s, 1H), 7.90 (d, J=0.96 Hz, 8.0 Hz, 1H), 7.79 (d, J=2.04 Hz, 1H), 7.68 (d, J=8.2 Hz, 1H), 6.83 (d, J=1 Hz, 1H), 4.14 (t, J=6.36 Hz, 5.48 Hz, 1H), 2.37 (s, 3H), 1.86 (m, 1H), 1.60 (m, 1H), 0.92 (t, J=7.44 Hz, 3H). LCMS: (ES) C$_{13}$H$_{15}$NO$_2$ requires 217, found 218 [M+H]$^+$.

Step 5: Synthesis of tert-butyl (1-(benzofuran-6-yl)-1-oxobutan-2-yl)(methyl)carbamate (Boc-Bk-6-MBPB): To a stirred solution of 1-(benzofuran-6-yl)-2-(methylamino)butan-1-one (Bk-6-MBPB) (2.75 g, 12.65 mmol, 1 eq.) in dry DCM (30 mL) was added triethylamine (3.65 mL, 25.31 mmol, 2 eq.) and Boc anhydride (5.8 mL, 25.31 mmol, 2 eq.) and the resulting reaction mixture was allowed to stir at room temperature for 4 hours. Upon completion of the reaction (monitored by TLC, 10% EA in hexane), the reaction mixture was extracted with DCM (2×50 ml) and washed with water followed by brine solution. The combined organic layers were dried over anhydrous sodium sulphate, solvent was evaporated under vacuum, and the crude material purified by silica gel column chromatography using ethyl acetate/hexane (10:90 v/v) as eluent to afford pure tert-butyl (1-(benzofuran-6-yl)-1-oxobutan-2-yl)(methyl)carbamate (Boc-Bk-6-MBPB) as yellow sticky gum (3.4 g, 84%). $^1$H NMR (400 MHz, CDCl$_3$) δ 8.24 (s, 1H), 7.97 (dd, J=8.2 Hz, 1H), 7.76 (bs, 1H), 7.63 (bm, 1H), 6.80 (bs, 1H), 5.61 (t, J=5.64 Hz, 8.88 Hz, 1H), 2.66 (s, 3H), 1.99 (q, 2H), 1.55 (s, 9H), 0.98 (m, 3H). Rotamer observed. LCMS: (ES) C$_{18}$H$_{23}$NO$_4$ requires 317, found 318 [M+H]$^+$.

Step 6: Synthesis of 1-(benzofuran-6-yl)-2-(methylamino)butan-1-one hydrochloride Bk-6-MBPB HCl): To a stirred solution of tert-butyl (1-(benzofuran-6-yl)-1-oxobutan-2-yl)(methyl)carbamate (Boc-Bk-6-MBPB) (1.5 g, 4.73 mmol, 1 eq.) in dry DCM (15 mL) was added 4(M) HCl in 1,4 dioxane (15 mL) at 0° C. and the resulting reaction mixture was allowed to stir at room temperature for 3 hours. Upon completion of the reaction (monitored by TLC, 10% EA in hexane), the solvent were evaporated and the crude was washed twice with diethyl ether (2×50 ml) and pentane and dried under vacuum to afford 1-(benzofuran-6-yl)-2-(methylamino)butan-1-one hydrochloride (Bk-6-MBPB HCl) (1 g, 83%) as a white solid. $^1$H NMR (400 MHz, CDCl$_3$) δ 10.78 (s, 1H), 8.95 (s, 1H), 8.15 (s, 1H), 7.87 (m, 2H), 7.72 (d, J=8.08 Hz, 1H), 6.86 (d, J=1.88 Hz, 1H), 4.99 (bs, 1H), 2.86 (bs, 3H), 2.48 (m, 1H), 2.71 (m, 1H), 1.05 (m, 3H). LCMS: (ES) C$_{13}$H$_{15}$NO$_2$ requires 217, found 218 [M+H]$^+$. HPLC: Purity (λ 300 nm): 99.68%.

Synthesis 20. Synthesis of (R)-1-(benzofuran-5-yl)-N-methylpropan-2-amine (R-5-MAPB)

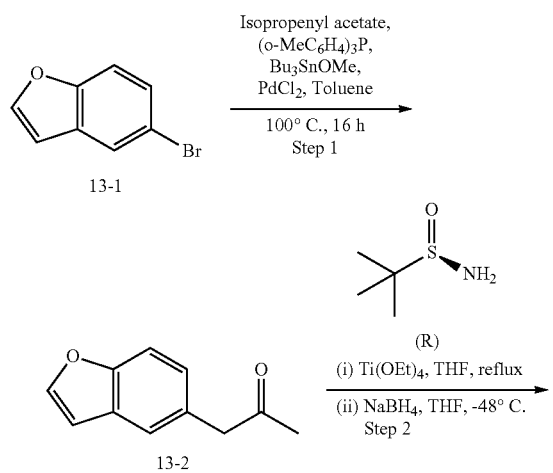

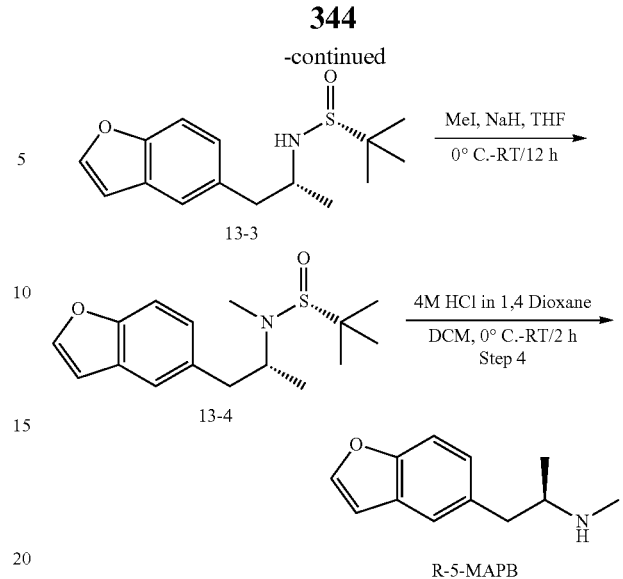

Step 1: To a stirred solution of 5-bromobenzofuran (13-1) (20 g, 101.52 mmol, 1 eq.) in dry Toluene (400 ml) was added tri(o-tolyl)phosphine (1.84 g, 6.091 mmol, 0.06 eq.), tributyl tin methoxide (48.89 mL, 152.28 mmol, 1.5 eq.) and Isopropenyl acetate (16.99 mL, 156.34 mmol, 1.54 eq.) and the resulting reaction mixture was degassed under nitrogen for 15 minutes. Then palladium (II) chloride (1.26 g, 7.10 mmol, 0.07 eq.) was added to the reaction mixture and the resulting reaction mixture was heated to 100° C. for 16 hrs. Upon completion, monitored by TLC (10% EA in Hexane), the reaction mixture was filtered through celite bed, extracted with ethyl acetate (2×400 ml), washed with water, followed by saturated potassium fluoride solution, and brine solution. Combined organic layer was dried over anhydrous sodium sulphate, solvent was removed under vacuum and purified by silica gel column chromatography using ethyl acetate/hexane (10:90 v/v) as eluent to afford 1-(benzofuran-5-yl)propan-2-one (13-2) as light yellow gum (17 g, 96%). $^1$H NMR (400 MHz, DMSO-d$_6$) δ 7.96 (d, J=2.08 Hz, 1H), 7.53 (d, J=8.48 Hz, 1H), 7.46 (s, 1H), 7.13 (dd, J=1.52 Hz, 8.44 Hz, 1H), 6.92 (d, J=0.76 Hz, 1H), 3.83 (s, 2H), 2.12 (s, 3H). LCMS: (ES) C$_{11}$H$_{10}$O$_2$ requires 174, found 175 [M+H]$^+$.

Step 2: To a stirred solution of 1-(benzofuran-5-yl)propan-2-one (13-2) (9 g, 51.66 mmol, 1 eq.) in dry THF (150 ml) was added Ti(OEt)$_4$ (37.91 ml, 180.82 mmol, 3.5eq.) and (R)-2-methylpropane-2-sulfinamide (6.26 g, 51.66 mmol, 1 eq.) (dissolved in 30 ml dry THF) and the resulting reaction mixture was allowed to stir at 70° C. for 12 hrs. Upon completion, monitored by TLC (50% EA in Hexane), the reaction mixture was cooled to 0° C., gradually to −48° C. and NaBH$_4$ (7.81 g, 206.65 mmol, 4 eq.) (dissolved in 30 ml dry THF) was added into the reaction mixture at −48° C. and the resulting reaction mixture was allowed to stir at −48° C. for 3 hrs. Upon completion, monitored by TLC (50% EA in Hexane), the reaction mixture was taken to room temperature and was quenched with Methanol and Sat NaCl solution (until white precipitate observed). The reaction mixture was then filtered through celite bed, washed with methanol (2×150 ml) and ethyl acetate (2×150 ml), evaporated under vacuum to remove the volatiles. Then the reaction mixture was extracted with ethyl acetate, washed with water, followed by brine solution. Combined organic layer was dried over anhydrous sodium sulphate, solvent was removed under vacuum to afford crude (R)-N-((R)-1-(benzofuran-5-yl)propan-2-yl)-2-methylpropane-2-sulfinamide (13-3) as yellow sticky gum (14 g, 96%). $^1$H NMR (400 MHz, DMSO-d$_6$) δ 7.94 (s, 1H), 7.48 (m, 2H), 7.15 (d, J=8.32 Hz, 1H), 6.89 (d, J=7.76 Hz, 1H), 4.97 (d, J=6.04 Hz, 1H), 3.48 (m, 1H), 3.07 (m, 1H), 2.76 (m, 1H), 1.09 (s, 12H), 1.08 (m, 3H) LCMS: (ES) C$_{15}$H$_{21}$NO$_2$S requires 279, found 280 [M+H]$^+$.

Step 3: To a stirred solution of (R)-N-((R)-1-(benzofuran-5-yl)propan-2-yl)-2-methylpropane-2-sulfinamide (13-3) (15 g, 53.57 mmol, 1 eq.) in dry THF (100 mL) (In a sealed tube) was added NaH (60%) (4.28 g, 107.14 mmol, 2 eq.) at 0° C. and the resulting reaction mixture was allowed to stir at 0° C. for 30 min. Then Iodomethane (6.7 ml, 107.14 mmol, 2 eq.) was added at 0° C. and the resulting reaction mixture was allowed to stir at room temperature for 12 h. Upon completion, monitored by TLC (50% EA in Hexane), the reaction mixture was quenched with ice water, extracted with ethyl acetate (2×250 ml), washed with saturated ammonium chloride solution, followed by brine solution. Combined organic layer was dried over anhydrous sodium sulphate, solvent was removed under vacuum and purified by silica gel column chromatography using ethyl acetate/hexane (50:50 v/v) as eluent to afford (R)-N-((R)-1-(benzofuran-5-yl)propan-2-yl)-N,2-dimethylpropane-2-sulfinamide (13-4) as light yellow gum (8 g, 50.9%). $^1$H NMR (400 MHz, DMSO-d$_6$) δ 7.93 (s, 1H), 7.49 (m, 2H), 7.14 (d, J=7.4, 1H), 6.89 (s, 1H), 3.54 (m, 1H), 2.92 (m, 1H), 2.81 (m, 1H), 2.49 (s, 3H), 1.09 (d, J=6.64 Hz, 3H), 1.02 (s, 9H). LCMS: (ES) C$_{16}$H$_{23}$NO$_2$S requires 293, found 294 [M+H]$^+$.

Step 4: To a stirred solution of (R)-N-((R)-1-(benzofuran-5-yl)propan-2-yl)-N,2-dimethylpropane-2-sulfinamide (13-4) (10.5 g, 37.58 mmol, 1 eq.) in dry DCM (50 ml) was added 4M HCl in 1,4 dioxane (100 mL) at 0° C. and then the resulting reaction mixture was allowed to stir at room temperature for 2 h. Upon completion of reaction (monitored by TLC, 30% EA in Hexane), the solvent were evaporated and the crude was washed twice with diethyl ether (2×60 ml) and pentane and dried under vacuum to afford (R)-1-(benzofuran-5-yl)-N-methylpropan-2-amine hydrochloride (R-5-MAPB) (5.8 g, 81%) as off white solid. $^1$HNMR (400 MHz, DMSO-d$_6$) δ 9.00 (bs, 2H), 7.99 (d, J=1.6 Hz, 1H), 7.57 (m, 2H), 7.21 (d, J=7.8 Hz, 1H), 6.93 (s, 1H), 3.38 (bs, 1H), 3.25 (m, 1H), 2.77 (m, 1H), 2.56 (s, 3H), 1.11 (d, J=6.28 Hz, 3H). LCMS: (ES) C$_{12}$H$_{15}$NO requires 189, found 190 [M+H]$^+$. HPLC: Purity (λ 210 nm): 99.26%.

Synthesis 21. Synthesis of (S)-1-(benzofuran-5-yl)-N-methylpropan-2-amine (S-5-MAPB)

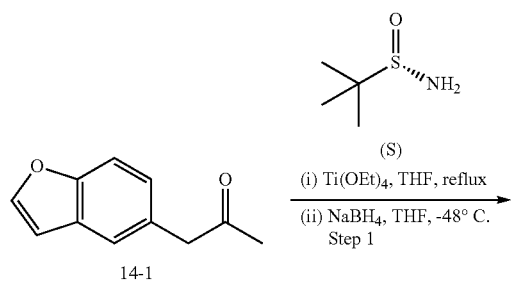

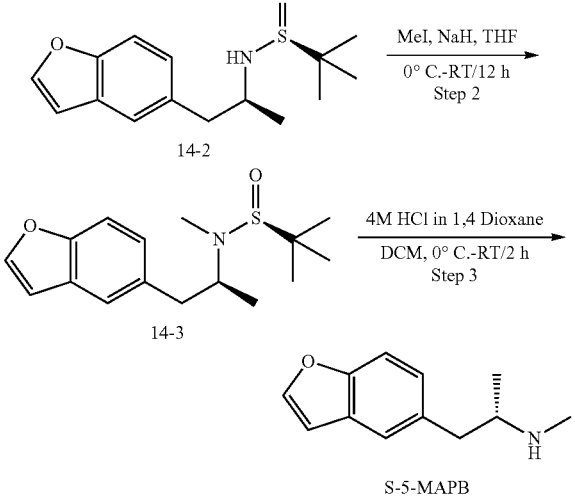

Step 1: To a stirred solution of 1-(benzofuran-5-yl)propan-2-one (14-1) (5 g, 28.70 mmol, 1 eq.) in dry THF (100 ml) was added Ti(OEt)$_4$ (21.06 ml, 100.45 mmol, 3.5 eq.) and (S)-2-methylpropane-2-sulfinamide (3.47 g, 28.73 mmol, 1 eq.) (dissolved in 20 ml dry THF) and the resulting reaction mixture was allowed to stir at 70° C. for 12 hrs. Upon completion (monitored by TLC, 50% EA in Hexane), the reaction mixture was cooled to 0° C., gradually to −48° C. and NaBH$_4$ (4.34 g, 114.81 mmol, 4 eq.) (dissolved in 20 ml dry THF) was added into the reaction mixture at −48° C. and the resulting reaction mixture was allowed to stir at −48° C. for 3 hrs. Upon completion (monitored by TLC, 50% EA in Hexane), the reaction mixture was taken to room temperature and was quenched with Methanol and Sat. NaCl solution (until white precipitate observed). The reaction mixture was then filtered through celite bed, washed with methanol (2×100 ml) and ethyl acetate (2×100 ml), evaporated under vacuum to remove the volatiles. Then the reaction mixture was extracted with ethyl acetate, washed with water, followed by brine solution. Combined organic layer was dried over anhydrous sodium sulphate, solvent was removed under vacuum to afford crude (S)-N-((S)-1-(benzofuran-5-yl)propan-2-yl)-2-methylpropane-2-sulfinamide (14-2) as yellow sticky gum (6.5 g, 81%). Crude 1H NMR (400 MHz, DMSO-d$_6$) δ 7.94 (d, J=7.8 Hz, 1H), 7.50 (m, 2H), 7.14 (m, 1H), 6.90 (d, J=6.36 Hz, 1H), 6.90 (d, J=6.36 Hz, 1H), 4.97 (d, J=5.96 Hz, 1H), 3.48 (m, 1H), 3.08 (m, 1H), 2.76 (m, 1H), 1.18 (m, 12H). LCMS: (ES) C$_{15}$H$_{21}$NO$_2$S requires 279, found 280 [M+H]$^+$.

Step 2: To a stirred solution of (S)-N-((S)-1-(benzofuran-5-yl)propan-2-yl)-2-methylpropane-2-sulfinamide (14-2) (7 g, 25 mmol, 1 eq.) in dry THF (50 mL) (In a sealed tube) was added NaH (60%) (2 g, 50 mmol, 2 eq.) at 0° C. and the resulting reaction mixture was allowed to stir at 0° C. for 30 min. Then Iodomethane (3.11 ml, 50 mmol, 2 eq.) was added at 0° C. and the resulting reaction mixture was allowed to stir at room temperature for 12 h. Upon completion (monitored by TLC, 50% EA in Hexane), the reaction mixture was quenched with ice water, extracted with ethyl acetate (2×200 ml), washed with saturated ammonium chloride solution, followed by brine solution. Combined organic layer was dried over anhydrous sodium sulphate, solvent was removed under vacuum and purified by silica gel column chromatography using ethyl acetate/hexane (50:50 v/v) as eluent to afford (S)-N-((S)-1-(benzofuran-5-yl)propan-2-yl)-N,2-dimethylpropane-2-sulfinamide (14-3) as light yellow gum (4 g, 54%). 1H NMR (400 MHz, DMSO-$d_6$) δ 7.94 (s, 1H), 7.49 (t, J=8.4 Hz, 9.04 Hz, 2H), 7.14 (d, J=8.2, 1H), 6.89 (s, 1H), 3.55 (m, 1H), 2.92 (m, 1H), 2.88 (m, 1H), 2.51 (s, 3H), 1.27 (m, 3H), 1.07 (S, 9H). LCMS: (ES) $C_{16}H_{23}NO_2S$ requires 293, found 294 [M+H]$^+$.

Step 3: To a stirred solution of (S)-N-((S)-1-(benzofuran-5-yl)propan-2-yl)-N,2-dimethylpropane-2-sulfinamide (14-3) (7 g, 23.89 mmol, 1 eq.) in dry DCM (35 mL) was added 4M-HCl in 1,4 dioxane (70 mL) at 0° C. and the resulting reaction mixture was allowed to stir at room temperature for 2 h. Upon completion of reaction (monitored by TLC, 30% EA in Hexane), the solvent was evaporated, and the crude was washed twice with diethyl ether (2×60 ml) and pentane and dried under vacuum to afford (S)-1-(benzofuran-5-yl)-N-methylpropan-2-amine hydrochloride (S-5-MAPB) (5 g, 97%) as off white solid. $^1$HNMR (400 MHz, DMSO-$d_6$) δ 9.06 (bs, 2H), 7.99 (d, J=1.88 Hz, 1H), 7.57 (m, 2H), 7.21 (d, J=8.28 Hz, 1H), 6.93 (d, J=1.32 Hz, 1H), 3.33 (m, 1H), 3.26 (m, 1H), 2.77 (q, 1H), 2.56 (s, 3H), 1.11 (d, J=6.4 Hz, 3H), LCMS: (ES) $C_{12}H_{15}NO$ requires 189, found 190 [M+H]$^+$. HPLC: Purity (λ 250 nm): 99.81%.

Synthesis 22. Synthesis of (R)-1-(benzofuran-6-yl)-N-methylpropan-2-amine (R-6-MAPB)

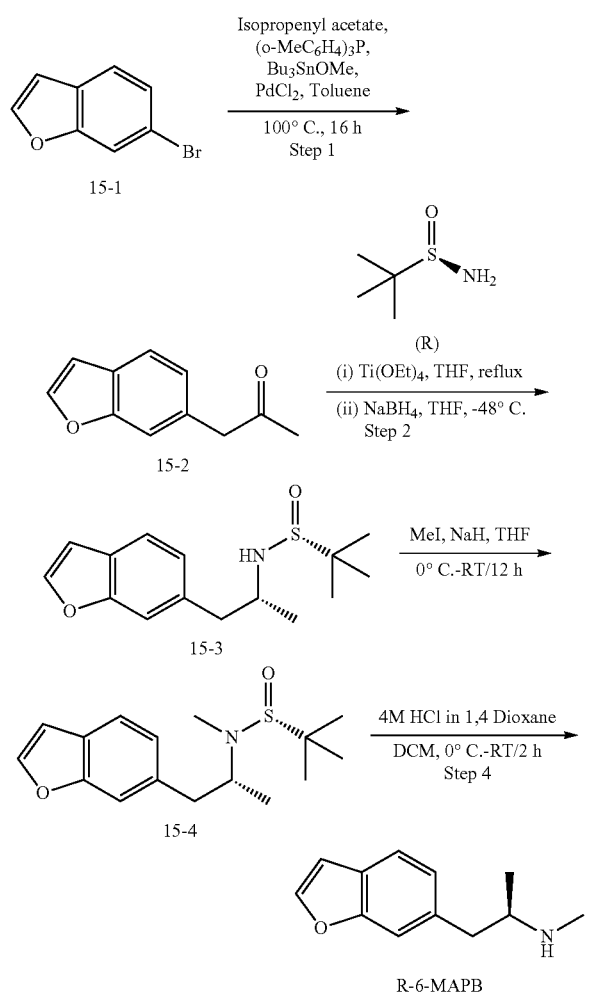

Step 1: A mixture of 6-bromobenzofuran (15-1) (10 g, 50.761 mmol), tri(o-tolyl)phosphine (0.92 g, 3.046 mmol), tributyl tin methoxide (24.4 mL, 76.14 mmol) and Isopropenyl acetate (8.49 mL, 78.17 mmol) in toluene (200 mL) was degassed under nitrogen for 15 minutes. Then palladium (II) chloride (0.63 g, 3.55 mmol) was added to this reaction mixture and continue to stir at 100° C. for 16 hours. Completion of the reaction was monitored by TLC (10% EA in Hexane). Upon completion, the reaction mixture was cooled to RT and concentrated under reduced pressure. The residue was filtered through celite bed and washed with water (100 mL) and DCM (100 mL). The reaction mixture was extracted with DCM twice (2×200 ml) and washed with water followed by brine solution. Combined organic layer was dried over anhydrous sodium sulphate, solvent was removed under vacuum and purified by silica gel column chromatography using ethyl acetate/hexane (20:80 v/v) as eluent to afford pure 1-(benzofuran-6-yl)propan-2-one (15-2) as light yellow liquid (7.0 g, 79%). 1H NMR (400 MHz, DMSO) δ 7.94 (d, J=2.0 Hz, 1H), 7.58 (d, J=7.92 Hz, 1H), 7.42 (s, 1H), 7.07 (d, J=7.84 Hz, 1H), 6.92 (d, J=1.12 Hz, 1H), 3.86 (s, 2H), 2.13 (s, 3H). LCMS: (ES) $C_{11}H_{10}O_2$ requires 174, found 175 [M+H]$^+$.

Step 2: To a stirred solution of 1-(benzofuran-6-yl)propan-2-one (15-2) (5.5 g, 31.60 mmol) in THF (80 ml) was added Ti(OEt)$_4$ (23.20 mL, 110 mmol) followed by 2-methylpropane-2-sulfinamide (R)(dissolved in 5 ml THF) (3.82 g, 31.60) and the reaction mixture was allowed to stir at 70° C. for 12 h. Completion of the reaction was monitored by TLC (50% EA in Hexane). The reaction mixture was cooled to 0° C. and NaBH4 (4.8 g, 126.4 mmol) was added to it at −45° C. and then it was allowed to stir at −45° C. for 2.5 h. Completion of the reaction was observed in TLC (50% EA in Hexane) and crude LCMS. The reaction mixture was taken to RT and then it was quenched with methanol and Saturated NaCl solution (white precipitation observed). It was filtered through celite bed, washed the celite bed with methanol and DCM then the solvent was evaporated under vacuum to remove the volatiles. Then the reaction mixture was extracted with EA twice (2×200 ml) and washed with water followed by brine solution. Combined organic layer was dried over anhydrous sodium sulphate, solvent was removed under vacuum to afford the crude (R)-N-((R)-1-(benzofuran-6-yl)propan-2-yl)-2-methylpropane-2-sulfinamide (15-3) (8.0 g), which was used for next step without further purification. 1H NMR (400 MHz, DMSO) δ 7.92 (d, J=1.96 Hz, 1H), 7.56 (d, J=7.84 Hz, 1H), 7.44 (s, 1H), 7.11 (d, J=8.08 Hz, 1H), 6.90 (d, J=1.04 Hz, 1H), 4.98 (d, J=6.0 Hz, 1H), 3.49 (m, 1H), 3.08 (m, 1H), 2.79 (m, 1H), 1.08 (m, 12H). LCMS: (ES) C15H21NO2S, requires 279, found 280 [M+H]$^+$.

Step 3: To a stirred solution of crude (R)-N-((R)-1-(benzofuran-6-yl)propan-2-yl)-2-methylpropane-2-sulfinamide (15-3) (8.0 g, 28.67 mmol) in THF (100 mL), NaH (60%) (2.2 g, 57.34 mmol) at 0° C. was added portion-wise then the reaction mixture was stirred at 0° C. for 30 min after that Iodomethane (3.54 mL, 57.34 mmol) was added to it and the reaction mixture was stirred at RT for 12 h. Completion of the reaction was monitored by TLC (20% EA in Hexane). Upon completion, the reaction mixture was diluted with cold water (100 mL) extracted with EA twice (2×200 ml) and organic layer was washed with NaHCO3 solution (100 mL) followed by brine solution. Combined organic layer was dried over anhydrous sodium sulphate, solvent was removed under vacuum and purified by silica gel column chromatography using 15-20% ethyl acetate hexane to afford pure (R)-N-((R)-1-(benzofuran-6-yl)propan-2-yl)-

N,2-dimethylpropane-2-sulfinamide (15-4) (4.0 g, 47%) as a colorless sticky solid. 1H NMR (400 MHz, DMSO) δ 7.91 (d, J=2.04 Hz, 1H), 7.56 (d, J=7.92 Hz, 1H), 7.42 (s, 1H), 7.10 (d, J=8.04 Hz, 1H), 6.90 (d, J=1.36 Hz, 1H), 3.59 (m, 1H), 2.95 (dd, J=13.42 Hz 1H), 2.84 (dd, J=13.38 Hz 1H), 2.51 (s, 3H), 1.10 (d, J=6.68 Hz, 3H), 1.02 (S, 9H). LCMS: (ES) C16H23NO2S, requires 293, found 294 [M+H]+.

Step 4: To a stirred solution of (R)-N-((R)-1-(benzofuran-6-yl)propan-2-yl)-N,2-dimethylpropane-2-sulfinamide (15-4) (9.4 g, 32.03 mmol) in 1,4 dioxane (60 mL) was added 4(M) HCl in 1,4 dioxane (30.0 mL) at 0° C. and the resulting reaction mixture was allowed to stir at room temperature for 5 h. Upon completion of reaction (monitored by TLC, 10% EA in Hexane), the solvent were evaporated and the residue was dissolved in methanol and diethyl ether was added to it for precipitation, finally filter to get pure (R)-1-(benzofuran-6-yl)-N-methylpropan-2-amine hydrochloride (R-6-MAPB) (6.1 g, 84%) as white solid. 1H NMR (400 MHz, DMSO) δ 9.00 (bs, 2H), 7.96 (d, J=2.08 Hz, 1H), 7.62 (d, J=7.92 Hz, 1H), 7.53 (s, 1H), 7.16 (d, J=7.52 Hz, 1H), 6.93 (d, J=1.48 Hz, 1H), 3.41 (bs, 1H), 3.30 (dd, J=13.28 Hz, 1H), 2.80 (dd, J=13.2 Hz, 1H), 2.56 (s, 3H), 1.12 (d, J=6.48 Hz, 3H). LCMS: (ES) C12H16ClNO, requires 189, found 190 [M+H]+. HPLC: Purity (λ 250 nm): 99.58%.

Synthesis 23. Synthesis of (S)-1-(benzofuran-6-yl)-N-methylpropan-2-amine (S-6-MAPB)

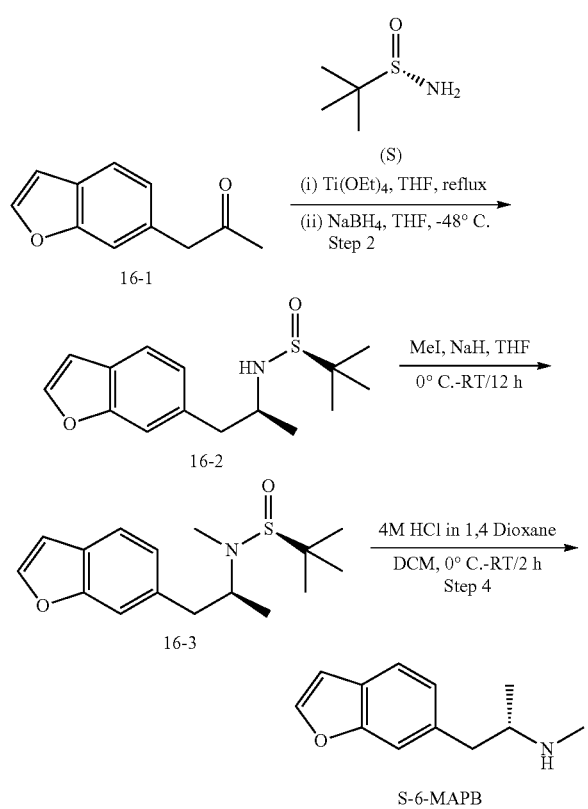

Step 1: To a stirred solution of 1-(benzofuran-6-yl)propan-2-one (16-1) (5 g, 28.70 mmol, 1 eq.) in dry THF (100 mL) was added Ti(OEt)4 (21.06 mL, 100.45 mmol, 3.5 eq.) and (S)-2-methylpropane-2-sulfinamide (3.47 g, 28.73 mmol, 1 eq.) (dissolved in 20 mL dry THF) and the resulting reaction mixture was allowed to stir at 70° C. for 12 h. Upon completion, monitored by TLC (50% EA in Hexane), the reaction mixture was cooled to 0° C., gradually to −48° C. and NaBH4 (4.34 g, 114.81 mmol, 4 eq.) (dissolved in 20 mL dry THF) was added into the reaction mixture at −48° C. and the resulting reaction mixture was allowed to stir at −48° C. for 3 h. Upon completion, monitored by TLC (50% EA in Hexane), the reaction mixture was taken to room temperature and was quenched with Methanol and saturated NaCl solution (until white precipitate observed). The reaction mixture was then filtered through celite bed, washed the celite bed with methanol (2×100 ml) and ethyl acetate (2×100 mL), and evaporated under vacuum to remove the volatiles. Then the reaction mixture was extracted with ethyl acetate, washed with water, followed by brine solution. Combined organic layer was dried over anhydrous sodium sulphate, solvent was removed under vacuum to afford crude (S)-N-((S)-1-(benzofuran-6-yl)propan-2-yl)-2-methylpropane-2-sulfinamide (16-2) as yellow sticky gum (7.5 g, 93%). Crude 1H NMR (400 MHz, DMSO-$d_6$) δ 7.92 (d, J=2.08 Hz 1H), 7.56 (d, J=7.92 Hz, 1H), 7.44 (s, 1H), 7.11 (d, J=7.96 Hz, 1H), 6.90 (d, J=1.84 Hz, 1H), 4.96 (d, J=6.08 Hz, 1H), 3.30 (m, 1H), 3.08 (m, 1H), 2.80 (m, 1H), 1.10 (m, 9H), 1.08 (m, 3H). LCMS: (ES) $C_{15}H_{21}NO_2S$, requires 279, found 280 [M+H]+.

Step 2: To a stirred solution of (S)-N-((S)-1-(benzofuran-6-yl)propan-2-yl)-2-methylpropane-2-sulfinamide (16-2) (8 g, 28.67 mmol, 1 eq.) in dry THF (60 mL) (In a sealed tube) was added NaH (60%) (2.28 g, 57.26 mmol, 2 eq.) at 0° C. and the resulting reaction mixture was allowed to stir at 0° C. for 30 min. Then Iodomethane (3.56 mL, 57.26 mmol, 2 eq.) was added at 0° C. and the resulting reaction mixture was allowed to stir at room temperature for 12 h. Upon completion, monitored by TLC (50% EA in Hexane), the reaction mixture was quenched with ice water, extracted with ethyl acetate (2×200 ml), washed with saturated ammonium chloride solution followed by brine solution. Combined organic layer was dried over anhydrous sodium sulphate, solvent was removed under vacuum and purified by silica gel column chromatography using ethyl acetate/hexane (50:50 v/v) as eluent to afford (S)-N-((S)-1-(benzofuran-6-yl)propan-2-yl)-N,2-dimethylpropane-2-sulfinamide (16-3) as light yellow gum (4.5 g, 53%). 1H NMR (400 MHz, DMSO-$d_6$) δ 7.92 (d, J=1.84 Hz, 1H), 7.56 (d, J=7.84 Hz, 1H), 7.42 (s, 1H), 7.10 (d, J=7.96 Hz, 1H), 6.90 (S, 1H), 3.57 (d, J=7.32 Hz, 1H), 2.92 (m, 1H), 2.84 (m, 1H), 2.51 (s, 3H), 1.10 (d, J=6.6 Hz, 3H), 1.02 (s, 9H). LCMS: (ES) $C_{16}H_{23}NO_2S$, requires 293, found 294 [M+H]+.

Step 3: To a stirred solution of (S)-N-((S)-1-(benzofuran-6-yl)propan-2-yl)-N,2-dimethylpropane-2-sulfinamide (16-3) (5.4 g, 18.40 mmol, 1 eq.) in dry DCM (45 mL) was added 4(M) HCl in 1,4 dioxane (90 mL) at 0° C. and the resulting reaction mixture was allowed to stir at room temperature for 2 h. Upon completion of reaction (monitored by TLC, 30% EA in Hexane), the solvent was evaporated, and the crude was washed twice with diethyl ether (2×100 ml) and pentane and dried under vacuum to afford (S)-1-(benzofuran-6-yl)-N-methylpropan-2-amine hydrochloride S-6-MAPB (3.5 g, 84%) as white solid. ¹HNMR (400 MHz, DMSO-$d_6$) δ 9.01 (bs, 2H), 7.96 (d, J=2.04 Hz, 1H), 7.62 (d, J=7.88 Hz, 1H), 7.53 (s, 1H), 7.16 (d, J=7.88 Hz, 1H), 6.93 (d, J=1.64 Hz, 1H), 3.44 (bs, 1H), 3.30 (q, 1H), 2.80 (m, 1H), 2.56 (s, 3H), 1.12 (d, J=6.48 Hz, 3H). LCMS: (ES) $C_{12}H_{15}NO$, requires 189, found 190 [M+H]+. HPLC:Purity (λ 200 nm): 99.61%.

Example 3: nAChR α4β2 Receptor Agonism

An IonFlux™ automated patch-clamp system is used to measure activity of S-5-MAPB, R-5-MAPB at nAChR α4β2 receptors (Eurofins, cat. No. CYL3106) expressed in HEK-293 cells as described in Yehia & Wei, 2020, Current Protocols in Pharmacology, 88(1). Acetylcholine is used as a positive control. Results show that the compounds of the current invention are active as agonists, with enantioselective effects in which the R-enantiomers have greater potency.

Example 4: Serum Serotonin Concentrations to Index Drug Interactions with the Serotonin Transporter (SERT, SLC6A4)

Serum serotonin is measured using High Performance Liquid Chromatography and Fluorescence Detection. Venipuncture is used to collect at least 1 mL of sample, which is spun with serum frozen to below −20° C. within 2 hours of collection. Assay results show robust and enantioselective increases in serum serotonin, indicating that the S-enantiomers are more potent releasers of serotonin.

Example 5: Marble Burying Measure of Decreased Anxiety and Neuroticism

The marble burying test is a model of neophobia, anxiety, and obsessive-compulsive behavior that has been proposed to have predictive validity for the screening of novel antidepressants and anxiolytics. It is well established to be sensitive to the effects of SSRIs as well as serotonin releasers such as fenfluramine and MDMA (De Brouwer et al., Cognitive, Affective, and Behavioral Neuroscience, 2019, 19(1), 1-39).

The test involved the placement of a standardized number of marbles gently onto the surface of a layer of bedding material within a testing arena. Mice were then introduced into the arena for a standardized amount of time and allowed to explore the environment. The outcome measure of the test was the number of marbles covered as scored by automatic scoring software or blinded observers. General locomotor activity, often operationalized as total distance traveled, was used as a control measure. Compounds that attenuate anxiety, neuroticism, or obsessive-compulsive behavior decrease marble burying. The racemates and individual enantiomers of 5-MAPB, 6-MAPB, BK-5-MAPB, and BK-5-MBPB were assessed with the marble burying assay. The results, which are shown graphically in FIG. 2 to FIG. 6, indicate that every tested compound had CNS modulating effects within 30 minutes. Every tested compound besides Bk-5-MAPB showed differences in activity between the two possible enantiomers. Surprisingly, a strong non-additive interaction was also observed between the enantiomers of 5-MAPB.

Figure 5:
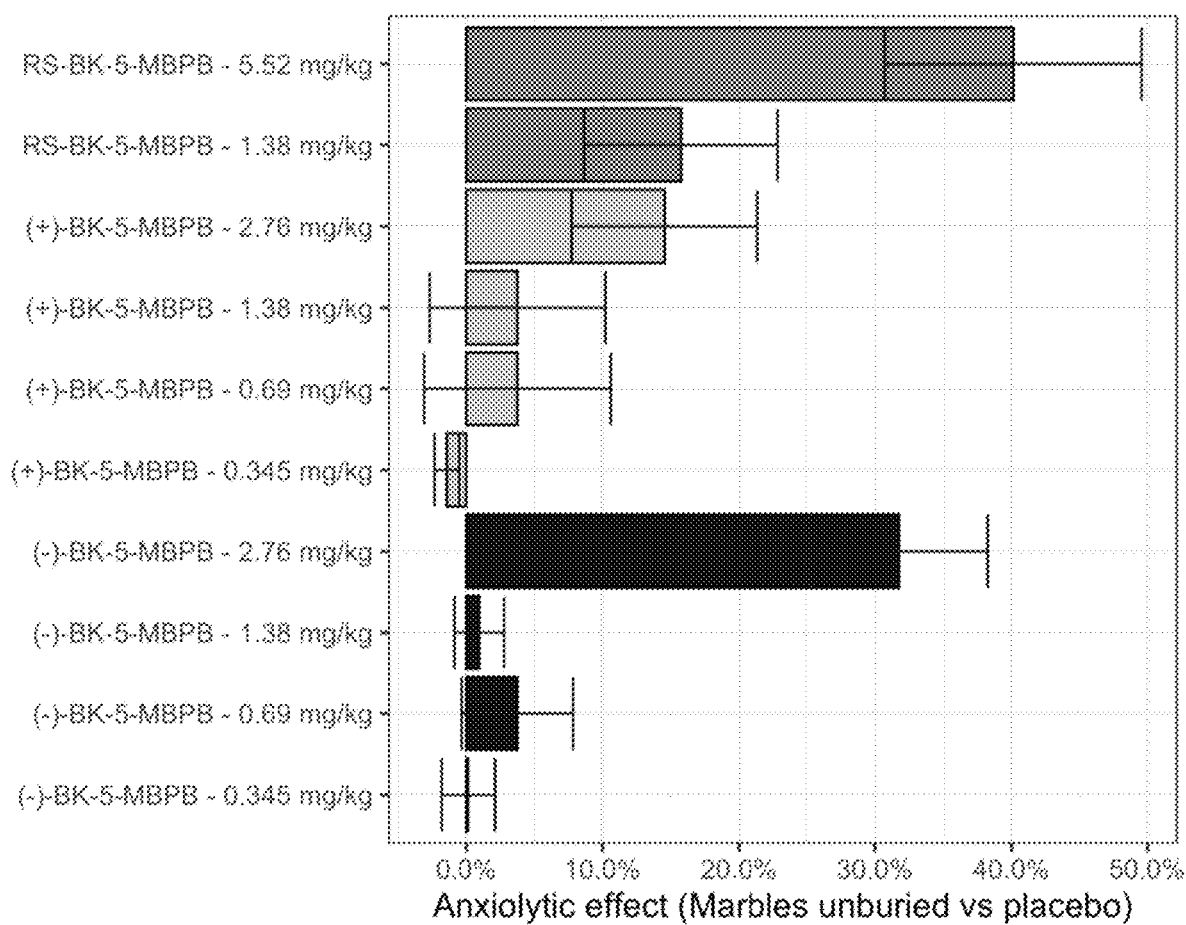
FIG. 5 is a chart showing results from the marble burying assay to measure decreased anxiety and neuroticism resulting from treatment with (+)-Bk-5-MBPB, RS-Bk-5-MBPB, and (−)-Bk-R-5-MBPB. The x-axis of the chart displays anxiolytic effect, described as the percent of marbles left unburied versus placebo. The y-axis gives the compound and dose. Error bars indicate 95% confidence intervals. Details and procedural information for this assay are described in Example 5.
Figure 6:
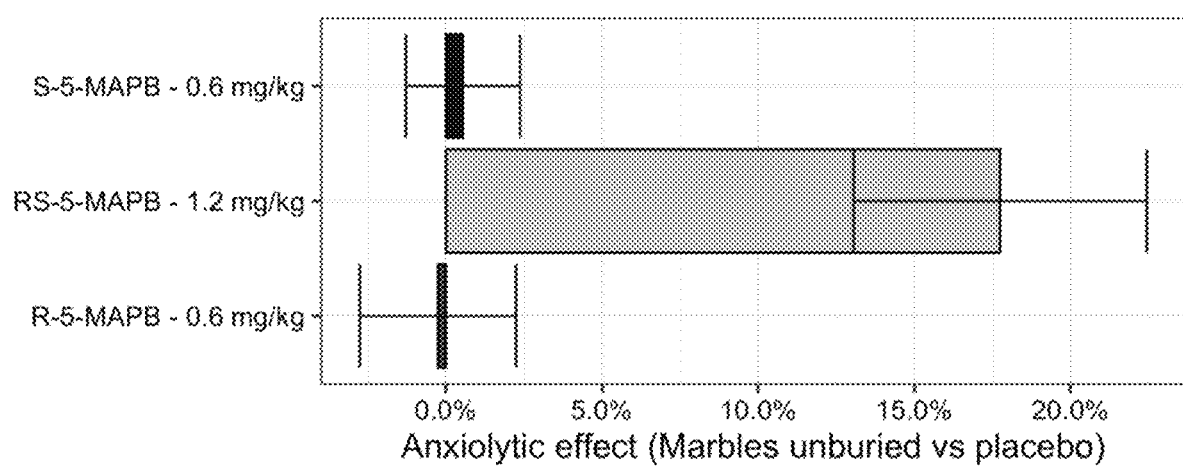
FIG. 6 is a chart showing results from the marble burying assay to measure decreased anxiety and neuroticism resulting from treatment with individual enantiomers of 5-MAPB vs the racemic mixture, demonstrating the non-additive effects of the two enantiomers. The x-axis of the chart displays anxiolytic effect, described as the percent of marbles left unburied versus placebo. The y-axis gives the compound and dose. Error bars indicate 95% confidence intervals. Details and procedural information for this assay are described in Example 5.

While 0.6 mg/kg of either enantiomer was ineffective, clear effects were seen when the two enantiomers were given simultaneously as 1.2 mg/kg of the racemate, illustrated in FIG. 5. In contrast, other compounds appeared to have roughly linear interactions where the effects of the racemate appeared to be adequately approximated by the sum of the effects of the individual enantiomers.

Based on this finding of potential non-additive effects, further experiments were conducted in which the ratio of 5-MAPB enantiomers was varied. Including the previous results, this resulted in the following dose combinations:

0 mg/kg S-enantiomer+0 mg/kg R-enantiomer;
0.3 mg/kg S-enantiomer+0 mg/kg R-enantiomer;
0.6 mg/kg S-enantiomer+0 mg/kg R-enantiomer;
1.2 mg/kg S-enantiomer+0 mg/kg R-enantiomer;
0 mg/kg S-enantiomer+0.3 mg/kg R-enantiomer;
0 mg/kg S-enantiomer+0.6 mg/kg R-enantiomer;
0 mg/kg S-enantiomer+1.2 mg/kg R-enantiomer;
0.6 mg/kg S-enantiomer+0.15 mg/kg R-enantiomer;
0.6 mg/kg S-enantiomer+0.3 mg/kg R-enantiomer;
0.6 mg/kg S-enantiomer+0.45 mg/kg R-enantiomer; and
0.6 mg/kg S-enantiomer+0.6 mg/kg R-enantiomer.

The resulting data were analyzed with a linear model in which marble burying was predicted by S-dose, R-dose and an interaction term. The overall model was significant (F-statistic: 20.3 on 3 and 216 DF, p-value: <0.001, adjusted $R^2$: 0.2091) and there were significant effects of S-dose (T-value −4.382, p<0.001), R-dose (T-value −2.388, p=0.018), and the interaction term (T-value −2.073, p=0.039). This confirmed a surprising interactive effect when both enantiomers were given simultaneously that was not explainable by dose of either enantiomer alone.

Marble Burying Experimental Methods

Marble burying experiments were conducted by trained and authorized personnel and were in compliance with applicable guidelines for experiments with laboratory animals. Manipulation of animals was conducted carefully to reduce stress to a minimum.

Animal Care

Test animals are Swiss CD1 mice, 5-6 weeks old, that have not been subjected to prior experiments.

Housing Conditions

| | |
|---|---|
| Housing | Group housing (8-9 mice/cage): 1290D Eurostandard Type III cages (Tecniplast, Italy) in transparent polycarbonate (42.5 cm deep; 26.6 cm large; 15.5 cm high, area = 820 cm²). Cages are covered with a stainless steel grid in which food and a bottle are placed. A stainless steel removable divider separates food and water |
| Litter | Aspen Small (SDS Dietex, France) |
| Enrichment | Cell huts |
| Temperature | 21.5 ± 1.5° C. |
| Hygrometry | 50 ± 30% (measured but not controlled) |
| Air renewal | Fresh air, 12-25 vol/h |
| Lighting | 20-30 Lux |
| Day/night cycle | Normal 12 h/12 h cycle; light on 8:00-20:00/off: 20:00-8:00 |
| Food | Rat-mouse A04 (Safe, France) available ad libitum |
| Drink | Tap water, available ad libitum |

Experimental Arenas

The experiment was conducted in eight Plexiglas transparent open boxes (42 cm L, 42 cm W, 40 cm H) filled with 5 cm sawdust. Twenty-five clean glass marbles (15 mm diameter) were evenly spaced 5 cm apart on sawdust.

Testing Procedure

Testing was carried out during the dark phase, in standardized conditions (T°=22.0±1.5° C.), with artificial light (20 Lux at the level of the apparatus) and low ambient noise (mostly coming from the ventilation system and the experimental apparatus).

Test compounds or placebo vehicle were administered intraperitoneally 30 minutes before animals were individually placed in an experimental apparatus for a 30-min session.

The number of marbles at least ⅔ buried was counted at the end of the session as the primary outcome measure. Results were generally displayed with scores inverted (proportion of marble left unburied) and expressed as magnitude difference-from-placebo with error bars indicating 95% confidence intervals.

Example 6: In Vitro Binding Site Studies

Select compounds of the present invention were tested for agonist and antagonist activity against $5\text{-HT}_{1B}$ and $5\text{-HT}_{2A}$ and the results are shown in Table 1. Select compounds were also tested for adrenergic β2 receptor antagonist activity, MAO-A inhibition, and the ability to inhibit nicotinic acetylcholine α4/β2 receptors. The results are shown in Table 2.

Adrenergic β2 Receptor cAMP Secondary Messenger Antagonist Assay Methods

This assay used a panel of CHO-K1 cell lines stably expressing non-tagged GPCRs that endogenously signal through cAMP. Hit Hunter® cAMP assays monitored the activation of a GPCR via Gi and Gs secondary messenger signaling in a homogenous, non-imaging assay format using DiscoverX Enzyme Fragment Complementation (EFC) with β-galactosidase as the functional endpoint.

The enzyme was split into two complementary portions: Enzyme Acceptor (EA) and Enzyme Donor (ED). In the assay, exogenously introduced ED fused to cAMP (ED-cAMP) competed with endogenously generated cAMP for binding to an anti-cAMP-specific antibody. Active β-galactosidase was formed by complementation of exogenous EA to any unbound ED-cAMP. Active enzyme could then convert a chemiluminescent substrate, generating an output signal detectable on a standard microplate reader.

Cell lines were expanded from freezer stocks according to standard procedures. Cells were seeded in a total volume of 20 µL into white walled, 384-well microplates and incubated at 37° C. for the appropriate time prior to testing. cAMP modulation was determined using the DiscoverX HitHunter cAMP XS+ assay.

Test compounds were assayed at 10 concentrations with the highest concentration either 30 or 10 µM and subsequent concentrations using a 0.33 dilution factor.

For agonist determination, cells were incubated with sample (in the presence of EC80 forskolin to induce response if measuring Gi secondary messenger signaling). Media was aspirated from cells and replaced with 15 µL 2:1 HBSS/10 mM Hepes:cAMP XS+ Ab reagent. Intermediate dilution of sample stocks was performed to generate 4X sample in assay buffer (optionally containing 4× EC80 forskolin). 5 µL of 4× sample was added to cells and incubated at 37° C. or room temperature for 30 or 60 minutes, as appropriate. Final assay vehicle concentration was 1%.

For antagonist determination, cells were pre-incubated with sample followed by agonist challenge at the EC80 concentration. Media was aspirated from cells and replaced with 1O L 1:1 HBSS/Hepes:cAMP XS+ Ab reagent. 5 µL of 4× compound was added to the cells and incubated at 37° C. or room temperature for 30 minutes. 5 µL of 4× EC80 agonist was added to cells and incubated at 37° C. or room temperature for 30 or 60 minutes. For Gi coupled GPCRs, EC80 forskolin was included.

After appropriate compound incubation, assay signal was generated through incubation with 20 µL cAMP XS+ ED/CL lysis cocktail for one hour followed by incubation with 20 µL cAMP XS+ EA reagent for three hours at room temperature. Microplates were read following signal generation with a PerkinElmer Envision™ instrument for chemiluminescent signal detection.

Compound activity was analyzed using CBIS data analysis suite (ChemInnovation, CA). For Gs antagonist mode assays, percentage inhibition was calculated as 100%×(1−(mean RLU of test sample−mean RLU of vehicle control)/(mean RLU of EC80 control−mean RLU of vehicle control)).

5-HT2A and 5-HT2B Agonist and Antagonist Assays

The DiscoveRx Calcium NWPLUS Assay was used for detection of changes in intracellular calcium as signalled by an increase of dye fluorescence in cells expressing 5-HT2A receptors. Signal was measured on a fluorescent plate reader equipped with fluidic handling capable of detecting rapid changes in fluorescence upon compound stimulation.

To conduct the assay, cell lines were expanded from freezer stocks according to standard procedures. Cells (10, 000 cells/well) were seeded in a total volume of 50 µL (200 cells/µL) into black-walled, clear-bottom, Poly-D-lysine coated 384-well microplates and incubated at 37° C. for the appropriate time prior to testing. DMSO concentration for all readouts was ≤0.2%.

Assays were performed in 1× DyeLoading Buffer consisting of 1× Dye (DiscoverX, Calcium No WashPLUS kit, Catalog No. 90-0091), 1× Additive A and 2.5 mM Probenecid in HBSS/20 mM Hepes. Probenecid was prepared fresh. Cells were loaded with dye prior to testing. Media was aspirated from cells and replaced with 25 µL Dye Loading Buffer. Test compounds were assayed at 10 concentrations with the highest concentration either 30 or 10 µM and subsequent concentrations using a 0.33 dilution factor. Cells with testing sample were incubated for 45 minutes at 37° C. and then 20 minutes at room temperature. After dye loading, cells were removed from the incubator and 25 µL of 2× compound in HBSS/20 mM Hepes was added using a FLIPR Tetra (MDS). For 5-HT2A assays, serotonin and altanserin were used as agonist and antagonist reference controls. For 5-HT2B assays, these were serotonin and LY272015.

For antagonist determination, cells were pre-incubated with sample followed by agonist challenge at the $EC_{80}$ concentration. After dye loading, cells were removed from the incubator and 25 µL 2× sample was added. Cells were incubated for 30 minutes at room temperature in the dark to equilibrate plate temperature. After incubation, antagonist determination was initiated with addition of 25 µL 1× compound with 3× $EC_{80}$ agonist using FLIPR.

Compound agonist activity was measured on a FLIPR Tetra. Calcium mobilization was monitored for 2 minutes with a 5 second baseline read. FLIPR read-Area under the curve was calculated for the two minute read. Compound activity was analyzed using CBIS data analysis suite (ChemInnovation, CA). Percentage activity was calculated as 100%×(mean RFU of test sample−mean RFU of vehicle control)/(mean MAX RFU control ligand−mean RFU of vehicle control). For antagonist mode assays, percentage inhibition was calculated as 100%×(1−(mean RFU of test sample−mean RFU of vehicle control)/(mean RFU of $EC_{80}$ control−mean RFU of vehicle control)).

MAO-A Inhibition Assay

MAO-A and test compounds were preincubated at 37° C. for 15 minutes before substrate addition. Test compounds were assayed at 10 concentrations with the highest concentration either 30 or 10 µM and subsequent concentrations using a 0.33 dilution factor. The reaction was initiated by addition of kynuramine and incubated at 37° C. for 30 minutes. The reaction was terminated by addition of NaOH. The amount of 4-hydroquioline formed was determined through spectrofluorimetric readout with the emission detection at 380 nm and excitation wavelength 310 nm. Clorgyline ($IC_{50}$ 0.00438 µM) was used as a positive control.

Nicotinic acetylcholine receptor α4β2 (nAchRa4/b2) Ion Channel Blocking Assay

Cell lines were expanded from freezer stocks according to standard procedures. Cells were seeded in a total volume of 20 µL into black-walled, clear-bottom, Poly-D-lysine coated 384-well microplates and incubated at 37° C. for the appropriate time prior to testing.

Assays were performed in 1× Dye Loading Buffer consisting of 1× Dye, and 2.5 mM freshly-prepared Probenecid when applicable.

Test compounds were assayed at 10 concentrations with the highest concentration either 30 or 10 μM and subsequent concentrations using a 0.33 dilution factor.

Prior to testing, cells were loaded with dye then incubated for 30-60 minutes at 37° C. For antagonist determination, cells were pre-incubated with sample. Dihydro-β-erythroidine was used as a positive control. Intermediate dilution of sample stocks was performed to generate 2-5× sample in assay buffer.

After dye loading, cells were moved from the incubator and 10-25 μL 2-5× sample was added to cells in the presence of EC80 agonist when appropriate. Cells were incubated for 30 minutes at room temperature in the dark to equilibrate plate temperature. Vehicle concentration was 1%.

Compound activity was measured on a FLIPRTetra (MDS) and analyzed using CBIS data analysis suite (ChemInnovation, CA). Percentage inhibition was calculated using the following formula: % Inhibition=100%×(1−(mean RLU of test sample−mean RLU of vehicle control)/(mean RLU of EC80 control−mean RLU of vehicle control)).

TABLE 1

Agonist and Antagonist activity against $5\text{-HT}_{1B}$ and $5\text{-HT}_{2A}$

| Compound | $5HT_{1B}$ Agonist (μM) | $5HT_{2A}$ Agonist (μM) | $5HT_{2A}$ Antagonist (μM) | $5HT_{2B}$ Agonist (μM) | $5HT_{2B}$ Antagonist (μM) |
|---|---|---|---|---|---|
| 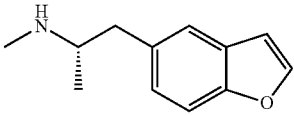<br>S-5-MAPB<br>[1-(1-benzofuran-5-yl)propan-2-yl](methyl)amine | 0.16 | ND | ND | ND | ND |
| 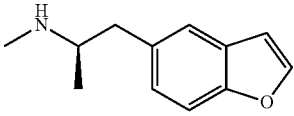<br>R-5-MAPB<br>[1-(1-benzofuran-5-yl)propan-2-yl](methyl)amine | 0.98 | 2.40 | 5.34 | ND | 0.36 |
| 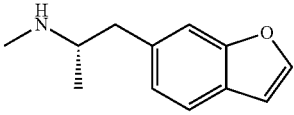<br>S-6-MAPB<br>[1-(1-benzofuran-6-yl)propan-2-yl](methyl)amine | 0.10 | ND | ND | ND | ND |
| 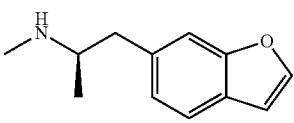<br>R-6-MAPB<br>[1-(1-benzofuran-6-yl)propan-2-yl](methyl)amine | 1.48 | 4.62 | ND | ND | 0.40 |
| 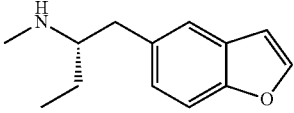<br>S-5-MBPB<br>[1-(1-benzofuran-5-yl)butan-2-yl](methyl)amine | 3.06 | ND | ND | ND | ND |

TABLE 1-continued

Agonist and Antagonist activity against 5-HT$_{1B}$ and 5-HT$_{2A}$

| Compound | 5HT$_{1B}$ Agonist (µM) | 5HT$_{2A}$ Agonist (µM) | 5HT$_{2A}$ Antagonist (µM) | 5HT$_{2B}$ Agonist (µM) | 5HT$_{2B}$ Antagonist (µM) |
|---|---|---|---|---|---|
| 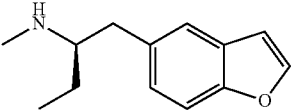 R-5-MBPB [1-(1-benzofuran-5-yl)butan-2-yl](methyl)amine | ND | ND | ND | ND | ND |
| 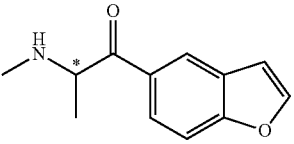 Enantiomer 1 BK-5-MAPB 1-(1-benzofuran-5-yl)-2-(methylamino)propan-1-one | 0.08 | ND | ND | ND | ND |
| 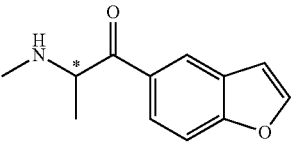 Enantiomer 2 BK-5-MAPB 1-(1-benzofuran-5-yl)-2-(methylamino)propan-1-one | 3.07 | ND | ND | ND | ND |

TABLE 2

Adrenergic β$_2$ receptor antagonist activity, MAO-A inhibition, and nicotinic acetylcholine α4/β2 receptor blocking activity of select compounds

| Compound | ADREN R β 2 Antagonist (µM) | MAO-A Inhibitor (µM) | nAChR(α4/β2) Blocker (µM) |
|---|---|---|---|
| 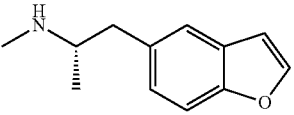 S-5-MAPB [1-(1-benzofuran-5-yl)propan-2-yl](methyl)amine | ND | 1.29 | ND |
| 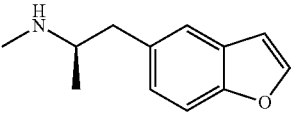 R-5-MAPB [1-(1-benzofuran-5-yl)propan-2-yl](methyl)amine | ND | 3.94 | 4.24 |

TABLE 2-continued

Adrenergic β2 receptor antagonist activity, MAO-A inhibition, and nicotinic acetylcholine α4/β2 receptor blocking activity of select compounds

| Compound | ADREN R β 2 Antagonist (μM) | MAO-A Inhibitor (μM) | nAChR(α4/β2) Blocker (μM) |
|---|---|---|---|
| S-6-MAPB [1-(1-benzofuran-6-yl)propan-2-yl](methyl)amine | ND | 5.39 | ND |
| R-6-MAPB [1-(1-benzofuran-6-yl)propan-2-yl](methyl)amine | 4.06 | 2.12 | 7.41 |
| S-5-MBPB [1-(1-benzofuran-5-yl)butan-2-yl](methyl)amine | ND | 2.66 | 9.98 |
| R-5-MBPB [1-(1-benzofuran-5-yl)butan-2-yl](methyl)amine | ND | ND | 6.33 |

Example 7: 5-HT1BR cAMP Secondary Messenger Agonist Assay

The 5-HT$_{1B}$R cAMP secondary messenger agonist assay used a panel of CHO-K1 cell lines stably expressing non-tagged GPCRs that endogenously signal through cAMP. Hit Hunter® cAMP assays monitored the activation of a GPCR via Gi and Gs secondary messenger signaling in a homogenous, non-imaging assay format using DiscoverX Enzyme Fragment Complementation (EFC) with β-galactosidase as the functional endpoint.

The enzyme was split into two complementary portions: Enzyme Acceptor (EA) and Enzyme Donor (ED). Exogenously introduced ED fused to cAMP (ED-cAMP) competed with endogenously generated cAMP for binding to an anti-cAMP-specific antibody. Active β-galactosidase was formed by complementation of exogenous EA to any unbound ED-cAMP. Active enzyme could then convert a chemiluminescent substrate, generating an output signal detectable on a standard microplate reader.

Cell lines were expanded from freezer stocks according to standard procedures. Cells were seeded in a total volume of 20 μL into white walled, 384-well microplates and incubated at 37° C. for the appropriate time prior to testing. cAMP modulation was determined using the DiscoverX HitHunter cAMP XS+ assay.

For agonist determination, cells were incubated with sample (in the presence of EC$_{80}$ forskolin to induce response if measuring Gi secondary messenger signaling). Media was aspirated from cells and replaced with 15 μL 2:1 HBSS/10 mM Hepes:cAMP XS+ Ab reagent. Intermediate dilution of sample stocks was performed to generate 4× sample in assay buffer (optionally containing 4× EC$_{80}$ forskolin). 5 μL of 4× sample was added to cells and incubated at 37° C. or room temperature for 30 or 60 minutes, as appropriate. Final assay vehicle concentration was 1%. The results are shown in Table 3.

Surprisingly, several of the benzofuran derivatives of the current invention are 5-HT1BR agonists. Direct stimulation of 5-HT1BR has not been previously documented with drugs producing MDMA-like effects and MDMA itself does not bind to the 5-HT1BR (Ray. 2010. PloS one, 5(2), e9019). Indirect stimulation of 5-HT1BR, secondary to elevated extracellular serotonin, has been hypothesized to be required for the prosocial effects of MDMA (Heifets et al. 2019. Science translational medicine, 11(522)), while other aspects of entactogen effects have been attributed to monoamine release (e.g., Luethi & Liechti. 2020. Archives of toxicology, 94(4), 1085-1133).

Thus, in one embodiment, the unique ratios of 5-HT1BR stimulation and monoamine release displayed by the disclosed compounds enable different profiles of therapeutic effects that cannot be achieved by MDMA or other known entactogens.

TABLE 3

5-HT1B Agonist Effects of N-alkyl Benzofuran Compounds

| Compound | 5-HT1BR EC50 (μM) | Hill Coef. |
|---|---|---|
| S-5-MAPB | 0.16147 | 1.08 |
| R-5-MAPB | 0.98089 | 1.13 |
| S-6-MAPB | 0.10166 | 1.21 |
| R-6-MAPB | 1.48187 | 1.14 |
| rac-5-MBPB | 5.82237 | 0.96 |
| S-5-MBPB | 3.0638 | 1.5 |
| R-5-MBPB | >10 | |
| rac-6-MBPB | 1.95124 | 0.89 |
| S-6-MBPB | 1.72234 | 1.1131 |
| R-6-MBPB | 5.75045 | 0.8121 |
| rac-BK-5-MAPB | 0.13951 | 0.91 |
| (−)-BK-5-MAPB | 0.0777 | 1.5 |
| (+)-BK-5-MAPB | 3.06782 | 1.05 |
| rac-BK-6-MAPB | 0.5373 | 0.99 |
| (−)-BK-6-MAPB | 0.28804 | 0.8339 |

TABLE 3-continued

5-HT1B Agonist Effects of N-alkyl Benzofuran Compounds

| Compound | 5-HT1BR EC50 (μM) | Hill Coef. |
|---|---|---|
| (+)-BK-6-MAPB | >10 | |
| rac-BK-5-MBPB | 19.64355 | 1.01 |
| (−)-BK-5-MBPB | 6.61190 | 1.6241 |
| (+)-BK-5-MBPB | >30 | |
| rac-BK-6-MBPB | >30 | |
| (−)-BK-6-MBPB | 7.51594 | 1.9551 |
| (+)-BK-6-MBPB | >30 | |

Example 8: Human Serotonin Transporter (SERT, SLC6A4) Functional Antagonist Uptake Assay Benzofuran derivatives were evaluated for inhibiting the human 5-HT transporter (hSERT) as expressed in CHO cells using an antagonist radioligand assay (Tatsumi, M. et al. (1999), Eur. J. Pharmacol., 368: 277-283). Compound binding was calculated as a percent inhibition of the binding of 2 nM [$^3$H]imipramine using a scintillation method and inhibition constants (Ki) were calculated using the Cheng Prusoff equation. Test compounds were assayed in three trials at 300, 94.868, 30, 9.4868, 0.3, and 0.94868 μM.

All tested compounds showed inhibition of hSERT at the tested concentrations. However, in two cases (the enantiomers of 5-MBPB), the lowest concentration of 0.94868 μM was too high to accurately estimate $IC_{50}$ values and $K_i$ values. For S-(+)-5-MBPB the $IC_{50}$ appeared close to 0.094868 μM, while for R-(−)-5-MBPB the $IC_{50}$ appeared close to 0.94868 μM.

When compounds are substrates for monoamine transporters instead of solely inhibitors, it is known that $IC_{50}$ values underestimate their potency for interacting with these transporters (Ilic, M. et al. (2020), Frontiers in Pharmacology 11: 673).

TABLE 4

Human Serotonin Transporter Functional Antagonist Uptake Assay

| Compound | SERT IC50 (μM) | SERT Ki (μM) |
|---|---|---|
| S-(+)-5-MAPB | 3.40 | 1.50 |
| R-(−)-5-MAPB | 2.70 | 1.20 |
| S-(+)-6-MAPB | 6.70 | 3.10 |
| R-(−)-6-MAPB | 24.0 | 11.0 |
| S-(+)-5-MBPB | <0.95 | ND |
| S-(+)-5-MBPB | <0.95 | ND |

TABLE 4-continued

Human Serotonin Transporter Functional Antagonist Uptake Assay

| Compound | SERT IC50 (µM) | SERT Ki (µM) |
|---|---|---|
| R-(−)-5-MBPB | 2.70 | 1.20 |
| S-(+)-6-MBPB | 5.70 | 2.60 |
| R-(−)-6-MBPB | 6.90 | 3.20 |
| (−)-BK-5MAPB | 38.0 | 17.0 |
| (+)-BK-5MAPB | 12.0 | 5.40 |
| (−)-BK-6MAPB | 110 | 51.0 |
| (+)-BK-6MAPB | 1.60 | 0.720 |
| (−)-BK-5MBPB | 6.50 | 3.00 |
| (+)-BK-5MBPB | 3.70 | 1.70 |
| (−)-BK-6MBPB | 29.0 | 13.0 |
| (+)-BK-6MBPB | | |

Example 9: Effects of Substituted Benzofurans on Extracellular Serotonin

Select compounds of the present invention were studied for their effect on extracellular serotonin and compared to MDMA. The results are shown in Table 5.

TABLE 5

Effects of Substituted Benzofurans on Extracellular Serotonin

| Compound | Inhibition of [3H]5-HT Uptake at SERT IC$_{50}$ (nM) | [3H]5-HT release via SERT EC$_{50}$ (nM) |
|---|---|---|
| S-5-MAPB | 60.4 ± 2.8 | 13.0 ± 1.2 |
| R-5-MAPB | 149.6 ± 8.6 | 29.3 ± 3.7 |
| S-6-MAPB | 90.9 ± 5.9 | 20.6 ± 2.7 |

TABLE 5-continued

Effects of Substituted Benzofurans on Extracellular Serotonin

| Compound | Inhibition of [3H]5-HT Uptake at SERT IC$_{50}$ (nM) | [3H]5-HT release via SERT EC$_{50}$ (nM) |
|---|---|---|
| R-6-MAPB | 622.6 ± 31.2 | 111.9 ± 17.5 |
| S-5-MBPB | 123.7 ± 35.8 | 31.2 ± 14.3 |
| R-5-MBPB | 211.7 ± 36.2 | 49.5 ± 27.1 |
| S-6-MBPB | 216.8 ± 45.8 | 54.1 ± 33.9 |
| R-6-MBPB | 702.5 ± 261.7 | 171.7 ± 82.2 |
| (−)-BK-5-MAPB | 284.4 ± 11.9 | 80.0 ± 13.7 |
| (+)-BK-5-MAPB | 2087.0 ± 151.0 | 438.8 ± 72.5 |
| (−)-BK-6-MAPB | 274.6 ± 13.0 | 72.2 ± 16.6 |
| (+)-BK-6-MAPB | 5466.0 ± 424.0 | 1283.0 ± 268.0 |
| MDMA | 384.5 ± 32.8 | 94.3 ± 13.6 |

Figure 7A:
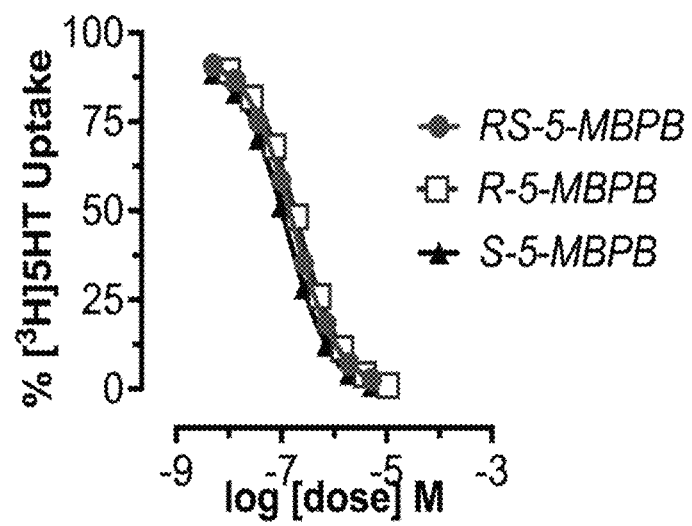
FIG. 7A is a graph showing results from an in vitro rat synaptosome serotonin uptake inhibition assay. The graphs display percent reuptake of [$^3$H]-labeled 5-HT as a function of concentration for RS-5-MBPB, R-5-MBPB, and S-5-MBPB. This data indicates that each tested compound rapidly increases extracellular serotonin by inhibiting reuptake. Details and procedural information for this assay are described in Example 9. The x-axis the log [dose] concentration measured in molar and the y-axis is the [$^3$H]-labeled 5-HT reuptake measured in percent.
Figure 7B:
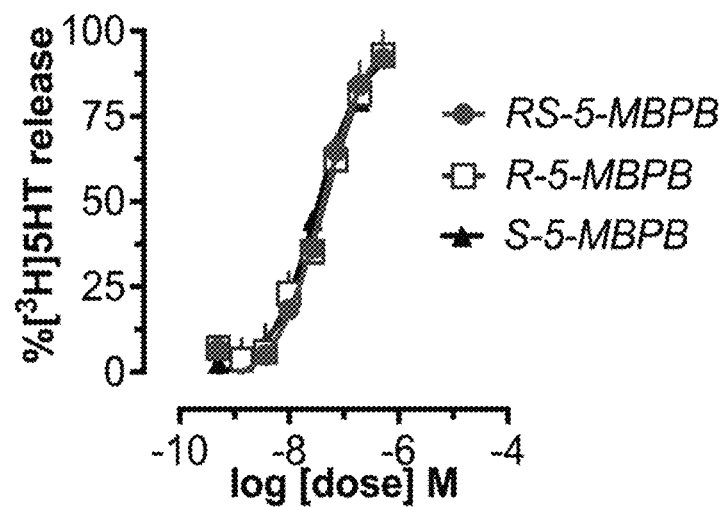
FIG. 7B is a graph showing results from an in vitro rat synaptosome serotonin release assay. The graphs display [$^3$H]-labeled 5-HT release as a function of concentration for RS-5-MBPB, R-5-MBPB, and S-5-MBPB. These data indicate that each tested compound rapidly increases extracellular serotonin by stimulating release. Details and procedural information for this assay are described in Example 9. The x-axis the log [dose] concentration measured in molar and the y-axis is the [$^3$H]-labeled 5-HT release measured in percent.
Figure 8A:
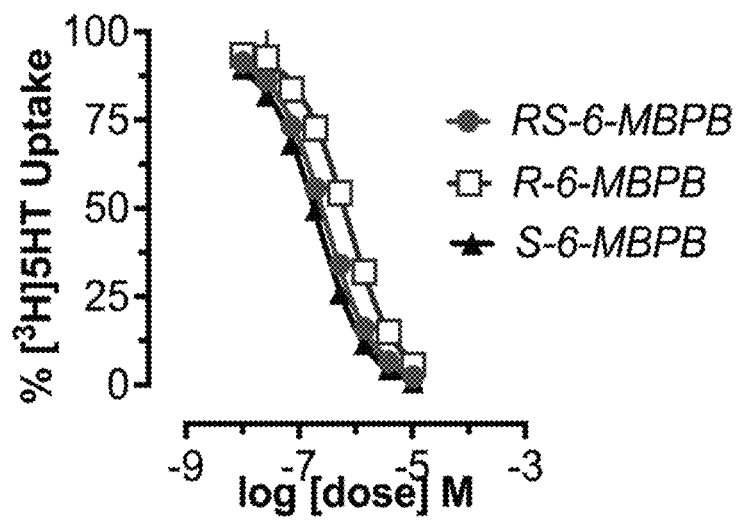
FIG. 8A is a graph showing results from an in vitro rat synaptosome serotonin uptake inhibition assay. The graphs display percent reuptake of [$^3$H]-labeled 5-HT as a function of concentration for RS-6-MBPB, R-6-MBPB, and S-6-MBPB. This data indicates that each tested compound rapidly increases extracellular serotonin by inhibiting reuptake. Details and procedural information for this assay are described in Example 9. The x-axis the log [dose] concentration measured in molar and the y-axis is the [$^3$H]-labeled 5-HT reuptake measured in percent.
Figure 8B:
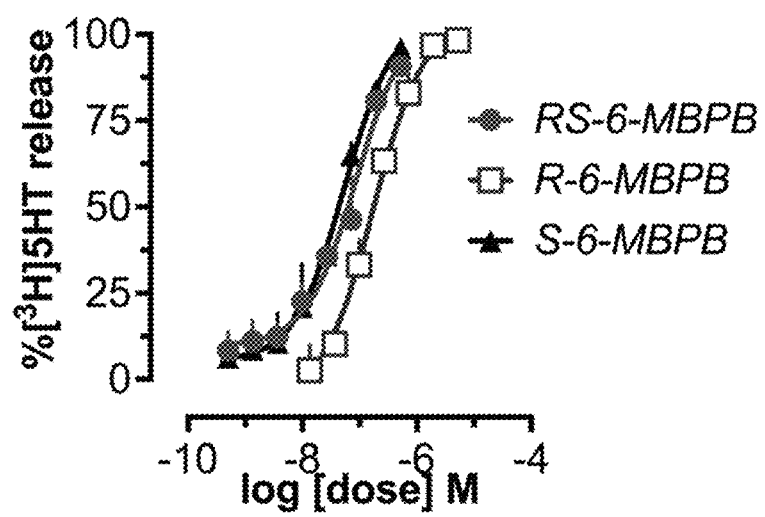
FIG. 8B is a graph showing results from an in vitro rat synaptosome serotonin release assay. The graphs display [$^3$H]-labeled 5-HT release as a function of concentration for RS-6-MBPB, R-6-MBPB, and S-6-MBPB. These data indicate that each tested compound rapidly increases extracellular serotonin by stimulating release. Details and procedural information for this assay are described in Example 9. The x-axis the log [dose] concentration measured in molar and the y-axis is the [$^3$H]-labeled 5-HT release measured in percent.
Figure 9A:
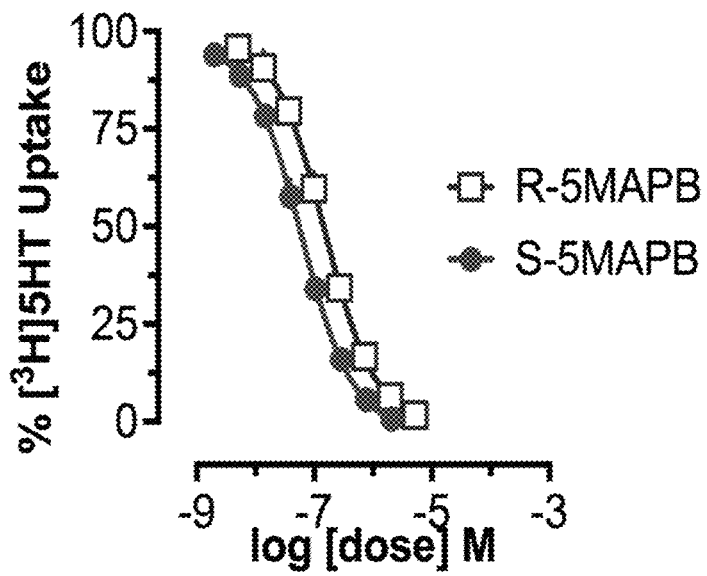
FIG. 9A is a graph showing results from an in vitro rat synaptosome serotonin uptake inhibition assay. The graphs display percent reuptake of [$^3$H]-labeled 5-HT as a function of concentration for R-5-MAPB and S-5-MAPB. This data indicates that each tested compound rapidly increases extracellular serotonin by inhibiting reuptake. Details and procedural information for this assay are described in Example 9. The x-axis the log [dose] concentration measured in molar and the y-axis is the [$^3$H]-labeled 5-HT reuptake measured in percent.
Figure 9B:
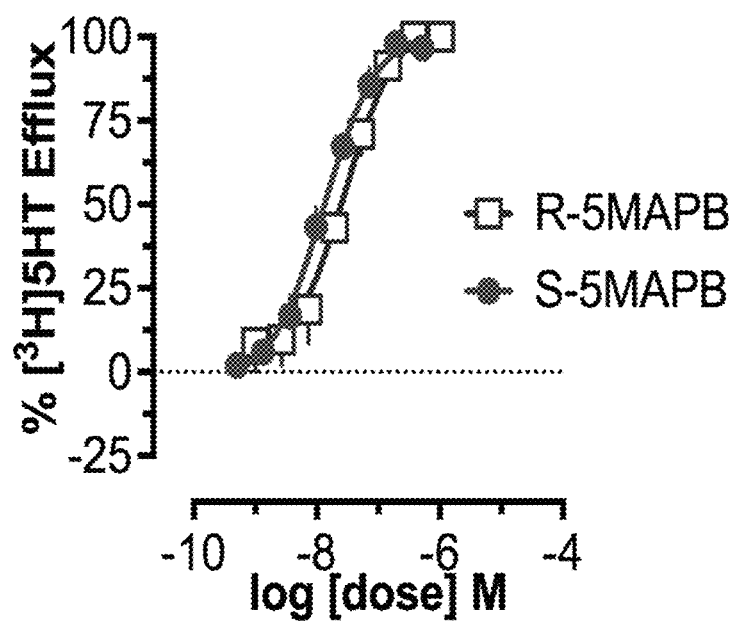
FIG. 9B is a graph showing results from an in vitro rat synaptosome serotonin efflux assay. The graphs display [$^3$H]-labeled 5-HT release as a function of concentration for R-5-MAPB and S-5-MAPB. These data indicate that each tested compound rapidly increases extracellular serotonin by stimulating release. Details and procedural information for this assay are described in Example 9. The x-axis the log [dose] concentration measured in molar and the y-axis is the [$^3$H]-labeled 5-HT release measured in percent.
Figure 10A:
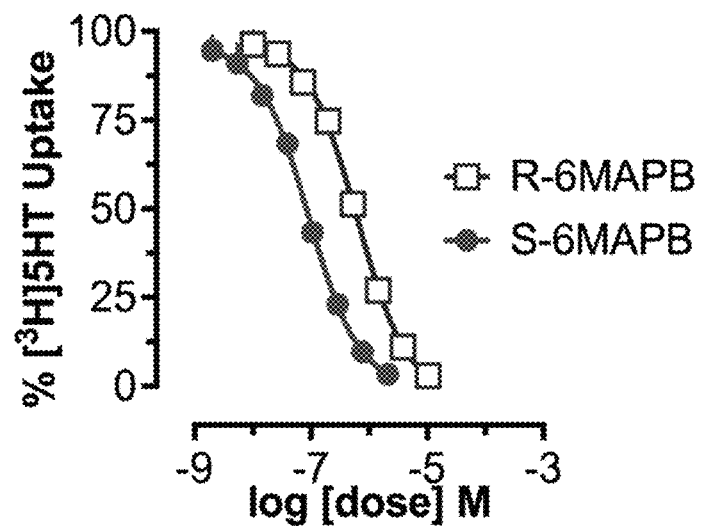
FIG. 10A is a graph showing results from an in vitro rat synaptosome serotonin uptake inhibition assay. The graphs display percent reuptake of [$^3$H]-labeled 5-HT as a function of concentration for R-6-MAPB and S-6-MAPB. This data indicates that each tested compound rapidly increases extracellular serotonin by inhibiting reuptake. Details and procedural information for this assay are described in Example 9. The x-axis the log [dose] concentration measured in molar and the y-axis is the [$^3$H]-labeled 5-HT reuptake measured in percent.
Figure 10B:
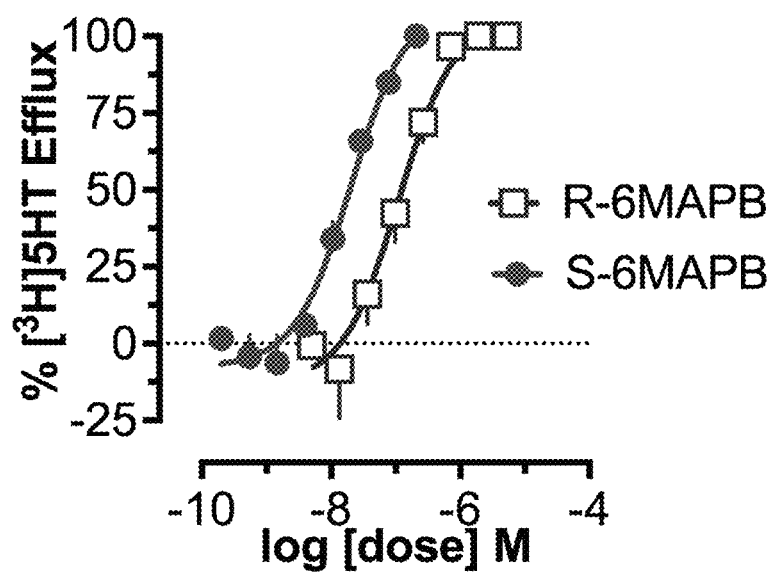
FIG. 10B is a graph showing results from an in vitro rat synaptosome serotonin efflux assay. The graphs display [$^3$H]-labeled 5-HT release as a function of concentration for R-6-MAPB and S-6-MAPB. These data indicate that each tested compound rapidly increases extracellular serotonin by stimulating release. Details and procedural information for this assay are described in Example 9. The x-axis the log [dose] concentration measured in molar and the y-axis is the [$^3$H]-labeled 5-HT release measured in percent.
Figure 11A:
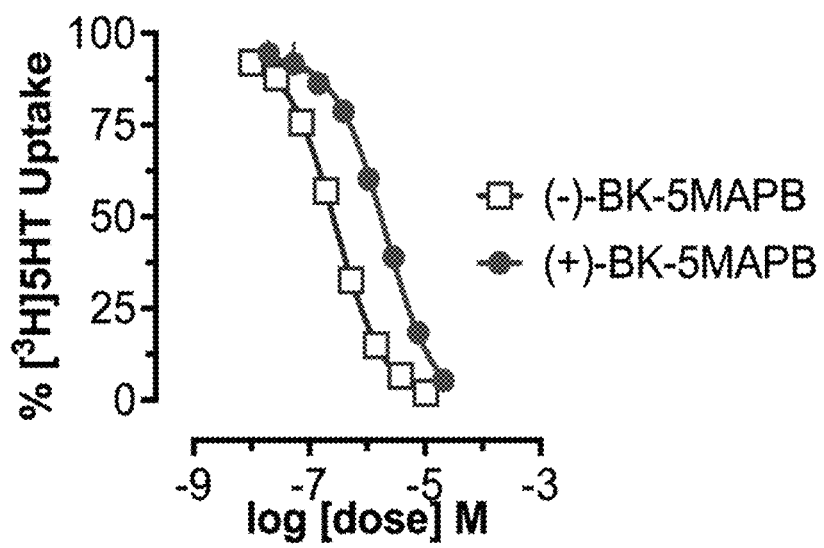
FIG. 11A is a graph showing results from an in vitro rat synaptosome serotonin uptake inhibition assay. The graphs display percent reuptake of [$^3$H]-labeled 5-HT as a function of concentration for (−)-Bk-5-MAPB and (+)-Bk-5-MAPB. This data indicates that each tested compound rapidly increases extracellular serotonin by inhibiting reuptake. Details and procedural information for this assay are described in Example 9. The x-axis the log [dose] concentration measured in molar and the y-axis is the [$^3$H]-labeled 5-HT reuptake measured in percent.
Figure 11B:
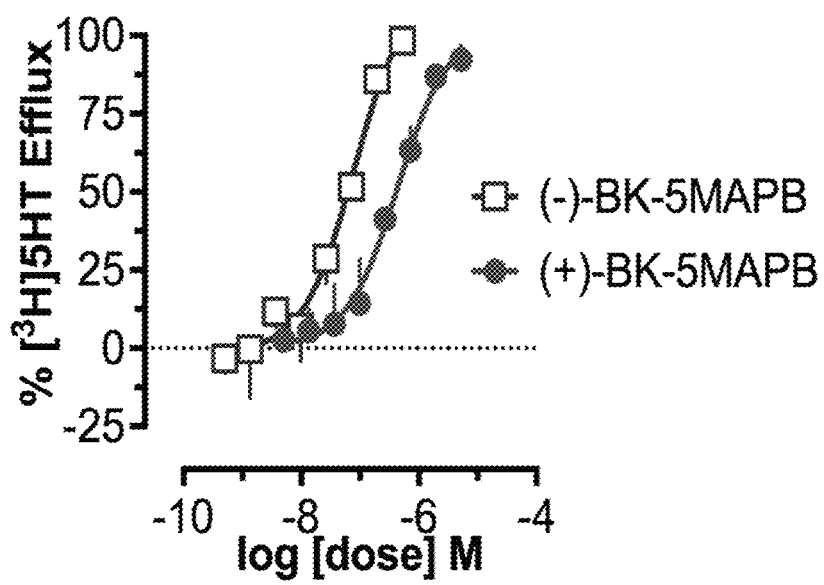
FIG. 11B is a graph showing results from an in vitro rat synaptosome serotonin efflux assay. The graphs display [$^3$H]-labeled 5-HT release as a function of concentration for (−)-Bk-5-MAPB and (+)-Bk-5-MAPB. These data indicate that each tested compound rapidly increases extracellular serotonin by stimulating release. Details and procedural information for this assay are described in Example 9. The x-axis the log [dose] concentration measured in molar and the y-axis is the [$^3$H]-labeled 5-HT release measured in percent.
Figure 12A:
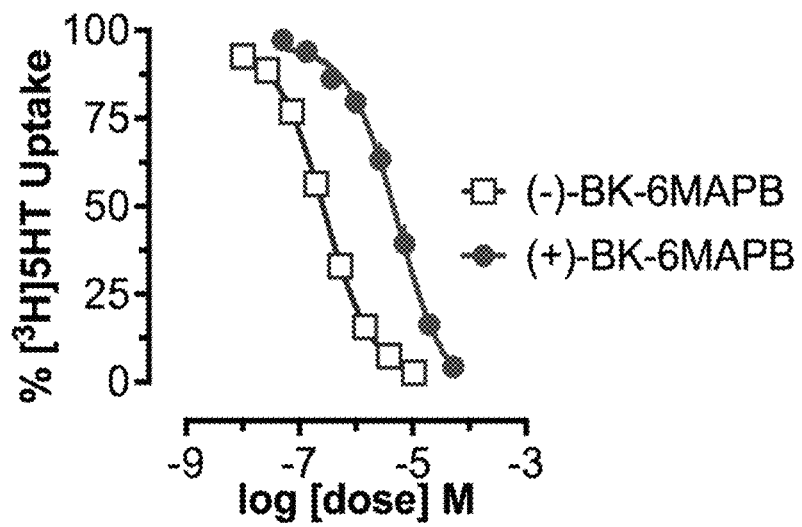
FIG. 12A is a graph showing results from an in vitro rat synaptosome serotonin uptake inhibition assay. The graphs display percent reuptake of [$^3$H]-labeled 5-HT as a function of concentration for (−)-Bk-6-MAPB and (+)-Bk-6-MAPB. This data indicates that each tested compound rapidly increases extracellular serotonin by inhibiting reuptake. Details and procedural information for this assay are described in Example 9. The x-axis the log [dose] concentration measured in molar and the y-axis is the [$^3$H]-labeled 5-HT reuptake measured in percent.
Figure 12B:
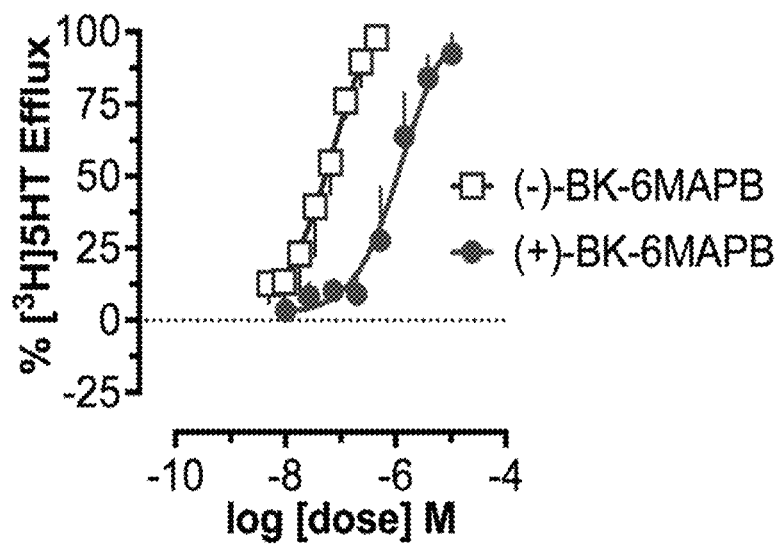
FIG. 12B is a graph showing results from an in vitro rat synaptosome serotonin efflux assay. The graphs display [$^3$H]-labeled 5-HT release as a function of concentration for (−)-Bk-6-MAPB and (+)-Bk-6-MAPB. These data indicate that each tested compound rapidly increases extracellular serotonin by stimulating release. Details and procedural information for this assay are described in Example 9. The x-axis the log [dose] concentration measured in molar and the y-axis is the [$^3$H]-labeled 5-HT release measured in percent.

The compounds were efficacious at rapidly increasing extracellular serotonin, which produces rapid therapeutic effects. FIG. 7A-FIG. 12B show in vitro rat synaptosome assay results that demonstrate serotonin reuptake inhibition and release of the compounds in Table 5. FIG. 7A is a graph of the effect of RS-5-MBPB, R-5-MBPB, and S-5-MBPB on 5HT uptake and FIG. 7B is a graph of the effect of RS-5-MBPB, R-5-MBPB, and S-5-MBPB on 5HT release. FIG. 8A is a graph of the effect of RS-6-MBPB, R-6-MBPB, and S-6-MBPB on 5HT uptake and FIG. 8B is a graph of the effect of RS-6-MBPB, R-6-MBPB, and S-6-MBPB on 5HT release. FIG. 9A and FIG. 9B are graphs of the effect of R-5-MAPB and S-5-MAPB on serotonin uptake and release, respectively. FIG. 10A and FIG. 10B are graphs of the effect of R-6-MAPB and S-6-MAPB on serotonin uptake and release, respectively. FIG. 11A and FIG. 11B are graphs of the effect of (−)-Bk-5-MAPB and (+)-Bk-5-MAPB on serotonin uptake and release, respectively. FIG. 12A and FIG. 12B are graphs of the effect of (−)-Bk-6-MAPB and (+)-Bk-6-MAPB on serotonin uptake and release, respectively.

Male Sprague-Dawley rats (Charles River, Kingston, NY, USA) were used for the synaptosome assays. Rats were group-housed with free access to food and water, under a 12 hour light/dark cycle with lights on at 0700 hours. Rats were euthanized by $CO_2$ narcosis, and synaptosomes were prepared from brains using standard procedures (Rothman, R. B., & Baumann, M. H. (2003) Monoamine transporters and psychostimulant drugs. European journal of pharmacology, 479(1-3), 23-40) Transporter uptake and release assays were performed as described previously (Solis et al. (2017). N-Alkylated analogs of 4-methylamphetamine (4-MA) differentially affect monoamine transporters and abuse liability. Neuropsychopharmacology, 42(10), 1950-1961). In brief, synaptosomes were prepared from whole brain minus caudate and cerebellum for serotonin (5-HT) transporter (SERT) assays.

For the SERT uptake inhibition assay, 5 nM [3H]5-HT was used. To optimize uptake for a single transporter, unlabeled blockers were included to prevent the uptake of [3H]5-HT by competing transporters. Uptake inhibition was initiated by incubating synaptosomes with various doses of test compound and [3H]5-HT in Krebs-phosphate buffer. Uptake assay was terminated by rapid vacuum filtration and retained radioactivity was quantified with liquid scintillation counting (Baumann et al. (2013) Powerful cocaine-like actions of 3,4-methylenedioxypyrovalerone (MDPV), a principal constituent of psychoactive 'bath salts' products. Neuropsychopharmacology, 38(4), 552-562). Results of the experiment are shown in FIG. 7A (for RS-5-MBPB, R-5-MBPB, and S-5-MBPB), FIG. 8A (for RS-6-MBPB, R-6-MBPB, and S-6-MBPB), FIG. 9A (for R-5-MAPB and S-5-MAPB), FIG. 10A (for R-6-MAPB and S-6-MAPB), FIG. 11A (for (−)-Bk-5-MAPB and (+)-Bk-5-MAPB), and FIG. 12A (for (−)-Bk-6-MAPB and (+)-Bk-6-MAPB).

For the release assay, 5 nM [3H]5-HT was used for SERT. All buffers used in the release assay contained 1 µM reserpine to block vesicular uptake of substrates. The selectivity of the release assay was optimized for a single transporter by including unlabeled blockers to prevent the uptake of [3H]5-HT by competing transporters. Synaptosomes were preloaded with radiolabeled substrate in Krebs-phosphate buffer for 1 hour to reach steady state. The release assay was initiated by incubating preloaded synaptosomes with various concentrations of the test drug. Release was terminated by vacuum filtration and retained radioactivity quantified by liquid scintillation counting. Results of the experiment are shown in FIG. 7B (for RS-5-MBPB, R-5-MBPB, and S-5-MBPB), FIG. 8B (for RS-6-MBPB, R-6-MBPB, and S-6-MBPB), FIG. 9B (for R-5-MAPB and S-5-MAPB), FIG. 10B (for R-6-MAPB and S-6-MAPB), FIG. 11B (for (−)-Bk-5-MAPB and (+)-Bk-5-MAPB), and FIG. 12B (for (−)-Bk-6-MAPB and (+)-Bk-6-MAPB).

Effects of test drugs on release were expressed as a percent of maximal release, with maximal release (i.e., 100% $E_{max}$) defined as the release produced by tyramine at doses that evoked the efflux of all 'releasable' tritium by synaptosomes (100 µM tyramine for SERT assay conditions). Effects of test drugs on uptake inhibition and release were analyzed by nonlinear regression. Dose-response values for the uptake inhibition and release were fit to the equation, $Y(x)=Y_{min}+(Y_{max}-Y_{min})/(1+10\exp[(\log P_{50}-\log x)]\times n)$, where x was the concentration of the compound tested, Y(x) was the response measured, $Y_{max}$ was the maximal response, $P_{50}$ was either $IC_{50}$ (the concentration that yielded half-maximal uptake inhibition response) or $EC_{50}$ (the concentration that yielded half-maximal release), and n was the Hill slope parameter.

Similarly, caudate tissue can be used for dopamine transporter (DAT) and whole brain minus caudate and cerebellum can be used for norepinephrine transporter (NET) assays. For other uptake inhibition assays, 5 nM [3H]dopamine or [3H]norepinephrine is used for DAT or NET assays respectively. To optimize uptake for a single transporter, unlabeled blockers are included to prevent the uptake of [3H]transmitter by competing transporters. Uptake inhibition is initiated by incubating synaptosomes with various doses of test compound and [3H]transmitter in Krebs-phosphate buffer. Uptake assays are terminated by rapid vacuum filtration and retained radioactivity is quantified with liquid scintillation counting (Baumann et al. (2013) Powerful cocaine-like actions of 3,4-methylenedioxypyrovalerone (MDPV), a principal constituent of psychoactive 'bath salts' products. Neuropsychopharmacology, 38(4), 552-562).

Alternatively, for similar release assays, 9 nM [3H]MPP+ is used as the radiolabeled substrate for DAT and NET. All buffers in the release assay contain 1 M reserpine to block vesicular uptake of substrates. The selectivity of release assays is optimized for a single transporter by including unlabeled blockers to prevent the uptake of [3H]MPP+ or [3H]5-HT by competing transporters. Synaptosomes are preloaded with radiolabeled substrate in Krebs-phosphate buffer for 1 h to reach steady state. Release assays are initiated by incubating preloaded synaptosomes with various concentrations of the test drug. Release is terminated by vacuum filtration and retained radioactivity quantified by liquid scintillation counting.

Example 10: In Vitro Absorption Assay

The permeability of 10 µM RS-5-MAPB in Caco-2, MDCKII, and MDR1-MDCKII cell line assays was assessed (Table 6). Both the AB and BA directions with and without the addition of a Pgp-specific inhibitor (verapamil), a MRP1 inhibitor (MK571), and an ATP-binding cassette subfamily G member 2 (ABCG2/BCRP) inhibitor (KO143) were measured. Trials were repeated twice, and values averaged. Results support that RS-5-MAPB was well absorbed and suggest that it is actively transported through a mechanism that was inhibited by verapamil.

TABLE 6

In vitro Absorption Assay of RS-5-MAPB

| Assay System & Conditions | Permeability (Papp, $10^{-6}$ cm/s) | | |
|---|---|---|---|
| | A-B | B-A | B-A/A-B |
| MDCKII, pH 7.4/7 4 | 82.1 | 19.8 | 0.241 |
| MDRI-MDCKII, pH 7.4/7 4 | 68.7 | 20.5 | 0.298 |
| MDR1-MDCKII, pH 7.4/7 4 + verapamil | 42.8 | 30.4 | 0.710 |
| Caco-2, pH 7.4/7.4 | 81 | 29.1 | 0.359 |
| Caco-2, pH 7.4/7.4 + verapamil | 37.6 | 23 | 0.612 |
| Caco-2, pH 7.4/7.4 + KO143 | 75.3 | 14 | 0.186 |

Example 11. 5-MAPB Freebase Isolation/Liquid-Liquid Extraction

Figure 13:
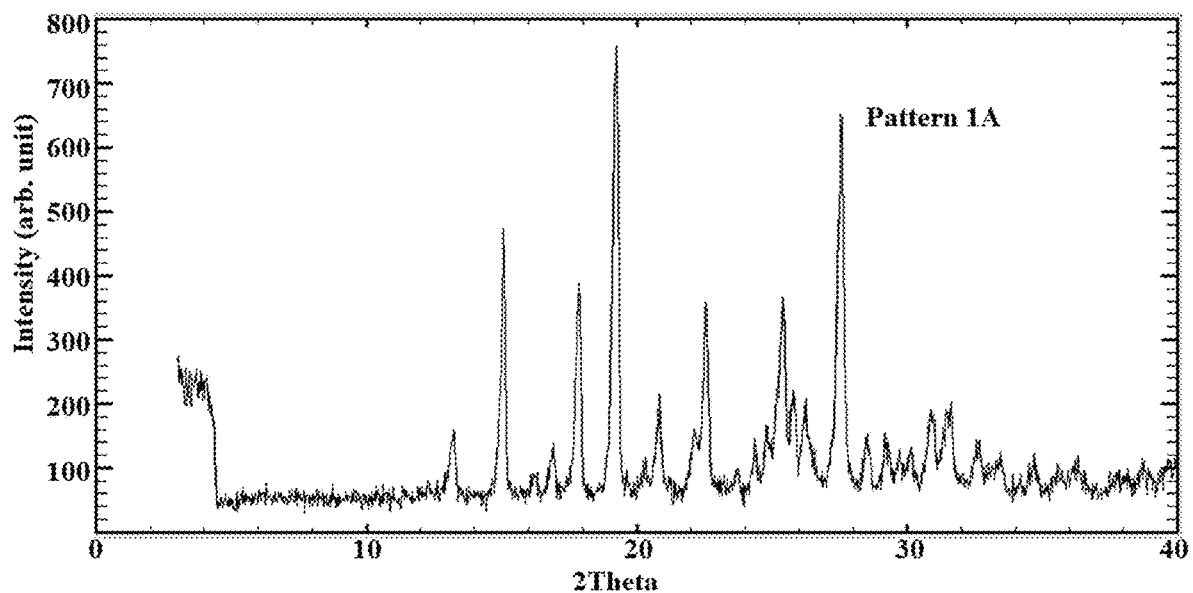
FIG. 13 is a powder XRPD Diffractogram of Pattern 1A (5-MAPB hydrochloride or 5-MAPB HCl). The diffractogram confirms the crystalline nature of Pattern 1A. The XRPD diffractogram showed that 5-MAPB Freebase was obtained as described in Example 11 and shown in Table 7. The x axis measures 2Theta in degrees and the y axis measures intensity measured in arb. units.
Figure 14:
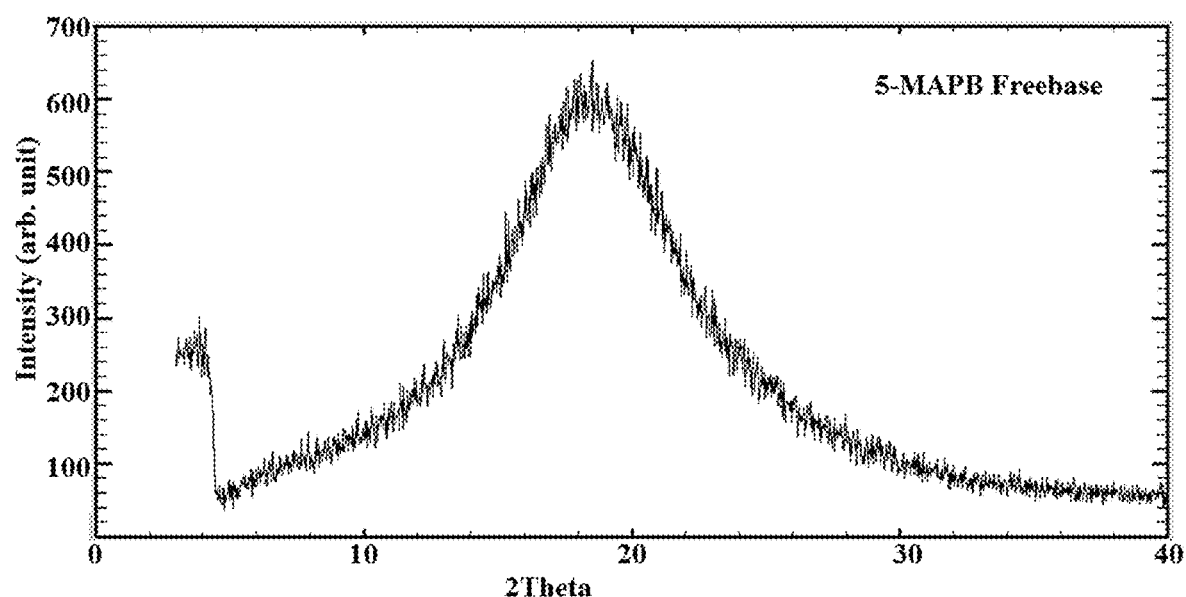
FIG. 14 is a powder XRPD Diffractogram of 5-MAPB Freebase recovered following Liquid-Liquid Extraction. The XRPD diffractogram showed that 5-MAPB Freebase was obtained as described in Example 11 and shown in Table 7. The diffractogram confirms the amorphous nature of 5-MAPB Freebase. The x axis measures 2Theta in degrees and the y axis measures intensity measured in arb. units.
Figure 15:
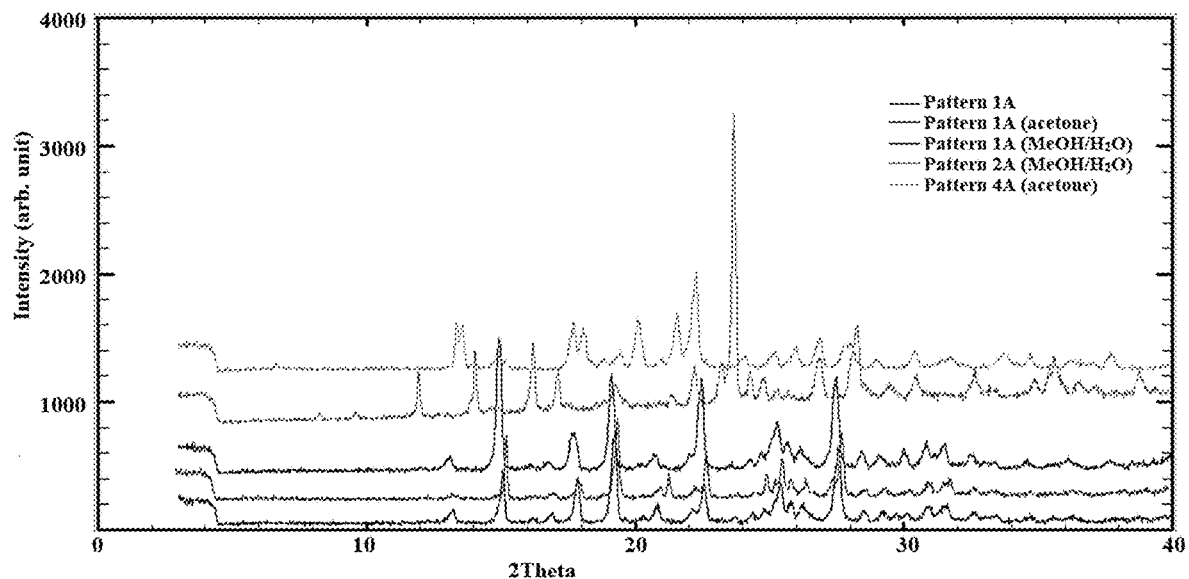
FIG. 15 is a comparison of XRPD Diffractogram salt screening of Pattern 1A, Pattern 2A (5-MAPB HBr) and Pattern 4A (5-MAPB H$_3$PO$_4$) in various solvents. The diffractogram confirms the crystalline nature of 5-MAPB in various counterions of Pattern 1A (5-MAPB HCl), Pattern 1A (5-MAPB HCl in acetone), Pattern 1A (5-MAPB HCl in MeOH:H$_2$O 90:10), Pattern 2A (5-MAPB HBr in MeOH:H$_2$O 90:10) and Pattern 4A (5-MAPB H$_3$PO$_4$ in acetone). The XRPD diffractogram showed that salt screening was obtained from most of the tested solutions as described in Example 13 and shown in Table 9. The x axis measures 2Theta in degrees and the y axis measures intensity measured in arb. units.
Figure 16:
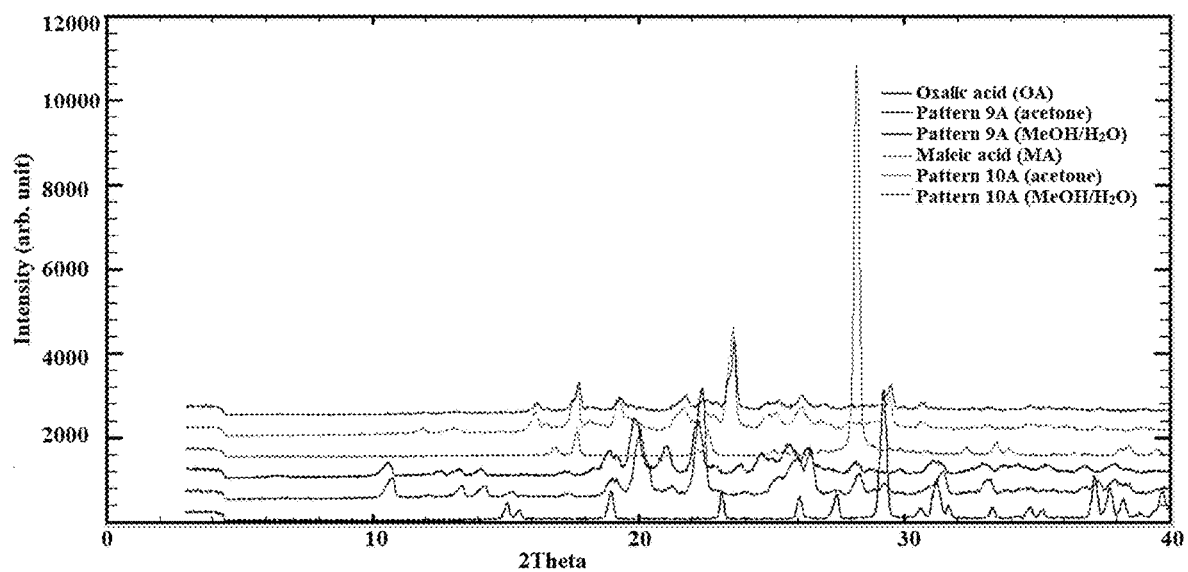
FIG. 16 is a comparison of XRPD Diffractogram of Pattern 9A (5-MAPB oxalic acid) and Pattern 10A (5-MAPB maleic acid) in various solvents, and solvents oxalic acid and maleic acid. The diffractogram confirms the crystalline nature of 5-MAPB in various counterions of Pattern 9A (5-MAPB oxalic acid in acetone), Pattern 9A (5-MAPB oxalic acid in MeOH:H$_2$O 90:10), Pattern 10A (5-MAPB maleic acid in acetone), and Pattern 10A (5-MAPB maleic acid in MeOH:H$_2$O 90:10). The XRPD diffractogram showed that salt screening was obtained from most of the tested solutions as described in Example 13 and shown in Table 9. The x axis measures 2Theta in degrees and the y axis measures intensity measured in arb. units.
Figure 17:
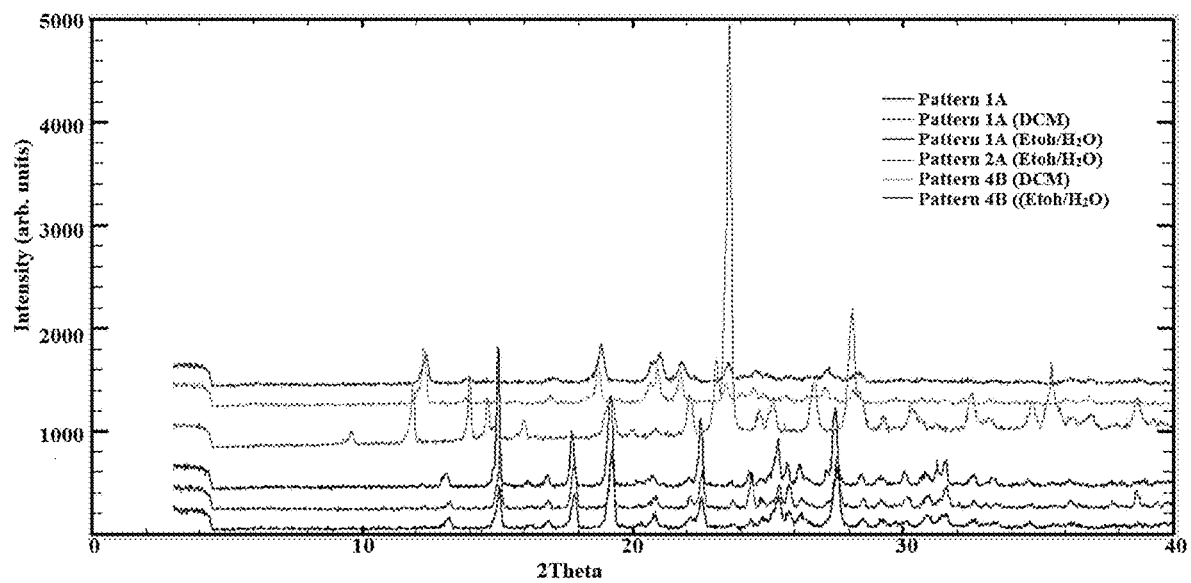
FIG. 17 is a comparison of XRPD Diffractogram of Pattern 1A, Pattern 2A (5-MAPB HBr) and Pattern 4B (5-MAPB H$_3$PO$_4$) in various solvents. The diffractogram confirms the crystalline nature of 5-MAPB in various counterions of Pattern 1A (5-MAPB HCl), Pattern 1A (5-MAPB HCl in DCM), Pattern 1A (5-MAPB HCl in EtOH:H$_2$O 90:10), Pattern 2A (5-MAPB HBr in EtOH:H$_2$O 90:10), Pattern 4B (5-MAPB H$_3$PO$_4$ in DCM) and Pattern 4B (5-MAPB H$_3$PO$_4$ in EtOH:H$_2$O 90:10). The XRPD diffractogram showed that salt screening was obtained from most of the tested solutions as described in Example 14 and shown in Table 10. The x axis measures 2Theta in degrees and the y axis measures intensity measured in arb. units.
Figure 18:
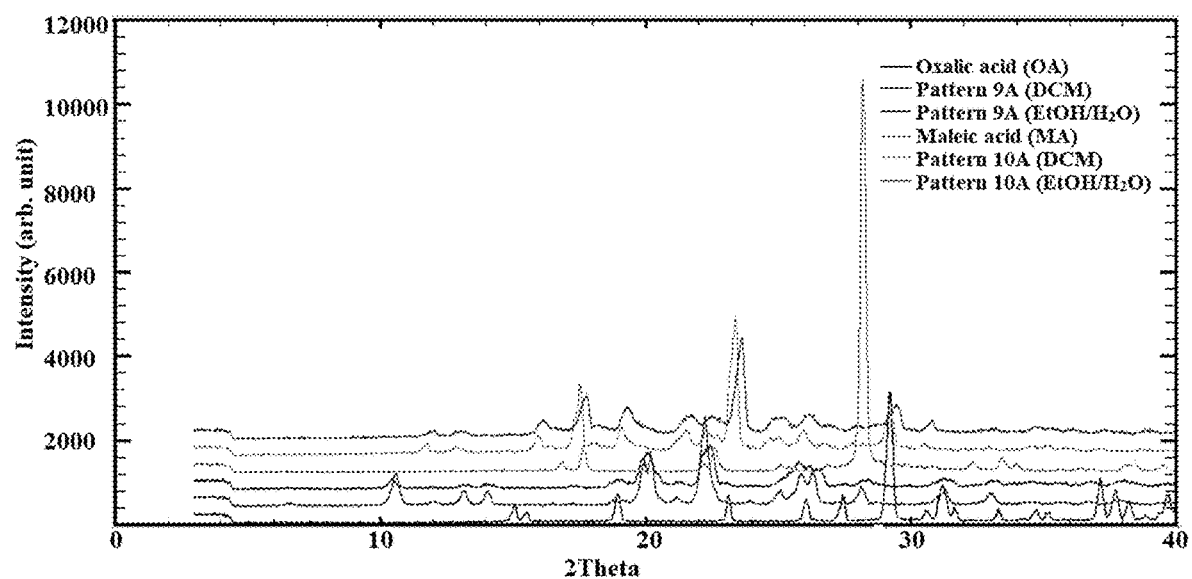
FIG. 18 is a comparison of XRPD Diffractogram of Pattern 9A (5-MAPB oxalic acid) and Pattern 10A (5-MAPB maleic acid) in various solvents, and solvents oxalic acid and maleic acid. The diffractogram confirms the crystalline nature of 5-MAPB in various counterions of Pattern 9A (5-MAPB oxalic acid in DCM), Pattern 9A (5-MAPB oxalic acid in EtOH:H$_2$O 90:10), Pattern 10A (5-MAPB maleic acid in DCM), and Pattern 10A (5-MAPB maleic acid in EtOH:H$_2$O 90:10). The XRPD diffractogram showed that salt screening was obtained from most of the tested solutions as described in Example 14 and shown in Table 10. The x axis measures 2Theta in degrees and the y axis measures intensity measured in arb. units.
Figure 19:
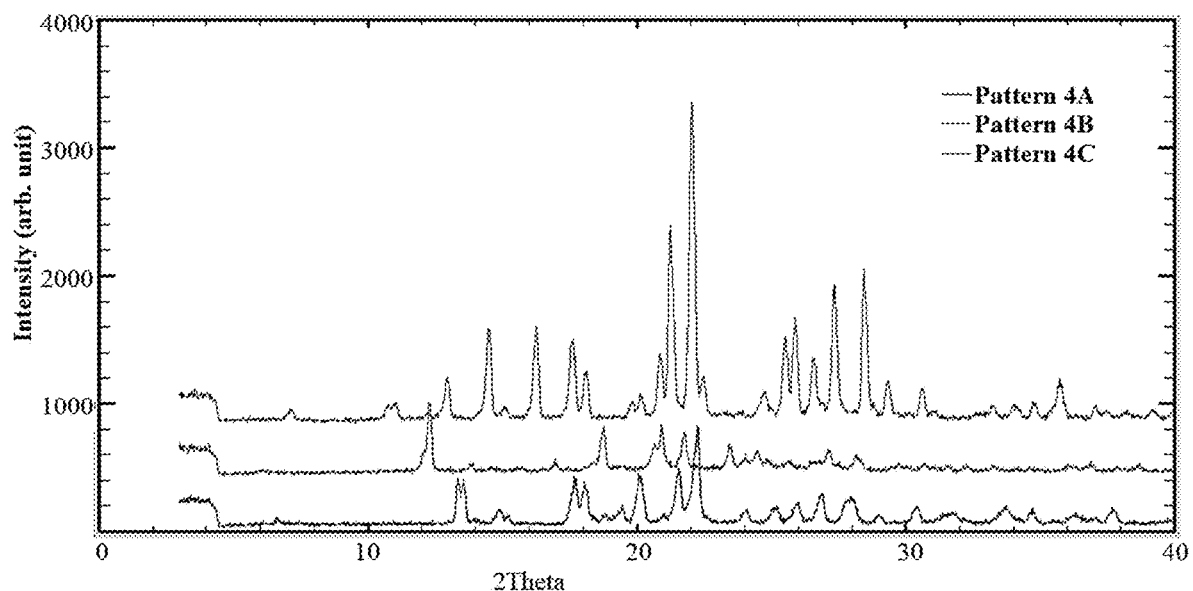
FIG. 19 is a comparison of XRPD Diffractogram of Pattern 4 (5-MAPB H$_3$PO$_4$) in various solvents. The diffractogram confirms the crystalline nature of 5-MAPB in various counterions of Pattern 4A (5-MAPB H$_3$PO$_4$ in acetone), Pattern 4B (5-MAPB H$_3$PO$_4$ in DCM) and Pattern 4C (5-MAPB H$_3$PO$_4$ in THF). The XRPD diffractogram showed that salt screening was obtained from most of the tested solutions as described in Example 15 and shown in Table 11. The x axis measures 2Theta in degrees and the y axis measures intensity measured in arb. units.
Figure 20:
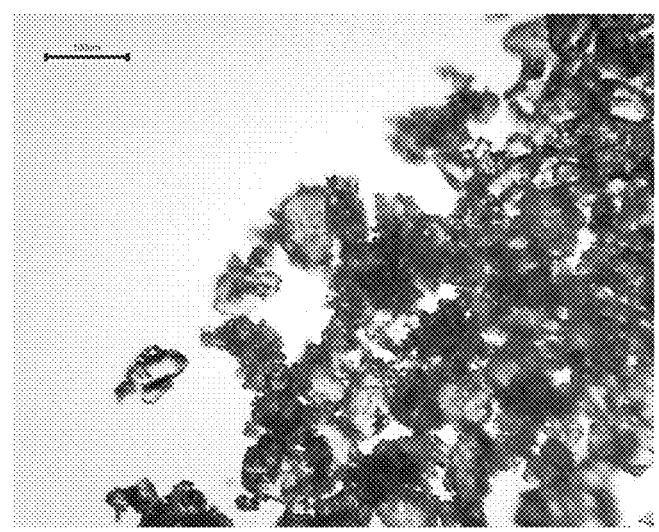
FIG. 20 is an optical micrograph of Pattern 1A. Pattern 1A appeared to have a morphology of irregular agglomerates.
Figure 21:
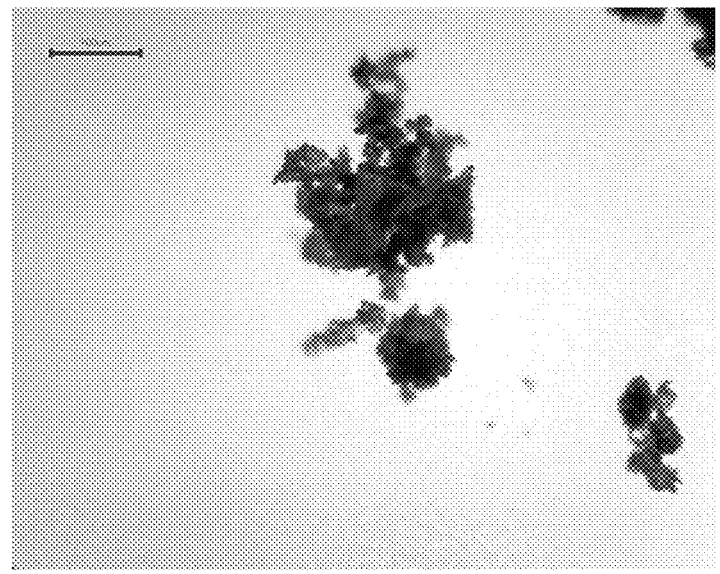
FIG. 21 is an optical micrograph of Pattern 2B (scale-up of Pattern 2A). Pattern 2B appeared to have a morphology of irregular agglomerates.
Figure 22:
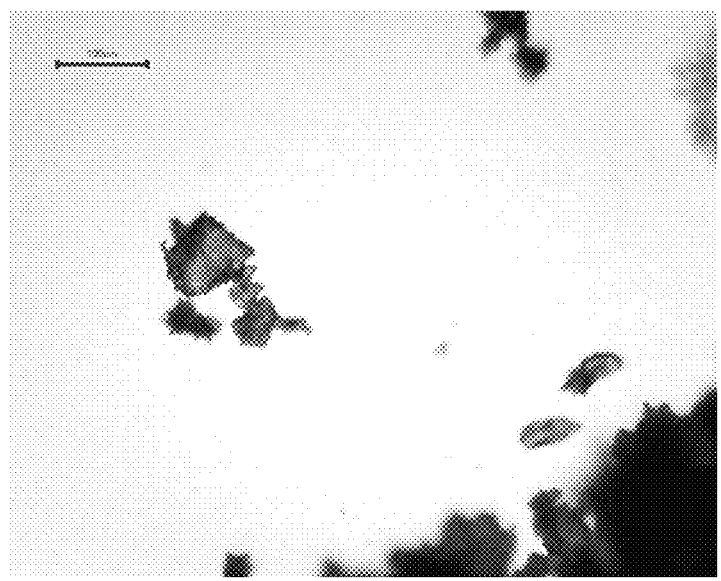
FIG. 22 is an optical micrograph of Pattern 10A. Pattern 10A appeared to have a morphology of irregular agglomerates.
Figure 23:
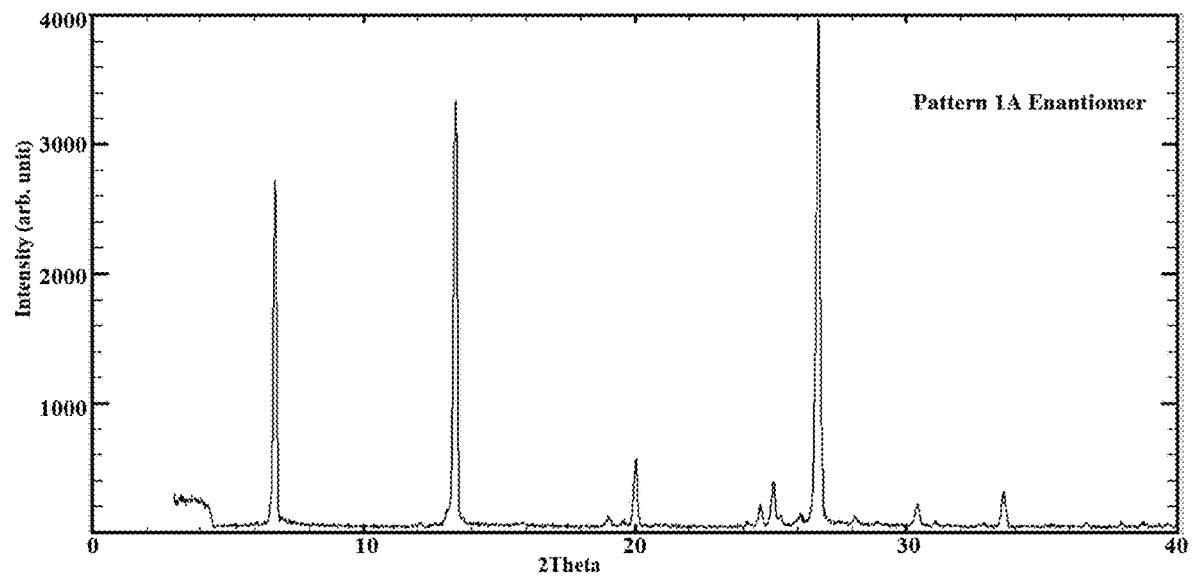
FIG. 23 is a powder XRPD Diffractogram of Pattern 1A Enantiomer (5-MAPB HCl, Pure Enantiomer). The diffractogram confirms the crystalline nature of Pattern 1A Enantiomer. The XRPD diffractogram showed that 5-MAPB Freebase was obtained as described in Examples 12. The x axis measures 2Theta in degrees and the y axis measures intensity measured in arb. units.
Figure 24:
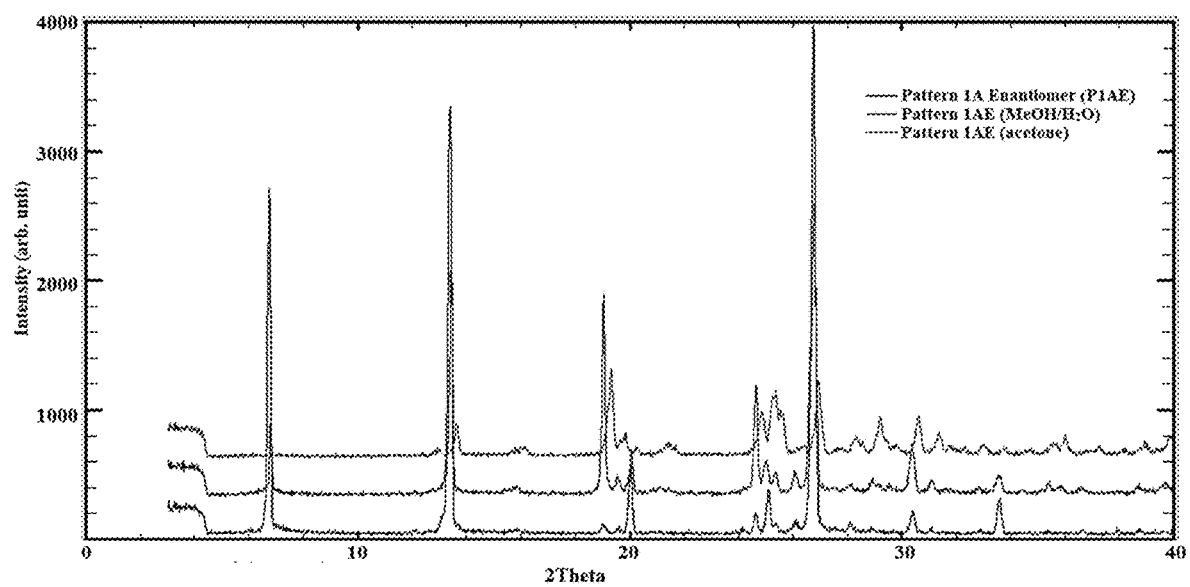
FIG. 24 is a comparison of XRPD Diffractogram of Pattern 1A Enantiomer (P1AE) in various solvents. The diffractogram confirms the crystalline nature of Pattern 1A Enantiomer (5-MAPB HCl Pure Enantiomer, P1AE) in various counterions of Pattern 1A Enantiomer (5-MAPB HCl Pure Enantiomer), Pattern 1AE (5-MAPB HCl Pure Enantiomer in MeOH:H$_2$O 90:10), and Pattern 1AE (5-MAPB HCl Pure Enantiomer in acetone). The XRPD diffractogram showed that salt screening was obtained from most of the tested solutions as described in Example 17 and shown in Table 13. The x axis measures 2Theta in degrees and the y axis measures intensity measured in arb. units.
Figure 25:
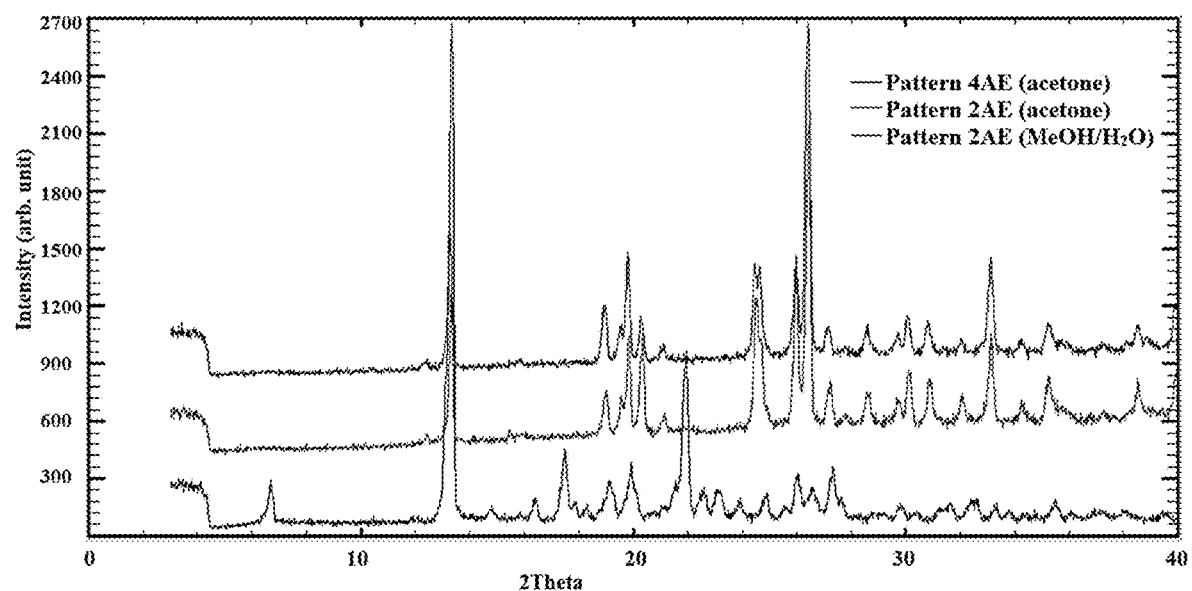
FIG. 25 is a comparison of XRPD Diffractogram of Pattern 2A (5-MAPB Enantiomer HBr) and Pattern 4A (5-MAPB Enantiomer H3PO$_4$) in various solvents. The diffractogram confirms the crystalline nature of Pattern 1A Enantiomer (5-MAPB HCl Pure Enantiomer, P1AE) in various counterions of Pattern 2A Enantiomer (Pattern 2AE, 5-MAPB Enantiomer HBr in acetone), Pattern 2A Enantiomer (Pattern 2AE, 5-MAPB Enantiomer HBr in MeOH:H$_2$O 90:10) and Pattern 4A Enantiomer (Pattern 4AE, 5-MAPB Enantiomer H3PO$_4$ in acetone). The XRPD diffractogram showed that salt screening was obtained from most of the tested solutions as described in Example 17 and shown in Table 13. The x axis measures 2Theta in degrees and the y axis measures intensity measured in arb. units.
Figure 26:
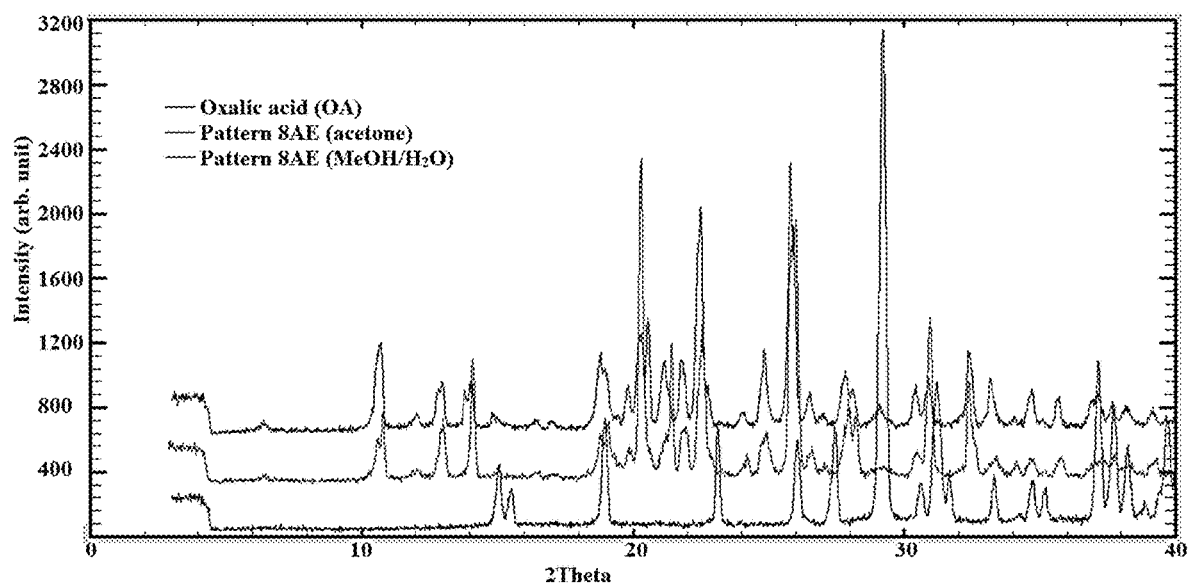
FIG. 26 is a comparison of XRPD Diffractogram of oxalic acid and Pattern 8A Enantiomer (Pattern 8AE, 5-MAPB Enantiomer oxalic acid) in various solvents. The diffractogram confirms the crystalline nature of Pattern 8A Enantiomer (5-MAPB Enantiomer oxalic acid) in various counterions of Pattern 8A Enantiomer (5-MAPB Enantiomer oxalic acid in acetone) and Pattern 8A Enantiomer (5-MAPB Enantiomer oxalic acid in MeOH:H$_2$O 90:10). The XRPD diffractogram showed that salt screening was obtained from most of the tested solutions as described in Example 17 and shown in Table 13. The x axis measures 2Theta in degrees and the y axis measures intensity measured in arb. units.
Figure 27:
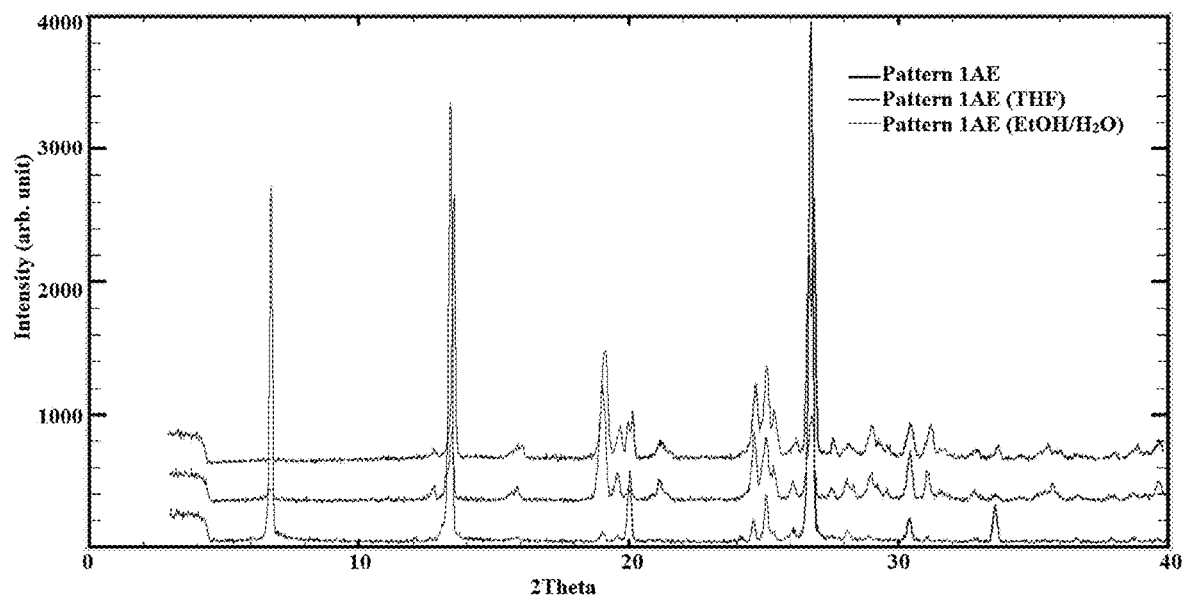
FIG. 27 is a comparison of XRPD Diffractogram of Pattern 1A Enantiomer (P1AE) in various solvents. The diffractogram confirms the crystalline nature of Pattern 1A Enantiomer (5-MAPB HCl Pure Enantiomer, P1AE) in various counterions of Pattern 1A Enantiomer (5-MAPB HCl Pure Enantiomer), Pattern 1AE (5-MAPB HCl Pure Enantiomer in EtOH:H$_2$O 90:10), and Pattern 1AE (5-MAPB HCl Pure Enantiomer in THF). The XRPD diffractogram showed that salt screening was obtained from most of the tested solutions as described in Example 18 and shown in Table 14. The x axis measures 2Theta in degrees and the y axis measures intensity measured in arb. units.
Figure 28:
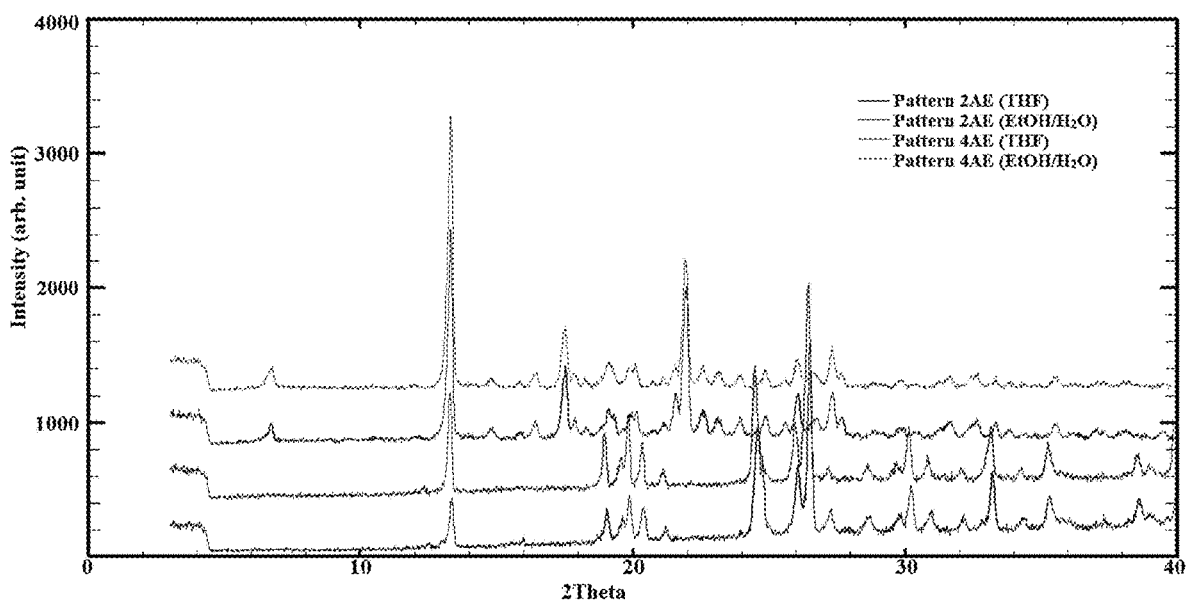
FIG. 28 is a comparison of XRPD Diffractogram of Pattern 2AE (5-MAPB Enantiomer HBr) and Pattern 4AE (5-MAPB Enantiomer H3PO$_4$) in various solvents. The diffractogram confirms the crystalline nature of Pattern 1A Enantiomer (5-MAPB HCl Pure Enantiomer, P1AE) in various counterions of Pattern 2A Enantiomer (Pattern 2AE, 5-MAPB Enantiomer HBr in THF), Pattern 2A Enantiomer (Pattern 2AE, 5-MAPB Enantiomer HBr in EtOH:H$_2$O 90:10), Pattern 4A Enantiomer (Pattern 4AE, 5-MAPB Enantiomer H3PO$_4$ in THF), and Pattern 4A Enantiomer (Pattern 4AE, 5-MAPB Enantiomer H3PO$_4$ in EtOH:H$_2$O 90:10). The XRPD diffractogram showed that salt screening was obtained from most of the tested solutions as described in Example 18 and shown in Table 14. The x axis measures 2Theta in degrees and the y axis measures intensity measured in arb. units.
Figure 29:
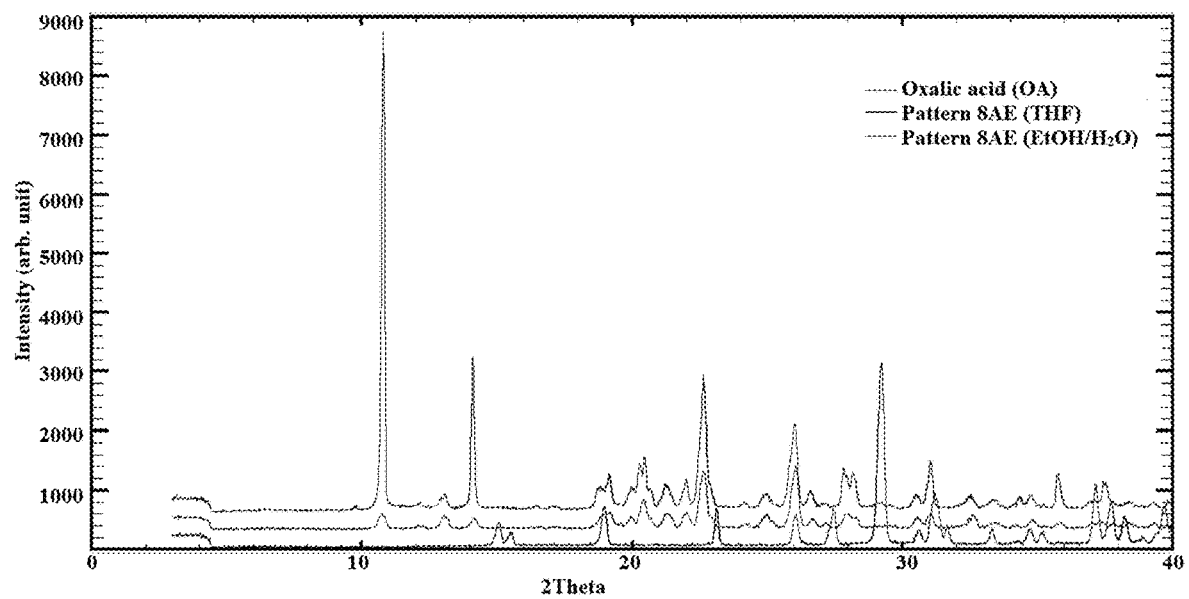
FIG. 29 is a comparison of XRPD Diffractogram of oxalic acid and Pattern 8A Enantiomer (Pattern 8AE, 5-MAPB Enantiomer oxalic acid) in various solvents. The diffractogram confirms the crystalline nature of Pattern 8A Enantiomer (5-MAPB Enantiomer oxalic acid) in various counterions of Pattern 8A Enantiomer (5-MAPB Enantiomer oxalic acid in THF) and Pattern 8A Enantiomer (5-MAPB Enantiomer oxalic acid in EtOH:H₂O 90:10). The XRPD diffractogram showed that salt screening was obtained from most of the tested solutions as described in Example 18 and shown in Table 14. The x axis measures 2Theta in degrees and the y axis measures intensity measured in arb. units.
Figure 30:
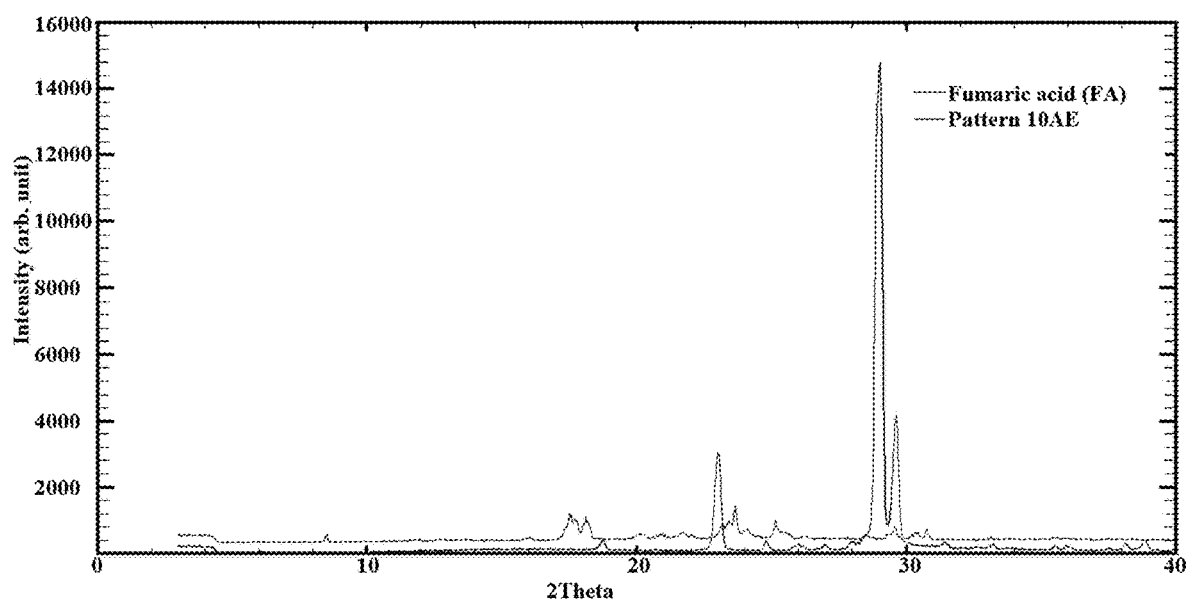
FIG. 30 is a comparison of XRPD Diffractogram of fumaric acid and Pattern 10A Enantiomer (Pattern 10AE, 5-MAPB Enantiomer fumaric acid) in EtOH/H₂O 90:10. The diffractogram confirms the crystalline nature of Pattern 10A Enantiomer (Pattern 10AE, 5-MAPB Enantiomer fumaric acid) in EtOH/H₂O 90:10. The XRPD diffractogram showed that salt screening was obtained from most of the tested solutions as described in Example 18 and shown in Table 14. The x axis measures 2Theta in degrees and the y axis measures intensity measured in arb. units.
Figure 31:
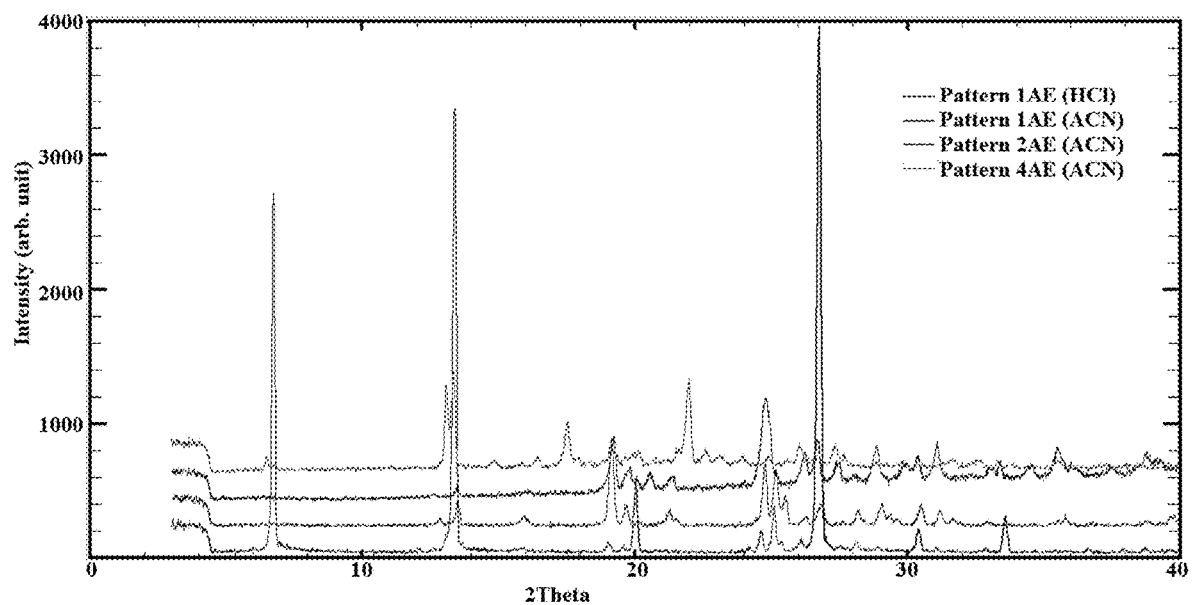
FIG. 31 is a comparison of XRPD Diffractogram of Pattern 1A Enantiomer (Pattern 1AE, 5-MAPB Enantiomer HCl), Pattern 1A Enantiomer (Pattern 1AE, 5-MAPB Enantiomer ACN), Pattern 2A Enantiomer (Pattern 2AE, 5-MAPB Enantiomer HBr) and Pattern 4A Enantiomer (Pattern 4AE, 5-MAPB Enantiomer H₃PO₄). The diffractogram confirms the crystalline nature of Pattern 1A Enantiomer in various counterions of Pattern 1AE (5-MAPB Enantiomer HCl), Pattern 1AE (5-MAPB Enantiomer ACN), Pattern 2AE (5-MAPB Enantiomer HBr in ACN) and Pattern 4A (5-MAPB Enantiomer H3PO4 in ACN). The XRPD diffractogram showed that salt screening was obtained from most of the tested solutions as described in Example 15 and shown in Table 15. The x axis measures 2Theta in degrees and the y axis measures intensity measured in arb. units.
Figure 32:
FIG. 32 is an optical micrograph of Pattern 1A Enantiomer (Pattern 1AE). Pattern 1A Enantiomer appeared to have an irregular morphology.
Figure 33:
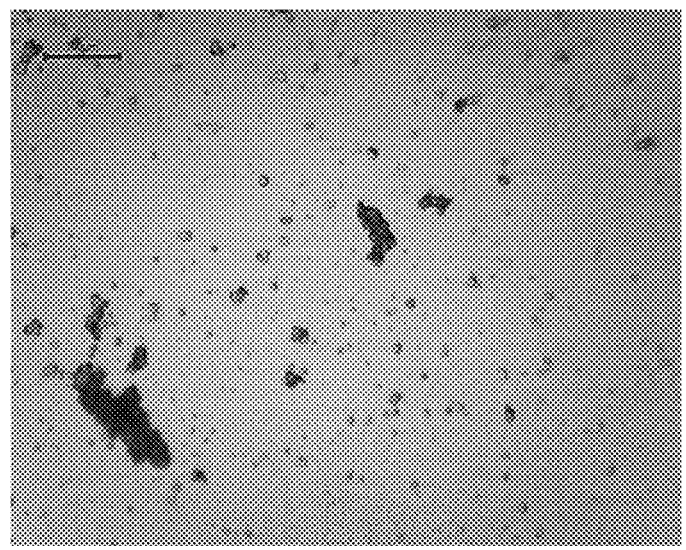
FIG. 33 is an optical micrograph of Pattern 4A Enantiomer (Pattern 4AE). Pattern 4AE appeared to have a morphology of irregular agglomerates and fines.
Figure 34:
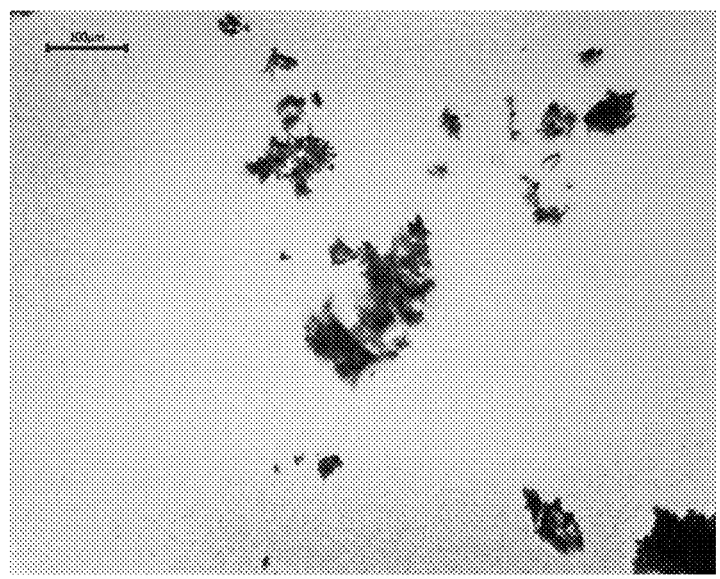
FIG. 34 is an optical micrograph of Pattern 8A Enantiomer (Pattern 8AE). Pattern 8AE appeared to have a morphology of irregular agglomerates.
Figure 35:
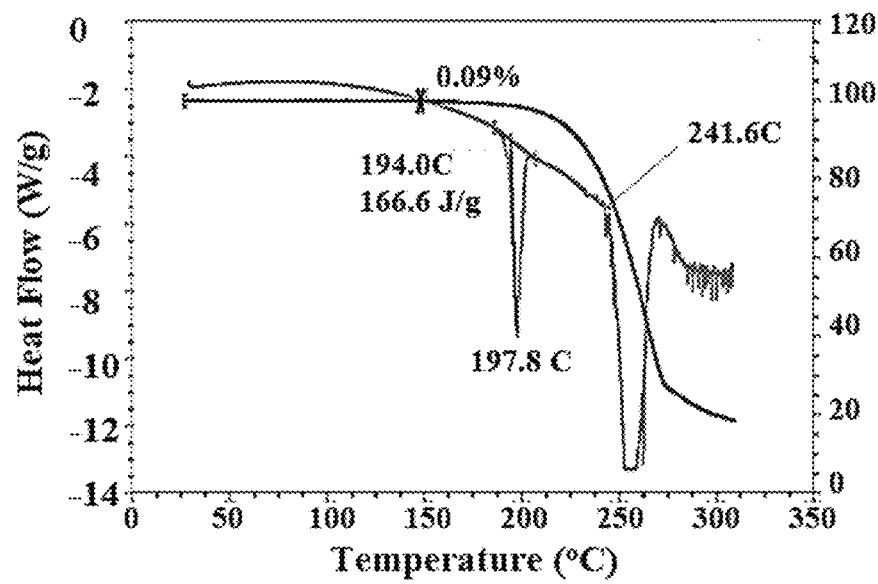
FIG. 35 is a differential scanning calorimetry (DSC) and thermogravimetric analysis (TGA) of Pattern 1A (HCl). The DSC shows an endotherm (likely melt) w/onset ~194° C. and the TGA shows ~0.09% weight loss up to 150° C. and decomposition at higher temperatures (>200° C.). The methods used for the DSC/TGA was conducted as described in Example 20 Table 16. The x-axis is temperature measured in degrees Celsius and the y-axis is Weight measured in percentage and Heat flow measured in W/g.
Figure 36:
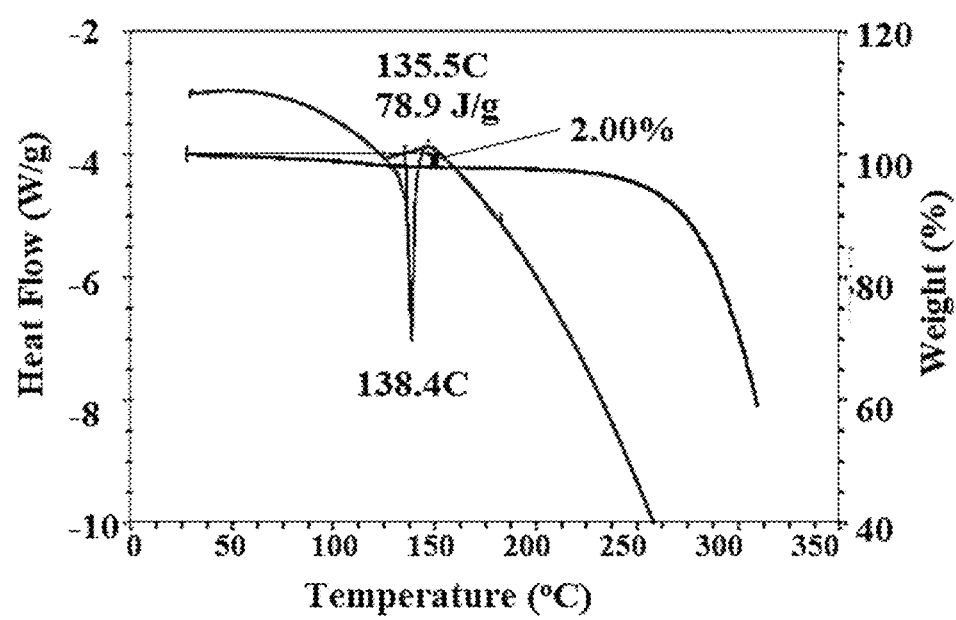
FIG. 36 is a differential scanning calorimetry (DSC) and thermogravimetric analysis (TGA) of Pattern 2A (HBr). The DSC shows an endotherm (likely melt) w/onset ~135° C. and the shows ~2.00% weight loss up to 150° C. and decomposition at higher temperatures (>240° C.). The methods used for the DSC/TGA was conducted as described in Example 20 Table 16. The x-axis is temperature measured in degrees Celsius and the y-axis is Weight measured in percentage and Heat flow measured in W/g.
Figure 37:
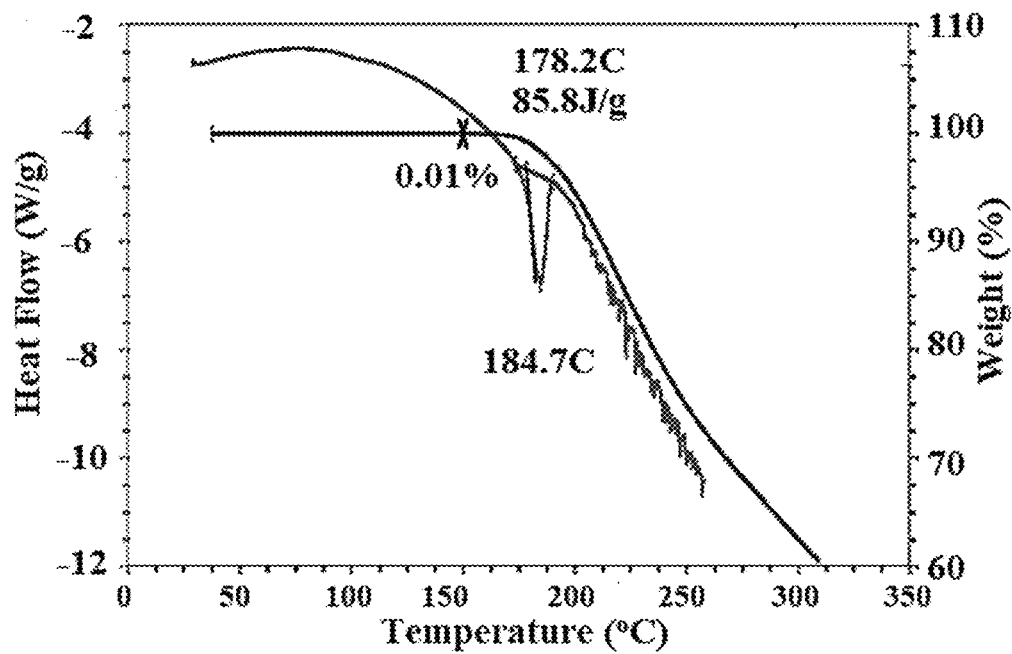
FIG. 37 is a differential scanning calorimetry (DSC) and thermogravimetric analysis (TGA) of Pattern 4A (H3P04). The DSC shows endotherm (likely melt and decomposition) w/onset ~178° C. and the TGA shows ~0.01% weight loss up to 150° C. and decomposition at higher temperatures (>180° C.). The methods used for the DSC/TGA was conducted as described in Example 20 Table 16. The x-axis is temperature measured in degrees Celsius and the y-axis is Weight measured in percentage and Heat flow measured in W/g.
Figure 38:
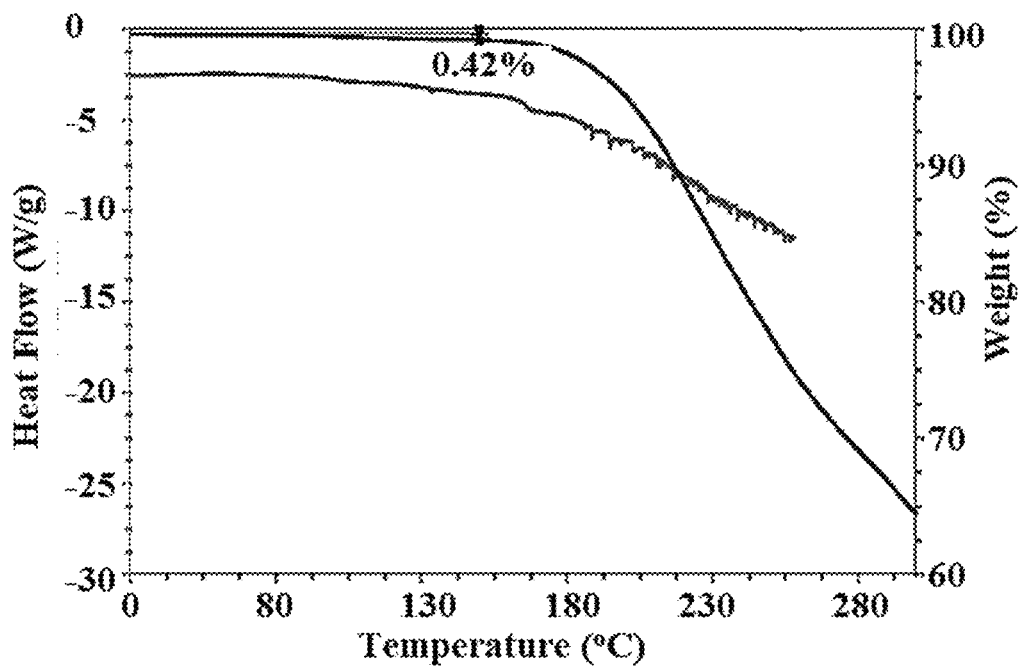
FIG. 38 is a differential scanning calorimetry (DSC) and thermogravimetric analysis (TGA) of Pattern 4B (H3P04). The DSC shows no clear thermal events and the TGA shows ~0.42% weight loss up to 150° C. The methods used for the DSC/TGA was conducted as described in Example 20 Table 16. The x-axis is temperature measured in degrees Celsius and the y-axis is Weight measured in percentage and Heat flow measured in W/g.
Figure 39:
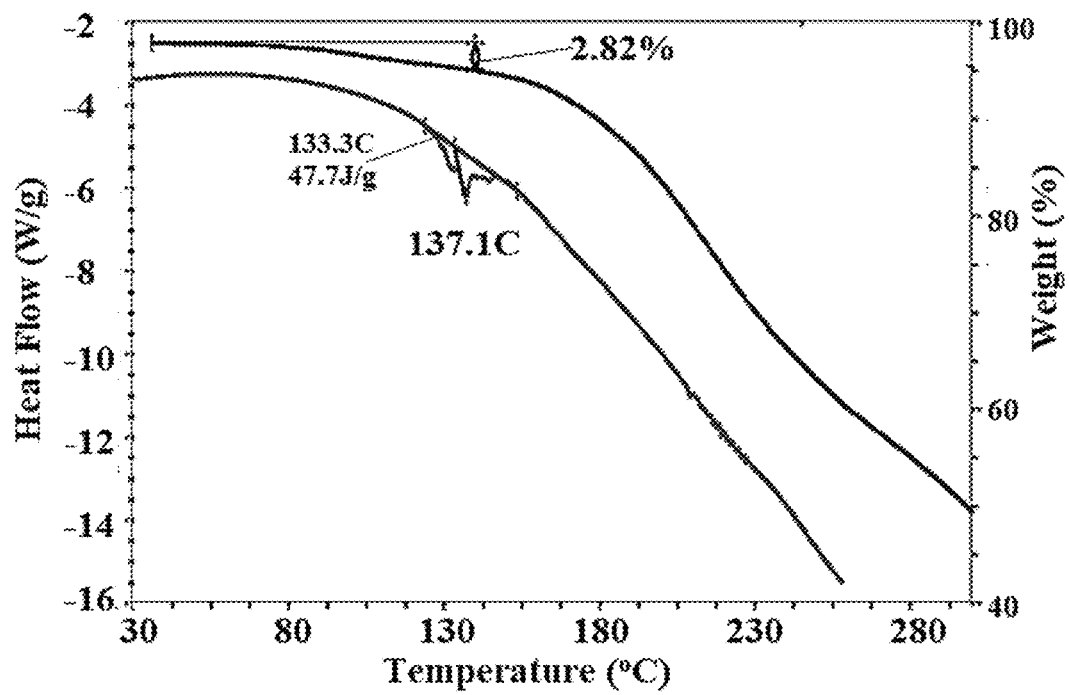
FIG. 39 is a differential scanning calorimetry (DSC) and thermogravimetric analysis (TGA) of Pattern 4C (H3P04). The DSC shows a broad endotherm w/onset at ~133° C. and the TGA shows ~2.82% weight loss up to 140° C. The methods used for the DSC/TGA was conducted as described in Example 20 Table 16. The x-axis is temperature measured in degrees Celsius and the y-axis is Weight measured in percentage and Heat flow measured in W/g.
Figure 40:
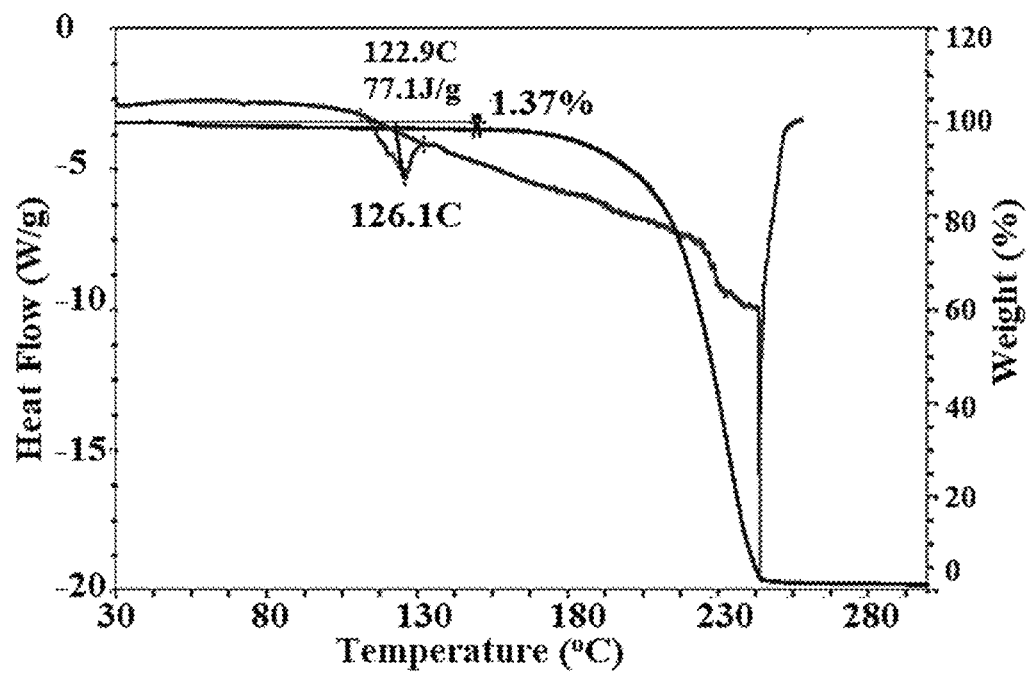
FIG. 40 is a differential scanning calorimetry (DSC) and thermogravimetric analysis (TGA) of Pattern 9A (Oxalic). The DSC shows an endotherm w/onset at ~122° C. and the TGA shows ~1.37% weight loss up to 150° C. and decomposition at higher temperatures (>180° C.). The methods used for the DSC/TGA was conducted as described in Example 20 Table 16. The x-axis is temperature measured in degrees Celsius and the y-axis is Weight measured in percentage and Heat flow measured in W/g.
Figure 41:
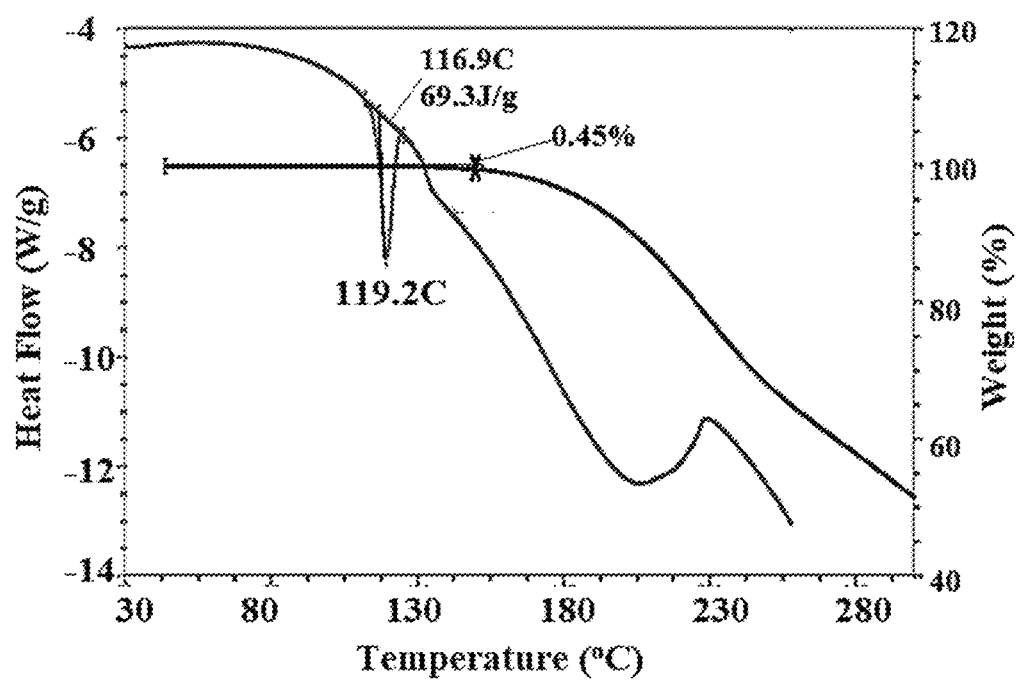
FIG. 41 is a differential scanning calorimetry (DSC) and thermogravimetric analysis (TGA) of Pattern 10A (Maleic). The DSC shows an endotherm w/onset at ~117° C. and the TGA shows ~0.45% weight loss up to 150° C. and decomposition at higher temperatures (>160° C.). The methods used for the DSC/TGA was conducted as described in Example 20 Table 16. The x-axis is temperature measured in degrees Celsius and the y-axis is Weight measured in percentage and Heat flow measured in W/g.
Figure 42:
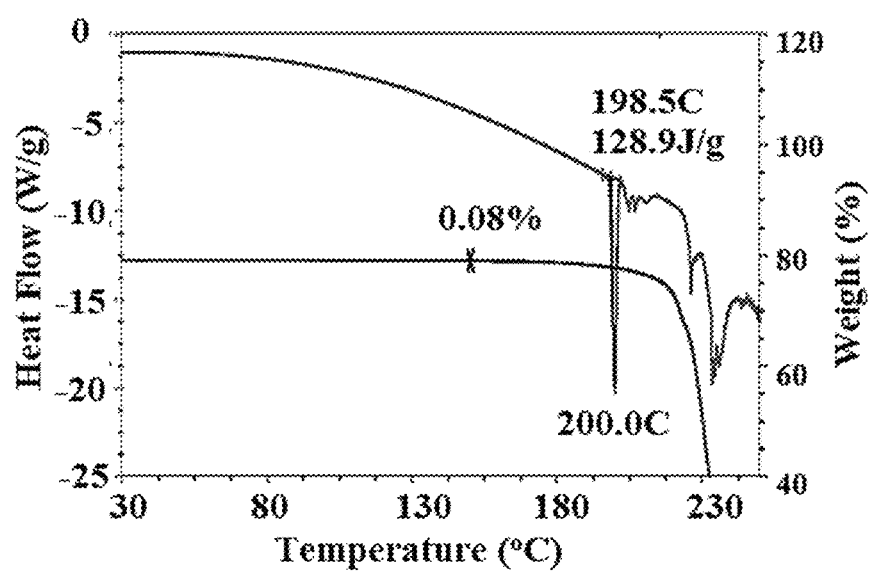
FIG. 42 is a differential scanning calorimetry (DSC) and thermogravimetric analysis (TGA) of Pattern 1A Enantiomer HCl. The DSC shows a sharp endotherm (likely melt) w/onset 199° C. and the TGA shows ~0.08% weight loss up to 150° C. and decomposition at higher temperatures (>200° C.). The methods used for the DSC/TGA was conducted as described in Example 20 Table 16. The x-axis is temperature measured in degrees Celsius and the y-axis is Weight measured in percentage and Heat flow measured in W/g.
Figure 43:
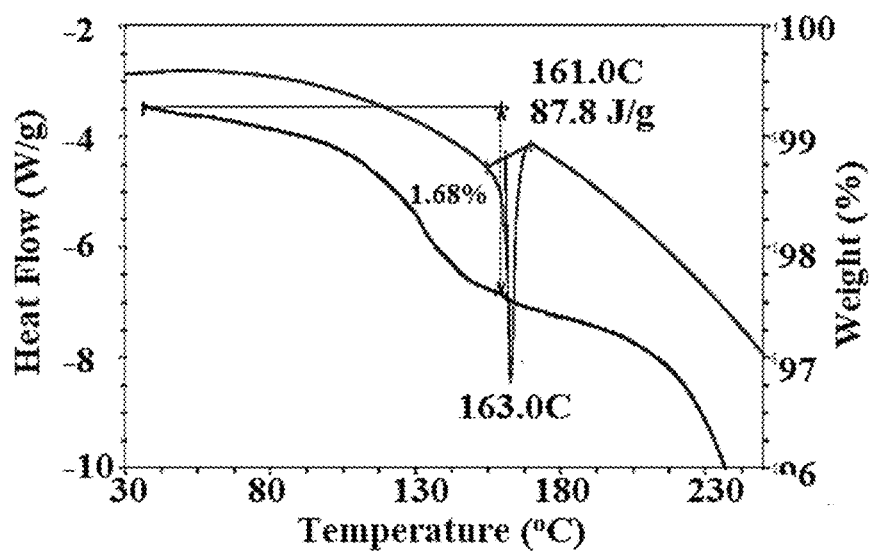
FIG. 43 is a differential scanning calorimetry (DSC) and thermogravimetric analysis (TGA) of Pattern 2A Enantiomer (HBr. The DSC shows a sharp endotherm (likely melt) w/onset ~161° C. and the TGA shows ~1.68% weight loss up to 160° C. The methods used for the DSC/TGA was conducted as described in Example 20 Table 16. The x-axis is temperature measured in degrees Celsius and the y-axis is Weight measured in percentage and Heat flow measured in W/g.
Figure 44:
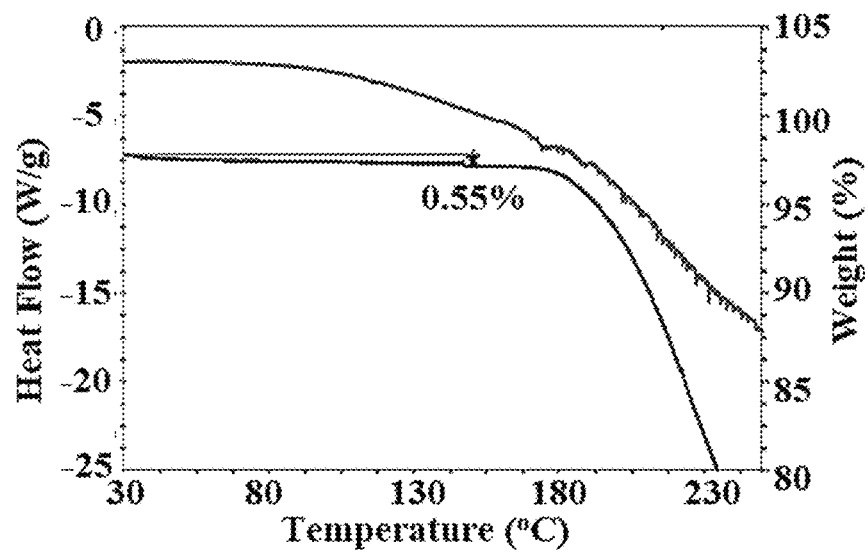
FIG. 44 is a differential scanning calorimetry (DSC) and thermogravimetric analysis (TGA) of Pattern 4A Enantiomer (H3PO₄. The DSC shows no clear thermal events and a noisy baseline at higher temps (>150° C.) and the TGA shows ~0.55% weight loss up to 150° C. and decomposition at higher temperatures (>180° C.). The methods used for the DSC/TGA was conducted as described in Example 20 Table 16. The x-axis is temperature measured in degrees Celsius and the y-axis is Weight measured in percentage and Heat flow measured in W/g.
Figure 45:
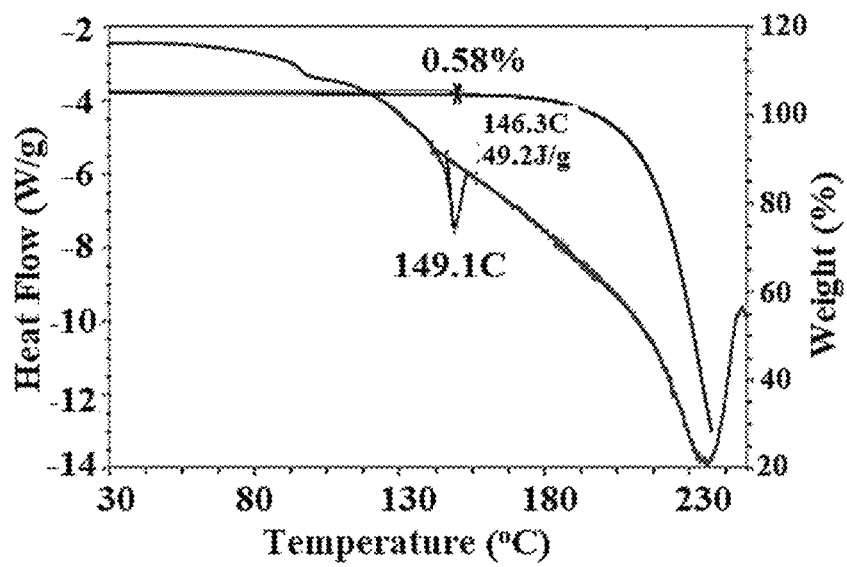
FIG. 45 is a differential scanning calorimetry (DSC) and thermogravimetric analysis (TGA) of Pattern 8A Enantiomer (Oxalic). The DSC shows an endotherm w/onset at ~146° C. and the TGA (blue curve) shows ~0.58% weight loss up to 150° C. The methods used for the DSC/TGA was conducted as described in Example 20 Table 16. The x-axis is temperature measured in degrees Celsius and the y-axis is Weight measured in percentage and Heat flow measured in W/g.
Figure 46:
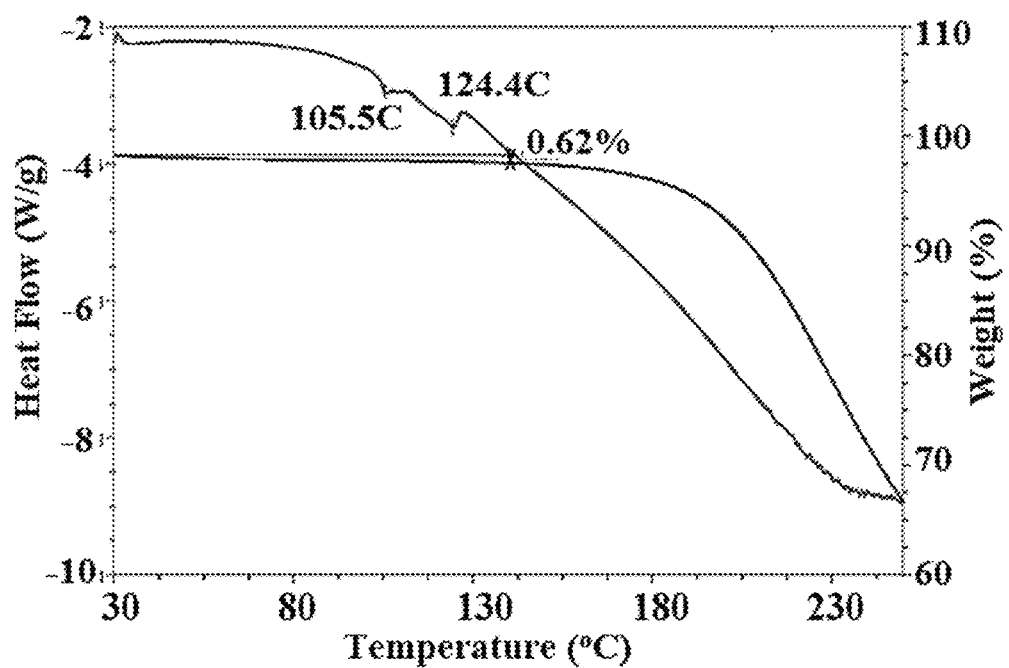
FIG. 46 is a differential scanning calorimetry (DSC) and thermogravimetric analysis (TGA) of Pattern 10A Enantiomer (Fumaric). The DSC shows a broad endotherm w/ peaks at ~106° C. and ~124° C. and the TGA shows ~0.62% weight loss up to 140° C. and decomposition at higher temperatures (>180° C.). The methods used for the DSC/TGA was conducted as described in Example 20 Table 16. The x-axis is temperature measured in degrees Celsius and the y-axis is Weight measured in percentage and Heat flow measured in W/g.

Liquid-Liquid Extraction (LLE) was used to isolate 5-MAPB freebase from 5-MAPB hydrochloride (5-MAPB HCl) using the conditions in Table 7. FIG. 13 is the XRPD pattern for 5-MAPB HCl. (for 50 mg of 5-MAPB HCl, 1 vol. solvent is equivalent to 50 µL). The below technique was used to generate the XRPD pattern of 5-MAPB freebase in FIG. 14.

TABLE 7

Liquid-Liquid Extraction of RS-5-MAPB Freebase
Liquid-Liquid Extraction Expts.

| Expt. No. | Coun-terion | Solvent (Density) | Procedure/Comments |
|---|---|---|---|
| 5-MAPB | NaOH | EtOAc (0.902 g/mL) | 50 mg of 5-MAPB (HCl salt) + 10 vols. solvent + NaOH stock soln. in water (1.1:1 molar ratio) + additional water (10 vols. water total) |

TABLE 7-continued

Liquid-Liquid Extraction of RS-5-MAPB Freebase
Liquid-Liquid Extraction Expts.

| Expt. No. | Counterion | Solvent (Density) | Procedure/Comments |
|---|---|---|---|
| 5-MAPB | NaOH | DCM (1.33 g/mL) | 50 mg of 5-MAPB (HCl salt) + 10 vols. solvent + NaOH stock soln. in water (1.1:1 molar ratio) + additional water (10 vols. water total) |

Example 12. Powder XRPD Diffractogram Procedure

The powder XRPD diffractogram of Pattern 1A, Pattern 2A, Pattern 4A, Pattern 4B, Pattern 4C and Pattern 10 were generated from RS-5-MAPB HCl. The below technique was used to generate the XRPD patterns in FIG. 13, FIG. 14, FIG. 15, FIG. 16, FIG. 17, FIG. 18, FIG. 19, FIG. 23, FIG. 24, FIG. 25, FIG. 26, FIG. 27, FIG. 28, FIG. 29, FIG. 30, and FIG. 31. Powder X-ray Diffraction (PXRD) patterns were collected on a Rigaku Miniflex Plus instrument. The instrument and method details are included below in the Table 8.

TABLE 8

| Powder XRPD diffractogram procedure | |
|---|---|
| Instrument: | Rigaku Miniflex Plus S/N ZD06186 |
| Sample Holder: | Aluminum Round Sample Holder with Zero Background Silicon Wafer |
| Scan Range: | 3° to 40° 2θ |
| Scan Axis: | 2θ/θ |
| Scan Method: | Continuous |
| Sampling Width: | 0.02° |
| Scan Speed: | 0.62°/minute |
| Wavelength: | Cu Kα 1.54 Å |
| X-ray Generator: | 30 kV/15 mA |
| Detector: | Scintillation Counter |
| Scattering Slit: | 4.2° |
| Receiving Slit: | 0.3 mm |

Example 13. Salt Studies of 5-MAPB in Acetone or MeOH:$H_2O$

Salt studies of 5-MAPB were conducted using the conditions in Table 9. A total of 30 salt experiments for 15 counterions in 2 different solvents, acetone and MeOH:$H_2O$ (90:10), were generated from RS-5-MAPB HCl. The below technique was used to generate the XRPD patterns in FIG. 15 and FIG. 16 (For 40 mg of 5-MAPB HCl, 1 vol. solvent=40 μL).

TABLE 9

Salt screening experiments

| Counterion | Solvent | Procedure/Comments | PXRD Result |
|---|---|---|---|
| HCl | Acetone | 40 mg 5-MAPB + 10 vols. solvent + 1:1 molar ratio counterion soln., stirred at 40° C., became a slurry after ~30 min of stirring, in solution after overnight stirring, opened for evaporation, solid after ~3 hrs of evaporation at 40° C., analyzed by PXRD, dried overnight at 40° C. in vacuum oven, analyzed by DSC and TGA | Pattern 1A |
| HBr | Acetone | 40 mg 5-MAPB + 10 vols. solvent + 1:1 molar ratio counterion soln., stirred at 40° C., in solution after overnight stirring, opened for evaporation, solid after overnight evaporation, turned into gel during PXRD sample prep, terminated | N/A (gel) |
| $H_2SO_4$ | Acetone | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| $H_3PO_4$ | Acetone | 40 mg 5-MAPB + 10 vols. solvent + 1:1 molar ratio counterion soln., stirred at 40° C., became a slurry after ~30 min of stirring, slurry after overnight stirring, centrifuged to harvest solids, analyzed by PXRD, dried overnight at 40° C. in vacuum oven, analyzed by DSC and TGA | Pattern 4A |
| $HNO_3$ | Acetone | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| Methane Sulfonic | Acetone | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| Tartaric | Acetone | 40 mg 5-MAPB + 10 vols. solvent + 1:1 molar ratio counterion soln., stirred at 40° C., in solution after overnight stirring, opened for evaporation, gel after 6 days evaporation, terminated | N/A (gel) |
| Succinic | Acetone | 40 mg 5-MAPB + 10 vols. solvent + 1:1 molar ratio counterion soln., stirred at 40° C., in solution after overnight stirring, opened for evaporation, gel after 6 days evaporation, terminated | N/A (gel) |
| Oxalic | Acetone | 40 mg 5-MAPB + 10 vols. solvent + 1:1 molar ratio counterion soln., stirred at 40° C., in solution after overnight stirring, opened for evaporation, solid | Pattern 9A with some |

TABLE 9-continued

Salt screening experiments

| Counterion | Solvent | Procedure/Comments | PXRD Result |
|---|---|---|---|
| | | after 6 days of evaporation, analyzed by PXRD, dried overnight at 40° C. in vacuum oven, analyzed by DSC and TGA | Oxalic Peaks |
| Maleic | Acetone | 40 mg 5-MAPB + 10 vols. solvent + 1:1 molar ratio counterion soln., stirred at 40° C., in solution after overnight stirring, opened for evaporation, solid after 6 days of evaporation, analyzed by PXRD, dried overnight at 40° C. in vacuum oven, analyzed by DSC and TGA | Pattern 10A |
| Malic | Acetone | 40 mg 5-MAPB + 10 vols. solvent + 1:1 molar ratio counterion soln., stirred at 40° C., in solution after overnight stirring, opened for evaporation, gel after 6 days evaporation, terminated | N/A (gel) |
| Citric | Acetone | 40 mg 5-MAPB + 10 vols. solvent + 1:1 molar ratio counterion soln., stirred at 40° C., in solution after overnight stirring, opened for evaporation, gel after 6 days evaporation, terminated | N/A (gel) |
| Fumaric | Acetone | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| Salicylic | Acetone | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| Hippuric | Acetone | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| HCl | MeOH:water 90:10 | 40 mg 5-MAPB + 10 vols. solvent + 1:1 molar ratio counterion soln., stirred at 40° C., in solution after overnight stirring, opened for evaporation, solid after overnight evaporation, analyzed by PXRD | Pattern 1A |
| HBr | MeOH:water 90:10 | 40 mg 5-MAPB + 10 vols. solvent + 1:1 molar ratio counterion soln., stirred at 40° C., in solution after overnight stirring, opened for evaporation, solid after overnight evaporation, analyzed by PXRD, dried overnight at 40° C. in vacuum oven, analyzed by DSC and TGA | Pattern 2A |
| $H_2SO_4$ | MeOH:water 90:10 | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| $H_3PO_4$ | MeOH:water 90:10 | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| $HNO_3$ | MeOH:water 90:10 | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| Methane Sulfonic | MeOH:water 90:10 | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| Tartaric | MeOH:water 90:10 | 40 mg 5-MAPB + 10 vols. solvent + 1:1 molar ratio counterion soln., stirred at 40° C., in solution after overnight stirring, opened for evaporation, gel after 7 days of evaporation, terminated | N/A (gel) |
| Succinic | MeOH:water 90:10 | 40 mg 5-MAPB + 10 vols. solvent + 1:1 molar ratio counterion soln., stirred at 40° C., in solution after overnight stirring, opened for evaporation, gel after 6 days evaporation, terminated | N/A (gel) |
| Oxalic | MeOH:water 90:10 | 40 mg 5-MAPB + 10 vols. solvent + 1:1 molar ratio counterion soln., stirred at 40° C., in solution after overnight stirring, opened for evaporation, solid after 6 days of evaporation, analyzed by PXRD | Pattern 9A |
| Maleic | MeOH:water 90:10 | 40 mg 5-MAPB + 10 vols. solvent + 1:1 molar ratio counterion soln., stirred at 40° C., in solution after overnight stirring, opened for evaporation, solid after 7 days of evaporation, analyzed by PXRD | Pattern 10A |
| Malic | MeOH:water 90:10 | 40 mg 5-MAPB + 10 vols. solvent + 1:1 molar ratio counterion soln., stirred at 40° C., in solution after overnight stirring, opened for evaporation, gel after 6 days evaporation, terminated | N/A (gel) |

TABLE 9-continued

Salt screening experiments

| Counterion | Solvent | Procedure/Comments | PXRD Result |
|---|---|---|---|
| Citric | MeOH:water 90:10 | 40 mg 5-MAPB + 10 vols. solvent + 1:1 molar ratio counterion soln., stirred at 40° C., in solution after overnight stirring, opened for evaporation, gel after 6 days evaporation, terminated | N/A (gel) |
| Fumaric | MeOH:water 90:10 | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| Salicylic | MeOH:water 90:10 | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |
| Hippuric | MeOH:water 90:10 | 40 mg 5-MAPB + 10 vols. solvent + 1:1 molar ratio counterion soln., stirred at 40° C., in solution after overnight stirring, opened for evaporation, gel after overnight evaporation, terminated | N/A (gel) |

In certain embodiments, the salt forms of RS-5-MAPB were prepared in a 1:1 molar ratio. In certain embodiments, the salt forms of RS-5-MAPB were prepared using excess amounts of RS-5-MAPB. In certain embodiments, the salt forms of RS-5-MAPB were prepared using excess amounts of salts. In certain embodiments, the solvent is acetone, methanol, water or methanol/water mixture.

In certain embodiments, salt forms of RS-5-MAPB were produced with counterions HCl, HBr, $H_3PO_4$, oxalic acid, and maleic acid. In certain embodiments, the solvents used to produce salt forms of RS-5-MAPB included acetone, MeOH:$H_2O$ ratio. In certain embodiments, the ratio of methanol to water is 9:1.

In certain embodiments, Pattern 1A is produced from HCl and acetone. In certain embodiments, Pattern 1A is produced from HCl and MeOH:$H_2O$ ratio. In certain embodiments, Pattern 1A is produced from HCl and MeOH:$H_2O$ 90:10 ratio.

In certain embodiments, Pattern 4A is produced from $H_3PO_4$ and acetone. In certain embodiments, Pattern 4A is produced from $H_3PO_4$ and MeOH:$H_2O$ ratio. In certain embodiments, Pattern 4A is produced from $H_3PO_4$ and MeOH:$H_2O$ 90:10 ratio.

In certain embodiments, Pattern 9A is produced from oxalic acid and acetone. In certain embodiments, Pattern 9A is produced from oxalic acid and MeOH:$H_2O$ ratio. In certain embodiments, Pattern 9A is produced from oxalic acid and MeOH:$H_2O$ 90:10 ratio.

In certain embodiments, Pattern 10A is produced from maleic acid and acetone. In certain embodiments, Pattern 10A is produced from maleic acid and MeOH:$H_2O$ ratio. In certain embodiments, Pattern 10A is produced from maleic acid and MeOH:$H_2O$ 90:10 ratio.

In certain embodiments, Pattern 2A is produced from HBr and MeOH:$H_2O$ ratio. In certain embodiments, Pattern 2A is produced from HBr and MeOH:$H_2O$ 90:10 ratio.

Example 14. Salt Studies of 5-MAPB in DCM or EtOH:$H_2O$

Salt studies of 5-MAPB were conducted as shown below in Table 10. A total of 30 salt studies for 15 counterions in 2 different solvents, DCM and EtOH:$H_2O$ (90:10), were generated from RS-5-MAPB HCl. The below technique was used to generate the XRPD patterns in FIG. 17 and FIG. 18. (For 40 mg of 5-MAPB, 1 vol. solvent=40 µL).

TABLE 10

Salt screening experiments

| Counterion | Solvent | Procedure/Comments | PXRD Result |
|---|---|---|---|
| HCl | DCM | 40 mg 5-MAPB + 10 vols. solvent + 1:1 molar ratio counterion soln., stirred at RT, in solution after overnight stirring, opened for evaporation, solid after 4 days of evaporation at RT, analyzed by PXRD | Pattern 1A |
| HBr | DCM | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| $H_2SO_4$ | DCM | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| $H_3PO_4$ | DCM | 40 mg 5-MAPB + 10 vols. solvent + 1:1 molar ratio counterion soln., stirred at RT, slurry after overnight stirring, centrifuged to harvest solids, analyzed by PXRD, dried overnight at 40° C. in vacuum oven, analyzed by DSC and TGA | Pattern 4B |

TABLE 10-continued

Salt screening experiments

| Counterion | Solvent | Procedure/Comments | PXRD Result |
|---|---|---|---|
| $HNO_3$ | DCM | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| Methane sulfonic | DCM | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| Tartaric | DCM | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, gel after 10 days of evaporation, terminated | N/A (gel) |
| Succinic | DCM | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, gel after 10 days of evaporation, terminated | N/A (gel) |
| Oxalic | DCM | 40 mg 5-MAPB + 10 vols. solvent + 1:1 molar ratio counterion soln., stirred at RT, centrifuged to harvest solids, analyzed by PXRD | Pattern 9A |
| Maleic | DCM | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, solid after 10 days of evaporation, analyzed by PXRD | Pattern 10A |
| Malic | DCM | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, gel after 10 days of evaporation, terminated | N/A (gel) |
| Citric | DCM | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, gel after 10 days of evaporation, terminated | N/A (gel) |
| Fumaric | DCM | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| Salicylic | DCM | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| Hippuric | DCM | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| HCl | EtOH:water 90:10 | 40 mg 5-MAPB + 10 vols. solvent + 1:1 molar ratio counterion soln., stirred at RT, in solution after overnight stirring, opened for evaporation, solid after 4 days of evaporation at RT, analyzed by PXRD | Pattern 1A |
| HBr | EtOH:water 90:10 | 40 mg 5-MAPB + 10 vols. solvent + 1:1 molar ratio counterion soln., stirred at RT, in solution after overnight stirring, opened for evaporation, solid after 4 days of evaporation at RT, analyzed by PXRD | Pattern 2A |
| $H_2SO_4$ | EtOH:water 90:10 | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| $H_3PO_4$ | EtOH:water 90:10 | 40 mg 5-MAPB + 10 vols. solvent + 1:1 molar ratio counterion soln., stirred at RT, in solution after overnight stirring, opened for evaporation, solid after 4 days of evaporation at RT, deliquesced during PXRD sample prep, reopened for evaporation, temp increased to 40° C. after 6 | Pattern 4B |

TABLE 10-continued

Salt screening experiments

| Counterion | Solvent | Procedure/Comments | PXRD Result |
|---|---|---|---|
| | | days of evaporation at RT, solid after 7 days of evaporation, analyzed by PXRD, dried overnight at 40° C. in vacuum oven | |
| HNO$_3$ | EtOH:water 90:10 | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| Methane sulfonic | EtOH:water 90:10 | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| Tartaric | EtOH:water 90:10 | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, gel after 10 days of evaporation, terminated | N/A (gel) |
| Succinic | EtOH:water 90:10 | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, gel after 10 days of evaporation, terminated | N/A (gel) |
| Oxalic | EtOH:water 90:10 | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, solid after 7 days of evaporation, analyzed by PXRD | Pattern 9A |
| Maleic | EtOH:water 90:10 | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, solid after 10 days of evaporation, analyzed by PXRD | Pattern 10A |
| Malic | EtOH:water 90:10 | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, gel after 10 days of evaporation, terminated | N/A (gel) |
| Citric | EtOH:water 90:10 | 40 mg 5-MAPB + 10 vols. solvent + 1:1 molar ratio counterion soln., stirred at RT, in solution after overnight stirring, opened for evaporation, temp increased to 40° C. after 6 days of evaporation at RT, gel after 10 days of evaporation, terminated | N/A (gel) |
| Fumaric | EtOH:water 90:10 | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| Salicylic | EtOH:water 90:10 | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |
| Hippuric | EtOH:water 90:10 | 40 mg 5-MAPB + 10 vols. solvent + 1:1 molar ratio counterion soln., stirred at RT, in solution after overnight stirring, opened for evaporation, gel after 4 days of evaporation at RT, terminated | N/A (gel) |

In certain embodiments, the salt forms of RS-5-MAPB were prepared in a 1:1 molar ratio. In certain embodiments, the salt forms of RS-5-MAPB were prepared using excess amounts of RS-5-MAPB. In certain embodiments, the salt forms of RS-5-MAPB were prepared using excess amounts of salts. In certain embodiments, the solvent is DCM, ethanol, water or ethanol/water mixture.

In certain embodiments, salt forms of RS-5-MAPB were produced with counterions HCl, HBr, H$_3$PO$_4$, oxalic acid, and maleic acid. In certain embodiments, the solvents used to produce salt forms of RS-5-MAPB included dichloromethane (DCM) and EtOH:H$_2$O ratio. In certain embodiments, the ratio of ethanol to water is 9:1.

In certain embodiments, Pattern 1A is produced from HCl and DCM. In certain embodiments, Pattern 1A is produced from HCl and EtOH:H$_2$O ratio. In certain embodiments, Pattern 1A is produced from HCl and EtOH:H$_2$O 90:10 ratio.

In certain embodiments, Pattern 4B is produced from H$_3$PO$_4$ and DCM. In certain embodiments, Pattern 4B is produced from H$_3$PO$_4$ and EtOH:H$_2$O ratio. In certain embodiments, Pattern 4B is produced from H$_3$PO$_4$ and EtOH:H$_2$O 90:10 ratio.

In certain embodiments, Pattern 9A is produced from oxalic acid and DCM. In certain embodiments, Pattern 9A is produced from oxalic acid and EtOH:$H_2O$ ratio. In certain embodiments, Pattern 9A is produced from oxalic acid and EtOH:$H_2O$ 90:10 ratio.

In certain embodiments, Pattern 10A is produced from maleic acid and DCM. In certain embodiments, Pattern 10A is produced from maleic acid and EtOH:$H_2O$ ratio. In certain embodiments, Pattern 10A is produced from maleic acid and EtOH:$H_2O$ 90:10 ratio.

In certain embodiments, Pattern 2A is produced from HBr and EtOH:$H_2O$ ratio. In certain embodiments, Pattern 2A is produced from HBr and EtOH:$H_2O$ 90:10 ratio.

Example 15. Salt Studies of 5-MAPB in THF

Salt studies of 5-MAPB were conducted as shown below in Table 11. A total of 30 salt screening experiments of 15 counterions in THF were generated from RS-5-MAPB HCl. The below technique was used to generate the XRPD patterns in FIG. 19. (For 40 mg of 5-MAPB, 1 vol. solvent=40 µL).

TABLE 11

| Salt screening experiments | | | |
|---|---|---|---|
| Counterion | Solvent | Procedure/Comments | PXRD Result |
| HBr | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| $H_2SO_4$ | THF | 50 mg 5-MAPB + 10 vols. solvent + 1:0.5 molar ratio counterion soln. (0.5 eq. counterion), stirred at 40° C., was in solution, opened for evaporation overnight, was amorphous gel, terminated | N/A (gel) |
| $H_2SO_4$ | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| $H_3PO_4$ | THF | 50 mg 5-MAPB + 10 vols. solvent + 1:0.33 molar ratio counterion soln. (0.33 eq. counterion), stirred at 40° C., was slurry after overnight stirring at 40° C., centrifuged, solids deliquesced, terminated | N/A (gel) |
| $H_3PO_4$ | THF | 50 mg 5-MAPB + 10 vols. solvent + 1:0.5 molar ratio counterion soln. (0.5 eq. counterion), stirred at 40° C., was slurry, centrifuged and analyzed by PXRD, dried overnight at 40° C. in vacuum oven, analyzed by DSC and TGA | Pattern 4C |
| $H_3PO_4$ | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| $HNO_3$ | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| Methane sulfonic | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| Tartaric | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| Succinic | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| Malic | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| Citric | THF | 40 mg 5-MAPB + 10 vols. solvent + 1:1 molar ratio counterion soln., stirred at 40° C., was in solution, opened for evaporation overnight, was amorphous gel, terminated | N/A (gel) |
| Fumaric | THF | 40 mg 5-MAPB + 10 vols. solvent + 1:1 molar ratio counterion soln., stirred at 40° C., was slurry after overnight stirring at 40° C., centrifuged, solids deliquesced, terminated | N/A (gel) |
| Salicylic | THF | 40 mg 5-MAPB + 10 vols. solvent + 1:1 molar ratio counterion soln., stirred at 40° C., was in solution, opened for evaporation overnight, was amorphous gel, terminated | N/A (gel) |

TABLE 11-continued

Salt screening experiments

| Counterion | Solvent | Procedure/Comments | PXRD Result |
|---|---|---|---|
| Hippuric | THF | 40 mg 5-MAPB + 10 vols. solvent + 1:1 molar ratio counterion soln., stirred at 40° C., was in solution, opened for evaporation overnight, was amorphous gel, terminated | N/A (gel) |

In certain embodiments, the salt forms of RS-5-MAPB were prepared in a 1:1 molar ratio. In certain embodiments, the salt forms of RS-5-MAPB were prepared using excess amounts of RS-5-MAPB. In certain embodiments, the salt forms of RS-5-MAPB were prepared using excess amounts of salts.

In certain embodiments, salt forms of RS-5-MAPB were produced with counterions HCl, HBr, $H_3PO_4$, oxalic acid, and maleic acid. In certain embodiments, the solvents used to produce salt forms of RS-5-MAPB included tetrahydrofuran (THF).

In certain embodiments, Pattern 4C is produced from $H_3PO_4$ and THF.

Example 16. 5-MAPB Freebase Isolation/Liquid-Liquid Extraction

Liquid-Liquid Extraction (LLE) was used to isolate 5-MAPB Freebase from Pattern 1A (5-MAPB HCl, Pure Enantiomer) using the conditions shown in Table 12 (for 2 g of 5-MAPB HCl Pure Enantiomer, 1 vol. solvent is equivalent to 2 mL).

TABLE 12

S-5-MAPB Freebase from Pattern 1A Enantiomer
(S-5-MAPB Pure Enantiomer)

| Counterion | Solvent (Density) | Procedure/Comments |
|---|---|---|
| NaOH | EtOAc (0.902 g/mL) | 2 g Pattern 1A Enantiomer (as HCl salt) + 10 vols. solvent + NaOH stock soln. in water (1.1:1 molar ratio) + additional water (10 vols. water total), did not dissolve in 10 vols. of EtOAc, went into solution and changed color after adding NaOH, EtOAc phase removed |

EXAMPLE 17. Salt Studies of Pattern 1A S-5-MAPB Pure Enantiomer in Acetone or MeOH:$H_2O$ Salt studies of Pattern 1A Enantiomer (S-5-MAPB Pure Enantiomer) were conducted as shown below in Table 13. A total of 24 salt experiments for 12 counterions (HCl, HBr, $H_2SO_4$, $H_3PO_4$, $HNO_3$, methansulfonic, succinic, oxalic, maleic, fumaric, L-arginine, L-lysine) in 2 different solvents, acetone and MeOH:$H_2O$, were generated from Pattern 1A Enantiomer (S-5-MAPB Pure Enantiomer). The below technique was used to generate the images in FIG. 24, FIG. 25 and FIG. 26. (for 35 mg of Pattern 1A Enantiomer, 1 vol. solvent=35 µL, (API=Pattern 1A Enantiomer (S-5-MAPB Pure Enantiomer)).

TABLE 13

Salt screening experiments of Pattern 1A Enantiomer
(S-5-MAPB Pure Enantiomer)

| Counterion | Solvent | Procedure/Comments | PXRD Result |
|---|---|---|---|
| HCl | Acetone | 35 mg API + 10 vols. solvent + 1:1 molar ratio counterion soln., stirred at 40° C., slurry after overnight stirring, centrifuged to recover solids, analyzed by PXRD, dried overnight at 40° C. in vacuum oven, analyzed by DSC and TGA | Enantiomer Pattern 1A |
| HBr | Acetone | 35 mg API + 10 vols. solvent + 1:1 molar ratio counterion soln., stirred at 40° C., in solution after overnight stirring, opened for evaporation, solid after 3 days of evaporation, analyzed by PXRD, dried overnight at 40° C. in vacuum oven, analyzed by DSC and TGA | Enantiomer Pattern 2A |
| $H_2SO_4$ | Acetone | 35 mg API + 10 vols. solvent + 1:1 molar ratio counterion soln., stirred at 40° C., in solution after overnight stirring, opened for evaporation, gel after 3 days of evaporation, terminated | N/A (gel) |
| $H_3PO_4$ | Acetone | 35 mg API + 10 vols. solvent + 1:1 molar ratio counterion soln., stirred at 40° C., slurry after overnight stirring, centrifuged to recover solids, analyzed by PXRD, dried overnight at 40° C. in vacuum oven, analyzed by DSC and TGA | Enantiomer Pattern 4A |

TABLE 13-continued

Salt screening experiments of Pattern 1A Enantiomer
(S-5-MAPB Pure Enantiomer)

| Counterion | Solvent | Procedure/Comments | PXRD Result |
|---|---|---|---|
| HNO₃ | Acetone | 35 mg API + 10 vols. solvent + 1:1 molar ratio counterion soln., stirred at 40° C., in solution after overnight stirring, opened for evaporation, gel after 3 days of evaporation, terminated | N/A (gel) |
| Methane Sulfonic | Acetone | 35 mg API + 10 vols. solvent + 1:1 molar ratio counterion soln., stirred at 40° C., in solution after overnight stirring, opened for evaporation, gel after 3 days of evaporation, terminated | N/A (gel) |
| Succinic | Acetone | 35 mg API + 10 vols. solvent + 1:1 molar ratio counterion soln., stirred at 40° C., in solution after overnight stirring, opened for evaporation, gel after 4 days of evaporation, terminated | N/A (gel) |
| Oxalic | Acetone | 35 mg API + 10 vols. solvent + 1:1 molar ratio counterion soln., stirred at 40° C., in solution after overnight stirring, opened for evaporation, solid after 3 days of evaporation, analyzed by PXRD, dried overnight at 40° C. in vacuum oven, analyzed by DSC and TGA | Enantiomer Pattern 8A |
| Maleic | Acetone | 35 mg API + 10 vols. solvent + 1:1 molar ratio counterion soln., stirred at 40° C., in solution after overnight stirring, opened for evaporation, gel after 4 days of evaporation, terminated | N/A (gel) |
| Fumaric | Acetone | 35 mg API + 10 vols. solvent + 1:1 molar ratio counterion soln., stirred at 40° C., in solution after overnight stirring, opened for evaporation, gel after 3 days of evaporation, terminated | N/A (gel) |
| L-Arginine | Acetone | 35 mg API + 10 vols. solvent + 1:1 molar ratio counterion soln., stirred at 40° C., in solution after overnight stirring, opened for evaporation, gel after 6 days of evaporation, terminated | N/A (gel) |
| L-Lysine | Acetone | 35 mg API + 10 vols. solvent + 1:1 molar ratio counterion soln., stirred at 40° C., in solution after overnight stirring, opened for evaporation, gel after 5 days of evaporation, terminated | N/A (gel) |
| HCl | MeOH:water 90:10 | 35 mg API + 10 vols. solvent + 1:1 molar ratio counterion soln., stirred at 40° C., in solution after overnight stirring, opened for evaporation, solid after 3 days of evaporation, analyzed by PXRD, dried overnight at 40° C. in vacuum oven, analyzed by DSC and TGA | Enantiomer Pattern 1A |
| HBr | MeOH:water 90:10 | 35 mg API + 10 vols. solvent + 1:1 molar ratio counterion soln., stirred at 40° C., in solution after overnight stirring, opened for evaporation, solid after 3 days of evaporation, analyzed by PXRD, dried overnight at 40° C. in vacuum oven | Enantiomer Pattern 2A |
| H₂SO₄ | MeOH:water 90:10 | 35 mg API + 10 vols. solvent + 1:1 molar ratio counterion soln., stirred at 40° C., in solution after overnight stirring, opened for evaporation, gel after 3 days of evaporation, terminated | N/A (gel) |
| H₃PO₄ | MeOH:water 90:10 | 35 mg API + 10 vols. solvent + 1:1 molar ratio counterion soln., stirred at 40° C., in solution after overnight stirring, opened for evaporation, gel after 3 days of evaporation, terminated | N/A (gel) |
| HNO₃ | MeOH:water 90:10 | 35 mg API + 10 vols. solvent + 1:1 molar ratio counterion soln., stirred at 40° C., in solution after overnight stirring, opened for evaporation, gel after 3 days of evaporation, terminated | N/A (gel) |
| Methane Sulfonic | MeOH:water 90:10 | 35 mg API + 10 vols. solvent + 1:1 molar ratio counterion soln., stirred at 40° C., in solution after overnight stirring, opened for evaporation, gel after 3 days of evaporation, terminated | N/A (gel) |
| Succinic | MeOH:water 90:10 | 35 mg API + 10 vols. solvent + 1:1 molar ratio counterion soln., stirred at 40° C., in solution after overnight stirring, opened for evaporation, gel after 5 days of evaporation, terminated | N/A (gel) |
| Oxalic | MeOH:water 90:10 | 35 mg API + 10 vols. solvent + 1:1 molar ratio counterion soln., stirred at 40° C., in solution after overnight stirring, opened for evaporation, solid after 3 days of evaporation, analyzed by PXRD | Enantiomer Pattern 8A |
| Maleic | MeOH:water 90:10 | 35 mg API + 10 vols. solvent + 1:1 molar ratio counterion soln., stirred at 40° C., in solution after overnight stirring, opened for evaporation, gel after 5 days of evaporation, terminated | N/A (gel) |

TABLE 13-continued

Salt screening experiments of Pattern 1A Enantiomer
(S-5-MAPB Pure Enantiomer)

| Counterion | Solvent | Procedure/Comments | PXRD Result |
|---|---|---|---|
| Fumaric | MeOH:water 90:10 | 35 mg API + 10 vols. solvent + 1:1 molar ratio counterion soln., stirred at 40° C., in solution after overnight stirring, opened for evaporation, gel after 3 days of evaporation, terminated | N/A (gel) |
| L-Arginine | MeOH:water 90:10 | 35 mg API + 10 vols. solvent + 1:1 molar ratio counterion soln., stirred at 40° C., in solution after overnight stirring, opened for evaporation, gel after 6 days of evaporation, terminated | N/A (gel) |
| L-Lysine | MeOH:water 90:10 | 35 mg API + 10 vols. solvent + 1:1 molar ratio counterion soln., stirred at 40° C., in solution after overnight stirring, opened for evaporation, gel after 6 days of evaporation, terminated | N/A (gel) |

In certain embodiments, the salt forms of S-5-MAPB were prepared in a 1:1 molar ratio. In certain embodiments, the salt forms of S-5-MAPB were prepared using excess amounts of S-5-MAPB. In certain embodiments, the salt forms of S-5-MAPB were prepared using excess amounts of salts.

In certain embodiments, salt forms of S-5-MAPB were produced with counterions HCl, HBr, $H_2SO_4$, $H_3PO_4$, $HNO_3$, Methansulfonic, Succinic, Oxalic, Maleic, Fumaric, L-Arginine, and L-Lysine. In certain embodiments, the solvent is acetone, methanol, water or methanol/water mixture.

In certain embodiments, Pattern 1A Enantiomer (Pattern 1AE) is produced from HCl and acetone. In certain embodiments, Pattern 1A Enantiomer (Pattern 1AE) is produced from HCl and MeOH:$H_2O$ ratio. In certain embodiments, Pattern 1A Enantiomer (Pattern 1AE) is produced from HCl and MeOH:$H_2O$ 90:10 ratio.

In certain embodiments, Pattern 4A Enantiomer (Pattern 4AE) is produced from $H_3PO_4$ and acetone.

In certain embodiments, Pattern 8A Enantiomer (Pattern 8AE) is produced from oxalic acid and acetone. In certain embodiments, Pattern 8A Enantiomer (Pattern 8AE) is produced from oxalic acid and MeOH:$H_2O$ ratio. In certain embodiments, Pattern 8AE Enantiomer (Pattern 8AE) is produced from oxalic acid and MeOH:$H_2O$ 90:10 ratio.

In certain embodiments, Pattern 2A Enantiomer (Pattern 2AE) is produced from HBr and acetone. In certain embodiments, Pattern 2A Enantiomer (Pattern 2AE) is produced from HBr and MeOH:$H_2O$ ratio. In certain embodiments, Pattern 2AE is produced from HBr and MeOH:$H_2O$ 90:10 ratio.

Example 18. Salt Screening Experiments of Pattern 1A S-5-MAPB Pure Enantiomer in THF or EtOH:$H_2O$ Salt screening experiments of Pattern 1A Enantiomer (S-5-MAPB Pure Enantiomer) were conducted as shown below in Table 14. A total of 24 salt screening experiments of 12 counterions (HCl, HBr, $H_2SO_4$, $H_3PO_4$, $HNO_3$, methansulfonic, succinic, oxalic, maleic, fumaric, L-arginine, L-lysine) in 2 different solvents, THF and EtOH:$H_2O$, were generated from Pattern A Enantiomer (S-5-MAPB Pure Enantiomer). The below technique was used to generate the images in FIG. 27, FIG. 28, FIG. 29 and FIG. 30. For 35 mg of Pattern A Enantiomer, 1 vol. solvent=35 µL; (API=Pattern 1A Enantiomer (S-5-MAPB Pure Enantiomer)).

TABLE 14

Salt screening experiments of Pattern 1A Enantiomer
(S-5-MAPB Pure Enantiomer)

| Counterion | Solvent | Procedure/Comments | PXRD Result |
|---|---|---|---|
| HCl | THF | 35 mg API + 10 vols. solvent + 1:1 molar ratio counterion soln., stirred at 40° C., slurry after overnight stirring, centrifuged to recover solids, analyzed by PXRD | Enantiomer Pattern 1A |
| HBr | THF | 35 mg API + 10 vols. solvent + 1:1 molar ratio counterion soln., stirred at 40° C., in solution after overnight stirring, opened for evaporation, solid after overnight evaporation, analyzed by PXRD | Enantiomer Pattern 2A |
| $H_2SO_4$ | THF | 35 mg API + 10 vols. solvent + 1:1 molar ratio counterion soln., stirred at 40° C., in solution after overnight stirring, opened for evaporation, gel after 5 days of evaporation, terminated | N/A (gel) |
| $H_3PO_4$ | THF | 35 mg API + 10 vols. solvent + 1:1 molar ratio counterion soln., stirred at 40° C., slurry after overnight stirring, centrifuged to recover solids, analyzed by PXRD | Enantiomer Pattern 4A |
| $HNO_3$ | THF | 35 mg API + 10 vols. solvent + 1:1 molar ratio counterion soln., stirred at 40° C., in solution after overnight stirring, opened for evaporation, gel after overnight evaporation, terminated | N/A (gel) |

TABLE 14-continued

Salt screening experiments of Pattern 1A Enantiomer
(S-5-MAPB Pure Enantiomer)

| Counterion | Solvent | Procedure/Comments | PXRD Result |
|---|---|---|---|
| Methane Sulfonic | THF | 35 mg API + 10 vols. solvent + 1:1 molar ratio counterion soln., stirred at 40° C., in solution after overnight stirring, opened for evaporation, gel after overnight evaporation, terminated | N/A (gel) |
| Succinic | THF | 35 mg API + 10 vols. solvent + 1:1 molar ratio counterion soln., stirred at 40° C., in solution after overnight stirring, opened for evaporation, gel after 2 days of evaporation, terminated | N/A (gel) |
| Oxalic | THF | 35 mg API + 10 vols. solvent + 1:1 molar ratio counterion soln., stirred at 40° C., in solution after overnight stirring, opened for evaporation, solid after 2 days of evaporation, analyzed by PXRD | Enantiomer Pattern 8A |
| Maleic | THF | 35 mg API + 10 vols. solvent + 1:1 molar ratio counterion soln., stirred at 40° C., in solution after overnight stirring, opened for evaporation, gel after 2 days of evaporation, terminated | N/A (gel) |
| Fumaric | THF | 35 mg API + 10 vols. solvent + 1:1 molar ratio counterion soln., stirred at 40° C., in solution after overnight stirring, opened for evaporation, gel after 2 days of evaporation, terminated | N/A (gel) |
| L-Arginine | THF | 35 mg API + 10 vols. solvent + 1:1 molar ratio counterion soln., stirred at 40° C., in solution after overnight stirring, opened for evaporation, gel after 5 days of evaporation, terminated | N/A (gel) |
| L-Lysine | THF | 35 mg API + 10 vols. solvent + 1:1 molar ratio counterion soln., stirred at 40° C., in solution after overnight stirring, opened for evaporation, solid after 5 days of evaporation, analyzed by PXRD | L-Lysine |
| HCl | EtOH: water 90:10 | 35 mg API + 10 vols. solvent + 1:1 molar ratio counterion soln., stirred at 40° C., in solution after overnight stirring, opened for evaporation, solid after overnight evaporation, analyzed by PXRD | Enantiomer Pattern 1A |
| HBr | EtOH: water 90:10 | 35 mg API + 10 vols. solvent + 1:1 molar ratio counterion soln., stirred at 40° C., in solution after overnight stirring, opened for evaporation, solid after 2 days of evaporation, analyzed by PXRD, dried overnight at 40° C. in vacuum oven, analyzed by DSC and TGA | Enantiomer Pattern 2A |
| $H_2SO_4$ | EtOH: water 90:10 | 35 mg API + 10 vols. solvent + 1:1 molar ratio counterion soln., stirred at 40° C., in solution after overnight stirring, opened for evaporation, gel after 2 days of evaporation, terminated | N/A (gel) |
| $H_3PO_4$ | EtOH: water 90:10 | 35 mg API + 10 vols. solvent + 1:1 molar ratio counterion soln., stirred at 40° C., in solution after overnight stirring, opened for evaporation, solid after overnight evaporation, analyzed by PXRD | Enantiomer Pattern 4A |
| $HNO_3$ | EtOH: water 90:10 | 35 mg API + 10 vols. solvent + 1:1 molar ratio counterion soln., stirred at 40° C., in solution after overnight stirring, opened for evaporation, gel after 2 days of evaporation, terminated | N/A (gel) |
| Methane Sulfonic | EtOH: water 90:10 | 35 mg API + 10 vols. solvent + 1:1 molar ratio counterion soln., stirred at 40° C., in solution after overnight stirring, opened for evaporation, gel after 2 days of evaporation, terminated | N/A (gel) |
| Succinic | EtOH: water 90:10 | 35 mg API + 10 vols. solvent + 1:1 molar ratio counterion soln., stirred at 40° C., in solution after overnight stirring, opened for evaporation, gel after 5 days of evaporation, terminated | N/A (gel) |
| Oxalic | EtOH: water 90:10 | 35 mg API + 10 vols. solvent + 1:1 molar ratio counterion soln., stirred at 40° C., in solution after overnight stirring, opened for evaporation, solid after 2 days of evaporation, analyzed by PXRD | Enantiomer Pattern 8A |
| Maleic | EtOH: water 90:10 | 35 mg API + 10 vols. solvent + 1:1 molar ratio counterion soln., stirred at 40° C., in solution after overnight stirring, opened for evaporation, gel after 5 days of evaporation, terminated | N/A (gel) |
| Fumaric | EtOH: water 90:10 | 35 mg API + 10 vols. solvent + 1:1 molar ratio counterion soln., stirred at 40° C., in solution after overnight stirring, opened for evaporation, solid after 5 days of evaporation, analyzed by PXRD, dried overnight at 40° C. in vacuum oven, analyzed by DSC and TGA | Enantiomer Pattern 10A |

TABLE 14-continued

Salt screening experiments of Pattern 1A Enantiomer
(S-5-MAPB Pure Enantiomer)

| Counterion | Solvent | Procedure/Comments | PXRD Result |
|---|---|---|---|
| L-Arginine | EtOH: water 90:10 | 35 mg API + 10 vols. solvent + 1:1 molar ratio counterion soln., stirred at 40° C., in solution after overnight stirring, opened for evaporation, gel after 5 days of evaporation, terminated | N/A (gel) |
| L-Lysine | EtOH: water 90:10 | 35 mg API + 10 vols. solvent + 1:1 molar ratio counterion soln., stirred at 40° C., in solution after overnight stirring, opened for evaporation, gel after 5 days of evaporation, terminated | N/A (gel) |

In certain embodiments, the salt forms of S-5-MAPB were prepared in a 1:1 molar ratio. In certain embodiments, the salt forms of S-5-MAPB were prepared using excess amounts of S-5-MAPB. In certain embodiments, the salt forms of S-5-MAPB were prepared using excess amounts of salts.

In certain embodiments, salt forms of S-5-MAPB were produced with counterions HCl, HBr, $H_2SO_4$, $H_3PO_4$, $HNO_3$, Methansulfonic, Succinic, Oxalic, Maleic, Fumaric, L-Arginine, and L-Lysine. In certain embodiments, the solvent is tetrahydrofuran, ethanol, water or ethanol/water mixture.

In certain embodiments, Pattern 1A Enantiomer (Pattern 1AE) is produced from HCl and THF. In certain embodiments, Pattern 1A Enantiomer (Pattern 1AE) is produced from HCl and EtOH:$H_2O$ ratio. In certain embodiments, Pattern 1A Enantiomer (Pattern 1AE) is produced from HCl and EtOH:$H_2O$ 90:10 ratio.

In certain embodiments, Pattern 4A Enantiomer (Pattern 4AE) is produced from $H_3PO_4$ and THF. In certain embodiments, Pattern 4A Enantiomer (Pattern 4AE) is produced from HCl and EtOH:$H_2O$ ratio. In certain embodiments, Pattern 4A Enantiomer (Pattern 4AE) is produced from HCl and EtOH:$H_2O$ 90:10 ratio.

In certain embodiments, Pattern 8A Enantiomer (Pattern 8AE) is produced from oxalic acid and THF. In certain embodiments, Pattern 8A Enantiomer (Pattern 8AE) is produced from oxalic acid and EtOH:$H_2O$ ratio. In certain embodiments, Pattern 8A Enantiomer (Pattern 8AE) is produced from oxalic acid and EtOH:$H_2O$ 90:10 ratio.

In certain embodiments, Pattern 2A Enantiomer (Pattern 2AE) is produced from HBr and THF. In certain embodiments, Pattern 2A Enantiomer (Pattern 2AE) is produced from HBr and EtOH:$H_2O$ ratio. In certain embodiments, Pattern 2AE is produced from HBr and EtOH:$H_2O$ 90:10 ratio.

In certain embodiments, Pattern 10A Enantiomer (Pattern 10AE) is produced from fumaric acid and EtOH:$H_2O$ ratio. In certain embodiments, Pattern 10AE is produced from fumaric acid and EtOH:$H_2O$ 90:10 ratio.

Example 19. Salt Screening Experiments of Pattern 1A S-5-MAPB Pure Enantiomer in ACN Salt screening experiments of Pattern 1A Enantiomer (S-5-MAPB Pure Enantiomer) were conducted as shown below in Table 15. A total of 13 salt screening experiments of 10 counterions in 1 solvent (ACN, acetonitrile) were generated from Pattern 1A Enantiomer (S-5-MAPB Pure Enantiomer). The below technique was used to generate the images in FIG. 31. For 35 mg of Pattern 1A Enantiomer, 1 vol. solvent=35 µL; (API=Pattern 1A Enantiomer (S-5-MAPB Pure Enantiomer)).

TABLE 15

Salt screening experiments of Pattern 1A Enantiomer
(S-5-MAPB Pure Enantiomer)

| Counterion | Solvent | Procedure/Comments | PXRD Result |
|---|---|---|---|
| HCl | ACN | 35 mg API + 10 vols. solvent + 1:1 molar ratio counterion soln., stirred at 40° C., slurry after overnight stirring, centrifuged to harvest solids, analyzed by PXRD | Enantiomer Pattern 1A |
| HBr | ACN | 35 mg API + 10 vols. solvent + 1:1 molar ratio counterion soln., stirred at 40° C., in solution after overnight stirring, opened for evaporation, solid after overnight evaporation, analyzed by PXRD | Enantiomer Pattern 2A |
| $H_2SO_4$ | ACN | 35 mg API + 10 vols. solvent + 1:0.5 molar ratio counterion soln. (0.5 eq. counterion), stirred at 40° C., in solution after overnight stirring, opened for evaporation, solid after overnight evaporation, became gel-like during PXRD sample prep, terminated | N/A (gel) |
| $H_2SO_4$ | ACN | 35 mg API + 10 vols. solvent + 1:1 molar ratio counterion soln., stirred at 40° C., in solution after overnight stirring, opened for evaporation, gel after 2 days of evaporation, terminated | N/A (gel) |
| $H_3PO_4$ | ACN | 35 mg API + 10 vols. solvent + 1:0.33 molar ratio counterion soln. (0.33 eq. counterion), stirred at 40° C., slurry after overnight stirring, centrifuged to harvest solids, became gel-like during PXRD sample prep, terminated | N/A (gel) |

TABLE 15-continued

Salt screening experiments of Pattern 1A Enantiomer
(S-5-MAPB Pure Enantiomer)

| Counterion | Solvent | Procedure/Comments | PXRD Result |
|---|---|---|---|
| $H_3PO_4$ | ACN | 35 mg API + 10 vols. solvent + 1:0.5 molar ratio counterion soln. (0.5 eq. counterion), stirred at 40° C., in solution after overnight stirring, opened for evaporation, gel after 2 days of evaporation, terminated | N/A (gel) |
| $H_3PO_4$ | ACN | 35 mg API + 10 vols. solvent + 1:1 molar ratio counterion soln., stirred at 40° C. slurry after overnight stirring, centrifuged to harvest solids, analyzed by PXRD | Enantiomer Pattern 4A |
| $HNO_3$ | ACN | 35 mg API + 10 vols. solvent + 1:1 molar ratio counterion soln., stirred at 40° C., in solution after overnight stirring, opened for evaporation, gel after overnight evaporation, terminated | N/A (gel) |
| Methane Sulfonic | ACN | 35 mg API + 10 vols. solvent + 1:1 molar ratio counterion soln., stirred at 40° C., in solution after overnight stirring, opened for evaporation, gel after overnight evaporation, terminated | N/A (gel) |
| Succinic | ACN | 35 mg API + 10 vols. solvent + 1:1 molar ratio counterion soln., stirred at 40° C., in solution after overnight stirring, opened for evaporation, gel after 5 days of evaporation, terminated | N/A (gel) |
| Fumaric | ACN | 35 mg API + 10 vols. solvent + 1:1 molar ratio counterion soln., stirred at 40° C., in solution after overnight stirring, opened for evaporation, gel after 2 days of evaporation, terminated | N/A (gel) |
| L-Arginine | ACN | 35 mg API + 10 vols. solvent + 1:1 molar ratio counterion soln., stirred at 40° C., in solution after overnight stirring, opened for evaporation, gel after 5 days of evaporation, terminated | N/A (gel) |
| L-Lysine | ACN | 35 mg API + 10 vols. solvent + 1:1 molar ratio counterion soln., stirred at 40° C., in solution after overnight stirring, opened for evaporation, gel after 5 days of evaporation, terminated | N/A (gel) |

In certain embodiments, the salt forms of S-5-MAPB were prepared in a 1:1 molar ratio. In certain embodiments, the salt forms of S-5-MAPB were prepared using excess amounts of S-5-MAPB. In certain embodiments, the salt forms of S-5-MAPB were prepared using excess amounts of salts.

In certain embodiments, salt forms of S-5-MAPB were produced with counterions HCl, HBr, $H_2SO_4$, $H_3PO_4$, $HNO_3$, Methansulfonic, Succinic, Oxalic, Maleic, Fumaric, L-Arginine, and L-Lysine. In certain embodiments, the solvent is acetonitrile.

In certain embodiments, Pattern 1A Enantiomer (Pattern 1AE) is produced from HCl and acetonitrile (ACN).

In certain embodiments, Pattern 2A Enantiomer (Pattern 2AE) is produced from HBr and acetonitrile (ACN).

In certain embodiments, Pattern 4A Enantiomer (Pattern 4AE) is produced from $H_3PO_4$ and acetonitrile (ACN).

Example 20. Differential Scanning Calorimetry (DSC) Thermogram Procedure

Differential Scanning Calorimetry (DSC) thermograms were collected on a Perkin Elmer Pyris 1 DSC with Intracooler. Thermogravimetric (TGA) thermograms were collected on a Perkin Elmer TGA-7 Instrument. The instrument and method details are included in the following table. The crystalline hits obtained during the salt screening experiments were further characterized by DSC and TGA. The instrument and method details are included below in the Table 16. The below technique was used to generate the images in FIG. 35, FIG. 36, FIG. 37, FIG. 38, FIG. 39, FIG. 40, FIG. 41, FIG. 42, FIG. 43, FIG. 44, FIG. 45, and FIG. 46.

TABLE 16

DSC/TGA thermogram procedure

| | | |
|---|---|---|
| Instrument: | Perkin Elmer Pyris 1 DSC with Intracooler (S/N 537N7063001) | Perkin Elmer TGA-7 (S/N 519N7100203) |
| Sample Holder: | Thermal Support Standard 6.7 mm Al Pans | Mettler Toledo Al Crucibles 40 µL |
| Scan Temp Range: | 30° C. to 250° C. | 30° C. to 300° C. |
| Scan Rate: | 10° C./min | 10° C./min |
| Purge: | Nitrogen, 20 cc/min | |

Example 21. Scale-Up and Stability Study

Scale up study of selected salts (Patterns 1A, 2A, and 10A) to ~70 mg was completed. Patterns 1A and 10A were successfully scaled up, however the attempt to scale up Pattern 2A was unsuccessful (new Pattern 2B was obtained instead). All three samples were then tested for their solid-state stability as shown below in Table 17. (API=5-MAPB HCl)

TABLE 17

Scale Up and Stability of Pattern 1A, 2A and 10A

| Counterion | Solvent | Procedure/Comments | PXRD Pattern (Wet cake) | PXRD Pattern (Vac. dried sample) | PXRD Pattern (40° C./ 75% RH sample) |
|---|---|---|---|---|---|
| HCl (Pattern 1A) | EtOH: water 90:10 | 70 mg API + 10 vols. solvent + 1:1 molar ratio counterion soln., stirred at 40° C., in solution after ~6 hrs of stirring, opened for evaporation, solid after 2 days of evaporation, analyzed by PXRD, dried overnight at 40° C. in vacuum oven, analyzed by PXRD, DSC, and TGA, analyzed by optical microscopy, ~10 mgs staged at 40° C./75% RH, pulled from staging after 1 day, analyzed by PXRD | Pattern 1A | Pattern 1A | Pattern 1A |
| HBr (Pattern 2A) | EtOH: water 90:10 | 70 mg API + 10 vols. solvent + 1:1 molar ratio counterion soln., stirred at 40° C., in solution after ~6 hrs of stirring, opened for evaporation, solid after 2 days of evaporation, analyzed by PXRD, dried overnight at 40° C. in vacuum oven, analyzed by PXRD, DSC, and TGA, analyzed by optical microscopy, ~10 mgs staged at 40° C./75% RH, pulled from staging after 1 day, analyzed by PXRD | Pattern 2B | Pattern 2B | Pattern 2B |
| Maleic (Pattern 10 A) | DCM | 65 mg API + 10 vols. solvent + 1:1 molar ratio counterion soln., stirred at 40° C., in solution after ~6 hrs of stirring, opened for evaporation, solid after 7 days of evaporation, analyzed by PXRD, dried overnight at 40° C. in vacuum oven, analyzed by PXRD, DSC, and TGA, analyzed by optical microscopy, ~10 mgs staged at 40° C./75% RH, pulled from staging after 1 day, analyzed by PXRD | Pattern 10A | Pattern 10A | Pattern 10A |

Example 22. Solubility Assessment in FaSSIF Media

The Patterns 1A, 2B and 10A scale up samples were tested for their approximate solubility in FaSSIF V2 media as shown below in Table 18. All three samples were found to have solubility of >10 mg/mL and remained in solution after overnight stirring.

TABLE 18

Solubility Assessment in FaSSIF Media of Patterns 1A, 2B and 10A

| Procedure/Comments | Solubility | PXRD Pattern |
|---|---|---|
| 10 mg of Pattern 1A + FaSSIF V2 media added in 1 mL steps at a rate of 1 mL/5 min until dissolved, stirred at room temp, dissolved after 1 mL, left stirring overnight, remained in solution after overnight stirring, terminated | >10 mg/mL | N/A (in solution) |
| 10 mg of Pattern 2B + FaSSIF V2 media added in 1 mL steps at a rate of 1 mL/5 min until dissolved, stirred at room temp, dissolved after 1 mL, left stirring overnight, remained in solution after overnight stirring, terminated | >10 mg/mL | N/A (in solution) |
| 10 mg of Pattern 10A + FaSSIF V2 media added in 1 mL steps at a rate of 1 mL/5 min until dissolved, stirred at room temp, dissolved after 1 mL, left stirring overnight, remained in solution after overnight stirring, terminated | >10 mg/mL | N/A (in solution) |

Example 23. Scale-Up and Stability Study

Scale up study of selected salts (Enantiomer Patterns 1A, 4A, and 8A) to ~250 mg completed. Enantiomer Patterns 1A, 4A, and 8A were all scaled up successfully. All three samples were then tested for their solid-state stability as shown below in Table 19. (API=S-5-MAPB Pure Enantiomer)

TABLE 19

Scale-up and stability study Enantiomer Pattern 1A, 4A, 8A

| Counterion | Solvent | Procedure/Comments | PXRD Pattern (overnight stirring) | PXRD Pattern (2 days of stirring) | PXRD Pattern (Vacuum Dried) | PXRD Pattern (40° C./ 75% RH sample) |
| --- | --- | --- | --- | --- | --- | --- |
| HCl (Pattern 1A) | THF | 240 mg API + 10 vols. solvent + 1:1 molar ratio counterion soln., stirred at 40° C., slurry after overnight stirring, sampled (.5 mL) and vacuum filtered for 30 min, analyzed by PXRD, cont stirring, slurry after 2 days of stirring, vacuum filtered for 30 min, analyzed by PXRD, dried overnight at 40° C. in vacuum oven, analyzed by optical microscopy, PXRD, DSC and TGA, ~10 mgs staged at 40° C./75% RH, pulled from staging after 1 day, analyzed by PXRD | Enantiomer Pattern 1A | Enantiomer Pattern 1A | Enantiomer Pattern 1A | Enantiomer Pattern 1A |
| $H_3PO_4$ (Pattern 4A) | Acetone | 250 mg API + 10 vols. solvent + 1:1 molar ratio counterion soln., stirred at 40° C., slurry after overnight stirring, sampled (.5 mL) and vacuum filtered for 30 min, analyzed by PXRD, cont stirring, slurry after 2 days of stirring, vacuum filtered for 30 min, analyzed by PXRD, dried overnight at 40° C. in vacuum oven, analyzed by optical microscopy, PXRD, DSC and TGA, ~10 mgs staged at 40° C./75% RH, pulled from staging after 1 day, analyzed by PXRD | Enantiomer Pattern 4A | Enantiomer Pattern 4A | Enantiomer Pattern 4A | Enantiomer Pattern 4A |
| Oxalic (Pattern 8A) | EtOH: water 90:10 | 240 mg API + 10 vols. solvent + 1:1 molar ratio counterion soln., stirred at 40° C., in solution after overnight stirring, opened for evaporation, solid after overnight evaporation, analyzed by PXRD, dried overnight at 40° C. in vacuum oven, analyzed by optical microscopy, PXRD, DSC and TGA, ~10 mgs staged at 40° C./75% RH, pulled from staging after 1 day, analyzed by PXRD | N/A | Enantiomer Pattern 8A | Enantiomer Pattern 8A | Enantiomer Pattern 8A |

Example 24. Solubility Assessment in FaSSIF Media

The approximate solubility of Enantiomer Patterns 1A, 4A and 8A scale up samples was measured in FaSSIF V2 media as shown below in Table 20. Enantiomer Patterns 1A and 4A were found to have a solubility >10 mg/mL. Enantiomer Pattern 8A was found to have a solubility between 10 mg/mL and 5 mg/mL. All three samples remained in solution after overnight stirring.

TABLE 20

Solubility Assessment in FaSSIF Media of Patterns 1A, 4A and 8A

| Procedure/Comments | Solubility mg/mL | PXRD Pattern |
|---|---|---|
| 10 mg of Pattern 1A + FaSSIF V2 media added in 1 mL steps at a rate of 1 mL/5 min until dissolved, stirred at room temp, dissolved after 1 mL, remained in solution after overnight stirring, terminated | >10 | N/A (in solution) |
| 10 mg of Pattern 4A + FaSSIF V2 media added in 1 mL steps at a rate of 1 mL/5 min until dissolved, stirred at room temp, dissolved after 1 mL, remained in solution after overnight stirring, terminated | >10 | N/A (in solution) |
| 10 mg of Pattern 8A + FaSSIF V2 media added in 1 mL steps at a rate of 1 mL/5 min until dissolved, stirred at room temp, dissolved after 2 mL, remained in solution after overnight stirring, terminated | 5 < S <10 | N/A (in solution) |

Example 25. R-5-MAPB Freebase Isolation/Liquid-Liquid Extraction

Figure 47:
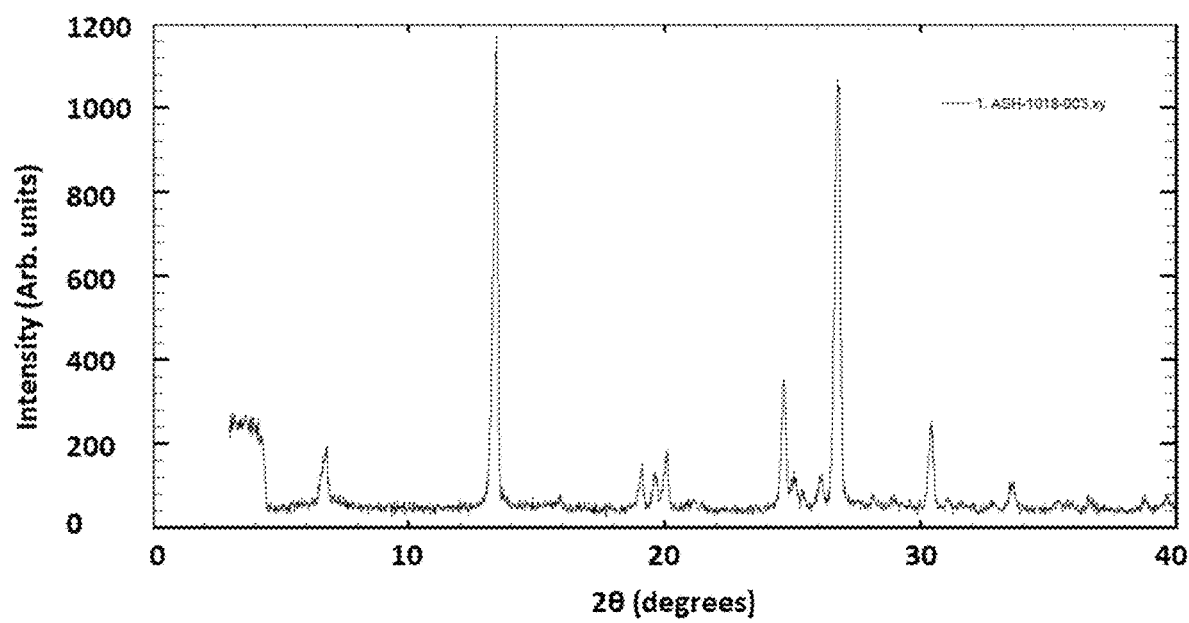
FIG. 47 is a powder XRPD Diffractogram of R-5-MAPB HCl used in the Liquid-Liquid Extraction to afford R-5-MAPB as described in Example 25. The x axis measures 2Theta in degrees and the y axis measures intensity measured in arb. units.
Figure 48:
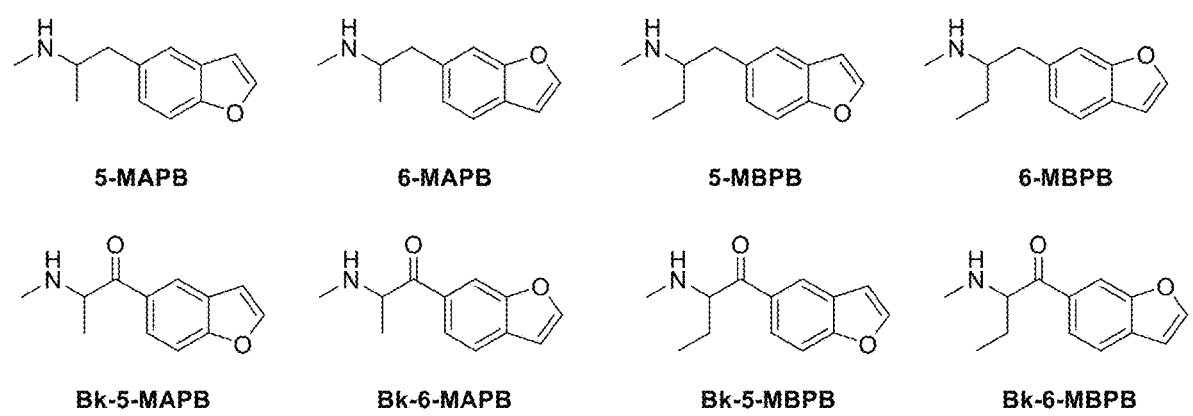
FIG. 48 provides the names and structures of select entactogenic compounds referred to herein.

Liquid-Liquid Extraction (LLE) was used to isolate R-5-MAPB freebase from R-5-MAPB hydrochloride (R5-MAPB HCl) using the conditions in Table 21. FIG. 47 is the XRPD pattern for R-5-MAPB HCl. This XRPD pattern is referred to as R-Enantiomer Pattern IA (for 300 mg of 5R-MAPB HCl, 1 vol. solvent is equivalent to 300 µL).

TABLE 21

R-5-MAPB Freebase from R-5-MAPB HCl

| Counterion | Solvent (Density) | Procedure/Comments |
|---|---|---|
| NaOH | EtOAc (0.902 g/mL) | 300 mg R-5-MAPB HCl + 10 vols. solvent + NaOH stock soln, in water (1.1:1 molar ratio) + additional water (10 vols. water total) |

Example 26. Salt Screening Experiments of R-5-MAPB Pure Enantiomer

Salt screening experiments of R-5-MAPB pure enantiomer were conducted as shown below in Table 22. All crystalline salts afford Pattern 1A, which was the same pattern observed from the R-5-MAPB HCl used as the starting material in Example 25 (for 27 mg of R-5-MAPB, 1 vol. solvent=27 µL).

TABLE 22

Salt screening experiments of R-5-MAPB Pure Enantiomer

| No. | Counterion | Solvent | Procedure/Comments | PXRD Result |
|---|---|---|---|---|
| 1 | HCl | Acetone | 27 mg R-5-MAPB + 10 vols. solvent + 1:1 molar ratio counterion soln., stirred at 40° C., slurry after overnight stirring, centrifuged to harvest solids, analyzed by PXRD | R-Enantiomer Pattern 1A |
| 2 | HCl | MeOH: water 90:10 | 27 mg R-5-MAPB + 10 vols. solvent + 1:1 molar ratio counterion soln., stirred at 40° C., in solution after overnight stirring, opened for evaporation, solid after overnight evaporation, analyzed by PXRD | R-Enantiomer Pattern 1A |
| 3 | HCl | THF | 27 mg R-5-MAPB + 10 vols. solvent + 1:1 molar ratio counterion soln., stirred at 40° C., slurry after overnight stirring, centrifuged to harvest solids, analyzed by PXRD | R-Enantiomer Pattern 1A |
| 4 | HCl | EtOH: water 90:10 | 27 mg R-5-MAPB + 10 vols. solvent + 1:1 molar ratio counterion soln., stirred at 40° C., in solution after overnight stirring, opened for evaporation, solid after overnight evaporation, analyzed by PXRD | R-Enantiomer Pattern 1A |
| 5 | HCl | CAN | 27 mg R-5-MAPB + 10 vols. solvent + 1:1 molar ratio counterion soln., stirred at 40° C., solid precipitate with solution after overnight stirring, solids harvested and analyzed by PXRD | R-Enantiomer Pattern 1A |

Example 27. Non-Racemic 5-MAPB Human Monoamine Transporter (hMAT) Release Assays Based on results from the marble burying assay that non-racemic mixtures of 5-MAPB enantiomers had non-additive effects, further in vitro measures of serotonin and dopamine release were made using cells that expressed human monoamine transporters, serotonin (hSERT) and dopamine (hDAT) transporter. Measures of in vitro serotonin and dopamine release using Chinese hamster ovary cells that expressed human serotonin (hSERT) or dopamine (hDAT) transporters were made. These produced surprising findings where non-racemic mixtures of 5-MAPB produced lower DAT to SERT ratios than the S-enantiomer or the racemate. This surprising finding suggests non-racemic mixtures may have lessened abuse liability compared to the S-enantiomer or the racemate. These findings could not be predicted from the activity of the individual enantiomers or the racemate.

TABLE 23

Effects of 5-MAPB on DAT and SERT

|  | $EC_{50}$ DAT (Mean ± SEM, nM) | $EC_{50}$ SERT (Mean ± SEM, nM) | DAT/SERT ratio* |
|---|---|---|---|
| S-5-MAPB | 258 ± 99 | 67 ± 15 | 0.26 |
| 75% S-5-MAPB | 632 ± 113 | 80 ± 7 | 0.13 |
| RS-5-MAPB | 459 ± 48 | 90 ± 16 | 0.20 |
| 75% R-5-MAPB | 794 ± 182 | 122 ± 13 | 0.15 |
| R-5-MAPB | 1951 ± 401 | 184 ± 3 | 0.09 |

*DAT/SERT ratios are calculated here as $(DAT\ EC_{50})^{-1}/(SERT\ EC_{50})^{-1}$ where larger number indicates higher DAT selectivity These data indicate that mixtures of enantiomers other than racemic produce lower DAT/SERT ratios than the simple racemic mixture. This could be the result of interactions between the reuptake inhibiting and release inducing properties of the individual enantiomers.

hSERT Release Measurement Methods

Chinese hamster ovary cells expressing human SERT were seeded in Cytostar™ (PerkinElmer) plate with standard culture medium the day before the experiment at a single density (5 000 cells/assay). Cells were incubated overnight with 5% $CO_2$ at 37° C. The day of experiment, the medium was replaced by incubation buffer (140 mM NaCl, 4.8 mM KCl, 1.2 mM $MgSO_4$, 0.1 mM $KH_2PO_4$, 10 mM HEPES, pH 7.4) with a single concentration of [$^3$H] Serotonin at 150 nM. Experiments comparing release in radioligand-free incubation buffer versus incubation buffer containing [$^3$H] Serotonin determined that the latter provided better signal stability. Therefore, this was used for experiments.

In control wells, the specificity of hSERT uptake was verified by adding the reference control imipramine (100 μM).

Two control conditions were used: (1) buffer only (with 1% DMSO concentration to match that in the test compound condition) to verify the background level of release; and (2) one reference SERT substrate compound, norfenfluramine, at 100 μM, to make it possible to calculate a relative Emax. Pilot studies varying DMSO concentration from 0.1 to 3% indicated that signal decreased at higher DMSO concentrations but that 1% DMSO retained good properties.

Cells were incubated at room temperature at different incubation times and radioactivity counted. Test compounds were measured at concentrations of 1e-10, 1e-09, 1e-08, 1e-07, 1e-06, 1e-05, and 1e-04 M. Each experiment was performed in duplicate (n=2) and results calculated at two inhibition times (60 and 90).

hDAT Release Measurement Methods

Chinese hamster ovary cells expressing human DAT were seeded in Cytostar™ plate with standard culture medium the day before experiment at one single density (2 500 cells/assay). Cells were incubated overnight with 5% $CO_2$ at 37° C. The day of experiment, the medium was replaced by incubation buffer (TrisHCl 5 mM, 120 mM NaCl, 5.4 mM KCl, 1.2 mM $MgSO_4$, 1.2 mM $CaCl_2$), Glucose 5 mM, 7.5 mM HEPES, pH 7.4) with a single concentration of [3H] dopamine at 300 nM. Experiments comparing release in radioligand-free incubation buffer versus incubation buffer containing [$^3$H]dopamine determined that the latter provided better signal stability. Therefore, this was used for experiments.

In control wells, the specificity of DAT uptake was verified by adding the reference control GBR 12909 (10 μM).

For all assays, three reference conditions were employed: (1) radioligand-containing buffer only, to verify the control level of release, (2) buffer with 1% DMSO (solvent used to solubilize the test compounds), (3) 100 uM amphetamine (in 1% DMSO) to make it possible to calculate a relative Emax.

Cells were incubated at room temperature at different incubation times and radioactivity counted. Test compounds were measured at concentrations of 1e-10, 1e-09, 1e-08, 1e-07, 1e-06, 1e-05, and 1e-04 M. Each experiment was performed in duplicate (n=2) and results calculated at two inhibition times (60 and 90).

Statistical Analysis

EC/IC50s were calculated using the R packages drm (to fit the regression model) and LL.4 (to define the structure of the log-logistic regression model). Values were fit to the following function:

$$f(x) = c + (d-c)/(1 + \exp(b(\log(x) - \log(e))))$$

where b=the Hill coefficient, c=minimum value, d=maximum value, and e=$EC_{50}/IC_{50}$.

Values were calculated for both experimental repetitions at both stable inhibition times (60 and 90 minutes), resulting in four estimates for each compound and transporter. These four values were averaged to produce a final estimate for each compound and transporter. Standard errors of the mean were also calculated based on the four values.

Example 28: Human Effects of Non-Racemic 5-MAPB

The effects of non-racemic 5-MAPB HCl were tested by a healthy human individual at four different ratios of enantiomers plus the racemate as a control:

54 mg S and 0 mg R (100% S)
47 mg S and 7 mg R (87% S)
36 mg S and 18 mg R (67% S)
27 mg S and 27 mg R (50% S)
7 mg S and 47 mg R (13% S)

Two trials were carried out at each ratio, except for 13% S where only one was conducted. Trials were at least 72 h apart.

5-MAPB HCl was dissolved in 1.5 ml distilled water and consumed in two halves, separated by 1 hour. Starting at 3 hours after administration, tablets of 250 mg ascorbic acid and capsules of 300 mg alpha lipoic acid were taken ad libitum (approximately every hour for a total of 4 administrations).

Measurements were 0-100 ratings of "good drug effects" (abbreviated as Good), "bad drug effects" (abbreviated as Bad), and "emotional openness" (abbreviated as Open), comparable to the visual analog ratings (e.g., Morean et al. 2013. Psychopharmacology, 227(1), 177-192) and verbal ratings (Mendelson et al. 1996. Clinical Pharmacology & Therapeutics, 60(1), 105-114) that are common in psychopharmacology research. Measurements were made approximately every 2 hours until post 6 hours and the maximum ratings per session were analyzed. Additionally, an index of good drug effects versus emotional openness, calculated as (Open−Good)/(200, the theoretical maximum of Open+Good), was constructed at each time point and the maximum analyzed. In healthy volunteers, Good Ratings can be considered a predictor of abuse liability. Accordingly, this index can be used as an indicator of the balance of a therapeutic effect (emotional openness) vs abuse liability.

Historic data of two trials 50 mg RS-5-MAPB Cl from the same individual were also included in the analysis for comparison. Methods for these data were similar except that doses were taken as a bolus and the setting was different.

Table 24 below indicates maximums for individual measures and for the open vs good index, averaged from all sessions (N=2, except for 13% S-5-MAPB where N=1). Qualitatively, all conditions produced subtle emotional effects, including decreases in negative affect and increases in stability of mood, without sensory distortion. 100% S appeared to have effects of less duration than conditions that included the R-enantiomer. A key finding was that non-racemic mixtures appeared to have a higher Open vs Good index, suggesting that they were better able to facilitate emotional openness while minimizing relative abuse liability.

TABLE 24

Self-Reported Ratings of Enantiomerically Enriched 5-MAPE

| Condition | Good | Bad | Open | Open vs Good Index |
|---|---|---|---|---|
| 100% S-5-MAPB | 55% | 1% | 65% | 0.17 |
| 87% S-5-MAPB | 40% | 5% | 65% | 0.20 |
| 67% S-5-MAPB | 37% | 5% | 55% | 0.21 |
| RS-5-MAPB | 50% | 10% | 45% | −0.03 |
| 13% S-5-MAPB | 13% | 15% | 15% | 0.05 |

Example 29 Evaluation of Entactogenic Effect of Decreased Neuroticism

The entactogenic effect of decreased neuroticism can be measured as a decrease in social anxiety using the Brief Fear of Negative Evaluation-revised (BFNE) (Carleton et al., 2006, Depression and Anxiety, 23(5), 297-303; Leary, 1983, Personality and Social Psychology bulletin, 9(3), 371-375). This 12-item Likert scale questionnaire measures apprehension and distress due to concerns about being judged disparagingly or with hostility by others. Ratings use a five-point Likert scale with the lowest, middle, and highest values labeled with "much less than normal," "normal," and "much more than normal." The BFNE can be administered before and repeatedly during therapeutic drug effects. Participants are instructed to answer how they have been feeling for the past hour, or otherwise during the effect of the drug. Baseline-subtracted responses are typically used in statistical models.

Example 30 Evaluation of Entactogenic Effect of Authenticity

The entactogenic effect of authenticity can be measured using the Authenticity Inventory (Kernis & Goldman. 2006. Advances in experimental social psychology, 38, 283-357) as modified by Baggott et al (Journal of Psychopharmacology 2016, 30.4: 378-87). Administration and scoring of the instrument is almost identical to that of the BFNE. The Authenticity Inventory consists of the following items, which are each rated on a 1-5 scale, with select items reverse scored as specified by Kernis & Goldman:

I am confused about my feelings.
I feel that I would pretend to enjoy something when in actuality I really didn't.
For better or worse, I am aware of who I truly am.
I understand why I believe the things I do about myself
I want the people with whom I am close to understand my strengths.
I actively understand which of my self-aspects fit together to form my core or true self.
I am very uncomfortable objectively considering my limitations and shortcomings.
I feel that I would use my silence or head-nodding to convey agreement with someone else's statement or position even though I really disagreed.
I have a very good understanding of why I do the things I do.
I am willing to change myself for others if the reward is desirable enough.
I would find it easy to pretend to be something other than my true self.
I want people with whom I am close to understand my weaknesses.
I find it difficult to critically assess myself (unchanged)
I am not in touch with my deepest thoughts and feelings.
I feel that I would make it a point to express to those I am close with how much I truly care for them.
I have difficulty accepting my personal faults, so I try to cast them in a more positive way.
I feel that I idealize the people close to me rather than objectively see them as they truly are.
If asked, people I am close to could accurately describe what kind of person I am.
I prefer to ignore my darkest thoughts and feelings
I am aware of times when I am not being my true self.
I am able to distinguish the self-aspects that are important to my core or true self from those that are unimportant.
People close to me would be shocked or surprised if they discovered what I am keeping inside me.
It is important for me to understand the needs and desires of those with whom I am close.
I want people close to me to understand the real me, rather than just my public persona or "image".
I could act in a manner that is consistent with my personally held values, even if others criticized me or rejected me for doing so.
If a close other and I were in disagreement, I would rather ignore the issue than constructively work it out.
I feel that I would do things that I don't want to do merely to avoid disappointing people.
My behavior expresses my values.

I actively attempt to understand myself as well as possible.
I feel that I'd rather feel good about myself than objectively assess my personal limitations and shortcomings.
My behavior expresses my personal needs and desires.
I have on a "false face" for others to see.
I feel that I would spend a lot of energy pursuing goals that are very important to other people even though they are unimportant to me.
I am not in touch with what is important to me.
I try to block out any unpleasant feelings I have about myself.
I question whether i really know what I want to accomplish in my lifetime.
I am overly critical about myself.
I am in touch with my motives and desires.
I feel that I would deny the validity of any compliments that I receive.
I place a good deal of importance on people close to me understanding who I truly am.
I find it difficult to embrace and feel good about the things I have accomplished.
If someone pointed out or focused on one of my shortcomings, I would quickly try to block it out of my mind and forget it.
The people close to me could count on me being who I am, regardless of what setting we were in.
My openness and honesty in close relationships are extremely important to me.
I am willing to endure negative consequences by expressing my true beliefs about things.

While the present invention is described in terms of particular embodiments and applications, it is not intended that these descriptions in any way limit its scope to any such embodiments and applications, and it will be understood that many modifications, substitutions, changes, and variations in the described embodiments, applications, and details of the invention illustrated herein can be made by those skilled in the art without departing from the spirit of the invention, or the scope of the invention as described in the appended claims.

I claim:
1. A compound of formula

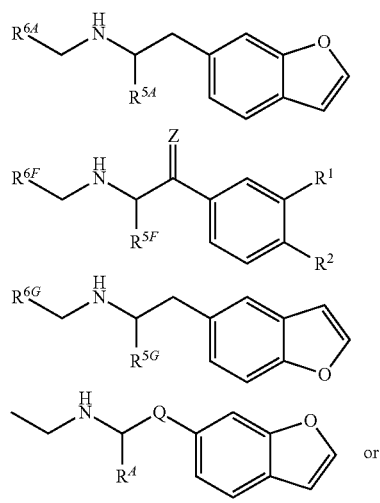

or

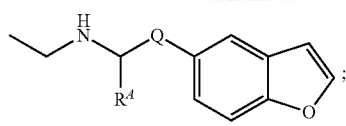

or a pharmaceutically acceptable salt or mixed salt thereof,
wherein:
$R^1$ and $R^2$ are taken together as —OCH=CH— or —CH=CHO—;
$R^{5A}$ and $R^{5G}$ are independently selected from the group consisting of —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_3$-C$_4$ alkyl;
$R^{5F}$ is —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, or C$_2$-C$_4$ alkyl;
$R^{6A}$, $R^{6F}$, and $R^{6G}$ are independently selected from the group consisting of —H and —CH$_3$;
$R^A$ is —CH$_3$, —CH$_2$Y, —CHY$_2$, —CY$_3$, —CH$_2$CH$_3$, —CH$_2$CH$_2$Y, —CH$_2$CHY$_2$, —CH$_2$CY$_3$, —CH$_2$OH, or —CH$_2$CH$_2$OH;
Q is

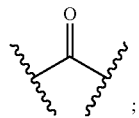 [SMILES: *C(*)=O]

Y is —F, —Cl, or —Br;
X is —F, —Cl, or —Br; and
Z is O or CH$_2$.

2. The compound of claim 1, wherein the compound is of formula

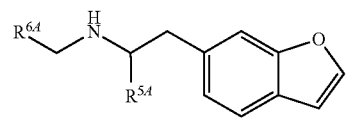

or a pharmaceutically acceptable salt or mixed salt thereof.

3. The compound of claim 1, wherein the compound is of formula

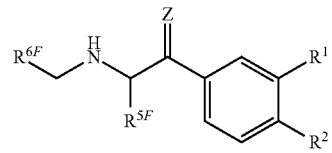

or a pharmaceutically acceptable salt or mixed salt thereof.

4. The compound of claim 1, wherein the compound is of formula

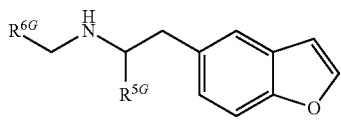

or a pharmaceutically acceptable salt or mixed salt thereof.

5. The compound of claim 1, wherein the compound is of formula

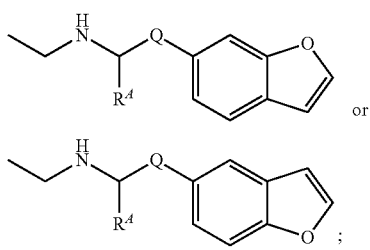

or a pharmaceutically acceptable salt or mixed salt thereof.

6. A compound selected from the group consisting of:

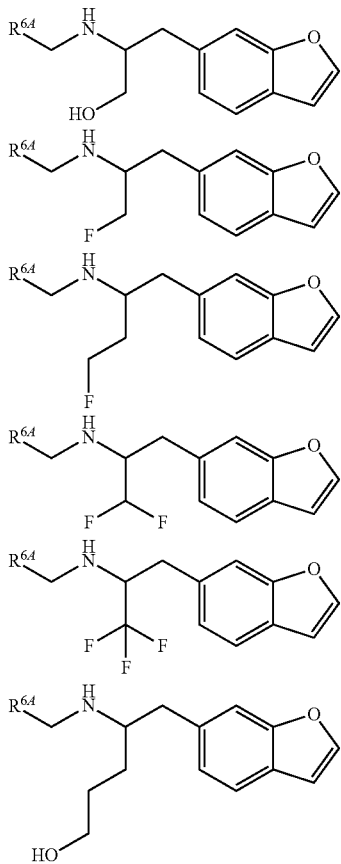

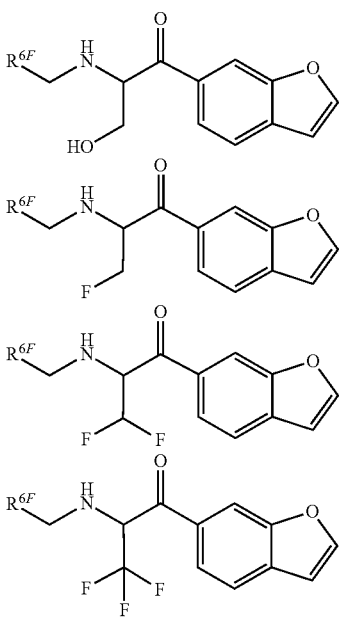

or a pharmaceutically acceptable salt or mixed salt thereof; wherein $R^{6A}$ is —H or —CH$_3$.

7. The compound of claim 3, wherein the compound is selected from the group consisting of:

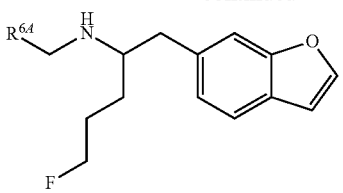

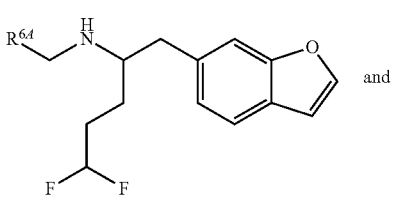

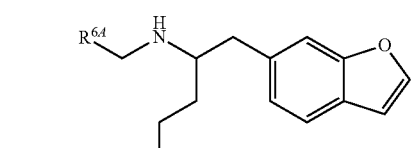

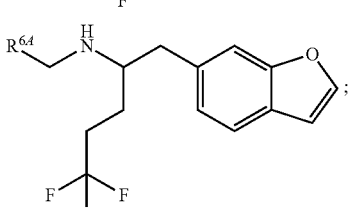

409
-continued
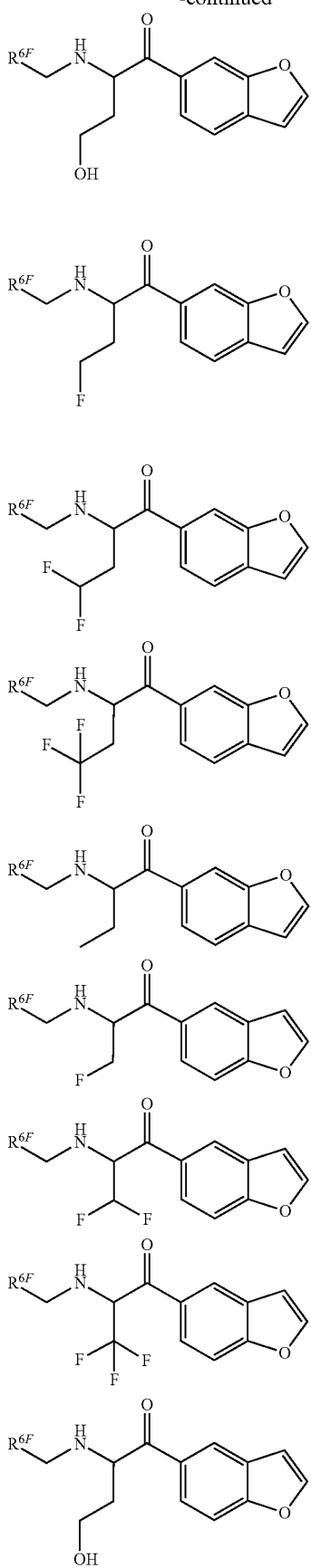
410
-continued
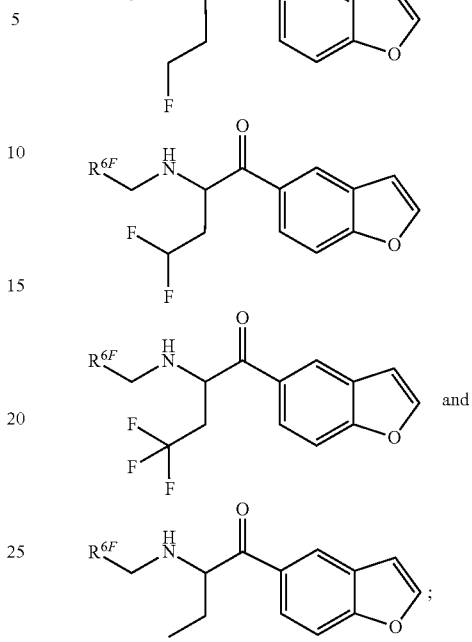
or a pharmaceutically acceptable sat or mixed sat thereof.
8. A compound selected from the group consisting of:
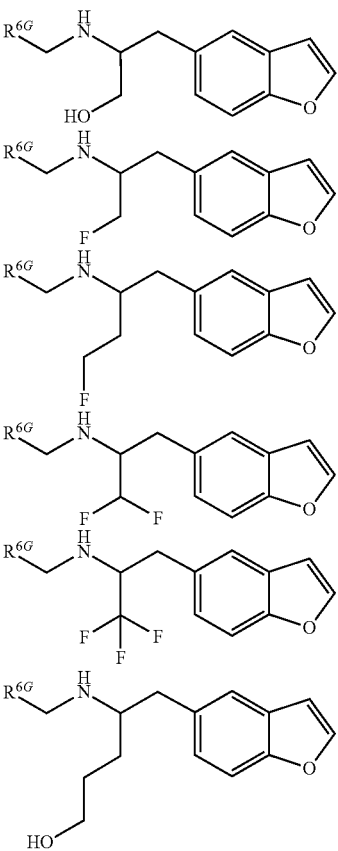

-continued

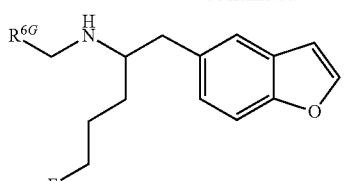

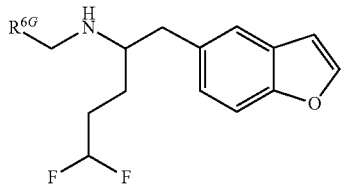 and

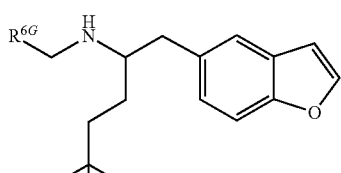 ;

or a pharmaceutically acceptable salt or mixed salt thereof; wherein $R^{6G}$ is —H or —CH$_3$.

9. The compound of claim 6 wherein the compound is selected from the group consisting of:

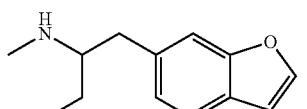

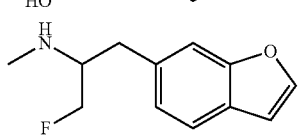

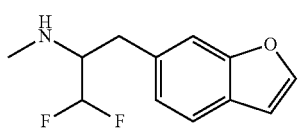

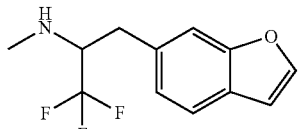

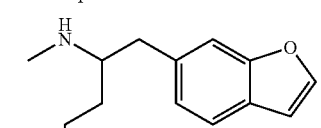

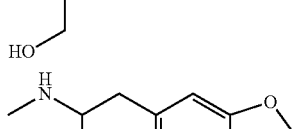

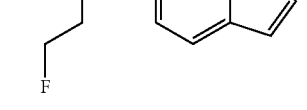

-continued

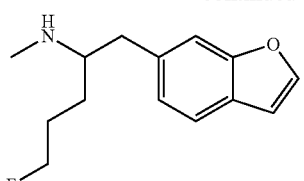

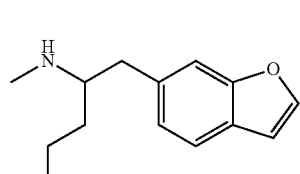 and

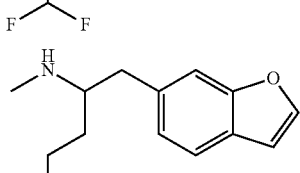 ;

or a pharmaceutically acceptable salt or mixed salt thereof.

10. The compound of claim 9 wherein the compound is

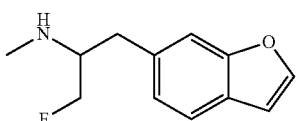

or a pharmaceutically acceptable salt or mixed salt thereof.

11. The compound of claim 9 wherein the compound is

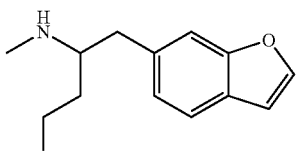

or a pharmaceutically acceptable salt or mixed salt thereof.

12. The compound of claim 5, wherein the compound is

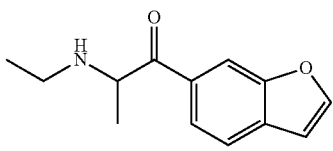 [SMILES: CCNC(C)C(=O)c1ccc2ccoc2c1]

or a pharmaceutically acceptable salt or mixed salt thereof.

13. The compound of claim 5, wherein the compound is
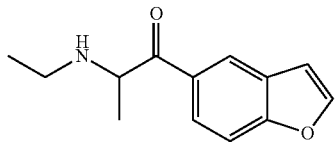 [SMILES: CCNC(C)C(=O)c1ccc2occc2c1]
or a pharmaceutically acceptable salt or mixed salt thereof.
14. A compound selected from the group consisting of:
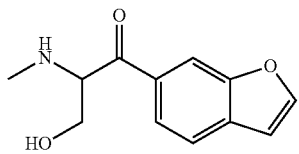
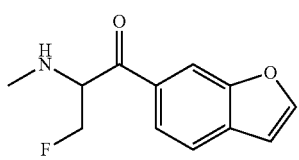
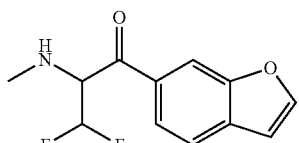
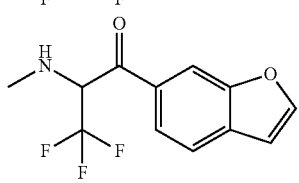
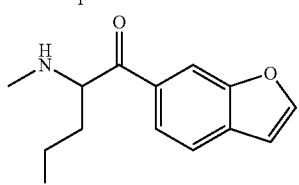
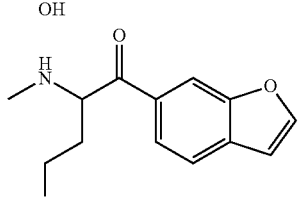
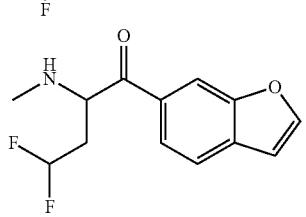
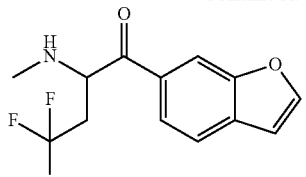
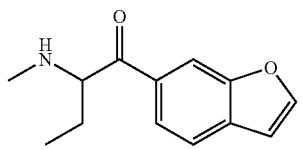
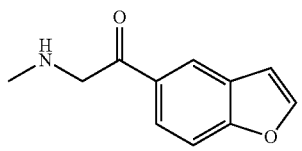
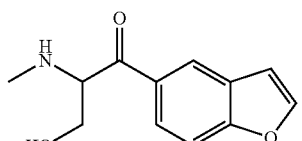
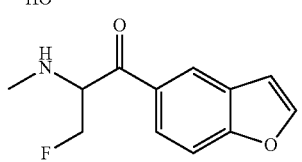
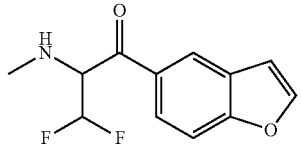
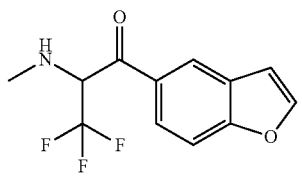
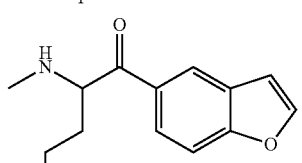
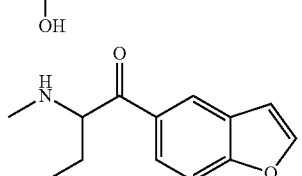 and -continued

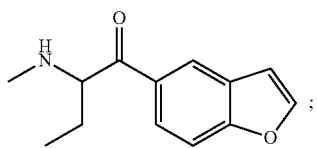 [SMILES: CCC(NC)C(=O)c1ccc2occc2c1];

or a pharmaceutically acceptable salt or mixed salt thereof.

15. A compound selected from the group consisting of:

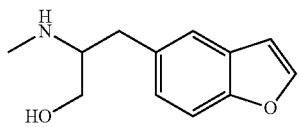

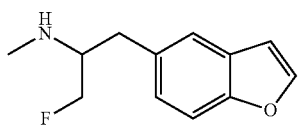

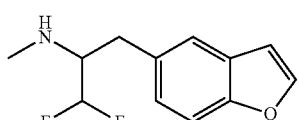

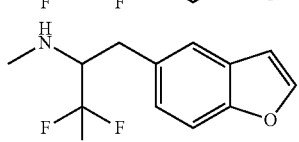

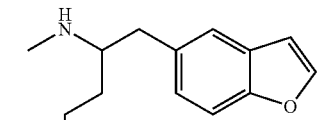

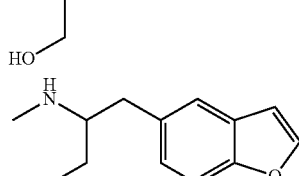

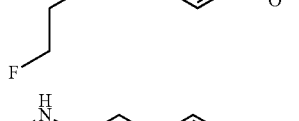

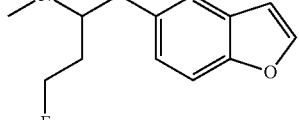

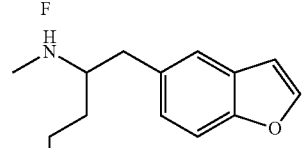 and

-continued

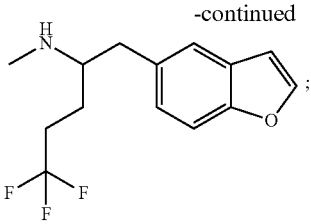;

or a pharmaceutically acceptable salt or mixed salt thereof.

16. The compound of claim 15, wherein the compound is

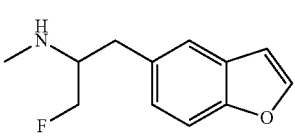

or a pharmaceutically acceptable salt or mixed salt thereof.

17. The compound of claim 15, wherein the compound is

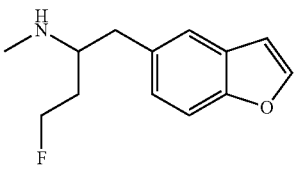 [SMILES: CNC(CCF)Cc1ccc2occc2c1]

or a pharmaceutically acceptable salt or mixed salt thereof.

18. An isolated enantiomerically enriched mixture of formula

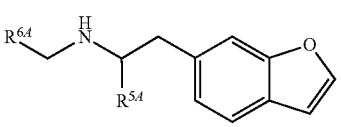

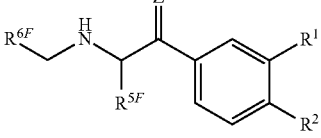

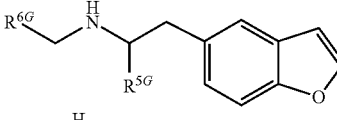

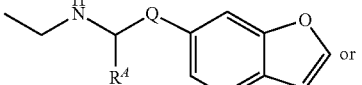 or

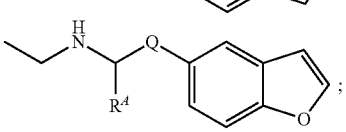;

or a pharmaceutically acceptable salt or mixed salt thereof, wherein the isolated enantiomerically enriched mixture comprises between 55% and 90% R-enantiomer or between 55% and 90% S-enantiomer, wherein:
R$^1$ and R$^2$ are taken together as —OCH=CH— or —CH=CHO—;
R$^{5A}$ and R$^{5G}$ are independently selected from the group consisting of —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, and C$_3$-C$_4$ alkyl;
R$^{5F}$ is —CH$_2$OH, —CH$_2$X, —CHX$_2$, —CX$_3$, —CH$_2$CH$_2$OH, —CH$_2$CH$_2$X, —CH$_2$CHX$_2$, —CH$_2$CX$_3$, C$_3$-C$_4$ cycloalkyl, or C$_2$-C$_4$ alkyl;
R$^{6A}$, R$^{6F}$, and R$^{6G}$ are independently selected from the group consisting of —H and —CH$_3$;
R$^A$ is —CH$_3$, —CH$_2$Y, —CHY$_2$, —CY$_3$, —CH$_2$CH$_3$, —CH$_2$CH$_2$Y, —CH$_2$CHY$_2$, —CH$_2$CY$_3$, —CH$_2$OH, or —CH$_2$CH$_2$OH;
Q is;

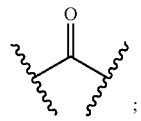

Y is —F;
X is —F; and
Z is O or CH$_2$.

19. The isolated enantiomerically enriched mixture of claim 18, wherein the isolated enantiomerically enriched mixture has between 55% and 90% S-enantiomer selected from those in a) through e) below:

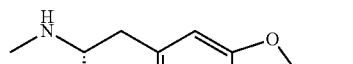

a)

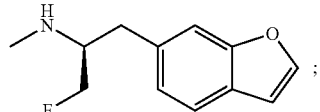

b)

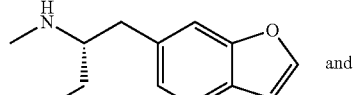

c)

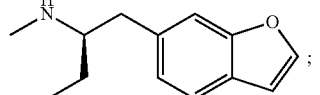

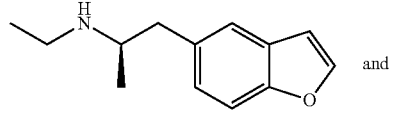

-continued

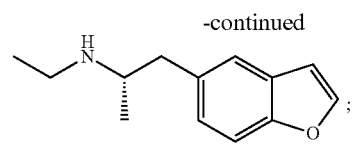

d)

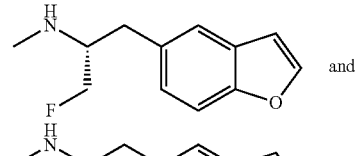

and

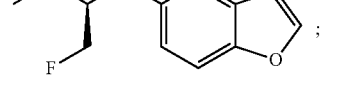

;

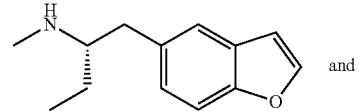

e)

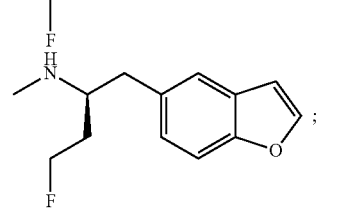

and or a pharmaceutically acceptable salt or a mixed salt thereof.

20. The isolated enantiomerically enriched mixture of claim 18, wherein the isolated enantiomerically enriched mixture has between 55% and 90% R-enantiomer selected from those in a) through e) below:

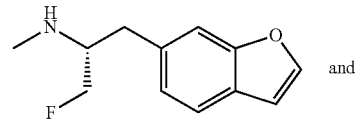

a)

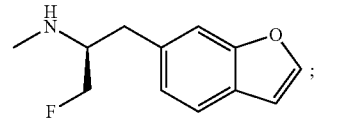

and

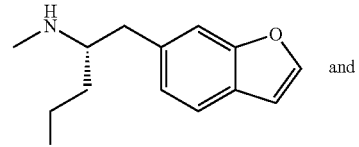

b)

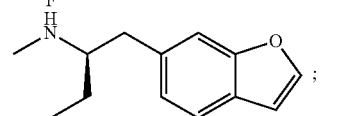

and

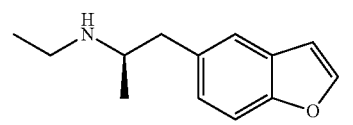

c)

and

-continued

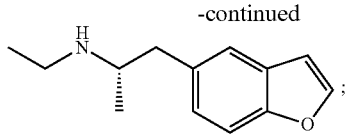

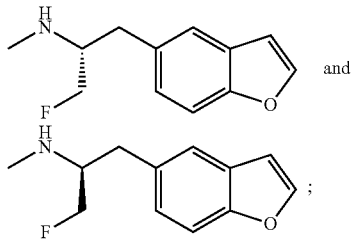
and

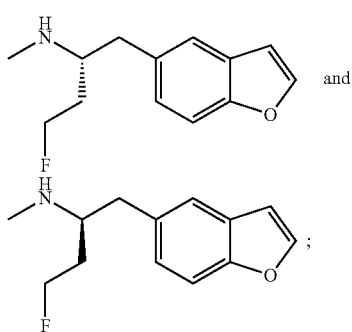
and or a pharmaceutically acceptable salt or a mixed salt thereof.

21. The isolated enantiomerically enriched mixture of claim 18 of formula

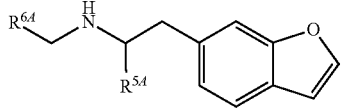

or a pharmaceutically acceptable salt or mixed salt thereof.

22. The isolated enantiomerically enriched mixture of claim 18 of formula

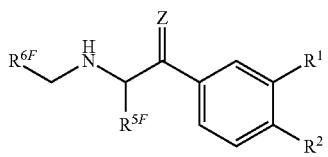

or a pharmaceutically acceptable salt or mixed salt thereof.

23. The isolated enantiomerically enriched mixture of claim 18 of formula

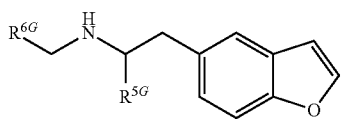

or a pharmaceutically acceptable salt or mixed salt thereof.

24. The isolated enantiomerically enriched mixture of claim 18 of formula d)
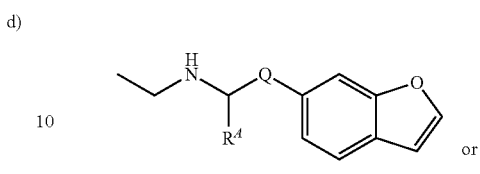
or e)
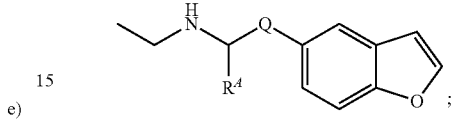
;

or a pharmaceutically acceptable salt or mixed salt thereof.

25. An isolated enantiomerically enriched mixture of formula:

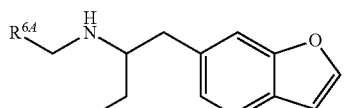

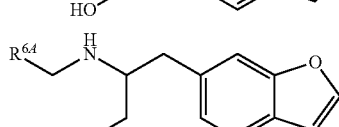

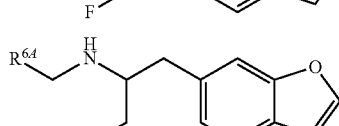

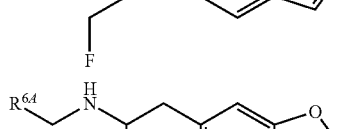

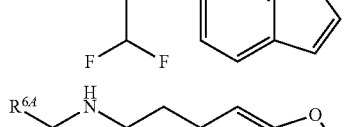

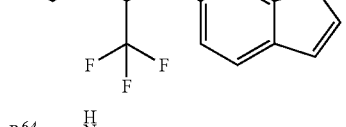

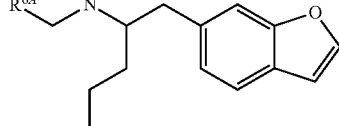

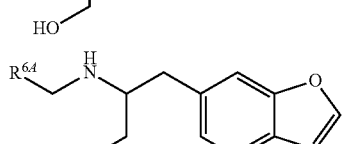

421
-continued
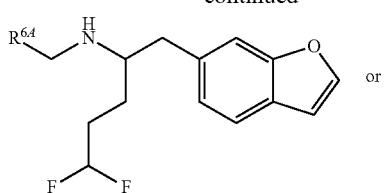
or
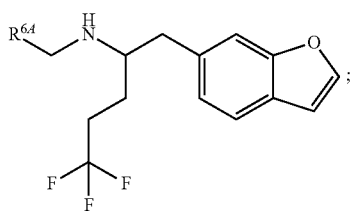
or a pharmaceutically acceptable salt or mixed salt thereof; wherein $R^{6A}$ is —H or —CH$_3$.
26. The isolated enantiomerically enriched mixture of claim 22 of formula:
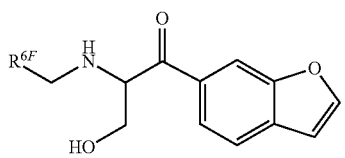
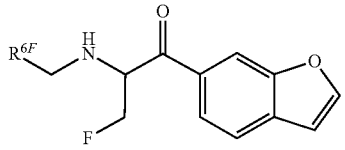
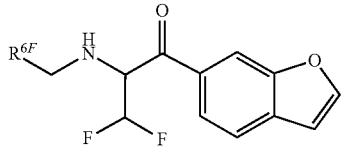
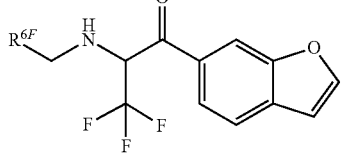
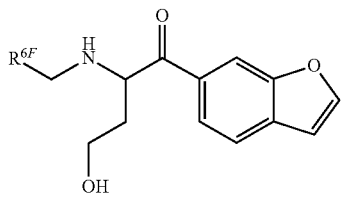
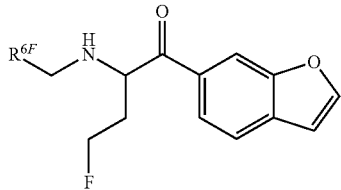
422
-continued
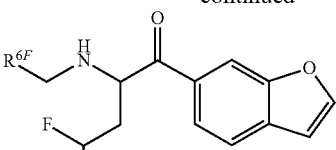
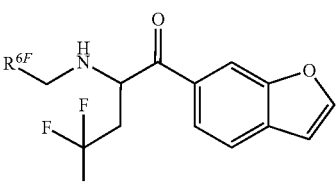
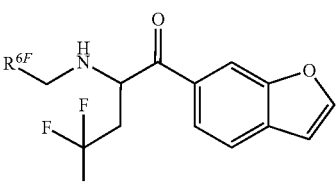
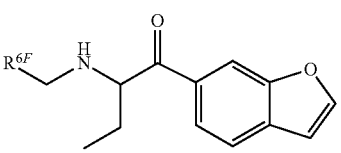
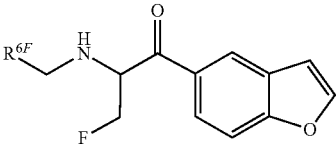
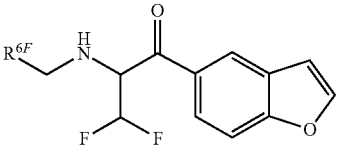
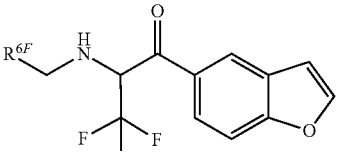
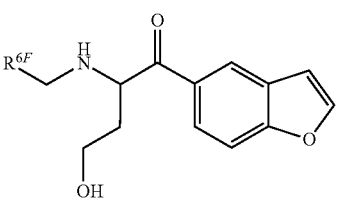
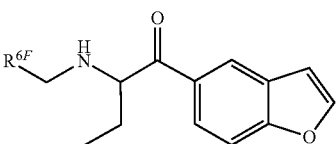
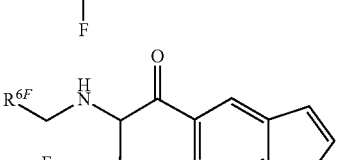

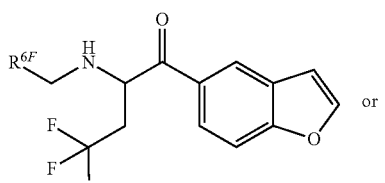
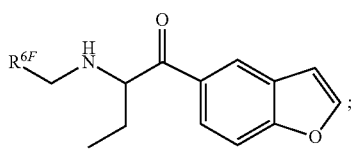
or a pharmaceutically acceptable salt or mixed salt thereof.
27. An isolated enantiomerically enriched mixture of formula:
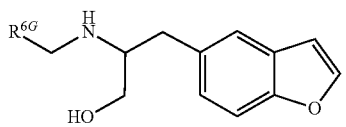
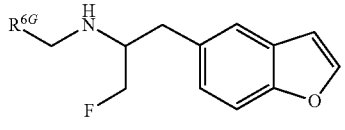
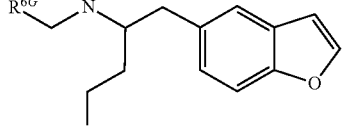
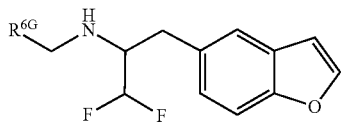
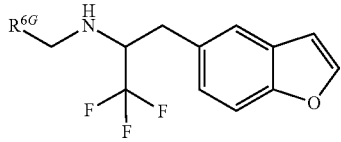
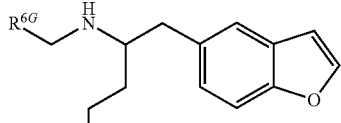
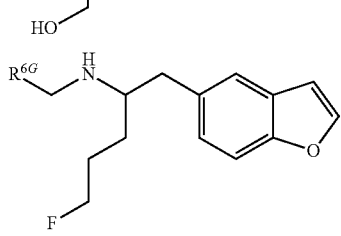
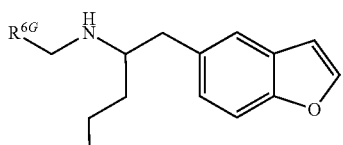
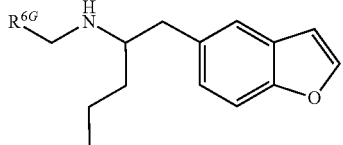
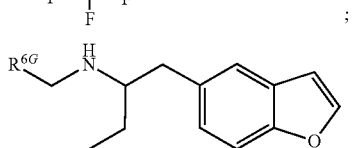
or a pharmaceutically acceptable salt or mixed salt thereof; wherein $R^{6G}$ is —H or —CH$_3$.
28. The isolated enantiomerically enriched mixture of claim 25 of formula:
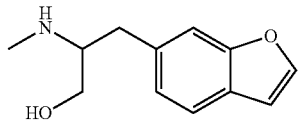
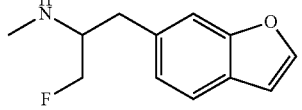
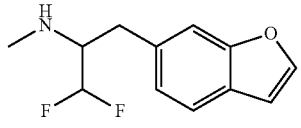
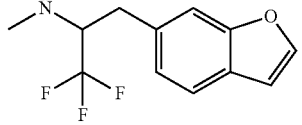
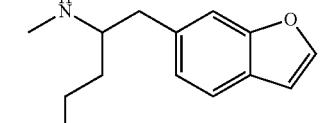
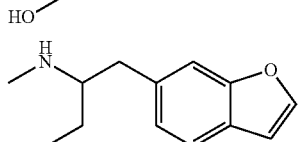

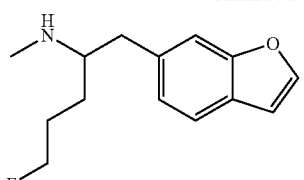
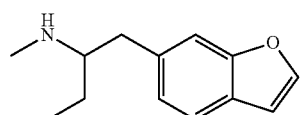
or
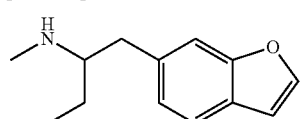
or a pharmaceutically acceptable salt or mixed salt thereof.
29. The isolated enantiomerically enriched mixture of claim 26 of formula:
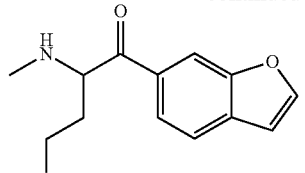
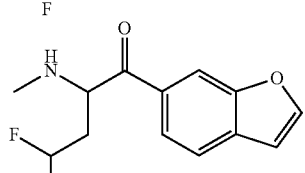
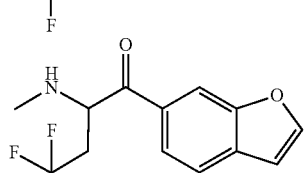
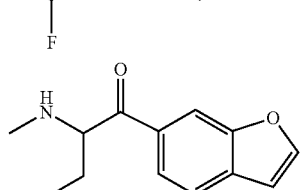
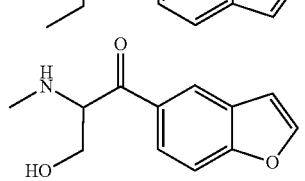
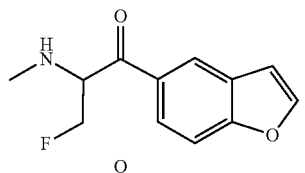
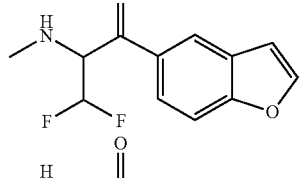
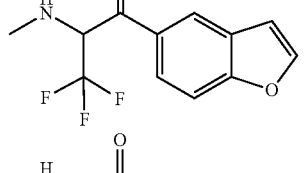
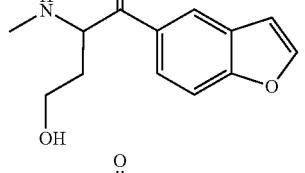
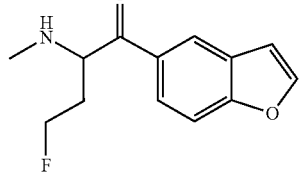
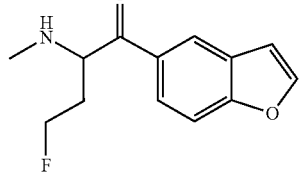

-continued
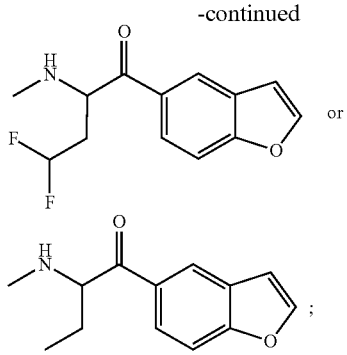
or
or a pharmaceutically acceptable salt or mixed salt thereof.
30. The isolated enantiomerically enriched mixture of claim 27 of formula:
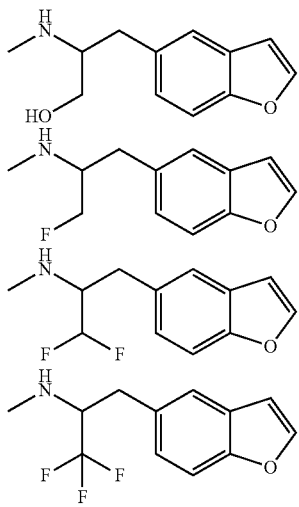
-continued
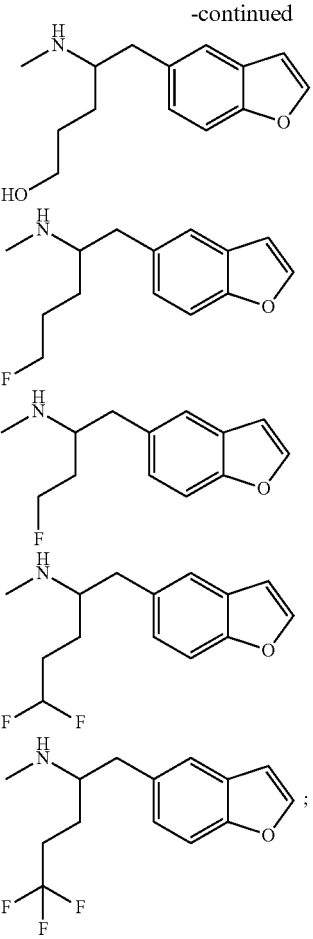
or
;
or a pharmaceutically acceptable salt or mixed salt thereof.
* * * * *